US011724992B2

(12) United States Patent
Franchi et al.

(10) Patent No.: US 11,724,992 B2
(45) **Date of Patent: *Aug. 15, 2023**

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Luigi Franchi, Ann Arbor, MI (US); Shomir Ghosh, Brookline, MA (US); Gary Glick, Ann Arbor, MI (US); Jason Katz, Newton, MA (US); Anthony William Opipari, Jr., Dexter, MI (US); William Roush, Boston, MA (US); Hans Martin Seidel, Concord, MA (US); Dong-Ming Shen, Edison, NJ (US); Shankar Venkatraman, Landsdale, PA (US); David Guenther Winkler, Arlington, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/496,375

(22) Filed: Oct. 7, 2021

(65) Prior Publication Data

US 2023/0062815 A1 Mar. 2, 2023

Related U.S. Application Data

(63) Continuation of application No. 16/632,849, filed as application No. PCT/US2018/043338 on Jul. 23, 2018, now Pat. No. 11,203,579.

(60) Provisional application No. 62/573,894, filed on Oct. 18, 2017, provisional application No. 62/536,271, filed on Jul. 24, 2017.

(51) Int. Cl.

| | |
|---|---|
| ***C07D 277/36*** | (2006.01) |
| ***C07D 215/36*** | (2006.01) |
| ***C07D 231/18*** | (2006.01) |
| ***C07D 239/26*** | (2006.01) |
| ***C07D 263/46*** | (2006.01) |
| ***C07D 307/64*** | (2006.01) |
| ***C07D 333/34*** | (2006.01) |
| ***C07C 307/06*** | (2006.01) |
| ***C07D 307/79*** | (2006.01) |
| ***C07D 317/62*** | (2006.01) |
| ***C07D 487/04*** | (2006.01) |
| *C07C 335/42* | (2006.01) |
| *C07D 213/71* | (2006.01) |
| *C07D 231/12* | (2006.01) |
| *C07D 405/12* | (2006.01) |
| *C07D 409/12* | (2006.01) |
| *C07D 417/12* | (2006.01) |
| *C07D 471/04* | (2006.01) |

(52) U.S. Cl.
CPC .......... *C07D 277/36* (2013.01); *C07C 307/06* (2013.01); *C07D 215/36* (2013.01); *C07D 231/18* (2013.01); *C07D 239/26* (2013.01); *C07D 263/46* (2013.01); *C07D 307/64* (2013.01); *C07D 307/79* (2013.01); *C07D 317/62* (2013.01); *C07D 333/34* (2013.01); *C07D 487/04* (2013.01); *C07C 335/42* (2013.01); *C07D 213/71* (2013.01); *C07D 231/12* (2013.01); *C07D 405/12* (2013.01); *C07D 409/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,666,506 A | 5/1987 | Hillemann | |
| 5,169,860 A | 12/1992 | Mohamadi et al. | |
| 5,258,406 A | 11/1993 | Toth et al. | |
| 10,654,816 B2 | 5/2020 | Franchi et al. | |
| 2002/0077486 A1 | 6/2002 | Scarborough et al. | |
| 2021/0171477 A1 | 6/2021 | Franchi et al. | |

FOREIGN PATENT DOCUMENTS

| | | |
|---|---|---|
| EP | 0 173 498 A1 | 3/1986 |
| EP | 0 552 553 A1 | 7/1993 |
| EP | 1236468 A1 | 4/2002 |
| EP | 2 314 593 A1 | 4/2011 |
| EP | 2 927 214 A1 | 10/2015 |
| WO | 98/32733 A1 | 7/1998 |

(Continued)

OTHER PUBLICATIONS

U.S. Appl. No. 16/572,528.
Coll, Rebecca C. et al.: "A small-molecule inhibitor of the NLRP3 inflammasome for the treatment of inflammatory diseases", Nature Medicine, vol. 21, No. 3, Mar. 2015, pp. 248-257.
Saxena, A. et al.: "Estimation of Antitumor Activity of Sulphonimidamide Analogs of Oncolytic Sulphonylureas", Oxidation Communications, vol. 26, No. 1, (2003), pp. 9-13.

(Continued)

*Primary Examiner* — Samantha L Shterengarts
(74) *Attorney, Agent, or Firm* — Sophie Binet Cross

(57) ABSTRACT

In one aspect, compounds of Formula AA, or a pharmaceutically acceptable salt thereof, are featured:

Formula AA

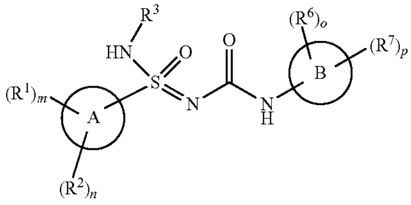

or a pharmaceutically acceptable salt thereof, wherein the variables shown in Formula A can be as defined anywhere herein.

20 Claims, 3 Drawing Sheets

Specification includes a Sequence Listing.

(56) References Cited

FOREIGN PATENT DOCUMENTS

| | | | |
|---|---|---|---|
| WO | 01/19390 | A1 | 3/2001 |
| WO | 2016/131098 | A1 | 8/2016 |
| WO | 2017/184604 | A1 | 10/2017 |
| WO | 2017/184623 | A1 | 10/2017 |
| WO | 2017/184624 | A1 | 10/2017 |
| WO | 2018/136890 | A1 | 7/2018 |
| WO | 2018/152396 | A1 | 8/2018 |
| WO | 2018/225018 | A1 | 12/2018 |
| WO | 2019/008025 | A1 | 1/2019 |
| WO | 2019/023145 | A1 | 1/2019 |
| WO | 2019/023147 | A1 | 1/2019 |
| WO | 2019/068772 | A1 | 4/2019 |

OTHER PUBLICATIONS

Scozzafava, A. et al.: "Arylsulfonyl-N,N-diethyl-dithiocarbamates: A Novel Class of Antitumor Agents", Bioorganic & Medicinal Chemistry Letters, vol. 10, (2000), pp. 1887-1891.

Supuran, C. et al.: "Carbonic anhydrase inhibitors—Part 94.1,3.4-Thiadiazole-2-sulfonamide derivatives as antitumor agents?", Eur. J. Med. Chem., vol. 35, (2000), pp. 867-874.

Toth, J. E. et al.: "Synthesis and Resolution of Sulfonimidamide Analogs of Sulfonylureas", J. Org. Chem., vol. 58, (1993), pp. 3469-3472.

Toth, J. E. et al.: "Sulfonimidamide Analogs of Oncolytic Sulfonylureas", J. Med. Chem., vol. 40, (1997), pp. 1018-1025.

Sehgelmeble,Fernando et al. Sulfonimidamides as Sulfonamides Bioisosteres: Rational Evaluation through Synthetic, in Vitro, and in Vivo Studies with y-Secretase Inhibitors:, Chem. Med. Chem 2012, 7, 396-399.

COMPOUNDS AND COMPOSITIONS FOR TREATING CONDITIONS ASSOCIATED WITH NLRP ACTIVITY

PRIORITY CLAIM

This application is a continuation of U.S. application Ser. No. 16/632,849, filed Mar. 31, 2020 which is a national stage of PCT Application No. PCT/US2018/043338, filed Jul. 23, 2018 which claims the benefit of U.S. Provisional Application No. 62/536,271, filed on Jul. 24, 2017; and U.S. Provisional Application No. 62/573,894, filed on Oct. 18, 2017; which are both incorporated herein by reference in their entirety.

TECHNICAL FIELD

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

NLRP3 can form a complex and has been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP3.

SUMMARY

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling).

In some embodiments, provided herein is a compound of Formula AA

Formula AA

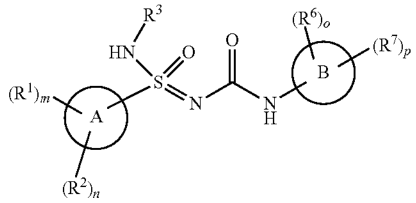

or a pharmaceutically acceptable salt thereof, wherein the variables in Formula AA can be as defined anywhere herein.

This disclosure also features compositions as well as other methods of using and making the same.

An "antagonist" of NLRP3 includes compounds that inhibit the ability of NLRP3 to induce the production of IL-1β and/or IL-18 by directly binding to NLRP3, or by inactivating, destabilizing, altering distribution, of NLRP3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3, as well as in vivo methods.

In a further aspect, methods of treatment of a disease in which NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP3, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21*st ed*.; Lippincott Williams & Wilkins: Philadelphia, Pa., 2005*; Handbook of Pharmaceutical Excipients,* 6*th ed*.; Rowe et al., Eds.; The Pharmaceutical Press and the American Pharmaceutical Association: 2009*; Handbook of Pharmaceutical Additives,* 3*rd ed*.; Ash and Ash Eds.; Gower Publishing Company: 2007*; Pharmaceutical Preformulation and Formulation,* 2*nd ed*.; Gibson Ed.; CRC Press LLC: Boca Raton, Fla., 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —$OCH_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclic rings include five-membered, six-membered, and seven-membered heterocyclic rings.

The term "cycloalkyl" as used herein includes an nonaromatic cyclic, bicylic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an nonaromatic 5-8 membered monocyclic, 8-12 membered bicyclic, or 11-14 membered tricyclic ring, fused, or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons. Examples include phenyl and naphthyl.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxy" refers to an OH group.

The term "amino" refers to an $NH_2$ group.

The term "oxo" refers to O. By way of example, substitution of a $CH_2$ a group with oxo gives a C=O group.

As used herein, the terms "the ring A" or "A" are used interchangeably to denote

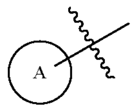

in formula AA, wherein the bond that is shown as being broken by the wavy line connects A to the S(O)($NHR^3$)=N moiety of Formula AA.

As used herein, the terms "the ring B" or "B" are used interchangeably to denote

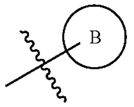

in formula AA wherein the bond that is shown as being broken by the wavy line connects B to the NH(CO) group of Formula AA.

As used herein, the term "the optionally substituted ring A" is used to denote

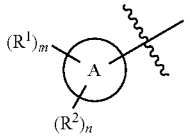

in formula AA, wherein the bond that is shown as being broken by the wavy line connects A to the S(O)($NHR^3$)=N moiety of Formula AA.

As used herein, the term "the substituted ring B" is used to denote

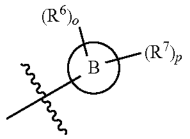

in formula AA, wherein the bond that is shown as being broken by the wavy line / connects B to the NH(CO) group of Formula AA.

As used herein, the recitation "$S(O_2)$", alone or as part of a larger recitation, refers to the group

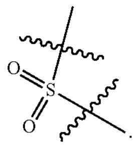 [SMILES: *S(*)(=O)=O]

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The scope of the compounds disclosed herein includes tautomeric form of the compounds. Thus, by way of example, a compound that is represented as containing the moiety

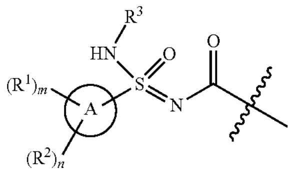

is also intended to include the tautomeric form containing the moiety

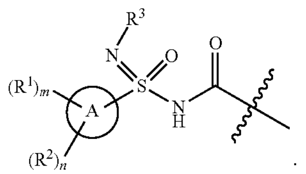

In addition, by way of example, a compound that is represented as containing the moiety

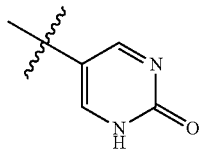 [SMILES: *c1cnc(=O)[nH]c1]

is also intended to include the tautomeric form containing the moiety

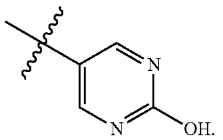 [SMILES: *c1cnc(O)nc1]

Non-limiting exemplified compounds of the formulae described herein include a stereogenic sulfur atom and optionally one or more stereogenic carbon atoms. This disclosure provides examples of stereoisomer mixtures (e.g., racemic mixture of enantiomers; mixture of diastereomers). This disclosure also describes and exemplifies methods for separating individual components of said stereoisomer mixtures (e.g., resolving the enantiomers of a racemic mixture). In cases of compounds containing only a stereogenic sulfur atom, resolved enantiomers are graphically depicted using one of the two following formats: formulas A/B (hashed and solid wedge three-dimensional representation); and formula C ("flat structures with *-labelled stereogenic sulfur).

Formula A

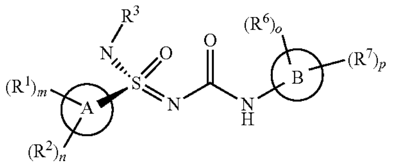

Formula B

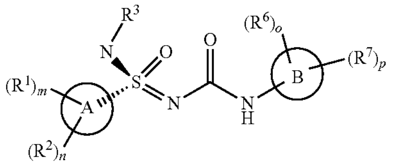

Formula C

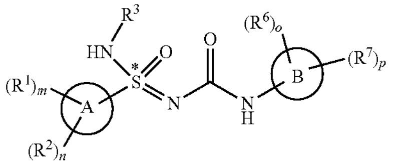

In reaction schemes showing resolution of a racemic mixture, Formulas A/B and C are intended only to convey that the constituent enantiomers were resolved in enantiopure pure form (about 98% ee or greater). The schemes that show resolution products using the formula A/B format are not intended to disclose or imply any correlation between absolute configuration and order of elution. Some of the compounds shown in the tables below are graphically represented using the formula A/B format. However, with the exception of compounds 181a and 181b, the depicted stereochemistry shown for each of the tabulated compounds drawn in the formula A/B format is a tentative assignment and based, by analogy, on the absolute stereochemistry assigned to compounds 181b (see, e.g., FIGS. 1 and 2).

The details of one or more embodiments of the invention are set forth in the accompanying drawings and the description below. Other features and advantages of the invention will be apparent from the description and drawings, and from the claims.

DETAILED DESCRIPTION

Figure 1:
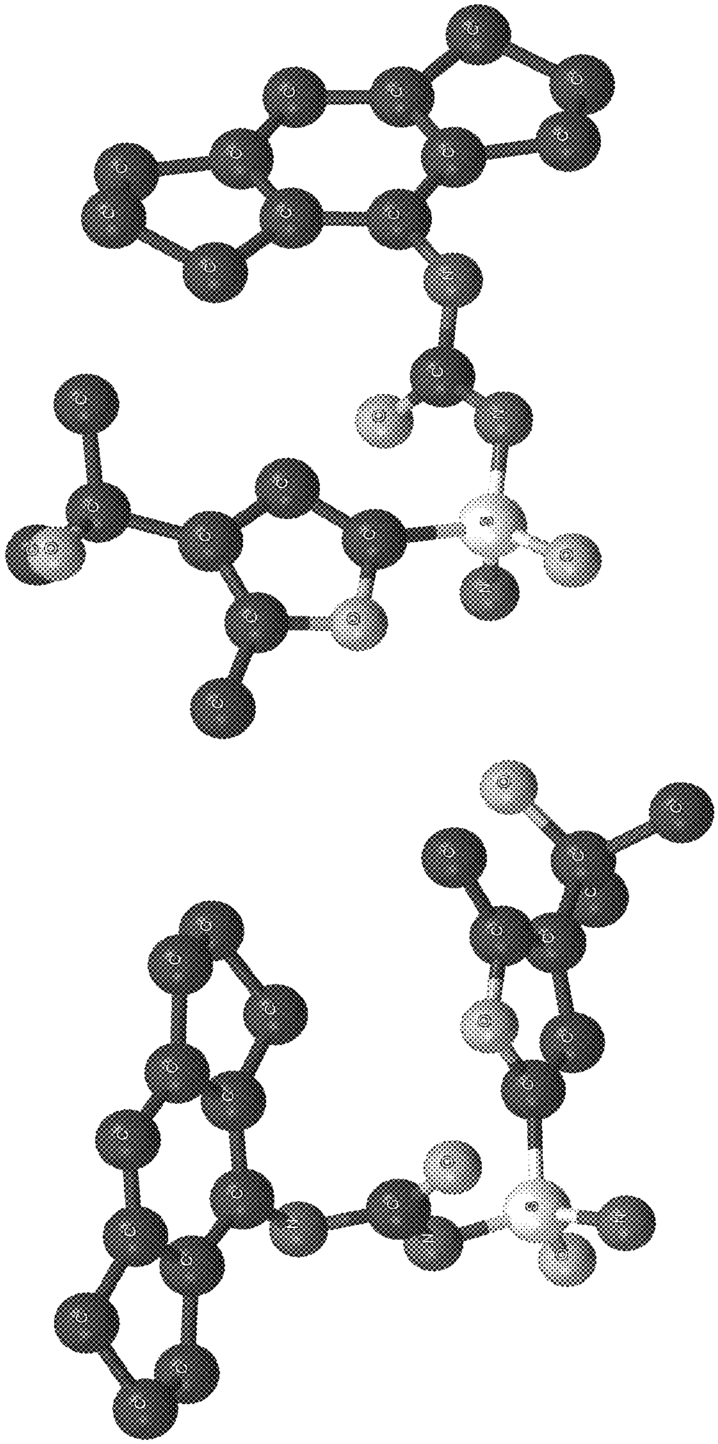
FIG. 1 depicts ball-and-stick representations of two crystallographically independent molecules of compound 181a in the asymmetrical unit.

In some embodiments, provided herein is a compound of Formula AA

Formula AA

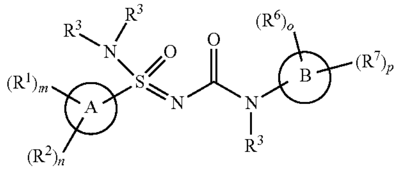

wherein
m=0, 1, or 2;
n=0, 1, or 2;
o=1 or 2;
p=0, 1, 2, or 3;
wherein
A is a 5-10-membered heteroaryl or a $C_6$-$C_{10}$ aryl;
B is a 5-10-membered heteroaryl or a $C_6$-$C_{10}$ aryl;
wherein
at least one $R^6$ is ortho to the bond connecting the B ring to the $NR^3$(CO) group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $COOC_1$-$C_6$ alkyl, $NR^8R^9$, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;
wherein the 3- to 7-membered heterocycloalkyl, $C_6$-$C_{10}$ aryl, or 5- to 10-membered heteroaryl, of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, oxo, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 4- to 8-membered heterocyclic ring containing 1 or 2 heteroatoms independently selected from O, N, $NR^{20}$, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$; each of $R^4$ and $R^5$ is independently selected from hydrogen and $C_1$-$C_6$ alkyl;
$R^{10}$ is $C_1$-$C_6$ alkyl;
each of $R^8$ and $R^9$ at each occurrence is independently selected from hydrogen, $C_1$-$C_6$ alkyl, $C_2$-$C_6$ alkenyl, $C_2$-$C_6$ alkynyl, (C=$NR^{13}$)$NR^{11}R^{12}$, $S(O_2)C_1$-$C_6$ alkyl, $S(O_2)$ $NR^{11}R^{12}$, $COR^{13}$, $CO_2R^{13}$ and $CONR^{11}R^{12}$; wherein the $C_1$-$C_6$ alkyl, $C_2$-$C_6$ alkenyl, or $C_2$-$C_6$ alkynyl is optionally substituted with one or more hydroxy, halo, oxo, $C_1$-$C_6$ alkoxy, $C_2$-$C_6$ alkynyl, $CO_2R^{13}$, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl; each $R^3$ is independently selected from hydrogen, cyano, hydroxy, $C_1$-$C_6$ alkoxy, $C_1$-$C_6$ alkyl, $CO_2C_1$-$C_6$ alkyl, and

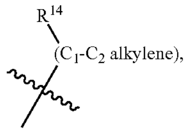

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

Formula AA

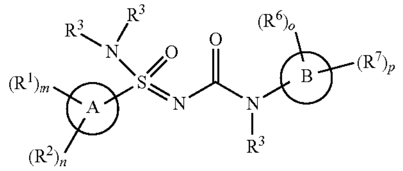

wherein m=0, 1, or 2;

n=0, 1, or 2;

o=1 or 2;

p=0, 1, 2, or 3;

wherein

A is a 5-10-membered heteroaryl or a $C_6$-$C_{10}$ aryl;

B is a 5-10-membered heteroaryl or a $C_6$-$C_{10}$ aryl;

wherein at least one $R^6$ is ortho to the bond connecting the B ring to the $NR^3$(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C═$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $COOC_1$-$C_6$ alkyl, $NR^8R^9$, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;

wherein the 3- to 7-membered heterocycloalkyl, $C_6$-$C_{10}$ aryl, or 5- to 10-membered heteroaryl, of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, oxo, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, ═$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, ═$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $C_2$-$C_6$ alkenyl, $C_2$-$C_6$ alkynyl, $(C{=}NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl, $C_2$-$C_6$ alkenyl, or $C_2$-$C_6$ alkynyl is optionally substituted with one or more hydroxy, halo, oxo, $C_1$-$C_6$ alkoxy, $C_2$-$C_6$ alkynyl, $CO_2R^{13}$, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl;

each $R^3$ is independently selected from hydrogen, cyano, hydroxy, $C_1$-$C_6$ alkoxy, $C_1$-$C_6$ alkyl, $CO_2C_1$-$C_6$ alkyl, and

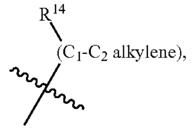

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

Formula AA

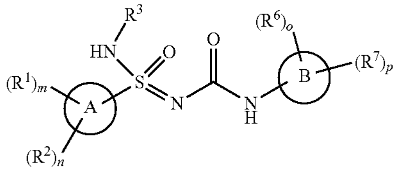

wherein m=0, 1, or 2;

n=0, 1, or 2;

o=1 or 2;

p=0, 1, 2, or 3;

wherein

A is a 5-10-membered heteroaryl or a $C_6$-$C_{10}$ aryl;

B is a 5-10-membered heteroaryl or a $C_6$-$C_{10}$ aryl;

wherein at least one $R^6$ is ortho to the bond connecting the B ring to the $NR^3(CO)$ group of Formula AA; $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, $NH$—$(C{=}NR^{13})NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen and optionally substituted with halo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $(C{=}NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, $CO_2C_1$-$C_6$ alkyl, and

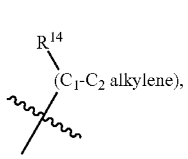

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

Formula AA

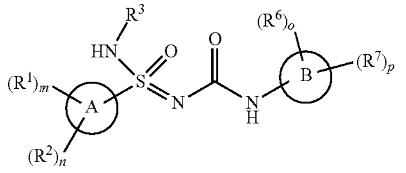

wherein
m=0, 1, or 2;
n=0, 1, or 2;
o=1 or 2;
p=0, 1, 2, or 3;
wherein
A is a 5- to 10-membered monocyclic or bicyclic heteroaryl or a $C_6$-$C_{10}$ monocyclic or bicyclic aryl;
B is a 5- to 10-membered monocyclic or bicyclic heteroaryl or a $C_6$-$C_{10}$ monocyclic or bicyclic aryl;
wherein
at least one $R^6$ is ortho to the bond connecting the B ring to the $NR^3$(CO) group of Formula AA; $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—$(C{=}NR^{13})NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl and 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl; and $R^3$ is selected from hydrogen, cyano, hydroxy, $C_1$-$C_6$ alkoxy, $C_1$-$C_6$ alkyl, and

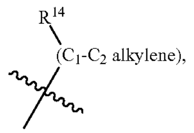

wherein the $C_1$-$C_2$ alkylene group is optionally substituted with oxo;

$R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

In some embodiments, provided herein is a compound of Formula AA

Formula AA

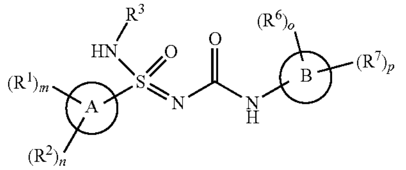

wherein m=0, 1, or 2;

n=0, 1, or 2;

o=1 or 2;

p=0, 1, 2, or 3, wherein

A is a 5- to 10-membered monocyclic or bicyclic heteroaryl or a $C_6$-$C_{10}$ monocyclic or bicyclic aryl;

B is a 5- to 10-membered monocyclic or bicyclic heteroaryl or a $C_6$-$C_{10}$ monocyclic or bicyclic aryl;

wherein at least one $R^6$ is ortho to the bond connecting the B ring to the NH(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, $(C{=}NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

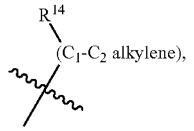

wherein the $C_1$-$C_2$ alkylene group is optionally substituted by oxo;

$R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

with the proviso that the compound of Formula AA is not a compound selected from the group consisting of:

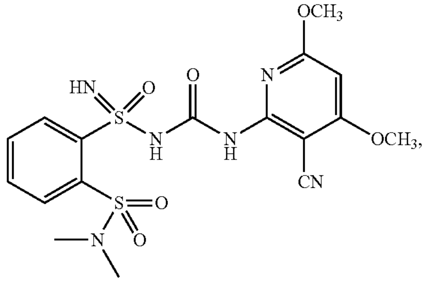

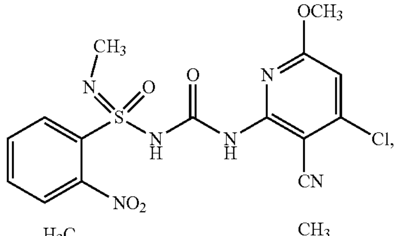

and

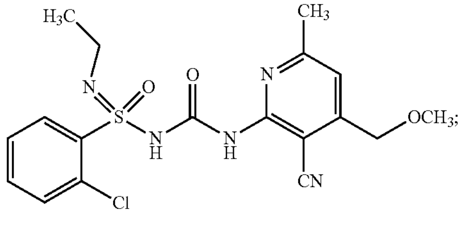

or a pharmaceutically acceptable salt thereof.

In some embodiments, provided herein is a compound of Formula AA

Formula AA

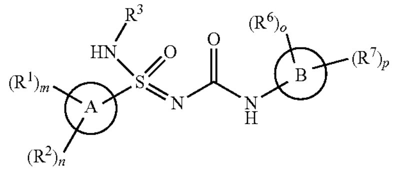

wherein m=0, 1, or 2;

n=0, 1, or 2;

o=1 or 2;

p=0, 1, 2, or 3, wherein

A is a 5- to 10-membered monocyclic or bicyclic heteroaryl or a $C_6$-$C_{10}$ monocyclic or bicyclic aryl;

B is a 5-membered heteroaryl, a 7-10 membered monocyclic or bicyclic heteroaryl, or a $C_6$-$C_{10}$ monocyclic or bicyclic aryl;

wherein at least one $R^6$ is ortho to the bond connecting the B ring to the NH(CO) group of Formula AA; $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C═$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, ═$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, ═$NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, ═$NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, ═$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, ═$NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, (C═$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

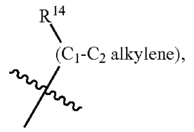

wherein the $C_1$-$C_2$ alkylene group is optionally substituted by oxo; and $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

In some embodiments the variables shown in the formulae herein are as follows:

The Variables m and n

In some embodiments m=0, 1, or 2.

In some embodiments m=0 or 1.

In some embodiments m=1 or 2.

In some embodiments m=0 or 2.

In some embodiments m=0.

In some embodiments m=1.

In some embodiments m=2.

In some embodiments n=0, 1, or 2.

In some embodiments n=0 or 1.

In some embodiments n=1 or 2.

In some embodiments n=0 or 2.

In some embodiments n=0.

In some embodiments n=1.

In some embodiments n=2.

In some embodiments, m=0 and n=0.

In some embodiments, m=1 and n=0.

In some embodiments, m=1 and n=1.

The Ring A and Substitutions on the Ring A

In some embodiments, A is a 5- to 10-membered (e.g., 5- to 6-membered) monocyclic or bicyclic heteroaryl or a $C_6$-$C_{10}$ (e.g., $C_6$) monocyclic or bicyclic aryl, such as phenyl.

In some embodiments, A is a 5- to 10-membered (e.g., 5- to 6-membered) monocyclic or bicyclic heteroaryl.

In some embodiments, A is a 5-membered heteroaryl containing a sulfur and optionally one or more nitrogens.

In some embodiments, A is a $C_6$-$C_{10}$ monocyclic or bicyclic aryl.

In some embodiments, A is phenyl optionally substituted with 1 or 2 $R^1$ and optionally substituted with 1 or 2 $R^2$.

In some embodiments, A is naphthyl optionally substituted with 1 or 2 $R^1$ and optionally substituted with 1 or 2 $R^2$.

In some embodiments, A is furanyl optionally substituted with 1 or 2 $R^1$ and optionally substituted with 1 $R^2$.

In some embodiments, A is furanyl optionally substituted with 1 $R^1$ and optionally substituted with 1 or 2 $R^2$.

In some embodiments, A is thiophenyl optionally substituted with 1 or 2 $R^1$ and optionally substituted with 1 or 2 $R^2$.

In some embodiments, A is oxazolyl optionally substituted with 1 or 2 $R^1$ and optionally substituted with 1 or 2 $R^2$.

In some embodiments, A is thiazolyl optionally substituted with 1 or 2 $R^1$ and optionally substituted with 1 or 2 $R^2$.

In some embodiments, A is oxazolyl optionally substituted with 2 $R^1$ or optionally substituted with 2 $R^2$.

In some embodiments, A is thiazolyl optionally substituted with 2 $R^1$ or optionally substituted with 2 $R^2$.

In some embodiments, A is pyrazolyl optionally substituted with 1 or 2 $R^1$ and optionally substituted with 1 or 2 $R^2$.

In some embodiments, A is pyrazolyl optionally substituted with 1 $R^1$ and optionally substituted with 1 or 2 $R^2$.

In some embodiments, A is pyrazolyl optionally substituted with 1 or 2 $R^1$ and optionally substituted with 1 $R^2$.

In some embodiments, A is pyridyl optionally substituted with 1 or 2 $R^1$ and optionally substituted with 1 or 2 $R^2$.

In some embodiments, A is indazolyl optionally substituted with 1 or 2 $R^1$ and optionally substituted with 1 or 2 $R^2$.

In some embodiments, A is phenyl substituted with 1 $R^1$ and optionally substituted with 1 $R^2$.

In some embodiments, A is naphthyl substituted with 1 $R^1$ and optionally substituted with 1 $R^2$.

In some embodiments, A is furanyl substituted with 1 $R^1$ and optionally substituted with 1 $R^2$.

In some embodiments, A is thiophenyl substituted with 1 $R^1$ and optionally substituted with 1 $R^2$.

In some embodiments, A is oxazolyl substituted with 1 $R^1$ and optionally substituted with 1 $R^2$.

In some embodiments, A is thiazolyl substituted with 1 $R^1$ and optionally substituted with 1 $R^2$.

In some embodiments, A is pyrazolyl substituted with 1 $R^1$ and optionally substituted with 1 $R^2$.

In some embodiments, A is pyridyl substituted with 1 $R^1$ and optionally substituted with 1 $R^2$.

In some embodiments, A is indazolyl optionally substituted with 1 $R^1$ and optionally substituted with 1 $R^2$.

In some embodiments, A is phenyl substituted with 1 $R^1$ and substituted with 1 $R^2$.

In some embodiments, A is furanyl substituted with 1 $R^1$ and substituted with 1 $R^2$.

In some embodiments, A is thiophenyl substituted with 1 $R^1$ and substituted with 1 $R^2$.

In some embodiments, A is oxazolyl substituted with 1 $R^1$ and substituted with 1 $R^2$.

In some embodiments, A is thiazolyl substituted with 1 $R^1$ and substituted with 1 $R^2$.

In some embodiments, A is pyrazolyl substituted with 1 $R^1$ and substituted with 1 $R^2$.

In some embodiments, A is pyridyl substituted with 1 $R^1$ and substituted with 1 $R^2$.

In some embodiments, A is phenyl, m is 0 or 1, and n is 0, 1, or 2.

In some embodiments, A is furanyl, m is 0 or 1, and n is 0, 1, or 2.

In some embodiments, A is thiophenyl, m is 0 or 1, and n is 0, 1, or 2.

In some embodiments, A is oxazolyl, m is 0 or 1, and n is 0, 1, or 2.

In some embodiments, A is thiazolyl, m is 0 or 1, and n is 0, 1, or 2.

In some embodiments, A is pyrazolyl, m is 0 or 1, and n is 0, 1, or 2.

In some embodiments, A is pyridyl, m is 0 or 1, and n is 0, 1, or 2.

In some embodiments, A is indazolyl, m is 0 or 1, and n is 0, 1, or 2.

In some embodiments, A is phenyl, m is 0, and n is 0 or 1.

In some embodiments, A is furanyl, m is 0, and n is 0 or 1.

In some embodiments, A is thiophenyl, m is 0, and n is 0 or 1.

In some embodiments, A is oxazolyl, m is 0, and n is 0 or 1.

In some embodiments, A is thiazolyl, m is 0, and n is 0 or 1.

In some embodiments, A is pyrazolyl, m is 0, and n is 0 or 1.

In some embodiments, A is pyridyl, m is 0, and n is 0 or 1.

In some embodiments, A is one of the rings disclosed hereinbelow optionally substituted as disclosed hereinbelow, wherein in each case the bond that is shown as being broken by the wavy line connects A to the $S(O)(NR^3R^3)$=N moiety of Formula AA.

In some embodiments, the optionally substituted ring A ( 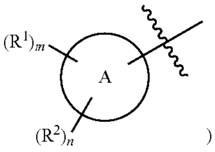 ) is 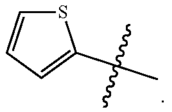

In some embodiments, the optionally substituted ring A is

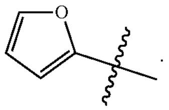 [SMILES: *c1ccco1]

In some embodiments, the optionally substituted ring A is

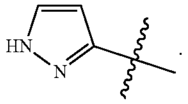

In some embodiments, the optionally substituted ring A is

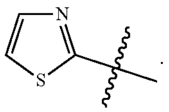 [SMILES: *c1nccs1]

In some embodiments, the optionally substituted ring A is

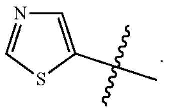 [SMILES: *c1cncs1]

In some embodiments, the optionally substituted ring A is

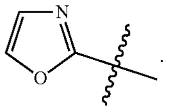 [SMILES: *c1ncco1]

In some embodiments, the optionally substituted ring A is

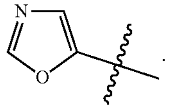 [SMILES: *c1cnco1]

In some embodiments, the optionally substituted ring A

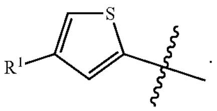

In some embodiments, the optionally substituted ring A is

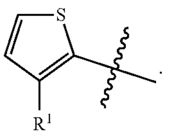

In some embodiments, the optionally substituted ring A is

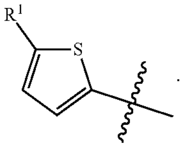

In some embodiments, the optionally substituted ring A is

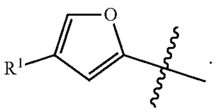

In some embodiments, the optionally substituted ring A is

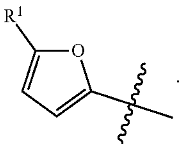

In some embodiments, the optionally substituted ring A is

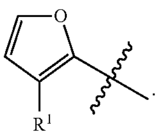

In some embodiments, the optionally substituted ring A is

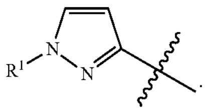

In some embodiments, the optionally substituted ring A is

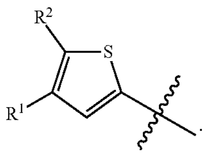

In some embodiments, the optionally substituted ring A is

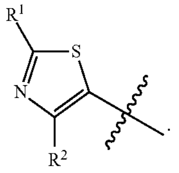

In some embodiments, the optionally substituted ring A is

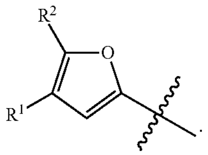

In some embodiments, the optionally substituted ring A is

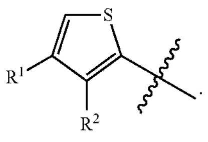

In some embodiments, the optionally substituted ring A is

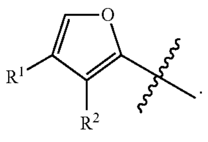

In some embodiments, the optionally substituted ring A is

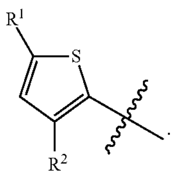

In some embodiments, the optionally substituted ring A is

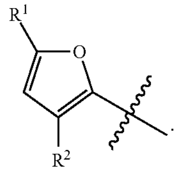

In some embodiments, the optionally substituted ring A is

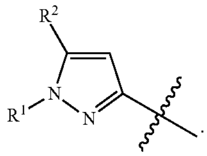

In some embodiments, the optionally substituted ring A is

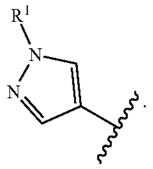

In some embodiments, the optionally substituted ring A is

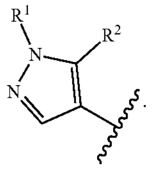

In some embodiments, the optionally substituted ring A is

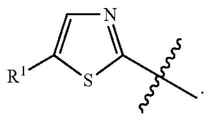

In some embodiments, the optionally substituted ring A is

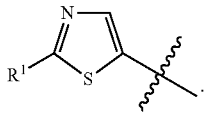

In some embodiments, the optionally substituted ring A is

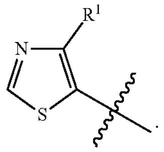

In some embodiments, the optionally substituted ring A is

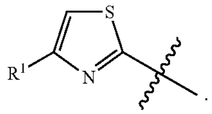

In some embodiments, the optionally substituted ring A is

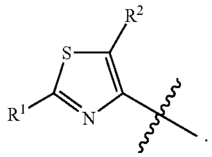

In some embodiments, the optionally substituted ring A is

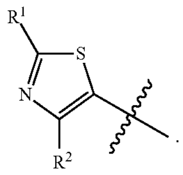

In some embodiments, the optionally substituted ring A is

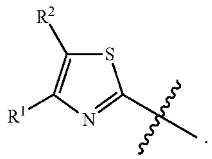

In some embodiments, the optionally substituted ring A is

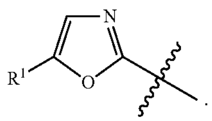

In some embodiments, the optionally substituted ring A is

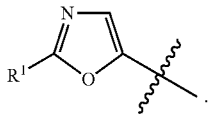

In some embodiments, the optionally substituted ring A is

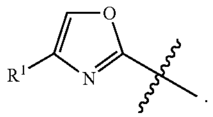

In some embodiments, the optionally substituted ring A is

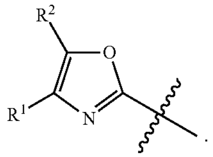

In some embodiments, the optionally substituted ring A is

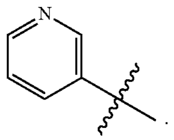 [SMILES: *c1cccnc1]

In some embodiments, the optionally substituted ring A is

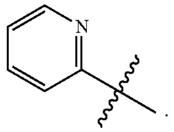 [SMILES: *c1ccccn1]

In some embodiments, the optionally substituted ring A is

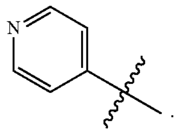 [SMILES: *c1ccncc1]

In some embodiments, the optionally substituted ring A is

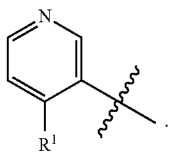

In some embodiments, the optionally substituted ring A is

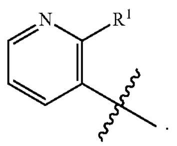

In some embodiments, the optionally substituted ring A is

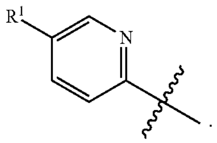

In some embodiments, the optionally substituted ring A is

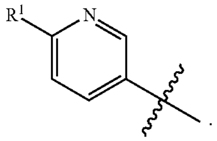

In some embodiments, the optionally substituted ring A is

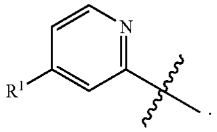

In some embodiments, the optionally substituted ring A is

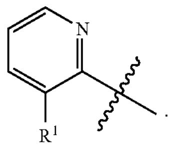

In some embodiments, the optionally substituted ring A is

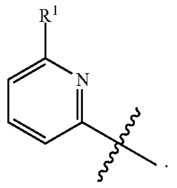

In some embodiments, the optionally substituted ring A is

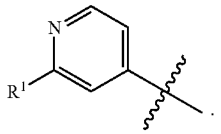

In some embodiments, the optionally substituted ring A is

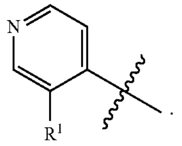

In some embodiments, the optionally substituted ring A is

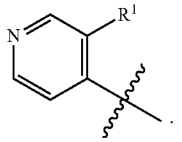

In some embodiments, the optionally substituted ring A is

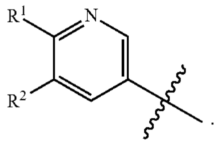

In some embodiments, the optionally substituted ring A is

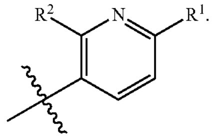

In some embodiments, the optionally substituted ring A is

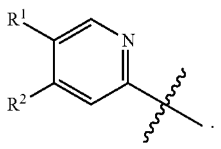

In some embodiments, the optionally substituted ring A is

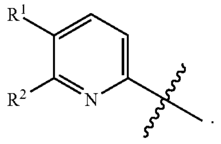

In some embodiments, the optionally substituted ring A is

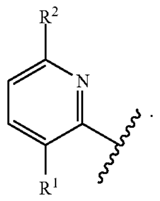

In some embodiments, the optionally substituted ring A is

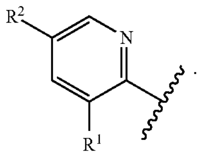

In some embodiments, the optionally substituted ring A is

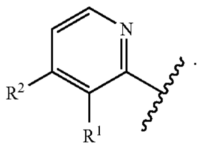

In some embodiments, the optionally substituted ring A is

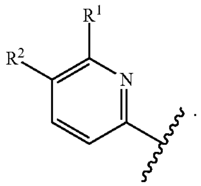

In some embodiments, the optionally substituted ring A is

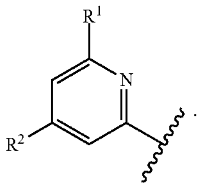

In some embodiments, the optionally substituted ring A is

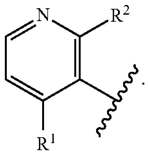

In some embodiments, the optionally substituted ring A is

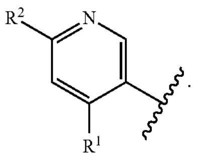

In some embodiments, the optionally substituted ring A is

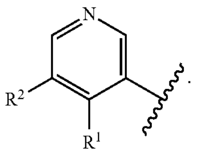

In some embodiments, the optionally substituted ring A is

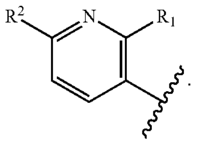

In some embodiments, the optionally substituted ring A is

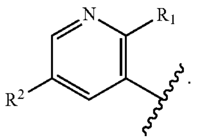

In some embodiments, the optionally substituted ring A is

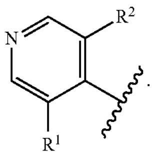

In some embodiments, the optionally substituted ring A is

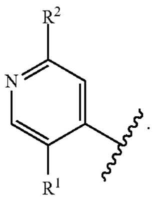

In some embodiments, the optionally substituted ring A is

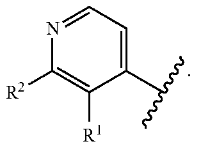

In some embodiments, the optionally substituted ring A is

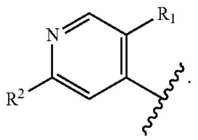

In some embodiments, the optionally substituted ring A is

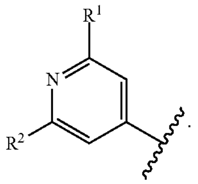

In some embodiments, the optionally substituted ring A is

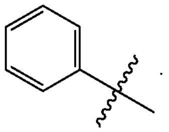 [SMILES: *c1ccccc1]

In some embodiments, the optionally substituted ring A is

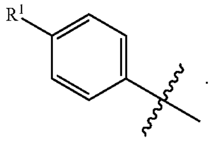

In some embodiments, the optionally substituted ring A is

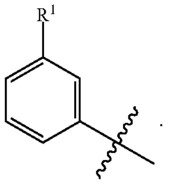

In some embodiments, the optionally substituted ring A is

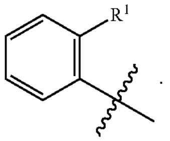

In some embodiments, the optionally substituted ring A is

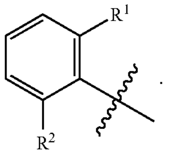

In some embodiments, the optionally substituted ring A is

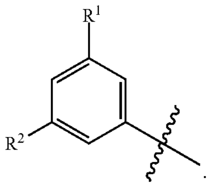

In some embodiments, the optionally substituted ring A is

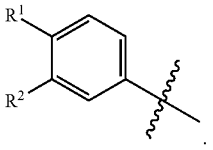

In some embodiments, the optionally substituted ring A is

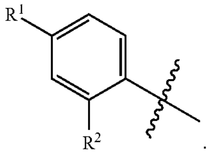

In some embodiments, the optionally substituted ring A is

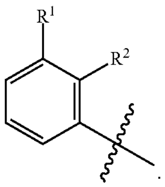

In some embodiments, the optionally substituted ring A is

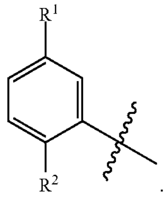

In some embodiments, the optionally substituted ring A is

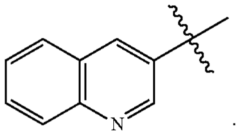 [SMILES: *c1cnc2ccccc2c1]

In some embodiments, the optionally substituted ring A is

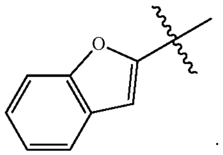 [SMILES: *c1cc2ccccc2o1]

In some embodiments, the optionally substituted ring A is

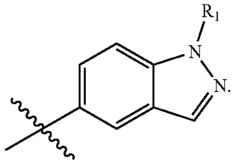

In some embodiments, the optionally substituted ring A is

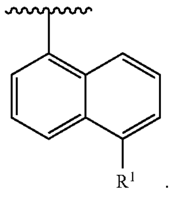

The Groups $R^1$ and $R^2$

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), and OCO(3- to 7-membered heterocycloalkyl);

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, and 5- to 10-membered heteroaryl are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;

In some embodiments, $R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo; wherein the 3- to 7-membered heterocycloalkyl, $C_6$-$C_{10}$ aryl, 5- to 10-membered heteroaryl, $NHCOC_6$-$C_{10}$ aryl, NHCO (5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo; wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl are each unsubstituted;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;

In some embodiments, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, $S(O)C_1$-$C_6$ alkyl, 5- to 10-membered heteroaryl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=0; and $R^1$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=0; and, $R^1$ is selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $—NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

In some embodiments, m=1; n=1; and, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are on adjacent atoms, and taken together with the atoms connecting them, form a $C_4$-$C_8$ carbocyclic ring or a 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_5$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_4$ $C_8$ carbocyclic ring or a 5- to 8-membered heterocyclic ring containing 1 or 2 heteroatoms independently selected from O, N, and S, wherein the carbocyclic ring or heterocyclic ring is unsubstituted.

Particular Embodiments Wherein m=1 and n=0:

In some embodiments, $R^1$ is $C_1$-$C_6$ alkyl optionally substituted with one or more hydroxy.

In some embodiments, $R^1$ is 1-hydroxy-2-methylpropan-2-yl.

In some embodiments, $R^1$ is 2-hydroxyethyl.

In some embodiments, $R^1$ is $C_1$-$C_6$ alkyl.

In some embodiments, $R^1$ is methyl.

In some embodiments, $R^1$ is isopropyl.

In some embodiments, $R^1$ is isopropyl.

In some embodiments, $R^1$ is $C_1$-$C_6$ alkyl substituted with hydroxy at the carbon directly connected to ring A.

In some embodiments, $R^1$ is 2-hydroxy-2-propyl.

In some embodiments, $R^1$ is hydroxymethyl.

In some embodiments, $R^1$ is 1-hydroxyethyl.

In some embodiments, $R^1$ is 1-hydroxy-2-propyl.

In some embodiments, $R^1$ is $C_1$-$C_6$ alkyl substituted with two or more hydroxy groups.

In some embodiments, $R^1$ is $C_1$-$C_6$ alkyl substituted with two or more hydroxy groups, wherein one of the two or more hydroxy groups is bonded to the carbon directly connected to ring A.

In some embodiments, $R^1$ is 1,2-dihydroxy-prop-2-yl.

In some embodiments, $R^1$ is $C_3$-$C_7$ cycloalkyl optionally substituted with one or more hydroxy.

In some embodiments, $R^1$ is $C_3$-$C_7$ cycloalkyl.

In some embodiments, $R^1$ is $C_3$-$C_7$ cycloalkyl substituted with hydroxy at the carbon directly connected to ring A.

In some embodiments, $R^1$ is 1-hydroxy-1-cyclopropyl.

In some embodiments, $R^1$ is 1-hydroxy-1-cyclobutyl.

In some embodiments, $R^1$ is 1-hydroxy-1-cyclopentyl.

In some embodiments, $R^1$ is 1-hydroxy-1-cyclohexyl.

In some embodiments, $R^1$ is 3- to 7-membered heterocycloalkyl optionally substituted with one or more hydroxy.

In some embodiments, $R^1$ is 3- to 7-membered heterocycloalkyl.

In some embodiments, $R^1$ is morpholinyl (e.g., 1-morpholinyl).

In some embodiments, $R^1$ is 1,3-dioxolan-2-yl.

In some embodiments, $R^1$ is 3- to 7-membered heterocycloalkyl optionally substituted with one or more $C_1$-$C_6$ alkyl.

In some embodiments, $R^1$ is 1-methylpyrrolidin-2-yl.

In some embodiments, $R^1$ is 3- to 7-membered heterocycloalkyl substituted with hydroxy at the carbon directly connected to ring A.

In some embodiments, $R^1$ is $C_1$-$C_6$ alkyl optionally substituted with one or more oxo.

In some embodiments, $R^1$ is $COCH_3$.

In some embodiments, $R^1$ is $COCH_2CH_3$.

In some embodiments, $R^1$ is $C_3$-$C_7$ cycloalkyl optionally substituted with one or more oxo.

In some embodiments, $R^1$ is 3- to 7-membered heterocycloalkyl optionally substituted with one or more oxo.

In some embodiments, $R^1$ is $C_1$-$C_6$ alkyl optionally substituted with one or more $C_1$-$C_6$ alkoxy.

In some embodiments, $R^1$ is 2-methoxy-2-propyl.

In some embodiments, $R^1$ is methoxymethyl.

In some embodiments, $R^1$ is $C_3$-$C_7$ cycloalkyl optionally substituted with one or more $C_1$-$C_6$ alkoxy.

In some embodiments, $R^1$ is 3- to 7-membered heterocycloalkyl optionally substituted with one or more $C_1$-$C_6$ alkoxy.

In some embodiments, $R^1$ is $C_1$-$C_6$ alkyl optionally substituted with one or more $NR^8R^9$.

In some embodiments, $R^1$ is $C_1$-$C_6$ alkyl substituted with $NR^8R^9$ at the carbon directly connected to ring A.

In some embodiments, $R^1$ is (methylamino)methyl.

In some embodiments, $R^1$ is (dimethylamino)methyl.

In some embodiments, $R^1$ is aminomethyl.

In some embodiments, $R^1$ is N-methylacetamidomethyl.

In some embodiments, $R^1$ is 1-(dimethylamino)eth-1-yl.

In some embodiments, $R^1$ is 2-(dimethylamino)prop-2-yl.

In some embodiments, $R^1$ is (2-methoxy-eth-1-yl)(methyl)aminomethyl.

In some embodiments, $R^1$ is (methyl)(acetyl)aminomethyl.

In some embodiments, $R^1$ is (methyl)(cyclopropylmethyl)aminomethyl.

In some embodiments, $R^1$ is (methyl)(2,2-difluoroeth-1-yl)aminomethyl.

In some embodiments, $R^1$ is $C_3$-$C_7$ cycloalkyl optionally substituted with one or more $NR^8R^9$.

In some embodiments, $R^1$ is 3- to 7-membered heterocycloalkyl optionally substituted with one or more $NR^8R^9$.

In some embodiments, $R^1$ is $C_1$-$C_6$ haloalkyl optionally substituted with one or more hydroxy.

In some embodiments, $R^1$ is $C_1$-$C_6$ alkoxy.

In some embodiments, $R^1$ is $C_1$-$C_6$ haloalkoxy.

In some embodiments, $R^1$ is $C_1$-$C_6$ alkyl optionally substituted with 3- to 7-membered heterocycloalkyl, wherein the 3- to 7-membered heterocycloalkyl is further optionally substituted as defined elsewhere herein.

In some embodiments, $R^1$ is pyrrolidinylmethyl (e.g., pyrrolidin-1-ylmethyl).

In some embodiments, $R^1$ is optionally substituted pyrrolidinylmethyl (e.g., 3,3-difluoropyrrolidin-1-ylmethyl).

In some embodiments, $R^1$ is azetidinylmethyl (e.g., azetidin-1-ylmethyl).

In some embodiments, $R^1$ is optionally substituted azetidinylmethyl (e.g., 3-methoxyazetidin-1-ylmethyl).

In some embodiments, $R^1$ is morpholinylmethyl (e.g., morpholin-4-ylmethyl).

In some embodiments, $R^1$ is halo.

In some embodiments, $R^1$ is fluoro.

In some embodiments, $R^1$ is chloro.

In some embodiments, $R^1$ is CN.

In some embodiments, $R^1$ is $NO_2$.

In some embodiments, $R^1$ is $COC_1$-$C_6$ alkyl.

In some embodiments, $R^1$ is CO—$C_6$-$C_{10}$ aryl.

In some embodiments, $R^1$ is CO(5- to 10-membered heteroaryl).

In some embodiments, $R^1$ is $CO_2C_1$-$C_6$ alkyl.

In some embodiments, $R^1$ is $CO_2C_3$-$C_8$ cycloalkyl.

In some embodiments, $R^1$ is $OCOC_1$-$C_6$ alkyl.

In some embodiments, $R^1$ is $OCOC_6$-$C_{10}$ aryl.

In some embodiments, $R^1$ is OCO(5- to 10-membered heteroaryl).

In some embodiments, $R^1$ is OCO(3- to 7-membered heterocycloalkyl).

In some embodiments, $R^1$ is $C_6$-$C_{10}$ aryl.

In some embodiments, $R^1$ is phenyl.

In some embodiments, $R^1$ is 5- to 10-membered heteroaryl.

In some embodiments, $R^1$ is pyridyl (e.g., 4-pyridyl).

In some embodiments, $R^1$ is pyrazolyl (e.g., 1-pyrazolyl).

In some embodiments, $R^1$ is $NH_2$.

In some embodiments, $R^1$ is $NHC_1$-$C_6$ alkyl.

In some embodiments, $R^1$ is $N(C_1$-$C_6$ alkyl$)_2$.

In some embodiments, $R^1$ is $CONR^8R^9$.

In some embodiments, $R^1$ is $SF_5$.

In some embodiments, $R^1$ is $SC_1$-$C_6$ alkyl,

In some embodiments, $R^1$ is $S(O_2)C_1$-$C_6$ alkyl.

In some embodiments, $R^1$ is $S(O_2)CH_3$.

In some embodiments, $R^1$ is $S(O_2)NR^{11}R^{12}$

In some embodiments, $R^1$ is $S(O_2)N(CH_3)_2$.

In some embodiments, $R^1$ is $S(O)C_1$-$C_6$ alkyl.

In some embodiments, $R^1$ is $S(O)CH_3$.

In some embodiments, $R^1$ is attached to a carbon of an aryl ring A.

In some embodiments, $R^1$ is attached to a carbon of a heteroaryl ring A.

In some embodiments, $R^1$ is attached to a nitrogen of a heteroaryl ring A.

Particular Embodiments Wherein m=1 and n=1:

In some embodiments, $R^1$ is $C_1$-$C_6$ alkyl optionally substituted with one or more hydroxy, and $R^2$ is $C_1$-$C_6$ alkyl optionally substituted with one or more hydroxy.

In some embodiments, $R^1$ is 1-hydroxy-2-methylpropan-2-yl, and $R^2$ is methyl.

In some embodiments, $R^1$ is 2-hydroxy-2-propyl and $R^2$ is methyl.

In some embodiments, $R^1$ is 2-hydroxy-2-propyl and $R^2$ is isopropyl.

In some embodiments, $R^1$ is 2-hydroxy-2-propyl and $R^2$ is 2-hydroxy-2-propyl.

In some embodiments, $R^1$ is 2-hydroxy-2-propyl and $R^2$ is 1-hydroxyethyl.

In some embodiments, $R^1$ is hydroxymethyl and $R^2$ is methyl.

In some embodiments, $R^1$ is 1-hydroxyethyl and $R^2$ is methyl.

In some embodiments, $R^1$ is 2-hydroxyethyl and $R^2$ is methyl.

In some embodiments, $R^1$ is 1-hydroxy-2-propyl and $R^2$ is methyl.

In some embodiments, $R^1$ is $C_1$-$C_6$ alkyl optionally substituted with one or more hydroxy, and $R^2$ is $C_6$-$C_{10}$ aryl.

In some embodiments, $R^1$ is 2-hydroxy-2-propyl and $R^2$ is phenyl.

In some embodiments, $R^1$ is $C_1$-$C_6$ alkyl optionally substituted with one or more hydroxy, and $R^2$ is 5- to 10-membered heteroaryl.

In some embodiments, $R^1$ is 2-hydroxy-2-propyl and $R^2$ is pyridyl.

In some embodiments, $R^1$ is 2-hydroxy-2-propyl and $R^2$ is pyrazolyl.

In some embodiments, $R^1$ is $C_1$-$C_6$ alkyl optionally substituted with one or more hydroxy, and $R^2$ is $SF_5$.

In some embodiments, $R^1$ is $C_1$-$C_6$ alkyl optionally substituted with one or more hydroxy, and $R^2$ is $SC_1$-$C_6$ alkyl, In some embodiments, $R^1$ is $C_1$-$C_6$ alkyl optionally substituted with one or more hydroxy, and $R^2$ is $S(O_2)C_1$-$C_6$ alkyl.

In some embodiments, $R^1$ is $C_1$-$C_6$ alkyl optionally substituted with one or more hydroxy, and $R^2$ is $S(O_2)CH_3$.

In some embodiments, $R^1$ is $C_1$-$C_6$ alkyl optionally substituted with one or more hydroxy, and $R^2$ is halo.

In some embodiments, $R^1$ is 2-hydroxy-2-propyl and $R^2$ is chloro.

In some embodiments, $R^1$ is 2-hydroxy-2-propyl and $R^2$ is fluoro.

In some embodiments, $R^1$ is $C_3$-$C_7$ cycloalkyl optionally substituted with one or more hydroxy, and $R^2$ is $C_1$-$C_6$ alkyl.

In some embodiments, $R^1$ is 1-hydroxy-1-cyclopropyl, and $R^2$ is methyl.

In some embodiments, $R^1$ is 1-hydroxy-1-cyclobutyl, and $R^2$ is methyl.

In some embodiments, $R^1$ is 1-hydroxy-1-cyclopentyl, and $R^2$ is methyl.

In some embodiments, $R^1$ is 1-hydroxy-1-cyclohexyl, and $R^2$ is methyl.

In some embodiments, $R^1$ is 3- to 7-membered heterocycloalkyl optionally substituted with one or more hydroxy, and $R^2$ is $C_1$-$C_6$ alkyl.

In some embodiments, $R^1$ is morpholinyl, and $R^2$ is methyl.

In some embodiments, $R^1$ is 1,3-dioxolan-2-yl, and $R^2$ is methyl.

In some embodiments, $R^1$ is 3- to 7-membered heterocycloalkyl optionally substituted with one or more hydroxy, and $R^2$ is halo.

In some embodiments, $R^1$ is 1,3-dioxolan-2-yl, and $R^2$ is fluoro.

In some embodiments, $R^1$ is 1,3-dioxolan-2-yl, and $R^2$ is chloro.

In some embodiments, $R^1$ is $C_1$-$C_6$ alkyl optionally substituted with one or more oxo, and $R^2$ is methyl.

In some embodiments, $R^1$ is $COCH_3$, and $R^2$ is methyl.

In some embodiments, $R^1$ is $C_1$-$C_6$ alkyl optionally substituted with one or more $C_1$-$C_6$ alkoxy, and $R^2$ is $C_1$-$C_6$ alkyl.

In some embodiments, $R^1$ is 2-methoxy-2-propyl, and $R^2$ is methyl.

In some embodiments, $R^1$ is $C_1$-$C_6$ alkyl optionally substituted with one or more $NR^8R^9$, and $R^2$ is $C_1$-$C_6$ alkyl.

In some embodiments, $R^1$ is (dimethylamino)methyl, and $R^2$ is methyl.

In some embodiments, $R^1$ is $C_1$-$C_6$ alkyl optionally substituted with one or more $NR^8R^9$, and $R^2$ is halo.

In some embodiments, $R^1$ is (dimethylamino)methyl, and $R^2$ is fluoro.

In some embodiments, $R^1$ is (dimethylamino)methyl, and $R^2$ is fluoro.

In some embodiments, $R^1$ is (methylamino)methyl, and $R^2$ is fluoro.

In some embodiments, $R^1$ is aminomethyl, and $R^2$ is fluoro.

In some embodiments, $R^1$ is $C_1$-$C_6$ alkyl, and $R^2$ is $C_1$-$C_6$ alkyl.

In some embodiments, $R^1$ is methyl, and $R^2$ is methyl.

In some embodiments, $R^2$ is 1-hydroxy-2-methylpropan-2-yl, and $R^1$ is methyl.

In some embodiments, $R^2$ is 2-hydroxy-2-propyl and $R^1$ is methyl.

In some embodiments, $R^2$ is 2-hydroxy-2-propyl and $R^1$ is isopropyl.

In some embodiments, $R^2$ is 2-hydroxy-2-propyl and $R^1$ is 1-hydroxyethyl.

In some embodiments, $R^2$ is hydroxymethyl and $R^1$ is methyl.

In some embodiments, $R^2$ is 1-hydroxyethyl and $R^1$ is methyl.

In some embodiments, $R^2$ is 2-hydroxyethyl and $R^1$ is methyl.

In some embodiments, $R^2$ is 1-hydroxy-2-propyl and $R^1$ is methyl.

In some embodiments, $R^2$ is $C_1$-$C_6$ alkyl optionally substituted with one or more hydroxy, and $R^1$ is $C_6$-$C_{10}$ aryl.

In some embodiments, $R^2$ is 2-hydroxy-2-propyl and $R^1$ is phenyl.

In some embodiments, $R^2$ is $C_1$-$C_6$ alkyl optionally substituted with one or more hydroxy, and $R^1$ is 5- to 10-membered heteroaryl.

In some embodiments, $R^2$ is 2-hydroxy-2-propyl and $R^1$ is pyridyl.

In some embodiments, $R^2$ is 2-hydroxy-2-propyl and $R^1$ is pyrazolyl.

In some embodiments, $R^2$ is $C_1$-$C_6$ alkyl optionally substituted with one or more hydroxy, and $R^1$ is $SF_5$.

In some embodiments, $R^2$ is $C_1$-$C_6$ alkyl optionally substituted with one or more hydroxy, and $R^1$ is $SC_1$-$C_6$ alkyl.

In some embodiments, $R^2$ is $C_1$-$C_6$ alkyl optionally substituted with one or more hydroxy, and $R^1$ is $S(O_2)C_1$-$C_6$ alkyl.

In some embodiments, $R^2$ is $C_1$-$C_6$ alkyl optionally substituted with one or more hydroxy, and $R^1$ is $S(O_2)CH_3$.

In some embodiments, $R^2$ is $C_1$-$C_6$ alkyl optionally substituted with one or more hydroxy, and $R^1$ is halo.

In some embodiments, $R^2$ is 2-hydroxy-2-propyl and $R^1$ is chloro.

In some embodiments, $R^2$ is 2-hydroxy-2-propyl and $R^1$ is fluoro.

In some embodiments, $R^2$ is $C_3$-$C_7$ cycloalkyl optionally substituted with one or more hydroxy, and $R^1$ is $C_1$-$C_6$ alkyl.

In some embodiments, $R^2$ is 1-hydroxy-1-cyclopropyl, and $R^1$ is methyl.

In some embodiments, $R^2$ is 1-hydroxy-1-cyclobutyl, and $R^1$ is methyl.

In some embodiments, $R^2$ is 1-hydroxy-1-cyclopentyl, and $R^1$ is methyl.

In some embodiments, $R^2$ is 1-hydroxy-1-cyclohexyl, and $R^1$ is methyl.

In some embodiments, $R^2$ is 3- to 7-membered heterocycloalkyl optionally substituted with one or more hydroxy, and $R^1$ is $C_1$-$C_6$ alkyl.

In some embodiments, $R^2$ is morpholinyl, and $R^1$ is methyl.

In some embodiments, $R^2$ is 1,3-dioxolan-2-yl, and $R^1$ is methyl.

In some embodiments, $R^2$ is 3- to 7-membered heterocycloalkyl optionally substituted with one or more hydroxy, and $R^1$ is halo.

In some embodiments, $R^2$ is 1,3-dioxolan-2-yl, and $R^1$ is fluoro.

In some embodiments, $R^2$ is 1,3-dioxolan-2-yl, and $R^1$ is chloro.

In some embodiments, $R^2$ is $C_1$-$C_6$ alkyl optionally substituted with one or more oxo, and $R^1$ is methyl.

In some embodiments, $R^2$ is $COCH_3$, and $R^1$ is methyl.

In some embodiments, $R^2$ is $C_1$-$C_6$ alkyl optionally substituted with one or more $C_1$-$C_6$ alkoxy, and $R^1$ is $C_1$-$C_6$ alkyl.

In some embodiments, $R^2$ is 2-methoxy-2-propyl, and $R^1$ is methyl.

In some embodiments, $R^2$ is $C_1$-$C_6$ alkyl optionally substituted with one or more $NR^8R^9$, and $R^1$ is $C_1$-$C_6$ alkyl.

In some embodiments, $R^2$ is (dimethylamino)methyl, and $R^1$ is methyl.

In some embodiments, $R^2$ is $C_1$-$C_6$ alkyl optionally substituted with one or more $NR^8R^9$, and $R^1$ is halo.

In some embodiments, $R^2$ is (dimethylamino)methyl, and $R^1$ is fluoro.

In some embodiments, $R^2$ is (methylamino)methyl, and $R^1$ is fluoro.

In some embodiments, $R^2$ is aminomethyl, and $R^1$ is fluoro.

In some embodiments, $R^2$ is $C_1$-$C_6$ alkoxy, and $R^1$ is $C_1$-$C_6$ alkyl optionally substituted with one or more $NR^8R^9$.

In some embodiments, $R^2$ is methoxy, and $R^1$ is (dimethylamino)methyl.

In some embodiments, $R^1$ and $R^2$ are each attached to a carbon of an aryl ring A.

In some embodiments, $R^1$ and $R^2$ are each attached to a carbon of a heteroaryl ring A.

In some embodiments, $R^1$ is attached to a carbon and $R^2$ is attached to a nitrogen of a heteroaryl ring A.

In some embodiments, $R^2$ is attached to a carbon and $R^1$ is attached to a nitrogen of a heteroaryl ring A.

In some embodiments, $R^1$ and $R^2$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, —$NR^{10}$ $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_5$ aliphatic carbocyclic ring.

In some embodiments, $R^1$ and $R^2$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, —$NR^{10}$ $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_6$ aliphatic carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, —$NR^{10}$ $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 5-membered heteroaromatic ring containing 1 or 2 heteroatoms independently selected from O, N, and S.

In some embodiments, $R^1$ and $R^2$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, —$NR^{10}$ $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 6-membered heteroaromatic ring containing 1 or 2 heteroatoms independently selected from O, N, and S.

In some embodiments, $R^1$ and $R^2$ are different.

In some embodiments, $R^1$ and $R^2$ are different, and $R^2$ comprises a carbonyl group.

In some embodiments, $R^1$ and $R^2$ are different, and $R^2$ comprises 1 or 2 (e.g., 1) nitrogen atoms.

In some embodiments, $R^1$ and $R^2$ are different, and $R^2$ comprises 1 or 2 (e.g., 1) oxygen atoms.

In some embodiments, $R^1$ and $R^2$ are different, and $R^2$ comprises a sulfur atom.

In some embodiments, $R^2$ and $R^1$ are different, and $R^2$ comprises a carbonyl group.

In some embodiments, $R^2$ and $R^1$ are different, and $R^2$ comprises 1 or 2 (e.g., 1) nitrogen atoms.

In some embodiments, $R^2$ and $R^1$ are different, and $R^2$ comprises 1 or 2 (e.g., 1) oxygen atoms.

In some embodiments, $R^2$ and $R^1$ are different, and $R^2$ comprises a sulfur atom.

In some embodiments, $R^1$ and $R^2$ are the same.

In some embodiments, $R^1$ is para or meta to $R^2$.

In some embodiments, $R^1$ is para or ortho to $R^2$.

In some embodiments, $R^1$ is ortho or meta to $R^2$. In some embodiments, $R^1$ is para to $R^2$.

In some embodiments, $R^1$ is meta to $R^2$.

In some embodiments, $R^1$ is ortho to $R^2$.

The Variables o and p

In some embodiments, o=1 or 2.

In some embodiments, o=1.

In some embodiments, o=2.

In some embodiments, p=0, 1, 2, or 3.

In some embodiments, p=0.

In some embodiments, p=1.

In some embodiments, p=2.

In some embodiments, o=1 and p=0.

In some embodiments, o=2 and p=0.

In some embodiments, o=1 and p=1.

In some embodiments, o=1 and p=2.

In some embodiments, o=2 and p=1.

In some embodiments, o=2 and p=2.

In some embodiments, o=2 and p=3.

The Ring B and Substitutions on the Ring B

In some embodiments, B is a 5- to 10-membered monocyclic or bicyclic heteroaryl or a $C_6$-$C_{10}$ monocyclic or bicyclic aryl, such as phenyl.

In some embodiments, B is a 5- to 6-membered monocyclic heteroaryl or a $C_6$ monocyclic aryl.

In some embodiments, B is a 5- to 10-membered monocyclic or bicyclic heteroaryl.

In some embodiments, B is a $C_6$-$C_{10}$ monocyclic or bicyclic aryl.

In some embodiments, B is a 5-membered heteroaryl.

In some embodiments, B is a 7-10 membered monocyclic or bicyclic heteroaryl.

In some embodiments, B is phenyl substituted with 1 or 2 $R^6$ and optionally substituted with 1, 2, or 3 $R^7$.

In some embodiments, B is pyridyl substituted with 1 or 2 $R^6$ and optionally substituted with 1, 2, or 3 $R^7$.

In some embodiments, B is indazolyl substituted with 1 or 2 $R^6$ and optionally substituted with 1, 2, or 3 $R^7$.

In some embodiments, B is pyrazolyl substituted with 1 or 2 $R^6$ and optionally substituted with 1 or 2 $R^7$.

In some embodiments, B is phenyl, o is 1 or 2, and p is 0, 1, 2, or 3.

In some embodiments, B is phenyl, o is 1, and p is 0, 1, 2, or 3.

In some embodiments, B is phenyl, o is 2, and p is 0, 1, 2, or 3.

In some embodiments, B is one of the rings disclosed hereinbelow, substituted as disclosed hereinbelow, wherein in each case the bond that is shown as being broken by the wavy line  connects B to the NH(CO)group of Formula AA.

In some embodiments, the substituted ring B

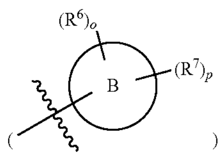 is 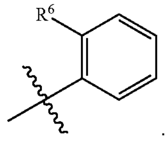 .

In some embodiments, the substituted ring B

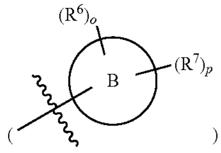 is 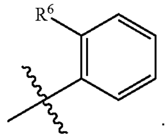 .

In some embodiments, the substituted ring B is

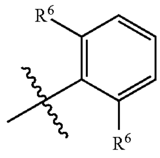 .

In some embodiments, the substituted ring B is

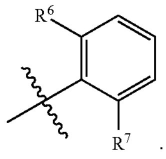 .

In some embodiments, the substituted ring B is

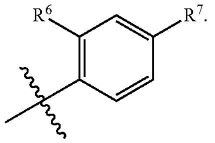

In some embodiments, the substituted ring B is

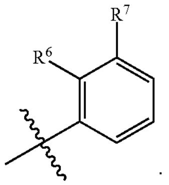

In some embodiments, the substituted ring B is

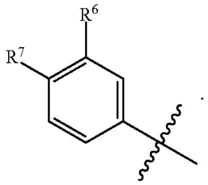

In some embodiments, the substituted ring B is

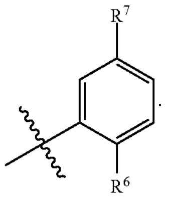

In some embodiments, the substituted ring B is

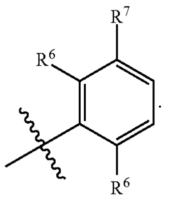

In some embodiments, the substituted ring B is

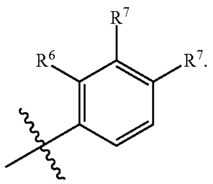

In some embodiments, the substituted ring B is

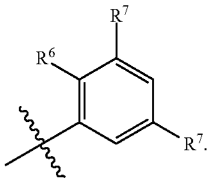

In some embodiments, the substituted ring B is

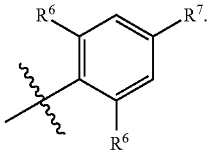

In some embodiments, the substituted ring B is

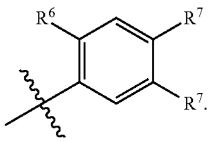

In some embodiments, the substituted ring B is

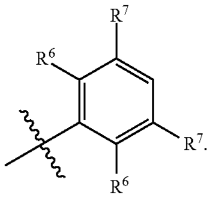

In some embodiments, the substituted ring B is

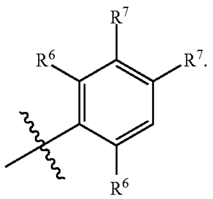

In some embodiments, the substituted ring B is

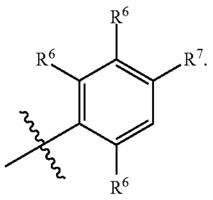

In some embodiments, the substituted ring B is

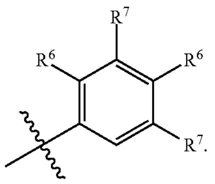

In some embodiments, the substituted ring B is

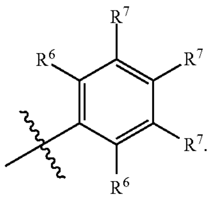

In some embodiments, the substituted ring B is

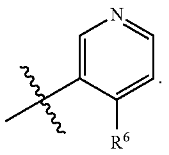

In some embodiments, the substituted ring B is

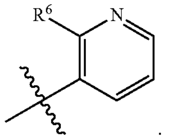

In some embodiments, the substituted ring B is

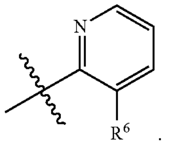

In some embodiments, the substituted ring B is

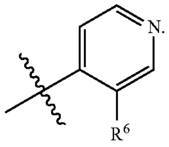

In some embodiments, the substituted ring B is

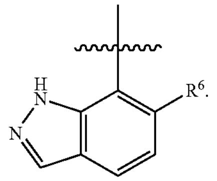

In some embodiments, the substituted ring B is

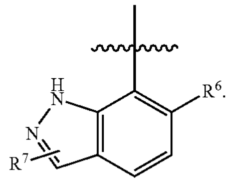

In some embodiments, the substituted ring B is

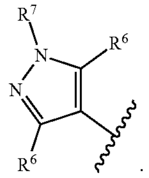

In some embodiments, the substituted ring B is

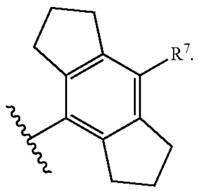

In some embodiments, the substituted ring B is

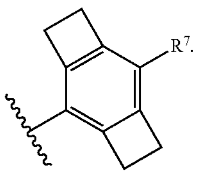

In some embodiments, the substituted ring B is

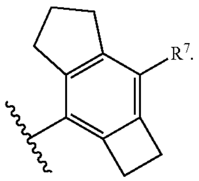

In some embodiments, the substituted ring B is

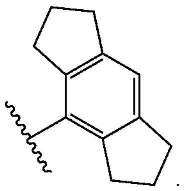 [SMILES: *c1c2c(cc3c1CCC3)CCC2]

In some embodiments, the substituted ring B is

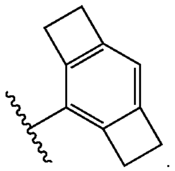 [SMILES: *c1c2c(cc3c1CC3)CC2]

In some embodiments, the substituted ring B is

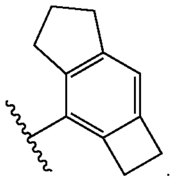 [SMILES: *c1c2c(cc3c1CC3)CCC2]

In some embodiments, the substituted ring B is

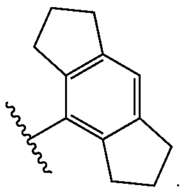 [SMILES: *c1c2c(cc3c1CCC3)CCC2]

In some embodiments, the substituted ring B is

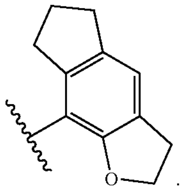 [SMILES: *c1c2c(cc3c1OCC3)CCC2]

In some embodiments, the substituted ring B is

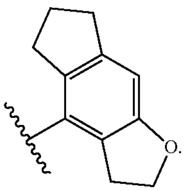 [SMILES: *c1c2c(cc3c1CCO3)CCC2]

In some embodiments, the substituted ring B is

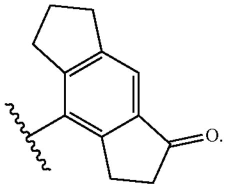 [SMILES: *c1c2c(cc3c1CCC3=O)CCC2]

In some embodiments, the substituted ring B is

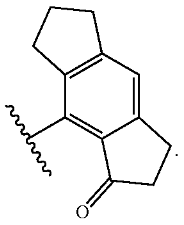 [SMILES: *c1c2c(cc3c1C(=O)CC3)CCC2]

In some embodiments, the substituted ring B is

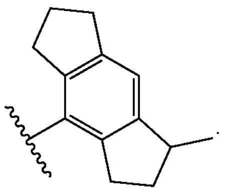 [SMILES: *c1c2c(cc3c1CCC3C)CCC2]

In some embodiments, the substituted ring B is

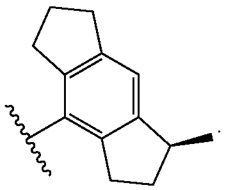 [SMILES: *c1c2c(cc3c1CC[C@@H]3C)CCC2]

In some embodiments, the substituted ring B is

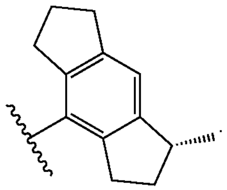 [SMILES: *c1c2c(cc3c1CC[C@H]3C)CCC2]

In some embodiments, the substituted ring B is

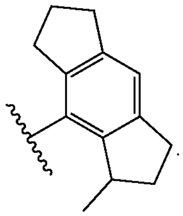 [SMILES: *c1c2c(cc3c1C(C)CC3)CCC2]

In some embodiments, the substituted ring B is

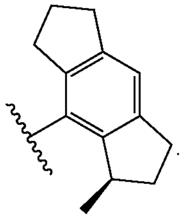 [SMILES: *c1c2c(cc3c1[C@H](C)CC3)CCC2]

In some embodiments, the substituted ring B is

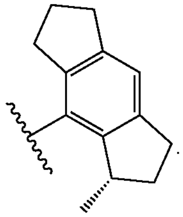 [SMILES: *c1c2c(cc3c1[C@@H](C)CC3)CCC2]

In some embodiments, the substituted ring B is

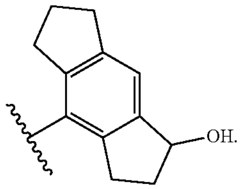 [SMILES: *c1c2c(cc3c1CCC3O)CCC2]

In some embodiments, the substituted ring B is

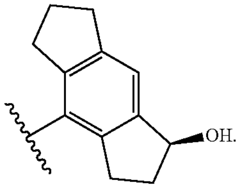 [SMILES: *c1c2c(cc3c1CC[C@@H]3O)CCC2]

In some embodiments, the substituted ring B is

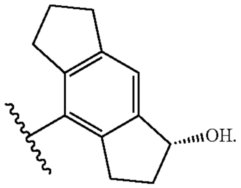 [SMILES: *c1c2c(cc3c1CC[C@H]3O)CCC2]

In some embodiments, the substituted ring B is

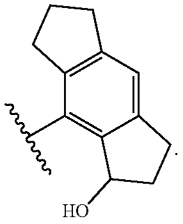 [SMILES: *c1c2c(cc3c1C(O)CC3)CCC2]

In some embodiments, the substituted ring B is

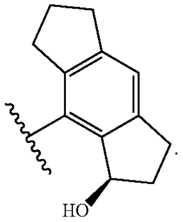 [SMILES: *c1c2c(cc3c1[C@H](O)CC3)CCC2]

In some embodiments, the substituted ring B is

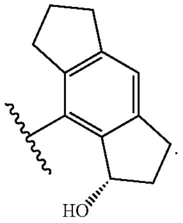 [SMILES: *c1c2c(cc3c1[C@@H](O)CC3)CCC2]

In some embodiments, the substituted ring B is.

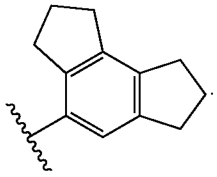 [SMILES: *c1cc2c(c3c1CCC3)CCC2]

In some embodiments, the substituted ring B is

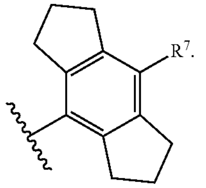

The Groups $R^6$ and $R^7$

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five- to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_6$ aliphatic carbocyclic ring or at least one 5- to 6-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5- to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more hydroxy or oxo.

In some embodiments, at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more hydroxy or oxo.

In some embodiments, at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more hydroxy or oxo.

In some embodiments, at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more $C_1$-$C_6$ alkyl.

In some embodiments, at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more $C_1$-$C_6$ alkyl.

In some embodiments, at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more $C_1$-$C_6$ alkyl.

In some embodiments, at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more $C_1$-$C_6$ alkyl.

In some embodiments, at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more $C_1$-$C_6$ alkyl.

In some embodiments, at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more $C_1$-$C_6$ alkyl.

In some embodiments, o=1; p=0; and $R^6$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, o=1; p=1; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, o=1 or 2; p=1, 2, or 3; and $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $—NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, o=2; p=1; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5- to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ (e.g., $C_4$-$C_6$) carbocyclic ring (e.g., aliphatic carbocyclic ring) or at least one 5- to-7-membered (e.g., 5- to-6-membered) heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, o=1 or 2; p=1, 2, or 3; and one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, —$NR^{10}$ $COOC_1$-$C_6$ alkyl, $C_6$-$C_{10}$ aryl, and $CONR^8R^9$.

In some embodiments, o=1 or 2; p=1, 2, or 3; and one $R^6$ and one $R^7$ are on adjacent atoms, and taken together with the atoms connecting them, form a $C_6$ carbocyclic ring or a 5- to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from 0, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_6$ carbocyclic ring or a 5- to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$ $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$ $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, one pair of one $R^6$ and one $R^7$ taken together with the atoms connecting them independently form a $C_4$ carbocyclic ring, and the other pair of one $R^6$ and one $R^7$ taken together with the atoms connecting them independently form a $C_5$ carbocyclic ring, wherein each of $C_4$ and $C_5$ carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, one pair of one $R^6$ and one $R^7$ taken together with the atoms connecting them independently form a $C_5$ carbocyclic ring, and the other pair of one $R^6$ and one $R^7$ taken together with the atoms connecting them independently form a 5- to 8-membered heterocyclic ring containing 1 or 2 heteroatoms independently selected from O, N, and S (e.g., a 5-membered heteorocyclic ring, e.g., 5-membered heterocyclic ring containing 1 heteroatom), wherein each of carbocyclic and heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

Particular Embodiments Wherein o=1; p=0:

In some embodiments, $R^6$ is $C_1$-$C_6$ alkyl.

In some embodiments, $R^6$ is isopropyl.

In some embodiments, $R^6$ is ethyl.

In some embodiments, $R^6$ is methyl.

In some embodiments, $R^6$ is $C_1$-$C_6$ alkyl substituted with one or more halo.

In some embodiments, $R^6$ is trifluoromethyl.

In some embodiments, $R^6$ is trifluoromethoxy.

In some embodiments, $R^6$ is $C_3$-$C_7$ cycloalkyl.

In some embodiments, $R^6$ is cyclopropyl.

In some embodiments, $R^6$ is halo.

In some embodiments, $R^6$ is chloro.

In some embodiments, $R^6$ is fluoro.

In some embodiments, $R^6$ is cyano.

In some embodiments, $R^6$ is attached to a carbon of an aryl ring B.

In some embodiments, $R^6$ is attached to a carbon of a heteroaryl ring B.

In some embodiments, $R^6$ is attached to a nitrogen of a heteroaryl ring B.

Particular Embodiments Wherein o=1 or 2: p=1, 2, or 3:

In some embodiments, at least one $R^6$ is $C_1$-$C_6$ alkyl, and at least one $R^7$ is $C_1$-$C_6$ alkyl optionally substituted with one or more halo.

In some embodiments, at least one $R^6$ is $C_1$-$C_6$ alkyl and at least one $R^7$ is $C_1$-$C_6$ alkyl.

In some embodiments, at least one $R^6$ is isopropyl and at least one $R^7$ is methyl.

In some embodiments, at least one $R^6$ is isopropyl and at least one $R^7$ is isopropyl.

In some embodiments, o=1; p=1; $R^6$ is isopropyl; and $R^7$ is isopropyl.

In some embodiments, at least one $R^6$ is $C_1$-$C_6$ alkyl, and at least one $R^7$ is $C_1$-$C_6$ alkyl substituted with one or more halo.

In some embodiments, at least one $R^6$ is isopropyl and at least one $R^7$ is trifluoromethyl.

In some embodiments, at least one $R^6$ is $C_1$-$C_6$ alkyl, and at least one $R^7$ is $C_3$-$C_7$ cycloalkyl.

In some embodiments, at least one $R^6$ is isopropyl and at least one $R^7$ is cyclopropyl.

In some embodiments, o=1; p=1; $R^6$ is isopropyl; and $R^7$ is cyclopropyl.

In some embodiments, at least one $R^6$ is $C_1$-$C_6$ alkyl, and at least one $R^7$ is halo.

In some embodiments, at least one $R^6$ is isopropyl and at least one $R^7$ is halo.

In some embodiments, at least one $R^6$ is isopropyl and at least one $R^7$ is chloro.

In some embodiments, at least one $R^6$ is isopropyl and at least one $R^7$ is fluoro.

In some embodiments, o=1; p=1; $R^6$ is isopropyl; and $R^7$ is chloro.

In some embodiments, o=2; p=1; at least one $R^6$ is isopropyl; and $R^7$ is chloro.

In some embodiments, o=1; p=1; $R^6$ is isopropyl; and $R^7$ is fluoro.

In some embodiments, o=2; p=1; at least one $R^6$ is isopropyl; and $R^7$ is fluoro.

In some embodiments, o=2; p=2; at least one $R^6$ is isopropyl; and at least one $R^7$ is fluoro.

In some embodiments, o=2; p=2; at least one $R^6$ is isopropyl; one $R^7$ is fluoro; and the other $R^7$ is cyano.

In some embodiments, o=2; p=3; at least one $R^6$ is isopropyl; two $R^7$ are fluoro; and one $R^7$ is chloro.

In some embodiments, o=2; p=1; at least one $R^6$ is ethyl; and $R^7$ is fluoro.

In some embodiments, o=2; p=1; one $R^6$ is isopropyl; the other $R^6$ is trifluoromethyl; and $R^7$ is chloro.

In some embodiments, at least one $R^6$ is $C_1$-$C_6$ alkyl, and at least one $R^7$ is cyano.

In some embodiments, at least one $R^6$ is isopropyl and at least one $R^7$ is cyano.

In some embodiments, o=1; p=1; $R^6$ is isopropyl; and $R^7$ is cyano.

In some embodiments, o=2; p=1; at least one $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl.

In some embodiments, at least one $R^6$ is cyclopropyl, and at least one $R^7$ is cyclopropyl.

In some embodiments, at least one $R^6$ is $C_3$-$C_7$ cycloalkyl, and at least one $R^7$ is halo.

In some embodiments, at least one $R^6$ is cyclopropyl and at least one $R^7$ is halo.

In some embodiments, at least one $R^6$ is cyclopropyl and at least one $R^7$ is chloro.

In some embodiments, at least one $R^6$ is cyclopropyl and at least one $R^7$ is fluoro.

In some embodiments, o=1; p=1; $R^6$ is cyclopropyl; and $R^7$ is chloro.

In some embodiments, o=1; p=1; $R^6$ is cyclopropyl; and $R^7$ is fluoro.

In some embodiments, at least one $R^6$ is $C_1$-$C_6$ alkyl, and at least one $R^7$ is $C_1$-$C_6$ alkoxy optionally substituted with one or more halo.

In some embodiments, at least one $R^6$ is isopropyl, and at least one $R^7$ is $C_1$-$C_6$ alkoxy.

In some embodiments, at least one $R^6$ is isopropyl, and at least one $R^7$ is methoxy.

In some embodiments, o=1; p=1; $R^6$ is isopropyl, and $R^7$ is methoxy.

In some embodiments, o=2; p=1; at least one $R^6$ is isopropyl, and $R^7$ is methoxy.

In some embodiments, at least one $R^6$ is $C_1$-$C_6$ alkyl, and at least one $R^7$ is $C_1$-$C_6$ alkoxy substituted with one or more halo.

In some embodiments, at least one $R^6$ is isopropyl, and at least one $R^7$ is trifluoromethoxy.

In some embodiments, at least one $R^6$ is isopropyl, and at least one $R^7$ is difluoromethoxy.

In some embodiments, at least one $R^6$ is halo, and at least one $R^7$ is $C_1$-$C_6$ haloalkyl optionally substituted with hydroxy.

In some embodiments, o=1; p=1; $R^6$ is chloro, and $R^7$ is trifluoromethyl.

In some embodiments, at least one $R^6$ is halo, and at least one $R^7$ is $C_1$-$C_6$ haloalkoxy.

In some embodiments, at least one $R^6$ is chloro, and at least one $R^7$ is trifluoromethoxy.

In some embodiments, o=1; p=1; $R^6$ is chloro, and $R^7$ is trifluoromethoxy.

In some embodiments, at least one $R^6$ is $C_1$-$C_6$ alkoxy; and at least one $R^7$ is halo.

In some embodiments, o=1; p=2; $R^6$ is $C_1$-$C_6$ alkoxy; and at least one $R^7$ is chloro.

In some embodiments, at least one $R^7$ is $C_1$-$C_6$ alkyl, and at least one $R^6$ is $C_1$-$C_6$ alkyl optionally substituted with one or more halo.

In some embodiments, at least one $R^7$ is isopropyl and at least one $R^6$ is methyl.

In some embodiments, at least one $R^7$ is $C_1$-$C_6$ alkyl, and at least one $R^6$ is $C_1$-$C_6$ alkyl substituted with one or more halo.

In some embodiments, at least one $R^7$ is isopropyl and at least one $R^6$ is trifluoromethyl.

In some embodiments, at least one $R^7$ is $C_1$-$C_6$ alkyl, and at least one $R^6$ is $C_3$-$C_7$ cycloalkyl.

In some embodiments, at least one $R^7$ is isopropyl and at least one $R^6$ is cyclopropyl.

In some embodiments, o=1; p=1; $R^7$ is isopropyl; and $R^6$ is cyclopropyl.

In some embodiments, at least one $R^7$ is $C_1$-$C_6$ alkyl, and at least one $R^6$ is halo.

In some embodiments, at least one $R^7$ is isopropyl and at least one $R^6$ is halo.

In some embodiments, at least one $R^7$ is isopropyl and at least one $R^6$ is chloro.

In some embodiments, at least one $R^7$ is isopropyl and at least one $R^6$ is fluoro.

In some embodiments, o=1; p=1; $R^7$ is isopropyl; and $R^6$ is chloro.

In some embodiments, o=2; p=1; $R^7$ is isopropyl; and at least one $R^6$ is chloro.

In some embodiments, o=1; p=1; $R^7$ is isopropyl; and $R^6$ is fluoro.

In some embodiments, o=2; p=1; $R^7$ is isopropyl; and at least one $R^6$ is fluoro.

In some embodiments, o=2; p=2; $R^7$ is isopropyl; and at least one $R^6$ is fluoro.

In some embodiments, o=2; p=2; at least one $R^7$ is isopropyl; one $R^6$ is fluoro; and the other $R^6$ is cyano.

In some embodiments, o=2; p=1; $R^7$ is ethyl; and at least one $R^6$ is fluoro.

In some embodiments, o=1; p=2; one $R^7$ is isopropyl; the other $R^7$ is trifluoromethyl; and $R^6$ is chloro.

In some embodiments, at least one $R^7$ is $C_1$-$C_6$ alkyl, and at least one $R^6$ is cyano.

In some embodiments, at least one $R^7$ is isopropyl and at least one $R^6$ is cyano.

In some embodiments, o=1; p=1; $R^7$ is isopropyl; and $R^6$ is cyano.

In some embodiments, o=2; p=1; $R^7$ is isopropyl; and at least one $R^6$ is cyano.

In some embodiments, at least one $R^7$ is $C_3$-$C_7$ cycloalkyl, and at least one $R^6$ is $C_3$-$C_7$ cycloalkyl.

In some embodiments, at least one $R^7$ is cyclopropyl, and at least one $R^6$ is cyclopropyl.

In some embodiments, at least one $R^7$ is $C_3$-$C_7$ cycloalkyl, and at least one $R^6$ is halo.

In some embodiments, at least one $R^7$ is cyclopropyl and at least one $R^6$ is halo.

In some embodiments, at least one $R^7$ is cyclopropyl and at least one $R^6$ is chloro.

In some embodiments, at least one $R^7$ is cyclopropyl and at least one $R^6$ is fluoro.

In some embodiments, o=1; p=1; $R^7$ is cyclopropyl; and $R^6$ is chloro.

In some embodiments, o=1; p=1; $R^7$ is cyclopropyl; and $R^6$ is fluoro.

In some embodiments, at least one $R^7$ is $C_1$-$C_6$ alkyl, and at least one $R^6$ is $C_1$-$C_6$ alkoxy optionally substituted with one or more halo.

In some embodiments, at least one $R^7$ is isopropyl, and at least one $R^6$ is $C_1$-$C_6$ alkoxy.

In some embodiments, at least one $R^7$ is isopropyl, and at least one $R^6$ is methoxy.

In some embodiments, o=1; p=1; $R^7$ is isopropyl, and $R^6$ is methoxy.

In some embodiments, o=2; p=1; $R^7$ is isopropyl, and at least one $R^6$ is methoxy.

In some embodiments, at least one $R^7$ is $C_1$-$C_6$ alkyl, and at least one $R^6$ is $C_1$-$C_6$ alkoxy substituted with one or more halo.

In some embodiments, at least one $R^7$ is isopropyl, and at least one $R^6$ is trifluoromethoxy.

In some embodiments, at least one $R^7$ is halo, and at least one $R^6$ is $C_1$-$C_6$ haloalkyl optionally substituted with one or more hydroxy.

In some embodiments, o=1; p=1; $R^7$ is chloro, and $R^6$ is trifluoromethyl.

In some embodiments, at least one $R^7$ is halo, and at least one $R^6$ is $C_1$-$C_6$ haloalkoxy.

In some embodiments, at least one $R^7$ is chloro, and at least one $R^6$ is trifluoromethoxy.

In some embodiments, o=1; p=1; $R^7$ is chloro, and $R^6$ is trifluoromethoxy.

In some embodiments, at least one $R^7$ is $C_1$-$C_6$ alkoxy; and at least one $R^6$ is halo.

In some embodiments, o=1; p=2; at least one $R^7$ is $C_1$-$C_6$ alkoxy; and $R^6$ is chloro.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_5$ aliphatic carbocyclic ring.

In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $—NR^{10}$ $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_6$ aliphatic carbocyclic ring.

In some embodiments, $R^6$ and $R^7$ are on adjacent atoms, and taken together with the atoms connecting them, form a $C_6$ aromatic carbocyclic ring.

In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $—NR^{10}$ $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 5-membered heteroaromatic ring containing 1 or 2 heteroatoms independently selected from O, N, and S.

In some embodiments, $R^6$ and $R^7$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $—NR^{10}$ $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 6-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 6-membered heteroaromatic ring containing 1 or 2 heteroatoms independently selected from O, N, and S.

In some embodiments, one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the ring is fused to the B ring at the 2- and 3-positions relative to the bond connecting the B ring to the NH(CO)group.

In some embodiments, o=1; p=2; and one pair of one $R^6$ and one $R^7$, are on adjacent atoms; and said pair of one $R^6$ and one $R^7$ taken together with the atoms connecting them form form a $C_4$-$C_8$ carbocyclic ring or a 5- to 8-membered heterocyclic ring containing 1 or 2 heteroatoms independently selected from O, N, and S, wherein the ring is fused to the B ring at the 2- and 3-positions relative to the bond connecting the B ring to the $NR^3$(CO) group.

In some embodiments, o=1; p=2; and one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2; and one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2; and one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_4$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $—NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_4$ aliphatic carbocyclic ring and the other pair of one $R^6$ and one $R^7$ taken together with the atoms connecting them form a $C_5$ aliphatic carbocyclic ring.

In some embodiments, o=2; p=2 or 3; and two pairs, each of one $R^6$ and one $R^7$, are on adjacent atoms, and each pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2 or 3; and two pairs, each of one $R^6$ and one $R^7$, are on adjacent atoms, and each pair of one $R^6$ and one $R^7$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, o=2; p=2 or 3; and two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, o=2; p=2 or 3; and two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_{4-8}$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 5- to 8-mebered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 6-mebered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3$(CO) group, and the other of the two rings is fused to the B ring at the 5- and 6-positions relative to the bond connecting the B ring to the NH(CO) group.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3$(CO) group, and the other of the two rings is fused to the B ring at the 4- and 5-positions relative to the bond connecting the B ring to the NH(CO) group.

In some embodiments, o=2; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_4$ aliphatic carbocyclic ring, and the other pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, and each pair of one $R^6$ and one $R^7$ taken together with the atoms connecting them form a $C_4$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_5$ aliphatic carbocyclic ring, and the other pair of one $R^6$ and one $R^7$ taken together with the atoms connecting them form a 5-membered heterocyclic ring containing 1 or 2 heteroatoms independently selected from O, N, and S.

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., Cl or F).

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

In some embodiments, one $R^7$ is pyrazolyl and is para to the bond connecting the B ring to the NH(CO) group of Formula AA.

In some embodiments, one $R^7$ is 3-pyrazolyl and is para to the bond connecting the B ring to the NH(CO) group of Formula AA.

In some embodiments, one $R^7$ is 4-pyrazolyl and is para to the bond connecting the B ring to the NH(CO) group of Formula AA.

In some embodiments, one $R^7$ is 5-pyrazolyl and is para to the bond connecting the B ring to the NH(CO) group of Formula AA.

In some embodiments, one $R^7$ is thiazolyl and is para to the bond connecting the B ring to the NH(CO) group of Formula AA.

In some embodiments, one $R^7$ is 4-thiazolyl and is para to the bond connecting the B ring to the NH(CO) group of Formula AA.

In some embodiments, one $R^7$ is 5-thiazolyl and is para to the bond connecting the B ring to the NH(CO) group of Formula AA.

In some embodiments, one $R^7$ is furyl and is para to the bond connecting the B ring to the NH(CO) group of Formula AA.

In some embodiments, one $R^7$ is 2-furyl and is para to the bond connecting the B ring to the NH(CO) group of Formula AA.

In some embodiments, one $R^7$ is thiophenyl and is para to the bond connecting the B ring to the NH(CO) group of Formula AA.

In some embodiments, one $R^7$ is 2-thiophenyl and is para to the bond connecting the B ring to the NH(CO) group of Formula AA.

In some embodiments, one $R^7$ is phenyl and is para to the bond connecting the B ring to the NH(CO) group of Formula AA.

In some embodiments, one $R^7$ is cycloalkenyl (e.g., cyclopentenyl, e.g., 1-cyclopentenyl) and is para to the bond connecting the B ring to the $NR^3$(CO) group of Formula AA.

In some embodiments, one $R^7$ is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the NH(CO) group of Formula AA.

In some embodiments, one $R^7$ is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the NH(CO) group of Formula AA.

In some embodiments, one $R^7$ is phenyl optionally substituted with one or more $C_6$-$C_{10}$ aryloxy (e.g., phenoxy) and is para to the bond connecting the B ring to the NH(CO) group of Formula AA.

In some embodiments, one $R^7$ is phenyl optionally substituted with one or more CN and is para to the bond connecting the B ring to the NH(CO) group of Formula AA.

In some embodiments, one $R^7$ is phenyl optionally substituted with one or more halo (e.g., F, Cl) and is para to the bond connecting the B ring to the NH(CO) group of Formula AA and is para to the bond connecting the B ring to the NH(CO) group of Formula AA.

In some embodiments, one $R^7$ is phenyl optionally substituted with one or more $COOC_1$-$C_6$ alkyl (e.g., $CO_2$t-Bu) and is para to the bond connecting the B ring to the NH(CO) group of Formula AA.

In some embodiments, one $R^7$ is phenyl optionally substituted with one or more $S(O_2)C_1$-$C_6$ alkyl (e.g., $S(O_2)$methyl) and is para to the bond connecting the B ring to the NH(CO) group of Formula AA.

In some embodiments, one $R^7$ is phenyl optionally substituted with one or more 3- to 7-membered heterocycloalkyl (e.g., morpholinyl) and is para to the bond connecting the B ring to the NH(CO) group of Formula AA.

In some embodiments, one $R^7$ is phenyl optionally substituted with one or more $CONR^8R^9$ (e.g., unsubstituted amido) and is para to the bond connecting the B ring to the NH(CO) group of Formula AA.

In some embodiments, one $R^7$ is phenyl optionally substituted with one or more $C_1$-$C_6$ alkyl (e.g., methyl or propyl, e.g., 2-propyl) and with one or more halo (e.g., F, Cl) and is para to the bond connecting the B ring to the NH(CO) group of Formula AA and is para to the bond connecting the B ring to the NH(CO) group of Formula AA.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments of any of the formulae herein, each of $R^1$ and $R^2$ is independently selected from the group consisting of $C_1$-$C_6$ alkyl optionally substituted with one or more hydroxy, halo, oxo, or $C_1$-$C_6$ alkoxy; $C_3$-$C_7$ cycloalkyl optionally substituted with one or more hydroxy, halo, oxo, $C_1$-$C_6$ alkoxy, or $C_1$-$C_6$ alkyl; wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, or $C_1$-$C_6$ alkyl wherein the $C_1$-$C_6$ alkoxy or $C_1$-$C_6$ alkyl is further optionally substituted with one to three hydroxy, halo, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of any of the formulae herein, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; $S(O_2)CH_3$; and $S(O_2)NR^{11}R^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; $S(O_2)CH_3$; and $S(O_2)NR^{11}R^{12}$.

In some embodiments, the substituted ring B is

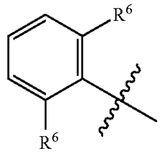

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO (5- to 10-membered heteroaryl), NHCO(4- to 6-membered heterocycloalkyl), and $NHCOC_2$-$C_6$ alkynyl.

In some embodiments, the substituted ring B is

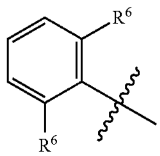

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

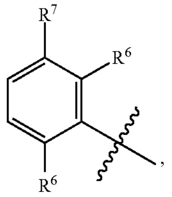

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5- to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

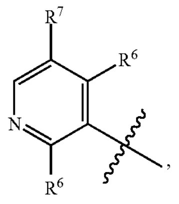

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5- to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

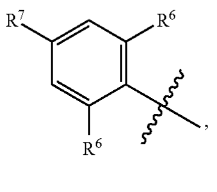

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In some embodiments, the substituted ring B is

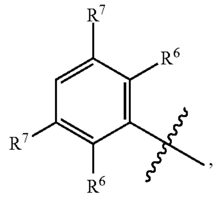

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $—NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

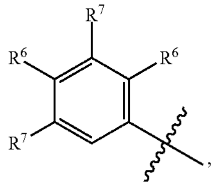

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

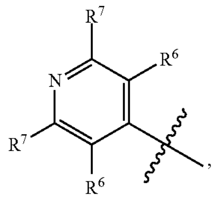

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

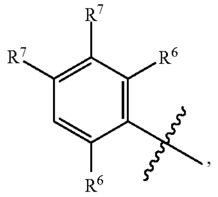

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form a $C_4$-$C_7$ carbocyclic ring or at least one 5- to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

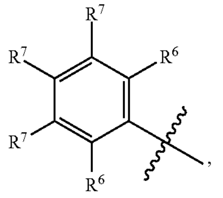

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

The Group $R^3$

In some embodiments, $R^3$ is selected from hydrogen, $C_1$-$C_6$ alkyl, and

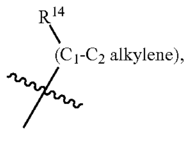

wherein the $C_1$-$C_2$ alkylene group is optionally substituted with oxo.

In some embodiments, $R^3$ is hydrogen.

In some embodiments, $R^3$ is cyano.

In some embodiments, $R^3$ is hydroxy.

In some embodiments, $R^3$ is $C_1$-$C_6$ alkoxy. In some embodiments, $R^3$ is $C_1$-$C_6$ alkyl.

In some embodiments, $R^3$ is methyl.

In some embodiments, $R^3$ is

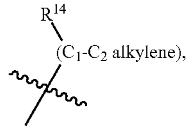

wherein the $C_1$-$C_2$ alkylene group is optionally substituted with oxo.

In some embodiments, $R^3$ is $—CH_2R^{14}$.

In some embodiments, $R^3$ is $—C(O)R^{14}$.

In some embodiments, $R^3$ is $—CH_2CH_2R^{14}$.

In some embodiments, $R^3$ is $—CHR^{14}CH_3$.

In some embodiments, $R^3$ is $—CH_2C(O)R^{14}$.

In some embodiments, $R^3$ is $—C(O)CH_2R^{14}$.

In some embodiments, $R^3$ is $CO_2C_1$-$C_6$ alkyl.

The Group $R^{14}$

In some embodiments, $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.

In some embodiments, $R^{14}$ is hydrogen or $C_1$-$C_6$ alkyl.

In some embodiments, $R^{14}$ is hydrogen, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.

In some embodiments, $R^{14}$ is hydrogen.

In some embodiments, $R^{14}$ is $C_1$-$C_6$ alkyl.

In some embodiments, $R^{14}$ is methyl.

In some embodiments, $R^{14}$ is 5- to 10-membered monocyclic or bicyclic heteroaryl optionally independently substituted with 1 or 2 $R^6$.

In some embodiments, $R^{14}$ is $C_6$-$C_{10}$ monocyclic or bicyclic aryl optionally independently substituted with 1 or 2 $R^6$.

The Moiety $S(=O)(NHR^3)=N—$

In some embodiments, the sulfur in the moiety $S(=O)(NHR^3)=N—$ has (S) stereochemistry.

In some embodiments, the sulfur in the moiety $S(=O)(NHR^3)=N—$ has (R) stereochemistry.

The Group $R^{10}$

In some embodiments, $R^{10}$ is $C_1$-$C_6$ alkyl.

In some embodiments, $R^{10}$ is methyl.

In some embodiments, $R^{10}$ is ethyl.

The Groups $R^8$ and $R^9$

In some embodiments, each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is independently selected from hydrogen, $C_1$-$C_6$ alkyl, (C═NR$^{13}$)NR$^{11}$R$^{12}$, S(O$_2$)C$_1$-C$_6$ alkyl, S(O$_2$)NR$^{11}$R$^{12}$, COR$^{13}$, CO$_2$R$^{13}$ and CONR$^{11}$R$^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is hydrogen,

In some embodiments, each $R^1$ at each occurrence is hydrogen and each $R^9$ at each occurrence is $C_1$-$C_6$ alkyl.

In some embodiments, each $R^1$ at each occurrence is hydrogen and each $R^9$ at each occurrence is methyl.

In some embodiments, each $R^1$ at each occurrence is hydrogen and each $R^9$ at each occurrence is ethyl.

In some embodiments, each of $R^8$ and $R^9$ at each occurrence is methyl.

In some embodiments, each of $R^8$ and $R^9$ at each occurrence is ethyl.

In some embodiments, $R^8$ and $R^9$ taken together with the nitrogen they are attached to form a 3-membered ring.

In some embodiments, $R^8$ and $R^9$ taken together with the nitrogen they are attached to form a 4-membered ring.

In some embodiments, $R^8$ and $R^9$ taken together with the nitrogen they are attached to form a 5-membered ring.

In some embodiments, $R^8$ and $R^9$ taken together with the nitrogen they are attached to form a 6-membered ring optionally containing one or more oxygen atoms in addition to the nitrogen they are attached to.

In some embodiments, $R^8$ and $R^9$ taken together with the nitrogen they are attached to form a 6-membered ring optionally containing one or more nitrogen atoms in addition to the nitrogen they are attached to.

In some embodiments, $R^8$ and $R^9$ taken together with the nitrogen they are attached to form a 7-membered ring.

The Group $R^{13}$

In some embodiments, $R^{13}$ is $C_1$-$C_6$ alkyl.

In some embodiments, $R^{13}$ is methyl.

In some embodiments, $R^{13}$ is ethyl.

In some embodiments, $R^{13}$ is $C_6$-$C_{10}$ aryl.

In some embodiments, $R^{13}$ is phenyl.

In some embodiments, $R^{13}$ is 5- to 10-membered heteroaryl.

The Groups $R^{11}$ and $R^{12}$

In some embodiments, each of $R^{11}$ and $R^{12}$ at each occurrence is independently selected from hydrogen and $C_1$-$C_6$ alkyl.

In some embodiments, each of $R^{11}$ and $R^{12}$ at each occurrence is hydrogen, In some embodiments, each $R^{11}$ at each occurrence is hydrogen and each $R^{12}$ at each occurrence is $C_1$-$C_6$ alkyl.

In some embodiments, each $R^{11}$ at each occurrence is hydrogen and each $R^{12}$ at each occurrence is methyl.

In some embodiments, each $R^{11}$ at each occurrence is hydrogen and each $R^{12}$ at each occurrence is ethyl.

In some embodiments, each of $R^{11}$ and $R^{12}$ at each occurrence is methyl.

In some embodiments, each of $R^{11}$ and $R^{12}$ at each occurrence is ethyl.

In some embodiments of the compound of formula AA, the substituted ring A is

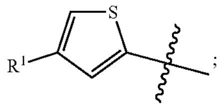

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

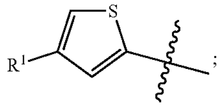

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

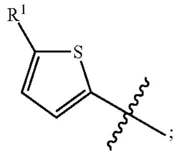

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy;

$C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

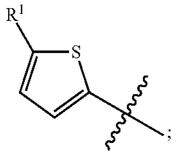

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

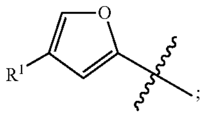

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

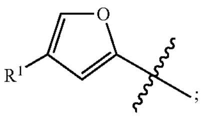

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

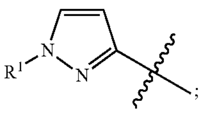

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

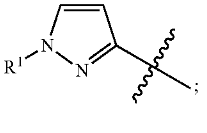

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

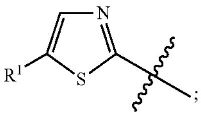
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

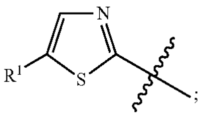
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

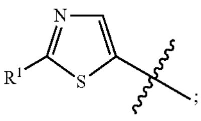
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

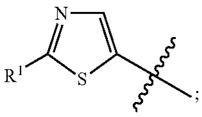
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

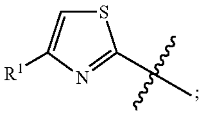
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

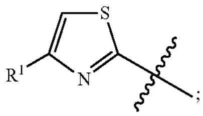
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

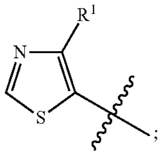
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

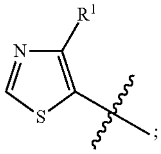
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

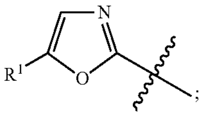
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

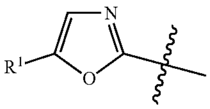
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

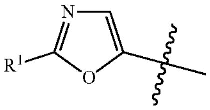
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

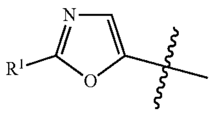

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

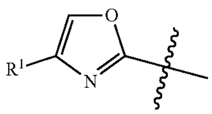

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

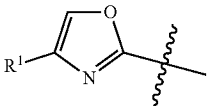

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

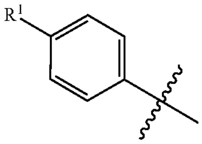

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

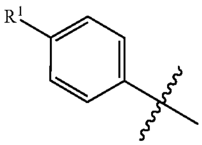

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

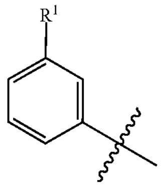

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

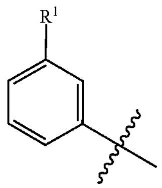

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

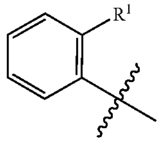

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

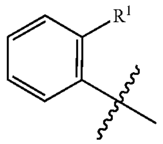

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

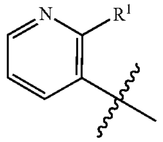

,

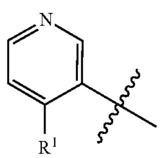

,

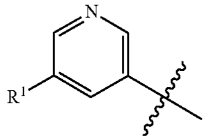

, or

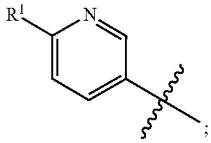

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

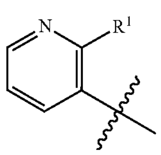
,
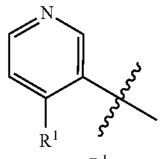
,
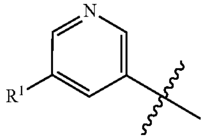
, or
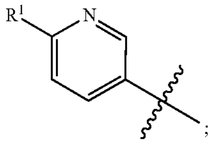
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

the substituted ring A is

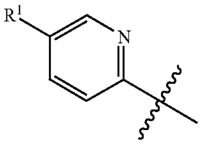
,
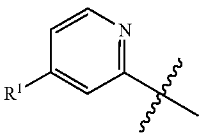
,
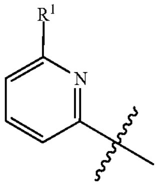
, or
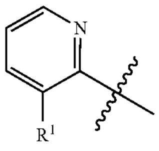
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

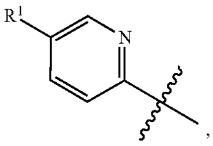
,
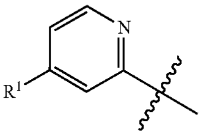
,
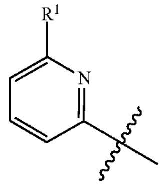
, or
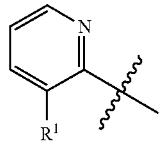
;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

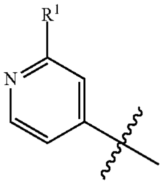
or
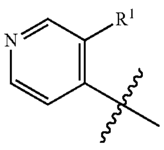
;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO-5- to 10-membered heteroaryl; $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

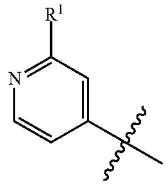

or

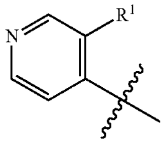

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

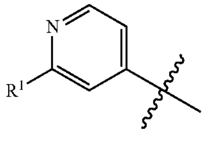

or

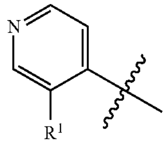

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

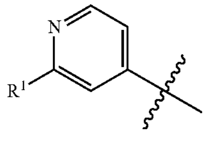

or

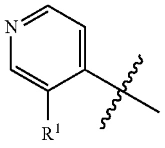

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino) ethyl; fluoro; chloro; phenyl; pyridyl; pyrazolyl; and $S(O_2)CH_3$.

In some embodiments of the compound of formula AA, the substituted ring A is

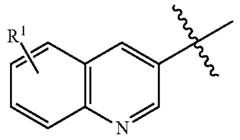

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $C_1$-$C_6$ alkyl substituted with one or more $NR^8R^9$; and $S(O_2)C_1$-$C_6$ alkyl.

the substituted ring A is

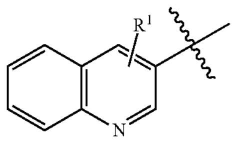

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; (dimethylamino)methyl; 1,3-dioxolan-2-yl; $COCH_3$; $COCH_2CH_3$; 2-methoxy-2-propyl; fluoro; chloro; phenyl; pyridyl; pyrazolyl; and $S(O_2)CH_3$.

the substituted ring A is

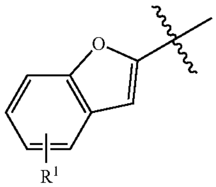

;

and $R^1$ is selected from:

$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $C_1$-$C_6$ alkyl substituted with one or more $NR^8R^9$; and $S(O_2)C_1$-$C_6$ alkyl.

the substituted ring A is

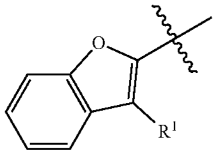

;

and $R^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; (dimethylamino)methyl; and $S(O_2)CH_3$.

In some embodiments of the compound of formula AA, the substituted ring A is

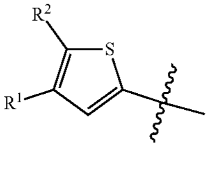

;

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy;

$R^1$ is $C_1$-$C_6$ alkyl optionally substituted with one or more hydroxy, and $R^2$ is $C_6$-$C_{10}$ aryl;

$R^1$ is $C_1$-$C_6$ alkyl optionally substituted with one or more hydroxy, and $R^2$ is 5- to 10-membered heteroaryl;

$R^1$ is $C_1$-$C_6$ alkyl optionally substituted with one or more hydroxy, and $R^2$ is $SF_5$;

$R^1$ is $C_1$-$C_6$ alkyl optionally substituted with one or more hydroxy, and $R^2$ is $S(O_2)C_1$-$C_6$ alkyl;

$R^1$ is $C_1$-$C_6$ alkyl optionally substituted with one or more hydroxy, and $R^2$ is halo;

$R^1$ is $C_3$-$C_7$ cycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is halo;

$R^1$ is $C_1$-$C_6$ alkyl optionally substituted with one or more oxo, and $R^2$ is methyl;

$R^1$ is $C_1$-$C_6$ alkyl optionally substituted with one or more $C_1$-$C_6$ alkoxy, and $R^2$ is $C_1$-$C_6$ alkyl;

$R^1$ is $C_1$-$C_6$ alkyl optionally substituted with one or more $NR^8R^9$, and $R^2$ is $C_1$-$C_6$ alkyl;

$R^1$ is $C_1$-$C_6$ alkyl optionally substituted with one or more $NR^8R^9$, and $R^2$ is halo;

$R^2$ is $C_1$-$C_6$ alkyl optionally substituted with one or more hydroxy, and $R^1$ is $C_6$-$C_{10}$ aryl;

$R^2$ is $C_1$-$C_6$ alkyl optionally substituted with one or more hydroxy, and $R^1$ is 5- to 10-membered heteroaryl;

$R^2$ is $C_1$-$C_6$ alkyl optionally substituted with one or more hydroxy, and $R^1$ is $SF_5$.

$R^2$ is $C_1$-$C_6$ alkyl optionally substituted with one or more hydroxy, and $R^1$ is $S(O_2)C_1$-$C_6$ alkyl;

$R^2$ is $C_1$-$C_6$ alkyl optionally substituted with one or more hydroxy, and $R^1$ is halo;

$R^2$ is $C_3$-$C_7$ cycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is halo;

$R^2$ is $C_1$-$C_6$ alkyl optionally substituted with one or more oxo, and $R^1$ is methyl;

$R^2$ is $C_1$-$C_6$ alkyl optionally substituted with one or more $C_1$-$C_6$ alkoxy, and $R^1$ is $C_1$-$C_6$ alkyl;

$R^2$ is $C_1$-$C_6$ alkyl optionally substituted with one or more $NR^8R^9$, and $R^1$ is $C_1$-$C_6$ alkyl;

$R^2$ is $C_1$-$C_6$ alkyl optionally substituted with one or more $NR^8R^9$, and $R^1$ is halo.

In some embodiments of the compound of formula AA, the substituted ring A is

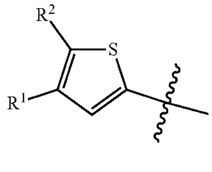

;

and $R^1$ and $R^2$ are one of the following combinations:

$R^1$ is 1-hydroxy-2-methylpropan-2-yl, and $R^2$ is methyl;

$R^1$ is 2-hydroxy-2-propyl and $R^2$ is methyl;

$R^1$ is 2-hydroxy-2-propyl and $R^2$ is isopropyl;

$R^1$ is 2-hydroxy-2-propyl and $R^2$ is 2-hydroxy-2-propyl;

$R^1$ is 2-hydroxy-2-propyl and $R^2$ is 1-hydroxyethyl;

$R^1$ is hydroxymethyl and $R^2$ is methyl;

$R^1$ is 1-hydroxyethyl and $R^2$ is methyl;

$R^1$ is 2-hydroxyethyl and $R^2$ is methyl;

$R^1$ is 1-hydroxy-2-propyl and $R^2$ is methyl;

$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^2$ is (dimethylamino)methyl, and $R^1$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

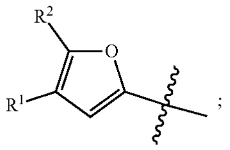

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.
$R^2$ is $C_1$-$C_6$ alkyl optionally substituted with one or more $NR^8R^9$, and $R^1$ is $C_1$-$C_6$ alkyl; or
$R^2$ is $C_1$-$C_6$ alkyl optionally substituted with one or more $NR^8R^9$, and $R^1$ is halo.

In some embodiments, of the compound of formula AA, the substituted ring A is

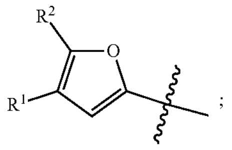

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;

$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

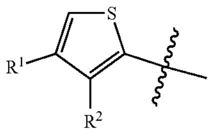

;

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;

$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

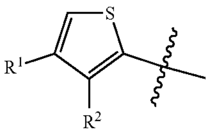

;

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;

$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

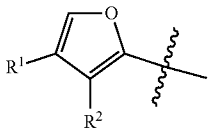

;

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;

$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

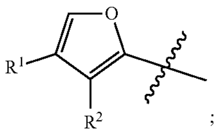

;

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;

$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

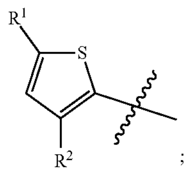

;

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

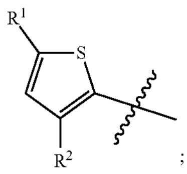

;

and $R^1$ and $R^2$ are one of the following combinations:

- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is (dimethylamino)methyl, and $R^2$ is methyl.
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is $C_1$-$C_6$ alkyl optionally substituted with one or more oxo, and $R^1$ is methyl;
- $R^2$ is (dimethylamino)methyl, and $R^1$ is methyl;
- $R^2$ is $COCH_3$, and $R^1$ is methyl; or
- $R^2$ is 2-methoxy-2-propyl, and $R^1$ is methyl.

In some embodiments, of the compound of formula AA, the substituted ring A is

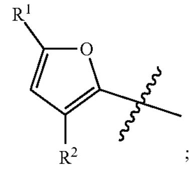

;

and $R^1$ and $R^2$ are one of the following combinations:

- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;
- $R^2$ is $C_1$-$C_6$ alkyl optionally substituted with one or more hydroxy, and $R^1$ is halo;
- $R^2$ is $C_3$-$C_7$ cycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is halo;
- $R^2$ is $C_1$-$C_6$ alkyl optionally substituted with one or more $NR^8R^9$, and $R^1$ is $C_1$-$C_6$ alkyl;
- $R^2$ is $C_1$-$C_6$ alkyl optionally substituted with one or more $NR^8R^9$, and $R^1$ is halo;
- $R^2$ is $C_1$-$C_6$ alkyl optionally substituted with one or more oxo, and $R^1$ is methyl; or
- $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

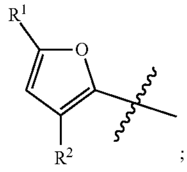

;

and $R^1$ and $R^2$ are one of the following combinations:

$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;

$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

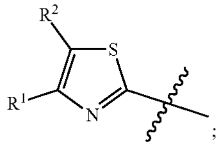

;

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;

$R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

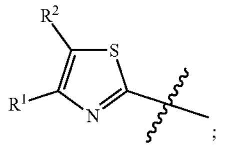

and $R^1$ and $R^2$ are one of the following combinations:

$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;

$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

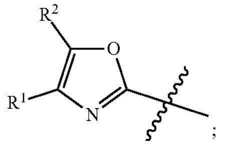

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;

$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

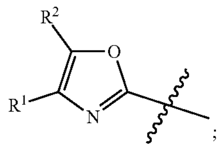

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

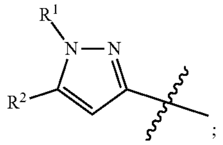

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;

$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

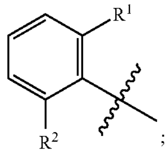

;

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

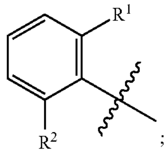

;

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;

$R^2$ is $C_3$-$C_7$ cycloalkyl optionally substituted with one or more hydroxy, and $R^1$ is $C_1$-$C_6$ alkyl;

$R^2$ is 1-hydroxy-1-cyclopropyl, and $R^1$ is methyl;

$R^2$ is 1-hydroxy-1-cyclobutyl, and $R^1$ is methyl;

$R^2$ is 1-hydroxy-1-cyclopentyl, and $R^1$ is methyl;

$R^2$ is 1-hydroxy-1-cyclohexyl, and $R^1$ is methyl;

$R^2$ is morpholinyl, and $R^1$ is methyl;

$R^2$ is 1,3-dioxolan-2-yl, and $R^1$ is methyl;

$R^2$ is 1,3-dioxolan-2-yl, and $R^1$ is fluoro;

$R^2$ is 1,3-dioxolan-2-yl, and $R^1$ is chloro;

$R^2$ is $C_1$-$C_6$ alkyl optionally substituted with one or more oxo, and $R^1$ is methyl;

$R^2$ is (dimethylamino)methyl, and $R^1$ is methyl;

$R^2$ is $COCH_3$, and $R^1$ is methyl; or $R^2$ is 2-methoxy-2-propyl, and $R^1$ is methyl.

In some embodiments, of the compound of formula AA, the substituted ring A is

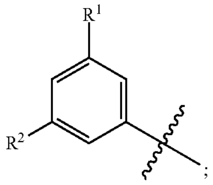

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy;

$R^1$ is $C_1$-$C_6$ alkyl optionally substituted with one or more hydroxy, and $R^2$ is $C_6$-$C_{10}$ aryl;

$R^1$ is $C_1$-$C_6$ alkyl optionally substituted with one or more hydroxy, and $R^2$ is 5- to 10-membered heteroaryl;

$R^1$ is $C_1$-$C_6$ alkyl optionally substituted with one or more hydroxy, and $R^2$ is $SF_5$;

$R^1$ is $C_1$-$C_6$ alkyl optionally substituted with one or more hydroxy, and $R^2$ is $S(O_2)C_1$-$C_6$ alkyl;

$R^1$ is $C_1$-$C_6$ alkyl optionally substituted with one or more hydroxy, and $R^2$ is halo;

$R^1$ is $C_3$-$C_7$ cycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is halo;

$R^1$ is $C_1$-$C_6$ alkyl optionally substituted with one or more oxo, and $R^2$ is methyl;

$R^1$ is $C_1$-$C_6$ alkyl optionally substituted with one or more $C_1$-$C_6$ alkoxy, and $R^2$ is $C_1$-$C_6$ alkyl;

$R^1$ is $C_1$-$C_6$ alkyl optionally substituted with one or more $NR^8R^9$, and $R^2$ is $C_1$-$C_6$ alkyl;

$R^1$ is $C_1$-$C_6$ alkyl optionally substituted with one or more $NR^8R^9$, and $R^2$ is halo;

$R^2$ is $C_1$-$C_6$ alkyl optionally substituted with one or more hydroxy, and $R^1$ is $C_6$-$C_{10}$ aryl;

$R^2$ is $C_1$-$C_6$ alkyl optionally substituted with one or more hydroxy, and $R^1$ is 5- to 10-membered heteroaryl;

$R^2$ is $C_1$-$C_6$ alkyl optionally substituted with one or more hydroxy, and $R^1$ is $SF_5$.

$R^2$ is $C_1$-$C_6$ alkyl optionally substituted with one or more hydroxy, and $R^1$ is $S(O_2)C_1$-$C_6$ alkyl;

$R^2$ is $C_1$-$C_6$ alkyl optionally substituted with one or more hydroxy, and $R^1$ is halo;

$R^2$ is $C_3$-$C_7$ cycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is halo;

$R^2$ is $C_1$-$C_6$ alkyl optionally substituted with one or more $NR^8R^9$, and $R^1$ is $C_1$-$C_6$ alkyl;

$R^2$ is $C_1$-$C_6$ alkyl optionally substituted with one or more $NR^8R^9$, and $R^1$ is halo;

$R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

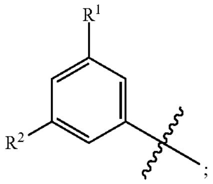

and $R^1$ and $R^2$ are one of the following combinations:

$R^1$ is 1-hydroxy-2-methylpropan-2-yl, and $R^2$ is methyl;

$R^1$ is 2-hydroxy-2-propyl and $R^2$ is methyl;

$R^1$ is 2-hydroxy-2-propyl and $R^2$ is isopropyl;

$R^1$ is 2-hydroxy-2-propyl and $R^2$ is 2-hydroxy-2-propyl;

$R^1$ is 2-hydroxy-2-propyl and $R^2$ is 1-hydroxyethyl;

$R^1$ is hydroxymethyl and $R^2$ is methyl;

$R^1$ is 1-hydroxyethyl and $R^2$ is methyl;

$R^1$ is 2-hydroxyethyl and $R^2$ is methyl;

$R^1$ is 1-hydroxy-2-propyl and $R^2$ is methyl;

$R^1$ is 2-hydroxy-2-propyl and $R^2$ is phenyl;

$R^1$ is 2-hydroxy-2-propyl and $R^2$ is pyridyl;

$R^1$ is 2-hydroxy-2-propyl and $R^2$ is pyrazolyl;

$R^1$ is 2-hydroxy-2-propyl, and $R^2$ is $S(O_2)CH_3$;

$R^1$ is 2-hydroxy-2-propyl and $R^2$ is chloro;

$R^1$ is 2-hydroxy-2-propyl and $R^2$ is fluoro;

$R^1$ is 1-hydroxy-1-cyclopropyl, and $R^2$ is methyl;

$R^1$ is 1-hydroxy-1-cyclobutyl, and $R^2$ is methyl;

$R^1$ is 1-hydroxy-1-cyclopentyl, and $R^2$ is methyl;

$R^1$ is 1-hydroxy-1-cyclohexyl, and $R^2$ is methyl;

$R^1$ is morpholinyl, and $R^2$ is methyl;

$R^1$ is 1,3-dioxolan-2-yl, and $R^2$ is methyl;

$R^1$ is 1,3-dioxolan-2-yl, and $R^2$ is fluoro;

$R^1$ is 1,3-dioxolan-2-yl, and $R^2$ is chloro;

$R^1$ is $COCH_3$, and $R^2$ is methyl;

$R^1$ is 2-methoxy-2-propyl, and $R^2$ is methyl;

$R^1$ is (dimethylamino)methyl, and $R^2$ is methyl.

$R^2$ is 1-hydroxy-2-methylpropan-2-yl, and $R^1$ is methyl;

$R^2$ is 2-hydroxy-2-propyl and $R^1$ is methyl;

$R^2$ is 2-hydroxy-2-propyl and $R^1$ is isopropyl;

$R^2$ is 2-hydroxy-2-propyl and $R^1$ is 1-hydroxyethyl;

$R^2$ is hydroxymethyl and $R^1$ is methyl;

$R^2$ is 1-hydroxyethyl and $R^1$ is methyl;

$R^2$ is 2-hydroxyethyl and $R^1$ is methyl;

$R^2$ is 1-hydroxy-2-propyl and $R^1$ is methyl;

$R^2$ is 2-hydroxy-2-propyl and $R^1$ is phenyl;

$R^2$ is $C_1$-$C_6$ alkyl optionally substituted with one or more hydroxy, and $R^1$ is 5- to 10-membered heteroaryl;

$R^2$ is 2-hydroxy-2-propyl and $R^1$ is pyridyl;

$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

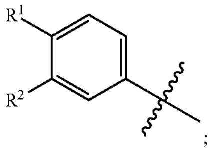

;

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

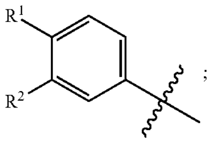

;

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;

$R^2$ is $C_1$-$C_6$ alkyl optionally substituted with one or more hydroxy, and $R^1$ is 5- to 10-membered heteroaryl;

$R^2$ is 2-hydroxy-2-propyl and $R^1$ is pyridyl;

$R^2$ is 2-hydroxy-2-propyl and $R^1$ is pyrazolyl;

$R^2$ is $C_1$-$C_6$ alkyl optionally substituted with one or more hydroxy, and $R^1$ is $S(O_2)CH_3$;

$R^2$ is 2-hydroxy-2-propyl and $R^1$ is chloro;

$R^2$ is 2-hydroxy-2-propyl and $R^1$ is fluoro;

$R^2$ is $C_3$-$C_7$ cycloalkyl optionally substituted with one or more hydroxy, and $R^1$ is $C_1$-$C_6$ alkyl;

$R^2$ is 1-hydroxy-1-cyclopropyl, and $R^1$ is methyl;

$R^2$ is 1-hydroxy-1-cyclobutyl, and $R^1$ is methyl;

$R^2$ is 1-hydroxy-1-cyclopentyl, and $R^1$ is methyl;

$R^2$ is 1-hydroxy-1-cyclohexyl, and $R^1$ is methyl;

$R^2$ is morpholinyl, and $R^1$ is methyl;

$R^2$ is 1,3-dioxolan-2-yl, and $R^1$ is methyl;

$R^2$ is 1,3-dioxolan-2-yl, and $R^1$ is fluoro;

$R^2$ is 1,3-dioxolan-2-yl, and $R^1$ is chloro;

$R^2$ is $C_1$-$C_6$ alkyl optionally substituted with one or more oxo, and $R^1$ is methyl;

$R^2$ is (dimethylamino)methyl, and $R^1$ is methyl;

$R^2$ is $COCH_3$, and $R^1$ is methyl; or $R^2$ is 2-methoxy-2-propyl, and $R^1$ is methyl.

In some embodiments, of the compound of formula AA, the substituted ring A is

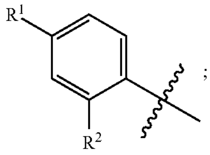

;

and $R^1$ and $R^2$ are one of the following combinations:

$R^1$ is $C_1$-$C_6$ alkyl optionally substituted with one or more hydroxy, and $R^2$ is $C_1$-$C_6$ alkyl optionally substituted with one or more hydroxy;

$R^1$ is $C_1$-$C_6$ alkyl optionally substituted with one or more hydroxy, and $R^2$ is $C_6$-$C_{10}$ aryl;

$R^1$ is $C_1$-$C_6$ alkyl optionally substituted with one or more hydroxy, and $R^2$ is 5- to 10-membered heteroaryl;

$R^1$ is $C_1$-$C_6$ alkyl optionally substituted with one or more hydroxy, and $R^2$ is $SF_5$;

$R^1$ is $C_1$-$C_6$ alkyl optionally substituted with one or more hydroxy, and $R^2$ is $S(O_2)C_1$-$C_6$ alkyl;

$R^1$ is $C_1$-$C_6$ alkyl optionally substituted with one or more hydroxy, and $R^2$ is halo;

$R^1$ is $C_3$-$C_7$ cycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is $C_1$-$C_6$ alkyl;

$R^1$ is 3- to 7-membered heterocycloalkyl optionally substituted with one or more hydroxy, and $R^2$ is halo;

$R^1$ is $C_1$-$C_6$ alkyl optionally substituted with one or more oxo, and $R^2$ is methyl;

$R^1$ is $C_1$-$C_6$ alkyl optionally substituted with one or more $C_1$-$C_6$ alkoxy, and $R^2$ is $C_1$-$C_6$ alkyl;

$R^1$ is $C_1$-$C_6$ alkyl optionally substituted with one or more $NR^8R^9$, and $R^2$ is $C_1$-$C_6$ alkyl;

$R^1$ is $C_1$-$C_6$ alkyl optionally substituted with one or more $NR^8R^9$, and $R^2$ is halo;

$R^2$ is $C_1$-$C_6$ alkyl optionally substituted with one or more hydroxy, and $R^1$ is $C_6$-$C_{10}$ aryl;

$R^2$ is $C_1$-$C_6$ alkyl optionally substituted with one or more hydroxy, and $R^1$ is 5- to 10-membered heteroaryl;

$R^2$ is $C_1$-$C_6$ alkyl optionally substituted with one or more hydroxy, and $R^1$ is $SF_5$.

$R^2$ is $C_1$-$C_6$ alkyl optionally substituted with one or more hydroxy, and $R^1$ is $S(O_2)C_1$-$C_6$ alkyl;

$R^2$ is $C_1$-$C_6$ alkyl optionally substituted with one or more hydroxy, and $R^1$ is halo;

$R^2$ is $C_3$-$C_7$ cycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is halo;

$R^2$ is $C_1$-$C_6$ alkyl optionally substituted with one or more $NR^8R^9$, and $R^1$ is $C_1$-$C_6$ alkyl;

$R^2$ is $C_1$-$C_6$ alkyl optionally substituted with one or more $NR^8R^9$, and $R^1$ is halo;

$R^2$ is $C_1$-$C_6$ alkyl optionally substituted with one or more oxo, and $R^1$ is methyl; or $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

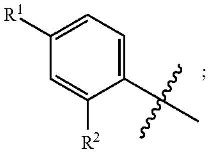

;

and $R^1$ and $R^2$ are one of the following combinations:

$R^1$ is 1-hydroxy-2-methylpropan-2-yl, and $R^2$ is methyl;

$R^1$ is 2-hydroxy-2-propyl and $R^2$ is methyl;

$R^1$ is 2-hydroxy-2-propyl and $R^2$ is isopropyl;

$R^1$ is 2-hydroxy-2-propyl and $R^2$ is 2-hydroxy-2-propyl;

$R^1$ is 2-hydroxy-2-propyl and $R^2$ is 1-hydroxyethyl;

$R^1$ is hydroxymethyl and $R^2$ is methyl;

$R^1$ is 1-hydroxyethyl and $R^2$ is methyl;

$R^1$ is 2-hydroxyethyl and $R^2$ is methyl;

$R^1$ is 1-hydroxy-2-propyl and $R^2$ is methyl;

$R^1$ is 2-hydroxy-2-propyl and $R^2$ is phenyl;

$R^1$ is 2-hydroxy-2-propyl and $R^2$ is pyridyl;

$R^1$ is 2-hydroxy-2-propyl and $R^2$ is pyrazolyl;

$R^1$ is 2-hydroxy-2-propyl, and $R^2$ is $S(O_2)CH_3$;

$R^1$ is 2-hydroxy-2-propyl and $R^2$ is chloro;

$R^1$ is 2-hydroxy-2-propyl and $R^2$ is fluoro;

$R^1$ is 1-hydroxy-1-cyclopropyl, and $R^2$ is methyl;

$R^1$ is 1-hydroxy-1-cyclobutyl, and $R^2$ is methyl;

$R^1$ is 1-hydroxy-1-cyclopentyl, and $R^2$ is methyl;

$R^1$ is 1-hydroxy-1-cyclohexyl, and $R^2$ is methyl;

$R^1$ is morpholinyl, and $R^2$ is methyl;

$R^1$ is 1,3-dioxolan-2-yl, and $R^2$ is methyl;

$R^1$ is 1,3-dioxolan-2-yl, and $R^2$ is fluoro;

$R^1$ is 1,3-dioxolan-2-yl, and $R^2$ is chloro;

$R^1$ is $COCH_3$, and $R^2$ is methyl;

$R^1$ is 2-methoxy-2-propyl, and $R^2$ is methyl;

$R^1$ is (dimethylamino)methyl, and $R^2$ is methyl.

$R^2$ is 1-hydroxy-2-methylpropan-2-yl, and $R^1$ is methyl;

$R^2$ is 2-hydroxy-2-propyl and $R^1$ is methyl;

$R^2$ is 2-hydroxy-2-propyl and $R^1$ is isopropyl;

$R^2$ is 2-hydroxy-2-propyl and $R^1$ is 1-hydroxyethyl;

$R^2$ is hydroxymethyl and $R^1$ is methyl;

$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is (dimethylamino)methyl, and $R^1$ is methyl;
$R^2$ is $C_1$-$C_6$ alkyl optionally substituted with one or more oxo, and $R^1$ is methyl; or
$R^2$ is $COCH_3$, and $R^1$ is methyl.

In some embodiments, of the compound of formula AA, the substituted ring A is

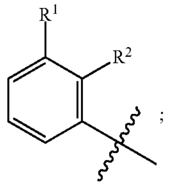

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;

$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

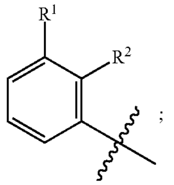

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;

$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

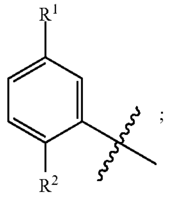

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

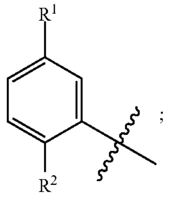

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;

$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments of the compound of formula AA, the substituted ring B is

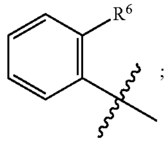

;

and $R^6$ is selected from:

$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

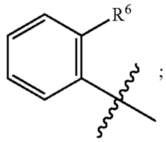

;

and $R^6$ is selected from:

isopropyl, ethyl, methyl, trifluoromethyl, trifluoromethoxy, cyclopropyl, halo, chloro, and fluoro.

In some embodiments of the compound of formula AA, the substituted ring B is

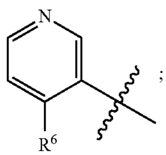

;

and $R^6$ is selected from:

$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

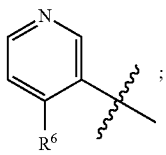

;

and $R^6$ is selected from:

isopropyl, ethyl, methyl, trifluoromethyl, trifluoromethoxy, cyclopropyl, halo, chloro, and fluoro.

In some embodiments of the compound of formula AA, the substituted ring B

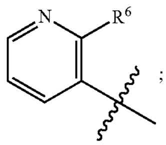

;

and $R^6$ is selected from:

$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

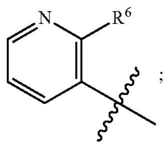

;

and $R^6$ is selected from:

isopropyl, ethyl, methyl, trifluoromethyl, trifluoromethoxy, cyclopropyl, halo, chloro, and fluoro.

In some embodiments of the compound of formula AA, the substituted ring B is

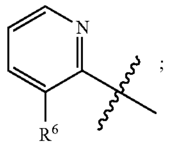

and $R^6$ is selected from:

$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

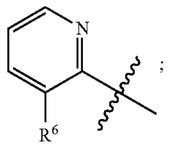

and $R^6$ is selected from:

isopropyl, ethyl, methyl, trifluoromethyl, trifluoromethoxy, cyclopropyl, halo, chloro, and fluoro.

In some embodiments of the compound of formula AA, the substituted ring B is

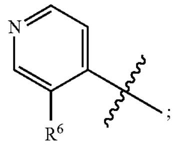

and $R^6$ is selected from:

$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

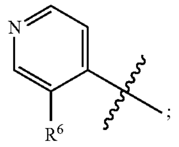

and $R^6$ is selected from:

isopropyl, ethyl, methyl, trifluoromethyl, trifluoromethoxy, cyclopropyl, halo, chloro, and fluoro.

In some embodiments, of the compound of formula AA, the substituted ring B is

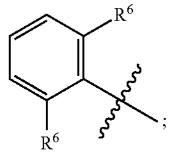

and the two $R^6$ are one of the following combinations:

(i) One $R^6$ is $C_1$-$C_6$ alkyl, and the other $R^6$ is $C_1$-$C_6$ alkyl optionally substituted with one or more halo;

(ii) One $R^6$ is $C_1$-$C_6$ alkyl and the other $R^6$ is $C_1$-$C_6$ alkyl;

(iii) One $R^6$ is $C_1$-$C_6$ alkyl, and the other $R^6$ is $C_1$-$C_6$ alkyl substituted with one or more halo;

(iv) One $R^6$ is $C_1$-$C_6$ alkyl, and the other $R^6$ is $C_3$-$C_7$ cycloalkyl;

(v) One $R^6$ is $C_1$-$C_6$ alkyl, and the other $R^6$ is halo;

(vi) One $R^6$ is $C_1$-$C_6$ alkyl, and the other $R^6$ is cyano;

(vii) One $R^6$ is $C_3$-$C_7$ cycloalkyl, and the other $R^6$ is $C_3$-$C_7$ cycloalkyl; (viii) One $R^6$ is $C_3$-$C_7$ cycloalkyl, and the other $R^6$ is halo;

(ix) One $R^6$ is cyclopropyl and the other $R^6$ is halo;

(x) One $R^6$ is $C_1$-$C_6$ alkyl, and the other $R^6$ is $C_1$-$C_6$ alkoxy optionally substituted with one or more halo;

(xi) One $R^6$ is $C_1$-$C_6$ alkyl, and the other $R^6$ is $C_1$-$C_6$ alkoxy;

(xii) One $R^6$ is $C_1$-$C_6$ alkyl, and the other $R^6$ is $C_1$-$C_6$ alkoxy substituted with one or more halo;

(xiii) One $R^6$ is halo, and the other $R^6$ is $C_1$-$C_6$ haloalkyl;

(xiv) One $R^6$ is halo, and the other $R^6$ is $C_1$-$C_6$ haloalkoxy;

(xv) One $R^6$ is $C_1$-$C_6$ alkoxy; and the other $R^6$ is halo;

(xvi) One $R^6$ is $C_1$-$C_6$ alkoxy; and the other $R^6$ is chloro.

In some embodiments, of the compound of formula AA, the substituted ring B is

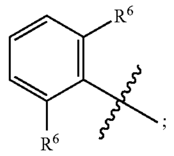

and the two $R^6$ are one of the following combinations:

(i) One $R^6$ is isopropyl; and the other $R^6$ is methyl;

(ii) One $R^6$ is isopropyl; and the other $R^6$ is n-propyl;

(iii) One $R^6$ is isopropyl; and the other $R^6$ is isopropyl;

(iv) One $R^6$ is isopropyl; and the other $R^6$ is trifluoromethyl;

(v) One $R^6$ is isopropyl; and the other $R^6$ is cyclopropyl;

(vi) One $R^6$ is isopropyl; and the other $R^6$ is chloro;

(vii) One $R^6$ is isopropyl; and the other $R^6$ is fluoro;

(viii) One $R^6$ is ethyl; and the other $R^6$ is fluoro;

(ix) One $R^6$ is isopropyl; and the other $R^6$ is cyano;

(x) One $R^6$ is cyclopropyl; and the other $R^6$ is cyclopropyl;

(xi) One $R^6$ is cyclopropyl; and the other $R^6$ is chloro;

(xii) One $R^6$ is cyclopropyl; and the other $R^6$ is fluoro;

(xiii) One $R^6$ is isopropyl; and the other $R^6$ is methoxy;

(xiv) One $R^6$ is isopropyl; and the other $R^6$ is methoxy; or (xv) One $R^6$ is isopropyl; and the other $R^6$ is trifluoromethoxy.

In some embodiments, of the compound of formula AA, the substituted ring B is

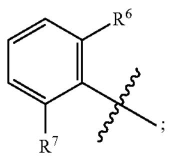

and $R^6$ and $R^7$ are one of the following combinations:

(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo; or
(xxxii) $R^7$ is $C_1$-$C_6$ alkoxy; and $R^6$ is chloro.

In some embodiments, of the compound of formula AA, the substituted ring B is

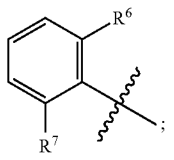

and $R^6$ and $R^7$ are one of the following combinations:

(i) $R^6$ is isopropyl; and $R^7$ is methyl;
(ii) $R^6$ is isopropyl; and $R^7$ is isopropyl;

(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro; $R^6$ is isopropyl; and $R^7$ is methoxy;
(xii) $R^6$ is isopropyl; and $R^7$ is trifluoromethoxy;
(xiii) $R^6$ is chloro; and $R^7$ is trifluoromethyl;
(xiv) $R^6$ is chloro; and $R^7$ is trifluoromethoxy;
(xv) $R^7$ is isopropyl; and $R^6$ is methyl;
(xvi) $R^7$ is isopropyl; and $R^6$ is trifluoromethyl;
(xvii) $R^7$ is isopropyl; and $R^6$ is cyclopropyl;
(xviii) $R^7$ is isopropyl; and $R^6$ is chloro;
(xix) $R^7$ is ethyl; and $R^6$ is fluoro;
(xx) $R^7$ is isopropyl; and $R^6$ is cyano;
(xxi) $R^7$ is cyclopropyl; and $R^6$ is cyclopropyl;
(xxii) $R^7$ is cyclopropyl; and $R^6$ is chloro;
(xxiii) $R^7$ is cyclopropyl; and $R^6$ is fluoro;
(xxiv) $R^7$ is isopropyl; and $R^6$ is methoxy;
(xxv) $R^7$ is isopropyl; and $R^6$ is trifluoromethoxy;
(xxvi) $R^7$ is chloro; and $R^6$ is trifluoromethyl; or
(xxvii) $R^7$ is chloro; and $R^6$ is trifluoromethoxy.

In some embodiments, of the compound of formula AA, the substituted ring B is

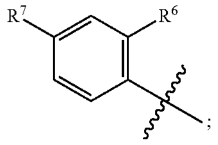

and $R^6$ and $R^7$ are one of the following combinations:

(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;

(xxiv) $R^7$ is $C_3$-$C_7$ cycloalkyl, and $R^6$ is halo;

(xxv) $R^7$ is $C_3$-$C_7$ cycloalkyl and $R^6$ is halo;

(xxvi) $R^7$ is $C_1$-$C_6$ alkyl, and $R^6$ is $C_1$-$C_6$ alkoxy optionally substituted with one or more halo;

(xxvii) $R^7$ is $C_1$-$C_6$ alkyl, and $R^6$ is $C_1$-$C_6$ alkoxy;

(xxviii) $R^7$ is $C_1$-$C_6$ alkyl, and $R^6$ is $C_1$-$C_6$ alkoxy substituted with one or more halo;

(xxix) $R^7$ is halo, and $R^6$ is $C_1$-$C_6$ haloalkyl;

(xxx) $R^7$ is halo, and $R^6$ is $C_1$-$C_6$ haloalkoxy;

(xxxi) $R^7$ is $C_1$-$C_6$ alkoxy; and $R^6$ is halo; or (xxxii) $R^7$ is $C_1$-$C_6$ alkoxy; and $R^6$ is chloro.

In some embodiments, of the compound of formula AA, the substituted ring B is

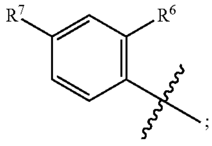
;

and $R^6$ and $R^7$ are one of the following combinations:

(i) $R^6$ is isopropyl; and $R^7$ is methyl;

(ii) $R^6$ is isopropyl; and $R^7$ is isopropyl;

(iii) $R^6$ is isopropyl; and $R^7$ is trifluoromethyl;

(iv) $R^6$ is isopropyl; and $R^7$ is cyclopropyl;

(v) $R^6$ is isopropyl; and $R^7$ is chloro;

(vi) $R^6$ is isopropyl; and $R^7$ is fluoro;

(vii) $R^6$ is ethyl; and $R^7$ is fluoro;

(viii) $R^6$ is isopropyl; and $R^7$ is cyano;

(ix) $R^6$ is cyclopropyl; and $R^7$ is cyclopropyl;

(x) $R^6$ is cyclopropyl; and $R^7$ is chloro;

(xi) $R^6$ is cyclopropyl; and $R^7$ is fluoro;

(xii) $R^6$ is isopropyl; and $R^7$ is methoxy;

(xiii) $R^6$ is isopropyl; and $R^7$ is trifluoromethoxy;

(xiv) $R^6$ is chloro; and $R^7$ is trifluoromethyl;

(xv) $R^6$ is chloro; and $R^7$ is trifluoromethoxy;

(xvi) $R^7$ is isopropyl; and $R^6$ is methyl;

(xvii) $R^7$ is isopropyl; and $R^6$ is trifluoromethyl;

(xviii) $R^7$ is isopropyl; and $R^6$ is cyclopropyl;

(xix) $R^7$ is isopropyl; and $R^6$ is chloro;

(xx) $R^7$ is ethyl; and $R^6$ is fluoro;

(xxi) $R^7$ is isopropyl; and $R^6$ is cyano;

(xxii) $R^7$ is cyclopropyl; and $R^6$ is cyclopropyl;

(xxiii) $R^7$ is cyclopropyl; and $R^6$ is chloro;

(xxiv) $R^7$ is cyclopropyl; and $R^6$ is fluoro;

(xxv) $R^7$ is isopropyl; and $R^6$ is methoxy;

(xxvi) $R^7$ is isopropyl; and $R^6$ is trifluoromethoxy;

(xxvii) $R^7$ is chloro; and $R^6$ is trifluoromethyl; or (xxviii) $R^7$ is chloro; and $R^6$ is trifluoromethoxy.

In some embodiments, of the compound of formula AA, the substituted ring B is

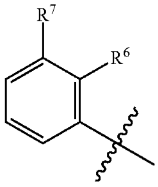
;

and $R^6$ and $R^7$ are one of the following combinations:

(i) $R^6$ is $C_1$-$C_6$ alkyl, and $R^7$ is $C_1$-$C_6$ alkyl optionally substituted with one or more halo;

(ii) $R^6$ is $C_1$-$C_6$ alkyl and $R^7$ is $C_1$-$C_6$ alkyl;

(iii) $R^6$ is $C_1$-$C_6$ alkyl, and $R^7$ is $C_1$-$C_6$ alkyl substituted with one or more halo;

(iv) $R^6$ is $C_1$-$C_6$ alkyl, and $R^7$ is $C_3$-$C_7$ cycloalkyl;

(v) $R^6$ is $C_1$-$C_6$ alkyl, and $R^7$ is halo;

(vi) $R^6$ is $C_1$-$C_6$ alkyl, and $R^7$ is cyano;

(vii) $R^6$ is $C_3$-$C_7$ cycloalkyl, and $R^7$ is $C_3$-$C_7$ cycloalkyl;

(viii) $R^6$ is $C_3$-$C_7$ cycloalkyl, and $R^7$ is halo;

(ix) $R^6$ is cyclopropyl and $R^7$ is halo;

(x) $R^6$ is $C_1$-$C_6$ alkyl, and $R^7$ is $C_1$-$C_6$ alkoxy optionally substituted with one or more halo;

(xi) $R^6$ is $C_1$-$C_6$ alkyl, and $R^7$ is $C_1$-$C_6$ alkoxy;

(xii) $R^6$ is $C_1$-$C_6$ alkyl, and $R^7$ is $C_1$-$C_6$ alkoxy substituted with one or more halo;

(xiii) $R^6$ is halo, and $R^7$ is $C_1$-$C_6$ haloalkyl;

(xiv) $R^6$ is halo, and $R^7$ is $C_1$-$C_6$ haloalkoxy;

(xv) $R^6$ is $C_1$-$C_6$ alkoxy; and $R^7$ is halo;

(xvi) $R^6$ is $C_1$-$C_6$ alkoxy; and $R^7$ is chloro;

(xvii) $R^7$ is $C_1$-$C_6$ alkyl, and $R^6$ is $C_1$-$C_6$ alkyl optionally substituted with one or more halo;

(xviii) $R^7$ is $C_1$-$C_6$ alkyl, and $R^6$ is $C_1$-$C_6$ alkyl substituted with one or more halo;

(xix) $R^7$ is $C_1$-$C_6$ alkyl, and $R^6$ is $C_3$-$C_7$ cycloalkyl;

(xx) $R^7$ is $C_1$-$C_6$ alkyl, and $R^6$ is halo;

(xxi) $R^7$ is $C_1$-$C_6$ alkyl and $R^6$ is halo;

(xxii) $R^7$ is $C_1$-$C_6$ alkyl, and $R^6$ is cyano;

(xxiii) $R^7$ is $C_3$-$C_7$ cycloalkyl, and $R^6$ is $C_3$-$C_7$ cycloalkyl;

(xxiv) $R^7$ is $C_3$-$C_7$ cycloalkyl, and $R^6$ is halo;

(xxv) $R^7$ is $C_3$-$C_7$ cycloalkyl and $R^6$ is halo;

(xxvi) $R^7$ is $C_1$-$C_6$ alkyl, and $R^6$ is $C_1$-$C_6$ alkoxy optionally substituted with one or more halo;

(xxvii) $R^7$ is $C_1$-$C_6$ alkyl, and $R^6$ is $C_1$-$C_6$ alkoxy;

(xxviii) $R^7$ is $C_1$-$C_6$ alkyl, and $R^6$ is $C_1$-$C_6$ alkoxy substituted with one or more halo;

(xxix) $R^7$ is halo, and $R^6$ is $C_1$-$C_6$ haloalkyl;

(xxx) $R^7$ is halo, and $R^6$ is $C_1$-$C_6$ haloalkoxy;

(xxxi) $R^7$ is $C_1$-$C_6$ alkoxy; and $R^6$ is halo; or (xxxii) $R^7$ is $C_1$-$C_6$ alkoxy; and $R^6$ is chloro;

(xxxiii) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or (xxxiv) $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

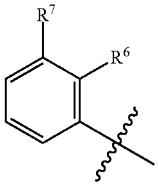
;

and $R^6$ and $R^7$ are one of the following combinations:

(i) $R^6$ is isopropyl; and $R^7$ is methyl;

(ii) $R^6$ is isopropyl; and $R^7$ is isopropyl;

(iii) $R^6$ is isopropyl; and $R^7$ is trifluoromethyl;

(iv) $R^6$ is isopropyl; and $R^7$ is cyclopropyl;

(v) $R^6$ is isopropyl; and $R^7$ is chloro;

(vi) $R^6$ is isopropyl; and $R^7$ is fluoro;

(vii) $R^6$ is ethyl; and $R^7$ is fluoro;

(viii) $R^6$ is isopropyl; and $R^7$ is cyano;

(ix) $R^6$ is cyclopropyl; and $R^7$ is cyclopropyl;

(x) $R^6$ is cyclopropyl; and $R^7$ is chloro;

(xi) $R^6$ is cyclopropyl; and $R^7$ is fluoro;

(xii) $R^6$ is isopropyl; and $R^7$ is methoxy;

(xiii) $R^6$ is isopropyl; and $R^7$ is trifluoromethoxy;

(xiv) $R^6$ is chloro; and $R^7$ is trifluoromethyl;

(xv) $R^6$ is chloro; and $R^7$ is trifluoromethoxy;

(xvi) $R^7$ is isopropyl; and $R^6$ is methyl;

(xvii) $R^7$ is isopropyl; and $R^6$ is trifluoromethyl;

(xviii) $R^7$ is isopropyl; and $R^6$ is cyclopropyl;

(xix) $R^7$ is isopropyl; and $R^6$ is chloro;

(xx) $R^7$ is ethyl; and $R^6$ is fluoro;

(xxi) $R^7$ is isopropyl; and $R^6$ is cyano;

(xxii) $R^7$ is cyclopropyl; and $R^6$ is cyclopropyl;

(xxiii) $R^7$ is cyclopropyl; and $R^6$ is chloro;

(xxiv) $R^7$ is cyclopropyl; and $R^6$ is fluoro;

(xxv) $R^7$ is isopropyl; and $R^6$ is methoxy;

(xxvi) $R^7$ is isopropyl; and $R^6$ is trifluoromethoxy;

(xxvii) $R^7$ is chloro; and $R^6$ is trifluoromethyl;

(xxviii) $R^7$ is chloro; and $R^6$ is trifluoromethoxy;

(xxix) $R^6$ and $R^7$ on adjacent atoms taken together with the atoms connecting them form a $C_4$ aliphatic carbocyclic ring;

(xxx) $R^6$ and $R^7$ on adjacent atoms taken together with the atoms connecting them form a $C_5$ aliphatic carbocyclic ring;

(xxxi) $R^6$ and $R^7$ on adjacent atoms taken together with the atoms connecting them form a $C_6$ aliphatic carbocyclic ring;

(xxxii) $R^6$ and $R^7$ on adjacent atoms taken together with the atoms connecting them form a 5-membered heterocyclic ring containing 1 heteroatoms independently selected from O, N, and S;

(xxxiii) $R^6$ and $R^7$ on adjacent atoms taken together with the atoms connecting them form a 6-membered heterocyclic ring containing 1 heteroatoms independently selected from O, N, and S; or (xxxiv) $R^6$ and $R^7$ on adjacent atoms taken together with the atoms connecting them form a $C_5$ aliphatic carbocyclic ring.

In some embodiments, of the compound of formula AA, the substituted ring B is

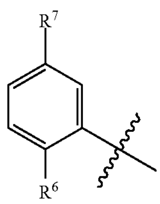

;

and $R^6$ and $R^7$ are one of the following combinations:

(i) $R^6$ is $C_1$-$C_6$ alkyl, and $R^7$ is $C_1$-$C_6$ alkyl optionally substituted with one or more halo;

(ii) $R^6$ is $C_1$-$C_6$ alkyl and $R^7$ is $C_1$-$C_6$ alkyl;

(iii) $R^6$ is $C_1$-$C_6$ alkyl, and $R^7$ is $C_1$-$C_6$ alkyl substituted with one or more halo;

(iv) $R^6$ is $C_1$-$C_6$ alkyl, and $R^7$ is $C_3$-$C_7$ cycloalkyl;

(v) $R^6$ is $C_1$-$C_6$ alkyl, and $R^7$ is halo;

(vi) $R^6$ is $C_1$-$C_6$ alkyl, and $R^7$ is cyano;

(vii) $R^6$ is $C_3$-$C_7$ cycloalkyl, and $R^7$ is $C_3$-$C_7$ cycloalkyl;

(viii) $R^6$ is $C_3$-$C_7$ cycloalkyl, and $R^7$ is halo;

(ix) $R^6$ is cyclopropyl and $R^7$ is halo;

(x) $R^6$ is $C_1$-$C_6$ alkyl, and $R^7$ is $C_1$-$C_6$ alkoxy optionally substituted with one or more halo;

(xi) $R^6$ is $C_1$-$C_6$ alkyl, and $R^7$ is $C_1$-$C_6$ alkoxy;

(xii) $R^6$ is $C_1$-$C_6$ alkyl, and $R^7$ is $C_1$-$C_6$ alkoxy substituted with one or more halo;

(xiii) $R^6$ is halo, and $R^7$ is $C_1$-$C_6$ haloalkyl;

(xiv) $R^6$ is halo, and $R^7$ is $C_1$-$C_6$ haloalkoxy;

(xv) $R^6$ is $C_1$-$C_6$ alkoxy; and $R^7$ is halo;

(xvi) $R^6$ is $C_1$-$C_6$ alkoxy; and $R^7$ is chloro;

(xvii) $R^7$ is $C_1$-$C_6$ alkyl, and $R^6$ is $C_1$-$C_6$ alkyl optionally substituted with one or more halo;

(xviii) $R^7$ is $C_1$-$C_6$ alkyl, and $R^6$ is $C_1$-$C_6$ alkyl substituted with one or more halo;

(xix) $R^7$ is $C_1$-$C_6$ alkyl, and $R^6$ is $C_3$-$C_7$ cycloalkyl;

(xx) $R^7$ is $C_1$-$C_6$ alkyl, and $R^6$ is halo;

(xxi) $R^7$ is $C_1$-$C_6$ alkyl and $R^6$ is halo;

(xxii) $R^7$ is $C_1$-$C_6$ alkyl, and $R^6$ is cyano;

(xxiii) $R^7$ is $C_3$-$C_7$ cycloalkyl, and $R^6$ is $C_3$-$C_7$ cycloalkyl;

(xxiv) $R^7$ is $C_3$-$C_7$ cycloalkyl, and $R^6$ is halo;

(xxv) $R^7$ is $C_3$-$C_7$ cycloalkyl and $R^6$ is halo;

(xxvi) $R^7$ is $C_1$-$C_6$ alkyl, and $R^6$ is $C_1$-$C_6$ alkoxy optionally substituted with one or more halo;

(xxvii) $R^7$ is $C_1$-$C_6$ alkyl, and $R^6$ is $C_1$-$C_6$ alkoxy;

(xxviii) $R^7$ is $C_1$-$C_6$ alkyl, and $R^6$ is $C_1$-$C_6$ alkoxy substituted with one or more halo;

(xxix) $R^7$ is halo, and $R^6$ is $C_1$-$C_6$ haloalkyl;

(xxx) $R^7$ is halo, and $R^6$ is $C_1$-$C_6$ haloalkoxy;

(xxxi) $R^7$ is $C_1$-$C_6$ alkoxy; and $R^6$ is halo; or (xxxii) $R^7$ is $C_1$-$C_6$ alkoxy; and $R^6$ is chloro.

In some embodiments, of the compound of formula AA, the substituted ring B is

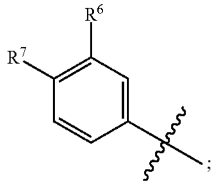

;

and $R^6$ and $R^7$ are one of the following combinations:

(i) $R^6$ is $C_1$-$C_6$ alkyl, and $R^7$ is $C_1$-$C_6$ alkyl optionally substituted with one or more halo;

(ii) $R^6$ is $C_1$-$C_6$ alkyl and $R^7$ is $C_1$-$C_6$ alkyl;

(iii) $R^6$ is $C_1$-$C_6$ alkyl, and $R^7$ is $C_1$-$C_6$ alkyl substituted with one or more halo;

(iv) $R^6$ is $C_1$-$C_6$ alkyl, and $R^7$ is $C_3$-$C_7$ cycloalkyl;

(v) $R^6$ is $C_1$-$C_6$ alkyl, and $R^7$ is halo;

(vi) $R^6$ is $C_1$-$C_6$ alkyl, and $R^7$ is cyano;

(vii) $R^6$ is $C_3$-$C_7$ cycloalkyl, and $R^7$ is $C_3$-$C_7$ cycloalkyl;

(viii) $R^6$ is $C_3$-$C_7$ cycloalkyl, and $R^7$ is halo;

(ix) $R^6$ is cyclopropyl and $R^7$ is halo;

(x) $R^6$ is $C_1$-$C_6$ alkyl, and $R^7$ is $C_1$-$C_6$ alkoxy optionally substituted with one or more halo;

(xi) $R^6$ is $C_1$-$C_6$ alkyl, and $R^7$ is $C_1$-$C_6$ alkoxy;

(xii) $R^6$ is $C_1$-$C_6$ alkyl, and $R^7$ is $C_1$-$C_6$ alkoxy substituted with one or more halo;

(xiii) $R^6$ is halo, and $R^7$ is $C_1$-$C_6$ haloalkyl;

(xiv) $R^6$ is halo, and $R^7$ is $C_1$-$C_6$ haloalkoxy;

(xv) $R^6$ is $C_1$-$C_6$ alkoxy; and $R^7$ is halo;

(xvi) $R^6$ is $C_1$-$C_6$ alkoxy; and $R^7$ is chloro;

(xvii) $R^7$ is $C_1$-$C_6$ alkyl, and $R^6$ is $C_1$-$C_6$ alkyl optionally substituted with one or more halo;

(xviii) $R^7$ is $C_1$-$C_6$ alkyl, and $R^6$ is $C_1$-$C_6$ alkyl substituted with one or more halo;

(xix) $R^7$ is $C_1$-$C_6$ alkyl, and $R^6$ is $C_3$-$C_7$ cycloalkyl;

(xx) $R^7$ is $C_1$-$C_6$ alkyl, and $R^6$ is halo;

(xxi) $R^7$ is $C_1$-$C_6$ alkyl and $R^6$ is halo;

(xxii) $R^7$ is $C_1$-$C_6$ alkyl, and $R^6$ is cyano;

(xxiii) $R^7$ is $C_3$-$C_7$ cycloalkyl, and $R^6$ is $C_3$-$C_7$ cycloalkyl;

(xxiv) $R^7$ is $C_3$-$C_7$ cycloalkyl, and $R^6$ is halo;

(xxv) $R^7$ is $C_3$-$C_7$ cycloalkyl and $R^6$ is halo;

(xxvi) $R^7$ is $C_1$-$C_6$ alkyl, and $R^6$ is $C_1$-$C_6$ alkoxy optionally substituted with one or more halo;

(xxvii) $R^7$ is $C_1$-$C_6$ alkyl, and $R^6$ is $C_1$-$C_6$ alkoxy;

(xxviii) $R^7$ is $C_1$-$C_6$ alkyl, and $R^6$ is $C_1$-$C_6$ alkoxy substituted with one or more halo;

(xxix) $R^7$ is halo, and $R^6$ is $C_1$-$C_6$ haloalkyl;

(xxx) $R^7$ is halo, and $R^6$ is $C_1$-$C_6$ haloalkoxy;

(xxxi) $R^7$ is $C_1$-$C_6$ alkoxy; and $R^6$ is halo;

(xxxii) $R^7$ is $C_1$-$C_6$ alkoxy; and $R^6$ is chloro;

(xxxiii) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or (xxxiv) $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

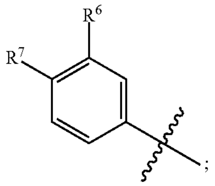

and $R^6$ and $R^7$ are one of the following combinations:

(i) $R^6$ is isopropyl; and $R^7$ is methyl;

(ii) $R^6$ is isopropyl; and $R^7$ is isopropyl;

(iii) $R^6$ is isopropyl; and $R^7$ is trifluoromethyl;

(iv) $R^6$ is isopropyl; and $R^7$ is cyclopropyl;

(v) $R^6$ is isopropyl; and $R^7$ is chloro;

(vi) $R^6$ is isopropyl; and $R^7$ is fluoro;

(vii) $R^6$ is ethyl; and $R^7$ is fluoro;

(viii) $R^6$ is isopropyl; and $R^7$ is cyano;

(ix) $R^6$ is cyclopropyl; and $R^7$ is cyclopropyl;

(x) $R^6$ is cyclopropyl; and $R^7$ is chloro;

(xi) $R^6$ is cyclopropyl; and $R^7$ is fluoro;

(xii) $R^6$ is isopropyl; and $R^7$ is methoxy;

(xiii) $R^6$ is isopropyl; and $R^7$ is trifluoromethoxy;

(xiv) $R^6$ is chloro; and $R^7$ is trifluoromethyl;

(xv) $R^6$ is chloro; and $R^7$ is trifluoromethoxy;

(xvi) $R^7$ is isopropyl; and $R^6$ is methyl;

(xvii) $R^7$ is isopropyl; and $R^6$ is trifluoromethyl;

(xviii) $R^7$ is isopropyl; and $R^6$ is cyclopropyl;

(xix) $R^7$ is isopropyl; and $R^6$ is chloro;

(xx) $R^7$ is ethyl; and $R^6$ is fluoro;

(xxi) $R^7$ is isopropyl; and $R^6$ is cyano;

(xxii) $R^7$ is cyclopropyl; and $R^6$ is cyclopropyl;

(xxiii) $R^7$ is cyclopropyl; and $R^6$ is chloro;

(xxiv) $R^7$ is cyclopropyl; and $R^6$ is fluoro;

(xxv) $R^7$ is isopropyl; and $R^6$ is methoxy;

(xxvi) $R^7$ is isopropyl; and $R^6$ is trifluoromethoxy;

(xxvii) $R^7$ is chloro; and $R^6$ is trifluoromethyl;

(xxviii) $R^7$ is chloro; and $R^6$ is trifluoromethoxy;

(xxix) $R^6$ and $R^7$ on adjacent atoms taken together with the atoms connecting them form a $C_4$ aliphatic carbocyclic ring;

(xxx) $R^6$ and $R^7$ on adjacent atoms taken together with the atoms connecting them form a $C_5$ aliphatic carbocyclic ring;

(xxxi) $R^6$ and $R^7$ on adjacent atoms taken together with the atoms connecting them form a $C_6$ aliphatic carbocyclic ring;

(xxxii) $R^6$ and $R^7$ on adjacent atoms taken together with the atoms connecting them form a 5-membered heterocyclic ring containing 1 heteroatoms independently selected from O, N, and S;

(xxxiii) $R^6$ and $R^7$ on adjacent atoms taken together with the atoms connecting them form a 6-membered heterocyclic ring containing 1 heteroatoms independently selected from O, N, and S; or (xxxiv) $R^6$ and $R^7$ on adjacent atoms taken together with the atoms connecting them form a $C_5$ aliphatic carbocyclic ring.

In some embodiments, of the compound of formula AA, the substituted ring B is

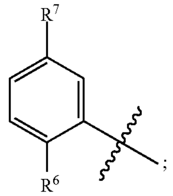

and $R^6$ and $R^7$ are one of the following combinations:

(i) $R^6$ is isopropyl; and $R^7$ is methyl;

(ii) $R^6$ is isopropyl; and $R^7$ is isopropyl;

(iii) $R^6$ is isopropyl; and $R^7$ is trifluoromethyl;

(iv) $R^6$ is isopropyl; and $R^7$ is cyclopropyl;

(v) $R^6$ is isopropyl; and $R^7$ is chloro;

(vi) $R^6$ is isopropyl; and $R^7$ is fluoro;

(vii) $R^6$ is ethyl; and $R^7$ is fluoro;

(viii) $R^6$ is isopropyl; and $R^7$ is cyano;

(ix) $R^6$ is cyclopropyl; and $R^7$ is cyclopropyl;

(x) $R^6$ is cyclopropyl; and $R^7$ is chloro;

(xi) $R^6$ is cyclopropyl; and $R^7$ is fluoro;

(xii) $R^6$ is isopropyl; and $R^7$ is methoxy;

(xiii) $R^6$ is isopropyl; and $R^7$ is trifluoromethoxy;

(xiv) $R^6$ is chloro; and $R^7$ is trifluoromethyl;

(xv) $R^6$ is chloro; and $R^7$ is trifluoromethoxy;

(xvi) $R^7$ is isopropyl; and $R^6$ is methyl;

(xvii) $R^7$ is isopropyl; and $R^6$ is trifluoromethyl;

(xviii) $R^7$ is isopropyl; and $R^6$ is cyclopropyl;

(xix) $R^7$ is isopropyl; and $R^6$ is chloro;

(xx) $R^7$ is ethyl; and $R^6$ is fluoro;

(xxi) $R^7$ is isopropyl; and $R^6$ is cyano;

(xxii) $R^7$ is cyclopropyl; and $R^6$ is cyclopropyl;

(xxiii) $R^7$ is cyclopropyl; and $R^6$ is chloro;

(xxiv) $R^7$ is cyclopropyl; and $R^6$ is fluoro;

(xxv) $R^7$ is isopropyl; and $R^6$ is methoxy;

(xxvi) $R^7$ is isopropyl; and $R^6$ is trifluoromethoxy;

(xxvii) $R^7$ is chloro; and $R^6$ is trifluoromethyl; or (xxviii) $R^7$ is chloro; and $R^6$ is trifluoromethoxy.

In some embodiments, of the compound of formula AA, the substituted ring B is

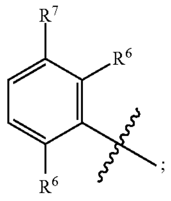

and $R^6$ and $R^7$ are one of the following combinations:

(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo;
(xxxii) $R^7$ is $C_1$-$C_6$ alkoxy; and $R^6$ is chloro;
(xxxiii) $R^6$ and $R^7$ on adjacent atoms taken together with the atoms connecting them form a $C_5$ aliphatic carbocyclic ring;
(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
(xxxv) $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

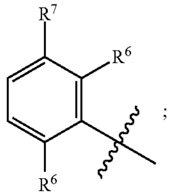

and $R^6$ and $R^7$ are one of the following combinations:

(i) each $R^6$ is isopropyl; and $R^7$ is methyl;
(ii) each $R^6$ is isopropyl; and $R^7$ is isopropyl;
(iii) each $R^6$ is isopropyl; and $R^7$ is trifluoromethyl;
(iv) each $R^6$ is isopropyl; and $R^7$ is cyclopropyl;
(v) each $R^6$ is isopropyl; and $R^7$ is chloro;
(vi) each $R^6$ is isopropyl; and $R^7$ is fluoro;
(vii) each $R^6$ is ethyl; and $R^7$ is fluoro;
(viii) each $R^6$ is isopropyl; and $R^7$ is cyano;
(ix) each $R^6$ is cyclopropyl; and $R^7$ is cyclopropyl;
(x) each $R^6$ is cyclopropyl; and $R^7$ is chloro;
(xi) each $R^6$ is cyclopropyl; and $R^7$ is fluoro;
(xii) each $R^6$ is isopropyl; and $R^7$ is methoxy;
(xiii) each $R^6$ is isopropyl; and $R^7$ is trifluoromethoxy;
(xiv) each $R^6$ is chloro; and $R^7$ is trifluoromethyl;
(xv) each $R^6$ is chloro; and $R^7$ is trifluoromethoxy;
(xvi) $R^7$ is isopropyl; and each $R^6$ is methyl;
(xvii) $R^7$ is isopropyl; and each $R^6$ is trifluoromethyl;
(xviii) $R^7$ is isopropyl; and each $R^6$ is cyclopropyl;
(xix) $R^7$ is isopropyl; and each $R^6$ is chloro;
(xx) $R^7$ is ethyl; and each $R^6$ is fluoro;
(xxi) $R^7$ is isopropyl; and each $R^6$ is cyano;
(xxii) $R^7$ is cyclopropyl; and each $R^6$ is cyclopropyl;
(xxiii) $R^7$ is cyclopropyl; and each $R^6$ is chloro;
(xxiv) $R^7$ is cyclopropyl; and each $R^6$ is fluoro;
(xxv) $R^7$ is isopropyl; and each $R^6$ is methoxy;
(xxvi) $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy;
(xxix) one $R^6$ is isopropyl; the other $R^6$ is trifluoromethyl; and $R^7$ is chloro;

(xxx) $R^6$ and $R^7$ on adjacent atoms taken together with the atoms connecting them form a $C_4$ aliphatic carbocyclic ring; and one $R^6$ is fluoro, chloro, or cyano;

(xxxi) $R^6$ and $R^7$ on adjacent atoms taken together with the atoms connecting them form a $C_5$ aliphatic carbocyclic ring; and one $R^6$ is fluoro, chloro, or cyano;

(xxxii) $R^6$ and $R^7$ on adjacent atoms taken together with the atoms connecting them form a $C_6$ aliphatic carbocyclic ring; and one $R^6$ is fluoro, chloro, or cyano;

(xxxiii) $R^6$ and $R^7$ on adjacent atoms taken together with the atoms connecting them form a 5-membered heterocyclic ring containing 1 heteroatoms independently selected from O, N, and S; and one $R^6$ is fluoro, chloro, or cyano; or (xxxiv) $R^6$ and $R^7$ on adjacent atoms taken together with the atoms connecting them form a 6-membered heterocyclic ring containing 1 heteroatoms independently selected from O, N, and S; and one $R^6$ is fluoro, chloro, or cyano.

In some embodiments, of the compound of formula AA, the substituted ring B is

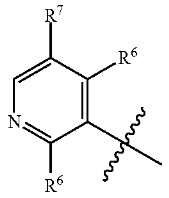

;

and $R^6$ and $R^7$ are one of the following combinations:

(i) each $R^6$ is independently $C_1$-$C_6$ alkyl, and $R^7$ is $C_1$-$C_6$ alkyl optionally substituted with one or more halo;

(ii) each $R^6$ is independently $C_1$-$C_6$ alkyl and $R^7$ is $C_1$-$C_6$ alkyl;

(iii) each $R^6$ is independently $C_1$-$C_6$ alkyl, and $R^7$ is $C_1$-$C_6$ alkyl substituted with one or more halo;

(iv) each $R^6$ is independently $C_1$-$C_6$ alkyl, and $R^7$ is $C_3$-$C_7$ cycloalkyl;

(v) each $R^6$ is independently $C_1$-$C_6$ alkyl, and $R^7$ is halo;

(vi) each $R^6$ is independently $C_1$-$C_6$ alkyl, and $R^7$ is cyano;

(vii) each $R^6$ is independently $C_3$-$C_7$ cycloalkyl, and $R^7$ is $C_3$-$C_7$ cycloalkyl;

(viii) each $R^6$ is independently $C_3$-$C_7$ cycloalkyl, and $R^7$ is halo;

(ix) each $R^6$ is independently cyclopropyl and $R^7$ is halo;

(x) each $R^6$ is independently $C_1$-$C_6$ alkyl, and $R^7$ is $C_1$-$C_6$ alkoxy optionally substituted with one or more halo;

(xi) each $R^6$ is independently $C_1$-$C_6$ alkyl, and $R^7$ is $C_1$-$C_6$ alkoxy;

(xii) each $R^6$ is independently $C_1$-$C_6$ alkyl, and $R^7$ is $C_1$-$C_6$ alkoxy substituted with one or more halo;

(xiii) each $R^6$ is independently halo, and $R^7$ is $C_1$-$C_6$ haloalkyl;

(xiv) each $R^6$ is independently halo, and $R^7$ is $C_1$-$C_6$ haloalkoxy;

(xv) each $R^6$ is independently $C_1$-$C_6$ alkoxy; and $R^7$ is halo;

(xvi) each $R^6$ is independently $C_1$-$C_6$ alkoxy; and $R^7$ is chloro;

(xvii) $R^7$ is $C_1$-$C_6$ alkyl, and each $R^6$ is independently $C_1$-$C_6$ alkyl optionally substituted with one or more halo;

(xviii) $R^7$ is $C_1$-$C_6$ alkyl, and each $R^6$ is independently $C_1$-$C_6$ alkyl substituted with one or more halo;

(xix) $R^7$ is $C_1$-$C_6$ alkyl, and each $R^6$ is independently $C_3$-$C_7$ cycloalkyl;

(xx) $R^7$ is $C_1$-$C_6$ alkyl, and each $R^6$ is independently halo;

(xxi) $R^7$ is $C_1$-$C_6$ alkyl and each $R^6$ is independently halo;

(xxii) $R^7$ is $C_1$-$C_6$ alkyl, and $R^6$ is cyano;

(xxiii) $R^7$ is $C_3$-$C_7$ cycloalkyl, and each $R^6$ is independently $C_3$-$C_7$ cycloalkyl;

(xxiv) $R^7$ is $C_3$-$C_7$ cycloalkyl, and each $R^6$ is independently halo;

(xxv) $R^7$ is $C_3$-$C_7$ cycloalkyl and each $R^6$ is independently halo;

(xxvi) $R^7$ is $C_1$-$C_6$ alkyl, and each $R^6$ is independently $C_1$-$C_6$ alkoxy optionally substituted with one or more halo;

(xxvii) $R^7$ is $C_1$-$C_6$ alkyl, and each $R^6$ is independently $C_1$-$C_6$ alkoxy;

(xxviii) $R^7$ is $C_1$-$C_6$ alkyl, and each $R^6$ is independently $C_1$-$C_6$ alkoxy substituted with one or more halo;

(xxix) $R^7$ is halo, and each $R^6$ is independently $C_1$-$C_6$ haloalkyl;

(xxx) $R^7$ is halo, and each $R^6$ is independently $C_1$-$C_6$ haloalkoxy;

(xxxi) $R^7$ is $C_1$-$C_6$ alkoxy; and each $R^6$ is independently halo; or (xxxii) $R^7$ is $C_1$-$C_6$ alkoxy; and $R^6$ is chloro.

In some embodiments, of the compound of formula AA, the substituted ring B is

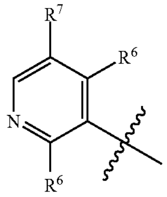

;

and $R^6$ and $R^7$ are one of the following combinations:

(i) each $R^6$ is isopropyl; and $R^7$ is methyl;

(ii) each $R^6$ is isopropyl; and $R^7$ is isopropyl;

(iii) each $R^6$ is isopropyl; and $R^7$ is trifluoromethyl;

(iv) each $R^6$ is isopropyl; and $R^7$ is cyclopropyl;

(v) each $R^6$ is isopropyl; and $R^7$ is chloro;

(vi) each $R^6$ is isopropyl; and $R^7$ is fluoro;

(vii) each $R^6$ is ethyl; and $R^7$ is fluoro;

(viii) each $R^6$ is isopropyl; and $R^7$ is cyano;

(ix) each $R^6$ is cyclopropyl; and $R^7$ is cyclopropyl;

(x) each $R^6$ is cyclopropyl; and $R^7$ is chloro;

(xi) each $R^6$ is cyclopropyl; and $R^7$ is fluoro;

(xii) each $R^6$ is isopropyl; and $R^7$ is methoxy;

(xiii) each $R^6$ is isopropyl; and $R^7$ is trifluoromethoxy;

(xiv) each $R^6$ is chloro; and $R^7$ is trifluoromethyl;

(xv) each $R^6$ is chloro; and $R^7$ is trifluoromethoxy;

(xvi) $R^7$ is isopropyl; and each $R^6$ is methyl;

(xvii) $R^7$ is isopropyl; and each $R^6$ is trifluoromethyl;

(xviii) $R^7$ is isopropyl; and each $R^6$ is cyclopropyl;

(xix) $R^7$ is isopropyl; and each $R^6$ is chloro;

(xx) $R^7$ is ethyl; and each $R^6$ is fluoro;

(xxi) $R^7$ is isopropyl; and each $R^6$ is cyano;

(xxii) $R^7$ is cyclopropyl; and each $R^6$ is cyclopropyl;

(xxiii) $R^7$ is cyclopropyl; and each $R^6$ is chloro;

(xxiv) $R^7$ is cyclopropyl; and each $R^6$ is fluoro;

(xxv) $R^7$ is isopropyl; and each $R^6$ is methoxy;

(xxvi) $R^7$ is isopropyl; and each $R^6$ is trifluoromethoxy;

(xxvii) $R^7$ is chloro; and each $R^6$ is trifluoromethyl;

(xxviii) $R^7$ is chloro; and each $R^6$ is trifluoromethoxy; or (xxix) one $R^6$ is isopropyl; the other $R^6$ is trifluoromethyl; and $R^7$ is chloro.

In some embodiments, of the compound of formula AA, the substituted ring B is

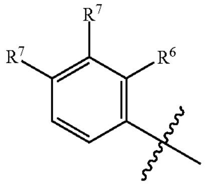

;

and $R^6$ and $R^7$ are one of the following combinations:

(i) $R^6$ is $C_1$-$C_6$ alkyl, and each $R^7$ is independently $C_1$-$C_6$ alkyl optionally substituted with one or more halo;

(ii) $R^6$ is $C_1$-$C_6$ alkyl and each $R^7$ is independently $C_1$-$C_6$ alkyl;

(iii) $R^6$ is $C_1$-$C_6$ alkyl, and each $R^7$ is independently $C_1$-$C_6$ alkyl substituted with one or more halo;

(iv) $R^6$ is $C_1$-$C_6$ alkyl, and each $R^7$ is independently $C_3$-$C_7$ cycloalkyl;

(v) $R^6$ is $C_1$-$C_6$ alkyl, and each $R^7$ is independently halo;

(vi) $R^6$ is $C_1$-$C_6$ alkyl, and $R^7$ is cyano;

(vii) $R^6$ is $C_3$-$C_7$ cycloalkyl, and each $R^7$ is independently $C_3$-$C_7$ cycloalkyl;

(viii) $R^6$ is $C_3$-$C_7$ cycloalkyl, and each $R^7$ is independently halo;

(ix) $R^6$ is cyclopropyl and each $R^7$ is independently halo;

(x) $R^6$ is $C_1$-$C_6$ alkyl, and each $R^7$ is independently $C_1$-$C_6$ alkoxy optionally substituted with one or more halo;

(xi) $R^6$ is $C_1$-$C_6$ alkyl, and each $R^7$ is independently $C_1$-$C_6$ alkoxy;

(xii) $R^6$ is $C_1$-$C_6$ alkyl, and each $R^7$ is independently $C_1$-$C_6$ alkoxy substituted with one or more halo;

(xiii) $R^6$ is halo, and each $R^7$ is independently $C_1$-$C_6$ haloalkyl;

(xiv) $R^6$ is halo, and each $R^7$ is independently $C_1$-$C_6$ haloalkoxy;

(xv) $R^6$ is $C_1$-$C_6$ alkoxy; and each $R^7$ is independently halo;

(xvi) $R^6$ is $C_1$-$C_6$ alkoxy; and $R^7$ is chloro;

(xvii) each $R^7$ is independently $C_1$-$C_6$ alkyl, and $R^6$ is $C_1$-$C_6$ alkyl optionally substituted with one or more halo;

(xviii) each $R^7$ is independently $C_1$-$C_6$ alkyl, and $R^6$ is $C_1$-$C_6$ alkyl substituted with one or more halo;

(xix) each $R^7$ is independently $C_1$-$C_6$ alkyl, and $R^6$ is $C_3$-$C_7$ cycloalkyl;

(xx) each $R^7$ is independently $C_1$-$C_6$ alkyl, and $R^6$ is halo;

(xxi) each $R^7$ is independently $C_1$-$C_6$ alkyl and $R^6$ is halo;

(xxii) each $R^7$ is independently $C_1$-$C_6$ alkyl, and $R^6$ is cyano;

(xxiii) each $R^7$ is independently $C_3$-$C_7$ cycloalkyl, and $R^6$ is $C_3$-$C_7$ cycloalkyl.

(xxiv) each $R^7$ is independently $C_3$-$C_7$ cycloalkyl, and $R^6$ is halo;

(xxv) each $R^7$ is independently $C_3$-$C_7$ cycloalkyl and $R^6$ is halo;

(xxvi) each $R^7$ is independently $C_1$-$C_6$ alkyl, and $R^6$ is $C_1$-$C_6$ alkoxy optionally substituted with one or more halo;

(xxvii) each $R^7$ is independently $C_1$-$C_6$ alkyl, and $R^6$ is $C_1$-$C_6$ alkoxy;

(xxviii) each $R^7$ is independently $C_1$-$C_6$ alkyl, and $R^6$ is $C_1$-$C_6$ alkoxy substituted with one or more halo;

(xxix) each $R^7$ is independently halo, and $R^6$ is $C_1$-$C_6$ haloalkyl;

(xxx) each $R^7$ is independently halo, and $R^6$ is $C_1$-$C_6$ haloalkoxy;

(xxxi) each $R^7$ is independently $C_1$-$C_6$ alkoxy; and $R^6$ is halo;

(xxxii) each $R^7$ is independently $C_1$-$C_6$ alkoxy; and $R^6$ is chloro;

(xxxiii) $R^6$ and $R^7$ on adjacent atoms taken together with the atoms connecting them form a $C_5$ aliphatic carbocyclic ring;

(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or (xxxv) $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

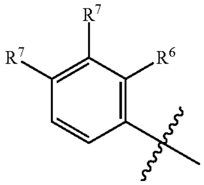

;

and $R^6$ and $R^7$ are one of the following combinations:

(i) $R^6$ is isopropyl; and each $R^7$ is methyl;

(ii) $R^6$ is isopropyl; and each $R^7$ is isopropyl;

(iii) $R^6$ is isopropyl; and each $R^7$ is trifluoromethyl;

(iv) $R^6$ is isopropyl; and each $R^7$ is cyclopropyl;

(v) $R^6$ is isopropyl; and each $R^7$ is chloro;

(vi) $R^6$ is isopropyl; and each $R^7$ is fluoro;

(vii) $R^6$ is ethyl; and each $R^7$ is fluoro;

(viii) $R^6$ is isopropyl; and each $R^7$ is cyano;

(ix) $R^6$ is cyclopropyl; and each $R^7$ is cyclopropyl;

(x) $R^6$ is cyclopropyl; and each $R^7$ is chloro;

(xi) $R^6$ is cyclopropyl; and each $R^7$ is fluoro;

(xii) $R^6$ is isopropyl; and $R^7$ is methoxy;

(xiii) $R^6$ is isopropyl; and each $R^7$ is trifluoromethoxy;

(xiv) $R^6$ is chloro; and each $R^7$ is trifluoromethyl;

(xv) $R^6$ is chloro; and each $R^7$ is trifluoromethoxy;

(xvi) each $R^7$ is isopropyl; and $R^6$ is methyl;

(xvii) each $R^7$ is isopropyl; and $R^6$ is trifluoromethyl;

(xviii) each $R^7$ is isopropyl; and $R^6$ is cyclopropyl;

(xix) each $R^7$ is isopropyl; and $R^6$ is chloro;

(xx) each $R^7$ is ethyl; and $R^6$ is fluoro;

(xxi) each $R^7$ is isopropyl; and $R^6$ is cyano;

(xxii) each $R^7$ is cyclopropyl; and $R^6$ is cyclopropyl;

(xxiii) each $R^7$ is cyclopropyl; and $R^6$ is chloro;

(xxiv) each $R^7$ is cyclopropyl; and $R^6$ is fluoro;

(xxv) each $R^7$ is isopropyl; and $R^6$ is methoxy;

(xxvi) each $R^7$ is isopropyl; and $R^6$ is trifluoromethoxy;

(xxvii) each $R^7$ is chloro; and $R^6$ is trifluoromethyl;

(xxviii) each $R^7$ is chloro; and $R^6$ is trifluoromethoxy;

(xxix) $R^6$ and $R^7$ on adjacent atoms taken together with the atoms connecting them form a $C_5$ aliphatic carbocyclic ring; and one $R^7$ is fluoro, chloro, or cyano;

(xxx) $R^6$ and $R^7$ on adjacent atoms taken together with the atoms connecting them form a $C_4$ aliphatic carbocyclic ring; and one $R^7$ is fluoro, chloro, or cyano;

(xxxi) $R^6$ and $R^7$ on adjacent atoms taken together with the atoms connecting them form a $C_6$ aliphatic carbocyclic ring; and one $R^7$ is fluoro, chloro, or cyano;

(xxxii) $R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or (xxxiii) $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

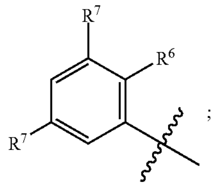

;

and $R^6$ and $R^7$ are one of the following combinations:

(i) $R^6$ is $C_1$-$C_6$ alkyl, and each $R^7$ is independently $C_1$-$C_6$ alkyl optionally substituted with one or more halo;

(ii) $R^6$ is $C_1$-$C_6$ alkyl and each $R^7$ is independently $C_1$-$C_6$ alkyl;

(iii) $R^6$ is $C_1$-$C_6$ alkyl, and each $R^7$ is independently $C_1$-$C_6$ alkyl substituted with one or more halo;

(iv) $R^6$ is $C_1$-$C_6$ alkyl, and each $R^7$ is independently $C_3$-$C_7$ cycloalkyl;

(v) $R^6$ is $C_1$-$C_6$ alkyl, and each $R^7$ is independently halo;

(vi) $R^6$ is $C_1$-$C_6$ alkyl, and $R^7$ is cyano;

(vii) $R^6$ is $C_3$-$C_7$ cycloalkyl, and each $R^7$ is independently $C_3$-$C_7$ cycloalkyl;

(viii) $R^6$ is $C_3$-$C_7$ cycloalkyl, and each $R^7$ is independently halo;

(ix) $R^6$ is cyclopropyl and each $R^7$ is independently halo;

(x) $R^6$ is $C_1$-$C_6$ alkyl, and each $R^7$ is independently $C_1$-$C_6$ alkoxy optionally substituted with one or more halo;

(xi) $R^6$ is $C_1$-$C_6$ alkyl, and each $R^7$ is independently $C_1$-$C_6$ alkoxy;

(xii) $R^6$ is $C_1$-$C_6$ alkyl, and each $R^7$ is independently $C_1$-$C_6$ alkoxy substituted with one or more halo;

(xiii) $R^6$ is halo, and each $R^7$ is independently $C_1$-$C_6$ haloalkyl;

(xiv) $R^6$ is halo, and each $R^7$ is independently $C_1$-$C_6$ haloalkoxy;

(xv) $R^6$ is $C_1$-$C_6$ alkoxy; and each $R^7$ is independently halo;

(xvi) $R^6$ is $C_1$-$C_6$ alkoxy; and $R^7$ is chloro;

(xvii) each $R^7$ is independently $C_1$-$C_6$ alkyl, and $R^6$ is $C_1$-$C_6$ alkyl optionally substituted with one or more halo;

(xviii) each $R^7$ is independently $C_1$-$C_6$ alkyl, and $R^6$ is $C_1$-$C_6$ alkyl substituted with one or more halo;

(xix) each $R^7$ is independently $C_1$-$C_6$ alkyl, and $R^6$ is $C_3$-$C_7$ cycloalkyl;

(xx) each $R^7$ is independently $C_1$-$C_6$ alkyl, and $R^6$ is halo;

(xxi) each $R^7$ is independently $C_1$-$C_6$ alkyl and $R^6$ is halo;

(xxii) each $R^7$ is independently $C_1$-$C_6$ alkyl, and $R^6$ is cyano;

(xxiii) each $R^7$ is independently $C_3$-$C_7$ cycloalkyl, and $R^6$ is $C_3$-$C_7$ cycloalkyl;

(xxiv) each $R^7$ is independently $C_3$-$C_7$ cycloalkyl, and $R^6$ is halo;

(xxv) each $R^7$ is independently $C_3$-$C_7$ cycloalkyl and $R^6$ is halo;

(xxvi) each $R^7$ is independently $C_1$-$C_6$ alkyl, and $R^6$ is $C_1$-$C_6$ alkoxy optionally substituted with one or more halo;

(xxvii) each $R^7$ is independently $C_1$-$C_6$ alkyl, and $R^6$ is $C_1$-$C_6$ alkoxy;

(xxviii) each $R^7$ is independently $C_1$-$C_6$ alkyl, and $R^6$ is $C_1$-$C_6$ alkoxy substituted with one or more halo;

(xxix) each $R^7$ is independently halo, and $R^6$ is $C_1$-$C_6$ haloalkyl;

(xxx) each $R^7$ is independently halo, and $R^6$ is $C_1$-$C_6$ haloalkoxy;

(xxxi) each $R^7$ is independently $C_1$-$C_6$ alkoxy; and $R^6$ is halo;

(xxxii) each $R^6$ is independently $C_1$-$C_6$ alkoxy; and $R^6$ is chloro;

(xxxiii) $R^6$ and $R^7$ on adjacent atoms taken together with the atoms connecting them form a $C_5$ aliphatic carbocyclic ring;

(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or (xxxiv) $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

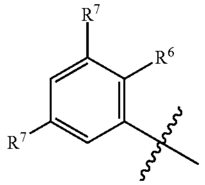

;

and $R^6$ and $R^7$ are one of the following combinations:

(i) $R^6$ is isopropyl; and each $R^7$ is methyl;

(ii) $R^6$ is isopropyl; and each $R^7$ is isopropyl;

(iii) $R^6$ is isopropyl; and each $R^7$ is trifluoromethyl;

(iv) $R^6$ is isopropyl; and each $R^7$ is cyclopropyl;

(v) $R^6$ is isopropyl; and each $R^7$ is chloro;

(vi) $R^6$ is isopropyl; and each $R^7$ is fluoro;

(vii) $R^6$ is ethyl; and each $R^7$ is fluoro;

(viii) $R^6$ is isopropyl; and each $R^7$ is cyano;

(ix) $R^6$ is cyclopropyl; and each $R^7$ is cyclopropyl;

(x) $R^6$ is cyclopropyl; and each $R^7$ is chloro;

(xi) $R^6$ is cyclopropyl; and each $R^7$ is fluoro;

(xii) $R^6$ is isopropyl; and each $R^7$ is methoxy;

(xiii) $R^6$ is isopropyl; and each $R^7$ is trifluoromethoxy;

(xiv) $R^6$ is chloro; and each $R^7$ is trifluoromethyl;
(xv) $R^6$ is chloro; and each $R^7$ is trifluoromethoxy;
(xvi) each $R^7$ is isopropyl; and $R^6$ is methyl;
(xvii) each $R^7$ is isopropyl; and $R^6$ is trifluoromethyl;
(xviii) each $R^7$ is isopropyl; and $R^6$ is cyclopropyl;
(xix) each $R^7$ is isopropyl; and $R^6$ is chloro;
(xx) each $R^7$ is ethyl; and $R^6$ is fluoro;
(xxi) each $R^7$ is isopropyl; and $R^6$ is cyano;
(xxii) each $R^7$ is cyclopropyl; and $R^6$ is cyclopropyl;
(xxiii) each $R^7$ is cyclopropyl; and $R^6$ is chloro;
(xxiv) each $R^7$ is cyclopropyl; and $R^6$ is fluoro;
(xxv) each $R^7$ is isopropyl; and $R^6$ is methoxy;
(xxvi) each $R^7$ is isopropyl; and $R^6$ is trifluoromethoxy;
(xxvii) each $R^7$ is chloro; and $R^6$ is trifluoromethyl;
(xxviii) each $R^7$ is chloro; and $R^6$ is trifluoromethoxy;
(xxix) $R^6$ and $R^7$ on adjacent atoms taken together with the atoms connecting them form a $C_5$ aliphatic carbocyclic ring; and one $R^7$ is fluoro, chloro, or cyano;
(xxx) $R^6$ and $R^7$ on adjacent atoms taken together with the atoms connecting them form a $C_4$ aliphatic carbocyclic ring; and one $R^7$ is fluoro, chloro, or cyano;
(xxxi) $R^6$ and $R^7$ on adjacent atoms taken together with the atoms connecting them form a $C_6$ aliphatic carbocyclic ring; and one $R^7$ is fluoro, chloro, or cyano;
(xxxii) $R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or
(xxxiii) $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

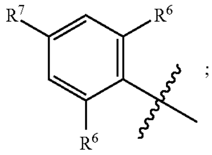
;

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo; or
(xxxii) $R^7$ is $C_1$-$C_6$ alkoxy; and $R^6$ is chloro.

In some embodiments, of the compound of formula AA, the substituted ring B is

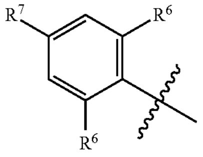
;

and $R^6$ and $R^7$ are one of the following combinations:
(i) each $R^6$ is isopropyl; and $R^7$ is methyl;
(ii) each $R^6$ is isopropyl; and $R^7$ is isopropyl;
(iii) each $R^6$ is isopropyl; and $R^7$ is trifluoromethyl;
(iv) each $R^6$ is isopropyl; and $R^7$ is cyclopropyl;
(v) each $R^6$ is isopropyl; and $R^7$ is chloro;
(vi) each $R^6$ is isopropyl; and $R^7$ is fluoro;
(vii) each $R^6$ is ethyl; and $R^7$ is fluoro;
(viii) each $R^6$ is isopropyl; and $R^7$ is cyano;
(ix) each $R^6$ is cyclopropyl; and $R^7$ is cyclopropyl;
(x) each $R^6$ is cyclopropyl; and $R^7$ is chloro;
(xi) each $R^6$ is cyclopropyl; and $R^7$ is fluoro;
(xii) each $R^6$ is isopropyl; and $R^7$ is methoxy;
(xiii) each $R^6$ is isopropyl; and $R^7$ is trifluoromethoxy;
(xiv) each $R^6$ is chloro; and $R^7$ is trifluoromethyl;

(xv) each $R^6$ is chloro; and $R^7$ is trifluoromethoxy;
(xvi) $R^7$ is isopropyl; and each $R^6$ is methyl;
(xvii) $R^7$ is isopropyl; and each $R^6$ is trifluoromethyl;
(xviii) $R^7$ is isopropyl; and each $R^6$ is cyclopropyl;
(xix) $R^7$ is isopropyl; and each $R^6$ is chloro;
(xx) $R^7$ is ethyl; and each $R^6$ is fluoro;
(xxi) $R^7$ is isopropyl; and each $R^6$ is cyano;
(xxii) $R^7$ is cyclopropyl; and each $R^6$ is cyclopropyl;
(xxiii) $R^7$ is cyclopropyl; and each $R^6$ is chloro;
(xxiv) $R^7$ is cyclopropyl; and each $R^6$ is fluoro;
(xxv) $R^7$ is isopropyl; and each $R^6$ is methoxy;
(xxvi) $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy; or
(xxix) one $R^6$ is isopropyl; the other $R^6$ is trifluoromethyl; and $R^7$ is chloro.

In some embodiments, of the compound of formula AA, the substituted ring B is

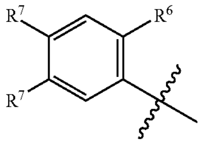

;

and $R^6$ and $R^7$ are one of the following combinations:
(i) $R^6$ is $C_1$-$C_6$ alkyl, and each $R^7$ is independently $C_1$-$C_6$ alkyl optionally substituted with one or more halo;
(ii) $R^6$ is $C_1$-$C_6$ alkyl and each $R^7$ is independently $C_1$-$C_6$ alkyl;
(iii) $R^6$ is $C_1$-$C_6$ alkyl, and each $R^7$ is independently $C_1$-$C_6$ alkyl substituted with one or more halo;
(iv) $R^6$ is $C_1$-$C_6$ alkyl, and each $R^7$ is independently $C_3$-$C_7$ cycloalkyl;
(v) $R^6$ is $C_1$-$C_6$ alkyl, and each $R^7$ is independently halo;
(vi) $R^6$ is $C_1$-$C_6$ alkyl, and $R^7$ is cyano;
(vii) $R^6$ is $C_3$-$C_7$ cycloalkyl, and each $R^7$ is independently $C_3$-$C_7$ cycloalkyl;
(viii) $R^6$ is $C_3$-$C_7$ cycloalkyl, and each $R^7$ is independently halo;
(ix) $R^6$ is cyclopropyl and each $R^7$ is independently halo;
(x) $R^6$ is $C_1$-$C_6$ alkyl, and each $R^7$ is independently $C_1$-$C_6$ alkoxy optionally substituted with one or more halo;
(xi) $R^6$ is $C_1$-$C_6$ alkyl, and each $R^7$ is independently $C_1$-$C_6$ alkoxy;
(xii) $R^6$ is $C_1$-$C_6$ alkyl, and each $R^7$ is independently $C_1$-$C_6$ alkoxy substituted with one or more halo;
(xiii) $R^6$ is halo, and each $R^7$ is independently $C_1$-$C_6$ haloalkyl;
(xiv) $R^6$ is halo, and each $R^7$ is independently $C_1$-$C_6$ haloalkoxy;
(xv) $R^6$ is $C_1$-$C_6$ alkoxy; and each $R^7$ is independently halo;
(xvi) $R^6$ is $C_1$-$C_6$ alkoxy; and $R^7$ is chloro;
(xvii) each $R^7$ is independently $C_1$-$C_6$ alkyl, and $R^6$ is $C_1$-$C_6$ alkyl optionally substituted with one or more halo;
(xviii) each $R^7$ is independently $C_1$-$C_6$ alkyl, and $R^6$ is $C_1$-$C_6$ alkyl substituted with one or more halo;
(xix) each $R^7$ is independently $C_1$-$C_6$ alkyl, and $R^6$ is $C_3$-$C_7$ cycloalkyl;
(xx) each $R^7$ is independently $C_1$-$C_6$ alkyl, and $R^6$ is halo;
(xxi) each $R^7$ is independently $C_1$-$C_6$ alkyl and $R^6$ is halo;
(xxii) each $R^7$ is independently $C_1$-$C_6$ alkyl, and $R^6$ is cyano;

(xxiii) each $R^7$ is independently $C_3$-$C_7$ cycloalkyl, and $R^6$ is $C_3$-$C_7$ cycloalkyl;
(xxiv) each $R^7$ is independently $C_3$-$C_7$ cycloalkyl, and $R^6$ is halo;
(xxv) each $R^7$ is independently $C_3$-$C_7$ cycloalkyl and $R^6$ is halo;
(xxvi) each $R^7$ is independently $C_1$-$C_6$ alkyl, and $R^6$ is $C_1$-$C_6$ alkoxy optionally substituted with one or more halo;
(xxvii) each $R^7$ is independently $C_1$-$C_6$ alkyl, and $R^6$ is $C_1$-$C_6$ alkoxy;
(xxviii) each $R^7$ is independently $C_1$-$C_6$ alkyl, and $R^6$ is $C_1$-$C_6$ alkoxy substituted with one or more halo;
(xxix) each $R^7$ is independently halo, and $R^6$ is $C_1$-$C_6$ haloalkyl;
(xxx) each $R^7$ is independently halo, and $R^6$ is $C_1$-$C_6$ haloalkoxy;
(xxxi) each $R^7$ is independently $C_1$-$C_6$ alkoxy; and $R^6$ is halo; or
(xxxii) each $R^7$ is independently $C_1$-$C_6$ alkoxy; and $R^6$ is chloro.

In some embodiments, of the compound of formula AA, the substituted ring B is

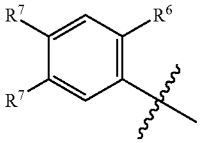

;

and $R^6$ and $R^7$ are one of the following combinations:
(i) $R^6$ is isopropyl; and each $R^7$ is methyl;
(ii) $R^6$ is isopropyl; and each $R^7$ is isopropyl;
(iii) $R^6$ is isopropyl; and each $R^7$ is trifluoromethyl;
(iv) $R^6$ is isopropyl; and each $R^7$ is cyclopropyl;
(v) $R^6$ is isopropyl; and each $R^7$ is chloro;
(vi) $R^6$ is isopropyl; and each $R^7$ is fluoro;
(vii) $R^6$ is ethyl; and each $R^7$ is fluoro;
(viii) $R^6$ is isopropyl; and each $R^7$ is cyano;
(ix) $R^6$ is cyclopropyl; and each $R^7$ is cyclopropyl;
(x) $R^6$ is cyclopropyl; and each $R^7$ is chloro;
(xi) $R^6$ is cyclopropyl; and each $R^7$ is fluoro;
(xii) $R^6$ is isopropyl; and each $R^7$ is methoxy;
(xiii) $R^6$ is isopropyl; and each $R^7$ is trifluoromethoxy;
(xiv) $R^6$ is chloro; and each $R^7$ is trifluoromethyl;
(xv) $R^6$ is chloro; and each $R^7$ is trifluoromethoxy;
(xvi) each $R^7$ is isopropyl; and $R^6$ is methyl;
(xvii) each $R^7$ is isopropyl; and $R^6$ is trifluoromethyl;
(xviii) each $R^7$ is isopropyl; and $R^6$ is cyclopropyl;
(xix) each $R^7$ is isopropyl; and $R^6$ is chloro;
(xx) each $R^7$ is ethyl; and $R^6$ is fluoro;
(xxi) each $R^7$ is isopropyl; and $R^6$ is cyano;
(xxii) each $R^7$ is cyclopropyl; and $R^6$ is cyclopropyl;
(xxiii) each $R^7$ is cyclopropyl; and $R^6$ is chloro;
(xxiv) each $R^7$ is cyclopropyl; and $R^6$ is fluoro;
(xxv) each $R^7$ is isopropyl; and $R^6$ is methoxy;
(xxvi) each $R^7$ is isopropyl; and $R^6$ is trifluoromethoxy;
(xxvii) each $R^7$ is chloro; and $R^6$ is trifluoromethyl; or
(xxviii) each $R^7$ is chloro; and $R^6$ is trifluoromethoxy.

In some embodiments, of the compound of formula AA, the substituted ring B is

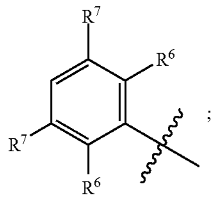

;

and $R^6$ and $R^7$ are one of the following combinations:

(i) each $R^6$ is independently $C_1$-$C_6$ alkyl, and each $R^7$ is independently $C_1$-$C_6$ alkyl optionally substituted with one or more halo;

(ii) each $R^6$ is independently $C_1$-$C_6$ alkyl and each $R^7$ is independently $C_1$-$C_6$ alkyl;

(iii) each $R^6$ is independently $C_1$-$C_6$ alkyl, and each $R^7$ is independently $C_1$-$C_6$ alkyl substituted with one or more halo;

(iv) each $R^6$ is independently $C_1$-$C_6$ alkyl, and each $R^7$ is independently $C_3$-$C_7$ cycloalkyl;

(v) each $R^6$ is independently $C_1$-$C_6$ alkyl, and each $R^7$ is independently halo;

(vi) each $R^6$ is independently $C_1$-$C_6$ alkyl, and $R^7$ is cyano;

(vii) each $R^6$ is independently $C_3$-$C_7$ cycloalkyl, and each $R^7$ is independently $C_3$-$C_7$ cycloalkyl;

(viii) each $R^6$ is independently $C_3$-$C_7$ cycloalkyl, and each $R^7$ is independently halo;

(ix) each $R^6$ is independently cyclopropyl and each $R^7$ is independently halo;

(x) each $R^6$ is independently $C_1$-$C_6$ alkyl, and each $R^7$ is independently $C_1$-$C_6$ alkoxy optionally substituted with one or more halo;

(xi) each $R^6$ is independently $C_1$-$C_6$ alkyl, and each $R^7$ is independently $C_1$-$C_6$ alkoxy;

(xii) each $R^6$ is independently $C_1$-$C_6$ alkyl, and each $R^7$ is independently $C_1$-$C_6$ alkoxy substituted with one or more halo;

(xiii) each $R^6$ is independently halo, and each $R^7$ is independently $C_1$-$C_6$ haloalkyl;

(xiv) each $R^6$ is independently halo, and each $R^7$ is independently $C_1$-$C_6$ haloalkoxy;

(xv) each $R^6$ is independently $C_1$-$C_6$ alkoxy; and each $R^7$ is independently halo;

(xvi) each $R^6$ is independently $C_1$-$C_6$ alkoxy; and $R^7$ is chloro;

(xvii) each $R^7$ is independently $C_1$-$C_6$ alkyl, and each $R^6$ is independently $C_1$-$C_6$ alkyl optionally substituted with one or more halo;

(xviii) each $R^7$ is independently $C_1$-$C_6$ alkyl, and each $R^6$ is independently $C_1$-$C_6$ alkyl substituted with one or more halo;

(xix) each $R^7$ is independently $C_1$-$C_6$ alkyl, and each $R^6$ is independently $C_3$-$C_7$ cycloalkyl;

(xx) each $R^7$ is independently $C_1$-$C_6$ alkyl, and each $R^6$ is independently halo;

(xxi) each $R^7$ is independently $C_1$-$C_6$ alkyl and each $R^6$ is independently halo;

(xxii) each $R^7$ is independently $C_1$-$C_6$ alkyl, and $R^6$ is cyano;

(xxiii) each $R^7$ is independently $C_3$-$C_7$ cycloalkyl, and each $R^6$ is independently $C_3$-$C_7$ cycloalkyl (xxiv) each $R^7$ is independently $C_3$-$C_7$ cycloalkyl, and each $R^6$ is independently halo;

(xxv) each $R^7$ is independently $C_3$-$C_7$ cycloalkyl and each $R^6$ is independently halo;

(xxvi) each $R^7$ is independently $C_1$-$C_6$ alkyl, and each $R^6$ is independently $C_1$-$C_6$ alkoxy optionally substituted with one or more halo;

(xxvii) each $R^7$ is independently $C_1$-$C_6$ alkyl, and each $R^6$ is independently $C_1$-$C_6$ alkoxy;

(xxviii) each $R^7$ is independently $C_1$-$C_6$ alkyl, and each $R^6$ is independently $C_1$-$C_6$ alkoxy substituted with one or more halo;

(xxix) each $R^7$ is independently halo, and each $R^6$ is independently $C_1$-$C_6$ haloalkyl;

(xxx) each $R^7$ is independently halo, and each $R^6$ is independently $C_1$-$C_6$ haloalkoxy;

(xxxi) each $R^7$ is independently $C_1$-$C_6$ alkoxy; and each $R^6$ is independently halo;

(xxxii) each $R^7$ is independently $C_1$-$C_6$ alkoxy; and $R^6$ is chloro;

(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;

(xxxiv) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;

(xxxv) two pairs, each of one $R^6$ and one $R^7$, are on adjacent atoms, and one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5- to-6-membered heterocyclic ring containing 1 heteroatom independently selected from O, N, and S, wherein the heterocyclic ring is optionally substituted with one or more hydroxy, oxo, or $C_1$-$C_6$ alkyl; or (xxxvi) two pairs, each of one $R^6$ and one $R^7$, are on adjacent atoms, and each pair of one $R^6$ and one $R^7$ taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

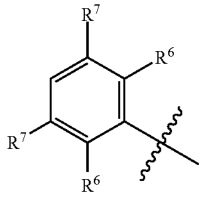

;

and $R^6$ and $R^7$ are one of the following combinations:

(i) each $R^6$ is isopropyl; and each $R^7$ is methyl;

(ii) each $R^6$ is isopropyl; and each $R^7$ is isopropyl;

(iii) each $R^6$ is isopropyl; and each $R^7$ is trifluoromethyl;

(iv) each $R^6$ is isopropyl; and each $R^7$ is cyclopropyl;

(v) each $R^6$ is isopropyl; and each $R^7$ is chloro;

(vi) each $R^6$ is isopropyl; and each $R^7$ is fluoro;

(vii) each $R^6$ is ethyl; and each $R^7$ is fluoro;

(viii) each $R^6$ is isopropyl; and each $R^7$ is cyano;

(ix) each $R^6$ is cyclopropyl; and each $R^7$ is cyclopropyl;

(x) each $R^6$ is cyclopropyl; and each $R^7$ is chloro;

(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and each $R^7$ is chloro;
(xxx) each $R^6$ is isopropyl; one $R^7$ is fluoro; and the other $R^7$ is cyano;
(xxxi) two pairs, each of one $R^6$ and one $R^7$, are on adjacent atoms, and each pair of one $R^6$ and one $R^7$ taken together with the atoms connecting them form a $C_5$ aliphatic carbocyclic ring;
(xxxii) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
(xxxiii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
(xxxiv) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
(xxxv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl;
(xxxvi) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvii) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

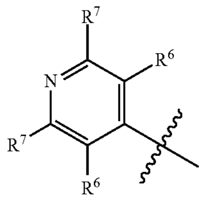

;

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;

(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo;
(xxxii) each $R^7$ is independently $C_1$-$C_6$ alkoxy; and $R^6$ is chloro;
(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
(xxxiv) two pairs, each of one $R^6$ and one $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxv) two pairs, each of one $R^6$ and one $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

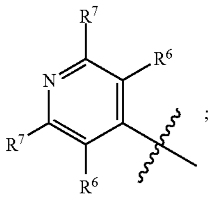

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and each $R^7$ is chloro;
(xxx) each $R^6$ is isopropyl; one $R^7$ is fluoro; and the other $R^7$ is cyano; or
(xxxi) two pairs, each of one $R^6$ and one $R^7$ on adjacent atoms taken together with the atoms connecting them form a $C_4$ aliphatic carbocyclic ring optionally substituted with one or more hydroxy, oxo, or methyl;
(xxxii) two pairs, each of one $R^6$ and one $R^7$ on adjacent atoms taken together with the atoms connecting them form a $C_5$ aliphatic carbocyclic ring optionally substituted with one or more hydroxy, oxo, or methyl;
(xxxiii) two pairs, each of one $R^6$ and one $R^7$ on adjacent atoms taken together with the atoms connecting them form a $C_6$ aliphatic carbocyclic ring optionally substituted with one or more hydroxy, oxo, or methyl;
(xxxiv) two pairs, each of one $R^6$ and one $R^7$ on adjacent atoms taken together with the atoms connecting them form a 5-membered heterocyclic ring containing 1 heteroatom independently selected from O, N, and S, wherein the heterocyclic ring is optionally substituted with one or more hydroxy, oxo, or methyl;
(xxxv) two pairs, each of one $R^6$ and one $R^7$ on adjacent atoms taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvi) two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, of the compound of formula AA, the substituted ring B is

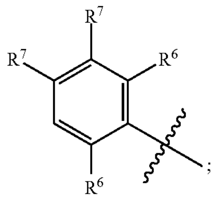

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;

(iii) each $R^6$ is independently $C_1$-$C_6$ alkyl, and each $R^7$ is independently $C_1$-$C_6$ alkyl substituted with one or more halo;

(iv) each $R^6$ is independently $C_1$-$C_6$ alkyl, and each $R^7$ is independently $C_3$-$C_7$ cycloalkyl;

(v) each $R^6$ is independently $C_1$-$C_6$ alkyl, and each $R^7$ is independently halo;

(vi) each $R^6$ is independently $C_1$-$C_6$ alkyl, and $R^7$ is cyano;

(vii) each $R^6$ is independently $C_3$-$C_7$ cycloalkyl, and each $R^7$ is independently $C_3$-$C_7$ cycloalkyl;

(viii) each $R^6$ is independently $C_3$-$C_7$ cycloalkyl, and each $R^7$ is independently halo;

(ix) each $R^6$ is independently cyclopropyl and each $R^7$ is independently halo;

(x) each $R^6$ is independently $C_1$-$C_6$ alkyl, and each $R^7$ is independently $C_1$-$C_6$ alkoxy optionally substituted with one or more halo;

(xi) each $R^6$ is independently $C_1$-$C_6$ alkyl, and each $R^7$ is independently $C_1$-$C_6$ alkoxy;

(xii) each $R^6$ is independently $C_1$-$C_6$ alkyl, and each $R^7$ is independently $C_1$-$C_6$ alkoxy substituted with one or more halo;

(xiii) each $R^6$ is independently halo, and each $R^7$ is independently $C_1$-$C_6$ haloalkyl;

(xiv) each $R^6$ is independently halo, and each $R^7$ is independently $C_1$-$C_6$ haloalkoxy;

(xv) each $R^6$ is independently $C_1$-$C_6$ alkoxy; and each $R^7$ is independently halo;

(xvi) each $R^6$ is independently $C_1$-$C_6$ alkoxy; and $R^7$ is chloro;

(xvii) each $R^7$ is independently $C_1$-$C_6$ alkyl, and each $R^6$ is independently $C_1$-$C_6$ alkyl optionally substituted with one or more halo;

(xviii) each $R^7$ is independently $C_1$-$C_6$ alkyl, and each $R^6$ is independently $C_1$-$C_6$ alkyl substituted with one or more halo;

(xix) each $R^7$ is independently $C_1$-$C_6$ alkyl, and each $R^6$ is independently $C_3$-$C_7$ cycloalkyl;

(xx) each $R^7$ is independently $C_1$-$C_6$ alkyl, and each $R^6$ is independently halo;

(xxi) each $R^7$ is independently $C_1$-$C_6$ alkyl and each $R^6$ is independently halo;

(xxii) each $R^7$ is independently $C_1$-$C_6$ alkyl, and $R^6$ is cyano;

(xxiii) each $R^7$ is independently $C_3$-$C_7$ cycloalkyl, and each $R^6$ is independently $C_3$-$C_7$ cycloalkyl;

(xxiv) each $R^7$ is independently $C_3$-$C_7$ cycloalkyl, and each $R^6$ is independently halo;

(xxv) each $R^7$ is independently $C_3$-$C_7$ cycloalkyl and each $R^6$ is independently halo;

(xxvi) each $R^7$ is independently $C_1$-$C_6$ alkyl, and each $R^6$ is independently $C_1$-$C_6$ alkoxy optionally substituted with one or more halo;

(xxvii) each $R^7$ is independently $C_1$-$C_6$ alkyl, and each $R^6$ is independently $C_1$-$C_6$ alkoxy;

(xxviii) each $R^7$ is independently $C_1$-$C_6$ alkyl, and each $R^6$ is independently $C_1$-$C_6$ alkoxy substituted with one or more halo;

(xxix) each $R^7$ is independently halo, and each $R^6$ is independently $C_1$-$C_6$ haloalkyl;

(xxx) each $R^7$ is independently halo, and each $R^6$ is independently $C_1$-$C_6$ haloalkoxy;

(xxxi) each $R^7$ is independently $C_1$-$C_6$ alkoxy; and each $R^6$ is independently halo; or (xxxii) each $R^7$ is independently $C_1$-$C_6$ alkoxy; and $R^6$ is chloro.

In some embodiments of the compound of formula AA, the substituted ring B is

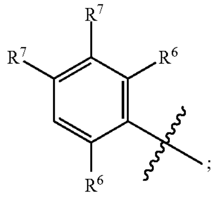

and $R^6$ and $R^7$ are one of the following combinations:

(i) each $R^6$ is isopropyl; and each $R^7$ is methyl;

(ii) each $R^6$ is isopropyl; and each $R^7$ is isopropyl;

(iii) each $R^6$ is isopropyl; and each $R^7$ is trifluoromethyl;

(iv) each $R^6$ is isopropyl; and each $R^7$ is cyclopropyl;

(v) each $R^6$ is isopropyl; and each $R^7$ is chloro;

(vi) each $R^6$ is isopropyl; and each $R^7$ is fluoro;

(vii) each $R^6$ is ethyl; and each $R^7$ is fluoro;

(viii) each $R^6$ is isopropyl; and each $R^7$ is cyano;

(ix) each $R^6$ is cyclopropyl; and each $R^7$ is cyclopropyl;

(x) each $R^6$ is cyclopropyl; and each $R^7$ is chloro;

(xi) each $R^6$ is cyclopropyl; and each $R^7$ is fluoro;

(xii) each $R^6$ is isopropyl; and each $R^7$ is methoxy;

(xiii) each $R^6$ is isopropyl; and each $R^7$ is trifluoromethoxy;

(xiv) each $R^6$ is chloro; and each $R^7$ is trifluoromethyl;

(xv) each $R^6$ is chloro; and each $R^7$ is trifluoromethoxy;

(xvi) each $R^7$ is isopropyl; and each $R^6$ is methyl;

(xvii) each $R^7$ is isopropyl; and each $R^6$ is trifluoromethyl;

(xviii) each $R^7$ is isopropyl; and each $R^6$ is cyclopropyl;

(xix) each $R^7$ is isopropyl; and each $R^6$ is chloro;

(xx) each $R^7$ is ethyl; and each $R^6$ is fluoro;

(xxi) each $R^7$ is isopropyl; and each $R^6$ is cyano;

(xxii) each $R^7$ is cyclopropyl; and each $R^6$ is cyclopropyl;

(xxiii) each $R^7$ is cyclopropyl; and each $R^6$ is chloro;

(xxiv) each $R^7$ is cyclopropyl; and each $R^6$ is fluoro;

(xxv) each $R^7$ is isopropyl; and each $R^6$ is methoxy;

(xxvi) each $R^7$ is isopropyl; and each $R^6$ is trifluoromethoxy;

(xxvii) each $R^7$ is chloro; and each $R^6$ is trifluoromethyl;

(xxviii) each $R^7$ is chloro; and each $R^6$ is trifluoromethoxy;

(xxix) one $R^6$ is isopropyl; the other $R^6$ is trifluoromethyl; and $R^7$ is chloro; or (xxx) $R^6$ is isopropyl; one $R^7$ is fluoro; and the other $R^7$ is cyano.

In some embodiments, of the compound of formula AA, the substituted ring B is

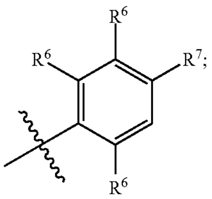

and $R^6$ and $R^7$ are one of the following combinations:

each $R^6$ is independently $C_1$-$C_6$ alkyl, and each $R^7$ is independently $C_1$-$C_6$ alkyl optionally substituted with one or more halo;

each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo;

each $R^6$ is independently $C_1$-$C_6$ alkyl, and each $R^7$ is independently $C_3$-$C_7$ cycloalkyl;

each $R^6$ is independently $C_1$-$C_6$ alkyl, and each $R^7$ is independently halo;

each $R^6$ is independently $C_1$-$C_6$ alkyl, and each $R^7$ is cyano;

each $R^6$ is independently $C_3$-$C_7$ cycloalkyl, and each $R^7$ is independently $C_3$-$C_7$ cycloalkyl;

each $R^6$ is independently $C_3$-$C_7$ cycloalkyl, and each $R^7$ is independently halo;

each $R^6$ is independently cyclopropyl and each $R^7$ is independently halo;

each $R^6$ is independently $C_1$-$C_6$ alkyl, and each $R^7$ is independently $C_1$-$C_6$ alkoxy optionally substituted with one or more halo;

each $R^6$ is independently $C_1$-$C_6$ alkyl, and each $R^7$ is independently $C_1$-$C_6$ alkoxy;

each $R^6$ is independently $C_1$-$C_6$ alkyl, and each $R^7$ is independently $C_1$-$C_6$ alkoxy substituted with one or more halo;

each $R^6$ is independently halo, and each $R^7$ is independently $C_1$-$C_6$ haloalkyl;

each $R^6$ is independently halo, and each $R^7$ is independently $C_1$-$C_6$ haloalkoxy;

each $R^6$ is independently $C_1$-$C_6$ alkoxy; and each $R^7$ is independently halo;

each $R^6$ is independently $C_1$-$C_6$ alkoxy; and each $R^7$ is chloro;

each $R^7$ is independently $C_1$-$C_6$ alkyl, and each $R^6$ is independently $C_1$-$C_6$ alkyl optionally substituted with one or more halo;

each $R^7$ is independently $C_1$-$C_6$ alkyl, and each $R^6$ is independently $C_1$-$C_6$ alkyl substituted with one or more halo;

each $R^7$ is independently $C_1$-$C_6$ alkyl, and each $R^6$ is independently $C_3$-$C_7$ cycloalkyl;

each $R^7$ is independently $C_1$-$C_6$ alkyl, and each $R^6$ is independently halo;

each $R^7$ is independently $C_1$-$C_6$ alkyl and each $R^6$ is independently halo;

each $R^7$ is independently $C_1$-$C_6$ alkyl, and each $R^6$ is cyano;

each $R^7$ is independently $C_3$-$C_7$ cycloalkyl, and each $R^6$ is independently $C_3$-$C_7$ cycloalkyl;

each $R^7$ is independently $C_3$-$C_7$ cycloalkyl, and each $R^6$ is independently halo;

each $R^7$ is independently $C_3$-$C_7$ cycloalkyl and each $R^6$ is independently halo;

each $R^7$ is independently $C_1$-$C_6$ alkyl, and each $R^6$ is independently $C_1$-$C_6$ alkoxy optionally substituted with one or more halo;

each $R^7$ is independently $C_1$-$C_6$ alkyl, and each $R^6$ is independently $C_1$-$C_6$ alkoxy;

each $R^7$ is independently $C_1$-$C_6$ alkyl, and each $R^6$ is independently $C_1$-$C_6$ alkoxy substituted with one or more halo;

each $R^7$ is independently halo, and each $R^6$ is independently $C_1$-$C_6$ haloalkyl;

each $R^7$ is independently halo, and each $R^6$ is independently $C_1$-$C_6$ haloalkoxy;

each $R^7$ is independently $C_1$-$C_6$ alkoxy; and each $R^6$ is independently halo;

each $R^7$ is independently $C_1$-$C_6$ alkoxy; and each $R^6$ is chloro;

$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or $R^6$ and $R^7$ on adjacent atoms taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

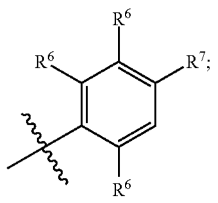

and $R^6$ and $R^7$ are one of the following combinations:

each $R^6$ is isopropyl; and each $R^7$ is methyl;

each $R^6$ is isopropyl; and each $R^7$ is isopropyl;

each $R^6$ is isopropyl; and each $R^7$ is trifluoromethyl;

each $R^6$ is isopropyl; and each $R^7$ is cyclopropyl;

each $R^6$ is isopropyl; and each $R^7$ is chloro;

each $R^6$ is isopropyl; and each $R^7$ is fluoro;

each $R^6$ is ethyl; and each $R^7$ is fluoro;

each $R^6$ is isopropyl; and each $R^7$ is cyano;

each $R^6$ is cyclopropyl; and each $R^7$ is cyclopropyl;

each $R^6$ is cyclopropyl; and each $R^7$ is chloro;

each $R^6$ is cyclopropyl; and each $R^7$ is fluoro;

each $R^6$ is isopropyl; and each $R^7$ is methoxy;

each $R^6$ is isopropyl; and each $R^7$ is trifluoromethoxy;

each $R^6$ is chloro; and each $R^7$ is trifluoromethyl;

each $R^6$ is chloro; and each $R^7$ is trifluoromethoxy;

each $R^7$ is isopropyl; and each $R^6$ is methyl;

each $R^7$ is isopropyl; and each $R^6$ is trifluoromethyl;

each $R^7$ is isopropyl; and each $R^6$ is cyclopropyl;

each $R^7$ is isopropyl; and each $R^6$ is chloro;

each $R^7$ is ethyl; and each $R^6$ is fluoro;

each $R^7$ is isopropyl; and each $R^6$ is cyano;

each $R^7$ is cyclopropyl; and each $R^6$ is cyclopropyl;

each $R^7$ is cyclopropyl; and each $R^6$ is chloro;

each $R^7$ is cyclopropyl; and each $R^6$ is fluoro;

each $R^7$ is isopropyl; and each $R^6$ is methoxy;

each $R^7$ is isopropyl; and each $R^6$ is trifluoromethoxy;

each $R^7$ is chloro; and each $R^6$ is trifluoromethyl;

each $R^7$ is chloro; and each $R^6$ is trifluoromethoxy;

one $R^6$ is isopropyl; the other $R^6$ is trifluoromethyl; and each $R^7$ is chloro;

each $R^6$ is isopropyl; one $R^7$ is fluoro; and the other $R^7$ is cyano;

$R^6$ and $R^7$ on adjacent atoms taken together with the atoms connecting them form a C aliphatic carbocyclic ring; and one $R^6$ is chloro, fluoro, or cyano;

$R^6$ and $R^7$ on adjacent atoms taken together with the atoms connecting them form a $C_5$ aliphatic carbocyclic ring; and one $R^6$ is chloro, fluoro, or cyano;

$R^6$ and $R^7$ on adjacent atoms taken together with the atoms connecting them form a $C_6$ aliphatic carbocyclic ring; and one $R^6$ is chloro, fluoro, or cyano;

$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;

$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or $R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

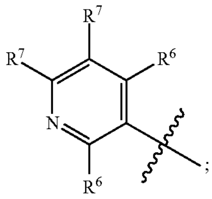

;

and $R^6$ and $R^7$ are one of the following combinations:

(i) each $R^6$ is independently $C_1$-$C_6$ alkyl, and each $R^7$ is independently $C_1$-$C_6$ alkyl optionally substituted with one or more halo;

(ii) each $R^6$ is independently $C_1$-$C_6$ alkyl and each $R^7$ is independently $C_1$-$C_6$ alkyl;

(iii) each $R^6$ is independently $C_1$-$C_6$ alkyl, and each $R^7$ is independently $C_1$-$C_6$ alkyl substituted with one or more halo;

(iv) each $R^6$ is independently $C_1$-$C_6$ alkyl, and each $R^7$ is independently $C_3$-$C_7$ cycloalkyl;

(v) each $R^6$ is independently $C_1$-$C_6$ alkyl, and each $R^7$ is independently halo;

(vi) each $R^6$ is independently $C_1$-$C_6$ alkyl, and $R^7$ is cyano;

(vii) each $R^6$ is independently $C_3$-$C_7$ cycloalkyl, and each $R^7$ is independently $C_3$-$C_7$ cycloalkyl;

(viii) each $R^6$ is independently $C_3$-$C_7$ cycloalkyl, and each $R^7$ is independently halo;

(ix) each $R^6$ is independently cyclopropyl and each $R^7$ is independently halo;

(x) each $R^6$ is independently $C_1$-$C_6$ alkyl, and each $R^7$ is independently $C_1$-$C_6$ alkoxy optionally substituted with one or more halo;

(xi) each $R^6$ is independently $C_1$-$C_6$ alkyl, and each $R^7$ is independently $C_1$-$C_6$ alkoxy;

(xii) each $R^6$ is independently $C_1$-$C_6$ alkyl, and each $R^7$ is independently $C_1$-$C_6$ alkoxy substituted with one or more halo;

(xiii) each $R^6$ is independently halo, and each $R^7$ is independently $C_1$-$C_6$ haloalkyl;

(xiv) each $R^6$ is independently halo, and each $R^7$ is independently $C_1$-$C_6$ haloalkoxy;

(xv) each $R^6$ is independently $C_1$-$C_6$ alkoxy; and each $R^7$ is independently halo;

(xvi) each $R^6$ is independently $C_1$-$C_6$ alkoxy; and $R^7$ is chloro;

(xvii) each $R^7$ is independently $C_1$-$C_6$ alkyl, and each $R^6$ is independently $C_1$-$C_6$ alkyl optionally substituted with one or more halo;

(xviii) each $R^7$ is independently $C_1$-$C_6$ alkyl, and each $R^6$ is independently $C_1$-$C_6$ alkyl substituted with one or more halo;

(xix) each $R^7$ is independently $C_1$-$C_6$ alkyl, and each $R^6$ is independently $C_3$-$C_7$ cycloalkyl;

(xx) each $R^7$ is independently $C_1$-$C_6$ alkyl, and each $R^6$ is independently halo;

(xxi) each $R^7$ is independently $C_1$-$C_6$ alkyl and each $R^6$ is independently halo;

(xxii) each $R^7$ is independently $C_1$-$C_6$ alkyl, and $R^6$ is cyano;

(xxiii) each $R^7$ is independently $C_3$-$C_7$ cycloalkyl, and each $R^6$ is independently $C_3$-$C_7$ cycloalkyl;

(xxiv) each $R^7$ is independently $C_3$-$C_7$ cycloalkyl, and each $R^6$ is independently halo;

(xxv) each $R^7$ is independently $C_3$-$C_7$ cycloalkyl and each $R^6$ is independently halo;

(xxvi) each $R^7$ is independently $C_1$-$C_6$ alkyl, and each $R^6$ is independently $C_1$-$C_6$ alkoxy optionally substituted with one or more halo;

(xxvii) each $R^7$ is independently $C_1$-$C_6$ alkyl, and each $R^6$ is independently $C_1$-$C_6$ alkoxy;

(xxviii) each $R^7$ is independently $C_1$-$C_6$ alkyl, and each $R^6$ is independently $C_1$-$C_6$ alkoxy substituted with one or more halo;

(xxix) each $R^7$ is independently halo, and each $R^6$ is independently $C_1$-$C_6$ haloalkyl;

(xxx) each $R^7$ is independently halo, and each $R^6$ is independently $C_1$-$C_6$ haloalkoxy;

(xxxi) each $R^7$ is independently $C_1$-$C_6$ alkoxy; and each $R^6$ is independently halo; or (xxxii) each $R^7$ is independently $C_1$-$C_6$ alkoxy; and $R^6$ is chloro.

In some embodiments, of the compound of formula AA, the substituted ring B is

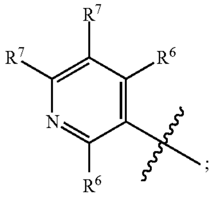

;

and $R^6$ and $R^7$ are one of the following combinations:

(i) each $R^6$ is isopropyl; and each $R^7$ is methyl;

(ii) each $R^6$ is isopropyl; and each $R^7$ is isopropyl;

(iii) each $R^6$ is isopropyl; and each $R^7$ is trifluoromethyl;

(iv) each $R^6$ is isopropyl; and each $R^7$ is cyclopropyl;

(v) each $R^6$ is isopropyl; and each $R^7$ is chloro;

(vi) each $R^6$ is isopropyl; and each $R^7$ is fluoro;

(vii) each $R^6$ is ethyl; and each $R^7$ is fluoro;

(viii) each $R^6$ is isopropyl; and each $R^7$ is cyano;

(ix) each $R^6$ is cyclopropyl; and each $R^7$ is cyclopropyl;

(x) each $R^6$ is cyclopropyl; and each $R^7$ is chloro;

(xi) each $R^6$ is cyclopropyl; and each $R^7$ is fluoro;

(xii) each $R^6$ is isopropyl; and each $R^7$ is methoxy;

(xiii) each $R^6$ is isopropyl; and each $R^7$ is trifluoromethoxy;

(xiv) each $R^6$ is chloro; and each $R^7$ is trifluoromethyl;

(xv) each $R^6$ is chloro; and each $R^7$ is trifluoromethoxy;

(xvi) each $R^7$ is isopropyl; and each $R^6$ is methyl;

(xvii) each $R^7$ is isopropyl; and each $R^6$ is trifluoromethyl;

(xviii) each $R^7$ is isopropyl; and each $R^6$ is cyclopropyl;

(xix) each $R^7$ is isopropyl; and each $R^6$ is chloro;

(xx) each $R^7$ is ethyl; and each $R^6$ is fluoro;

(xxi) each $R^7$ is isopropyl; and each $R^6$ is cyano;

(xxii) each $R^7$ is cyclopropyl; and each $R^6$ is cyclopropyl;

(xxiii) each $R^7$ is cyclopropyl; and each $R^6$ is chloro;

(xxiv) each $R^7$ is cyclopropyl; and each $R^6$ is fluoro;

(xxv) each $R^7$ is isopropyl; and each $R^6$ is methoxy;

(xxvi) each $R^7$ is isopropyl; and each $R^6$ is trifluoromethoxy;

(xxvii) each $R^7$ is chloro; and each $R^6$ is trifluoromethyl;

(xxviii) each $R^7$ is chloro; and each $R^6$ is trifluoromethoxy;

(xxix) one $R^6$ is isopropyl; the other $R^6$ is trifluoromethyl; and each $R^7$ is chloro; or (xxx) each $R^6$ is isopropyl; one $R^7$ is fluoro; and the other $R^7$ is cyano.

In some embodiments, of the compound of formula AA, the substituted ring B is

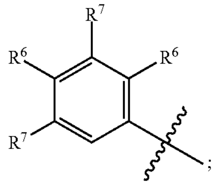

and $R^6$ and $R^7$ are one of the following combinations:

(i) each $R^6$ is independently $C_1$-$C_6$ alkyl, and each $R^7$ is independently $C_1$-$C_6$ alkyl optionally substituted with one or more halo;

(ii) each $R^6$ is independently $C_1$-$C_6$ alkyl and each $R^7$ is independently $C_1$-$C_6$ alkyl;

(iii) each $R^6$ is independently $C_1$-$C_6$ alkyl, and each $R^7$ is independently $C_1$-$C_6$ alkyl substituted with one or more halo;

(iv) each $R^6$ is independently $C_1$-$C_6$ alkyl, and each $R^7$ is independently $C_3$-$C_7$ cycloalkyl;

(v) each $R^6$ is independently $C_1$-$C_6$ alkyl, and each $R^7$ is independently halo;

(vi) each $R^6$ is independently $C_1$-$C_6$ alkyl, and $R^7$ is cyano;

(vii) each $R^6$ is independently $C_3$-$C_7$ cycloalkyl, and each $R^7$ is independently $C_3$-$C_7$ cycloalkyl;

(viii) each $R^6$ is independently $C_3$-$C_7$ cycloalkyl, and each $R^7$ is independently halo;

(ix) each $R^6$ is independently cyclopropyl and each $R^7$ is independently halo;

(x) each $R^6$ is independently $C_1$-$C_6$ alkyl, and each $R^7$ is independently $C_1$-$C_6$ alkoxy optionally substituted with one or more halo;

(xi) each $R^6$ is independently $C_1$-$C_6$ alkyl, and each $R^7$ is independently $C_1$-$C_6$ alkoxy;

(xii) each $R^6$ is independently $C_1$-$C_6$ alkyl, and each $R^7$ is independently $C_1$-$C_6$ alkoxy substituted with one or more halo;

(xiii) each $R^6$ is independently halo, and each $R^7$ is independently $C_1$-$C_6$ haloalkyl;

(xiv) each $R^6$ is independently halo, and each $R^7$ is independently $C_1$-$C_6$ haloalkoxy;

(xv) each $R^6$ is independently $C_1$-$C_6$ alkoxy; and each $R^7$ is independently halo;

(xvi) each $R^6$ is independently $C_1$-$C_6$ alkoxy; and $R^7$ is chloro;

(xvii) each $R^7$ is independently $C_1$-$C_6$ alkyl, and each $R^6$ is independently $C_1$-$C_6$ alkyl optionally substituted with one or more halo;

(xviii) each $R^7$ is independently $C_1$-$C_6$ alkyl, and each $R^6$ is independently $C_1$-$C_6$ alkyl substituted with one or more halo;

(xix) each $R^7$ is independently $C_1$-$C_6$ alkyl, and each $R^6$ is independently $C_3$-$C_7$ cycloalkyl;

(xx) each $R^7$ is independently $C_1$-$C_6$ alkyl, and each $R^6$ is independently halo;

(xxi) each $R^7$ is independently $C_1$-$C_6$ alkyl and each $R^6$ is independently halo;

(xxii) each $R^7$ is independently $C_1$-$C_6$ alkyl, and $R^6$ is cyano;

(xxiii) each $R^7$ is independently $C_3$-$C_7$ cycloalkyl, and each $R^6$ is independently $C_3$-$C_7$ cycloalkyl;

(xxiv) each $R^7$ is independently $C_3$-$C_7$ cycloalkyl, and each $R^6$ is independently halo;

(xxv) each $R^7$ is independently $C_3$-$C_7$ cycloalkyl and each $R^6$ is independently halo;

(xxvi) each $R^7$ is independently $C_1$-$C_6$ alkyl, and each $R^6$ is independently $C_1$-$C_6$ alkoxy optionally substituted with one or more halo;

(xxvii) each $R^7$ is independently $C_1$-$C_6$ alkyl, and each $R^6$ is independently $C_1$-$C_6$ alkoxy;

(xxviii) each $R^7$ is independently $C_1$-$C_6$ alkyl, and each $R^6$ is independently $C_1$-$C_6$ alkoxy substituted with one or more halo;

(xxix) each $R^7$ is independently halo, and each $R^6$ is independently $C_1$-$C_6$ haloalkyl;

(xxx) each $R^7$ is independently halo, and each $R^6$ is independently $C_1$-$C_6$ haloalkoxy;

(xxxi) each $R^7$ is independently $C_1$-$C_6$ alkoxy; and each $R^6$ is independently halo;

(xxxvi) each $R^7$ is independently $C_1$-$C_6$ alkoxy; and $R^6$ is chloro;

(xxxvii) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;

(xxxii) two pairs, each of one $R^6$ and one $R^7$, are on adjacent atoms, and each pair of one $R^6$ and one $R^7$ taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl; or (xxxiii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

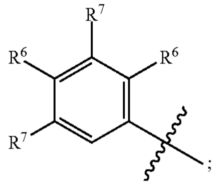

and $R^6$ and $R^7$ are one of the following combinations:

(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy;
(xxix) one $R^6$ is isopropyl; the other $R^6$ is trifluoromethyl; and $R^7$ is chloro;
(xxx) $R^6$ is isopropyl; one $R^7$ is fluoro; and the other $R^7$ is cyano; two pairs, each of one $R^6$ and one $R^7$, are on adjacent atoms, and each pair of one $R^6$ and one $R^7$ taken together with the atoms connecting them form a $C_5$ aliphatic carbocyclic ring;
(xxxi) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
(xxxii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
(xxxiii) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
(xxxiv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl
(xxxv) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvi) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

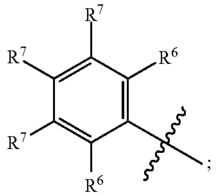

and $R^6$ and $R^7$ are one of the following combinations:

(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;

(xvi) each $R^6$ is independently $C_1$-$C_6$ alkoxy; and $R^7$ is chloro;

(xvii) $R^7$ is $C_1$-$C_6$ alkyl, and each $R^6$ is independently $C_1$-$C_6$ alkyl optionally substituted with one or more halo;

(xviii) $R^7$ is $C_1$-$C_6$ alkyl, and each $R^6$ is independently $C_1$-$C_6$ alkyl substituted with one or more halo;

(xix) $R^7$ is $C_1$-$C_6$ alkyl, and each $R^6$ is independently $C_3$-$C_7$ cycloalkyl;

(xx) $R^7$ is $C_1$-$C_6$ alkyl, and each $R^6$ is independently halo;

(xxi) $R^7$ is $C_1$-$C_6$ alkyl and each $R^6$ is independently halo;

(xxii) $R^7$ is $C_1$-$C_6$ alkyl, and $R^6$ is cyano;

(xxiii) $R^7$ is $C_3$-$C_7$ cycloalkyl, and each $R^6$ is independently $C_3$-$C_7$ cycloalkyl;

(xxiv) $R^7$ is $C_3$-$C_7$ cycloalkyl, and each $R^6$ is independently halo;

(xxv) $R^7$ is $C_3$-$C_7$ cycloalkyl and each $R^6$ is independently halo;

(xxvi) $R^7$ is $C_1$-$C_6$ alkyl, and each $R^6$ is independently $C_1$-$C_6$ alkoxy optionally substituted with one or more halo;

(xxvii) $R^7$ is $C_1$-$C_6$ alkyl, and each $R^6$ is independently $C_1$-$C_6$ alkoxy;

(xxviii) $R^7$ is $C_1$-$C_6$ alkyl, and each $R^6$ is independently $C_1$-$C_6$ alkoxy substituted with one or more halo;

(xxix) $R^7$ is halo, and each $R^6$ is independently $C_1$-$C_6$ haloalkyl;

(xxx) $R^7$ is halo, and each $R^6$ is independently $C_1$-$C_6$ haloalkoxy;

(xxxi) $R^7$ is $C_1$-$C_6$ alkoxy; and each $R^6$ is independently halo;

(xxxii) $R^7$ is $C_1$-$C_6$ alkoxy; and $R^6$ is chloro;

(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is halo;

(xxxiv) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is cyano;

(xxxv) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; and one $R^7$ is halo or cyano;

(xxxvi) two pairs, each of one $R^6$ and one $R^7$, are on adjacent atoms, and each pair of one $R^6$ and one $R^7$ taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano; or (xxxvii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5- to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano.

In some embodiments, of the compound of formula AA, the substituted ring B is

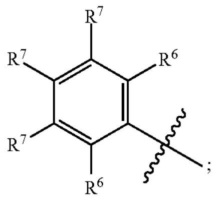

and $R^6$ and $R^7$ are one of the following combinations:

(i) each $R^6$ is isopropyl; and each $R^7$ is methyl;

(ii) each $R^6$ is isopropyl; and each $R^7$ is isopropyl;

(iii) each $R^6$ is isopropyl; and each $R^7$ is trifluoromethyl;

(iv) each $R^6$ is isopropyl; and each $R^7$ is cyclopropyl;

(v) each $R^6$ is isopropyl; and each $R^7$ is chloro;

(vi) each $R^6$ is isopropyl; and each $R^7$ is fluoro;

(vii) each $R^6$ is ethyl; and each $R^7$ is fluoro;

(viii) each $R^6$ is isopropyl; and each $R^7$ is cyano;

(ix) each $R^6$ is cyclopropyl; and each $R^7$ is cyclopropyl;

(x) each $R^6$ is cyclopropyl; and each $R^7$ is chloro;

(xi) each $R^6$ is cyclopropyl; and each $R^7$ is fluoro;

(xii) each $R^6$ is isopropyl; and each $R^7$ is methoxy;

(xiii) each $R^6$ is isopropyl; and each $R^7$ is trifluoromethoxy;

(xiv) each $R^6$ is chloro; and each $R^7$ is trifluoromethyl;

(xv) each $R^6$ is chloro; and each $R^7$ is trifluoromethoxy;

(xvi) each $R^7$ is isopropyl; and each $R^6$ is methyl;

(xvii) each $R^7$ is isopropyl; and each $R^6$ is trifluoromethyl;

(xviii) each $R^7$ is isopropyl; and each $R^6$ is cyclopropyl;

(xix) each $R^7$ is isopropyl; and each $R^6$ is chloro;

(xx) each $R^7$ is ethyl; and each $R^6$ is fluoro;

(xxi) each $R^7$ is isopropyl; and each $R^6$ is cyano;

(xxii) each $R^7$ is cyclopropyl; and each $R^6$ is cyclopropyl;

(xxiii) each $R^7$ is cyclopropyl; and each $R^6$ is chloro;

(xxiv) each $R^7$ is cyclopropyl; and each $R^6$ is fluoro;

(xxv) each $R^7$ is isopropyl; and each $R^6$ is methoxy;

(xxvi) each $R^7$ is isopropyl; and each $R^6$ is trifluoromethoxy;

(xxvii) each $R^7$ is chloro; and each $R^6$ is trifluoromethyl;

(xxviii) each $R^7$ is chloro; and each $R^6$ is trifluoromethoxy;

(xxix) each $R^6$ is isopropyl; two $R^7$ are fluoro; and one $R^7$ is chloro;

(xxx) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is chloro;

(xxxi) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is fluoro;

(xxxii) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; and one $R^7$ is fluoro or chloro;

(xxxiii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro;

(xxxiv) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl; and one $R^7$ is fluoro or chloro;

(xxxv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; and one $R^7$ is fluoro or chloro;

(xxxvi) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; and one $R^7$ is fluoro or chloro; or (xxxvii) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro.

Additional Features of the Embodiments Herein

In some embodiments of the compound of Formula AA (e.g., Formula AA-1, Formula AA-2, Formula AA-3, Formula AA-4, or Formula AA-5), $R^6$ is not CN.

In some embodiments, the compound of Formula AA is not a compound selected from the group consisting of:

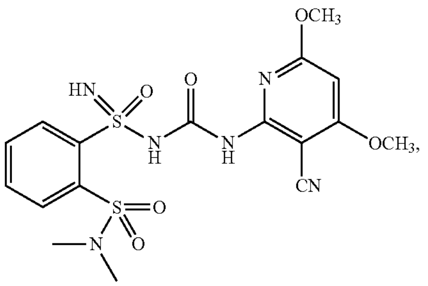

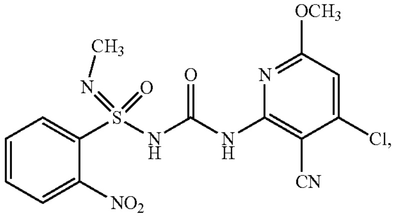

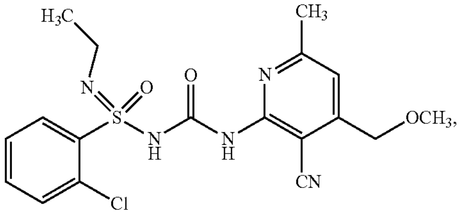

and

-continued

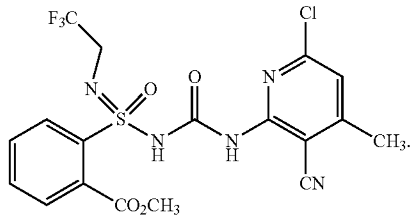

In some embodiments, the compound of Formula AA is not a compound selected from the group consisting of:

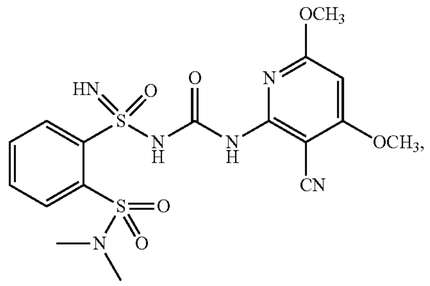

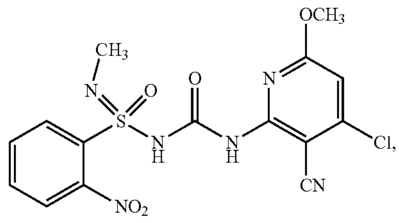

and

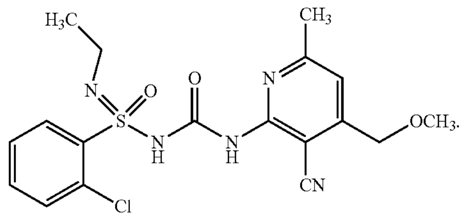

In some embodiments the compound of any of the formulae herein is not a compound disclosed in EP 0173498, which is incorporated herein by reference in its entirety.

In some embodiments the compound of any of the formulae herein is not a compound disclosed in U.S. Pat. No. 4,666,506, which is incorporated herein by reference in its entirety.

It is understood that the combination of variables in the formulae herein is such that the compounds are stable.

In some embodiments, provided herein is a compound that is selected from the group consisting of the compounds in Table 1:

TABLE 1
| Compound | Structure |
| --- | --- |
| 101' | 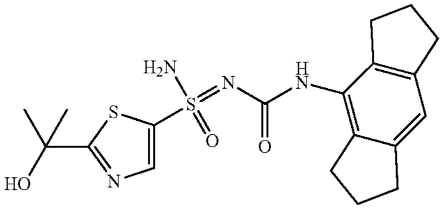 |
| 101 | 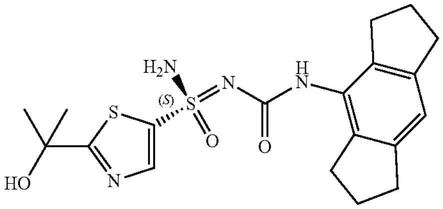 |
| 102 | 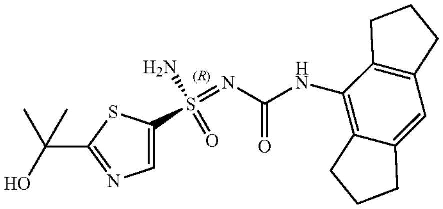 |
| 103' | 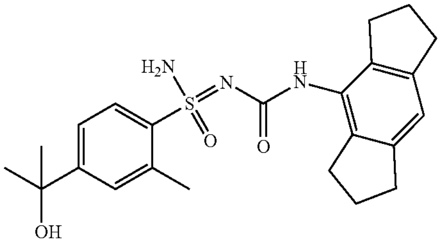 [SMILES: Cc1cc(C(C)(C)O)ccc1S(N)(=O)=NC(=O)Nc1c2c(cc3c1CCC3)CCC2] |
| 103 | 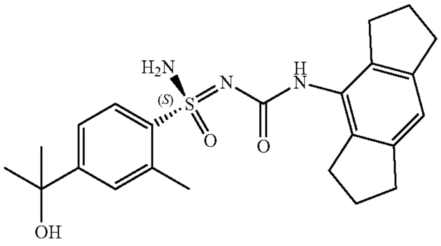 |
| 104 | 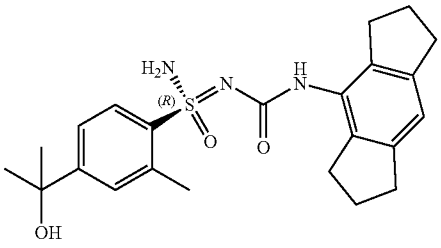 |

TABLE 1-continued
| Compound | Structure |
| --- | --- |
| 105 | 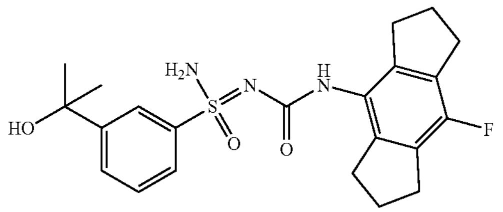 [SMILES: CC(C)(O)c1cccc(S(N)(=O)=NC(=O)Nc2c3c(c(F)c4c2CCC4)CCC3)c1] |
| 105a | 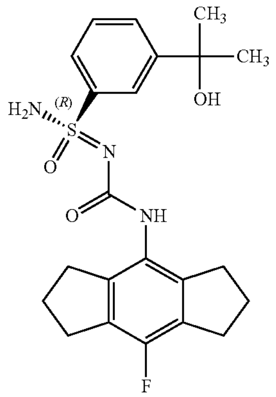 |
| 105b | 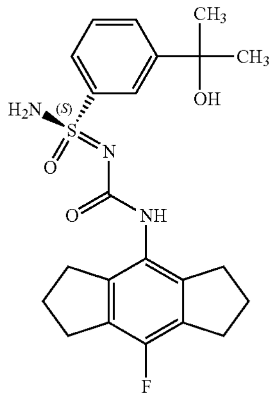 |
| 106 | 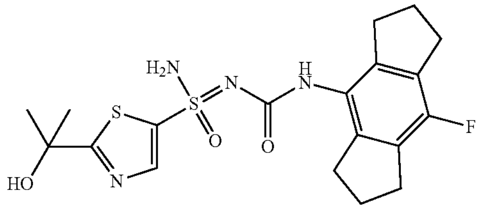 |

TABLE 1-continued
| Compound | Structure |
| --- | --- |
| 106a | 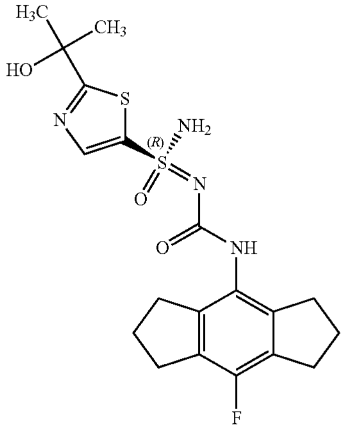 |
| 106b | 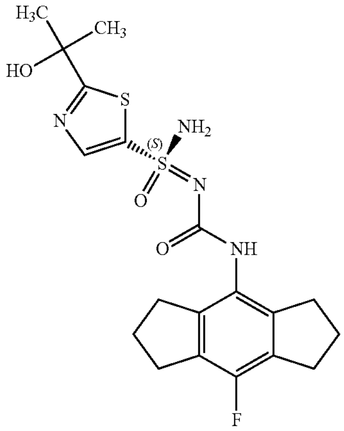 |
| 107 | 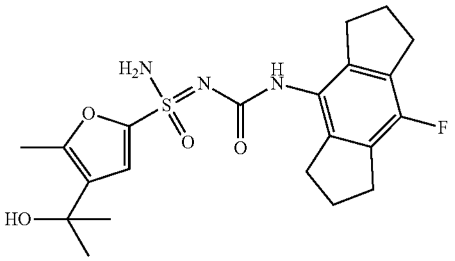 [SMILES: Cc1oc(S(N)(=O)=NC(=O)Nc2c3c(c(F)c4c2CCC4)CCC3)cc1C(C)(C)O] |
| 107a | 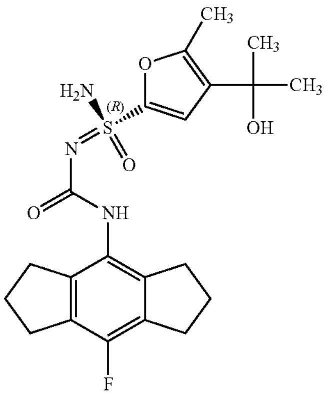 |

TABLE 1-continued
| Compound | Structure |
| --- | --- |
| 107b | 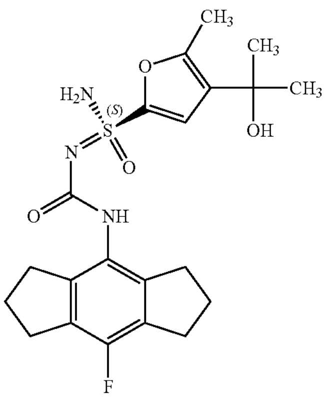 |
| 108 | 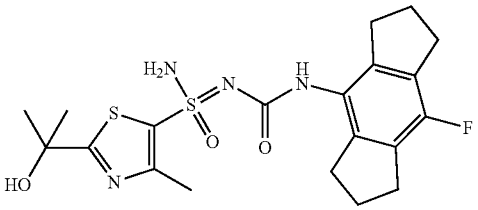 [SMILES: Cc1nc(C(C)(C)O)sc1S(N)(=O)=NC(=O)Nc1c2c(c(F)c3c1CCC3)CCC2] |
| 108a | 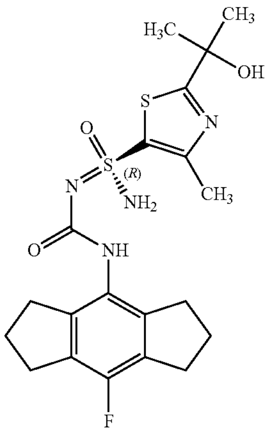 |
| 108b | 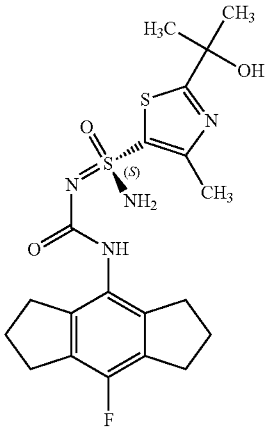 |

TABLE 1-continued
| Compound | Structure |
|---|---|
| 109 | 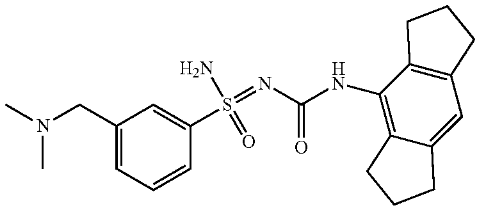 [SMILES: CN(C)Cc1cccc(S(N)(=O)=NC(=O)Nc2c3c(cc4c2CCC4)CCC3)c1] |
| 109a | 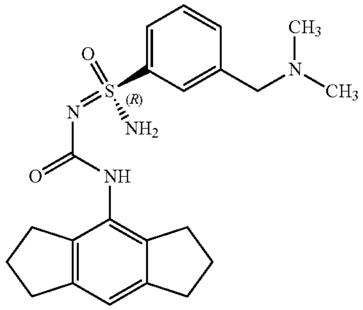 |
| 109b | 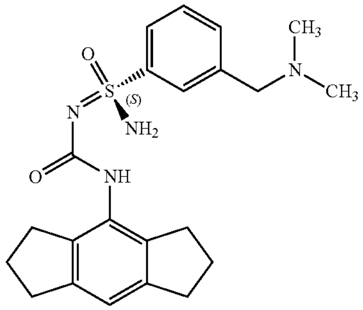 |
| 110 | 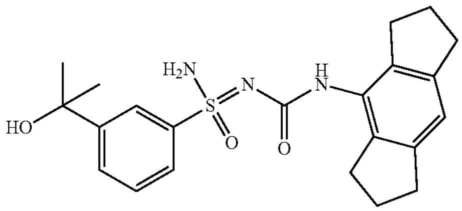 [SMILES: CC(C)(O)c1cccc(S(N)(=O)=NC(=O)Nc2c3c(cc4c2CCC4)CCC3)c1] |
| 110a | 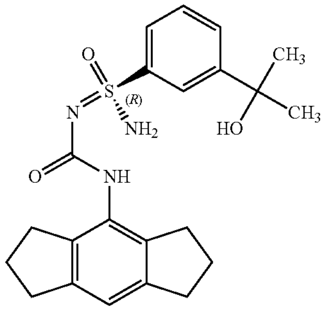 |

TABLE 1-continued
| Compound | Structure |
|---|---|
| 110b | 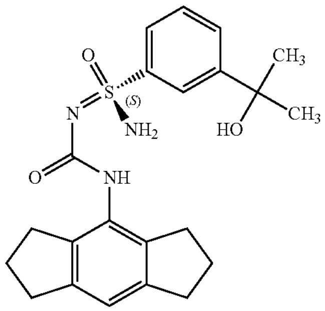 |
| 111 | 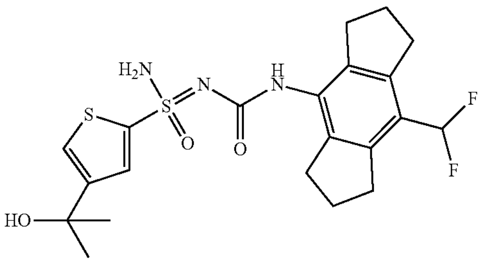 [SMILES: CC(C)(O)c1csc(S(N)(=O)=NC(=O)Nc2c3c(c(C(F)F)c4c2CCC4)CCC3)c1] |
| 112 | 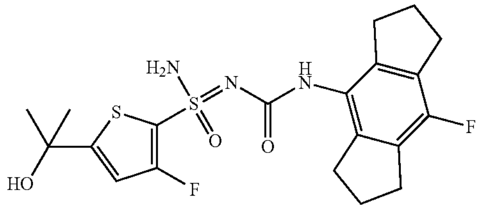 [SMILES: CC(C)(O)c1cc(F)c(S(N)(=O)=NC(=O)Nc2c3c(c(F)c4c2CCC4)CCC3)s1] |
| 112a | 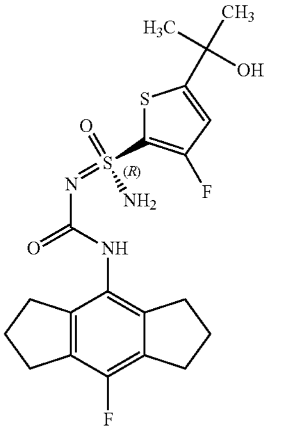 |

TABLE 1-continued
| Compound | Structure |
|---|---|
| 112b | 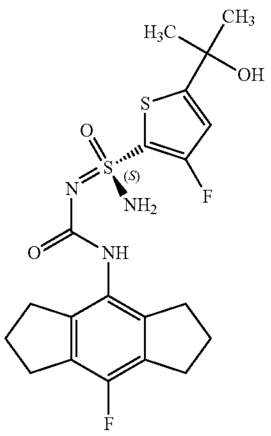 |
| 113 | 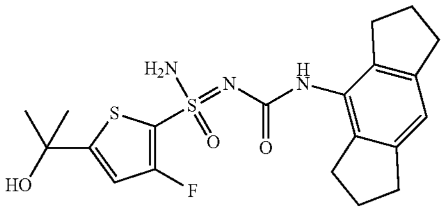 [SMILES: CC(C)(O)c1cc(F)c(S(N)(=O)=NC(=O)Nc2c3c(cc4c2CCC4)CCC3)s1] |
| 113a | 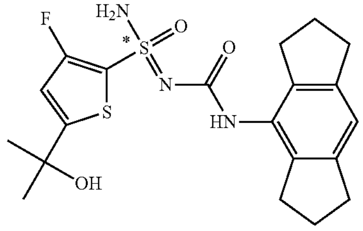 [SMILES: CC(C)(O)c1cc(F)c(S(N)(=O)=NC(=O)Nc2c3c(cc4c2CCC4)CCC3)s1] |
| 113b | 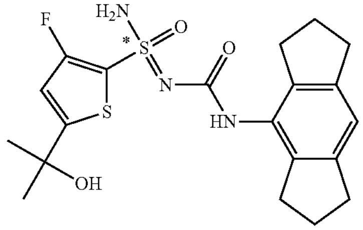 [SMILES: CC(C)(O)c1cc(F)c(S(N)(=O)=NC(=O)Nc2c3c(cc4c2CCC4)CCC3)s1] |
| 114 | 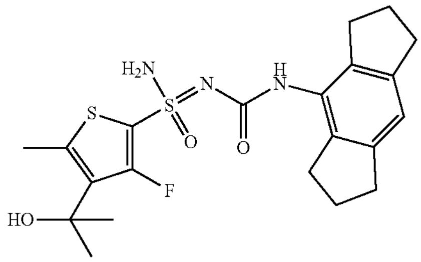 [SMILES: Cc1sc(S(N)(=O)=NC(=O)Nc2c3c(cc4c2CCC4)CCC3)c(F)c1C(C)(C)O] |

TABLE 1-continued
| Compound | Structure |
| --- | --- |
| 115 | 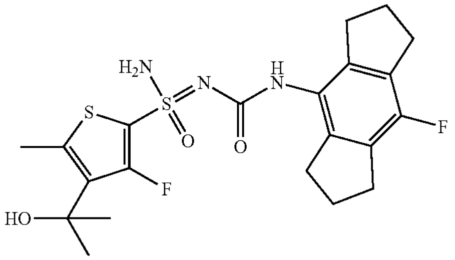 [SMILES: Cc1sc(S(N)(=O)=NC(=O)Nc2c3c(c(F)c4c2CCC4)CCC3)c(F)c1C(C)(C)O] |
| 116 | 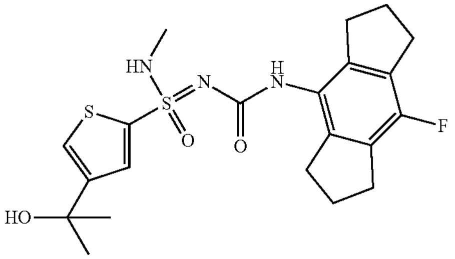 [SMILES: CNS(=O)(=NC(=O)Nc1c2c(c(F)c3c1CCC3)CCC2)c1cc(C(C)(C)O)cs1] |
| 116a | 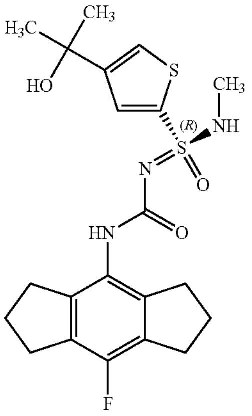 |
| 116b | 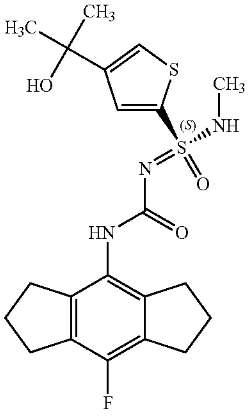 |
| 117 | 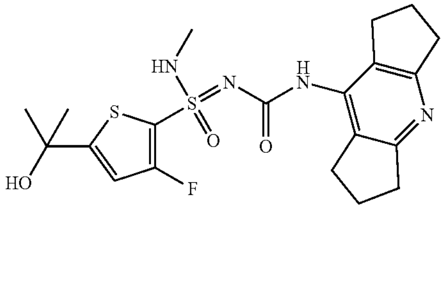 [SMILES: CNS(=O)(=NC(=O)Nc1c2c(nc3c1CCC3)CCC2)c1sc(C(C)(C)O)cc1F] |

TABLE 1-continued
| Compound | Structure |
|---|---|
| 118 | 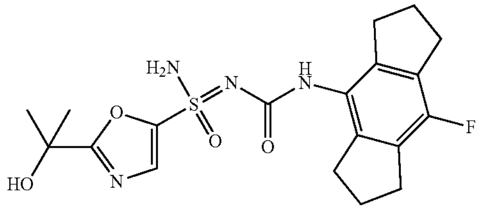 [SMILES: CC(C)(O)c1ncc(S(N)(=O)=NC(=O)Nc2c3c(c(F)c4c2CCC4)CCC3)o1] |
| 119 | 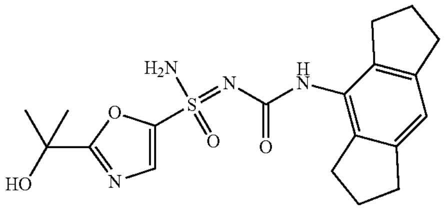 [SMILES: CC(C)(O)c1ncc(S(N)(=O)=NC(=O)Nc2c3c(cc4c2CCC4)CCC3)o1] |
| 120 | 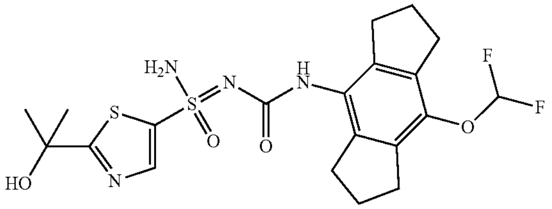 [SMILES: CC(C)(O)c1ncc(S(N)(=O)=NC(=O)Nc2c3c(c(OC(F)F)c4c2CCC4)CCC3)s1] |
| 120a | 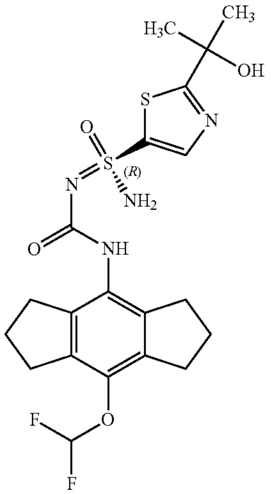 |

TABLE 1-continued
| Compound | Structure |
|---|---|
| 120b | 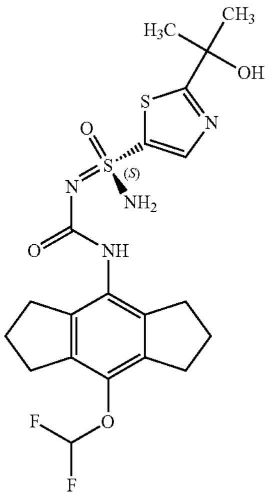 |
| 121 | 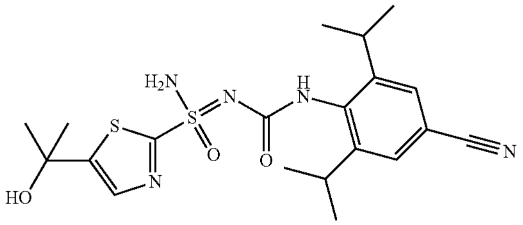 [SMILES: CC(C)c1cc(C#N)cc(C(C)C)c1NC(=O)N=S(N)(=O)c1ncc(C(C)(C)O)s1] |
| 121a | 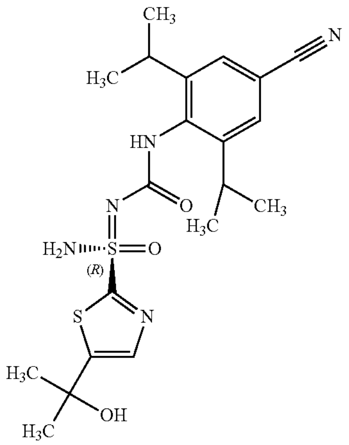 |
| 121b | 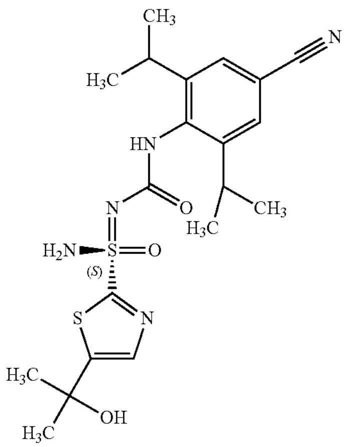 |

TABLE 1-continued
| Compound | Structure |
|---|---|
| 122 | 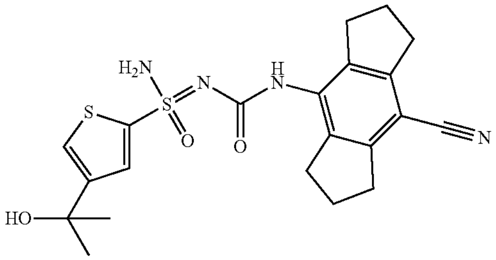 [SMILES: CC(C)(O)c1csc(S(N)(=O)=NC(=O)Nc2c3c(c(C#N)c4c2CCC4)CCC3)c1] |
| 122a | 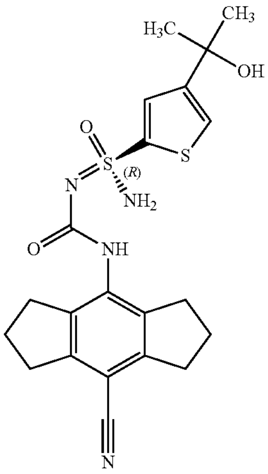 |
| 122b | 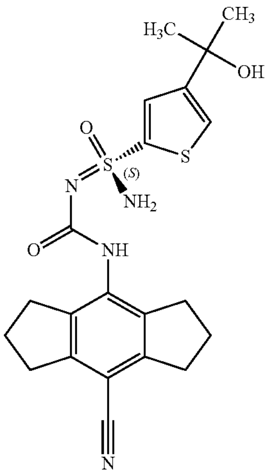 |
| 123 | 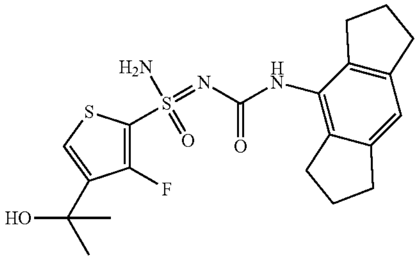 [SMILES: CC(C)(O)c1csc(S(N)(=O)=NC(=O)Nc2c3c(cc4c2CCC4)CCC3)c1F] |

TABLE 1-continued
| Compound | Structure |
| --- | --- |
| 124 | 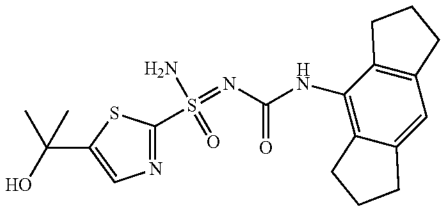 [SMILES: CC(C)(O)c1cnc(S(N)(=O)=NC(=O)Nc2c3c(cc4c2CCC4)CCC3)s1] |
| 125 | 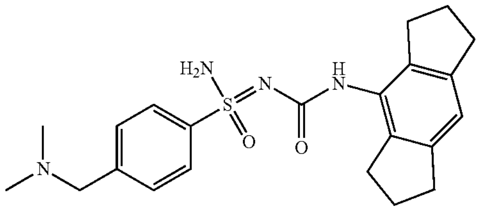 [SMILES: CN(C)Cc1ccc(S(N)(=O)=NC(=O)Nc2c3c(cc4c2CCC4)CCC3)cc1] |
| 125a | 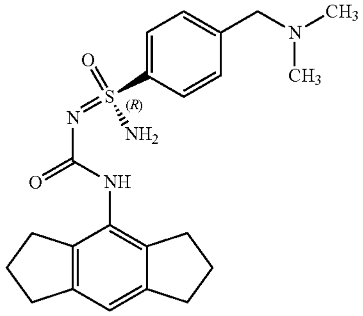 |
| 125b | 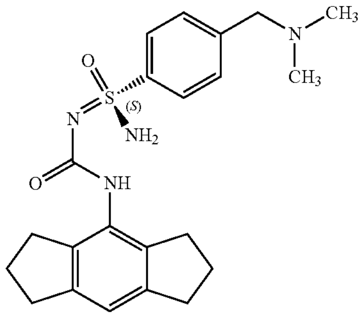 |
| 126 | 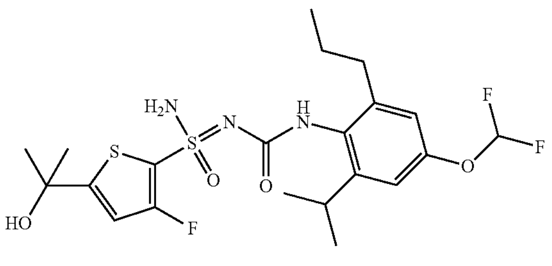 [SMILES: CCCc1cc(OC(F)F)cc(C(C)C)c1NC(=O)N=S(N)(=O)c1sc(C(C)(C)O)cc1F] |
| 127 | 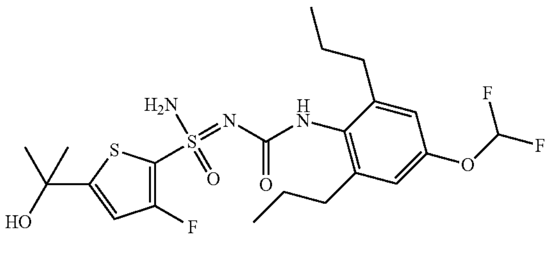 [SMILES: CCCc1cc(OC(F)F)cc(CCC)c1NC(=O)N=S(N)(=O)c1sc(C(C)(C)O)cc1F] |

TABLE 1-continued
| Compound | Structure |
| --- | --- |
| 128 | 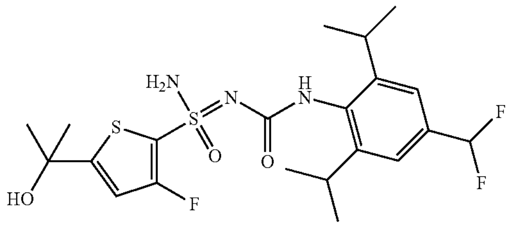 [SMILES: CC(C)c1cc(C(F)F)cc(C(C)C)c1NC(=O)N=S(N)(=O)c1sc(C(C)(C)O)cc1F] |
| 129 | 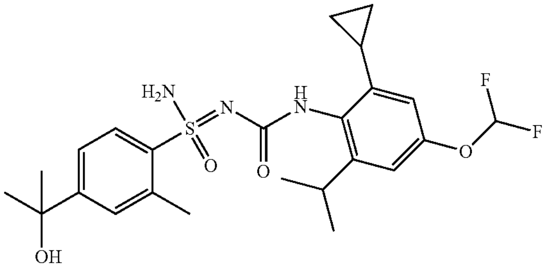 [SMILES: Cc1cc(C(C)(C)O)ccc1S(N)(=O)=NC(=O)Nc1c(C(C)C)cc(OC(F)F)cc1C1CC1] |
| 129a | 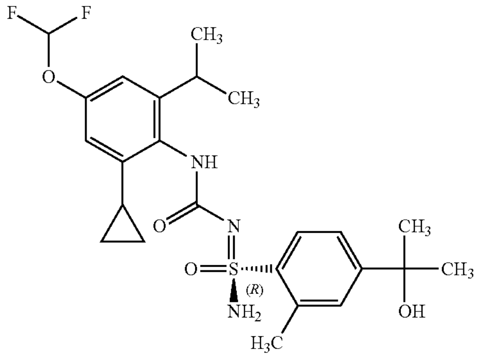 |
| 129b | 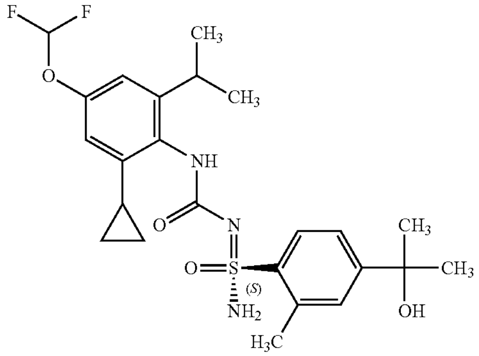 |
| 130 | 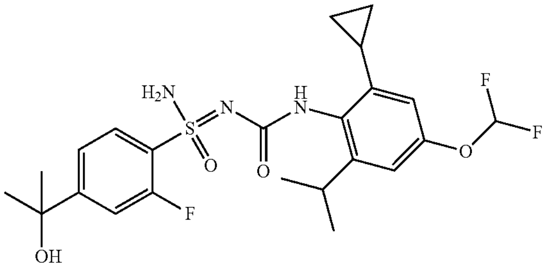 |

TABLE 1-continued
| Compound | Structure |
|---|---|
| 130a | 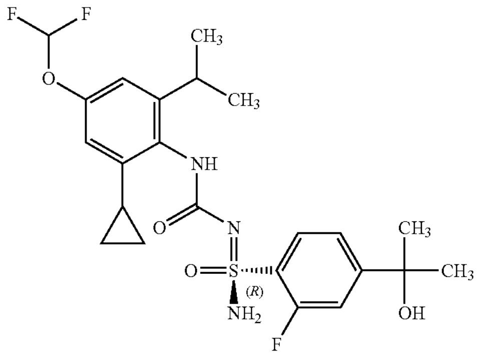 |
| 130b | 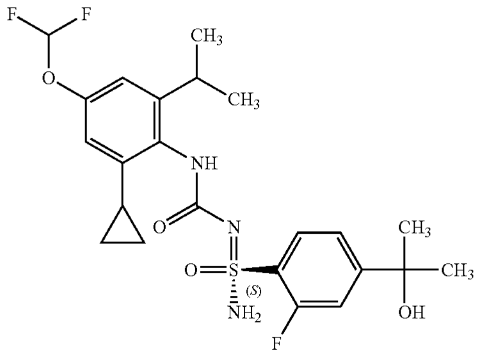 |
| 131 | 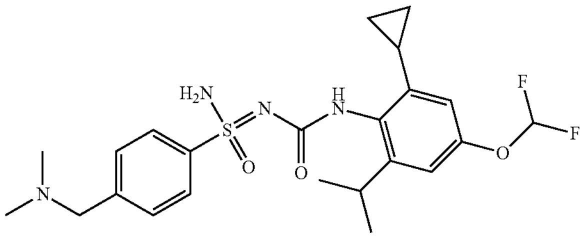 [SMILES: CC(C)c1cc(OC(F)F)cc(C2CC2)c1NC(=O)N=S(N)(=O)c1ccc(CN(C)C)cc1] |
| 131a | 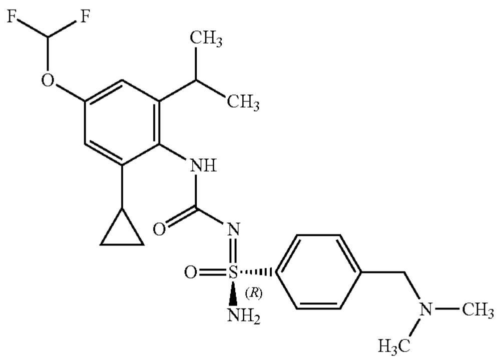 |

TABLE 1-continued
| Compound | Structure |
|---|---|
| 131b | 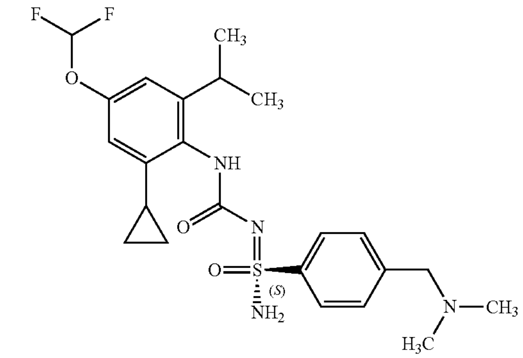 |
| 132 | 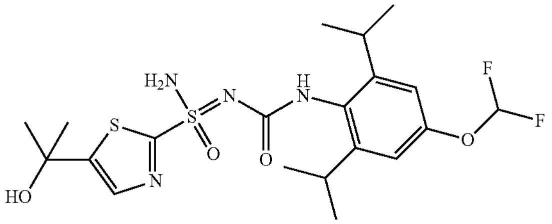 [SMILES: CC(C)c1cc(OC(F)F)cc(C(C)C)c1NC(=O)N=S(N)(=O)c1ncc(C(C)(C)O)s1] |
| 133 | 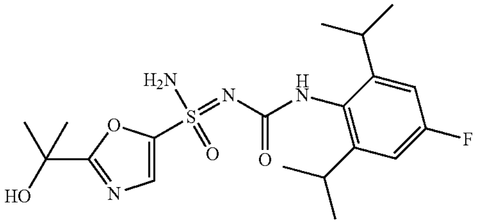 [SMILES: CC(C)c1cc(F)cc(C(C)C)c1NC(=O)N=S(N)(=O)c1cnc(C(C)(C)O)o1] |
| 134 | 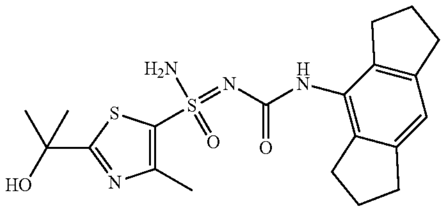 [SMILES: Cc1nc(C(C)(C)O)sc1S(N)(=O)=NC(=O)Nc1c2c(cc3c1CCC3)CCC2] |
| 134a | 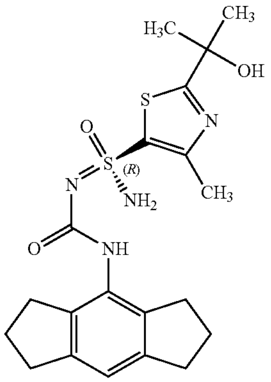 |

TABLE 1-continued
| Compound | Structure |
|---|---|
| 134b | 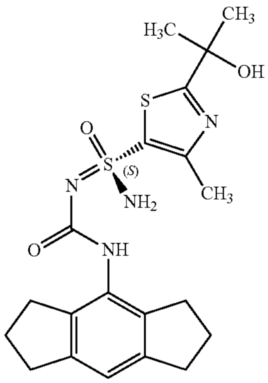 |
| 135 | 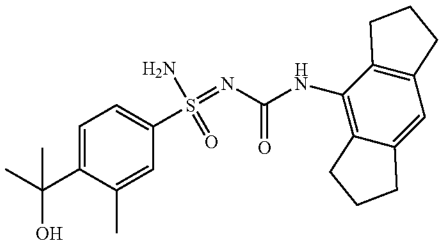 [SMILES: Cc1cc(S(N)(=O)=NC(=O)Nc2c3c(cc4c2CCC4)CCC3)ccc1C(C)(C)O] |
| 135a | 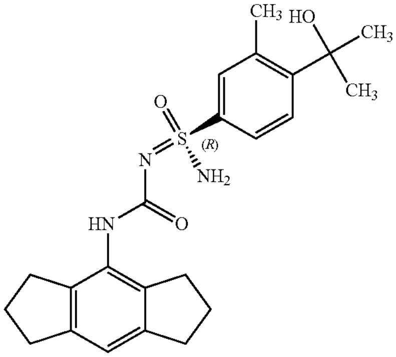 |
| 135b | 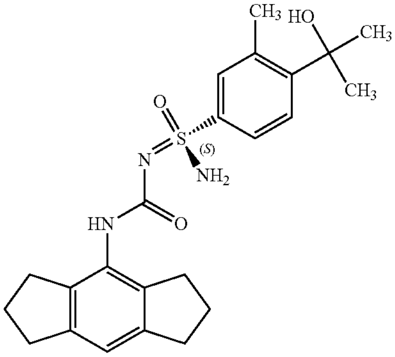 |

TABLE 1-continued
| Compound | Structure |
|---|---|
| 136 | 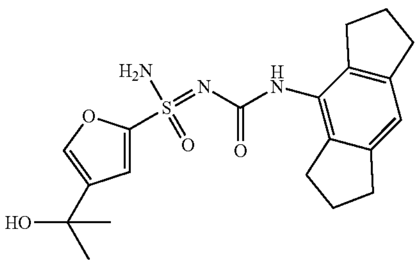 [SMILES: CC(C)(O)c1coc(S(N)(=O)=NC(=O)Nc2c3c(cc4c2CCC4)CCC3)c1] |
| 136a | 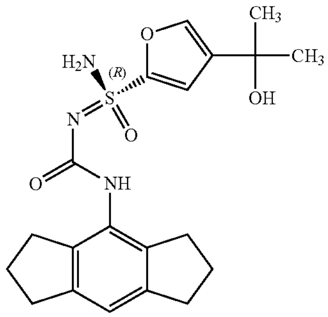 |
| 136b | 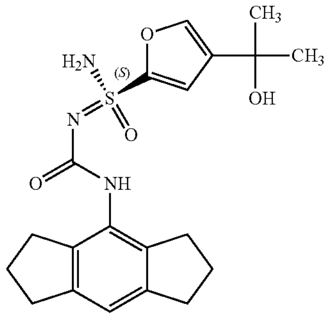 |
| 137 | 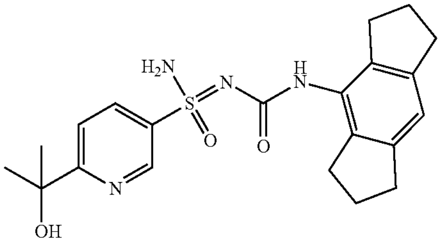 [SMILES: CC(C)(O)c1ccc(S(N)(=O)=NC(=O)Nc2c3c(cc4c2CCC4)CCC3)cn1] |
| 137a | 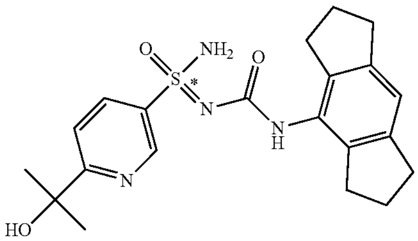 [SMILES: CC(C)(O)c1ccc(S(N)(=O)=NC(=O)Nc2c3c(cc4c2CCC4)CCC3)cn1] |

TABLE 1-continued
| Compound | Structure |
|---|---|
| 137b | 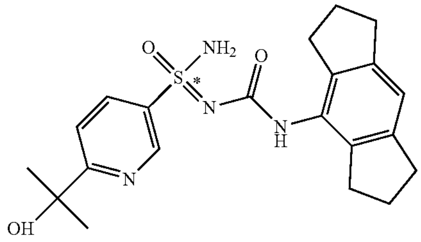 [SMILES: CC(C)(O)c1ccc(S(N)(=O)=NC(=O)Nc2c3c(cc4c2CCC4)CCC3)cn1] |
| 138 | 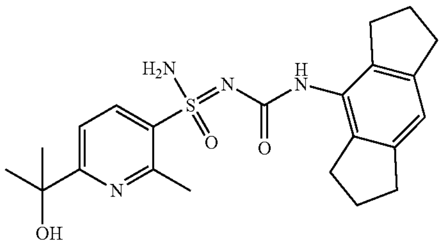 [SMILES: Cc1nc(C(C)(C)O)ccc1S(N)(=O)=NC(=O)Nc1c2c(cc3c1CCC3)CCC2] |
| 138a | 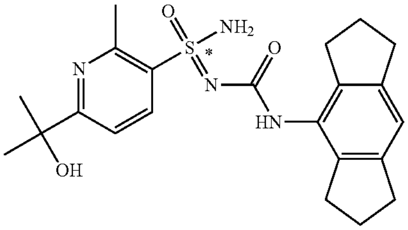 [SMILES: Cc1nc(C(C)(C)O)ccc1S(N)(=O)=NC(=O)Nc1c2c(cc3c1CCC3)CCC2] |
| 138b | 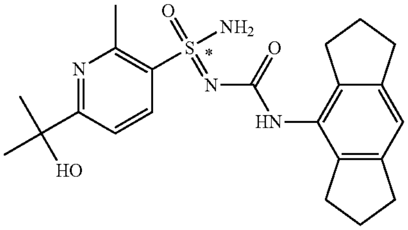 [SMILES: Cc1nc(C(C)(C)O)ccc1S(N)(=O)=NC(=O)Nc1c2c(cc3c1CCC3)CCC2] |
| 139 | 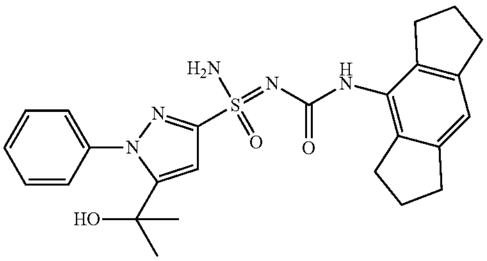 [SMILES: CC(C)(O)c1cc(S(N)(=O)=NC(=O)Nc2c3c(cc4c2CCC4)CCC3)nn1-c1ccccc1] |
| 139a | 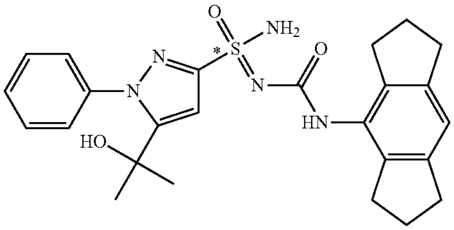 [SMILES: CC(C)(O)c1cc(S(N)(=O)=NC(=O)Nc2c3c(cc4c2CCC4)CCC3)nn1-c1ccccc1] |

TABLE 1-continued
| Compound | Structure |
| --- | --- |
| 139b | 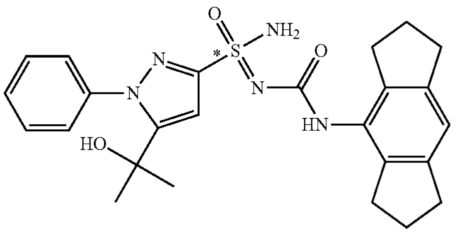 [SMILES: CC(C)(O)c1cc(S(N)(=O)=NC(=O)Nc2c3c(cc4c2CCC4)CCC3)nn1-c1ccccc1] |
| 140 | 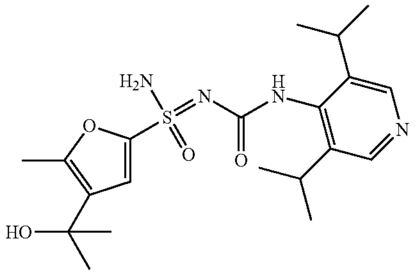 [SMILES: Cc1oc(S(N)(=O)=NC(=O)Nc2c(C(C)C)cncc2C(C)C)cc1C(C)(C)O] |
| 141 | 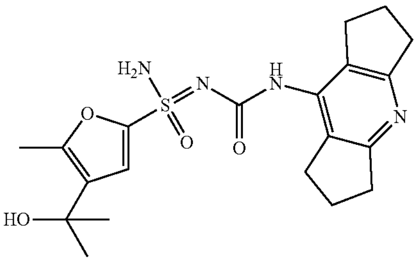 [SMILES: Cc1oc(S(N)(=O)=NC(=O)Nc2c3c(nc4c2CCC4)CCC3)cc1C(C)(C)O] |
| 142 | 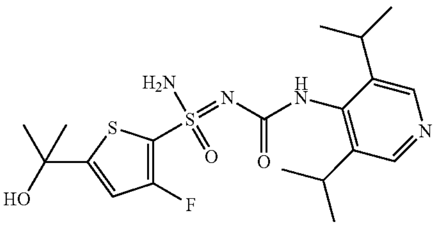 [SMILES: CC(C)c1cncc(C(C)C)c1NC(=O)N=S(N)(=O)c1sc(C(C)(C)O)cc1F] |
| 143 | 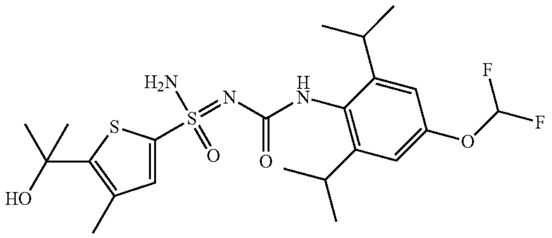 [SMILES: Cc1cc(S(N)(=O)=NC(=O)Nc2c(C(C)C)cc(OC(F)F)cc2C(C)C)sc1C(C)(C)O] |

TABLE 1-continued
| Compound | Structure |
|---|---|
| 143a | 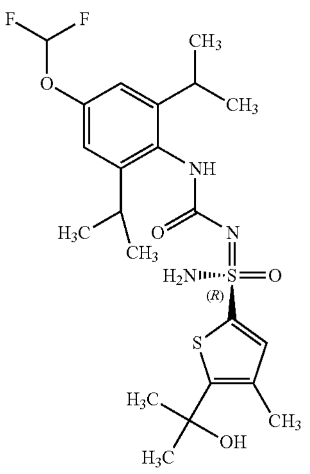 |
| 143b | 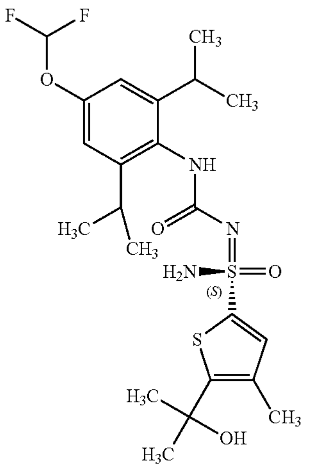 |
| 144 | 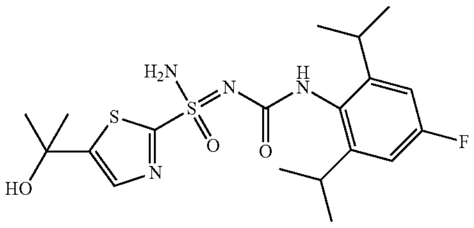 [SMILES: CC(C)c1cc(F)cc(C(C)C)c1NC(=O)N=S(N)(=O)c1ncc(C(C)(C)O)s1] |
| 144a | 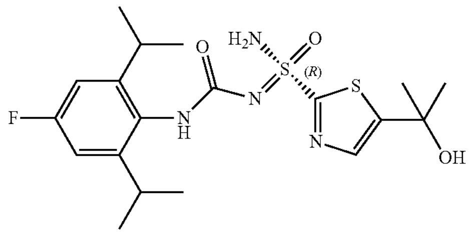 |

TABLE 1-continued
| Compound | Structure |
| --- | --- |
| 144b | 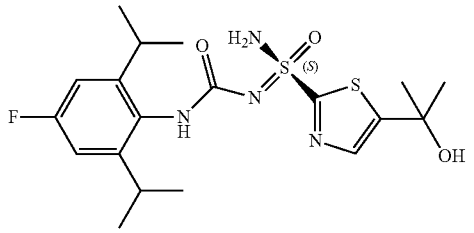 |
| 145 | 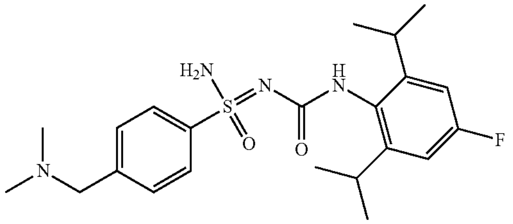 [SMILES: CC(C)c1cc(F)cc(C(C)C)c1NC(=O)N=S(N)(=O)c1ccc(CN(C)C)cc1] |
| 145a | 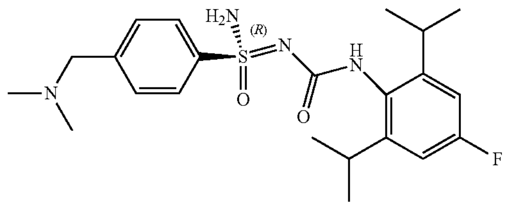 |
| 145b | 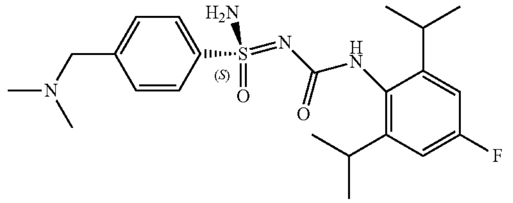 |
| 146 | 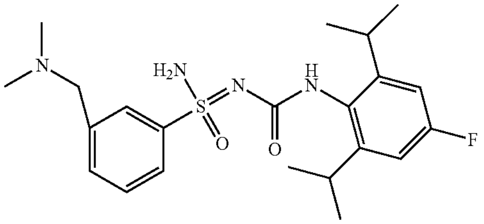 [SMILES: CC(C)c1cc(F)cc(C(C)C)c1NC(=O)N=S(N)(=O)c1cccc(CN(C)C)c1] |
| 147 | 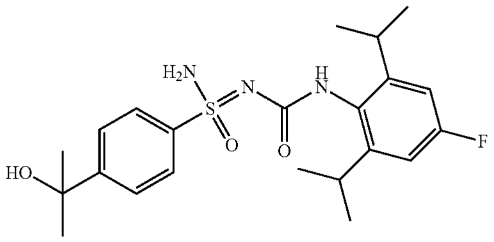 [SMILES: CC(C)c1cc(F)cc(C(C)C)c1NC(=O)N=S(N)(=O)c1ccc(C(C)(C)O)cc1] |

TABLE 1-continued
| Compound | Structure |
|---|---|
| 148 | 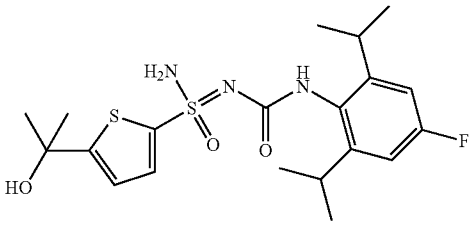 [SMILES: CC(C)c1cc(F)cc(C(C)C)c1NC(=O)N=S(N)(=O)c1ccc(C(C)(C)O)s1] |
| 148a | 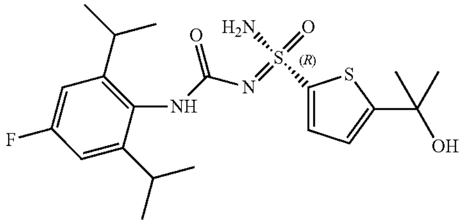 |
| 148b | 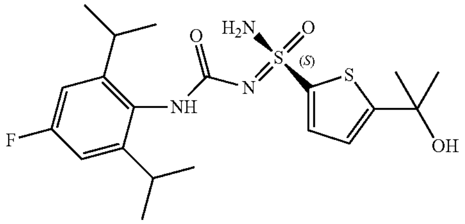 |
| 149 | 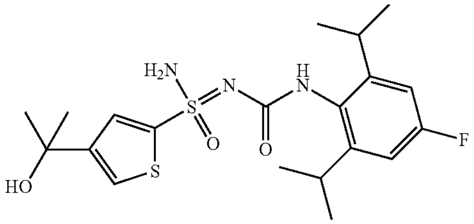 [SMILES: CC(C)c1cc(F)cc(C(C)C)c1NC(=O)N=S(N)(=O)c1cc(C(C)(C)O)cs1] |
| 149a | 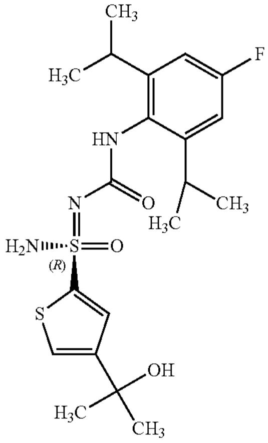 |

TABLE 1-continued
| Compound | Structure |
|---|---|
| 149b | 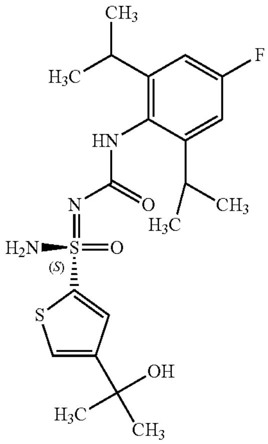 |
| 150 | 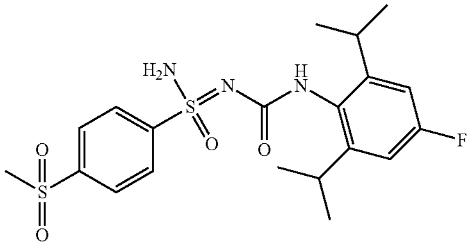 [SMILES: CC(C)c1cc(F)cc(C(C)C)c1NC(=O)N=S(N)(=O)c1ccc(S(C)(=O)=O)cc1] |
| 151a' | 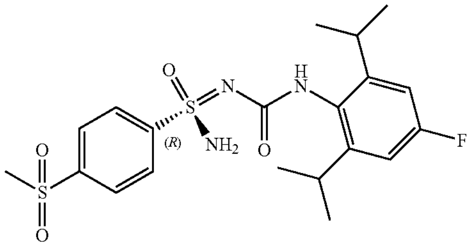 |
| 151b' | 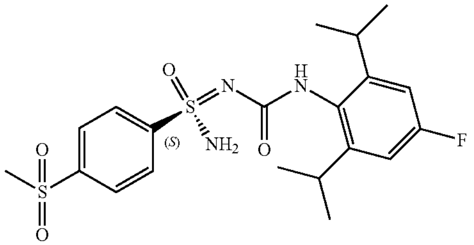 |
| 151 | 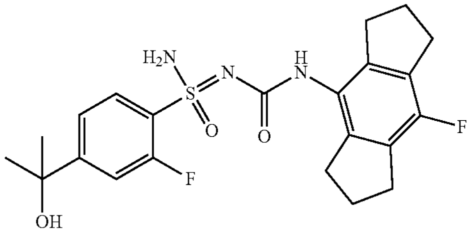 [SMILES: CC(C)(O)c1ccc(S(N)(=O)=NC(=O)Nc2c3c(c(F)c4c2CCC4)CCC3)c(F)c1] |

TABLE 1-continued
| Compound | Structure |
| --- | --- |
| 151a | 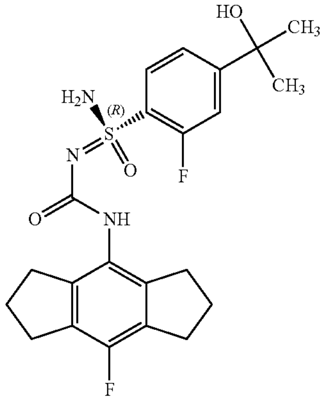 |
| 151b | 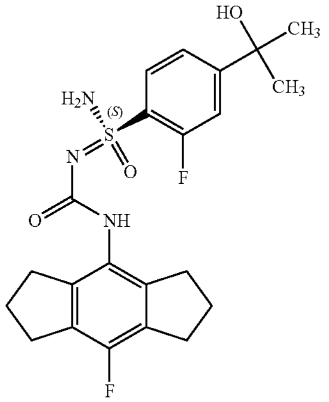 |
| 152 | 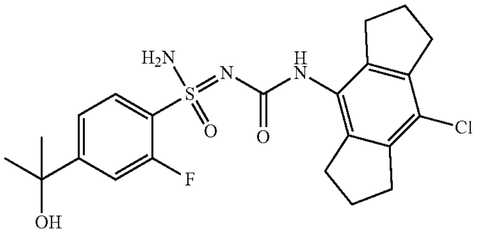 [SMILES: CC(C)(O)c1ccc(S(N)(=O)=NC(=O)Nc2c3c(c(Cl)c4c2CCC4)CCC3)c(F)c1] |
| 152a | 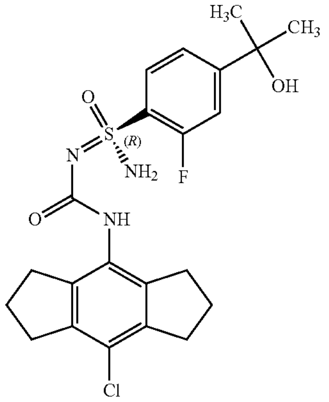 |

TABLE 1-continued
| Compound | Structure |
|---|---|
| 152b | 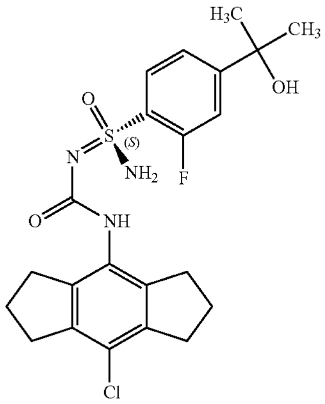 |
| 153 | 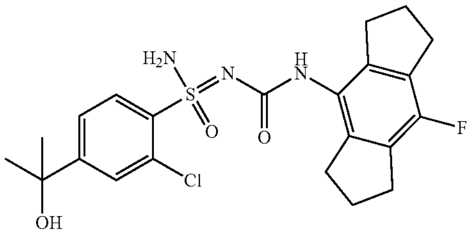 [SMILES: CC(C)(O)c1ccc(S(N)(=O)=NC(=O)Nc2c3c(c(F)c4c2CCC4)CCC3)c(Cl)c1] |
| 153a | 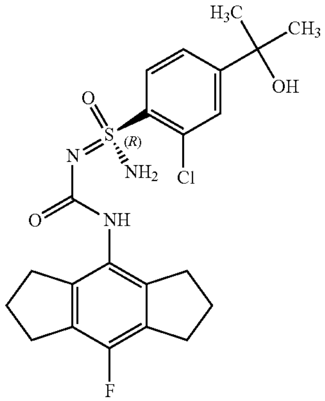 |
| 153b | 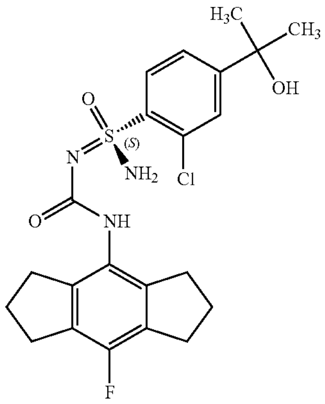 |

TABLE 1-continued
| Compound | Structure |
|---|---|
| 154 | 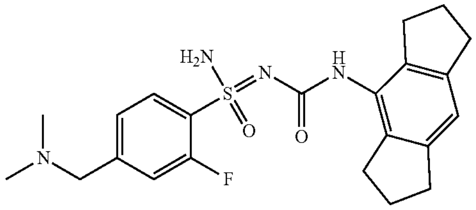 [SMILES: CN(C)Cc1ccc(S(N)(=O)=NC(=O)Nc2c3c(cc4c2CCC4)CCC3)c(F)c1] |
| 154a | 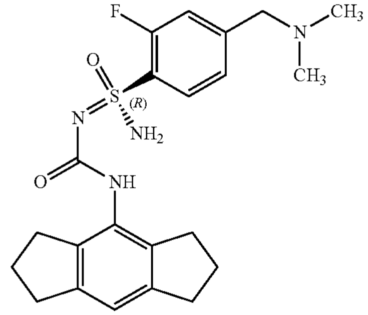 |
| 154b | 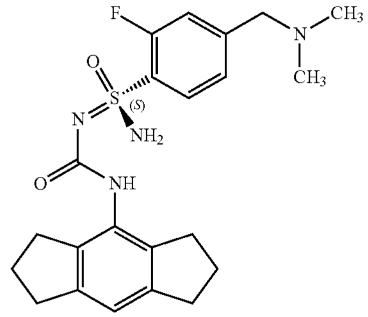 |
| 155 | 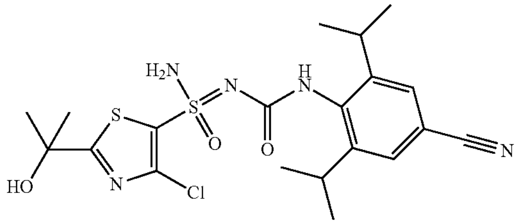 [SMILES: CC(C)c1cc(C#N)cc(C(C)C)c1NC(=O)N=S(N)(=O)c1sc(C(C)(C)O)nc1Cl] |
| 156 | 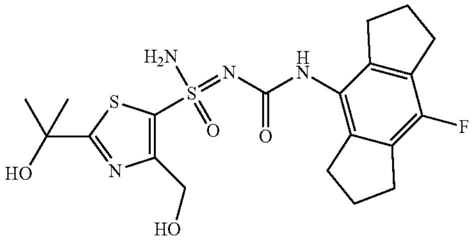 [SMILES: CC(C)(O)c1nc(CO)c(S(N)(=O)=NC(=O)Nc2c3c(c(F)c4c2CCC4)CCC3)s1] |
| 157 | 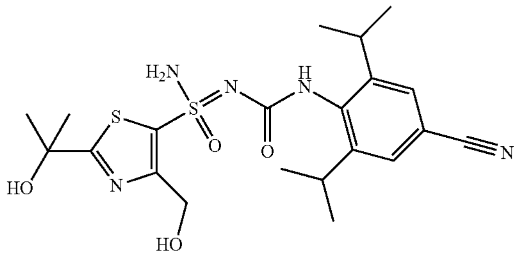 [SMILES: CC(C)c1cc(C#N)cc(C(C)C)c1NC(=O)N=S(N)(=O)c1sc(C(C)(C)O)nc1CO] |

TABLE 1-continued
| Compound | Structure |
|---|---|
| 157a | 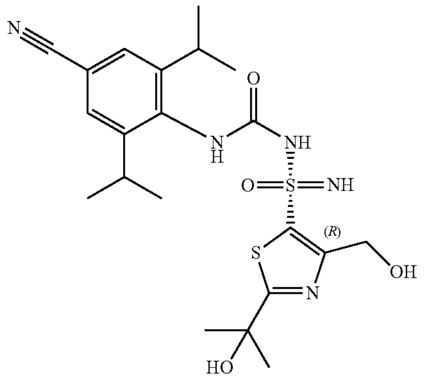 |
| 157b | 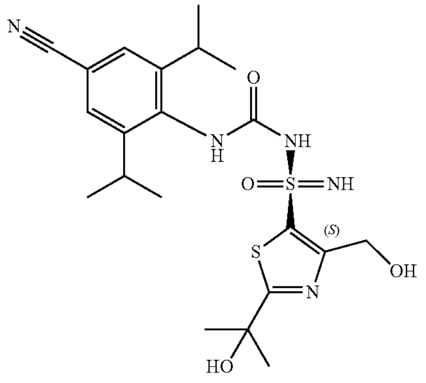 |
| 158 | 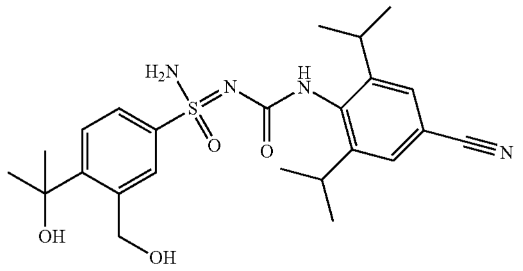 [SMILES: CC(C)c1cc(C#N)cc(C(C)C)c1NC(=O)N=S(N)(=O)c1ccc(C(C)(C)O)c(CO)c1] |
| 158a | 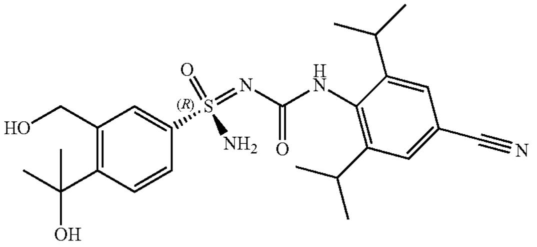 |
| 158b | 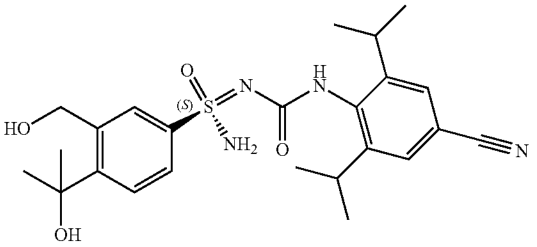 |

TABLE 1-continued
| Compound | Structure |
| --- | --- |
| 159 | 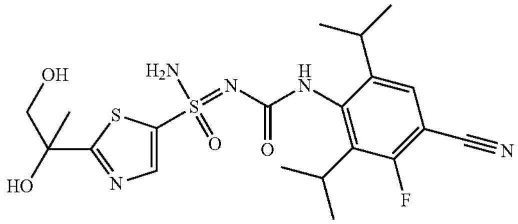 [SMILES: CC(C)c1cc(C#N)c(F)c(C(C)C)c1NC(=O)N=S(N)(=O)c1cnc(C(C)(O)CO)s1] |
| 159a | 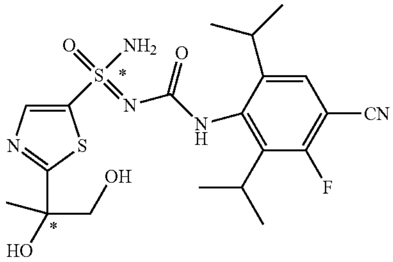 [SMILES: CC(C)c1cc(C#N)c(F)c(C(C)C)c1NC(=O)N=S(N)(=O)c1cnc(C(C)(O)CO)s1] |
| 159ba | 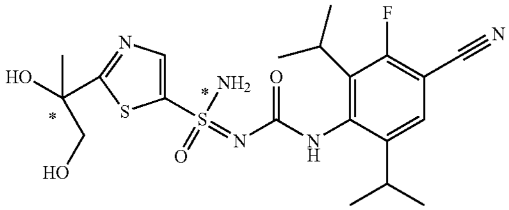 [SMILES: CC(C)c1cc(C#N)c(F)c(C(C)C)c1NC(=O)N=S(N)(=O)c1cnc(C(C)(O)CO)s1] |
| 159ab | 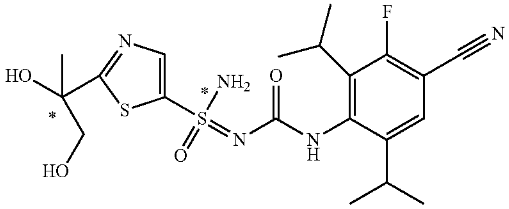 [SMILES: CC(C)c1cc(C#N)c(F)c(C(C)C)c1NC(=O)N=S(N)(=O)c1cnc(C(C)(O)CO)s1] |
| 160 | 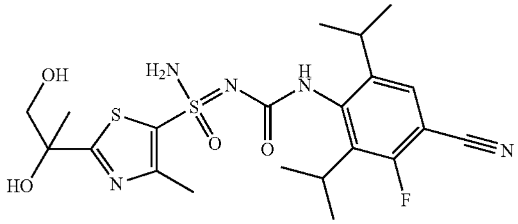 [SMILES: Cc1nc(C(C)(O)CO)sc1S(N)(=O)=NC(=O)Nc1c(C(C)C)cc(C#N)c(F)c1C(C)C] |
| 161 | 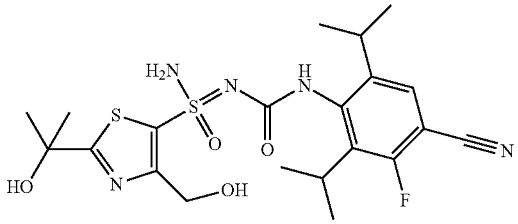 [SMILES: CC(C)c1cc(C#N)c(F)c(C(C)C)c1NC(=O)N=S(N)(=O)c1sc(C(C)(C)O)nc1CO] |

TABLE 1-continued
| Compound | Structure |
| --- | --- |
| 161a | 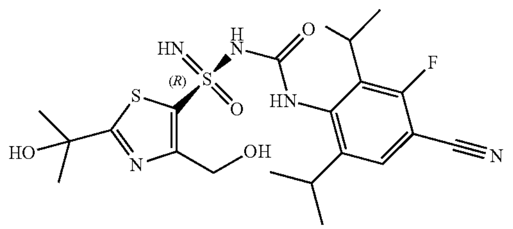 |
| 161b | 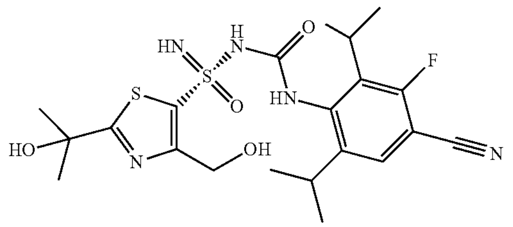 [SMILES: CC(C)c1cc(C#N)c(F)c(C(C)C)c1NC(=O)N[S@](=N)(=O)c1sc(C(C)(C)O)nc1CO] |
| 162 | 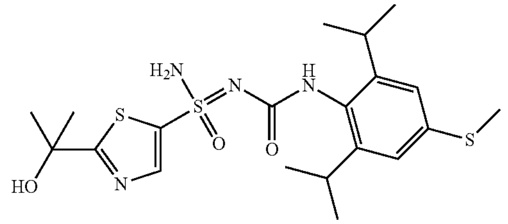 [SMILES: CSc1cc(C(C)C)c(NC(=O)N=S(N)(=O)c2cnc(C(C)(C)O)s2)c(C(C)C)c1] |
| 163 | 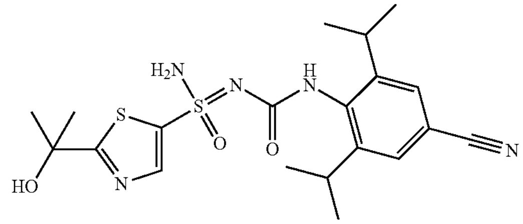 [SMILES: CC(C)c1cc(C#N)cc(C(C)C)c1NC(=O)N=S(N)(=O)c1cnc(C(C)(C)O)s1] |
| 164 | 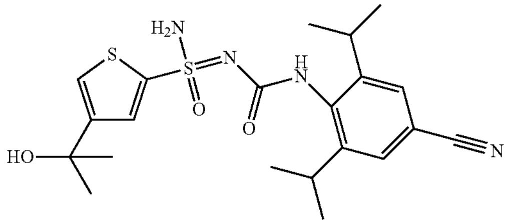 [SMILES: CC(C)c1cc(C#N)cc(C(C)C)c1NC(=O)N=S(N)(=O)c1cc(C(C)(C)O)cs1] |
| 165 | 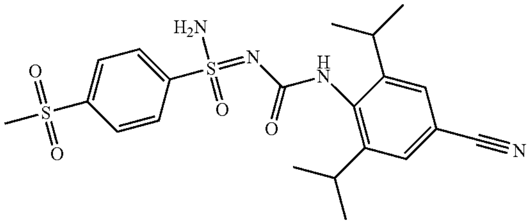 [SMILES: CC(C)c1cc(C#N)cc(C(C)C)c1NC(=O)N=S(N)(=O)c1ccc(S(C)(=O)=O)cc1] |

TABLE 1-continued
| Compound | Structure |
|---|---|
| 165a | 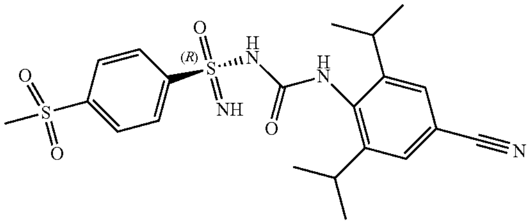 |
| 165b | 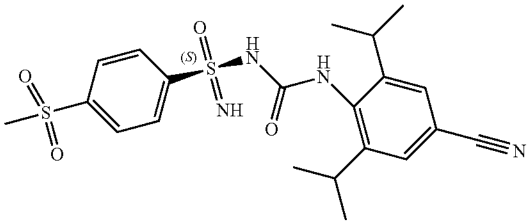 |
| 166 | 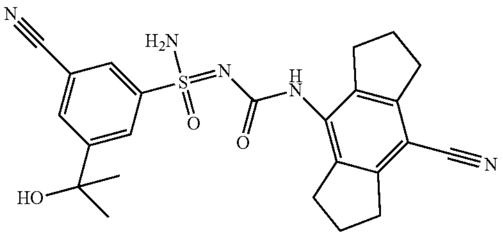 [SMILES: CC(C)(O)c1cc(C#N)cc(S(N)(=O)=NC(=O)Nc2c3c(c(C#N)c4c2CCC4)CCC3)c1] |
| 167 | 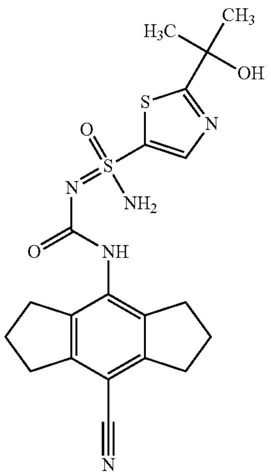 [SMILES: CC(C)(O)c1ncc(S(N)(=O)=NC(=O)Nc2c3c(c(C#N)c4c2CCC4)CCC3)s1] |

TABLE 1-continued
| Compound | Structure |
| --- | --- |
| 167a | 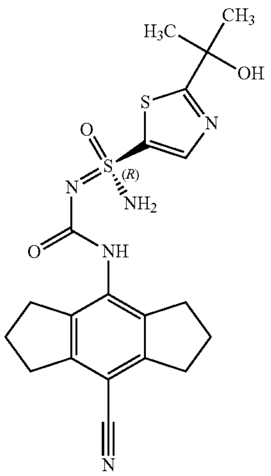 |
| 167b | 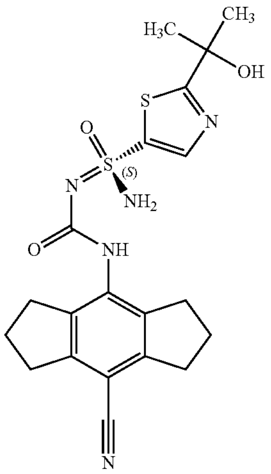 |
| 168 | 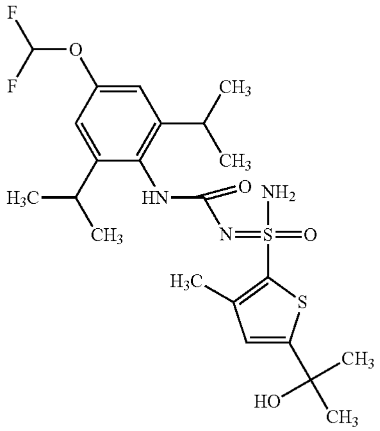 [SMILES: Cc1cc(C(C)(C)O)sc1S(N)(=O)=NC(=O)Nc1c(C(C)C)cc(OC(F)F)cc1C(C)C] |

TABLE 1-continued
| Compound | Structure |
| --- | --- |
| 168a | 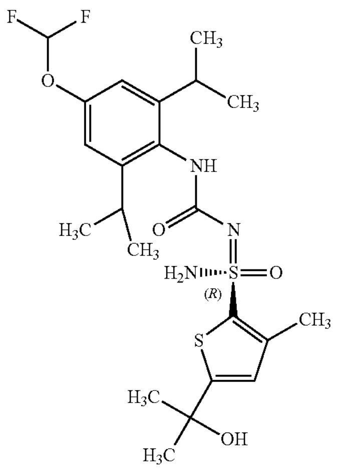 |
| 168b | 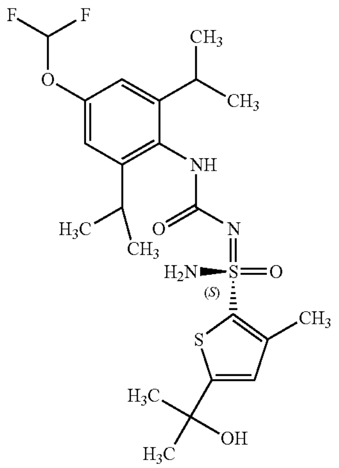 |
| 170 | 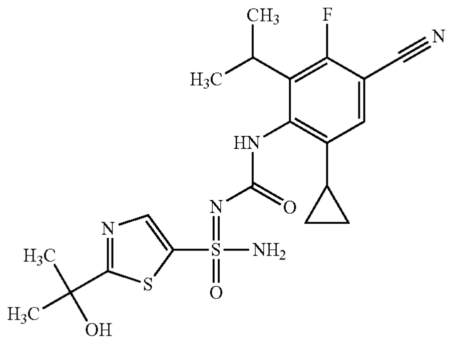 [SMILES: CC(C)c1c(F)c(C#N)cc(C2CC2)c1NC(=O)N=S(N)(=O)c1cnc(C(C)(C)O)s1] |

TABLE 1-continued
| Compound | Structure |
| --- | --- |
| 170a | 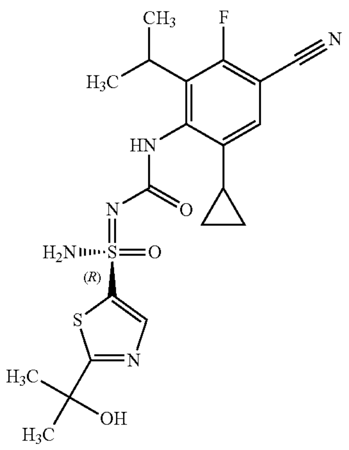 |
| 170b | 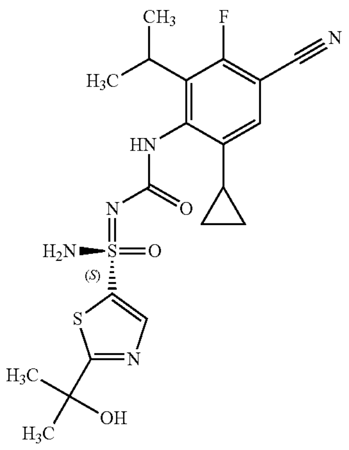 |
| 171 | 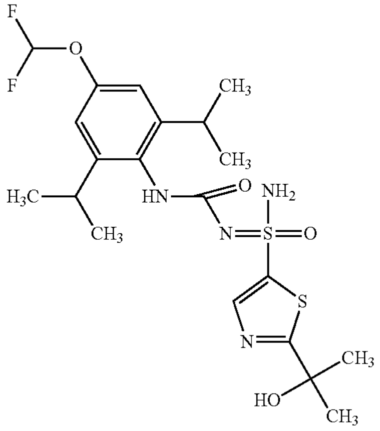 [SMILES: CC(C)c1cc(OC(F)F)cc(C(C)C)c1NC(=O)N=S(N)(=O)c1cnc(C(C)(C)O)s1] |

TABLE 1-continued
| Compound | Structure |
| --- | --- |
| 171a | 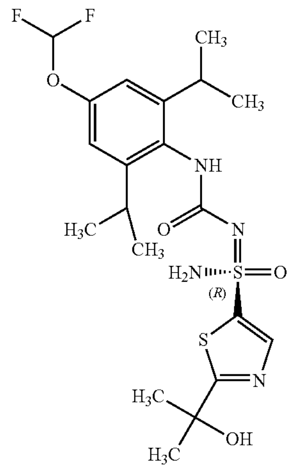 |
| 171b | 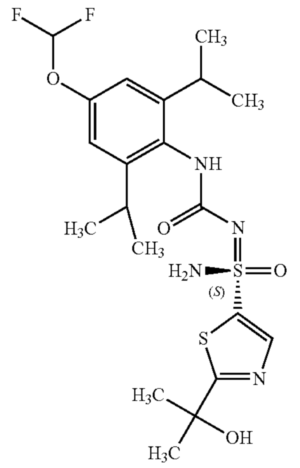 |
| 172 | 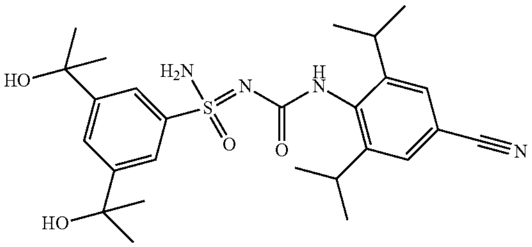 [SMILES: CC(C)c1cc(C#N)cc(C(C)C)c1NC(=O)N=S(N)(=O)c1cc(C(C)(C)O)cc(C(C)(C)O)c1] |
| 172a | 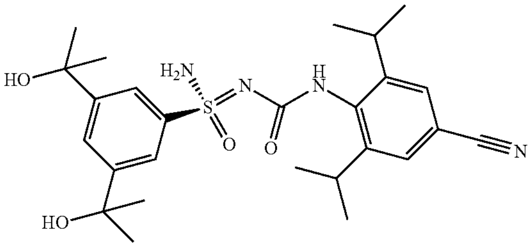 [SMILES: CC(C)c1cc(C#N)cc(C(C)C)c1NC(=O)N=[S@@](N)(=O)c1cc(C(C)(C)O)cc(C(C)(C)O)c1] |

TABLE 1-continued
| Compound | Structure |
| --- | --- |
| 172b | 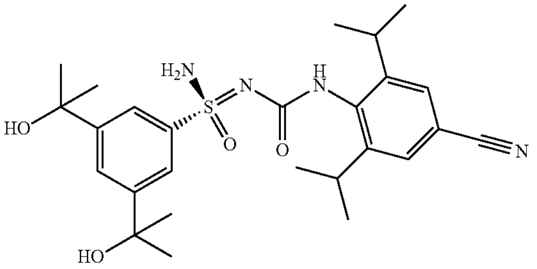 [SMILES: CC(C)c1cc(C#N)cc(C(C)C)c1NC(=O)N=[S@](N)(=O)c1cc(C(C)(C)O)cc(C(C)(C)O)c1] |
| 173 | 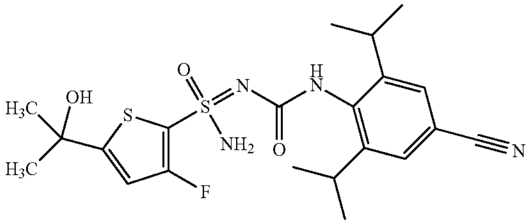 [SMILES: CC(C)c1cc(C#N)cc(C(C)C)c1NC(=O)N=S(N)(=O)c1sc(C(C)(C)O)cc1F] |
| 173a | 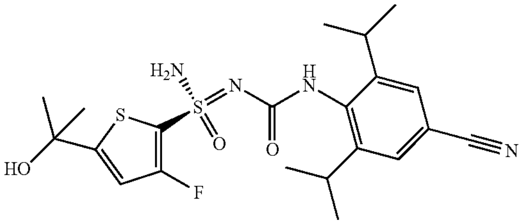 [SMILES: CC(C)c1cc(C#N)cc(C(C)C)c1NC(=O)N=[S@@](N)(=O)c1sc(C(C)(C)O)cc1F] |
| 173b | 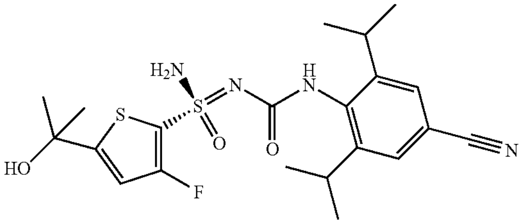 [SMILES: CC(C)c1cc(C#N)cc(C(C)C)c1NC(=O)N=[S@](N)(=O)c1sc(C(C)(C)O)cc1F] |
| 174 | 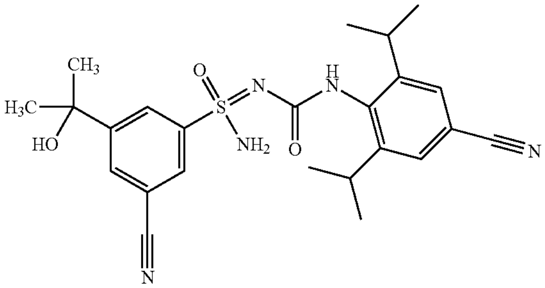 [SMILES: CC(C)c1cc(C#N)cc(C(C)C)c1NC(=O)N=S(N)(=O)c1cc(C#N)cc(C(C)(C)O)c1] |
| 174a | 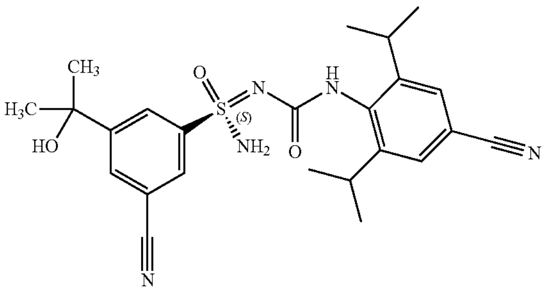 |

TABLE 1-continued
| Compound | Structure |
|---|---|
| 174b | 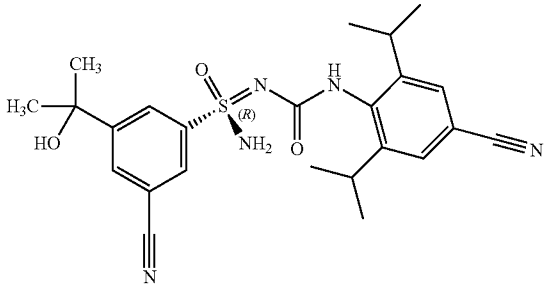 |
| 176 | 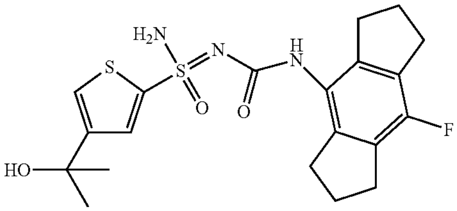 [SMILES: CC(C)(O)c1csc(S(N)(=O)=NC(=O)Nc2c3c(c(F)c4c2CCC4)CCC3)c1] |
| 176a | 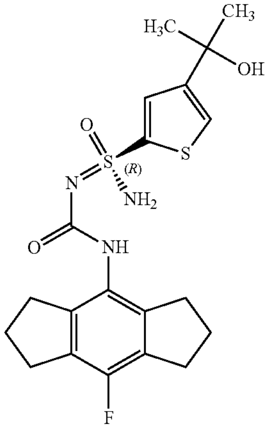 |
| 176b | 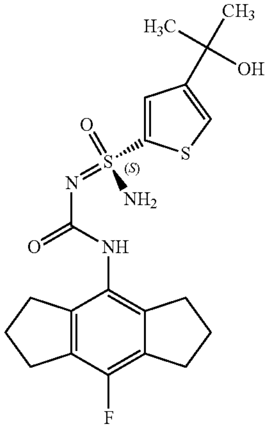 |
| 177 | 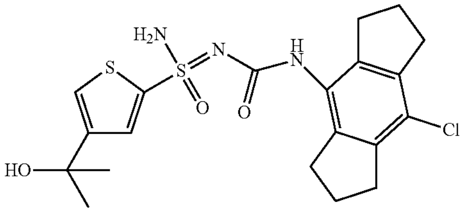 [SMILES: CC(C)(O)c1csc(S(N)(=O)=NC(=O)Nc2c3c(c(Cl)c4c2CCC4)CCC3)c1] |

TABLE 1-continued
| Compound | Structure |
|---|---|
| 177a | 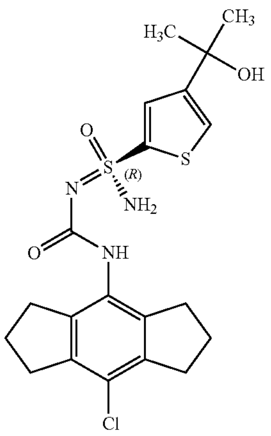 |
| 177b | 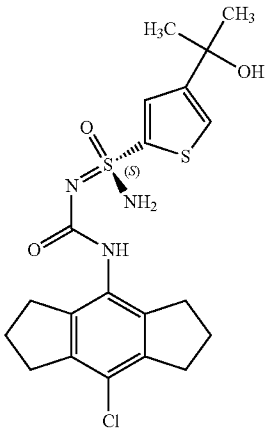 |
| 178 | 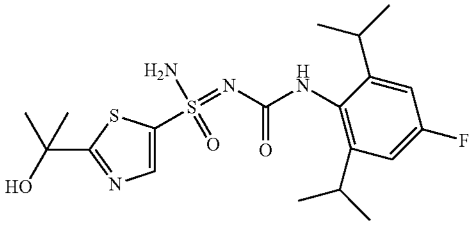 [SMILES: CC(C)c1cc(F)cc(C(C)C)c1NC(=O)N=S(N)(=O)c1cnc(C(C)(C)O)s1] |
| 178a | 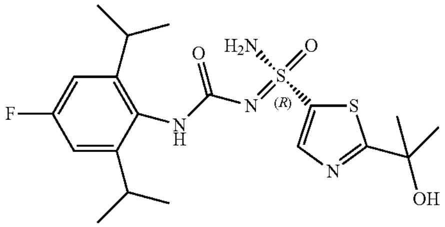 |
| 178b | 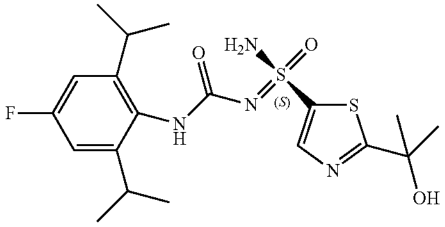 |

TABLE 1-continued
| Compound | Structure |
| --- | --- |
| 179 | 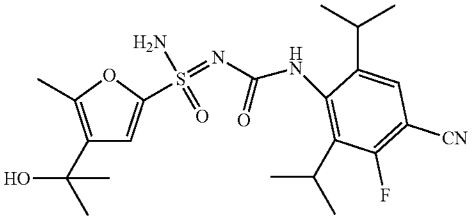 [SMILES: Cc1oc(S(N)(=O)=NC(=O)Nc2c(C(C)C)cc(C#N)c(F)c2C(C)C)cc1C(C)(C)O] |
| 179a | 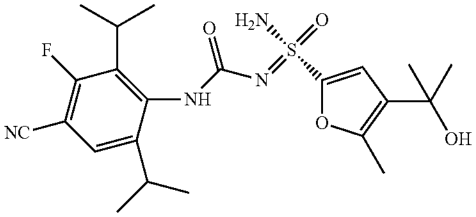 [SMILES: Cc1oc([S@](N)(=O)=NC(=O)Nc2c(C(C)C)cc(C#N)c(F)c2C(C)C)cc1C(C)(C)O] |
| 179b | 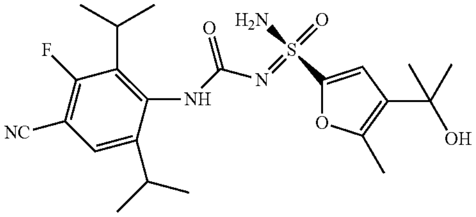 [SMILES: Cc1oc([S@@](N)(=O)=NC(=O)Nc2c(C(C)C)cc(C#N)c(F)c2C(C)C)cc1C(C)(C)O] |
| 180 | 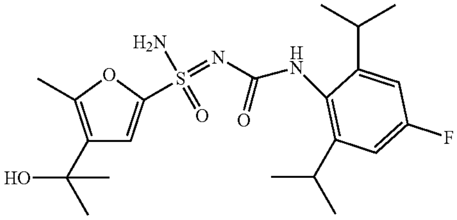 [SMILES: Cc1oc(S(N)(=O)=NC(=O)Nc2c(C(C)C)cc(F)cc2C(C)C)cc1C(C)(C)O] |
| 180a | 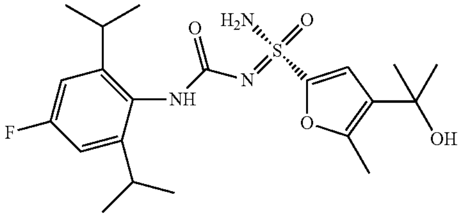 [SMILES: Cc1oc([S@](N)(=O)=NC(=O)Nc2c(C(C)C)cc(F)cc2C(C)C)cc1C(C)(C)O] |
| 180b | 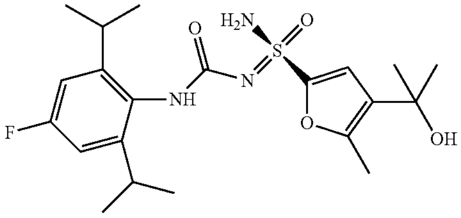 [SMILES: Cc1oc([S@@](N)(=O)=NC(=O)Nc2c(C(C)C)cc(F)cc2C(C)C)cc1C(C)(C)O] |
| 181 | 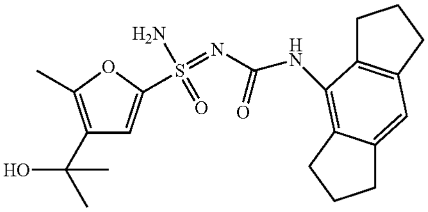 [SMILES: Cc1oc(S(N)(=O)=NC(=O)Nc2c3c(cc4c2CCC4)CCC3)cc1C(C)(C)O] |

TABLE 1-continued
| Compound | Structure |
|---|---|
| 181a | 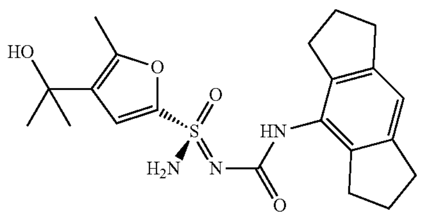 [SMILES: Cc1oc([S@](N)(=O)=NC(=O)Nc2c3c(cc4c2CCC4)CCC3)cc1C(C)(C)O] |
| 181b | 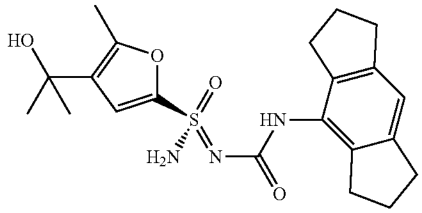 [SMILES: Cc1oc([S@@](N)(=O)=NC(=O)Nc2c3c(cc4c2CCC4)CCC3)cc1C(C)(C)O] |
| 182 | 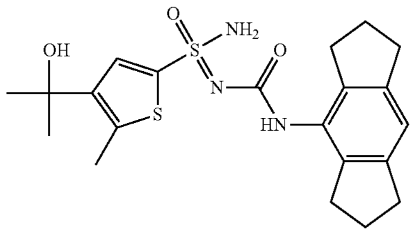 [SMILES: Cc1sc(S(N)(=O)=NC(=O)Nc2c3c(cc4c2CCC4)CCC3)cc1C(C)(C)O] |
| 182a | 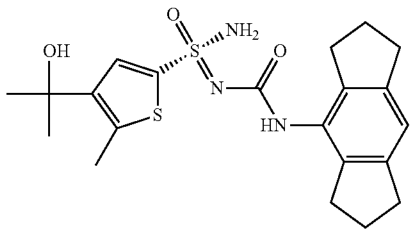 [SMILES: Cc1sc([S@@](N)(=O)=NC(=O)Nc2c3c(cc4c2CCC4)CCC3)cc1C(C)(C)O] |
| 182b | 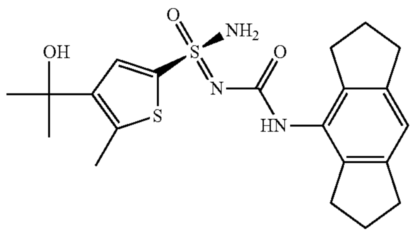 [SMILES: Cc1sc([S@](N)(=O)=NC(=O)Nc2c3c(cc4c2CCC4)CCC3)cc1C(C)(C)O] |
| 183 | 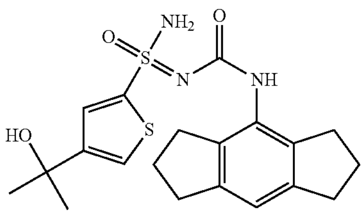 [SMILES: CC(C)(O)c1csc(S(N)(=O)=NC(=O)Nc2c3c(cc4c2CCC4)CCC3)c1] |

TABLE 1-continued
| Compound | Structure |
| --- | --- |
| 183a | 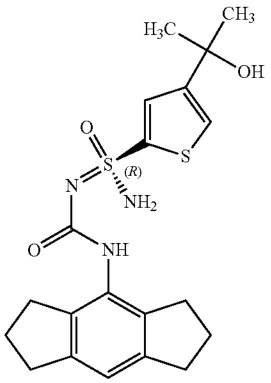 |
| 183b | 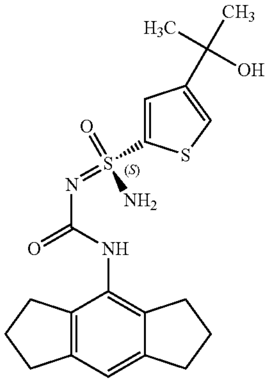 |
| 184 | 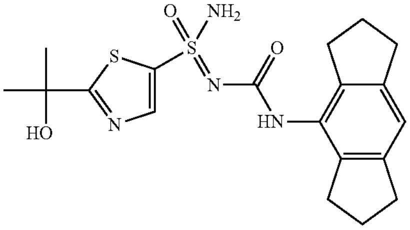 [SMILES: CC(C)(O)c1ncc(S(N)(=O)=NC(=O)Nc2c3c(cc4c2CCC4)CCC3)s1] |
| 185 | 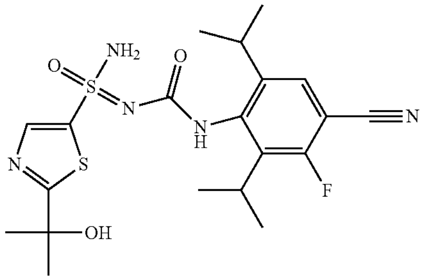 [SMILES: CC(C)c1cc(C#N)c(F)c(C(C)C)c1NC(=O)N=S(N)(=O)c1cnc(C(C)(C)O)s1] |
| 185a | 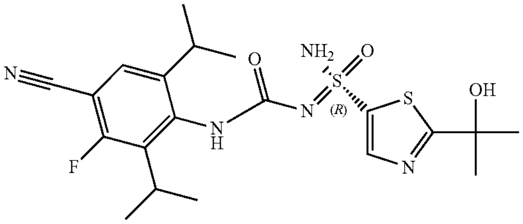 |

TABLE 1-continued
| Compound | Structure |
| --- | --- |
| 185b | 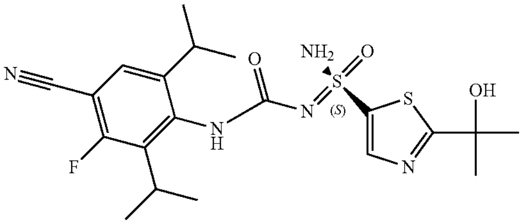 |
| 186 | 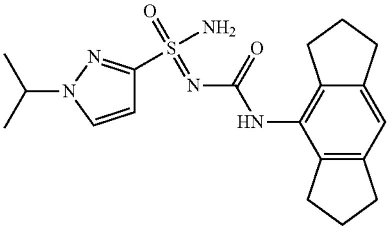 [SMILES: CC(C)n1ccc(S(N)(=O)=NC(=O)Nc2c3c(cc4c2CCC4)CCC3)n1] |
| 186a | 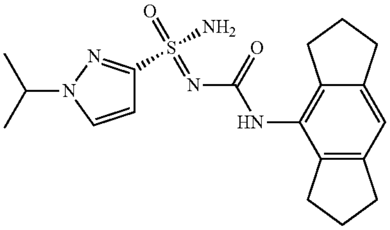 [SMILES: CC(C)n1ccc([S@@](N)(=O)=NC(=O)Nc2c3c(cc4c2CCC4)CCC3)n1] |
| 186b | 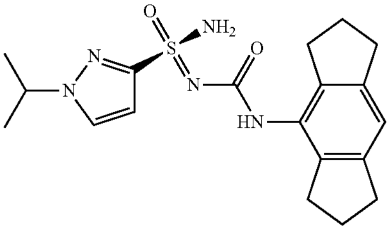 [SMILES: CC(C)n1ccc([S@](N)(=O)=NC(=O)Nc2c3c(cc4c2CCC4)CCC3)n1] |
| 187 | 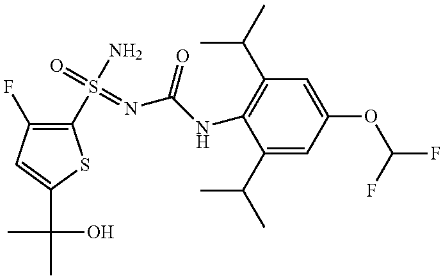 [SMILES: CC(C)c1cc(OC(F)F)cc(C(C)C)c1NC(=O)N=S(N)(=O)c1sc(C(C)(C)O)cc1F] |
| 187a | 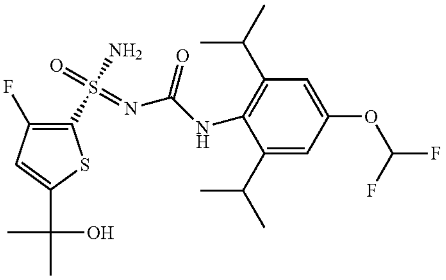 [SMILES: CC(C)c1cc(OC(F)F)cc(C(C)C)c1NC(=O)N=[S@](N)(=O)c1sc(C(C)(C)O)cc1F] |

TABLE 1-continued
| Compound | Structure |
|---|---|
| 187b | 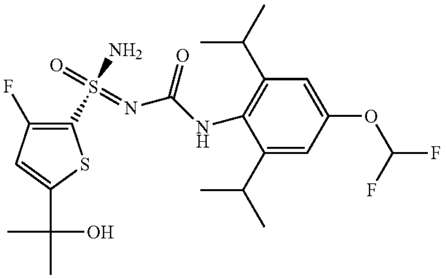 |
| 188 | 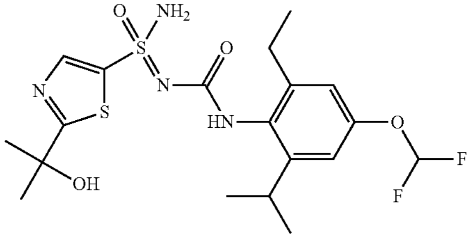 [SMILES: CCc1cc(OC(F)F)cc(C(C)C)c1NC(=O)N=S(N)(=O)c1cnc(C(C)(C)O)s1] |
| 188a | 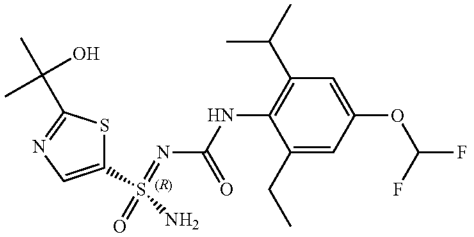 |
| 188b | 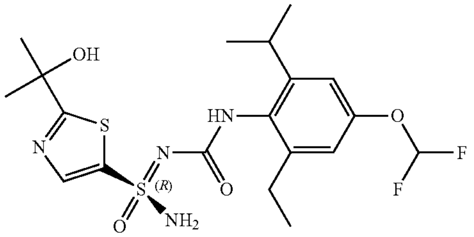 |
| 189 | 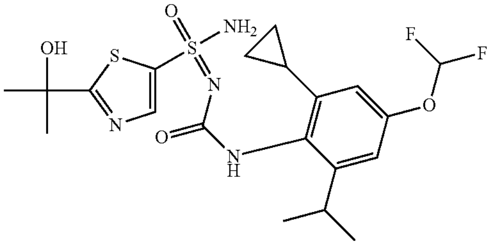 [SMILES: CC(C)c1cc(OC(F)F)cc(C2CC2)c1NC(=O)N=S(N)(=O)c1cnc(C(C)(C)O)s1] |
| 189a | 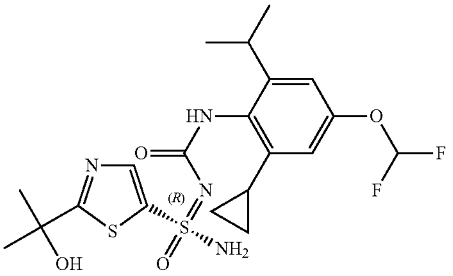 |

TABLE 1-continued
| Compound | Structure |
| --- | --- |
| 189b | 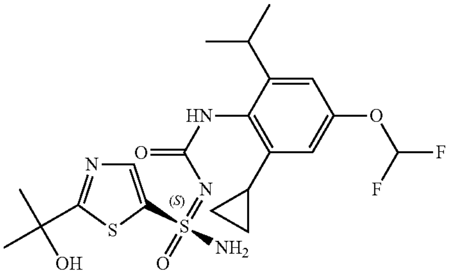 |
| 190 | 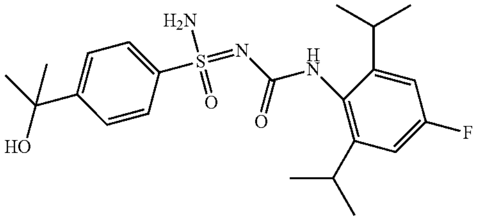 [SMILES: CC(C)c1cc(F)cc(C(C)C)c1NC(=O)N=S(N)(=O)c1ccc(C(C)(C)O)cc1] |
| 190a | 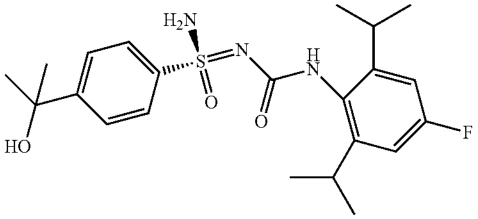 [SMILES: CC(C)c1cc(F)cc(C(C)C)c1NC(=O)N=[S@](N)(=O)c1ccc(C(C)(C)O)cc1] |
| 190b | 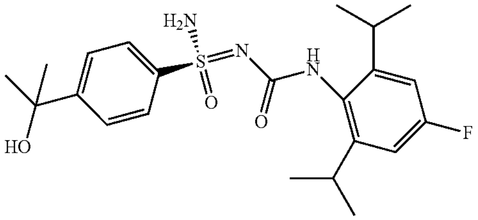 [SMILES: CC(C)c1cc(F)cc(C(C)C)c1NC(=O)N=[S@@](N)(=O)c1ccc(C(C)(C)O)cc1] |
| 191 | 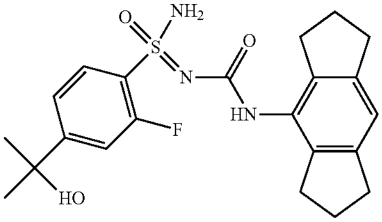 [SMILES: CC(C)(O)c1ccc(S(N)(=O)=NC(=O)Nc2c3c(cc4c2CCC4)CCC3)c(F)c1] |
| 191a | 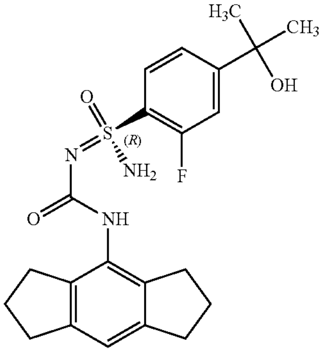 |

TABLE 1-continued
| Compound | Structure |
| --- | --- |
| 191b | 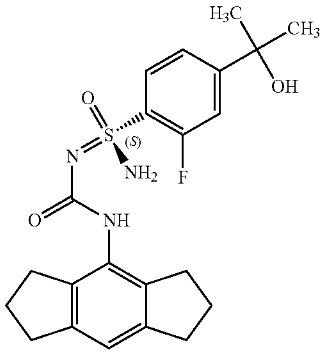 |
| 192 | 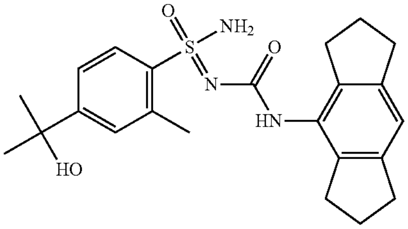 [SMILES: Cc1cc(C(C)(C)O)ccc1S(N)(=O)=NC(=O)Nc1c2c(cc3c1CCC3)CCC2] |
| 192a | 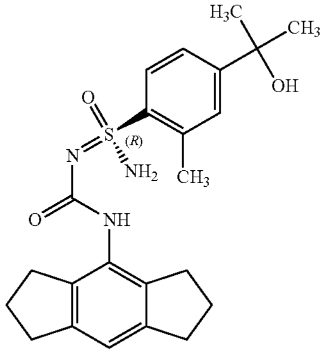 |
| 192b | 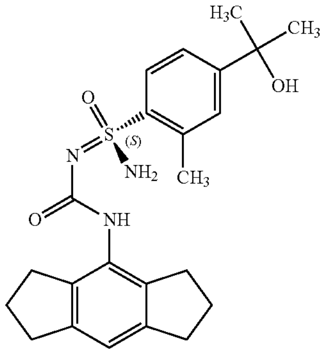 |
| 193 | 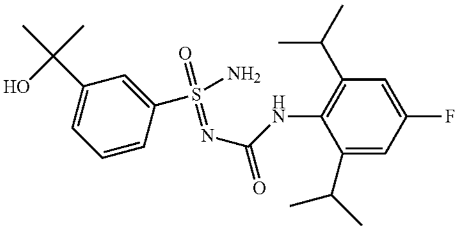 [SMILES: CC(C)c1cc(F)cc(C(C)C)c1NC(=O)N=S(N)(=O)c1cccc(C(C)(C)O)c1] |

TABLE 1-continued
| Compound | Structure |
|---|---|
| 193a | 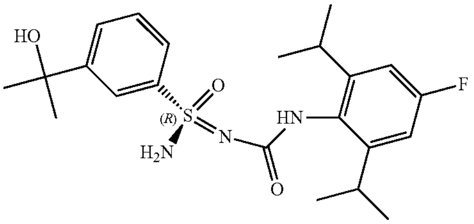 |
| 193b | 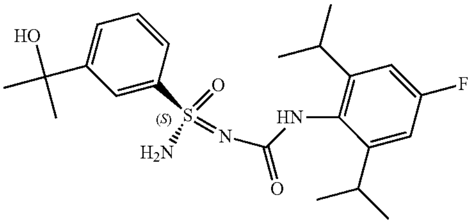 |
| 194 | 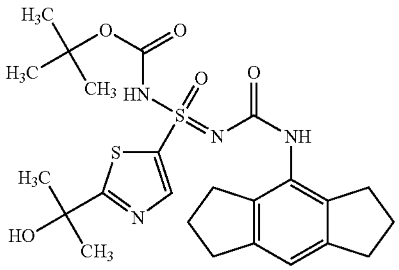 [SMILES: CC(C)(C)OC(=O)NS(=O)(=NC(=O)Nc1c2c(cc3c1CCC3)CCC2)c1cnc(C(C)(C)O)s1] |
| 195 | 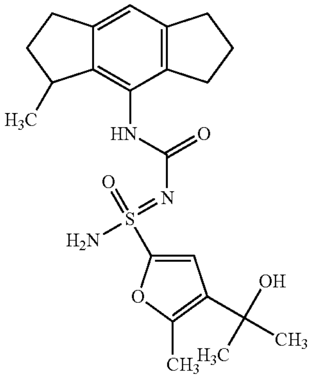 [SMILES: Cc1oc(S(N)(=O)=NC(=O)Nc2c3c(cc4c2C(C)CC4)CCC3)cc1C(C)(C)O] |
| 195a | 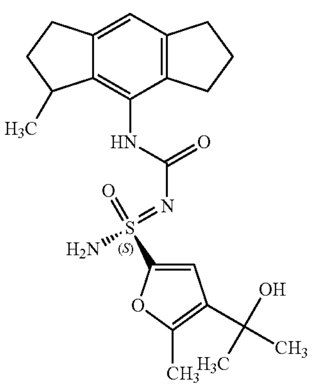 |

TABLE 1-continued
| Compound | Structure |
|---|---|
| 195ba | 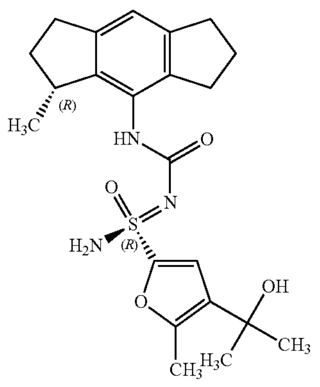 |
| 195bb | 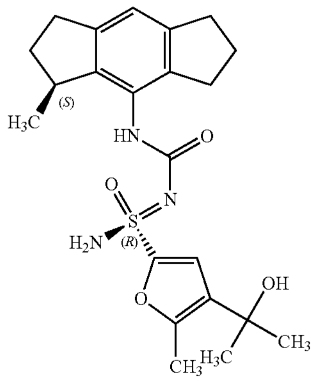 |
| 195e | 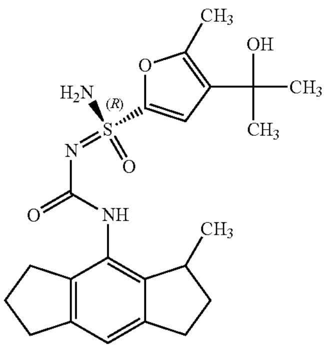 |
| 196 | 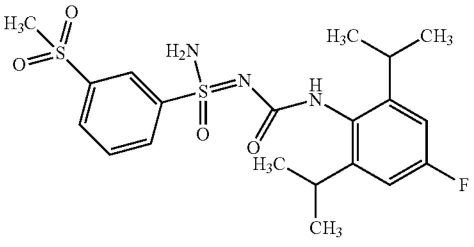 [SMILES: CC(C)c1cc(F)cc(C(C)C)c1NC(=O)N=S(N)(=O)c1cccc(S(C)(=O)=O)c1] |

TABLE 1-continued
| Compound | Structure |
|---|---|
| 197 | 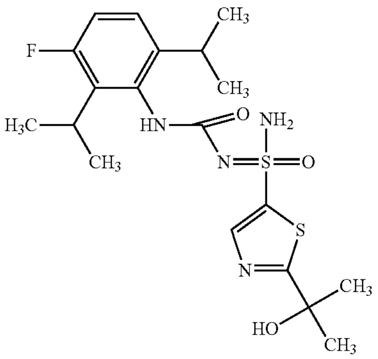 [SMILES: CC(C)c1ccc(F)c(C(C)C)c1NC(=O)N=S(N)(=O)c1cnc(C(C)(C)O)s1] |
| 198 | 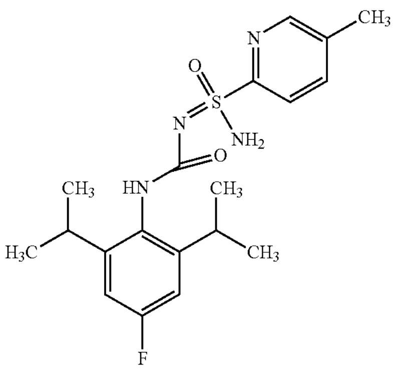 [SMILES: Cc1ccc(S(N)(=O)=NC(=O)Nc2c(C(C)C)cc(F)cc2C(C)C)nc1] |
| 199 | 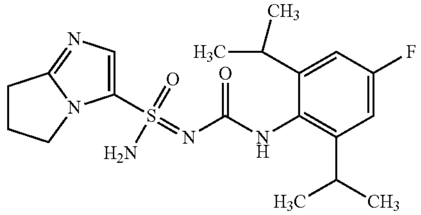 [SMILES: CC(C)c1cc(F)cc(C(C)C)c1NC(=O)N=S(N)(=O)c1cnc2n1CCC2] |
| 200 | 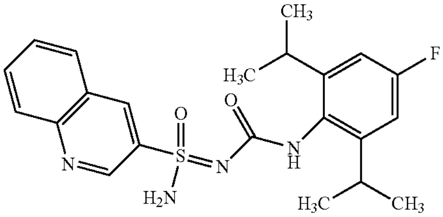 [SMILES: CC(C)c1cc(F)cc(C(C)C)c1NC(=O)N=S(N)(=O)c1cnc2ccccc2c1] |
| 201 | 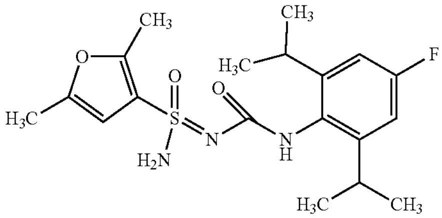 [SMILES: Cc1cc(S(N)(=O)=NC(=O)Nc2c(C(C)C)cc(F)cc2C(C)C)c(C)o1] |

TABLE 1-continued
| Compound | Structure |
|---|---|
| 202 | 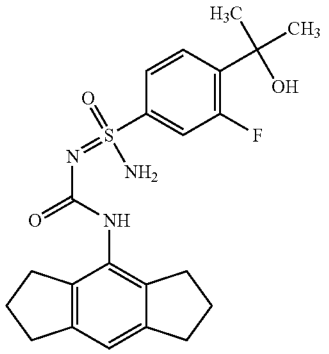 [SMILES: CC(C)(O)c1ccc(S(N)(=O)=NC(=O)Nc2c3c(cc4c2CCC4)CCC3)cc1F] |
| 202a | 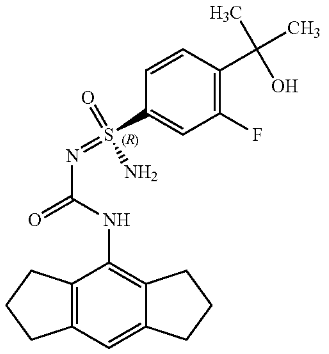 |
| 202b | 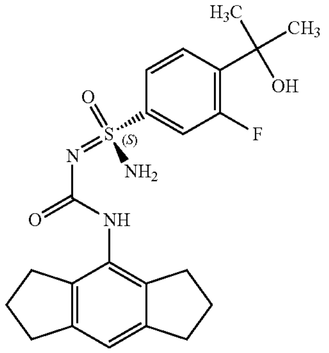 |
| 203 | 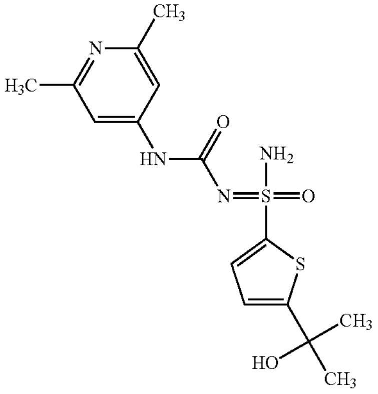 [SMILES: Cc1cc(NC(=O)N=S(N)(=O)c2ccc(C(C)(C)O)s2)cc(C)n1] |

TABLE 1-continued
| Compound | Structure |
|---|---|
| 204 | 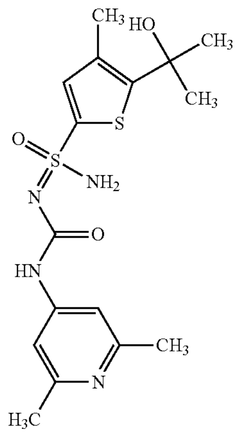 [SMILES: Cc1cc(NC(=O)N=S(N)(=O)c2cc(C)c(C(C)(C)O)s2)cc(C)n1] |
| 205 | 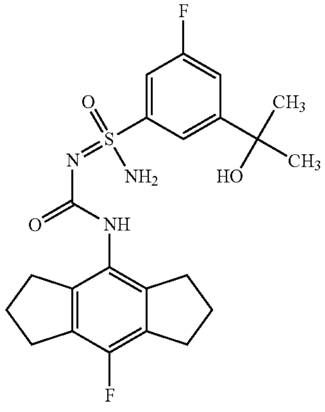 [SMILES: CC(C)(O)c1cc(F)cc(S(N)(=O)=NC(=O)Nc2c3c(c(F)c4c2CCC4)CCC3)c1] |
| 205a | 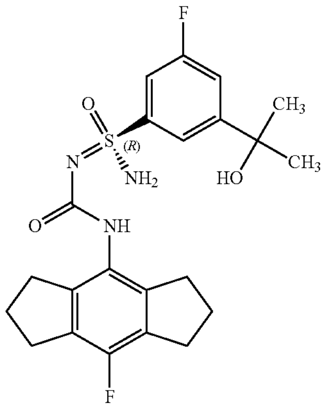 |

TABLE 1-continued
| Compound | Structure |
| --- | --- |
| 205b | 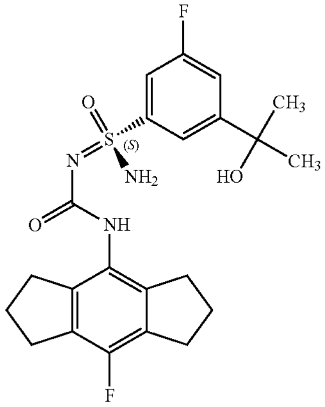 |
| 206 | 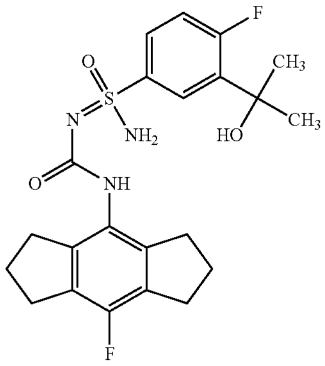 [SMILES: CC(C)(O)c1cc(S(N)(=O)=NC(=O)Nc2c3c(c(F)c4c2CCC4)CCC3)ccc1F] |
| 206a | 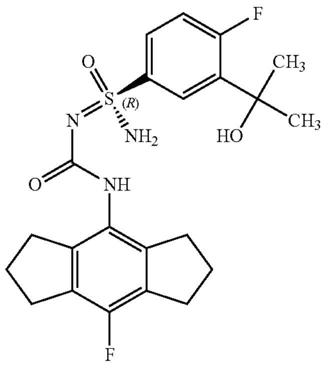 |
| 206b | 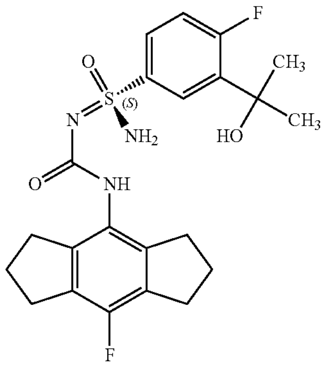 |

TABLE 1-continued
| Compound | Structure |
| --- | --- |
| 207 | 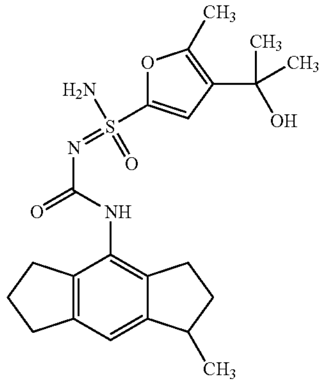 [SMILES: Cc1oc(S(N)(=O)=NC(=O)Nc2c3c(cc4c2CCC4C)CCC3)cc1C(C)(C)O] |
| 207a | 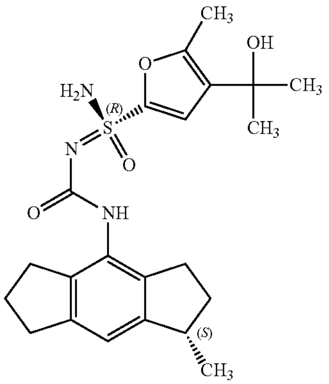 |
| 207b | 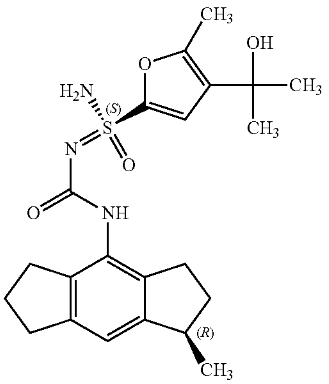 |
| 207bb | 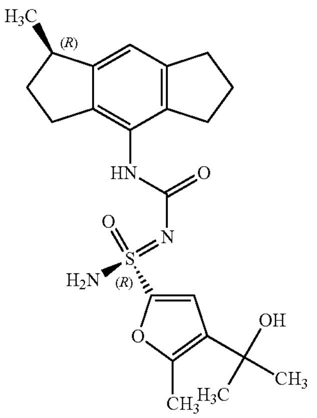 |

TABLE 1-continued
| Compound | Structure |
| --- | --- |
| 207aa | 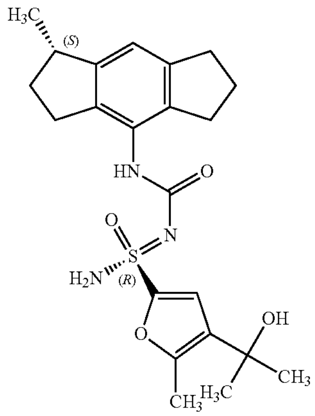 |
| 207c | 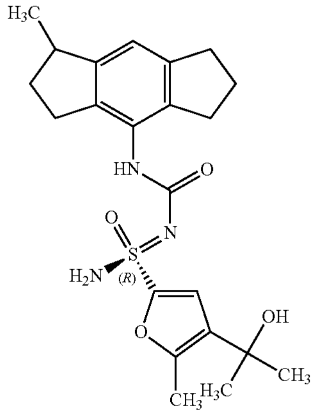 |
| 208 | 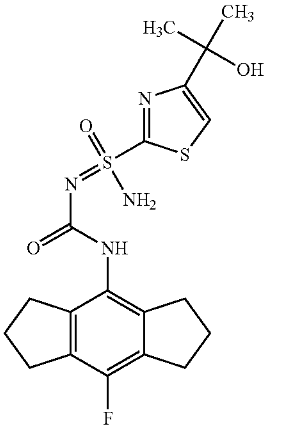 [SMILES: CC(C)(O)c1csc(S(N)(=O)=NC(=O)Nc2c3c(c(F)c4c2CCC4)CCC3)n1] |

TABLE 1-continued
| Compound | Structure |
|---|---|
| 209 | 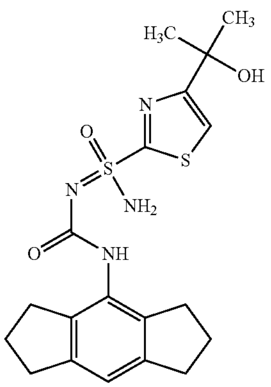 [SMILES: CC(C)(O)c1csc(S(N)(=O)=NC(=O)Nc2c3c(cc4c2CCC4)CCC3)n1] |
| 210 | 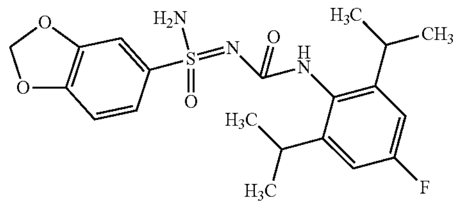 [SMILES: CC(C)c1cc(F)cc(C(C)C)c1NC(=O)N=S(N)(=O)c1ccc2c(c1)OCO2] |
| 211 | 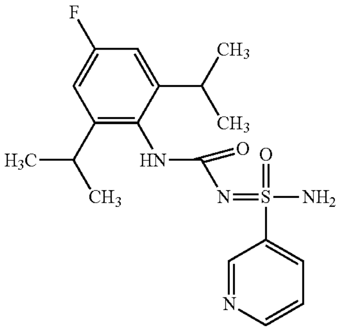 [SMILES: CC(C)c1cc(F)cc(C(C)C)c1NC(=O)N=S(N)(=O)c1cccnc1] |
| 212 | 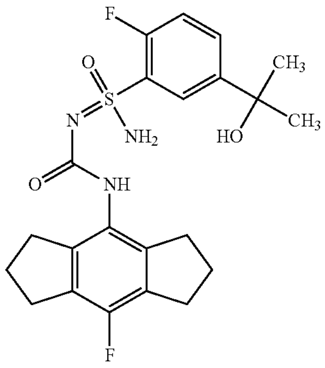 [SMILES: CC(C)(O)c1ccc(F)c(S(N)(=O)=NC(=O)Nc2c3c(c(F)c4c2CCC4)CCC3)c1] |

TABLE 1-continued
| Compound | Structure |
|---|---|
| 212a | 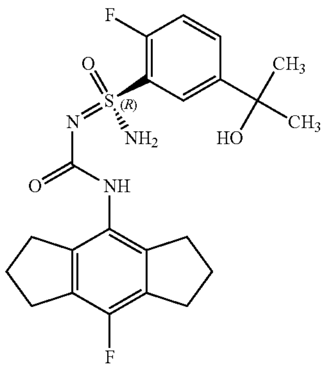 |
| 212b | 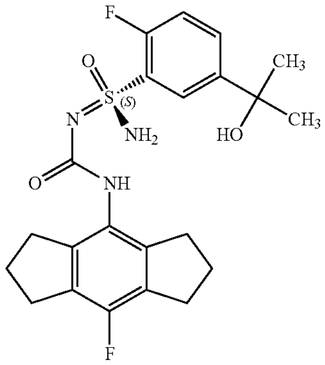 |
| 213 | 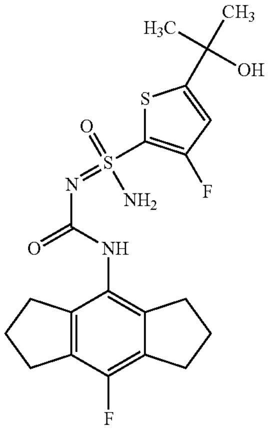 [SMILES: CC(C)(O)c1cc(F)c(S(N)(=O)=NC(=O)Nc2c3c(c(F)c4c2CCC4)CCC3)s1] |
| 214 | 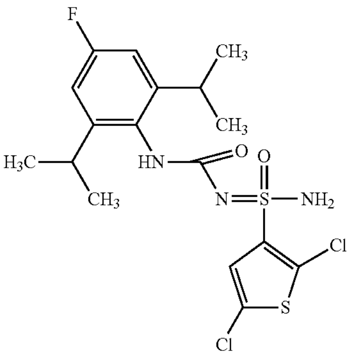 [SMILES: CC(C)c1cc(F)cc(C(C)C)c1NC(=O)N=S(N)(=O)c1cc(Cl)sc1Cl] |

TABLE 1-continued
| Compound | Structure |
| --- | --- |
| 215 | 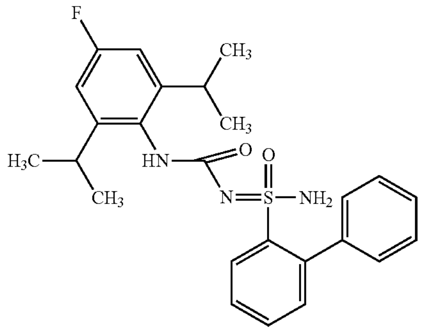 [SMILES: CC(C)c1cc(F)cc(C(C)C)c1NC(=O)N=S(N)(=O)c1ccccc1-c1ccccc1] |
| 216 | 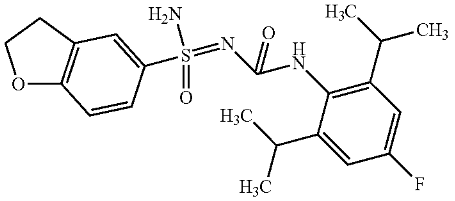 [SMILES: CC(C)c1cc(F)cc(C(C)C)c1NC(=O)N=S(N)(=O)c1ccc2c(c1)CCO2] |
| 217 | 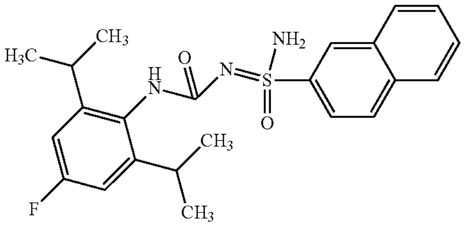 [SMILES: CC(C)c1cc(F)cc(C(C)C)c1NC(=O)N=S(N)(=O)c1ccc2ccccc2c1] |
| 218 | 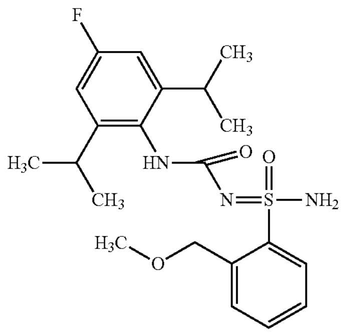 [SMILES: COCc1ccccc1S(N)(=O)=NC(=O)Nc1c(C(C)C)cc(F)cc1C(C)C] |
| 219 | 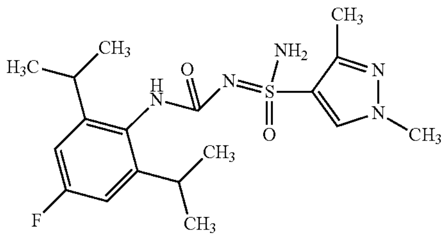 [SMILES: Cc1nn(C)cc1S(N)(=O)=NC(=O)Nc1c(C(C)C)cc(F)cc1C(C)C] |

TABLE 1-continued
| Compound | Structure |
| --- | --- |
| 220 | 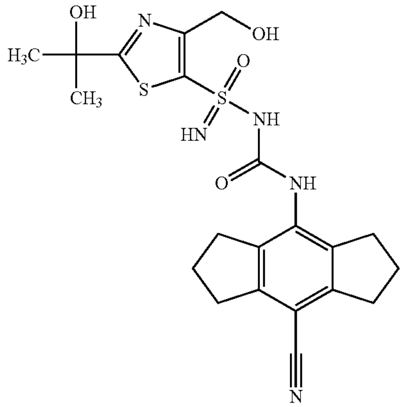 [SMILES: CC(C)(O)c1nc(CO)c(S(=N)(=O)NC(=O)Nc2c3c(c(C#N)c4c2CCC4)CCC3)s1] |
| 220a | 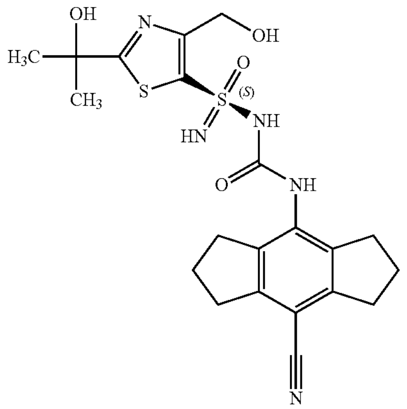 |
| 220b | 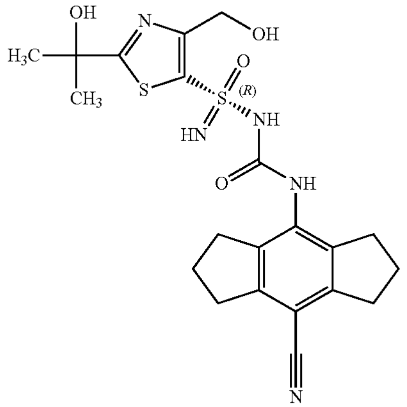 |
| 221 | 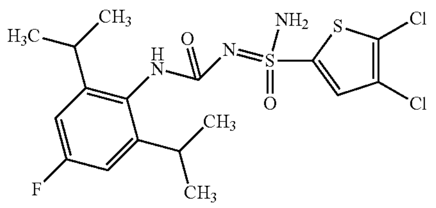 [SMILES: CC(C)c1cc(F)cc(C(C)C)c1NC(=O)N=S(N)(=O)c1cc(Cl)c(Cl)s1] |

TABLE 1-continued
| Compound | Structure |
| --- | --- |
| 223 | 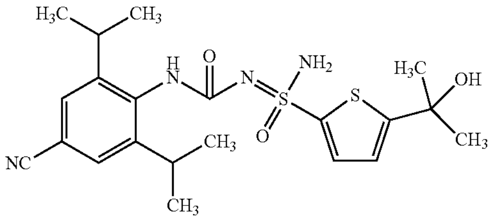 [SMILES: CC(C)c1cc(C#N)cc(C(C)C)c1NC(=O)N=S(N)(=O)c1ccc(C(C)(C)O)s1] |
| 223a | 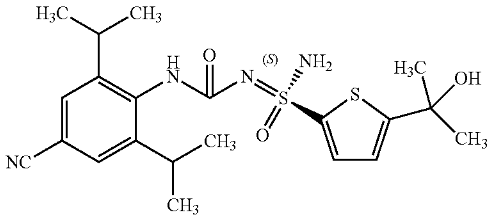 |
| 223b | 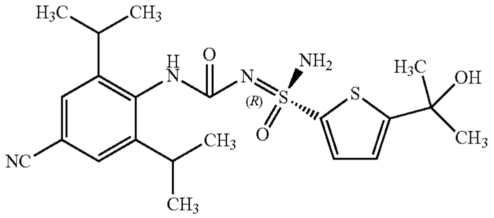 |
| 225 | 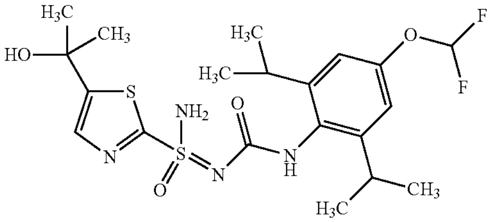 [SMILES: CC(C)c1cc(OC(F)F)cc(C(C)C)c1NC(=O)N=S(N)(=O)c1ncc(C(C)(C)O)s1] |
| 225a | 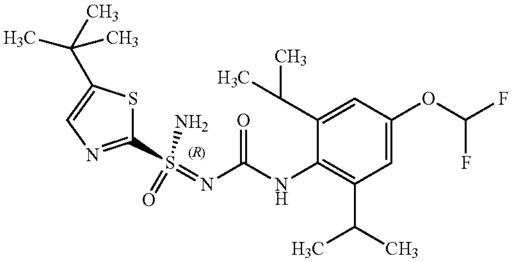 |
| 225b | 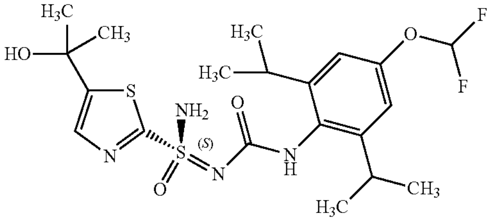 |

TABLE 1-continued
| Compound | Structure |
| --- | --- |
| 226 | 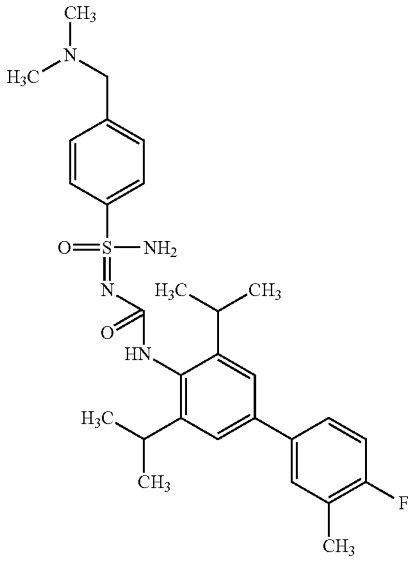 [SMILES: Cc1cc(-c2cc(C(C)C)c(NC(=O)N=S(N)(=O)c3ccc(CN(C)C)cc3)c(C(C)C)c2)ccc1F] |
| 227 | 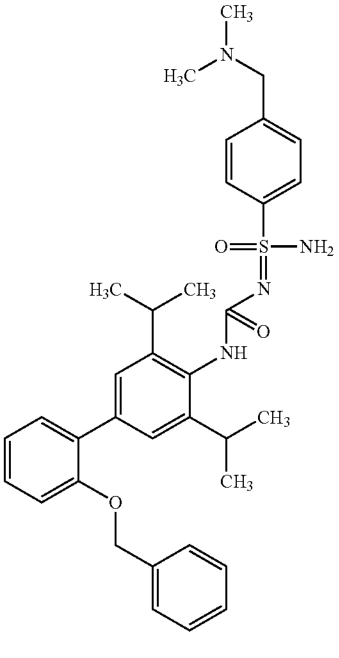 [SMILES: CC(C)c1cc(-c2ccccc2OCc2ccccc2)cc(C(C)C)c1NC(=O)N=S(N)(=O)c1ccc(CN(C)C)cc1] |

TABLE 1-continued
| Compound | Structure |
|---|---|
| 228 | 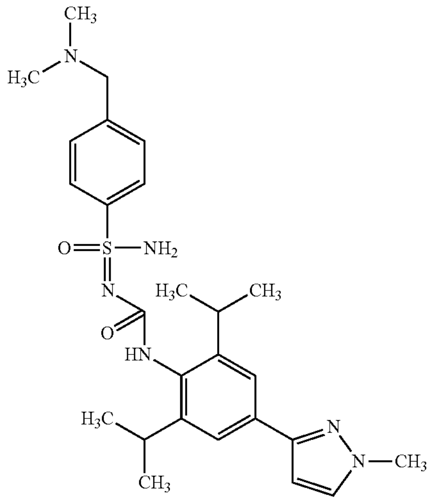 |
| 229 | 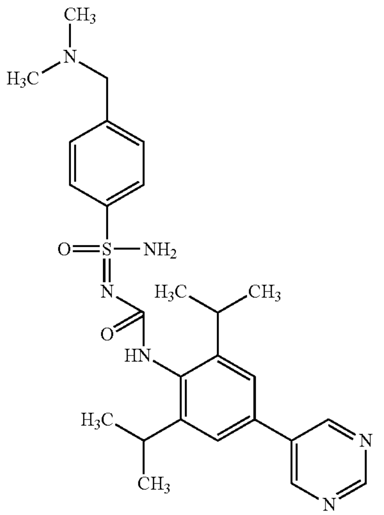 [SMILES: CC(C)c1cc(-c2cncnc2)cc(C(C)C)c1NC(=O)N=S(N)(=O)c1ccc(CN(C)C)cc1] |
| 230 | 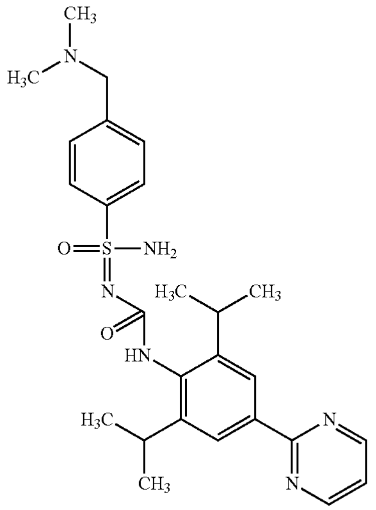 [SMILES: CC(C)c1cc(-c2ncccn2)cc(C(C)C)c1NC(=O)N=S(N)(=O)c1ccc(CN(C)C)cc1] |

TABLE 1-continued
| Compound | Structure |
| --- | --- |
| 231 | 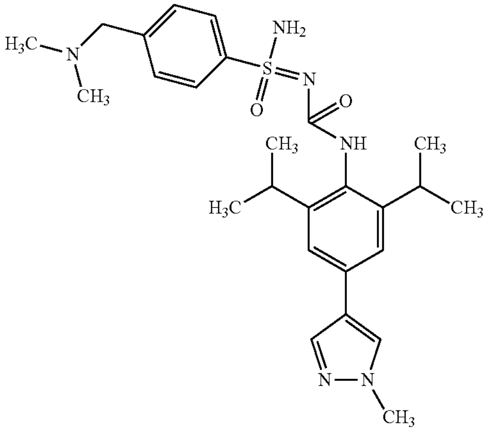 [SMILES: CC(C)c1cc(-c2cnn(C)c2)cc(C(C)C)c1NC(=O)N=S(N)(=O)c1ccc(CN(C)C)cc1] |
| 232 | 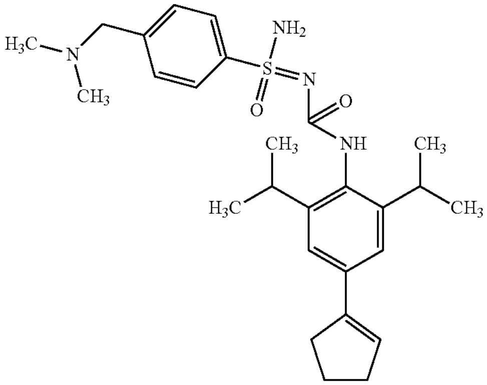 [SMILES: CC(C)c1cc(C2=CCCC2)cc(C(C)C)c1NC(=O)N=S(N)(=O)c1ccc(CN(C)C)cc1] |
| 233 | 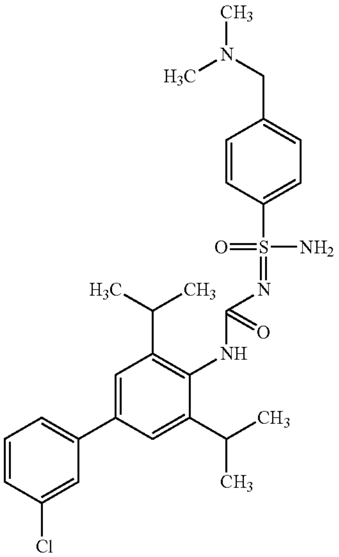 [SMILES: CC(C)c1cc(-c2cccc(Cl)c2)cc(C(C)C)c1NC(=O)N=S(N)(=O)c1ccc(CN(C)C)cc1] |

TABLE 1-continued
| Compound | Structure |
|---|---|
| 234 | 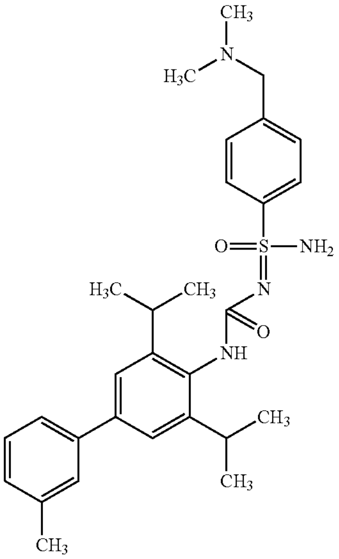 [SMILES: Cc1cccc(-c2cc(C(C)C)c(NC(=O)N=S(N)(=O)c3ccc(CN(C)C)cc3)c(C(C)C)c2)c1] |
| 235 | 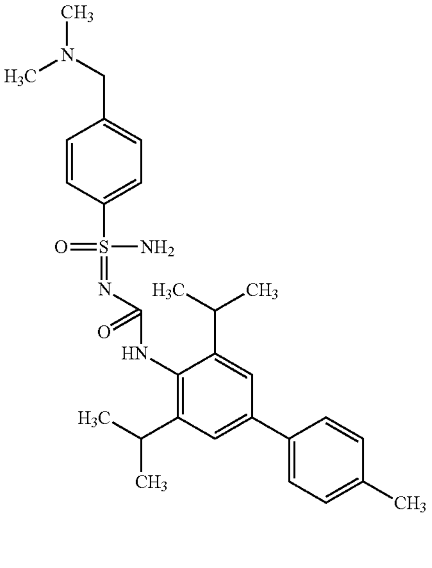 |

TABLE 1-continued
| Compound | Structure |
| --- | --- |
| 236 | 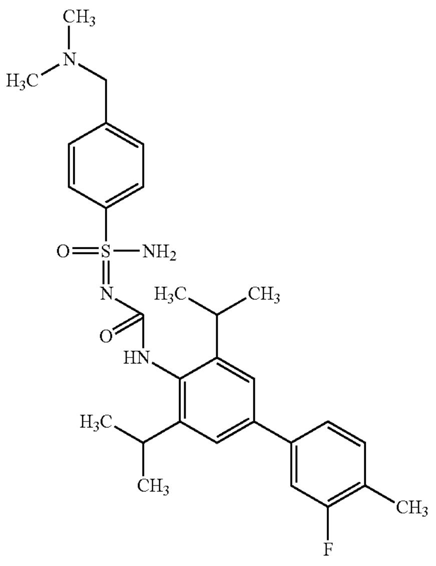 |
| 237 | 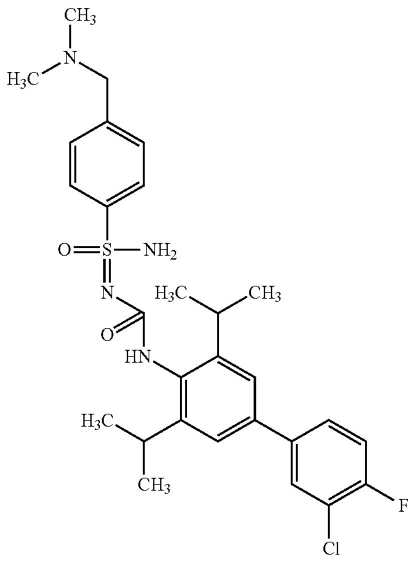 [SMILES: CC(C)c1cc(-c2ccc(F)c(Cl)c2)cc(C(C)C)c1NC(=O)N=S(N)(=O)c1ccc(CN(C)C)cc1] |
| 238 | 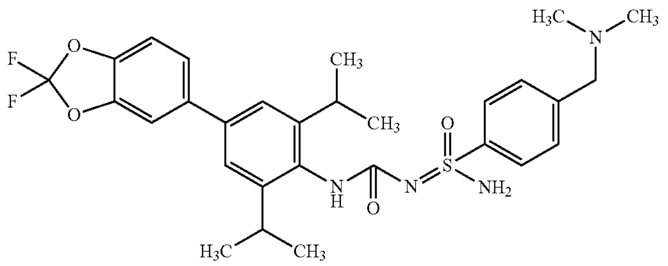 [SMILES: CC(C)c1cc(-c2ccc3c(c2)OC(F)(F)O3)cc(C(C)C)c1NC(=O)N=S(N)(=O)c1ccc(CN(C)C)cc1] |

TABLE 1-continued
| Compound | Structure |
| --- | --- |
| 239 | 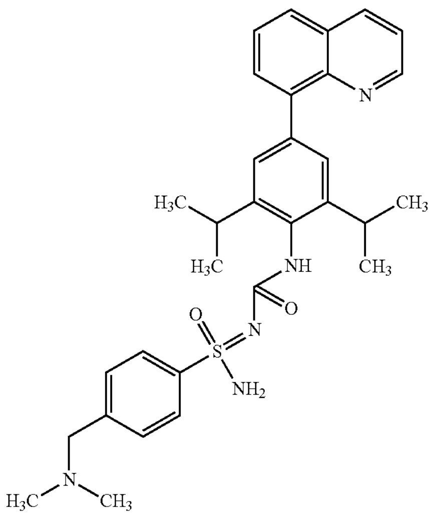 [SMILES: CC(C)c1cc(-c2cccc3cccnc23)cc(C(C)C)c1NC(=O)N=S(N)(=O)c1ccc(CN(C)C)cc1] |
| 240 | 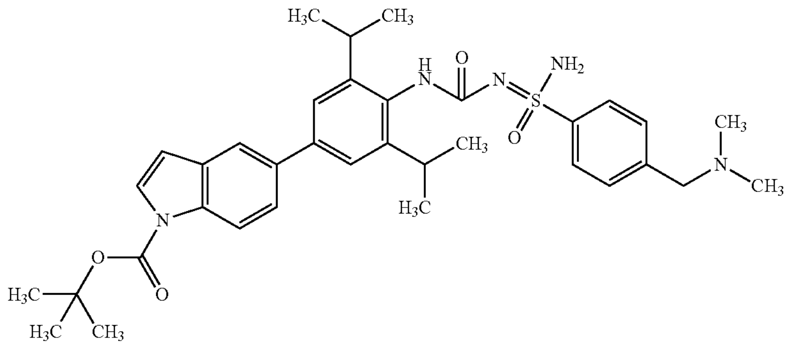 [SMILES: CC(C)c1cc(-c2ccc3c(ccn3C(=O)OC(C)(C)C)c2)cc(C(C)C)c1NC(=O)N=S(N)(=O)c1ccc(CN(C)C)cc1] |
| 241 | 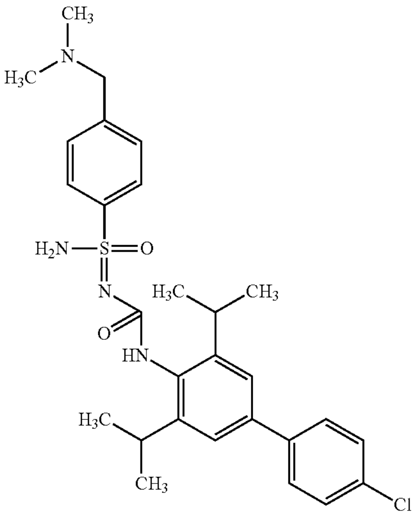 [SMILES: CC(C)c1cc(-c2ccc(Cl)cc2)cc(C(C)C)c1NC(=O)N=S(N)(=O)c1ccc(CN(C)C)cc1] |

TABLE 1-continued
| Compound | Structure |
| --- | --- |
| 242 | 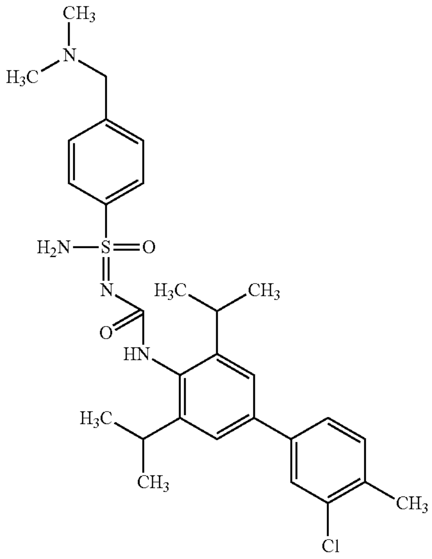 |
| 243 | 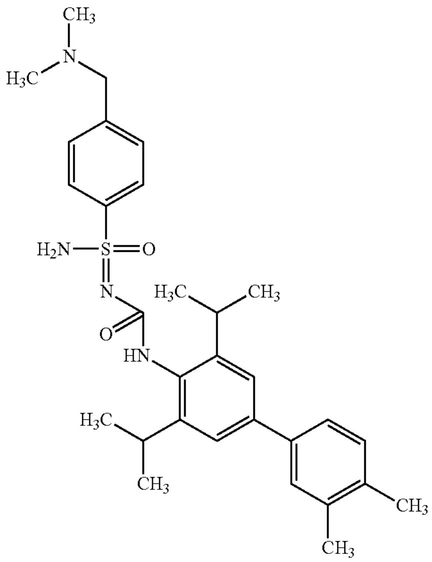 |

TABLE 1-continued
| Compound | Structure |
|---|---|
| 244 | 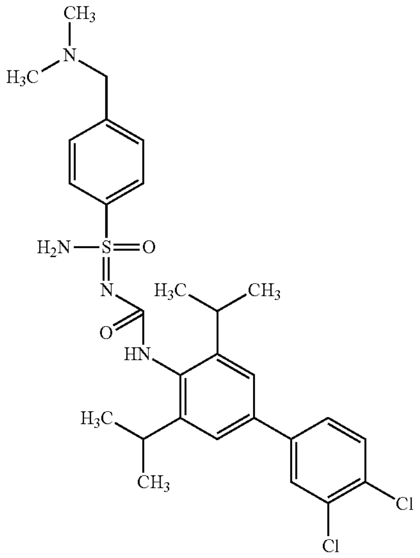 [SMILES: CC(C)c1cc(-c2ccc(Cl)c(Cl)c2)cc(C(C)C)c1NC(=O)N=S(N)(=O)c1ccc(CN(C)C)cc1] |
| 245 | 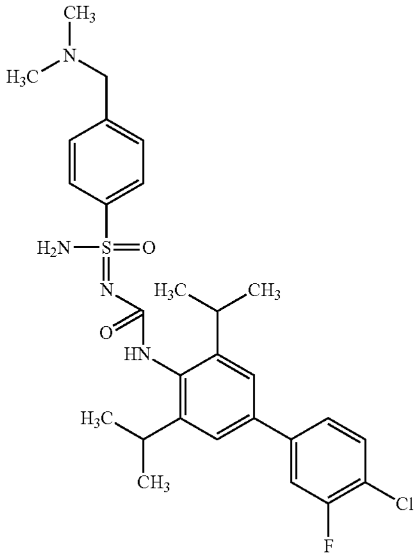 [SMILES: CC(C)c1cc(-c2ccc(Cl)c(F)c2)cc(C(C)C)c1NC(=O)N=S(N)(=O)c1ccc(CN(C)C)cc1] |

TABLE 1-continued
| Compound | Structure |
| --- | --- |
| 246 | 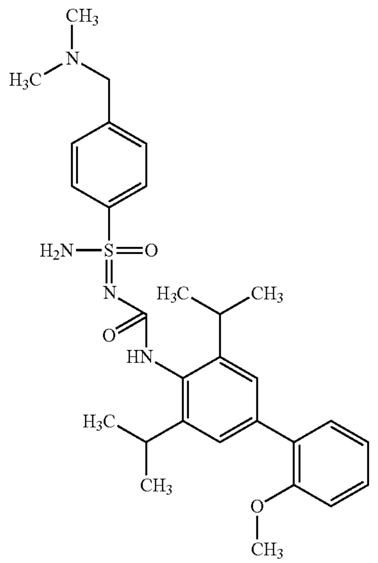 [SMILES: COc1ccccc1-c1cc(C(C)C)c(NC(=O)N=S(N)(=O)c2ccc(CN(C)C)cc2)c(C(C)C)c1] |
| 247 | 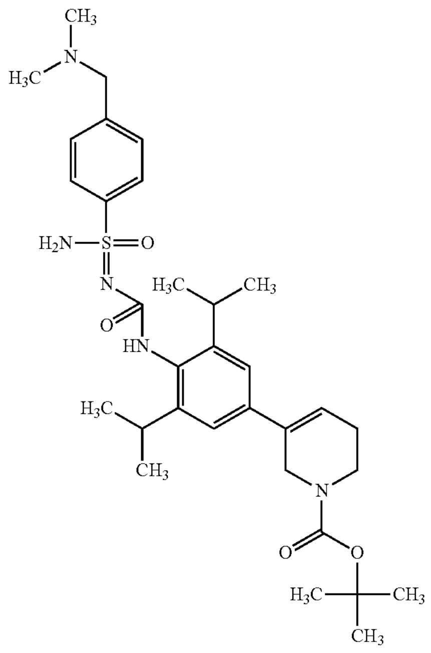 [SMILES: CC(C)c1cc(C2=CCCN(C(=O)OC(C)(C)C)C2)cc(C(C)C)c1NC(=O)N=S(N)(=O)c1ccc(CN(C)C)cc1] |

TABLE 1-continued
| Compound | Structure |
| --- | --- |
| 248 | 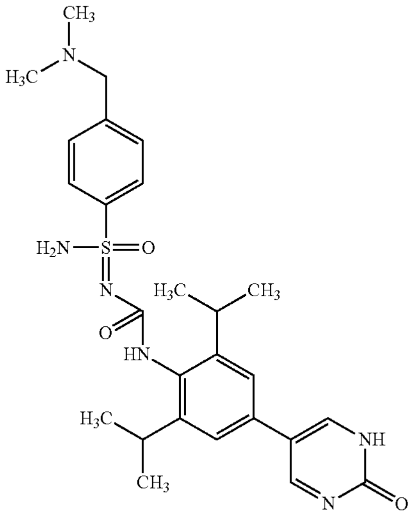 [SMILES: CC(C)c1cc(-c2cnc(=O)[nH]c2)cc(C(C)C)c1NC(=O)N=S(N)(=O)c1ccc(CN(C)C)cc1] |
| 249 | 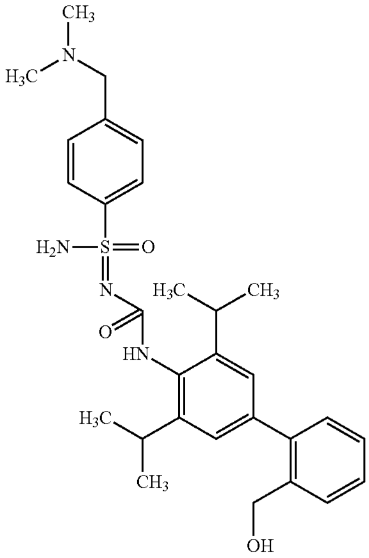 [SMILES: CC(C)c1cc(-c2ccccc2CO)cc(C(C)C)c1NC(=O)N=S(N)(=O)c1ccc(CN(C)C)cc1] |
| 250 | 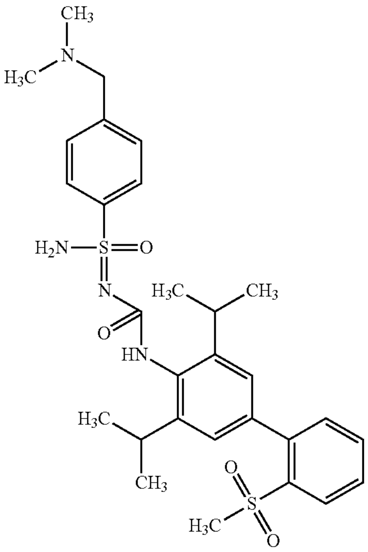 [SMILES: CC(C)c1cc(-c2ccccc2S(C)(=O)=O)cc(C(C)C)c1NC(=O)N=S(N)(=O)c1ccc(CN(C)C)cc1] |

TABLE 1-continued
| Compound | Structure |
|---|---|
| 251 | 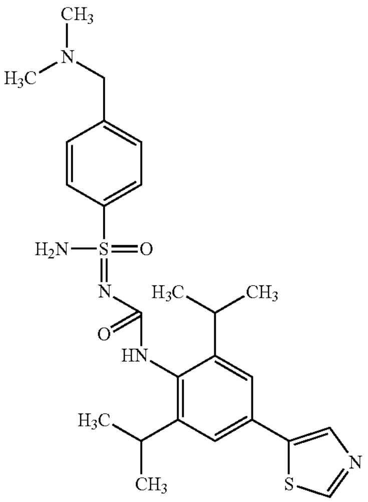 [SMILES: CC(C)c1cc(-c2cncs2)cc(C(C)C)c1NC(=O)N=S(N)(=O)c1ccc(CN(C)C)cc1] |
| 252 | 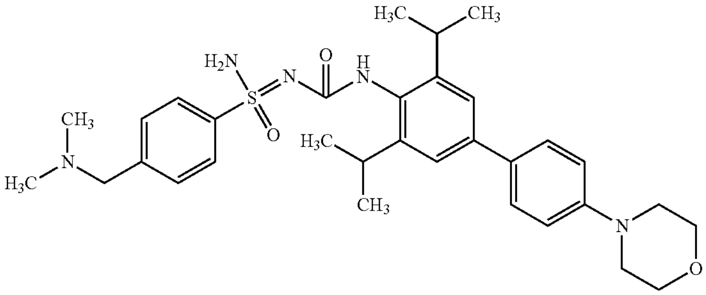 [SMILES: CC(C)c1cc(-c2ccc(N3CCOCC3)cc2)cc(C(C)C)c1NC(=O)N=S(N)(=O)c1ccc(CN(C)C)cc1] |
| 253 | 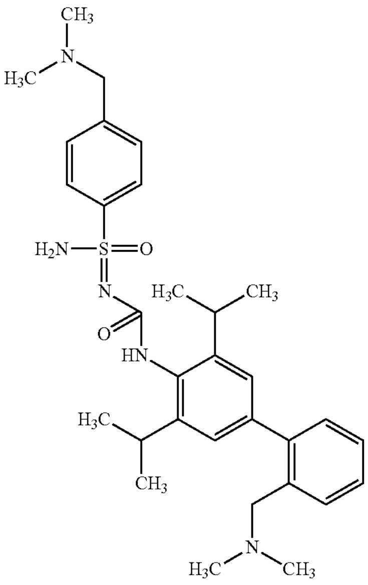 [SMILES: CC(C)c1cc(-c2ccccc2CN(C)C)cc(C(C)C)c1NC(=O)N=S(N)(=O)c1ccc(CN(C)C)cc1] |

TABLE 1-continued
| Compound | Structure |
|---|---|
| 254 | 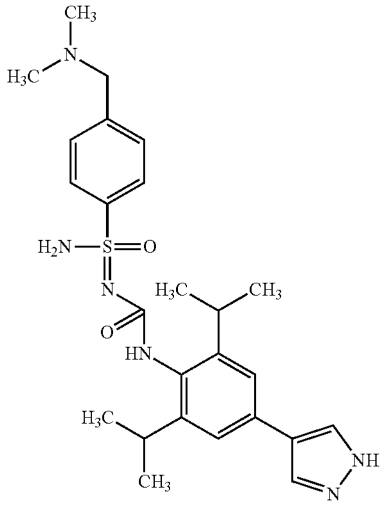 [SMILES: CC(C)c1cc(-c2cn[nH]c2)cc(C(C)C)c1NC(=O)N=S(N)(=O)c1ccc(CN(C)C)cc1] |
| 255 | 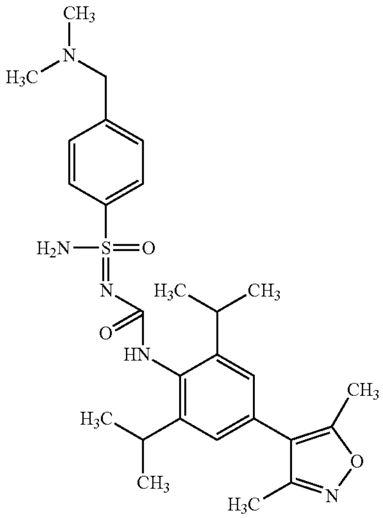 [SMILES: Cc1noc(C)c1-c1cc(C(C)C)c(NC(=O)N=S(N)(=O)c2ccc(CN(C)C)cc2)c(C(C)C)c1] |

TABLE 1-continued
| Compound | Structure |
|---|---|
| 256 | 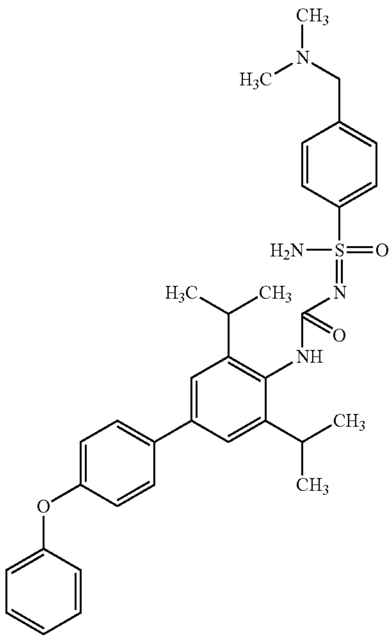 [SMILES: CC(C)c1cc(-c2ccc(Oc3ccccc3)cc2)cc(C(C)C)c1NC(=O)N=S(N)(=O)c1ccc(CN(C)C)cc1] |
| 257 | 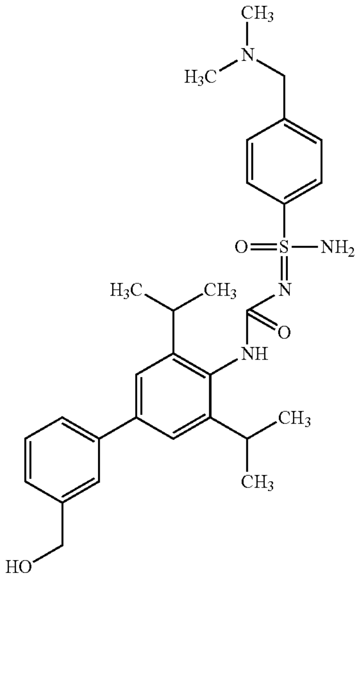 [SMILES: CC(C)c1cc(-c2cccc(CO)c2)cc(C(C)C)c1NC(=O)N=S(N)(=O)c1ccc(CN(C)C)cc1] |

TABLE 1-continued
| Compound | Structure |
|---|---|
| 258 | 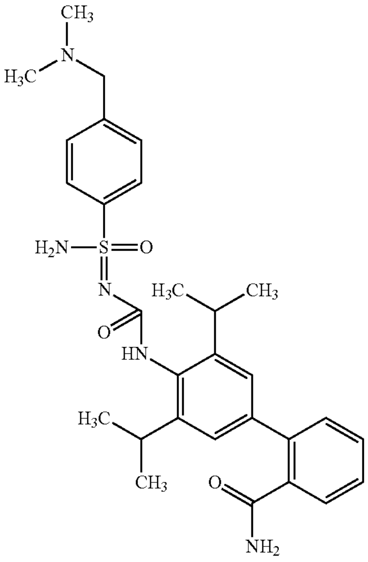 [SMILES: CC(C)c1cc(-c2ccccc2C(N)=O)cc(C(C)C)c1NC(=O)N=S(N)(=O)c1ccc(CN(C)C)cc1] |
| 259 | 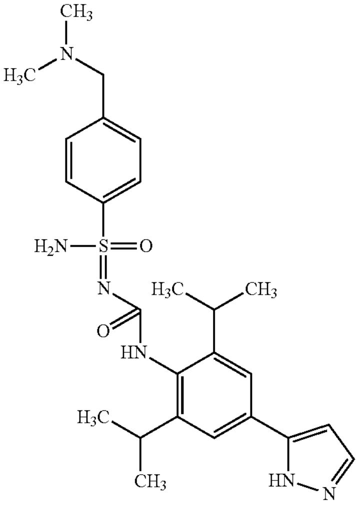 [SMILES: CC(C)c1cc(-c2ccn[nH]2)cc(C(C)C)c1NC(=O)N=S(N)(=O)c1ccc(CN(C)C)cc1] |
| 260 | 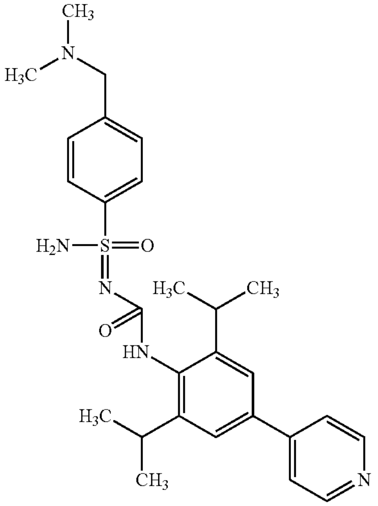 [SMILES: CC(C)c1cc(-c2ccncc2)cc(C(C)C)c1NC(=O)N=S(N)(=O)c1ccc(CN(C)C)cc1] |

TABLE 1-continued
| Compound | Structure |
| --- | --- |
| 261 | 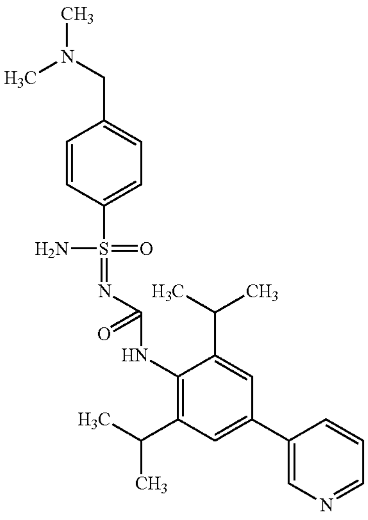 [SMILES: CC(C)c1cc(-c2cccnc2)cc(C(C)C)c1NC(=O)N=S(N)(=O)c1ccc(CN(C)C)cc1] |
| 262 | 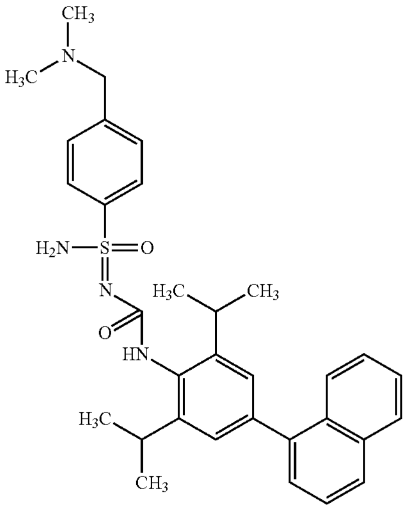 [SMILES: CC(C)c1cc(-c2cccc3ccccc23)cc(C(C)C)c1NC(=O)N=S(N)(=O)c1ccc(CN(C)C)cc1] |
| 263 | 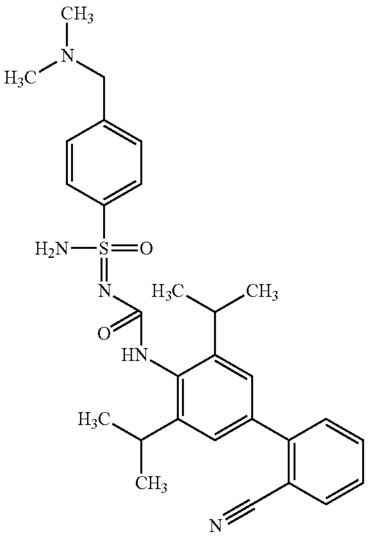 [SMILES: CC(C)c1cc(-c2ccccc2C#N)cc(C(C)C)c1NC(=O)N=S(N)(=O)c1ccc(CN(C)C)cc1] |

TABLE 1-continued
| Compound | Structure |
| --- | --- |
| 264 | 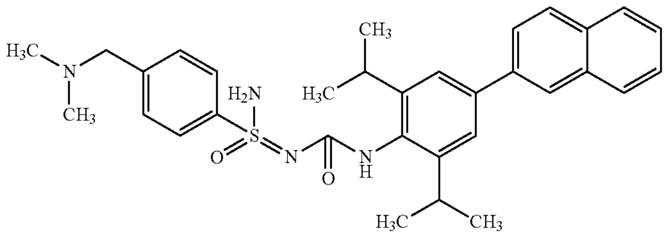 [SMILES: CC(C)c1cc(-c2ccc3ccccc3c2)cc(C(C)C)c1NC(=O)N=S(N)(=O)c1ccc(CN(C)C)cc1] |
| 265 | 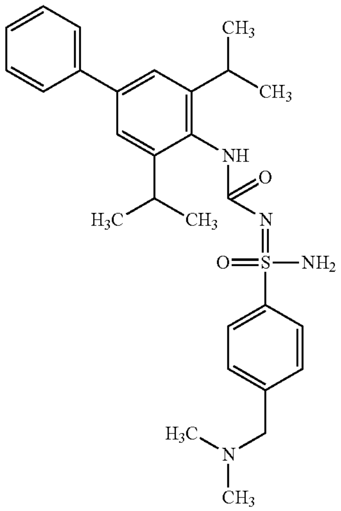 [SMILES: CC(C)c1cc(-c2ccccc2)cc(C(C)C)c1NC(=O)N=S(N)(=O)c1ccc(CN(C)C)cc1] |
| 266 | 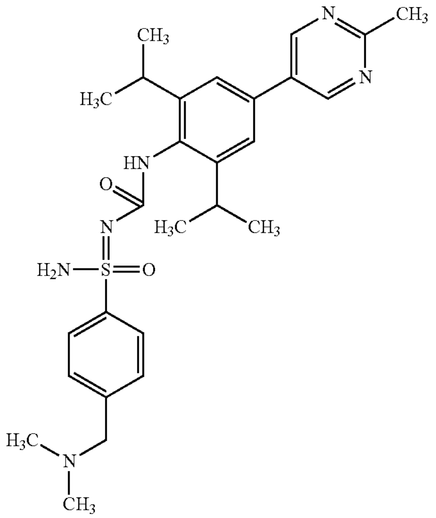 |

TABLE 1-continued
| Compound | Structure |
|---|---|
| 267 | 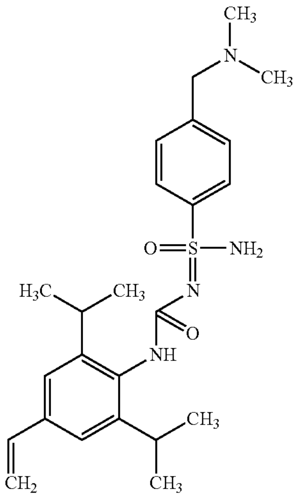 [SMILES: C=Cc1cc(C(C)C)c(NC(=O)N=S(N)(=O)c2ccc(CN(C)C)cc2)c(C(C)C)c1] |
| 268 | 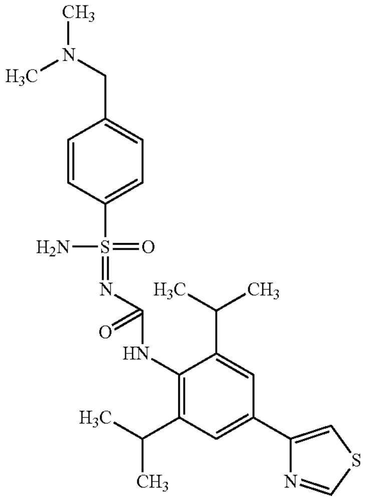 [SMILES: CC(C)c1cc(-c2cscn2)cc(C(C)C)c1NC(=O)N=S(N)(=O)c1ccc(CN(C)C)cc1] |
| 269 | 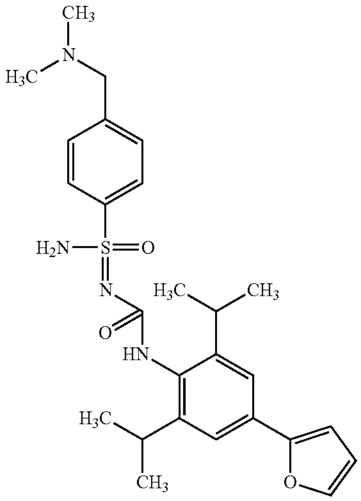 [SMILES: CC(C)c1cc(-c2ccco2)cc(C(C)C)c1NC(=O)N=S(N)(=O)c1ccc(CN(C)C)cc1] |

TABLE 1-continued
| Compound | Structure |
| --- | --- |
| 270 | 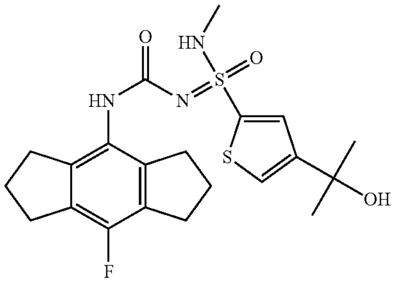 [SMILES: CNS(=O)(=NC(=O)Nc1c2c(c(F)c3c1CCC3)CCC2)c1cc(C(C)(C)O)cs1] |
and pharmaceutically acceptable salts thereof.
In some embodiments, provided herein is a compound that is selected from the group consisting of the compounds in the following table:
| | |
| --- | --- |
| 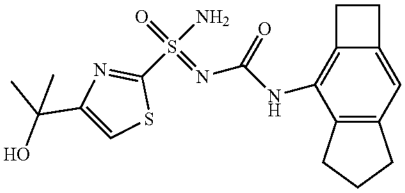 [SMILES: CC(C)(O)c1csc(S(N)(=O)=NC(=O)Nc2c3c(cc4c2CC4)CCC3)n1] | 303 |
| 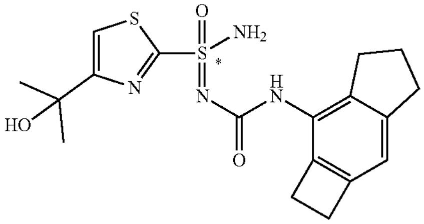 [SMILES: CC(C)(O)c1csc(S(N)(=O)=NC(=O)Nc2c3c(cc4c2CC4)CCC3)n1] | 303a |
| 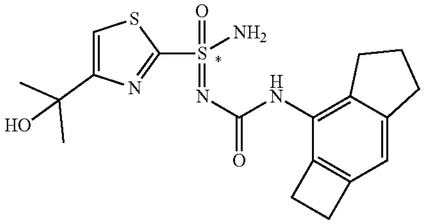 [SMILES: CC(C)(O)c1csc(S(N)(=O)=NC(=O)Nc2c3c(cc4c2CC4)CCC3)n1] | 303b |
| 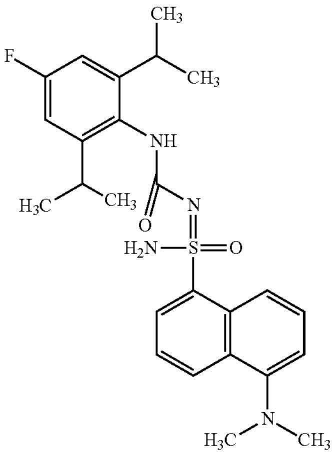 [SMILES: CC(C)c1cc(F)cc(C(C)C)c1NC(=O)N=S(N)(=O)c1cccc2c(N(C)C)cccc12] | 306 |

-continued
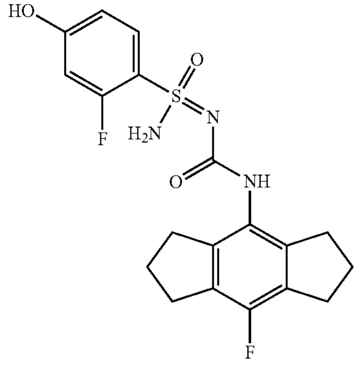 [SMILES: NS(=O)(=NC(=O)Nc1c2c(c(F)c3c1CCC3)CCC2)c1ccc(O)cc1F]
307
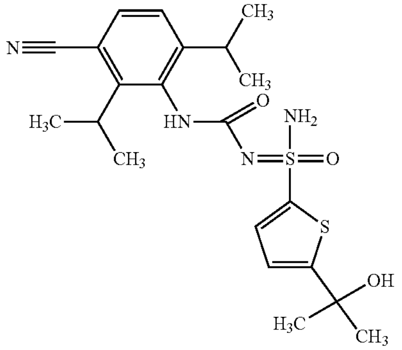 [SMILES: CC(C)c1ccc(C#N)c(C(C)C)c1NC(=O)N=S(N)(=O)c1ccc(C(C)(C)O)s1]
308
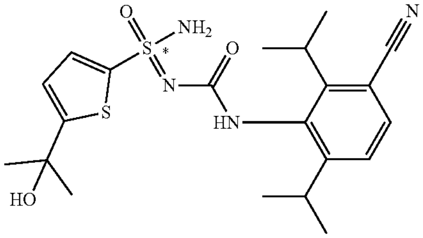 [SMILES: CC(C)c1ccc(C#N)c(C(C)C)c1NC(=O)N=S(N)(=O)c1ccc(C(C)(C)O)s1]
308a
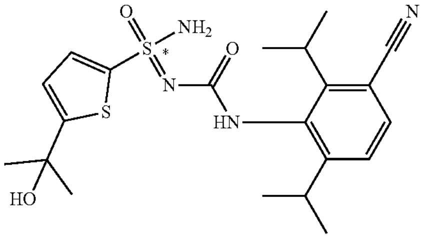 [SMILES: CC(C)c1ccc(C#N)c(C(C)C)c1NC(=O)N=S(N)(=O)c1ccc(C(C)(C)O)s1]
308b
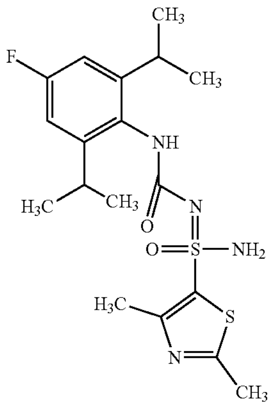 [SMILES: Cc1nc(C)c(S(N)(=O)=NC(=O)Nc2c(C(C)C)cc(F)cc2C(C)C)s1]
309

-continued
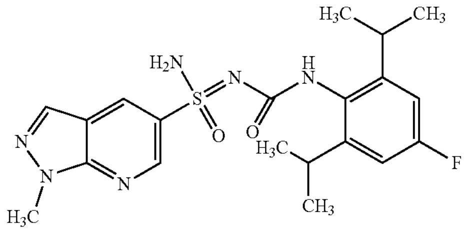 [SMILES: CC(C)c1cc(F)cc(C(C)C)c1NC(=O)N=S(N)(=O)c1cnc2c(cnn2C)c1]
310
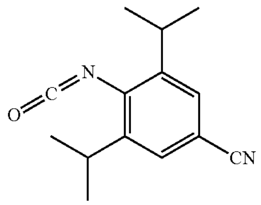 [SMILES: CC(C)c1cc(C#N)cc(C(C)C)c1N=C=O]
311
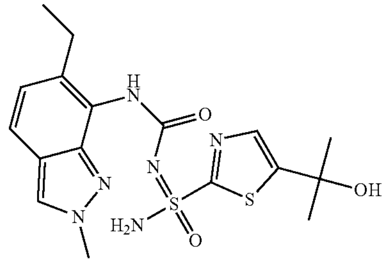 [SMILES: CCc1ccc2cn(C)nc2c1NC(=O)N=S(N)(=O)c1ncc(C(C)(C)O)s1]
312
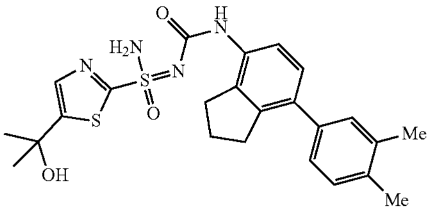 [SMILES: Cc1ccc(-c2ccc(NC(=O)N=S(N)(=O)c3ncc(C(C)(C)O)s3)c3c2CCC3)cc1C]
313
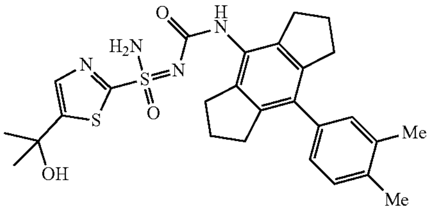 [SMILES: Cc1ccc(-c2c3c(c(NC(=O)N=S(N)(=O)c4ncc(C(C)(C)O)s4)c4c2CCC4)CCC3)cc1C]
314
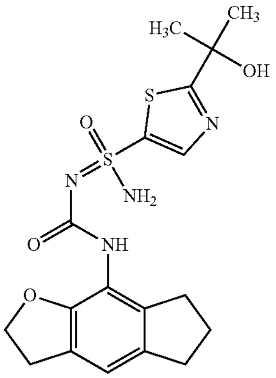 [SMILES: CC(C)(O)c1ncc(S(N)(=O)=NC(=O)Nc2c3c(cc4c2OCC4)CCC3)s1]
315

-continued
315b
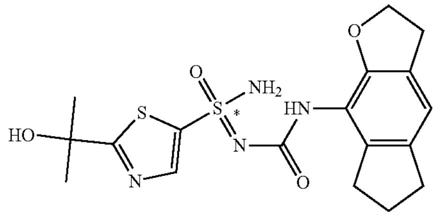 [SMILES: CC(C)(O)c1ncc(S(N)(=O)=NC(=O)Nc2c3c(cc4c2OCC4)CCC3)s1]
315a
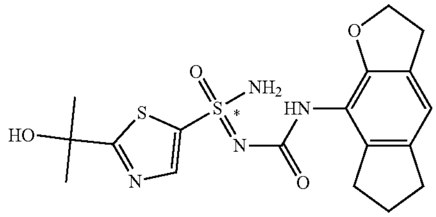 [SMILES: CC(C)(O)c1ncc(S(N)(=O)=NC(=O)Nc2c3c(cc4c2OCC4)CCC3)s1]
316
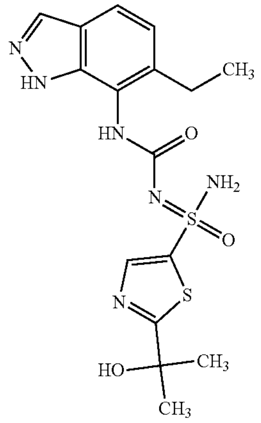 [SMILES: CCc1ccc2cn[nH]c2c1NC(=O)N=S(N)(=O)c1cnc(C(C)(C)O)s1]
316a
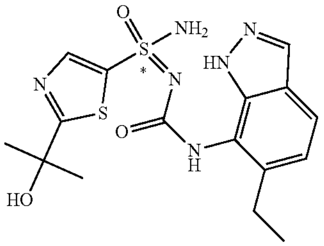 [SMILES: CCc1ccc2cn[nH]c2c1NC(=O)N=S(N)(=O)c1cnc(C(C)(C)O)s1]
316b
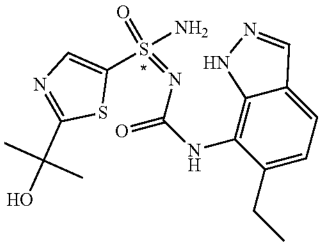 [SMILES: CCc1ccc2cn[nH]c2c1NC(=O)N=S(N)(=O)c1cnc(C(C)(C)O)s1]
317
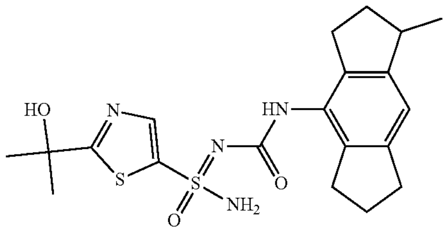 [SMILES: CC1CCc2c1cc1c(c2NC(=O)N=S(N)(=O)c2cnc(C(C)(C)O)s2)CCC1]

-continued
317ab
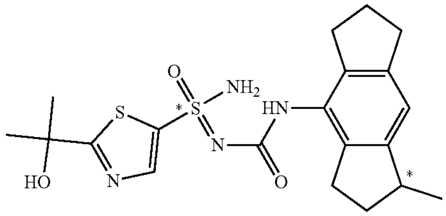 [SMILES: CC1CCc2c1cc1c(c2NC(=O)N=S(N)(=O)c2cnc(C(C)(C)O)s2)CCC1]
317aa
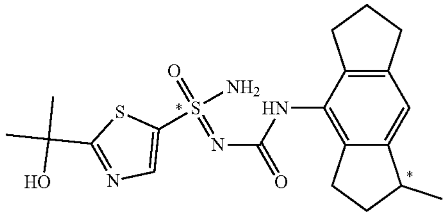 [SMILES: CC1CCc2c1cc1c(c2NC(=O)N=S(N)(=O)c2cnc(C(C)(C)O)s2)CCC1]
317bb
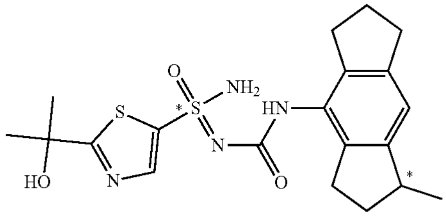 [SMILES: CC1CCc2c1cc1c(c2NC(=O)N=S(N)(=O)c2cnc(C(C)(C)O)s2)CCC1]
317ba
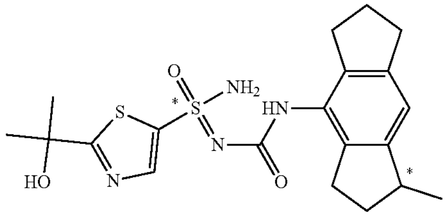 [SMILES: CC1CCc2c1cc1c(c2NC(=O)N=S(N)(=O)c2cnc(C(C)(C)O)s2)CCC1]
318
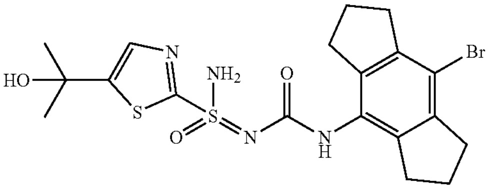 [SMILES: CC(C)(O)c1cnc(S(N)(=O)=NC(=O)Nc2c3c(c(Br)c4c2CCC4)CCC3)s1]
318a
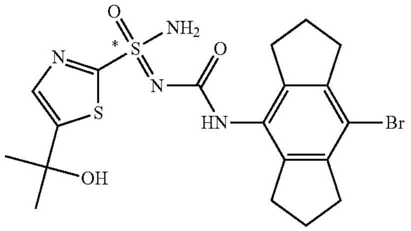 [SMILES: CC(C)(O)c1cnc(S(N)(=O)=NC(=O)Nc2c3c(c(Br)c4c2CCC4)CCC3)s1]
318b
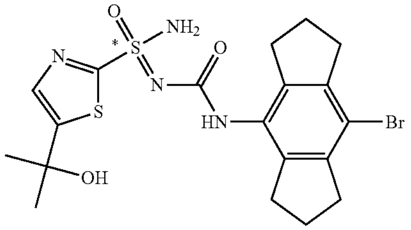 [SMILES: CC(C)(O)c1cnc(S(N)(=O)=NC(=O)Nc2c3c(c(Br)c4c2CCC4)CCC3)s1]

-continued
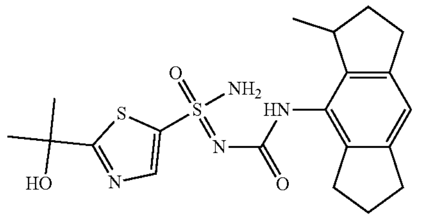 [SMILES: CC1CCc2cc3c(c(NC(=O)N=S(N)(=O)c4cnc(C(C)(C)O)s4)c21)CCC3]
319
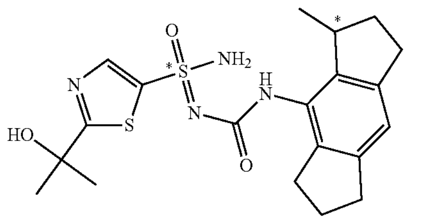 [SMILES: CC1CCc2cc3c(c(NC(=O)N=S(N)(=O)c4cnc(C(C)(C)O)s4)c21)CCC3]
319ab
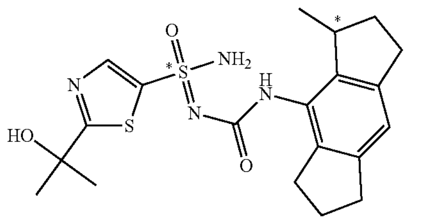 [SMILES: CC1CCc2cc3c(c(NC(=O)N=S(N)(=O)c4cnc(C(C)(C)O)s4)c21)CCC3]
319ba
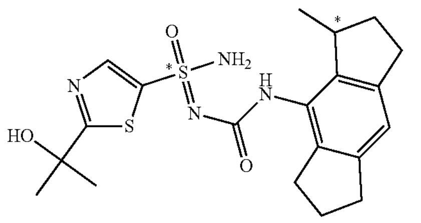 [SMILES: CC1CCc2cc3c(c(NC(=O)N=S(N)(=O)c4cnc(C(C)(C)O)s4)c21)CCC3]
319aa
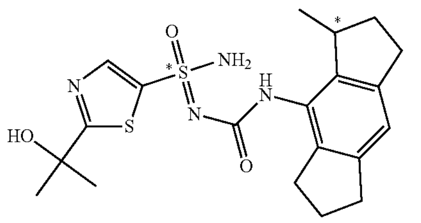 [SMILES: CC1CCc2cc3c(c(NC(=O)N=S(N)(=O)c4cnc(C(C)(C)O)s4)c21)CCC3]
319bb
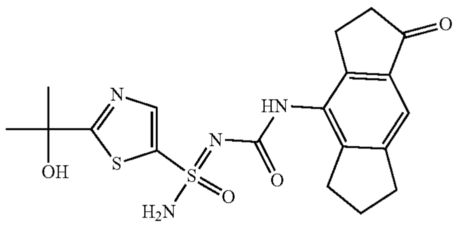 [SMILES: CC(C)(O)c1ncc(S(N)(=O)=NC(=O)Nc2c3c(cc4c2CCC4=O)CCC3)s1]
320
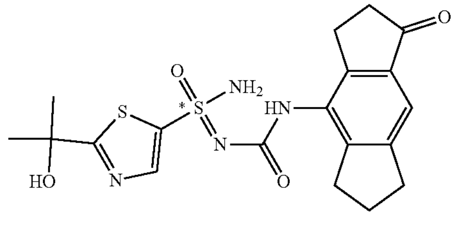 [SMILES: CC(C)(O)c1ncc(S(N)(=O)=NC(=O)Nc2c3c(cc4c2CCC4=O)CCC3)s1]
320a -continued
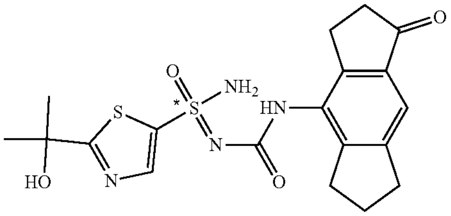 [SMILES: CC(C)(O)c1ncc(S(N)(=O)=NC(=O)Nc2c3c(cc4c2CCC4=O)CCC3)s1]
320b
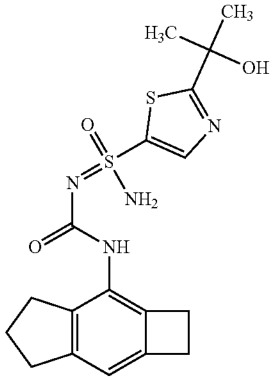 [SMILES: CC(C)(O)c1ncc(S(N)(=O)=NC(=O)Nc2c3c(cc4c2CC4)CCC3)s1]
321
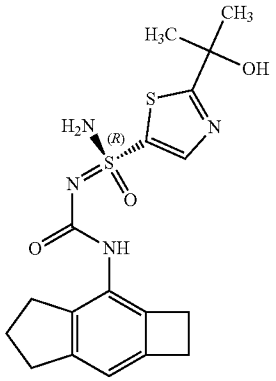
321b
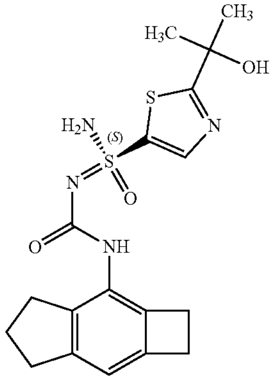
321a
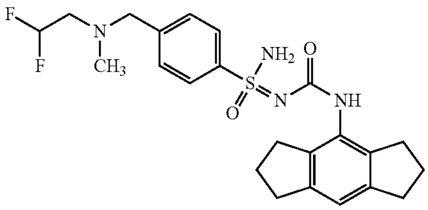 [SMILES: CN(Cc1ccc(S(N)(=O)=NC(=O)Nc2c3c(cc4c2CCC4)CCC3)cc1)CC(F)F]
322

-continued
323
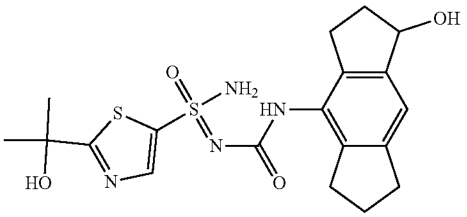 [SMILES: CC(C)(O)c1ncc(S(N)(=O)=NC(=O)Nc2c3c(cc4c2CCC4O)CCC3)s1]
323ab
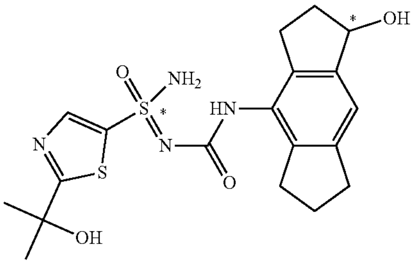 [SMILES: CC(C)(O)c1ncc(S(N)(=O)=NC(=O)Nc2c3c(cc4c2CCC4O)CCC3)s1]
323aa
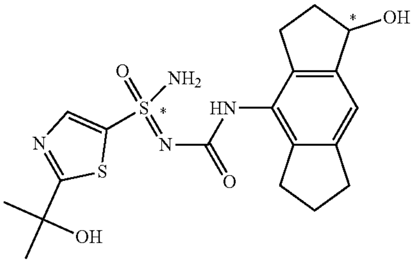 [SMILES: CC(C)(O)c1ncc(S(N)(=O)=NC(=O)Nc2c3c(cc4c2CCC4O)CCC3)s1]
323bb
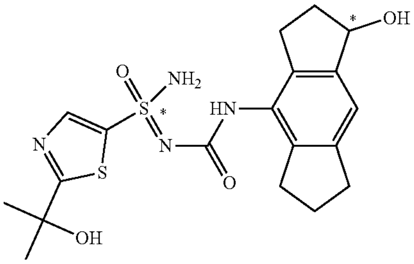 [SMILES: CC(C)(O)c1ncc(S(N)(=O)=NC(=O)Nc2c3c(cc4c2CCC4O)CCC3)s1]
323ba
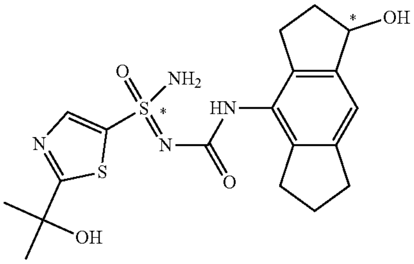 [SMILES: CC(C)(O)c1ncc(S(N)(=O)=NC(=O)Nc2c3c(cc4c2CCC4O)CCC3)s1]

-continued
324
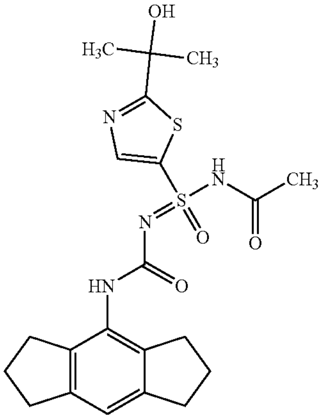 [SMILES: CC(=O)NS(=O)(=NC(=O)Nc1c2c(cc3c1CCC3)CCC2)c1cnc(C(C)(C)O)s1]
325
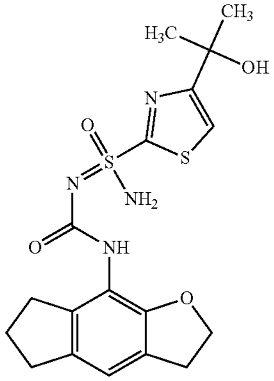 [SMILES: CC(C)(O)c1csc(S(N)(=O)=NC(=O)Nc2c3c(cc4c2OCC4)CCC3)n1]
325a
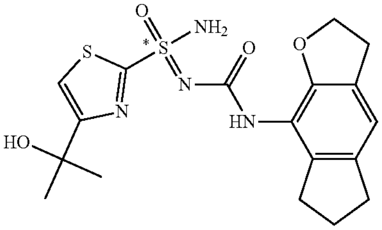 [SMILES: CC(C)(O)c1csc(S(N)(=O)=NC(=O)Nc2c3c(cc4c2OCC4)CCC3)n1]
325b
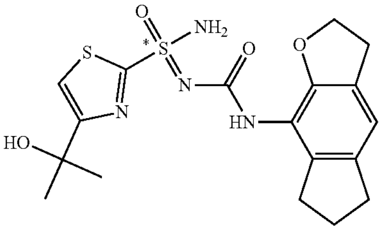

-continued
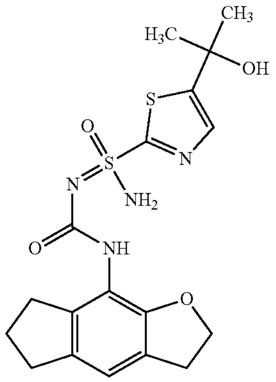 [SMILES: CC(C)(O)c1cnc(S(N)(=O)=NC(=O)Nc2c3c(cc4c2OCC4)CCC3)s1]
326
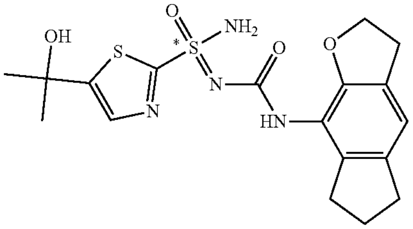 [SMILES: CC(C)(O)c1cnc(S(N)(=O)=NC(=O)Nc2c3c(cc4c2OCC4)CCC3)s1]
326b
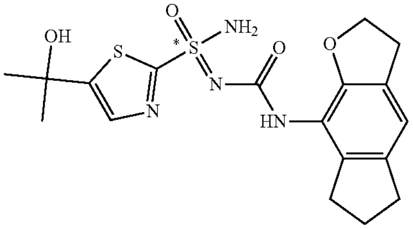 [SMILES: CC(C)(O)c1cnc(S(N)(=O)=NC(=O)Nc2c3c(cc4c2OCC4)CCC3)s1]
326a
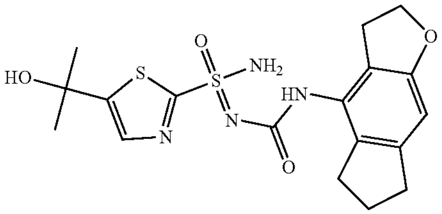 [SMILES: CC(C)(O)c1cnc(S(N)(=O)=NC(=O)Nc2c3c(cc4c2CCO4)CCC3)s1]
327
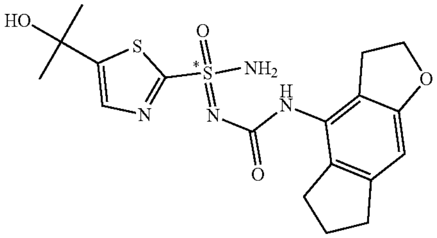 [SMILES: CC(C)(O)c1cnc(S(N)(=O)=NC(=O)Nc2c3c(cc4c2CCO4)CCC3)s1]
328b
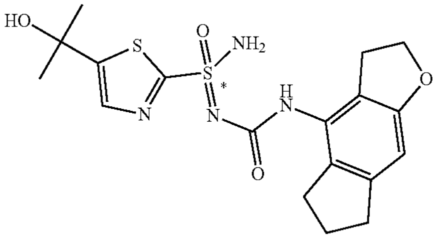 [SMILES: CC(C)(O)c1cnc(S(N)(=O)=NC(=O)Nc2c3c(cc4c2CCO4)CCC3)s1]
328a -continued
329
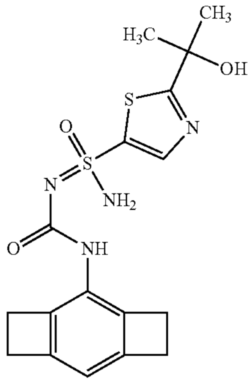 [SMILES: CC(C)(O)c1ncc(S(N)(=O)=NC(=O)Nc2c3c(cc4c2CC4)CC3)s1]
329a
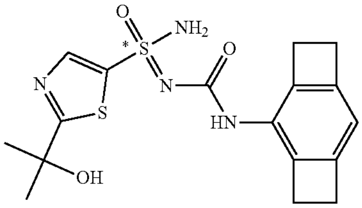 [SMILES: CC(C)(O)c1ncc(S(N)(=O)=NC(=O)Nc2c3c(cc4c2CC4)CC3)s1]
329b
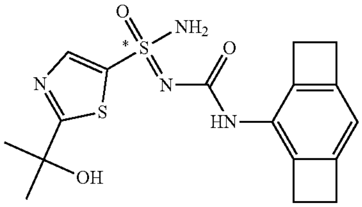 [SMILES: CC(C)(O)c1ncc(S(N)(=O)=NC(=O)Nc2c3c(cc4c2CC4)CC3)s1]
330
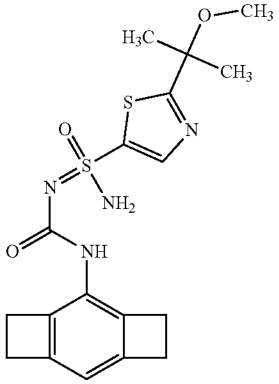 [SMILES: COC(C)(C)c1ncc(S(N)(=O)=NC(=O)Nc2c3c(cc4c2CC4)CC3)s1]
330a
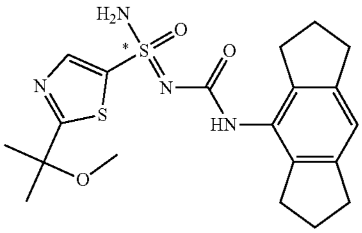 [SMILES: COC(C)(C)c1ncc(S(N)(=O)=NC(=O)Nc2c3c(cc4c2CCC4)CCC3)s1]

-continued
330b
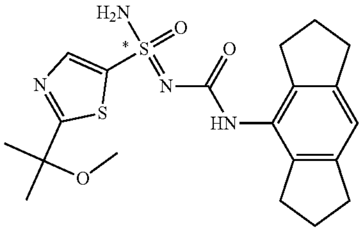 [SMILES: COC(C)(C)c1ncc(S(N)(=O)=NC(=O)Nc2c3c(cc4c2CCC4)CCC3)s1]
331
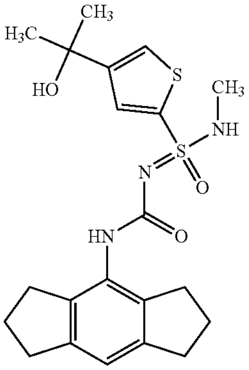 [SMILES: CNS(=O)(=NC(=O)Nc1c2c(cc3c1CCC3)CCC2)c1cc(C(C)(C)O)cs1]
332
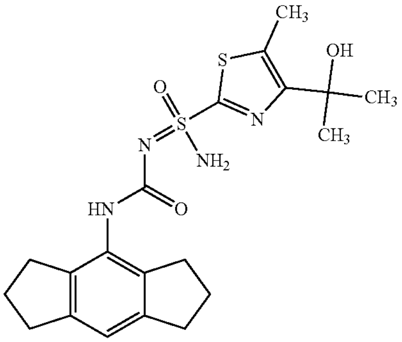 [SMILES: Cc1sc(S(N)(=O)=NC(=O)Nc2c3c(cc4c2CCC4)CCC3)nc1C(C)(C)O]
332a
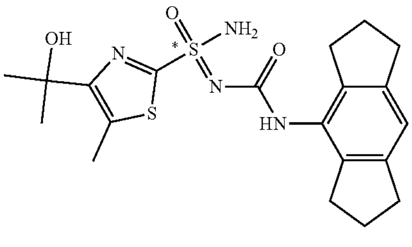 [SMILES: Cc1sc(S(N)(=O)=NC(=O)Nc2c3c(cc4c2CCC4)CCC3)nc1C(C)(C)O]
332b
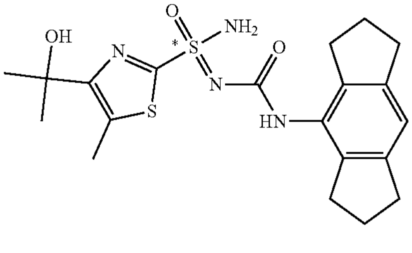 [SMILES: Cc1sc(S(N)(=O)=NC(=O)Nc2c3c(cc4c2CCC4)CCC3)nc1C(C)(C)O]

-continued
333
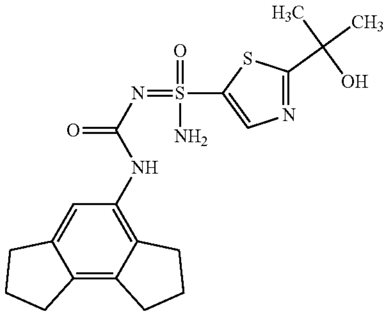 [SMILES: CC(C)(O)c1ncc(S(N)(=O)=NC(=O)Nc2cc3c(c4c2CCC4)CCC3)s1]
333a
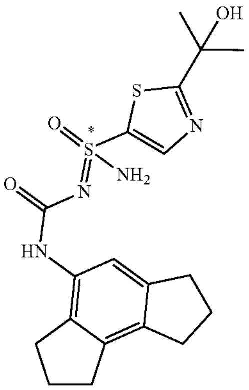 [SMILES: CC(C)(O)c1ncc(S(N)(=O)=NC(=O)Nc2cc3c(c4c2CCC4)CCC3)s1]
333b
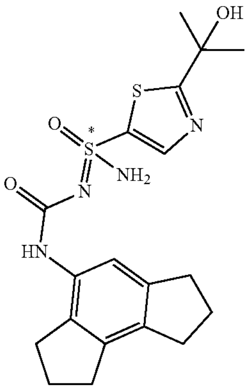 [SMILES: CC(C)(O)c1ncc(S(N)(=O)=NC(=O)Nc2cc3c(c4c2CCC4)CCC3)s1]
334
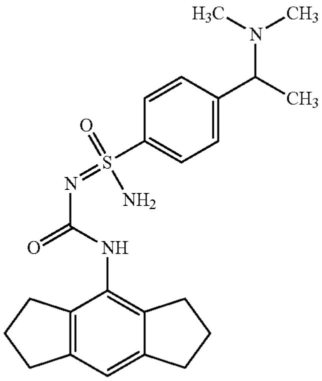 [SMILES: CC(c1ccc(S(N)(=O)=NC(=O)Nc2c3c(cc4c2CCC4)CCC3)cc1)N(C)C]

-continued
334ba
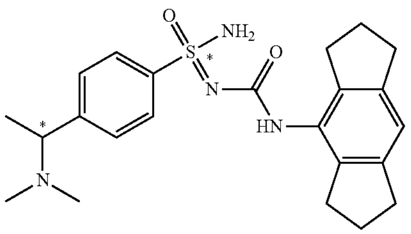 [SMILES: CC(c1ccc(S(N)(=O)=NC(=O)Nc2c3c(cc4c2CCC4)CCC3)cc1)N(C)C]
334bb
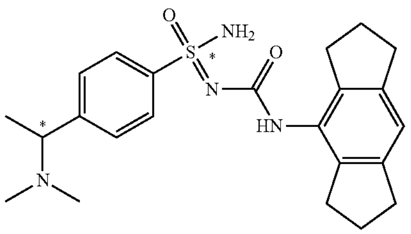 [SMILES: CC(c1ccc(S(N)(=O)=NC(=O)Nc2c3c(cc4c2CCC4)CCC3)cc1)N(C)C]
334aa
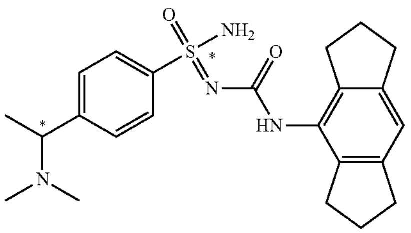
334ab
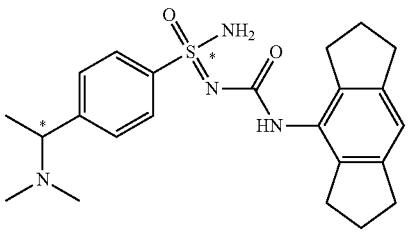
334b
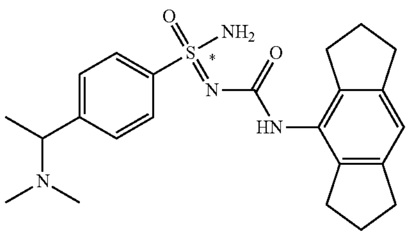
334a
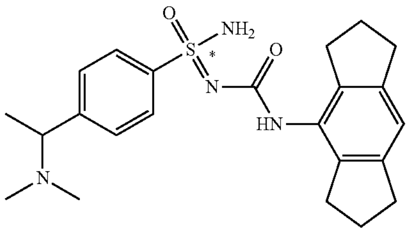

-continued
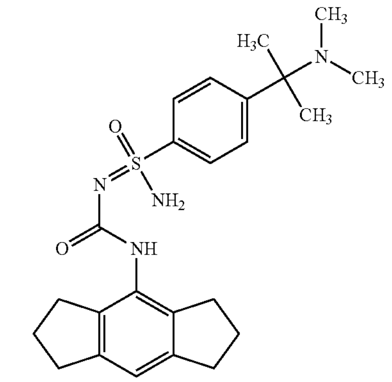 [SMILES: CN(C)C(C)(C)c1ccc(S(N)(=O)=NC(=O)Nc2c3c(cc4c2CCC4)CCC3)cc1]
335
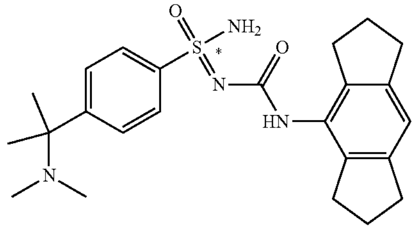 [SMILES: CN(C)C(C)(C)c1ccc(S(N)(=O)=NC(=O)Nc2c3c(cc4c2CCC4)CCC3)cc1]
335b
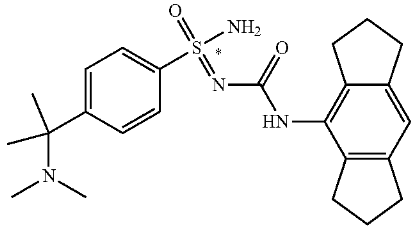
335a
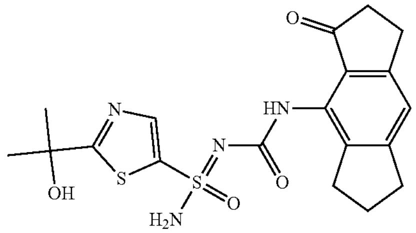 [SMILES: CC(C)(O)c1ncc(S(N)(=O)=NC(=O)Nc2c3c(cc4c2C(=O)CC4)CCC3)s1]
336
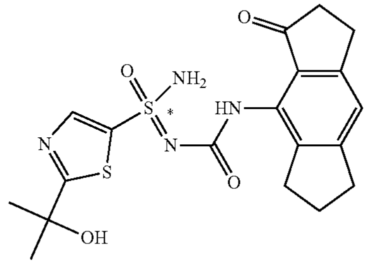 [SMILES: CC(C)(O)c1ncc(S(N)(=O)=NC(=O)Nc2c3c(cc4c2C(=O)CC4)CCC3)s1]
336a
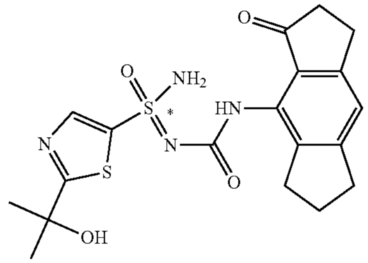 [SMILES: CC(C)(O)c1ncc(S(N)(=O)=NC(=O)Nc2c3c(cc4c2C(=O)CC4)CCC3)s1]
336b -continued
337
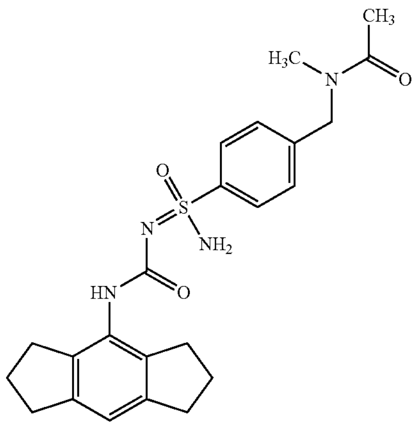 [SMILES: CC(=O)N(C)Cc1ccc(S(N)(=O)=NC(=O)Nc2c3c(cc4c2CCC4)CCC3)cc1]
337a
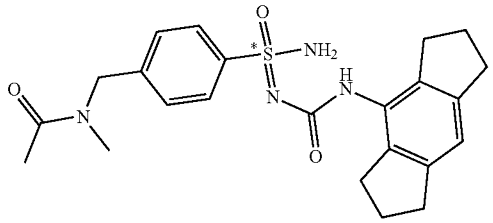 [SMILES: CC(=O)N(C)Cc1ccc(S(N)(=O)=NC(=O)Nc2c3c(cc4c2CCC4)CCC3)cc1]
337b
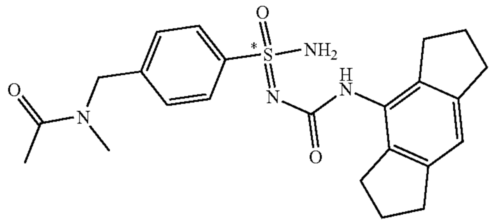 [SMILES: CC(=O)N(C)Cc1ccc(S(N)(=O)=NC(=O)Nc2c3c(cc4c2CCC4)CCC3)cc1]
338
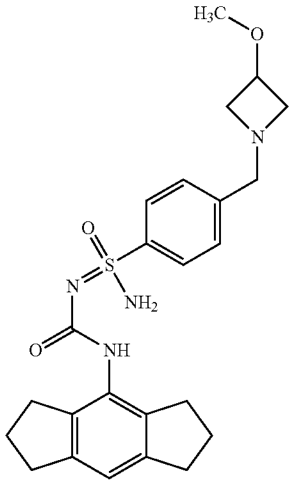 [SMILES: COC1CN(Cc2ccc(S(N)(=O)=NC(=O)Nc3c4c(cc5c3CCC5)CCC4)cc2)C1]
338a
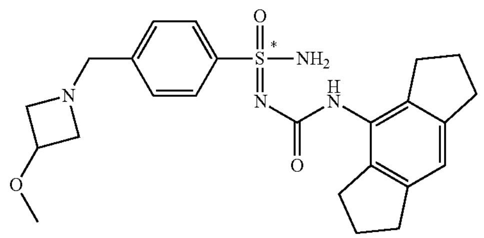 [SMILES: COC1CN(Cc2ccc(S(N)(=O)=NC(=O)Nc3c4c(cc5c3CCC5)CCC4)cc2)C1]

-continued
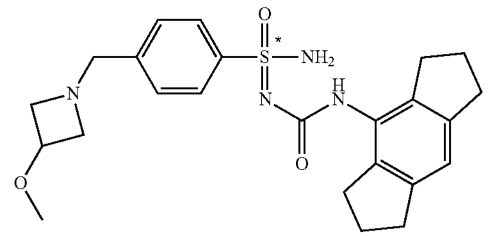 [SMILES: COC1CN(Cc2ccc(S(N)(=O)=NC(=O)Nc3c4c(cc5c3CCC5)CCC4)cc2)C1]
338b
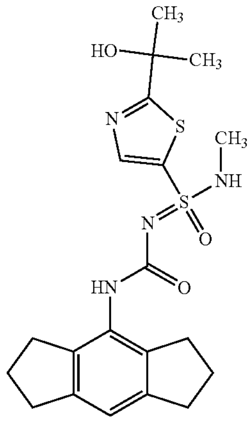 [SMILES: CNS(=O)(=NC(=O)Nc1c2c(cc3c1CCC3)CCC2)c1cnc(C(C)(C)O)s1]
339
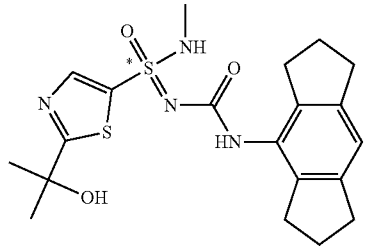 [SMILES: CNS(=O)(=NC(=O)Nc1c2c(cc3c1CCC3)CCC2)c1cnc(C(C)(C)O)s1]
339a
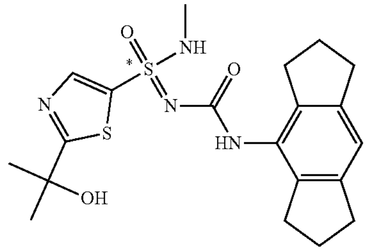 [SMILES: CNS(=O)(=NC(=O)Nc1c2c(cc3c1CCC3)CCC2)c1cnc(C(C)(C)O)s1]
339b
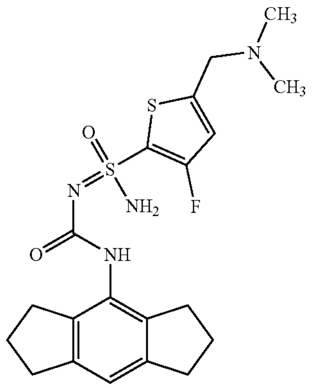 [SMILES: CN(C)Cc1cc(F)c(S(N)(=O)=NC(=O)Nc2c3c(cc4c2CCC4)CCC3)s1]
340

-continued
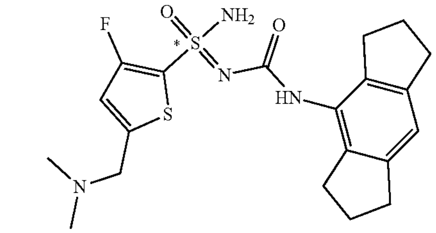 [SMILES: CN(C)Cc1cc(F)c(S(N)(=O)=NC(=O)Nc2c3c(cc4c2CCC4)CCC3)s1]
340a
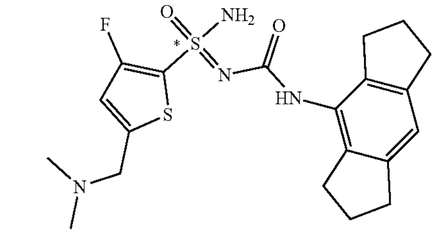 [SMILES: CN(C)Cc1cc(F)c(S(N)(=O)=NC(=O)Nc2c3c(cc4c2CCC4)CCC3)s1]
340b
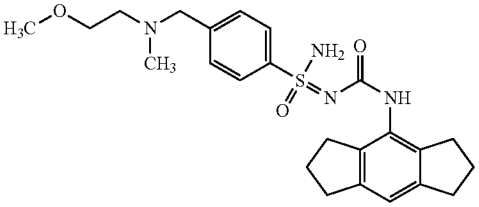 [SMILES: COCCN(C)Cc1ccc(S(N)(=O)=NC(=O)Nc2c3c(cc4c2CCC4)CCC3)cc1]
341
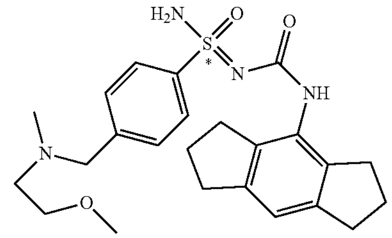 [SMILES: COCCN(C)Cc1ccc(S(N)(=O)=NC(=O)Nc2c3c(cc4c2CCC4)CCC3)cc1]
341b
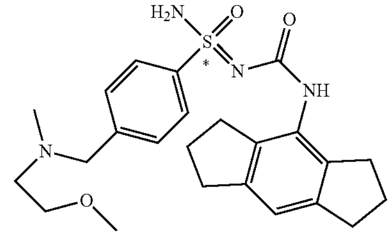 [SMILES: COCCN(C)Cc1ccc(S(N)(=O)=NC(=O)Nc2c3c(cc4c2CCC4)CCC3)cc1]
341a
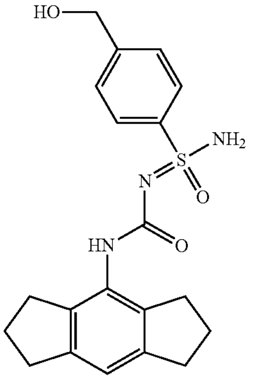 [SMILES: NS(=O)(=NC(=O)Nc1c2c(cc3c1CCC3)CCC2)c1ccc(CO)cc1]
342

-continued
343
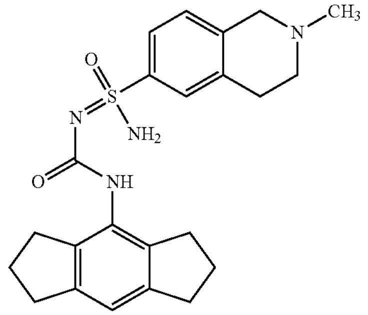 [SMILES: CN1CCc2cc(S(N)(=O)=NC(=O)Nc3c4c(cc5c3CCC5)CCC4)ccc2C1]
343a
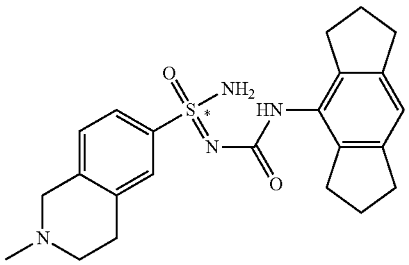 [SMILES: CN1CCc2cc(S(N)(=O)=NC(=O)Nc3c4c(cc5c3CCC5)CCC4)ccc2C1]
343b
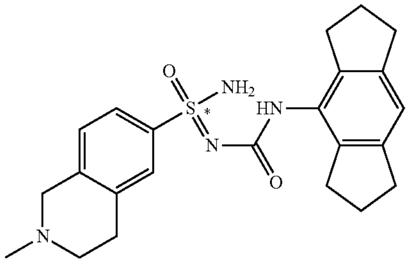 [SMILES: CN1CCc2cc(S(N)(=O)=NC(=O)Nc3c4c(cc5c3CCC5)CCC4)ccc2C1]
344
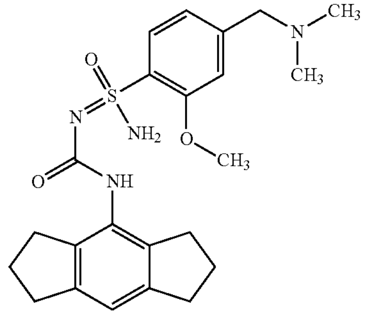 [SMILES: COc1cc(CN(C)C)ccc1S(N)(=O)=NC(=O)Nc1c2c(cc3c1CCC3)CCC2]

-continued
345
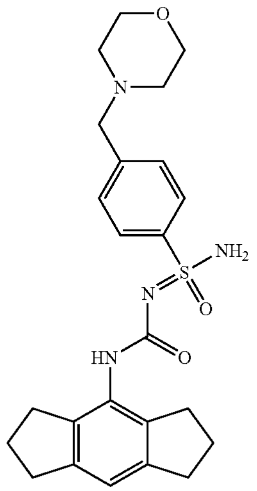 [SMILES: NS(=O)(=NC(=O)Nc1c2c(cc3c1CCC3)CCC2)c1ccc(CN2CCOCC2)cc1]
346
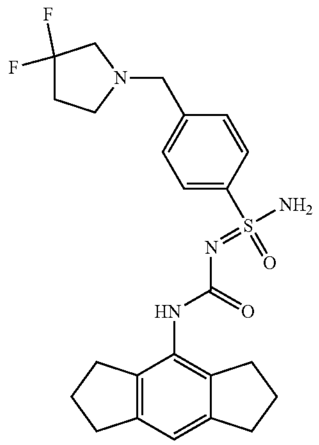 [SMILES: NS(=O)(=NC(=O)Nc1c2c(cc3c1CCC3)CCC2)c1ccc(CN2CCC(F)(F)C2)cc1]
347
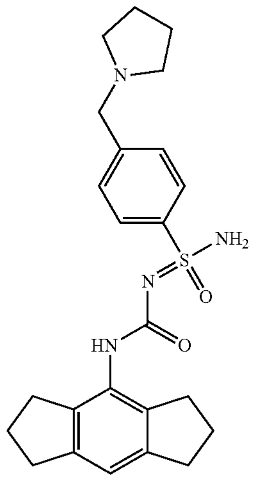 [SMILES: NS(=O)(=NC(=O)Nc1c2c(cc3c1CCC3)CCC2)c1ccc(CN2CCCC2)cc1]

-continued
348
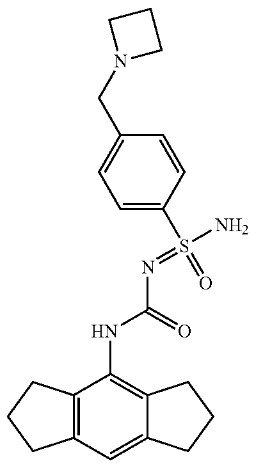 [SMILES: NS(=O)(=NC(=O)Nc1c2c(cc3c1CCC3)CCC2)c1ccc(CN2CCC2)cc1]
349
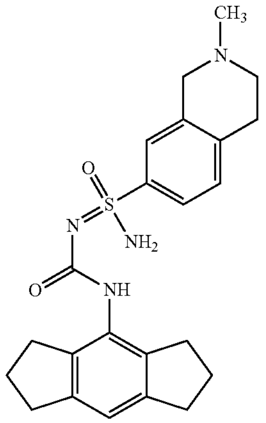 [SMILES: CN1CCc2ccc(S(N)(=O)=NC(=O)Nc3c4c(cc5c3CCC5)CCC4)cc2C1]
350
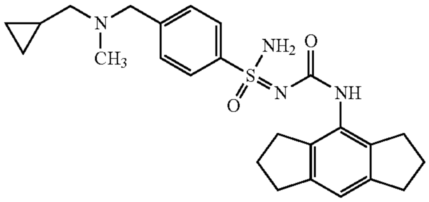 [SMILES: CN(Cc1ccc(S(N)(=O)=NC(=O)Nc2c3c(cc4c2CCC4)CCC3)cc1)CC1CC1]
351
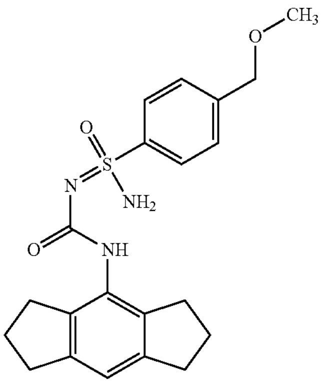 [SMILES: COCc1ccc(S(N)(=O)=NC(=O)Nc2c3c(cc4c2CCC4)CCC3)cc1]

-continued
352
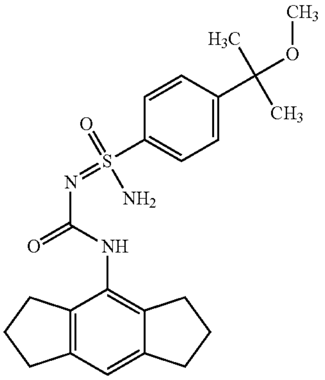 [SMILES: COC(C)(C)c1ccc(S(N)(=O)=NC(=O)Nc2c3c(cc4c2CCC4)CCC3)cc1]
352b
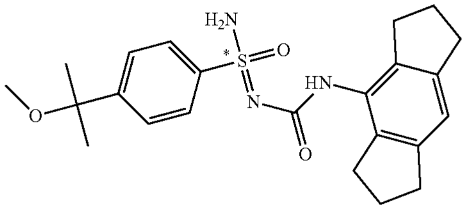 [SMILES: COC(C)(C)c1ccc(S(N)(=O)=NC(=O)Nc2c3c(cc4c2CCC4)CCC3)cc1]
352a
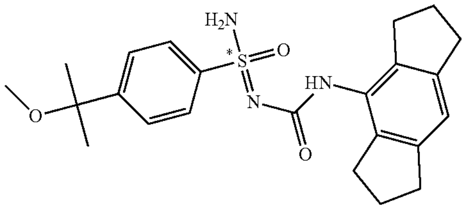 [SMILES: COC(C)(C)c1ccc(S(N)(=O)=NC(=O)Nc2c3c(cc4c2CCC4)CCC3)cc1]
353
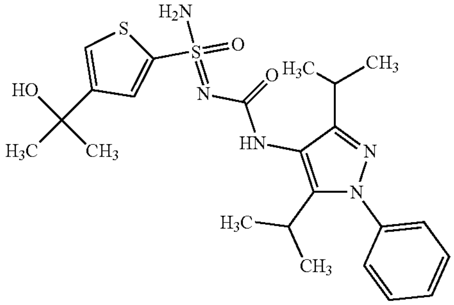 [SMILES: CC(C)c1nn(-c2ccccc2)c(C(C)C)c1NC(=O)N=S(N)(=O)c1cc(C(C)(C)O)cs1]
354
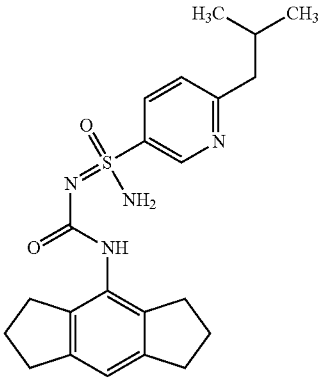 [SMILES: CC(C)Cc1ccc(S(N)(=O)=NC(=O)Nc2c3c(cc4c2CCC4)CCC3)cn1]

-continued
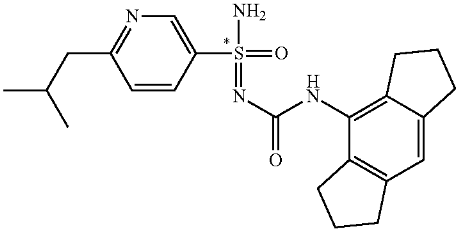 [SMILES: CC(C)Cc1ccc(S(N)(=O)=NC(=O)Nc2c3c(cc4c2CCC4)CCC3)cn1]
354a
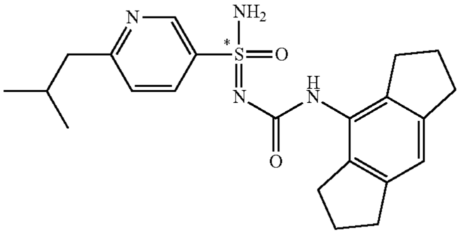 [SMILES: CC(C)Cc1ccc(S(N)(=O)=NC(=O)Nc2c3c(cc4c2CCC4)CCC3)cn1]
354b
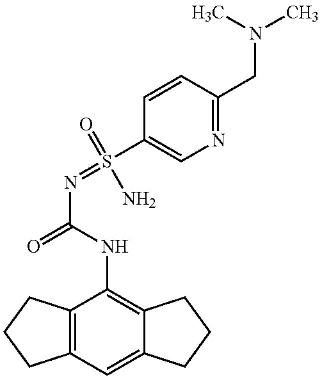 [SMILES: CN(C)Cc1ccc(S(N)(=O)=NC(=O)Nc2c3c(cc4c2CCC4)CCC3)cn1]
355
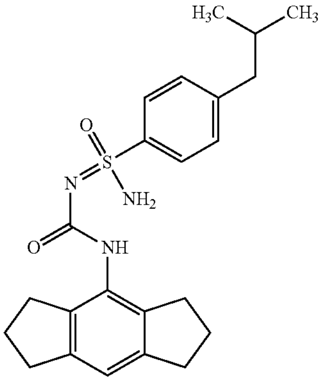 [SMILES: CC(C)Cc1ccc(S(N)(=O)=NC(=O)Nc2c3c(cc4c2CCC4)CCC3)cc1]
356
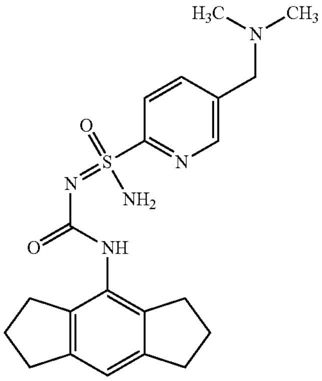 [SMILES: CN(C)Cc1ccc(S(N)(=O)=NC(=O)Nc2c3c(cc4c2CCC4)CCC3)nc1]
357

-continued
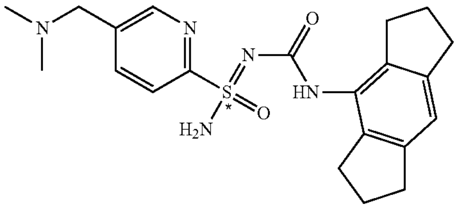 [SMILES: CN(C)Cc1ccc(S(N)(=O)=NC(=O)Nc2c3c(cc4c2CCC4)CCC3)nc1]
357a
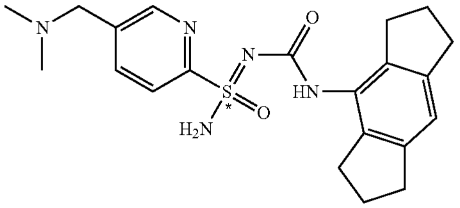 [SMILES: CN(C)Cc1ccc(S(N)(=O)=NC(=O)Nc2c3c(cc4c2CCC4)CCC3)nc1]
357b
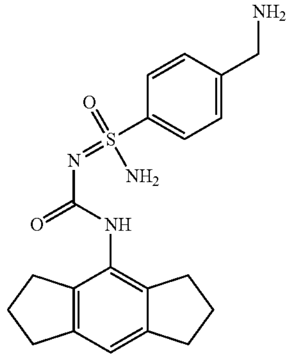 [SMILES: NCc1ccc(S(N)(=O)=NC(=O)Nc2c3c(cc4c2CCC4)CCC3)cc1]
358
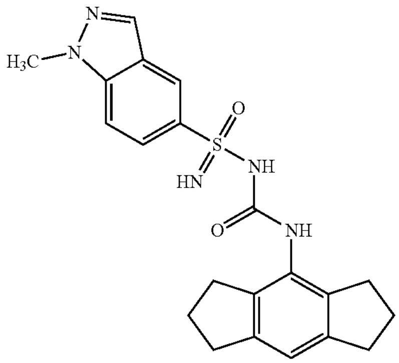 [SMILES: Cn1ncc2cc(S(=N)(=O)NC(=O)Nc3c4c(cc5c3CCC5)CCC4)ccc21]
359
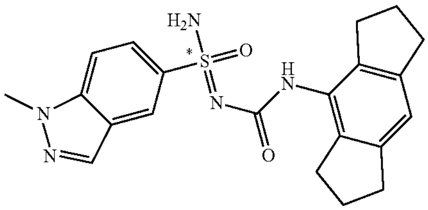 [SMILES: Cn1ncc2cc(S(N)(=O)=NC(=O)Nc3c4c(cc5c3CCC5)CCC4)ccc21]
359a
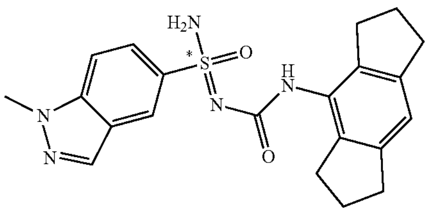 [SMILES: Cn1ncc2cc(S(N)(=O)=NC(=O)Nc3c4c(cc5c3CCC5)CCC4)ccc21]
359b -continued
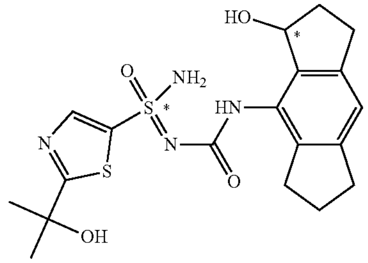 [SMILES: CC(C)(O)c1ncc(S(N)(=O)=NC(=O)Nc2c3c(cc4c2C(O)CC4)CCC3)s1]
360ba
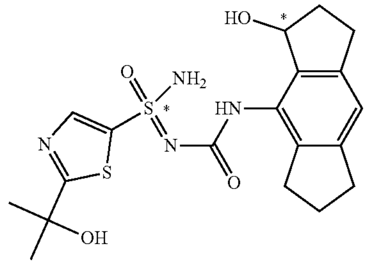 [SMILES: CC(C)(O)c1ncc(S(N)(=O)=NC(=O)Nc2c3c(cc4c2C(O)CC4)CCC3)s1]
360bb
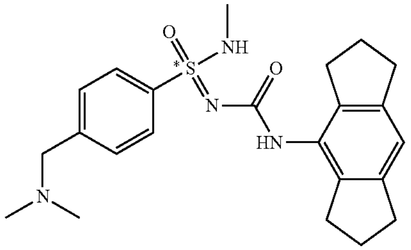 [SMILES: CNS(=O)(=NC(=O)Nc1c2c(cc3c1CCC3)CCC2)c1ccc(CN(C)C)cc1]
361b
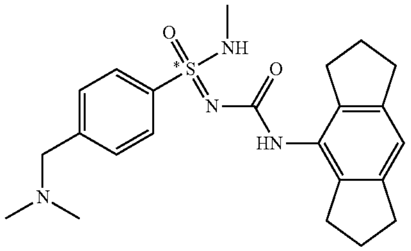 [SMILES: CNS(=O)(=NC(=O)Nc1c2c(cc3c1CCC3)CCC2)c1ccc(CN(C)C)cc1]
361a
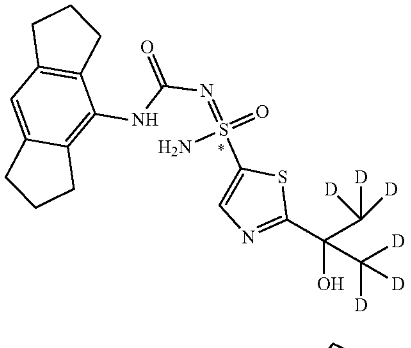
363b
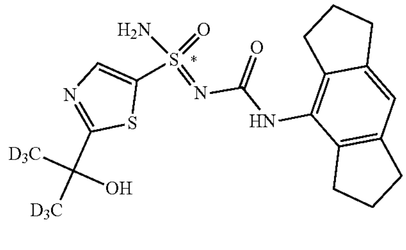 [SMILES: [2H]C([2H])([2H])C(O)(c1ncc(S(N)(=O)=NC(=O)Nc2c3c(cc4c2CCC4)CCC3)s1)C([2H])([2H])[2H]]
363a -continued
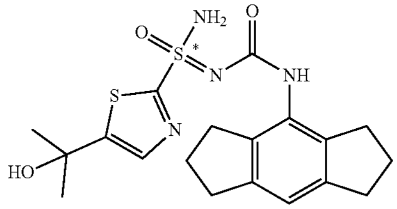 [SMILES: CC(C)(O)c1cnc(S(N)(=O)=NC(=O)Nc2c3c(cc4c2CCC4)CCC3)s1]
364a
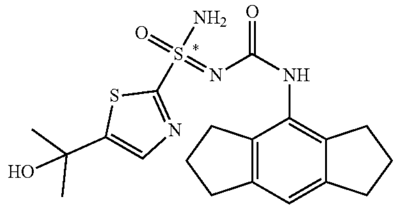 [SMILES: CC(C)(O)c1cnc(S(N)(=O)=NC(=O)Nc2c3c(cc4c2CCC4)CCC3)s1]
364b
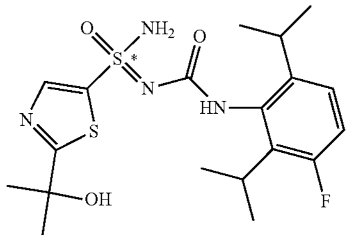 [SMILES: CC(C)c1ccc(F)c(C(C)C)c1NC(=O)N=S(N)(=O)c1cnc(C(C)(C)O)s1]
365a
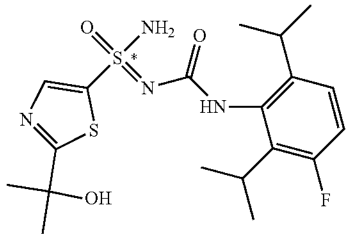 [SMILES: CC(C)c1ccc(F)c(C(C)C)c1NC(=O)N=S(N)(=O)c1cnc(C(C)(C)O)s1]
365b
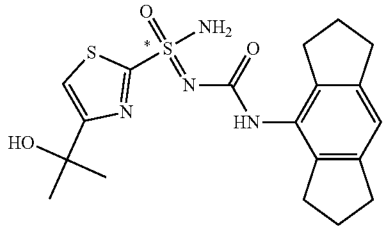 [SMILES: CC(C)(O)c1csc(S(N)(=O)=NC(=O)Nc2c3c(cc4c2CCC4)CCC3)n1]
366a
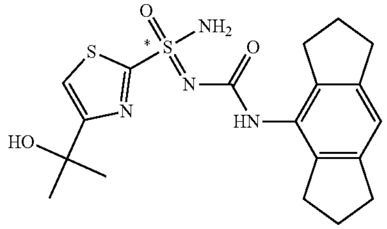 [SMILES: CC(C)(O)c1csc(S(N)(=O)=NC(=O)Nc2c3c(cc4c2CCC4)CCC3)n1]
366b
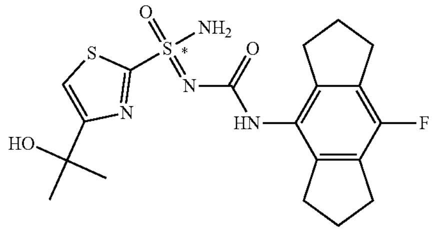 [SMILES: CC(C)(O)c1csc(S(N)(=O)=NC(=O)Nc2c3c(c(F)c4c2CCC4)CCC3)n1]
367a -continued
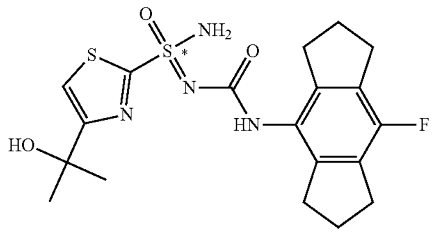 [SMILES: CC(C)(O)c1csc(S(N)(=O)=NC(=O)Nc2c3c(c(F)c4c2CCC4)CCC3)n1]
367b
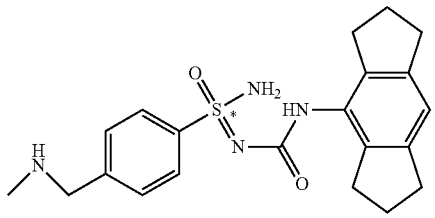 [SMILES: CNCc1ccc(S(N)(=O)=NC(=O)Nc2c3c(cc4c2CCC4)CCC3)cc1]
369a
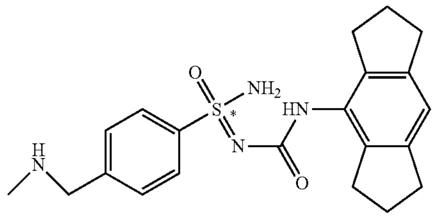 [SMILES: CNCc1ccc(S(N)(=O)=NC(=O)Nc2c3c(cc4c2CCC4)CCC3)cc1]
369b
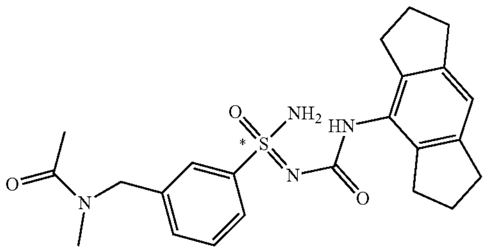 [SMILES: CC(=O)N(C)Cc1cccc(S(N)(=O)=NC(=O)Nc2c3c(cc4c2CCC4)CCC3)c1]
371a
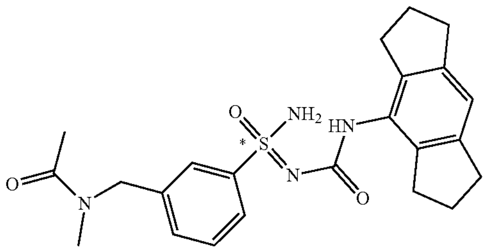 [SMILES: CC(=O)N(C)Cc1cccc(S(N)(=O)=NC(=O)Nc2c3c(cc4c2CCC4)CCC3)c1]
371b
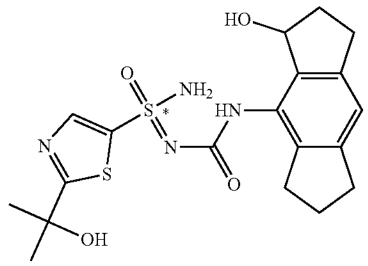 [SMILES: CC(C)(O)c1ncc(S(N)(=O)=NC(=O)Nc2c3c(cc4c2C(O)CC4)CCC3)s1]
372a -continued
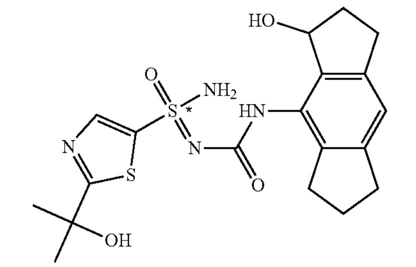 [SMILES: CC(C)(O)c1ncc(S(N)(=O)=NC(=O)Nc2c3c(cc4c2C(O)CC4)CCC3)s1]
372b
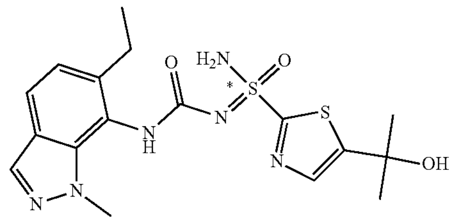 [SMILES: CCc1ccc2cnn(C)c2c1NC(=O)N=S(N)(=O)c1ncc(C(C)(C)O)s1]
373a
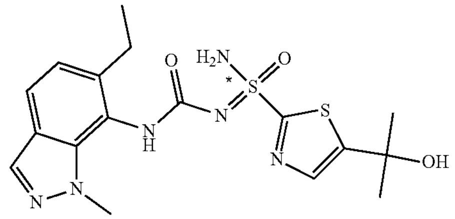 [SMILES: CCc1ccc2cnn(C)c2c1NC(=O)N=S(N)(=O)c1ncc(C(C)(C)O)s1]
373b
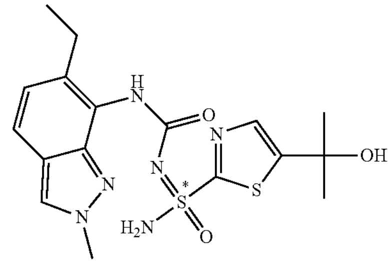 [SMILES: CCc1ccc2cn(C)nc2c1NC(=O)N=S(N)(=O)c1ncc(C(C)(C)O)s1]
374a
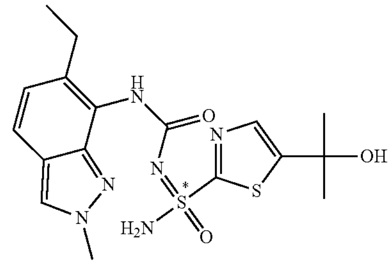 [SMILES: CCc1ccc2cn(C)nc2c1NC(=O)N=S(N)(=O)c1ncc(C(C)(C)O)s1]
374b
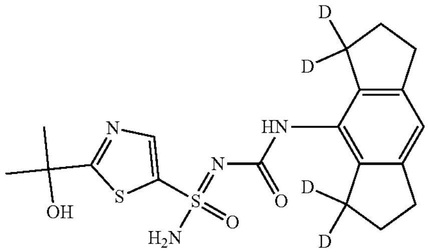 [SMILES: [2H]C1([2H])CCc2cc3c(c(NC(=O)N=S(N)(=O)c4cnc(C(C)(C)O)s4)c21)C([2H])([2H])CC3]
375

-continued
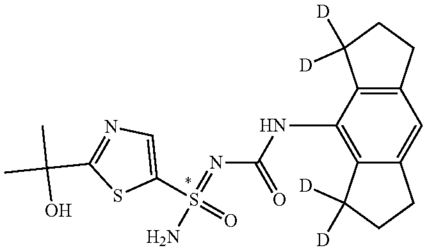 [SMILES: [2H]C1([2H])CCc2cc3c(c(NC(=O)N=S(N)(=O)c4cnc(C(C)(C)O)s4)c21)C([2H])([2H])CC3]
375a
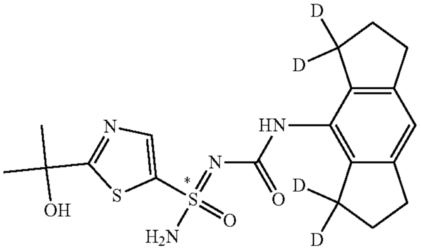 [SMILES: [2H]C1([2H])CCc2cc3c(c(NC(=O)N=S(N)(=O)c4cnc(C(C)(C)O)s4)c21)C([2H])([2H])CC3]
375b
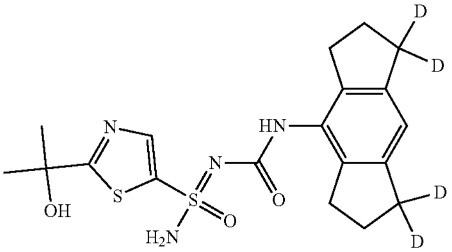 [SMILES: [2H]C1([2H])CCc2c1cc1c(c2NC(=O)N=S(N)(=O)c2cnc(C(C)(C)O)s2)CCC1([2H])[2H]]
376
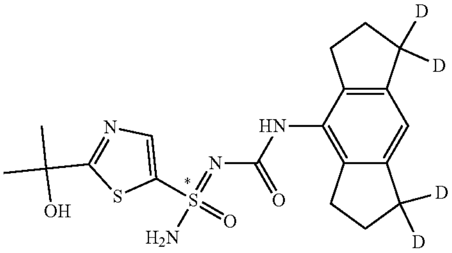 [SMILES: [2H]C1([2H])CCc2c1cc1c(c2NC(=O)N=S(N)(=O)c2cnc(C(C)(C)O)s2)CCC1([2H])[2H]]
376a
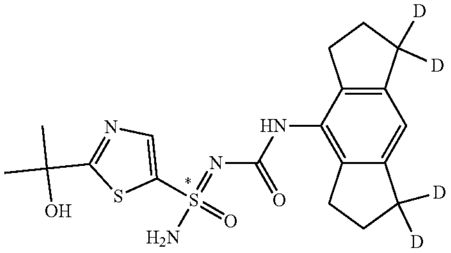 [SMILES: [2H]C1([2H])CCc2c1cc1c(c2NC(=O)N=S(N)(=O)c2cnc(C(C)(C)O)s2)CCC1([2H])[2H]]
376b
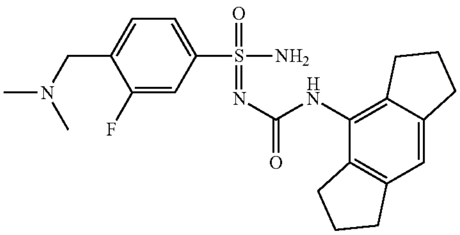 [SMILES: CN(C)Cc1ccc(S(N)(=O)=NC(=O)Nc2c3c(cc4c2CCC4)CCC3)cc1F]
377

-continued
378
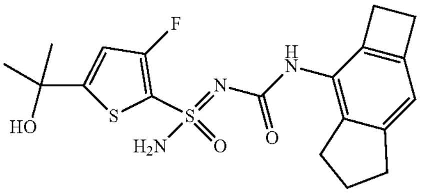 [SMILES: CC(C)(O)c1cc(F)c(S(N)(=O)=NC(=O)Nc2c3c(cc4c2CC4)CCC3)s1]
379
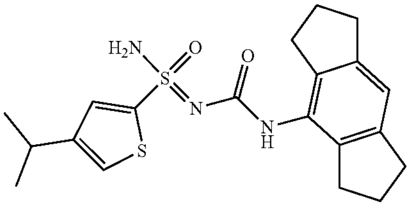 [SMILES: CC(C)c1csc(S(N)(=O)=NC(=O)Nc2c3c(cc4c2CCC4)CCC3)c1]
379a
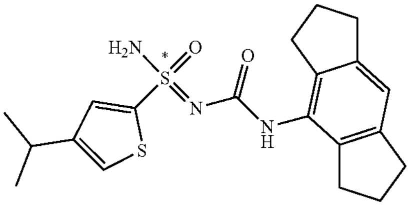 [SMILES: CC(C)c1csc(S(N)(=O)=NC(=O)Nc2c3c(cc4c2CCC4)CCC3)c1]
379b
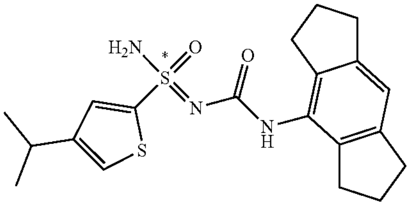 [SMILES: CC(C)c1csc(S(N)(=O)=NC(=O)Nc2c3c(cc4c2CCC4)CCC3)c1]
380
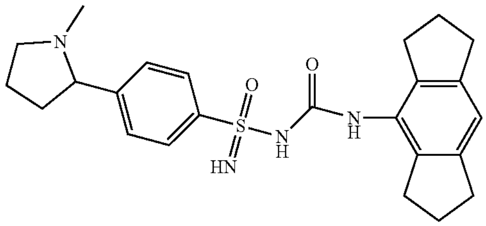 [SMILES: CN1CCCC1c1ccc(S(=N)(=O)NC(=O)Nc2c3c(cc4c2CCC4)CCC3)cc1]
380a
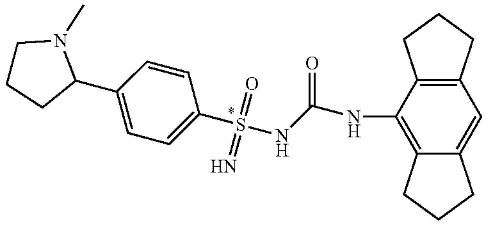 [SMILES: CN1CCCC1c1ccc(S(=N)(=O)NC(=O)Nc2c3c(cc4c2CCC4)CCC3)cc1]
380b
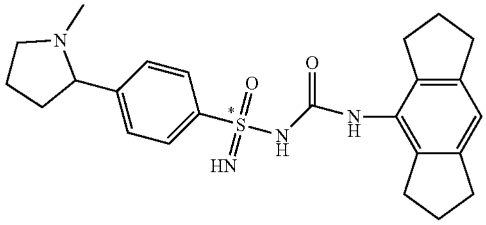 [SMILES: CN1CCCC1c1ccc(S(=N)(=O)NC(=O)Nc2c3c(cc4c2CCC4)CCC3)cc1]

-continued
380c
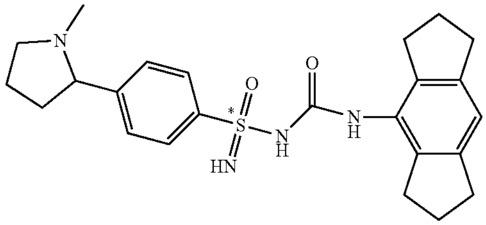 [SMILES: CN1CCCC1c1ccc(S(=N)(=O)NC(=O)Nc2c3c(cc4c2CCC4)CCC3)cc1]
380d
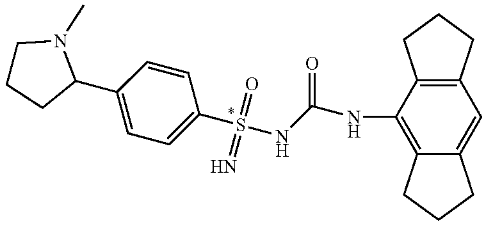 [SMILES: CN1CCCC1c1ccc(S(=N)(=O)NC(=O)Nc2c3c(cc4c2CCC4)CCC3)cc1]
382
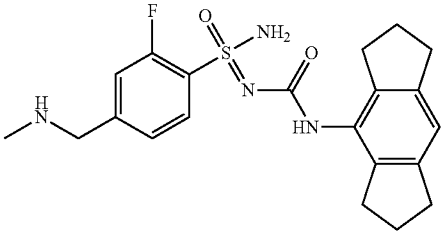 [SMILES: CNCc1ccc(S(N)(=O)=NC(=O)Nc2c3c(cc4c2CCC4)CCC3)c(F)c1]
382a
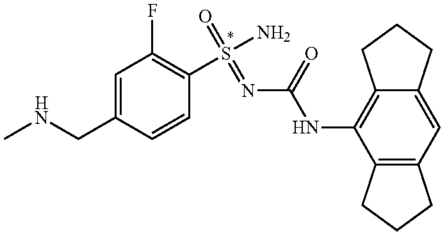 [SMILES: CNCc1ccc(S(N)(=O)=NC(=O)Nc2c3c(cc4c2CCC4)CCC3)c(F)c1]
382b
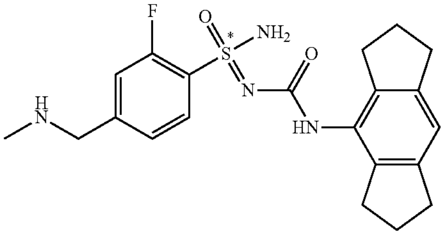
383
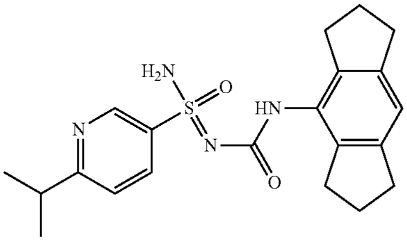

-continued
383a
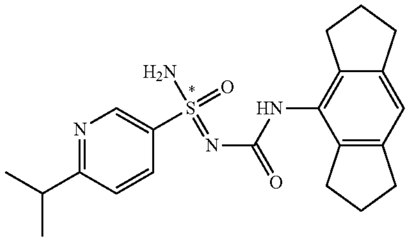
383b
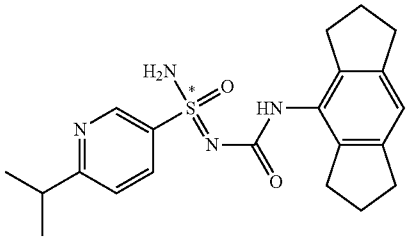
384a
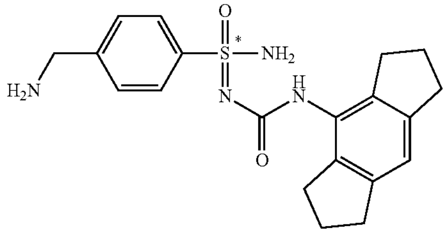 [SMILES: NCc1ccc(S(N)(=O)=NC(=O)Nc2c3c(cc4c2CCC4)CCC3)cc1]
384b
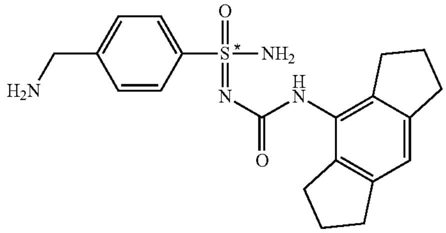 [SMILES: NCc1ccc(S(N)(=O)=NC(=O)Nc2c3c(cc4c2CCC4)CCC3)cc1]
387a
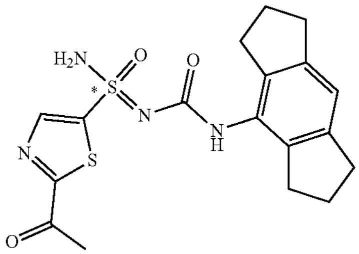 [SMILES: CC(=O)c1ncc(S(N)(=O)=NC(=O)Nc2c3c(cc4c2CCC4)CCC3)s1]
387b
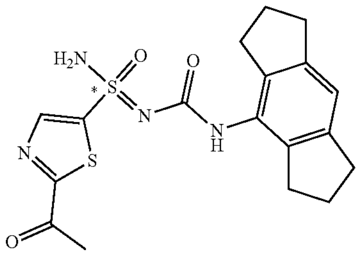 [SMILES: CC(=O)c1ncc(S(N)(=O)=NC(=O)Nc2c3c(cc4c2CCC4)CCC3)s1]
and pharmaceutically acceptable salts thereof.

In some embodiments, provided herein is a compound that is selected from the group consisting of the compounds in the following table.
401
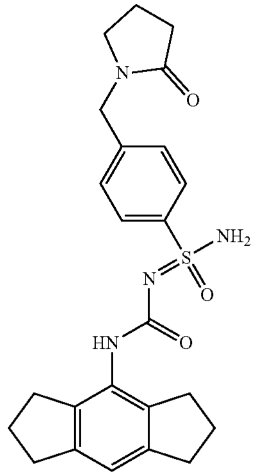 [SMILES: NS(=O)(=NC(=O)Nc1c2c(cc3c1CCC3)CCC2)c1ccc(CN2CCCC2=O)cc1]
402
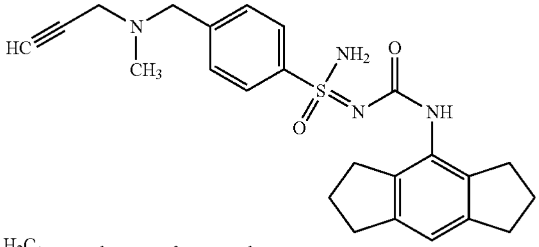
403
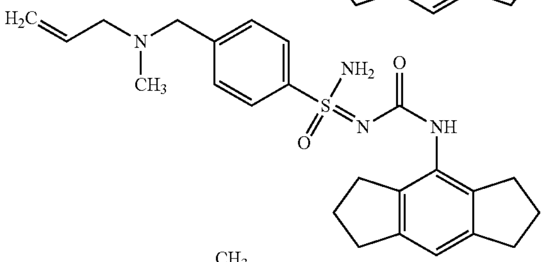
404
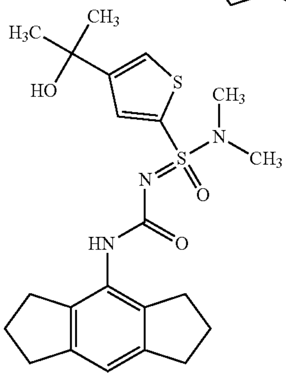
404a
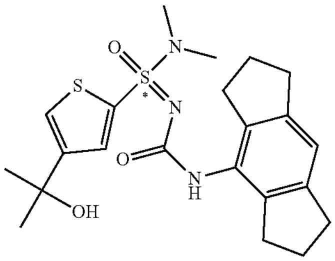 [SMILES: CN(C)S(=O)(=NC(=O)Nc1c2c(cc3c1CCC3)CCC2)c1cc(C(C)(C)O)cs1]

-continued
404b
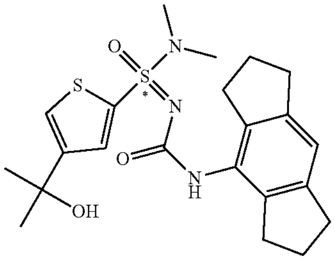 [SMILES: CN(C)S(=O)(=NC(=O)Nc1c2c(cc3c1CCC3)CCC2)c1cc(C(C)(C)O)cs1]
405
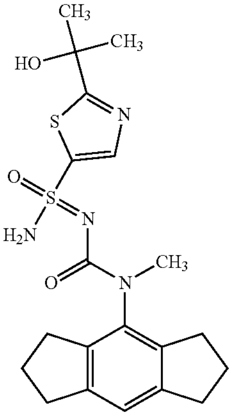 [SMILES: CN(C(=O)N=S(N)(=O)c1cnc(C(C)(C)O)s1)c1c2c(cc3c1CCC3)CCC2]
406
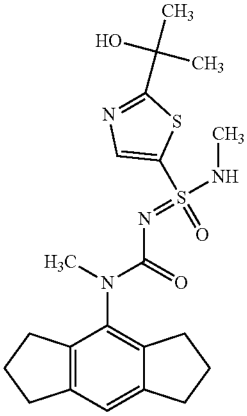 [SMILES: CNS(=O)(=NC(=O)N(C)c1c2c(cc3c1CCC3)CCC2)c1cnc(C(C)(C)O)s1]
407
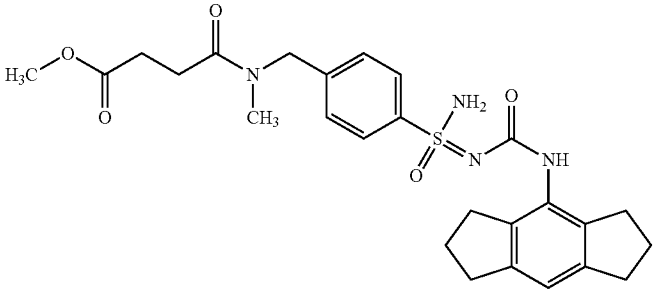 [SMILES: COC(=O)CCC(=O)N(C)Cc1ccc(S(N)(=O)=NC(=O)Nc2c3c(cc4c2CCC4)CCC3)cc1]
408
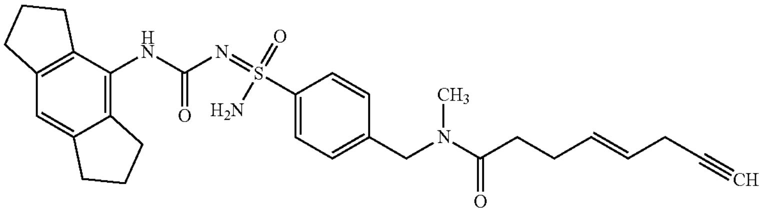 [SMILES: C#CC/C=C/CCC(=O)N(C)Cc1ccc(S(N)(=O)=NC(=O)Nc2c3c(cc4c2CCC4)CCC3)cc1]

-continued

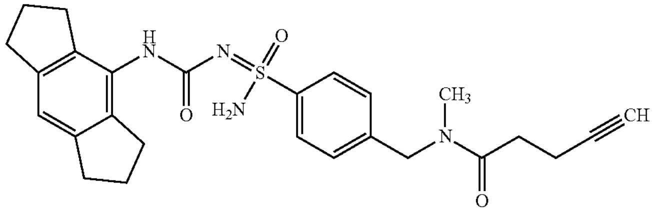 [SMILES: C#CCCC(=O)N(C)Cc1ccc(S(N)(=O)=NC(=O)Nc2c3c(cc4c2CCC4)CCC3)cc1]

409

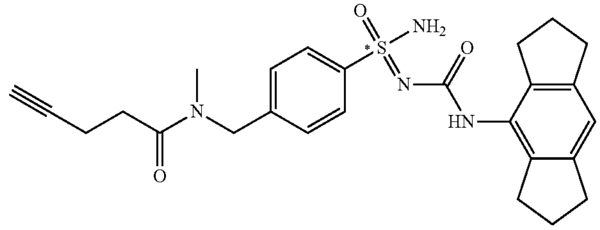 [SMILES: C#CCCC(=O)N(C)Cc1ccc(S(N)(=O)=NC(=O)Nc2c3c(cc4c2CCC4)CCC3)cc1]

409a

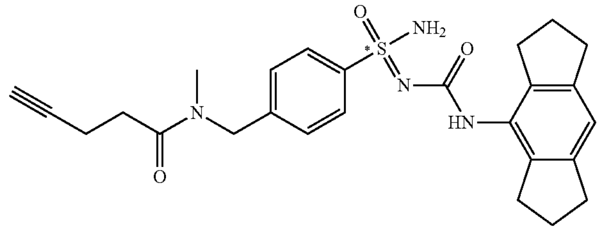 [SMILES: C#CCCC(=O)N(C)Cc1ccc(S(N)(=O)=NC(=O)Nc2c3c(cc4c2CCC4)CCC3)cc1]

409b

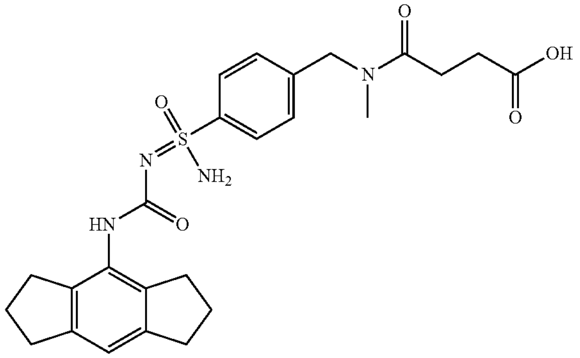 [SMILES: CN(Cc1ccc(S(N)(=O)=NC(=O)Nc2c3c(cc4c2CCC4)CCC3)cc1)C(=O)CCC(=O)O]

410

Pharmaceutical Compositions and Administration

General

In some embodiments, a chemical entity (e.g., a compound that modulates (e.g., antagonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22nd Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" *Neoplasia.* 2006, 10, 788-795.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry,* 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selelcted from thickeners, viscosity enhancing agents, bulking agents, mucoadhesive agents, penetration enhanceers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selelcted from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selelcted from thickeners, viscosity enhancing agents, bulking agents, mucoadhesive agents, buffers, preservatives, and fillers.

In certain embodiments, each of the one or more pharmaceutically acceptable excipients can be independently selelcted from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phospahate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dxtrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:

One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof, One or more (e.g., one or two; e.g., two) buffers, such as phosphate buffer system (e.g., sodium dihydrogen phospahate dehydrate, disodium phosphate dodecahydrate);

One or more (e.g., one or two, e.g., two) glidants and/or lubricants, such as magnesium stearate and/or talc;

One or more (e.g., one or two; e.g., one) disintegrants, such as crospovidone; and One or more (e.g., one or two; e.g., one) diluents, such as lactose (e.g., lactose monohydrate).

In certain of these embodiments, the chemical entity is a compound of Formula AA, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phospahate dehydrate, disodium phosphate dodecahydrate, crospovidone, lactose monohydrate, magnesium stearate, and talc. In certain of these embodiments, the chemical entity is a compound of Formula AA, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (i) and (ii) is provided in its own separate kit or pack.

In certain of these embodiments, component (i) includes the chemical entitiy (e.g., a compound of Formula AA, or a pharmaceutically acceptable salt and/or hydrate and/or cocrystal thereof, e.g., a compound of Formula AA) and one or more (e.g., all) of the following excipients:

(a) One or more (e.g., one) binders (e.g., a polyvinyl polymer, such as polyvinylpyrrolidone (povidone);

(b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a compound of Formula AA, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table A.

TABLE A

| Ingredient | Weight Percent |
|---|---|
| A compound of Formula AA | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |

TABLE A-continued

| Ingredient | Weight Percent |
|---|---|
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (i) includes the ingredients and amounts as shown in Table B.

TABLE B

| Ingredient | Weight Percent |
|---|---|
| A compound of Formula AA | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging.

In certain of the foregoing embodiments, component (ii) includes water and one or more (e.g., all) of the following excipients:

(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof, and (c') One or more (e.g., one or two; e.g., two) buffers, such as phosphate buffer system (e.g., sodium dihydrogen phospahate dihydrate, disodium phosphate dodecahydrate);

In certain of the foregoing embodiments, component (ii) includes water and one or more (e.g., all) of the following excipients:

(a") a first thickener, viscosity enhancing agent, binder, and/or mucoadhesive agent (e.g., a cellulose or cellulose ester or ether or derivative or salt thereof (e.g., methyl cellulose));

(a"') a second thickener, viscosity enhancing agent, binder, and/or mucoadhesive agent (e.g., a polyvinyl polymer, such as polyvinylpyrrolidone (povidone));

(b") a first preservative, such as a paraben, e.g., propyl 4-hydroxybenzoate (propylparaben), or a pharmaceutically acceptable salt or ester thereof;

(b") a second preservative, such as a paraben, e.g., methyl 4-hydroxybenzoate (methylparaben), or a pharmaceutically acceptable salt or ester thereof, (c") a first buffer, such as phosphate buffer system (e.g., disodium phosphate dodecahydrate);

(c"') a second buffer, such as phosphate buffer system (e.g., sodium dihydrogen phospahate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a"').

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b"').

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c"').

In certain of these embodiments, each of (a")-(c"') is present.

In certain embodiments, component (ii) includes water (up to 100%) and the ingredients and amounts as shown in Table C.

TABLE C

| Ingredient | Weight Percent |
|---|---|
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |

TABLE C-continued

| Ingredient | Weight Percent |
|---|---|
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 1000%) and the ingredients and amounts as shown in Table D.

TABLE D

| Ingredient | Weight Percent |
|---|---|
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum. In some embodiments, the enema formulation can be delivered in the device shown in FIGS. 3A-3C, which includes a plastic bottle, a breakable capsule, and a rectal cannula and single flow pack.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 10 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 150 mg of a compound of Formula AA in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 450 mg of a compound of Formula AA in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is a compound of Formula AA, or a pharmaceutically acceptable salt and/or hydrate and/or cocrystal thereof. For example, enema formulations can include about 2.5 mg/mL or about 7.5 mg/mL of a compound of Formula AA in liquid carrier.

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., an increase, e.g., NLRP3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as carbiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CML); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20.

In some embodiments, the methods described herein further include the step of identifying a subject (e.g., a patient) in need of treatment for an indication related to NLRP3 activity, such as an indication related to point mutation of NLRP3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibit reduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (INK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSF1A associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., *Cell Death Differentiation* 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., a cell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), INK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, INK, LBP, MEK1/2, MEK3/6, MEK4/7, MK2, MyD88, NF-κB, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, TKK, IκB, IRAK, INK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)2, a minibody, or a BiTE.

In some embodiments, an antibody can be a crossmab, a diabody, a scDiabody, a scDiabody-CH3, a Diabody-CH3, a DutaMab, a DT-IgG, a diabody-Fc, a scDiabody-HAS, a charge pair antibody, a Fab-arm exchange antibody, a SEEDbody, a Triomab, a LUZ-Y, a Fcab, a kλ-body, an orthogonal Fab, a DVD-IgG, an IgG(H)-scFv, a scFv-(H) IgG, an IgG(L)-scFv, a scFv-(L)-IgG, an IgG (L,H)-Fc, an IgG(H)-V, a V(H)-IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-CH3 KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., *Autoimmunity Rev.* 13(1):24-30, 2014; Bongartz et al., *JAMA* 295(19):2275-2285, 2006; Butler et al., *Eur. Cytokine Network* 6(4):225-230, 1994; Cohen et al., *Canadian J. Gastroenterol. Hepatol.* 15(6):376-384, 2001; Elliott et al., *Lancet* 1994; 344: 1125-1127, 1994; Feldmann et al., *Ann. Rev. Immunol.* 19(1):163-196, 2001; Rankin et al., *Br. J. Rheumatol.* 2:334-342, 1995; Knight et al., *Molecular Immunol.* 30(16):1443-1453, 1993; Lorenz et al., *J. Immunol.* 156(4):1646-1653, 1996; Hinshaw et al., *Circulatory Shock* 30(3):279-292, 1990; Ordas et al., *Clin. Pharmacol. Therapeutics* 91(4):635-646, 2012*; Feldman, Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Wanner et al., *Shock* 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBECO101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1\times10^{-5}$ M (e.g., less than $0.5\times10^{-5}$ M, less than $1\times10^{-6}$ M, less than $0.5\times10^{-6}$ M, less than $1\times10^{-7}$ M less than $0.5\times10^{-7}$ M, less than $1\times10^{-8}$ M, less than $0.5\times10^{-8}$ M, less than $1\times10^{-9}$ M, less than $0.5\times10^{-9}$ M, less than $1\times10^{-10}$ M, less than $0.5\times10^{-10}$ M, less than $1\times10^{-11}$ M, less than $0.5\times10^{-11}$ M, or less than $1\times10^{-12}$ M), e.g., as measured in phosphate buffered saline using surface plasmon resonance (SPR).

In some embodiments, any of the antibodies or antigen-binding fragments described herein has a $K_D$ of about $1\times10^{-12}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M about $0.5\times10^{-9}$ M, about $1\times10^{-10}$ M about $0.5\times10^{-10}$ M, about $1\times10^{-11}$ M, or about $0.5\times10^{-11}$ M (inclusive); about $0.5\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, or about $1\times10^{-11}$ M (inclusive); about $1\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, or about $0.5\times10^{-10}$ M (inclusive); about 0.5×10$^{-10}$ M to about 1×10$^{-5}$ M, about 0.5×10$^{-5}$ M, about 1×10$^{-6}$ M, about 0.5×10$^{-6}$ M, about 1×10$^{-7}$ M, about 0.5×10$^{-7}$ M, about 1×10$^{-8}$ M, about 0.5×10$^{-8}$ M, about 1×10$^{-9}$ M, about 0.5×10$^{-9}$ M, or about 1×10$^{-10}$ M (inclusive); about 1×10$^{-10}$ M to about 1×10$^{-5}$ M, about 0.5×10$^{-5}$ M, about 1×10$^{-6}$ M, about 0.5×10$^{-6}$ M, about 1×10$^{-7}$ M, about 0.5×10$^{-7}$ M, about 1×10$^{-8}$ M, about 0.5×10$^{-8}$ M, about 1×10$^{-9}$ M or about 0.5×10$^{-9}$ M (inclusive); about 0.5×10$^{-9}$ M to about 1×10$^{-5}$ M, about 0.5×10$^{-5}$ M, about 1×10$^{-6}$ M, about 0.5×10$^{-6}$ M, about 1×10$^{-7}$ M about 0.5×10$^{-7}$ M, about 1×10$^{-8}$ M, about 0.5×10$^{-8}$ M, or about 1×10$^{-9}$ M (inclusive); about 1×10$^{-9}$ M to about 1×10$^{-5}$ M, about 0.5×10$^{-5}$ M, about 1×10$^{-6}$ M, about 0.5×10$^{-6}$ M, about 1×10$^{-7}$ M, about 0.5×10$^{-7}$ M, about 1×10$^{-8}$ M, or about 0.5×10$^{-8}$ M (inclusive); about 0.5×10$^{-8}$ M to about 1×10$^{-5}$ M, about 0.5×10$^{-5}$ M, about 1×10$^{-6}$ M, about 0.5×10$^{-6}$ M, about 1×10$^{-7}$ M, about 0.5×10$^{-7}$ M, or about 1×10$^{-8}$ M (inclusive); about 1×10$^{-8}$ M to about 1×10$^{-5}$ M, about 0.5×10$^{-5}$ M, about 1×10$^{-6}$ M, about 0.5×10$^{-6}$ M, about 1×10$^{-7}$ M, or about 0.5×10$^{-7}$ M (inclusive); about 0.5×10$^{-7}$ M to about 1×10$^{-5}$ M, about 0.5×10$^{-5}$ M, about 1×10$^{-6}$ M, about 0.5×10$^{-6}$ M, or about 1×10$^{-7}$ M (inclusive); about 1×10$^{-7}$ M to about 1×10$^{-5}$ M, about 0.5×10$^{-5}$ M, about 1×10$^{-6}$ M, or about 0.5×10$^{-6}$ M (inclusive); about 0.5×10$^{-6}$ M to about 1×10$^{-5}$ M, about 0.5×10$^{-5}$ M, or about 1×10$^{-6}$ M (inclusive); about 1×10$^{-6}$ M to about 1×10$^{-5}$ M or about 0.5×10$^{-5}$ M (inclusive); or about 0.5×10$^{-5}$ M to about 1×10$^{-5}$ M (inclusive), e.g., as measured in phosphate buffered saline using surface plasmon resonance (SPR).

In some embodiments, any of the antibodies or antigen-binding fragments described herein has a K$_{off}$ of about 1×10$^{-6}$ s$^{-1}$ to about 1×10$^{-3}$ s$^{-1}$, about 0.5×10$^{-3}$ s$^{-1}$, about 1×10$^{-4}$ s$^{-1}$, about 0.5×10$^{-4}$ s$^{-1}$, about 1×10$^{-5}$ s$^{-1}$, or about 0.5×10$^{-5}$ s$^{-1}$ (inclusive); about 0.5×10$^{-5}$ s$^{-1}$ to about 1×10$^{-3}$ s$^{-1}$, about 0.5×10$^{-3}$ s$^{-1}$, about 1×10$^{-4}$ s$^{-1}$, about 0.5×10$^{-4}$ s$^{-1}$, or about 1×10$^{-5}$ s$^{-1}$ (inclusive); about 1×10$^{-5}$ s$^{-1}$ to about 1×10$^{-3}$ s$^{-1}$, about 0.5×10$^{-3}$ s$^{-1}$, about 1×10$^{-4}$ s$^{-1}$, or about 0.5×10$^{-4}$ s$^{-1}$ (inclusive); about 0.5×10$^{-4}$ s$^{-1}$ to about 1×10$^{-3}$ s$^{-1}$, about 0.5×10$^{-3}$ s$^{-1}$, or about 1×10$^{-4}$ s$^{-1}$ (inclusive); about 1×10$^{-4}$ s$^{-1}$ to about 1×10$^{-3}$ s$^{-1}$, or about 0.5×10$^{-3}$ s$^{-1}$ (inclusive); or about 0.5×10$^{-5}$ s$^{-1}$ to about 1×10$^{-3}$ s$^{-1}$ (inclusive), e.g., as measured in phosphate buffered saline using surface plasmon resonance (SPR).

In some embodiments, any of the antibodies or antigen-binding fragments described herein has a K$_{on}$ of about 1×10$^{2}$ M$^{-1}$s$^{-1}$ to about 1×10$^{6}$ M$^{-1}$s$^{-1}$, about 0.5×10$^{6}$ M$^{-1}$s$^{-1}$, about 1×10$^{5}$ M$^{-1}$s$^{-1}$, about 0.5×10$^{5}$ M$^{-1}$s$^{-1}$, about 1×10$^{4}$ M$^{-1}$s$^{-1}$, about 0.5×10$^{4}$ M$^{-1}$s$^{-1}$, about 1×10$^{3}$ M$^{-1}$s$^{-1}$, or about 0.5×10$^{3}$ M$^{-1}$s$^{-1}$ (inclusive); about 0.5×10$^{3}$ M$^{-1}$s$^{-1}$ to about 1×10$^{6}$ M$^{-1}$s$^{-1}$, about 0.5×10$^{6}$ M$^{-1}$s$^{-1}$, about 1×10$^{5}$ M$^{-1}$s$^{-1}$, about 0.5×10$^{5}$ M$^{-1}$s$^{-1}$, about 1×10$^{4}$ M$^{-1}$s$^{-1}$, about 0.5×10$^{4}$ M$^{-1}$s$^{-1}$, or about 1×10$^{3}$ M$^{-1}$s$^{-1}$ (inclusive); about 1×10$^{3}$ M$^{-1}$s$^{-1}$ to about 1×10$^{6}$ M$^{-1}$s$^{-1}$, about 0.5×10$^{6}$ M$^{-1}$s$^{-1}$, about 1×10$^{5}$ M$^{-1}$s$^{-1}$, about 0.5×10$^{5}$ M$^{-1}$s$^{-1}$, about 1×10$^{4}$ M$^{-1}$s$^{-1}$, or about 0.5×10$^{4}$ M$^{-1}$s$^{-1}$ (inclusive); about 0.5×10$^{4}$ M$^{-1}$s$^{-1}$ to about 1×10$^{6}$ M$^{-1}$s$^{-1}$, about 0.5×10$^{6}$ M$^{-1}$s$^{-1}$, about 1×10$^{5}$ M$^{-1}$s$^{-1}$, about 0.5×10$^{5}$ M$^{-1}$s$^{-1}$, or about 1×10$^{4}$ M$^{-1}$s$^{-1}$ (inclusive); about 1×10$^{4}$ M$^{-1}$s$^{-1}$ to about 1×10$^{6}$ M$^{-1}$s$^{-1}$, about 0.5×10$^{6}$ M$^{-1}$s$^{-1}$, about 1×10$^{5}$ M$^{-1}$s$^{-1}$, or about 0.5×10$^{5}$ M$^{-1}$s$^{-1}$ (inclusive); about 0.5×10$^{5}$ M$^{-1}$s$^{-1}$ to about 1×10$^{6}$ M$^{-1}$s$^{-1}$, about 0.5×10$^{6}$ M$^{-1}$s$^{-1}$, or about 1×10$^{5}$ M$^{-1}$s$^{-1}$ (inclusive); about 1×10$^{5}$ M$^{-1}$s$^{-1}$ to about 1×10$^{6}$ M$^{-1}$s$^{-1}$, or about 0.5×10$^{6}$ M$^{-1}$s$^{-1}$ (inclusive); or about 0.5×10$^{6}$ M$^{-1}$s$^{-1}$ to about 1×10$^{6}$ M$^{-1}$s$^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J. Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269 (1):R23-R29, 1995; Tsao et al., *Eur Respir J.* 14(3):490-495, 1999; Watt et al., *J Leukoc Biol.* 66(6):1005-1013, 1999; Mohler et al., *J. Immunol.* 151(3):1548-1561, 1993; Nophar et al., *EMBO J.* 9(10):3269, 1990; Piguet et al., *Eur. Respiratory J.* 7(3):515-518, 1994; and Gray et al., *Proc. Natl. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., *J. Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is complementary to all or part of a AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., complementary to all or a part of any one of SEQ ID NOs: 1-37).

Human TNFα CDS (SEQ ID NO: 1)
ATGAGCACTGAAAGCATGATCCGGGACGTGGAGCTGGCCGAGGAGGCGC

TCCCCAAGAAGACAGGGGGGCCCCAGGGCTCCAGGCGGTGCTTGTTCCT

CAGCCTCTTCTCCTTCCTGATCGTGGCAGGCGCCACCACGCTCTTCTGC

CTGCTGCACTTTGGAGTGATCGGCCCCCAGAGGGAAGAGTTCCCCAGGG

ACCTCTCTCTAATCAGCCCTCTGGCCCAGGCAGTCAGATCATCTTCTCG

AACCCCGAGTGACAAGCCTGTAGCCCATGTTGTAGCAAACCCTCAAGCT

GAGGGGCAGCTCCAGTGGCTGAACCGCCGGGCCAATGCCCTCCTGGCCA

ATGGCGTGGAGCTGAGAGATAACCAGCTGGTGGTGCCATCAGAGGGCCT

GTACCTCATCTACTCCCAGGTCCTCTTCAAGGGCCAAGGCTGCCCCTCC

ACCCATGTGCTCCTCACCCACACCATCAGCCGCATCGCCGTCTCCTACC

AGACCAAGGTCAACCTCCTCTCTGCCATCAAGAGCCCCTGCCAGAGGGA

GACCCCAGAGGGGGCTGAGGCCAAGCCCTGGTATGAGCCCATCTATCTG

GGAGGGGTCTTCCAGCTGGAGAAGGGTGACCGACTCAGCGCTGAGATCA

ATCGGCCCGACTATCTCGACTTTGCCGAGTCTGGGCAGGTCTACTTTGG

GATCATTGCCCTGTGA

-continued

Human TNFR1 CDS (SEQ ID NO: 2)

ATGGGCCTCTCCACCGTGCCTGACCTGCTGCTGCCACTGGTGCTCCTGG
AGCTGTTGGTGGGAATATACCCCTCAGGGGTTATTGGACTGGTCCCTCA
CCTAGGGGACAGGGAGAAGAGAGATAGTGTGTGTCCCCAAGGAAAATAT
ATCCACCCTCAAAATAATTCGATTTGCTGTACCAAGTGCCACAAAGGAA
CCTACTTGTACAATGACTGTCCAGGCCCGGGGCAGGATACGGACTGCAG
GGAGTGTGAGAGCGGCTCCTTCACCGCTTCAGAAAACCACCTCAGACAC
TGCCTCAGCTGCTCCAAATGCCGAAAGGAAATGGGTCAGGTGGAGATCT
CTTCTTGCACAGTGGACCGGGACACCGTGTGTGGCTGCAGGAAGAACCA
GTACCGGCATTATTGGAGTGAAAACCTTTTCCAGTGCTTCAATTGCAGC
CTCTGCCTCAATGGGACCGTGCACCTCTCCTGCCAGGAGAAACAGAACA
CCGTGTGCACCTGCCATGCAGGTTTCTTTCTAAGAGAAAACGAGTGTGT
CTCCTGTAGTAACTGTAAGAAAAGCCTGGAGTGCACGAAGTTGTGCCTA
CCCCAGATTGAGAATGTTAAGGGCACTGAGGACTCAGGCACCACAGTGC
TGTTGCCCCTGGTCATTTTCTTTGGTCTTTGCCTTTTATCCCTCCTCTT
CATTGGTTTAATGTATCGCTACCAACGGTGGAAGTCCAAGCTCTACTCC
ATTGTTTGTGGGAAATCGACACCTGAAAAAGAGGGGGAGCTTGAAGGAA
CTACTACTAAGCCCCTGGCCCCAAACCCAAGCTTCAGTCCCACTCCAGG
CTTCACCCCCACCCTGGGCTTCAGTCCCGTGCCCAGTTCCACCTTCACC
TCCAGCTCCACCTATACCCCCGGTGACTGTCCCAACTTTGCGGCTCCCC
GCAGAGAGGTGGCACCACCCTATCAGGGGGCTGACCCCATCCTTGCGAC
AGCCCTCGCCTCCGACCCCATCCCCAACCCCCTTCAGAAGTGGGAGGAC
AGCGCCCACAAGCCACAGAGCCTAGACACTGATGACCCCGCGACGCTGT
ACGCCGTGGTGGAGAACGTGCCCCCGTTGCGCTGGAAGGAATTCGTGCG
GCGCCTAGGGCTGAGCGACCACGAGATCGATCGGCTGGAGCTGCAGAAC
GGGCGCTGCCTGCGCGAGGCGCAATACAGCATGCTGGCGACCTGGAGGC
GGCGCACGCCGCGGCGCGAGGCCACGCTGGAGCTGCTGGGACGCGTGCT
CCGCGACATGGACCTGCTGGGCTGCCTGGAGGACATCGAGGAGGCGCTT
TGCGGCCCCGCCGCCCTCCCGCCCGCGCCCAGTCTTCTCAGATGA

Human TNFR2 CDS (SEQ ID NO: 3)

ATTCTTCCCCTGGTGGCCATGGGACCCAGGTCAATGTCACCTGCATCGT
GAACGTCTGTAGCAGCTCTGACCACAGCTCACAGTGCTCCTCCCAAGCC
AGCTCCACAATGGGAGACACAGATTCCAGCCCCTCGGAGTCCCCGAAGG
ACGAGCAGGTCCCCTTCTCCAAGGAGGAATGTGCCTTTCGGTCACAGCT
GGAGACGCCAGAGACCCTGCTGGGGAGCACCGAAGAGAAGCCCCTGCCC
CTTGGAGTGCCTGATGCTGGGATGAAGCCCAGTTAA

Human TRADD CDS (SEQ ID NO: 4)

ATGGCAGCTGGGCAAAATGGGCACGAAGAGTGGGTGGGCAGCGCATACC
TGTTTGTGGAGTCCTCGCTGGACAAGGTGGTCCTGTCGGATGCCTACGC
GCACCCCCAGCAGAAGGTGGCAGTGTACAGGGCTCTGCAGGCTGCCTTG
GCAGAGAGCGGCGGGAGCCCGGACGTGCTGCAGATGCTGAAGATCCACC
GCAGCGACCCGCAGCTGATCGTGCAGCTGCGATTCTGCGGGCGGCAGCC
CTGTGGCCGCTTCCTCCGCGCCTACCGCGAGGGGGCGCTGCGCGCCGCG
CTGCAGAGGAGCCTGGCGGCCGCGCTCGCCCAGCACTCGGTGCCGCTGC
AACTGGAGCTGCGCGCCGGCGCCGAGCGGCTGGACGCTTTGCTGGCGGA
CGAGGAGCGCTGTTTGAGTTGCATCCTAGCCCAGCAGCCCGACCGGCTC
CGGGATGAAGAACTGGCTGAGCTGGAGGATGCGCTGCGAAATCTGAAGT
GCGGCTCGGGGGCCCGGGGTGGCGACGGGGAGGTCGCTTCGGCCCCCTT
GCAGCCCCCGGTGCCCTCTCTGTCGGAGGTGAAGCCGCCGCCGCCGCCG
CCACCTGCCCAGACTTTTCTGTTCCAGGGTCAGCCTGTAGTGAATCGGC
CGCTGAGCCTGAAGGACCAACAGACGTTCGCGCGCTCTGTGGGTCTCAA
ATGGCGCAAGGTGGGGCGCTCACTGCAGCGAGGCTGCCGGGCGCTGCGG
GACCCGGCGCTGGACTCGCTGGCCTACGAGTACGAGCGCGAGGGACTGT
ACGAGCAGGCCTTCCAGCTGCTGCGGCGCTTCGTGCAGGCCGAGGGCCG
CCGCGCCACGCTGCAGCGCCTGGTGGAGGCACTCGAGGAGAACGAGCTC
ACCAGCCTGGCAGAGGACTTGCTGGGCCTGACCGATCCCAATGGCGGCC
TGGCCTAG

Human TRAF2 CDS (SEQ ID NO: 5)

ATGGCTGCAGCTAGCGTGACCCCCCCTGGCTCCCTGGAGTTGCTACAGC
CCGGCTTCTCCAAGACCCTCCTGGGGACCAAGCTGGAAGCCAAGTACCT
GTGCTCCGCCTGCAGAAACGTCCTCCGCAGGCCCTTCCAGGCGCAGTGT
GGCCACCGGTACTGCTCCTTCTGCCTGGCCAGCATCCTCAGCTCTGGGC
CTCAGAACTGTGCTGCCTGTGTTCACGAGGGCATATATGAAGAAGGCAT
TTCTATTTTAGAAAGCAGTTCGGCCTTCCCAGATAATGCTGCCCGCAGG
GAGGTGGAGAGCCTGCCGGCCGTCTGTCCCAGTGATGGATGCACCTGGA
AGGGGACCCTGAAAGAATACGAGAGCTGCCACGAAGGCCGCTGCCCGCT
CATGCTGACCGAATGTCCCGCGTGCAAAGGCCTGGTCCGCCTTGGTGAA
AAGGAGCGCCACCTGGAGCACGAGTGCCCGGAGAGAAGCCTGAGCTGCC
GGCATTGCCGGGCACCCTGCTGCGGAGCAGACGTGAAGGCGCACCACGA
GGTCTGCCCCAAGTTCCCCTTAACTTGTGACGGCTGCGGCAAGAAGAAG
ATCCCCCGGGAGAAGTTTCAGGACCACGTCAAGACTTGTGGCAAGTGTC
GAGTCCCTTGCAGATTCCACGCCATCGGCTGCCTCGAGACGGTAGAGGG
TGAGAAACAGCAGGAGCACGAGGTGCAGTGGCTGCGGGAGCACCTGGCC
ATGCTACTGAGCTCGGTGCTGGAGGCAAAGCCCCTCTTGGGAGACCAGA
GCCACGCGGGGTCAGAGCTCCTGCAGAGGTGCGAGAGCCTGGAGAAGAA
GACGGCCACTTTTGAGAACATTGTCTGCGTCCTGAACCGGGAGGTGGAG
AGGGTGGCCATGACTGCCGAGGCCTGCAGCCGGCAGCACCGGCTGGACC
AAGACAAGATTGAAGCCCTGAGTAGCAAGGTGCAGCAGCTGGAGAGGAG
CATTGGCCTCAAGGACCTGGCGATGGCTGACTTGGAGCAGAAGGTCTTG
GAGATGGAGGCATCCACCTACGATGGGGTCTTCATCTGGAAGATCTCAG
ACTTCGCCAGGAAGCGCCAGGAAGCTGTGGCTGGCCGCATACCCGCCAT

-continued

CTTCTCCCCAGCCTTCTACACCAGCAGGTACGGCTACAAGATGTGTCTG

CGTATCTACCTGAACGGCGACGGCACCGGGCGAGGAACACACCTGTCCC

TCTTCTTTGTGGTGATGAAGGGCCCGAATGACGCCCTGCTGCGGTGGCC

CTTCAACCAGAAGGTGACCTTAATGCTGCTCGACCAGAATAACCGGGAG

CACGTGATTGACGCCTTCAGGCCCGACGTGACTTCATCCTCTTTTCAGA

GGCCAGTCAACGACATGAACATCGCAAGCGGCTGCCCCCTCTTCTGCCC

CGTCTCCAAGATGGAGGCAAAGAATTCCTACGTGCGGGACGATGCCATC

TTCATCAAGGCCATTGTGGACCTGACAGGGCTCTAA

Human AP-1 CDS (SEQ ID NO: 6)

ATGGAAACACCCTTCTACGGCGATGAGGCGCTGAGCGGCCTGGGCGGCG

GCGCCAGTGGCAGCGGCGGCAGCTTCGCGTCCCCGGGCCGCTTGTTCCC

CGGGGCGCCCCCGACGGCCGCGGCCGGCAGCATGATGAAGAAGGACGCG

CTGACGCTGAGCCTGAGTGAGCAGGTGGCGGCAGCGCTCAAGCCTGCGG

CCGCGCCGCCTCCTACCCCCCTGCGCGCCGACGGCGCCCCCAGCGCGGC

ACCCCCCGACGGCCTGCTCGCCTCTCCCGACCTGGGGCTGCTGAAGCTG

GCCTCCCCCGAGCTCGAGCGCCTCATCATCCAGTCCAACGGGCTGGTCA

CCACCACGCCGACGAGCTCACAGTTCCTCTACCCCAAGGTGGCGGCCAG

CGAGGAGCAGGAGTTCGCCGAGGGCTTCGTCAAGGCCCTGGAGGATTTA

CACAAGCAGAACCAGCTCGGCGCGGGCGCGGCCGCTGCCGCCGCCGCCG

CCGCCGCCGGGGGGCCCTCGGGCACGGCCACGGGCTCCGCGCCCCCCGG

CGAGCTGGCCCCGGCGGCGGCCGCGCCCGAAGCGCCTGTCTACGCGAAC

CTGAGCAGCTACGCGGGCGGCGCCGGGGGCGCGGGGGGCGCCGCGACGG

TCGCCTTCGCTGCCGAACCTGTGCCCTTCCCGCCGCCGCCACCCCCAGG

CGCGTTGGGGCCGCCGCGCCTGGCTGCGCTCAAGGACGAGCCACAGACG

GTGCCCGACGTGCCGAGCTTCGGCGAGAGCCCGCCGTTGTCGCCCATCG

ACATGGACACGCAGGAGCGCATCAAGGCGGAGCGCAAGCGGCTGCGCAA

CCGCATCGCCGCCTCCAAGTGCCGCAAGCGCAAGCTGGAGCGCATCTCG

CGCCTGGAAGAGAAAGTGAAGACCCTCAAGAGTCAGAACACGGAGCTGG

CGTCCACGGCGAGCCTGCTGCGCGAGCAGGTGGCGCAGCTCAAGCAGAA

AGTCCTCAGCCACGTCAACAGCGGCTGCCAGCTGCTGCCCCAGCACCAG

GTGCCCGCGTACTGA

Human ASK1 CDS (SEQ ID NO: 7)

ATGAGCACGGAGGCGGACGAGGGCATCACTTTCTCTGTGCCACCCTTCG

CCCCCTCGGGCTTCTGCACCATCCCCGAGGGCGGCATCTGCAGGAGGGG

AGGAGCGGCGGCGGTGGGCGAGGGCGAGGAGCACCAGCTGCCACCGCCG

CCGCCGGGCAGTTTCTGGAACGTGGAGAGCGCCGCTGCCCCTGGCATCG

GTTGTCCGGCGGCCACCTCCTCGAGCAGTGCCACCCGAGGCCGGGGCAG

CTCTGTTGGCGGGGGCAGCCGACGGACCACGGTGGCATATGTGATCAAC

GAAGCGAGCCAAGGGCAACTGGTGGTGGCCGAGAGCGAGGCCCTGCAGA

GCTTGCGGGAGGCGTGCGAGACAGTGGGCGCCACCCTGGAACCCTGCAT

-continued

TTTGGGAAACTCGACTTTGGAGAAACCACCGTGCTGGACCGCTTTTACA

ATGCAGATATTGCGGTGGTGGAGATGAGCGATGCCTTCCGGCAGCCGTC

CTTGTTTTACCACCTTGGGGTGAGAGAAAGTTTCAGCATGGCCAACAAC

ATCATCCTCTACTGCGATACTAACTCGGACTCTCTGCAGTCACTGAAGG

AAATCATTTGCCAGAAGAATACTATGTGCACTGGGAACTACACCTTTGT

TCCTTACATGATAACTCCACATAACAAAGTCTACTGCTGTGACAGCAGC

TTCATGAAGGGGTTGACAGAGCTCATGCAACCGAACTTCGAGCTGCTTC

TTGGACCCATCTGCTTACCTCTTGTGGATCGTTTTATTCAACTTTTGAA

GGTGGCACAAGCAAGTTCTAGCCAGTACTTCCGGGAATCTATACTCAAT

GACATCAGGAAAGCTCGTAATTTATACACTGGTAAAGAATTGGCAGCTG

AGTTGGCAAGAATTCGGCAGCGAGTAGATAATATCGAAGTCTTGACAGC

AGATATTGTCATAAATCTGTTACTTTCCTACAGAGATATCCAGGACTAT

GATTCTATTGTGAAGCTGGTAGAGACTTTAGAAAAACTGCCAACCTTTG

ATTTGGCCTCCCATCACCATGTGAAGTTTCATTATGCATTTGCACTGAA

TAGGAGAAATCTCCCTGGTGACAGAGCAAAAGCTCTTGATATTATGATT

CCCATGGTGCAAAGCGAAGGACAAGTTGCTTCAGATATGTATTGCCTAG

TTGGTCGAATCTACAAAGATATGTTTTTGGACTCTAATTTCACGGACAC

TGAAAGCAGAGACCATGGAGCTTCTTGGTTCAAAAAGGCATTTGAATCT

GAGCCAACACTACAGTCAGGAATTAATTATGCGGTCCTCCTCCTGGCAG

CTGGACACCAGTTTGAATCTTCCTTTGAGCTCCGGAAAGTTGGGGTGAA

GCTAAGTAGTCTTCTTGGTAAAAAGGGAAACTTGGAAAAACTCCAGAGC

TACTGGGAAGTTGGATTTTTTCTGGGGGCCAGCGTCCTAGCCAATGACC

ACATGAGAGTCATTCAAGCATCTGAAAAGCTTTTTAAACTGAAGACACC

AGCATGGTACCTCAAGTCTATTGTAGAGACAATTTTGATATATAAGCAT

TTTGTGAAACTGACCACAGAACAGCCTGTGGCCAAGCAAGAACTTGTGG

ACTTTTGGATGGATTTCCTGGTCGAGGCCACAAAGACAGATGTTACTGT

GGTTAGGTTTCCAGTATTAATATTAGAACCAACCAAAATCTATCAACCT

TCTTATTTGTCTATCAACAATGAAGTTGAGGAAAAGACAATCTCTATTT

GGCACGTGCTTCCTGATGACAAGAAAGGTATACATGAGTGGAATTTTAG

TGCCTCTTCTGTCAGGGGAGTGAGTATTTCTAAATTTGAAGAAAGATGC

TGCTTTCTTTATGTGCTTCACAATTCTGATGATTTCCAAATCTATTTCT

GTACAGAACTTCATTGTAAAAAGTTTTTTGAGATGGTGAACACCATTAC

CGAAGAGAAGGGGAGAAGCACAGAGGAAGGAGACTGTGAAAGTGACTTG

CTGGAGTATGACTATGAATATGATGAAAATGGTGACAGAGTCGTTTTAG

GAAAAGGCACTTATGGGATAGTCTACGCAGGTCGGGACTTGAGCAACCA

AGTCAGAATTGCTATTAAGGAAATCCCAGAGAGAGACAGCAGATACTCT

CAGCCCCTGCATGAAGAAATAGCATTGCATAAACACCTGAAGCACAAAA

ATATTGTCCAGTATCTGGGCTCTTTCAGTGAGAATGGTTTCATTAAAAT

CTTCATGGAGCAGGTCCCTGGAGGAAGTCTTTCTGCTCTCCTTCGTTCC

AAATGGGGTCCATTAAAAGACAATGAGCAAACAATTGGCTTTTATACAA

AGCAAATACTGGAAGGATTAAAATATCTCCATGACAATCAGATAGTTCA

-continued

CCGGGACATAAAGGGTGACAATGTGTTGATTAATACCTACAGTGGTGTT

CTCAAGATCTCTGACTTCGGAACATCAAAGAGGCTTGCTGGCATAAACC

CCTGTACTGAAACTTTTACTGGTACCCTCCAGTATATGGCACCAGAAAT

AATAGATAAAGGACCAAGAGGCTACGGAAAAGCAGCAGACATCTGGTCT

CTGGGCTGTACAATCATTGAAATGGCCACAGGAAAACCCCCATTTTATG

AACTGGGAGAACCACAAGCAGCTATGTTCAAGGTGGGAATGTTTAAAGT

CCACCCTGAGATCCCAGAGTCCATGTCTGCAGAGGCCAAGGCATTCATA

CTGAAATGTTTTGAACCAGATCCTGACAAGAGAGCCTGTGCTAACGACT

TGCTTGTTGATGAGTTTTTAAAAGTTTCAAGCAAAAAGAAAAAGACACA

ACCTAAGCTTTCAGCTCTTTCAGCTGGATCAAATGAATATCTCAGGAGT

ATATCCTTGCCGGTACCTGTGCTGGTGGAGGACACCAGCAGCAGCAGTG

AGTACGGCTCAGTTTCACCCGACACGGAGTTGAAAGTGGACCCCTTCTC

TTTCAAAACAAGAGCCAAGTCCTGCGGAGAAAGAGATGTCAAGGGAATT

CGGACACTCTTTTTGGGCATTCCAGATGAGAATTTTGAAGATCACAGTG

CTCCTCCTTCCCCTGAAGAAAAAGATTCTGGATTCTTCATGCTGAGGAA

GGACAGTGAGAGGCGAGCTACCCTTCACAGGATCCTGACGGAAGACCAA

GACAAAATTGTGAGAAACCTAATGGAATCTTTAGCTCAGGGGGCTGAAG

AACCGAAACTAAAATGGGAACACATCACAACCCTCATTGCAAGCCTCAG

AGAATTTGTGAGATCCACTGACCGAAAAATCATAGCCACCACACTGTCA

AAGCTGAAACTGGAGCTGGACTTCGACAGCCATGGCATTAGCCAAGTCC

AGGTGGTACTCTTTGGTTTTCAAGATGCTGTCAATAAAGTTCTTCGGAA

TCATAACATCAAGCCGCACTGGATGTTTGCCTTAGACAGTATCATTCGG

AAGGCGGTACAGACAGCCATTACCATCCTGGTTCCAGAACTAAGGCCAC

ATTTCAGCCTTGCATCTGAGAGTGATACTGCTGATCAAGAAGACTTGGA

TGTAGAAGATGACCATGAGGAACAGCCTTCAAATCAAACTGTCCGAAGA

CCTCAGGCTGTCATTGAAGATGCTGTGGCTACCTCAGGCGTGAGCACGC

TCAGTTCTACTGTGTCTCATGATTCCCAGAGTGCTCACCGGTCACTGAA

TGTACAGCTTGGAAGGATGAAAATAGAAACCAATAGATTACTGGAAGAA

TTGGTTCGGAAAGAGAAAGAATTACAAGCACTCCTTCATCGAGCTATTG

AAGAAAAAGACCAAGAAATTAAACACCTGAAGCTTAAGTCCCAACCCAT

AGAAATTCCTGAATTGCCTGTATTTCATCTAAATTCTTCTGGCACAAAT

ACTGAAGATTCTGAACTTACCGACTGGCTGAGAGTGAATGGAGCTGATG

AAGACACTATAAGCCGGTTTTTGGCTGAAGATTATACACTATTGGATGT

TCTCTACTATGTTACACGTGATGACTTAAAATGCTTGAGACTAAGGGGA

GGGATGCTGTGCACACTGTGGAAGG CTATCATTGACTTTCGAAACAAA

CAGACTTGA

Human CD14 CDS (SEQ ID NO: 8)

ATGGAGCGCGCGTCCTGCTTGTTGCTGCTGCTGCTGCCGCTGGTGCACG

TCTCTGCGACCACGCCAGAACCTTGTGAGCTGGACGATGAAGATTTCCG

CTGCGTCTGCAACTTCTCCGAACCTCAGCCCGACTGGTCCGAAGCCTTC

-continued

CAGTGTGTGTCTGCAGTAGAGGTGGAGATCCATGCCGGCGGTCTCAACC

TAGAGCCGTTTCTAAAGCGCGTCGATGCGGACGCCGACCCGCGGCAGTA

TGCTGACACGGTCAAGGCTCTCCGCGTGCGGCGGCTCACAGTGGGAGCC

GCACAGGTTCCTGCTCAGCTACTGGTAGGCGCCCTGCGTGTGCTAGCGT

ACTCCCGCCTCAAGGAACTGACGCTCGAGGACCTAAAGATAACCGGCAC

CATGCCTCCGCTGCCTCTGGAAGCCACAGGACTTGCACTTTCCAGCTTG

CGCCTACGCAACGTGTCGTGGGCGACAGGGCGTTCTTGGCTCGCCGAGC

TGCAGCAGTGGCTCAAGCCAGGCCTCAAGGTACTGAGCATTGCCCAAGC

ACACTCGCCTGCCTTTTCCTGCGAACAGGTTCGCGCCTTCCCGGCCCTT

ACCAGCCTAGACCTGTCTGACAATCCTGGACTGGGCGAACGCGGACTGA

TGGCGGCTCTCTGTCCCCACAAGTTCCCGGCCATCCAGAATCTAGCGCT

GCGCAACACAGGAATGGAGACGCCCACAGGCGTGTGCGCCCGCACTGGCG

GCGGCAGGTGTGCAGCCCCACAGCCTAGACCTCAGCCACAACTCGCTGC

GCGCCACCGTAAACCCTAGCGCTCCGAGATGCATGTGGTCCAGCGCCCT

GAACTCCCTCAATCTGTCGTTCGCTGGGCTGGAACAGGTGCCTAAAGGA

CTGCCAGCCAAGCTCAGAGTGCTCGATCTCAGCTGCAACAGACTGAACA

GGGCGCCGCAGCCTGACGAGCTGCCCGAGGTGGATAACCTGACACTGGA

CGGGAATCCCTTCCTGGTCCCTGGAACTGCCCTCCCCCACGAGGGCTCA

ATGAACTCCGGCGTGGTCCCAGCCTGTGCACGTTCGACCCTGTCGGTGG

GGGTGTCGGGAACCCTGGTGCTGCTCCAAGGGGCCCGGGGCTTTGCCTA

A

Human ERK1 CDS (SEQ ID NO: 9)

ATGGCGGCGGCGGCGGCTCAGGGGGGCGGGGGCGGGGAGCCCCGTAGAA

CCGAGGGGGTCGGCCCGGGGGTCCCGGGGGAGGTGGAGATGGTGAAGGG

GCAGCCGTTCGACGTGGGCCCGCGCTACACGCAGTTGCAGTACATCGGC

GAGGGCGCGTACGGCATGGTCAGCTCGGCCTATGACCACGTGCGCAAGA

CTCGCGTGGCCATCAAGAAGATCAGCCCCTTCGAACATCAGACCTACTG

CCAGCGCACGCTCCGGGAGATCCAGATCCTGCTGCGCTTCCGCCATGAG

AATGTCATCGGCATCCGAGACATTCTGCGGGCGTCCACCCTGGAAGCCA

TGAGAGATGTCTACATTGTGCAGGACCTGATGGAGACTGACCTGTACAA

GTTGCTGAAAAGCCAGCAGCTGAGCAATGACCATATCTGCTACTTCCTC

TACCAGATCCTGCGGGGCCTCAAGTACATCCACTCCGCCAACGTGCTCC

ACCGAGATCTAAAGCCCTCCAACCTGCTCATCAACACCACCTGCGACCT

TAAGATTTGTGATTTCGGCCTGGCCCGGATTGCCGATCCTGAGCATGAC

CACACCGGCTTCCTGACGGAGTATGTGGCTACGCGCTGGTACCGGGCCC

CAGAGATCATGCTGAACTCCAAGGGCTATACCAAGTCCATCGACATCTG

GTCTGTGGGCTGCATTCTGGCTGAGATGCTCTCTAACCGGCCCATCTTC

CCTGGCAAGCACTACCTGGATCAGCTCAACCACATTCTGGGCATCCTGG

GCTCCCCATCCCAGGAGGACCTGAATTGTATCATCAACATGAAGGCCCG

AAACTACCTACAGTCTCTGCCCTCCAAGACCAAGGTGGCTTGGGCCAAG

CTTTTCCCCAAGTCAGACTCCAAAGCCCTTGACCTGCTGGACCGGATGT

-continued

TAACCTTTAACCCCAATAAACGGATCACAGTGGAGGAAGCGCTGGCTCA

CCCCTACCTGGAGCAGTACTATGACCCGACGGATGAGCCAGTGGCCGAG

GAGCCCTTCACCTTCGCCATGGAGCTGGATGACCTACCTAAGGAGCGGC

TGAAGGAGCTCATCTTCCAGGAGACAGCACGCTTCCAGCCCGGAGTGCT

GGAGGCCCCCTAG

Human ERK2 CDS (SEQ ID NO: 10)

ATGGCGGCGGCGGCGGCGGCGGGCGCGGGCCCGGAGATGGTCCGCGGGC

AGGTGTTCGACGTGGGGCCGCGCTACACCAACCTCTCGTACATCGGCGA

GGGCGCCTACGGCATGGTGTGCTCTGCTTATGATAATGTCAACAAAGTT

CGAGTAGCTATCAAGAAAATCAGCCCCTTTGAGCACCAGACCTACTGCC

AGAGAACCCTGAGGGAGATAAAAATCTTACTGCGCTTCAGACATGAGAA

CATCATTGGAATCAATGACATTATTCGAGCACCAACCATCGAGCAAATG

AAAGATGTATATATAGTACAGGACCTCATGGAAACAGATCTTTACAAGC

TCTTGAAGACACAACACCTCAGCAATGACCATATCTGCTATTTTCTCTA

CCAGATCCTCAGAGGGTTAAAATATATCCATTCAGCTAACGTTCTGCAC

CGTGACCTCAAGCCTTCCAACCTGCTGCTCAACACCACCTGTGATCTCA

AGATCTGTGACTTTGGCCTGGCCCGTGTTGCAGATCCAGACCATGATCA

CACAGGGTTCCTGACAGAATATGTGGCCACACGTTGGTACAGGGCTCCA

GAAATTATGTTGAATTCCAAGGGCTACACCAAGTCCATTGATATTTGGT

CTGTAGGCTGCATTCTGGCAGAAATGCTTTCTAACAGGCCCATCTTTCC

AGGGAAGCATTATCTTGACCAGCTGAACCACATTTTGGGTATTCTTGGA

TCCCCATCACAAGAAGACCTGAATTGTATAATAAATTTAAAAGCTAGGA

ACTATTTGCTTTCTCTTCCACACAAAAATAAGGTGCCATGGAACAGGCT

GTTCCCAAATGCTGACTCCAAAGCTCTGGACTTATTGGACAAAATGTTG

ACATTCAACCCACACAAGAGGATTGAAGTAGAACAGGCTCTGGCCCACC

CATATCTGGAGCAGTATTACGACCCGAGTGACGAGCCCATCGCCGAAGC

ACCATTCAAGTTCGACATGGAATTGGATGACTTGCCTAAGGAAAAGCTC

AAAGAACTAATTTTTGAAGAGACTGCTAGATTCCAGCCAGGATACAGAT

CTTAA

Human IKK CDS (SEQ ID NO: 11)

ATGTTTTCAGGGGGGTGTCATAGCCCCGGGTTTGGCCGCCCCAGCCCCG

CCTTCCCCGCCCCGGGGAGCCCGCCCCCTGCCCCGCGTCCCTGCCGACA

GGAAACAGGTGAGCAGATTGCCATCAAGCAGTGCCGGCAGGAGCTCAGC

CCCCGGAACCGAGAGCGGTGGTGCCTGGAGATCCAGATCATGAGAAGGC

TGACCCACCCCAATGTGGTGGCTGCCCGAGATGTCCCTGAGGGGATGCA

GAACTTGGCGCCCAATGACCTGCCCCTGCTGGCCATGGAGTACTGCCAA

GGAGGAGATCTCCGGAAGTACCTGAACCAGTTTGAGAACTGCTGTGGTC

TGCGGGAAGGTGCCATCCTCACCTTGCTGAGTGACATTGCCTCTGCGCT

TAGATACCTTCATGAAAACAGAATCATCCATCGGGATCTAAAGCCAGAA

AACATCGTCCTGCAGCAAGGAGAACAGAGGTTAATACACAAAATTATTG

-continued

ACCTAGGATATGCCAAGGAGCTGGATCAGGGCAGTCTTTGCACATCATT

CGTGGGGACCCTGCAGTACCTGGCCCCAGAGCTACTGGAGCAGCAGAAG

TACACAGTGACCGTCGACTACTGGAGCTTCGGCACCCTGGCCTTTGAGT

GCATCACGGGCTTCCGGCCCTTCCTCCCCAACTGGCAGCCCGTGCAGTG

GCATTCAAAAGTGCGGCAGAAGAGTGAGGTGGACATTGTTGTTAGCGAA

GACTTGAATGGAACGGTGAAGTTTTCAAGCTCTTTACCCTACCCCAATA

ATCTTAACAGTGTCCTGGCTGAGCGACTGGAGAAGTGGCTGCAACTGAT

GCTGATGTGGCACCCCCGACAGAGGGGCACGGATCCCACGTATGGGCCC

AATGGCTGCTTCAAGGCCCTGGATGACATCTTAAACTTAAAGCTGGTTC

ATATCTTGAACATGGTCACGGGCACCATCCACACCTACCCTGTGACAGA

GGATGAGAGTCTGCAGAGCTTGAAGGCCAGAATCCAACAGGACACGGGC

ATCCCAGAGGAGGACCAGGAGCTGCTGCAGGAAGCGGGCCTGGCGTTGA

TCCCCGATAAGCCTGCCACTCAGTGTATTTCAGACGGCAAGTTAAATGA

GGGCCACACATTGGACATGGATCTTGTTTTTCTCTTTGACAACAGTAAA

ATCACCTATGAGACTCAGATCTCCCCACGGCCCCAACCTGAAAGTGTCA

GCTGTATCCTTCAAGAGCCCAAGAGGAATCTCGCCTTCTTCCAGCTGAG

GAAGGTGTGGGGCCAGGTCTGGCACAGCATCCAGACCCTGAAGGAAGAT

TGCAACCGGCTGCAGCAGGGACAGCGAGCCGCCATGATGAATCTCCTCC

GAAACAACAGCTGCCTCTCCAAAATGAAGAATTCCATGGCTTCCATGTC

TCAGCAGCTCAAGGCCAAGTTGGATTTCTTCAAAACCAGCATCCAGATT

GACCTGGAGAAGTACAGCGAGCAAACCGAGTTTGGGATCACATCAGATA

AACTGCTGCTGGCCTGGAGGGAAATGGAGCAGGCTGTGGAGCTCTGTGG

GCGGGAGAACGAAGTGAAACTCCTGGTAGAACGGATGATGGCTCTGCAG

ACCGACATTGTGGACTTACAGAGGAGCCCCATGGGCCGGAAGCAGGGGG

GAACGCTGGACGACCTAGAGGAGCAAGCAAGGGAGCTGTACAGGAGACT

AAGGGAAAAACCTCGAGACCAGCGAACTGAGGGTGACAGTCAGGAAATG

GTACGGCTGCTGCTTCAGGCAATTCAGAGCTTCGAGAAGAAAGTGCGAG

TGATCTATACGCAGCTCAGTAAAACTGTGGTTTGCAAGCAGAAGGCGCT

GGAACTGTTGCCCAAGGTGGAAGAGGTGGTGAGCTTAATGAATGAGGAT

GAGAAGACTGTTGTCCGGCTGCAGGAGAAGCGGCAGAAGGAGCTCTGGA

ATCTCCTGAAGATTGCTTGTAGCAAGGTCCGTGGTCCTGTCAGTGGAAG

CCCGGATAGCATGAATGCCTCTCGACTTAGCCAGCCTGGGCAGCTGATG

TCTCAGCCCTCCACGGCCTCCAACAGCTTACCTGAGCCAGCCAAGAAGA

GTGAAGAACTGGTGGCTGAAGCACATAACCTCTGCACCCTGCTAGAAAA

TGCCATACAGGACACTGTGAGGGAACAAGACCAGAGTTTCACGGCCCTA

GACTGGAGCTGGTTACAGACGGAAGAAGAAGAGCACAGCTGCCTGGAGC

AGGCCTCATGA

Human IκB CDS (SEQ ID NO: 12)

ATGTTCCAGGCGGCCGAGCGCCCCCAGGAGTGGGCCATGGAGGGCCCCC

GCGACGGGCTGAAGAAGGAGCGGCTACTGGACGACCGCCACGACAGCGG

CCTGGACTCCATGAAAGACGAGGAGTACGAGCAGATGGTCAAGGAGCTG

-continued

CAGGAGATCCGCCTCGAGCCGCAGGAGGTGCCGCGCGGCTCGGAGCCCT

GGAAGCAGCAGCTCACCGAGGACGGGGACTCGTTCCTGCACTTGGCCAT

CATCCATGAAGAAAAGGCACTGACCATGGAAGTGATCCGCCAGGTGAAG

GGAGACCTGGCCTTCCTCAACTTCCAGAACAACCTGCAGCAGACTCCAC

TCCACTTGGCTGTGATCACCAACCAGCCAGAAATTGCTGAGGCACTTCT

GGGAGCTGGCTGTGATCCTGAGCTCCGAGACTTTCGAGGAAATACCCCC

CTACACCTTGCCTGTGAGCAGGGCTGCCTGGCCAGCGTGGGAGTCCTGA

CTCAGTCCTGCACCACCCCGCACCTCCACTCCATCCTGAAGGCTACCAA

CTACAATGGCCACACGTGTCTACACTTAGCCTCTATCCATGGCTACCTG

GGCATCGTGGAGCTTTTGGTGTCCTTGGGTGCTGATGTCAATGCTCAGG

AGCCCTGTAATGGCCGGACTGCCCTTCACCTCGCAGTGGACCTGCAAAA

TCCTGACCTGGTGTCACTCCTGTTGAAGTGTGGGGCTGATGTCAACAGA

GTTACCTACCAGGGCTATTCTCCCTACCAGCTCACCTGGGGCCGCCCAA

GCACCCGGATACAGCAGCAGCTGGGCCAGCTGACACTAGAAAACCTTCA

GATGCTGCCAGAGAGTGAGGATGAGGAGAGCTATGACACAGAGTCAGAG

TTCACGGAGTTCACAGAGGACGAGCTGCCCTATGATGACTGTGTGTTTG

GAGGCCAGCGTCTGACGTT ATGA

Human IRAK CDS (SEQ ID NO: 13)

ATGGCCGGGGGGCCGGGCCCGGGGGAGCCCGCAGCCCCCGGCGCCCAGC

ACTTCTTGTACGAGGTGCCGCCCTGGGTCATGTGCCGCTTCTACAAAGT

GATGGACGCCCTGGAGCCCGCCGACTGGTGCCAGTTCGCCGCCCTGATC

GTGCGCGACCAGACCGAGCTGCGGCTGTGCGAGCGCTCCGGGCAGCGCA

CGGCCAGCGTCCTGTGGCCCTGGATCAACCGCAACGCCCGTGTGGCCGA

CCTCGTGCACATCCTCACGCACCTGCAGCTGCTCCGTGCGCGGGACATC

ATCACAGCCTGGCACCCTCCCGCCCCGCTTCCGTCCCCAGGCACCACTG

CCCCGAGGCCCAGCAGCATCCCTGCACCCGCCGAGGCCGAGGCCTGGAG

CCCCCGGAAGTTGCCATCCTCAGCCTCCACCTTCCTCTCCCCAGCTTTT

CCAGGCTCCCAGACCCATTCAGGGCCTGAGCTCGGCCTGGTCCCAAGCC

CTGCTTCCCTGTGGCCTCCACCGCCATCTCCAGCCCCTTCTTCTACCAA

GCCAGGCCCAGAGAGCTCAGTGTCCCTCCTGCAGGGAGCCCGCCCCTTT

CCGTTTTGCTGGCCCCTCTGTGAGATTTCCCGGGGCACCCACAACTTCT

CGGAGGAGCTCAAGATCGGGGAGGGTGGCTTTGGGTGCGTGTACCGGGC

GGTGATGAGGAACACGGTGTATGCTGTGAAGAGGCTGAAGGAGAACGCT

GACCTGGAGTGGACTGCAGTGAAGCAGAGCTTCCTGACCGAGGTGGAGC

AGCTGTCCAGGTTTCGTCACCCAAACATTGTGGACTTTGCTGGCTACTG

TGCTCAGAACGGCTTCTACTGCCTGGTGTACGGCTTCCTGCCCAACGGC

TCCCTGGAGGACCGTCTCCACTGCCAGACCCAGGCCTGCCCACCTCTCT

CCTGGCCTCAGCGACTGGACATCCTTCTGGGTACAGCCCGGGCAATTCA

GTTTCTACATCAGGACAGCCCCAGCCTCATCCATGGAGACATCAAGAGT

TCCAACGTCCTTCTGGATGAGAGGCTGACACCCAAGCTGGGAGACTTTG

-continued

GCCTGGCCCGGTTCAGCCGCTTTGCCGGGTCCAGCCCCAGCCAGAGCAG

CATGGTGGCCCGGACACAGACAGTGCGGGGCACCCTGGCCTACCTGCCC

GAGGAGTACATCAAGACGGGAAGGCTGGCTGTGGACACGGACACCTTCA

GCTTTGGGGTGGTAGTGCTAGAGACCTTGGCTGGTCAGAGGGCTGTGAA

GACGCACGGTGCCAGGACCAAGTATCTGAAAGACCTGGTGGAAGAGGAG

GCTGAGGAGGCTGGAGTGGCTTTGAGAAGCACCCAGAGCACACTGCAAG

CAGGTCTGGCTGCAGATGCCTGGGCTGCTCCCATCGCCATGCAGATCTA

CAAGAAGCACCTGGACCCCAGGCCCGGGCCCTGCCCACCTGAGCTGGGC

CTGGGCCTGGGCCAGCTGGCCTGCTGCTGCCTGCACCGCCGGGCCAAAA

GGAGGCCTCCTATGACCCAGGTGTACGAGAGGCTAGAGAAGCTGCAGGC

AGTGGTGGCGGGGGTGCCCGGGCATTCGGAGGCCGCCAGCTGCATCCCC

CCTTCCCCGCAGGAGAACTCCTACGTGTCCAGCACTGGCAGAGCCCACA

GTGGGGCTGCTCCATGGCAGCCCCTGGCAGCGCCATCAGGAGCCAGTGC

CCAGGCAGCAGAGCAGCTGCAGAGAGGCCCCAACCAGCCCGTGGAGAGT

GACGAGAGCCTAGGCGGCCTCTCTGCTGCCCTGCGCTCCTGGCACTTGA

CTCCAAGCTGCCCTCTGGACCCAGCACCCCTCAGGGAGGCCGGCTGTCC

TCAGGGGGACACGGCAGGAGAATCGAGCTGGGGGAGTGGCCCAGGATCC

CGGCCCACAGCCGTGGAAGGACTGGCCCTTGGCAGCTCTGCATCATCGT

CGTCAGAGCCACCGCAGATTATCATCAACCCTGCCCGACAGAAGATGGT

CCAGAAGCTGGCCCTGTACGAGGATGGGGCCCTGGACAGCCTGCAGCTG

CTGTCGTCCAGCTCCCTCCCAGGCTTGGGCCTGGAACAGGACAGGCAGG

GGCCCGAAGAAAGTGATGAATTTCAGAGCTGA

Human JNK CDS (SEQ ID NO: 14)

ATGAGCAGAAGCAAGCGTGACAACAATTTTTATAGTGTAGAGATTGGAG

ATTCTACATTCACAGTCCTGAAACGATATCAGAATTTAAAACCTATAGG

CTCAGGAGCTCAAGGAATAGTATGCGCAGCTTATGATGCCATTCTTGAA

AGAAATGTTGCAATCAAGAAGCTAAGCCGACCATTTCAGAATCAGACTC

ATGCCAAGCGGGCCTACAGAGAGCTAGTTCTTATGAAATGTGTTAATCA

CAAAAATATAATTGGCCTTTTGAATGTTTTCACACCACAGAAATCCCTA

GAAGAATTTCAAGATGTTTACATAGTCATGGAGCTCATGGATGCAAATC

TTTGCCAAGTGATTCAGATGGAGCTAGATCATGAAAGAATGTCCTACCT

TCTCTATCAGATGCTGTGTGGAATCAAGCACCTTCATTCTGCTGGAATT

ATTCATCGGGACTTAAAGCCCAGTAATATAGTAGTAAAATCTGATTGCA

CTTTGAAGATTCTTGACTTCGGTCTGGCCAGGACTGCAGGAACGAGTTT

TATGATGACGCCTTATGTAGTGACTCGCTACTACAGAGCACCCGAGGTC

ATCCTTGGCATGGGCTACAAGGAAAACGTTGACATTTGGTCAGTTGGGT

GCATCATGGGAGAAATGATCAAAGGTGGTGTTTTGTTCCCAGGTACAGA

TCATATTGATCAGTGGAATAAAGTTATTGAACAGCTTGGAACACCATGT

CCTGAATTCATGAAGAAACTGCAACCAACAGTAAGGACTTACGTTGAAA

ACAGACCTAAATATGCTGGATATAGCTTTGAGAAACTCTTCCCTGATGT

CCTTTTCCCAGCTGACTCAGAACACAACAAACTTAAAGCCAGTCAGGCA

-continued

AGGGATTTGTTATCCAAAATGCTGGTAATAGATGCATCTAAAAGGATCT
CTGTAGATGAAGCTCTCCAACACCCGTACATCAAGTCTGGTATGATCCT
TCTGAAGCAGAAGCTCCACCACCAAAGATCCCTGACAAGCAGTTAGATG
AAAGGGAACACACAATAGAAGAGTGGAAAGAATTGATATATAAGGAAGT
TATGGACTTGGAGGAGAGAACCAAGAATGGAGTTATACGGGGGCAGCCC
TCTCCTTTAGGTGCAGCAGTGATCAATGGCTCTCAGCATCCATCATCAT
CGTCGTCTGTCAATGATGTGTCTTCAATGTCAACAGATCCGACTTTGGC
CTCTGATACAGACAGCAGTCTAGAAGCAGCAGCTGGGCCTCTGGGCTGC
TGTAGATGA

Human LBP CDS (SEQ ID NO: 15)

ATGGGGGCCTTGGCCAGAGCCCTGCCGTCCATACTGCTGGCATTGCTGC
TTACGTCCACCCCAGAGGCTCTGGGTGCCAACCCCGGCTTGGTCGCCAG
GATCACCGACAAGGGACTGCAGTATGCGGCCCAGGAGGGGCTATTAGCT
CTGCAGAGTGAGCTGCTCAGGATCACGCTGCCTGACTTCACCGGGGACT
TGAGGATCCCCCACGTCGGCCGTGGGCGCTATGAGTTCCACAGCCTGAA
CATCCACAGCTGTGAGCTGCTTCACTCTGCGCTGAGGCCTGTCCCTGGC
CAGGGCCTGAGTCTCAGCATCTCCGACTCCTCCATCCGGGTCCAGGGCA
GGTGGAAGGTGCGCAAGTCATTCTTCAAACTACAGGGCTCCTTTGATGT
CAGTGTCAAGGGCATCAGCATTTCGGTCAACCTCCTGTTGGGCAGCGAG
TCCTCCGGGAGGCCCACAGTTACTGCCTCCAGCTGCAGCAGTGACATCG
CTGACGTGGAGGTGGACATGTCGGGAGACTTGGGGTGGCTGTTGAACCT
CTTCCACAACCAGATTGAGTCCAAGTTCCAGAAAGTACTGGAGAGCAGG
ATTTGCGAAATGATCCAGAAATCGGTGTCCTCCGATCTACAGCCTTATC
TCCAAACTCTGCCAGTTACAACAGAGATTGACAGTTTCGCCGACATTGA
TTATAGCTTAGTGGAAGCCCCTCGGGCAACAGCCCAGATGCTGGAGGTG
ATGTTTAAGGGTGAAATCTTTCATCGTAACCACCGTTCTCCAGTTACCC
TCCTTGCTGCAGTCATGAGCCTTCCTGAGGAACACAACAAAATGGTCTA
CTTTGCCATCTCGGATTATGTCTTCAACACGGCCAGCCTGGTTTATCAT
GAGGAAGGATATCTGAACTTCTCCATCACAGATGACATGATACCGCCTG
ACTCTAATATCCGACTGACCACCAAGTCCTTCCGACCCTTCGTCCCACG
GTTAGCCAGGCTCTACCCCAACATGAACCTGGAACTCCAGGGATCAGTG
CCCTCTGCTCCGCTCCTGAACTTCAGCCCTGGGAATCTGTCTGTGGACC
CCTATATGGAGATAGATGCCTTTGTGCTCCTGCCCAGCTCCAGCAAGGA
GCCTGTCTTCCGGCTCAGTGTGGCCACTAATGTGTCCGCCACCTTGACC
TTCAATACCAGCAAGATCACTGGGTTCCTGAAGCCAGGAAAGGTAAAAG
TGGAACTGAAAGAATCCAAAGTTGGACTATTCAATGCAGAGCTGTTGGA
AGCGCTCCTCAACTATTACATCCTTAACACCCTCTACCCCAAGTTCAAT
GATAAGTTGGCCGAAGGCTTCCCCCTTCCTCTGCTGAAGCGTGTTCAGC
TCTACGACCTTGGGCTGCAGATCCATAAGGACTTCCTGTTCTTGGGTGC
CAATGTCCAATACATGAGAGTTTGA

Human MEK1 CDS (SEQ ID NO: 16)

ATGCCCAAGAAGAAGCCGACGCCCATCCAGCTGAACCCGGCCCCCGACG
GCTCTGCAGTTAACGGGACCAGCTCTGCGGAGACCAACTTGGAGGCCTT
GCAGAAGAAGCTGGAGGAGCTAGAGCTTGATGAGCAGCAGCGAAAGCGC
CTTGAGGCCTTTCTTACCCAGAAGCAGAAGGTGGGAGAACTGAAGGATG
ACGACTTTGAGAAGATCAGTGAGCTGGGGGCTGGCAATGGCGGTGTGGT
GTTCAAGGTCTCCCACAAGCCTTCTGGCCTGGTCATGGCCAGAAAGCTA
ATTCATCTGGAGATCAAACCCGCAATCCGGAACCAGATCATAAGGGAGC
TGCAGGTTCTGCATGAGTGCAACTCTCCGTACATCGTGGGCTTCTATGG
TGCGTTCTACAGCGATGGCGAGATCAGTATCTGCATGGAGCACATGGAT
GGAGGTTCTCTGGATCAAGTCCTGAAGAAAGCTGGAAGAATTCCTGAAC
AAATTTTAGGAAAAGTTAGCATTGCTGTAATAAAAGGCCTGACATATCT
GAGGGAGAAGCACAAGATCATGCACAGAGATGTCAAGCCCTCCAACATC
CTAGTCAACTCCCGTGGGGAGATCAAGCTCTGTGACTTTGGGGTCAGCG
GGCAGCTCATCGACTCCATGGCCAACTCCTTCGTGGGCACAAGGTCCTA
CATGTCGCCAGAAAGACTCCAGGGGACTCATTACTCTGTGCAGTCAGAC
ATCTGGAGCATGGGACTGTCTCTGGTAGAGATGGCGGTTGGGAGGTATC
CCATCCCTCCTCCAGATGCCAAGGAGCTGGAGCTGATGTTTGGGTGCCAG
GTGGAAGGAGATGCGGCTGAGACCCCACCCAGGCCAAGGACCCCCGGGA
GGCCCCTTAGCTCATACGGAATGGACAGCCGACCTCCCATGGCAATTTT
TGAGTTGTTGGATTACATAGTCAACGAGCCTCCTCCAAAACTGCCCAGT
GGAGTGTTCAGTCTGGAATTTCAAGATTTTGTGAATAAATGCTTAATAA
AAAACCCCGCAGAGAGAGCAGATTTGAAGCAACTCATGGTTCATGCTTT
TATCAAGAGATCTGATGCTGAGGAAGTGGATTTTGCAGGTTGGCTCTGC
TCCACCATCGGCCTTAACCAGCCCAGC ACACCAACCCATGCTGCTGGC
GTCTAA

Human MEK2 CDS (SEQ ID NO: 17)

ATGCTGGCCCGGAGGAAGCCGGTGCTGCCGGCGCTCACCATCAACCCTA
CCATCGCCGAGGGCCCATCCCCTACCAGCGAGGGCGCCTCCGAGGCAAA
CCTGGTGGACCTGCAGAAGAAGCTGGAGGAGCTGGAACTTGACGAGCAG
CAGAAGAAGCGGCTGGAAGCCTTTCTCACCCAGAAAGCCAAGGTCGGCG
AACTCAAAGACGATGACTTCGAAAGGATCTCAGAGCTGGGCGCGGGCAA
CGGCGGGGTGGTCACCAAAGTCCAGCACAGACCCTCGGGCCTCATCATG
GCCAGGAAGCTGATCCACCTTGAGATCAAGCCGGCCATCCGGAACCAGA
TCATCCGCGAGCTGCAGGTCCTGCACGAATGCAACTCGCCGTACATCGT
GGGCTTCTACGGGGCCTTCTACAGTGACGGGGAGATCAGCATTTGCATG
GAACACATGGACGGCGGCTCCCTGGACCAGGTGCTGAAAGAGGCCAAGA
GGATTCCCGAGGAGATCCTGGGGAAAGTCAGCATCGCGGTTCTCCGGGG
CTTGGCGTACCTCCGAGAGAAGCACCAGATCATGCACCGAGATGTGAAG
CCCTCCAACATCCTCGTGAACTCTAGAGGGGAGATCAAGCTGTGTGACT
TCGGGGTGAGCGGCCAGCTCATCGACTCCATGGCCAACTCCTTCGTGGG

-continued

CACGCGCTCCTACATGGCTCCGGAGCGGTTGCAGGGCACACATTACTCG

GTGCAGTCGGACATCTGGAGCATGGGCCTGTCCCTGGTGGAGCTGGCCG

TCGGAAGGTACCCCATCCCCCCGCCCGACGCCAAAGAGCTGGAGGCCAT

CTTTGGCCGGCCCGTGGTCGACGGGGAAGAAGGAGAGCCTCACAGCATC

TCGCCTCGGCCGAGGCCCCCCGGGCGCCCCGTCAGCGGTCACGGGATGG

ATAGCCGGCCTGCCATGGCCATCTTTGAACTCCTGGACTATATTGTGAA

CGAGCCACCTCCTAAGCTGCCCAACGGTGTGTTCACCCCCGACTTCCAG

GAGTTTGTCAATAAATGCCTCATCAAGAACCCAGCGGAGCGGGCGGACC

TGAAGATGCTCACAAACCACACCTTCATCAAGCGGTCCGAGGTGGAAGA

AGTGGATTTTGCCGGCTGGTTGTGTAAAACCCTGCGGCTGAACCAGCCC

GGCACACCCACGCGCACCGCCGTGTGA

Human MEK3 CDS (SEQ ID NO: 18)

ATGTCCAAGCCACCCGCACCCAACCCCACACCCCCCCGGAACCTGGACT

CCCGGACCTTCATCACCATTGGAGACAGAAACTTTGAGGTGGAGGCTGA

TGACTTGGTGACCATCTCAGAACTGGGCCGTGGAGCCTATGGGGTGGTA

GAGAAGGTGCGGCACGCCCAGAGCGGCACCATCATGGCCGTGAAGCGGA

TCCGGGCCACCGTGAACTCACAGGAGCAGAAGCGGCTGCTCATGGACCT

GGACATCAACATGCGCACGGTCGACTGTTTCTACACTGTCACCTTCTAC

GGGGCACTATTCAGAGAGGGAGACGTGTGGATCTGCATGGAGCTCATGG

ACACATCCTTGGACAAGTTCTACCGGAAGGTGCTGGATAAAAACATGAC

AATTCCAGAGGACATCCTTGGGGAGATTGCTGTGTCTATCGTGCGGGCC

CTGGAGCATCTGCACAGCAAGCTGTCGGTGATCCACAGAGATGTGAAGC

CCTCCAATGTCCTTATCAACAAGGAGGGCCATGTGAAGATGTGTGACTT

TGGCATCAGTGGCTACTTGGTGGACTCTGTGGCCAAGACGATGGATGCC

GGCTGCAAGCCCTACATGGCCCCTGAGAGGATCAACCCAGAGCTGAACC

AGAAGGGCTACAATGTCAAGTCCGACGTCTGGAGCCTGGGCATCACCAT

GATTGAGATGGCCATCCTGCGGTTCCCTTACGAGTCCTGGGGGACCCCG

TTCCAGCAGCTGAAGCAGGTGGTGGAGGAGCCGTCCCCCCAGCTCCCAG

CCGACCGTTTCTCCCCCGAGTTTGTGGACTTCACTGCTCAGTGCCTGAG

GAAGAACCCCGCAGAGCGTATGAGCTACCTGGAGCTGATGGAGCACCCC

TTCTTCACCTTGCACAAAACCAAGAAGACGGACATTGCTGCCTTCGTGA

AGGAGATCCTGGGAGAAGACTCATAG

Human MEK6 CDS (SEQ ID NO: 19)

ATGTCTCAGTCGAAAGGCAAGAAGCGAAACCCTGGCCTTAAAATTCCAA

AAGAAGCATTTGAACAACCTCAGACCAGTTCCACACCACCTCGAGATTT

AGACTCCAAGGCTTGCATTTCTATTGGAAATCAGAACTTTGAGGTGAAG

GCAGATGACCTGGAGCCTATAATGGAACTGGGACGAGGTGCGTACGGGG

TGGTGGAGAAGATGCGGCACGTGCCCAGCGGGCAGATCATGGCAGTGAA

GCGGATCCGAGCCACAGTAAATAGCCAGGAACAGAAACGGCTACTGATG

GATTTGGATATTTCCATGAGGACGGTGGACTGTCCATTCACTGTCACCT

-continued

TTTATGGCGCACTGTTTCGGGAGGGTGATGTGTGGATCTGCATGGAGCT

CATGGATACATCACTAGATAAATTCTACAAACAAGTTATTGATAAAGGC

CAGACAATTCCAGAGGACATCTTAGGGAAAATAGCAGTTTCTATTGTAA

AAGCATTAGAACATTTACATAGTAAGCTGTCTGTCATTCACAGAGACGT

CAAGCCTTCTAATGTACTCATCAATGCTCTCGGTCAAGTGAAGATGTGC

GATTTTGGAATCAGTGGCTACTTGGTGGACTCTGTTGCTAAAACAATTG

ATGCAGGTTGCAAACCATACATGGCCCCTGAAAGAATAAACCCAGAGCT

CAACCAGAAGGGATACAGTGTGAAGTCTGACATTTGGAGTCTGGGCATC

ACGATGATTGAGTTGGCCATCCTTCGATTTCCCTATGATTCATGGGGAA

CTCCATTTCAGCAGCTCAAACAGGTGGTAGAGGAGCCATCGCCACAACT

CCCAGCAGACAAGTTCTCTGCAGAGTTTGTTGACTTTACCTCACAGTGC

TTAAAGAAGAATTCCAAAGAACGGCCTACATACCCAGAGCTAATGCAAC

ATCCATTTTTCACCCTACATGAATCCAAAGGAACAGATGTGGCATCTTT

TGTAAAACTGATTCTTGGAGACTAA

Human MEKK1 CDS (SEQ ID NO: 20)

ATGGCGGCGGCGGCGGGGAATCGCGCCTCGTCGTCGGGATTCCCGGGCG

CCAGGGCTACGAGCCCTGAGGCAGGCGGCGGCGGAGGAGCCCTCAAGGC

GAGCAGCGCGCCCGCGGCTGCCGCGGGACTGCTGCGGGAGGCGGGCAGC

GGGGGCCGCGAGCGGGCGGACTGGCGGCGGCGGCAGCTGCGCAAAGTGC

GGAGTGTGGAGCTGGACCAGCTGCCTGAGCAGCCGCTCTTCCTTGCCGC

CTCACCGCCGGCCTCCTCGACTTCCCCGTCGCCGGAGCCCGCGGACGCA

GCGGGGAGTGGGACCGGCTTCCAGCCTGTGGCGGTGCCGCCGCCCCACG

GAGCCGCGAGCCGCGGCGGCGCCCACCTTACCGAGTCGGTGGCGGCGCC

GGACAGCGGCGCCTCGAGTCCCGCAGCGGCCGAGCCCGGGGAGAAGCGG

GCGCCCGCCGCCGAGCCGTCTCCTGCAGCGGCCCCCGCCGGTCGTGAGA

TGGAGAATAAAGAAACTCTCAAAGGGTTGCACAAGATGGATGATCGTCC

AGAGGAACGAATGATCAGGGAGAAACTGAAGGCAACCTGTATGCCAGCC

TGGAAGCACGAATGGTTGGAAAGGAGAAATAGGCGAGGGCCTGTGGTGG

TAAAACCAATCCCAGTTAAAGGAGATGGATCTGAAATGAATCACTTAGC

AGCTGAGTCTCCAGGAGAGGTCCAGGCAAGTGCGGCTTCACCAGCTTCC

AAAGGCCGACGCAGTCCTTCTCCTGGCAACTCCCCATCAGGTCGCACAG

TGAAATCAGAATCTCCAGGAGTAAGGAGAAAAAGAGTTTCCCCAGTGCC

TTTTCAGAGTGGCAGAATCACACCACCCCGAAGAGCCCCTTCACCAGAT

GGCTTCTCACCATATAGCCCTGAGGAAACAAACCGCCGTGTTAACAAAG

TGATGCGGGCCAGACTGTACTTACTGCAGCAGATAGGGCCTAACTCTTT

CCTGATTGGAGGAGACAGCCCAGACAATAAATACCGGGTGTTTATTGGG

CCTCAGAACTGCAGCTGTGCACGTGGAACATTCTGTATTCATCTGCTAT

TTGTGATGCTCCGGGTGTTTCAACTAGAACCTTCAGACCCAATGTTATG

GAGAAAAACTTTAAAGAATTTTGAGGTTGAGAGTTTGTTCCAGAAATAT

CACAGTAGGCGTAGCTCAAGGATCAAAGCTCCATCTCGTAACACCATCC

AGAAGTTTGTTTCACGCATGTCAAATTCTCATACATTGTCATCATCTAG

-continued

TACTTCTACGTCTAGTTCAGAAAACAGCATAAAGGATGAAGAGGAACAG
ATGTGTCCTATTTGCTTGTTGGGCATGCTTGATGAAGAAAGTCTTACAG
TGTGTGAAGACGGCTGCAGGAACAAGCTGCACCACCACTGCATGTCAAT
TTGGGCAGAAGAGTGTAGAAGAAATAGAGAACCTTTAATATGTCCCCTT
TGTAGATCTAAGTGGAGATCTCATGATTTCTACAGCCACGAGTTGTCAA
GTCCTGTGGATTCCCCTTCTTCCCTCAGAGCTGCACAGCAGCAAACCGT
ACAGCAGCAGCCTTTGGCTGGATCACGAAGGAATCAAGAGAGCAATTTT
AACCTTACTCATTATGGAACTCAGCAAATCCCTCCTGCTTACAAAGATT
TAGCTGAGCCATGGATTCAGGTGTTTGGAATGGAACTCGTTGGCTGCTT
ATTTTCTAGAAACTGGAATGTGAGAGAGATGGCCCTCAGGCGTCTTTCC
CATGATGTCAGTGGGGCCCTGCTGTTGGCAAATGGGGAGAGCACTGGAA
ATTCTGGGGGCAGCAGTGGAAGCAGCCCGAGTGGGGGAGCCACCAGTGG
GTCTTCCCAGACCAGTATCTCAGGAGATGTGGTGGAGGCATGCTGCAGC
GTTCTGTCAATGGTCTGTGCTGACCCTGTCTACAAAGTGTACGTTGCTG
CTTTAAAAACATTGAGAGCCATGCTGGTATATACTCCTTGCCACAGTTT
AGCGGAAAGAATCAAACTTCAGAGACTTCTCCAGCCAGTTGTAGACACC
ATCCTAGTCAAATGTGCAGATGCCAATAGCCGCACAAGTCAGCTGTCCA
TATCAACACTGTTGGAACTGTGCAAAGGCCAAGCAGGAGAGTTGGCAGT
TGGCAGAGAAATACTAAAAGCTGGATCCATTGGTATTGGTGGTGTTGAT
TATGTCTTAAATTGTATTCTTGGAAACCAAACTGAATCAAACAATTGGC
AAGAACTTCTTGGCCGCCTTTGTCTTATAGATAGACTGTTGTTGGAATT
TCCTGCTGAATTTTATCCTCATATTGTCAGTACTGATGTTTCACAAGCT
GAGCCTGTTGAAATCAGGTATAAGAAGCTGCTGTCCCTCTTAACCTTTG
CTTTGCAGTCCATTGATAATTCCCACTCAATGGTTGGCAAACTTTCCAG
AAGGATCTACTTGAGTTCTGCAAGAATGGTTACTACAGTACCCCATGTG
TTTTCAAAACTGTTAGAAATGCTGAGTGTTTCCAGTTCCACTCACTTCA
CCAGGATGCGTCGCCGTTTGATGGCTATTGCAGATGAGGTGGAAATTGC
CGAAGCCATCCAGTTGGGCGTAGAAGACACTTTGGATGGTCAACAGGAC
AGCTTCTTGCAGGCATCTGTTCCCAACAACTATCTGGAAACCACAGAGA
ACAGTTCCCCTGAGTGCACAGTCCATTTAGAGAAAACTGGAAAAGGATT
ATGTGCTACAAAATTGAGTGCCAGTTCAGAGGACATTTCTGAGAGACTG
GCCAGCATTTCAGTAGGACCTTCTAGTTCAACAACAACAACAACAACAA
CAACAGAGCAACCAAAGCCAATGGTTCAAACAAAAGGCAGACCCCACAG
TCAGTGTTTGAACTCCTCTCCTTTATCTCATCATTCCCAATTAATGTTT
CCAGCCTTGTCAACCCCTTCTTCTTCTACCCCATCTGTACCAGCTGGCA
CTGCAACAGATGTCTCTAAGCATAGACTTCAGGGATTCATTCCCTGCAG
AATACCTTCTGCATCTCCTCAAACACAGCGCAAGTTTTCTCTACAATTC
CACAGAAACTGTCCTGAAAACAAAGACTCAGATAAACTTTCCCCAGTCT
TTACTCAGTCAAGACCCTTGCCCTCCAGTAACATACACAGGCCAAAGCC
ATCTAGACCTACCCCAGGTAATACAAGTAAACAGGGAGATCCCTCAAAA

-continued

AATAGCATGACACTTGATCTGAACAGTAGTTCCAAATGTGATGACAGCT
TTGGCTGTAGCAGCAATAGTAGTAATGCTGTTATACCCAGTGACGAGAC
AGTGTTCACCCCAGTAGAGGAGAAATGCAGATTAGATGTCAATACAGAG
CTCAACTCCAGTATTGAGGACCTTCTTGAAGCATCTATGCCTTCAAGTG
ATACAACAGTAACTTTTAAGTCAGAAGTTGCTGTCCTGTCTCCTGAAAA
GGCTGAAAATGATGATACCTACAAAGATGATGTGAATCATAATCAAAAG
TGCAAAGAGAAGATGGAAGCTGAAGAAGAAGAAGCTTTAGCAATTGCCA
TGGCAATGTCAGCGTCTCAGGATGCCCTCCCCATAGTTCCTCAGCTGCA
GGTTGAAAATGGAGAAGATATCATCATTATTCAACAGGATACACCAGAG
ACTCTACCAGGACATACCAAAGCAAAACAACCGTATAGAGAAGACACTG
AATGGCTGAAAGGTCAACAGATAGGCCTTGGAGCATTTTCTTCTTGTTA
TCAGGCTCAAGATGTGGGAACTGGAACTTTAATGGCTGTTAAACAGGTG
ACTTATGTCAGAAACACATCTTCTGAGCAAGAAGAAGTAGTAGAAGCAC
TAAGAGAAGAGATAAGAATGATGAGCCATCTGAATCATCCAAACATCAT
TAGGATGTTGGGAGCCACGTGTGAGAAGAGCAATTACAATCTCTTCATT
GAATGGATGGCAGGGGGATCGGTGGCTCATTTGCTGAGTAAATATGGAG
CCTTCAAAGAATCAGTAGTTATTAACTACACTGAACAGTTACTCCGTGG
CCTTTCGTATCTCCATGAAAACCAAATCATTCACAGAGATGTCAAAGGT
GCCAATTTGCTAATTGACAGCACTGGTCAGAGACTAAGAATTGCAGATT
TTGGAGCTGCAGCCAGGTTGGCATCAAAAGGAACTGGTGCAGGAGAGTT
TCAGGGACAATTACTGGGGACAATTGCATTTATGGCACCTGAGGTACTA
AGAGGTCAACAGTATGGAAGGAGCTGTGATGTATGGAGTGTTGGCTGTG
CTATTATAGAAATGGCTTGTGCAAAACCACCATGGAATGCAGAAAAACA
CTCCAATCATCTTGCTTTGATATTTAAGATTGCTAGTGCAACTACTGCT
CCATCGATCCCTTCACATTTGTCTCCTGGTTTACGAGATGTGGCTCTTC
GTTGTTTAGAACTTCAACCTCAGGACAGACCTCCATCAAGAGAGCTACT
GAAGCATCCAGTCTTTCGTACTACATGGTAG

Human MEKK 3 CDS (SEQ ID NO: 21)

ATGGACGAACAGGAGGCATTGAACTCAATCATGAACGATCTGGTGGCCCT
CCAGATGAACCGACGTCACCGGATGCCTGGATATGAGACCATGAAGAACA
AAGACACAGGTCACTCAAATAGGCAGAAAAAACACAACAGCAGCAGCTCA
GCCCTTCTGAACAGCCCCACAGTAACAACAAGCTCATGTGCAGGGGCCAG
TGAGAAAAAGAAATTTTTGAGTGACGTCAGAATCAAGTTCGAGCACAACG
GGGAGAGGCGAATTATAGCGTTCAGCCGGCCTGTGAAATATGAAGATGTG
GAGCACAAGGTGACAACAGTATTTGGACAACCTCTTGATCTACATTACAT
GAACAATGAGCTCTCCATCCTGCTGAAAAACCAAGATGATCTTGATAAAG
CAATTGACATTTTAGATAGAAGCTCAAGCATGAAAAGCCTTAGGATATTG
CTGTTGTCCCAGGACAGAAACCATAACAGTTCCTCTCCCCACTCTGGGGT
GTCCAGACAGGTGCGGATCAAGGCTTCCCAGTCCGCAGGGGATATAAATA
CTATCTACCAGCCCCCCGAGCCCAGAAGCAGGCACCTCTCTGTCAGCTCC
CAGAACCCTGGCCGAAGCTCACCTCCCCCTGGCTATGTTCCTGAGCGGCA

-continued

GCAGCACATTGCCCGGCAGGGGTCCTACACCAGCATCAACAGTGAGGGGG

AGTTCATCCCAGAGACCAGCGAGCAGTGCATGCTGGATCCCCTGAGCAGT

GCAGAAAATTCCTTGTCTGGAAGCTGCCAATCCTTGGACAGGTCAGCAGA

CAGCCCATCCTTCCGGAAATCACGAATGTCCCGTGCCCAGAGCTTCCCTG

ACAACAGACAGGAATACTCAGATCGGGAAACTCAGCTTTATGACAAAGGG

GTCAAAGGTGGAACCTACCCCCGGCGCTACCACGTGTCTGTGCACCACAA

GGACTACAGTGATGGCAGAAGAACATTTCCCCGAATACGGCGTCATCAAG

GCAACTTGTTCACCCTGGTGCCCTCCAGCCGCTCCCTGAGCACAAATGGC

GAGAACATGGGTCTGGCTGTGCAATACCTGGACCCCCGTGGGCGCCTGCG

GAGTGCGGACAGCGAGAATGCCCTCTCTGTGCAGGAGAGGAATGTGCCAA

CCAAGTCTCCCAGTGCCCCCATCAACTGGCGCCGGGGAAAGCTCCTGGGC

CAGGGTGCCTTCGGCAGGGTCTATTTGTGCTATGACGTGGACACGGGACG

TGAACTTGCTTCCAAGCAGGTCCAATTTGATCCAGACAGTCCTGAGACAA

GCAAGGAGGTGAGTGCTCTGGAGTGCGAGATCCAGTTGCTAAAGAACTTG

CAGCATGAGCGCATCGTGCAGTACTATGGCTGTCTGCGGGACCGCGCTGA

GAAGACCCTGACCATCTTCATGGAGTACATGCCAGGGGGCTCGGTGAAAG

ACCAGTTGAAGGCTTACGGTGCTCTGACAGAGAGCGTGACCCGAAAGTAC

ACGCGGCAGATCCTGGAGGGCATGTCCTACCTGCACAGCAACATGATTGT

TCACCGGGACATTAAGGGAGCCAACATCCTCCGAGACTCTGCTGGGAATG

TAAAGCTGGGGGACTTTGGGGCCAGCAAACGCCTGCAGACGATCTGTATG

TCGGGGACGGGCATGCGCTCCGTCACTGGCACACCCTACTGGATGAGCCC

TGAGGTGATCAGCGGCGAGGGCTATGGAAGGAAAGCAGACGTGTGGAGCC

TGGGCTGCACTGTGGTGGAGATGCTGACAGAGAAACCACCGTGGGCAGAG

TATGAAGCTATGGCCGCCATCTTCAAGATTGCCACCCAGCCCACCAATCC

TCAGCTGCCCTCCCACATCTCTGAACATGGCCGGGACTTCCTGAGGCGCA

TTTTTGTGGAGGCTCGCCAGAGACCTTCAGCTGAGGAGCTGCTCACACAC

CACTTTGCACAGCTCATGTACTGA

Human MEKK4 CDS (SEQ ID NO: 22)

ATGAGAGAAGCCGCTGCCGCGCTGGTCCCTCCTCCCGCCTTTGCCGTCAC

GCCTGCCGCCGCCATGGAGGAGCCGCCGCCACCGCCGCCGCCGCCACCAC

CGCCACCGGAACCCGAGACCGAGTCAGAACCCGAGTGCTGCTTGGCGGCG

AGGCAAGAGGGCACATTGGGAGATTCAGCTTGCAAGAGTCCTGAATCTGA

TCTAGAAGACTTCTCCGATGAAACAAATACAGAGAATCTTTATGGTACCT

CTCCCCCCAGCACACCTCGACAGATGAAACGCATGTCAACCAAACATCAG

AGGAATAATGTGGGGAGGCCAGCCAGTCGGTCTAATTTGAAAGAAAAAAT

GAATGCACCAAATCAGCCTCCACATAAAGACACTGGAAAAACAGTGGAGA

ATGTGGAAGAATACAGCTATAAGCAGGAGAAAAAGATCCGAGCAGCTCTT

AGAACAACAGAGCGTGATCATAAAAAAAATGTACAGTGCTCATTCATGTT

AGACTCAGTGGGTGGATCTTTGCCAAAAAAATCAATTCCAGATGTGGATC

TCAATAAGCCTTACCTCAGCCTTGGCTGTAGCAATGCTAAGCTTCCAGTA

-continued

TCTGTGCCCATGCCTATAGCCAGACCTGCACGCCAGACTTCTAGGACTGA

CTGTCCAGCAGATCGTTTAAAGTTTTTTGAAACTTTACGACTTTTGCTAA

AGCTTACCTCAGTCTCAAAGAAAAAAGACAGGGAGCAAAGAGGACAAGAA

AATACGTCTGGTTTCTGGCTTAACCGATCTAACGAACTGATCTGGTTAGA

GCTACAAGCCTGGCATGCAGGACGGACAATTAACGACCAGGACTTCTTTT

TATATACAGCCCGTCAAGCCATCCCAGATATTATTAATGAAATCCTTACT

TTCAAAGTCGACTATGGGAGCTTCGCCTTTGTTAGAGATAGAGCTGGTTT

TAATGGTACTTCAGTAGAAGGGCAGTGCAAAGCCACTCCTGGAACAAAGA

TTGTAGGTTACTCAACACATCATGAGCATCTCCAACGCCAGAGGGTCTCA

TTTGAGCAGGTAAAACGGATAATGGAGCTGCTAGAGTACATAGAAGCACT

TTATCCATCATTGCAGGCTCTTCAGAAGGACTATGAAAAATATGCTGCAA

AAGACTTCCAGGACAGGGTGCAGGCACTCTGTTTGTGGTTAAACATCACA

AAAGACTTAAATCAGAAATTAAGGATTATGGGCACTGTTTTGGGCATCAA

GAATTTATCAGACATTGGCTGGCCAGTGTTTGAAATCCCTTCCCCTCGAC

CATCCAAAGGTAATGAGCCGGAGTATGAGGGTGATGACACAGAAGGAGAA

TTAAAGGAGTTGGAAAGTAGTACGGATGAGAGTGAAGAAGAACAAATCTC

TGATCCTAGGGTACCGGAAATCAGACAGCCCATAGATAACAGCTTCGACA

TCCAGTCGCGGGACTGCATATCCAAGAAGCTTGAGAGGCTCGAATCTGAG

GATGATTCTCTTGGCTGGGGAGCACCAGACTGGAGCACAGAAGCAGGCTT

TAGTAGACATTGTCTGACTTCTATTTATAGACCATTTGTAGACAAAGCAC

TGAAGCAGATGGGGTTAAGAAAGTTAATTTTAAGACTTCACAAGCTAATG

GATGGTTCCTTGCAAAGGGCACGTATAGCATTGGTAAAGAACGATCGTCC

AGTGGAGTTTTCTGAATTTCCAGATCCCATGTGGGGTTCAGATTATGTGC

AGTTGTCAAGGACACCACCTTCATCTGAGGAGAAATGCAGTGCTGTGTCG

TGGGAGGAGCTGAAGGCCATGGATTTACCTTCATTCGAACCTGCCTTCCT

AGTTCTCTGCCGAGTCCTTCTGAATGTCATACATGAGTGTCTGAAGTTAA

GATTGGAGCAGAGACCTGCTGGAGAACCATCTCTCTTGAGTATTAAGCAG

CTGGTGAGAGAGTGTAAGGAGGTCCTGAAGGGCGGCCTGCTGATGAAGCA

GTACTACCAGTTCATGCTGCAGGAGGTTCTGGAGGACTTGGAGAAGCCCG

ACTGCAACATTGACGCTTTTGAAGAGGATCTACATAAAATGCTTATGGTG

TATTTTGATTACATGAGAAGCTGGATCCAAATGCTACAGCAATTACCTCA

AGCATCGCATAGTTTAAAAAATCTGTTAGAAGAAGAATGGAATTTCACCA

AAGAAATAACTCATTACATACGGGGAGGAGAAGCACAGGCCGGGAAGCTT

TTCTGTGACATTGCAGGAATGCTGCTGAAATCTACAGGAAGTTTTTTAGA

ATTTGGCTTACAGGAGAGCTGTGCTGAATTTTGGACTAGTGCGGATGACA

GCAGTGCTTCCGACGAAATCAGGAGGTCTGTTATAGAGATCAGTCGAGCC

CTGAAGGAGCTCTTCCATGAAGCCAGAGAAAGGGCTTCCAAAGCACTTGG

ATTTGCTAAAATGTTGAGAAAGGACCTGGAAATAGCAGCAGAATTCAGGC

TTTCAGCCCCAGTTAGAGACCTCCTGGATGTTCTGAAATCAAAACAGTAT

GTCAAGGTGCAAATTCCTGGGTTAGAAAACTTGCAAATGTTTGTTCCAGA

CACTCTTGCTGAGGAGAAGAGTATTATTTTGCAGTTACTCAATGCAGCTG

-continued

CAGGAAAGGACTGTTCAAAAGATTCAGATGACGTACTCATCGATGCCTAT

CTGCTTCTGACCAAGCACGGTGATCGAGCCCGTGATTCAGAGGACAGCTG

GGGCACCTGGGAGGCACAGCCTGTCAAAGTCGTGCCTCAGGTGGAGACTG

TTGACACCCTGAGAAGCATGCAGGTGGATAATCTTTTACTAGTTGTCATG

CAGTCTGCGCATCTCACAATTCAGAGAAAAGCTTTCCAGCAGTCCATTGA

GGGACTTATGACTCTGTGCCAGGAGCAGACATCCAGTCAGCCGGTCATCG

CCAAAGCTTTGCAGCAGCTGAAGAATGATGCATTGGAGCTATGCAACAGG

ATAAGCAATGCCATTGACCGCGTGGACCACATGTTCACATCAGAATTTGA

TGCTGAGGTTGATGAATCTGAATCTGTCACCTTGCAACAGTACTACCGAG

AAGCAATGATTCAGGGGTACAATTTTGGATTTGAGTATCATAAAGAAGTT

GTTCGTTTGATGTCTGGGGAGTTTAGACAGAAGATAGGAGACAAATATAT

AAGCTTTGCCCGGAAGTGGATGAATTATGTCCTGACTAAATGTGAGAGTG

GTAGAGGTACAAGACCCAGGTGGGCGACTCAAGGATTTGATTTTCTACAA

GCAATTGAACCTGCCTTTATTTCAGCTTTACCAGAAGATGACTTCTTGAG

TTTACAAGCCTTGATGAATGAATGCATTGGCCATGTCATAGGAAAACCAC

ACAGTCCTGTTACAGGTTTGTACCTTGCCATTCATCGGAACAGCCCCCGT

CCTATGAAGGTACCTCGATGCCATAGTGACCCTCCTAACCCACACCTCAT

TATCCCCACTCCAGAGGGATTCAGCACTCGGAGCATGCCTTCCGACGCGC

GGAGCCATGGCAGCCCTGCTGCTGCTGCTGCTGCTGCTGCTGCTGCTGTT

GCTGCCAGTCGGCCCAGCCCCTCTGGTGGTGACTCTGTGCTGCCCAAATC

CATCAGCAGTGCCCATGATACCAGGGGTTCCAGCGTTCCTGAAAATGATC

GATTGGCTTCCATAGCTGCTGAATTGCAGTTTAGGTCCCTGAGTCGTCAC

TCAAGCCCCACGGAGGAGCGAGATGAACCAGCATATCCAAGAGGAGATTC

AAGTGGGTCCACAAGAAGAAGTTGGGAACTTCGGACACTAATCAGCCAGA

GTAAAGATACTGCTTCTAAACTAGGACCCATAGAAGCTATCCAGAAGTCA

GTCCGATTGTTTGAAGAAAAGAGGTACCGAGAAATGAGGAGAAAGAATAT

CATTGGTCAAGTTTGTGATACGCCTAAGTCCTATGATAATGTTATGCACG

TTGGCTTGAGGAAGGTGACCTTCAAATGGCAAAGAGGAAACAAAATTGGA

GAAGGCCAGTATGGGAAGGTGTACACCTGCATCAGCGTCGACACCGGGGA

GCTGATGGCCATGAAAGAGATTCGATTTCAACCTAATGACCATAAGACTA

TCAAGGAAACTGCAGACGAATTGAAAATATTCGAAGGCATCAAACACCCC

AATCTGGTTCGGTATTTTGGTGTGGAGCTCCATAGAGAAGAAATGTACAT

CTTCATGGAGTACTGCGATGAGGGGACTTTAGAAGAGGTGTCAAGGCTGG

GACTTCAGGAACATGTGATTAGGCTGTATTCAAAGCAGATCACCATTGCG

ATCAACGTCCTCCATGAGCATGGCATAGTCCACCGTGACATTAAAGGTGC

CAATATCTTCCTTACCTCATCTGGATTAATCAAACTGGGAGATTTTGGAT

GTTCAGTAAAGCTCAAAAACAATGCCCAGACCATGCCTGGTGAAGTGAAC

AGCACCCTGGGGACAGCAGCATACATGGCACCTGAAGTCATCACTCGTGC

CAAAGGAGAGGGCCATGGGCGTGCGGCCGACATCTGGAGTCTGGGGTGTG

TTGTCATAGAGATGGTGACTGGCAAGAGGCCTTGGCATGAGTATGAGCAC

-continued

AACTTTCAAATTATGTATAAAGTGGGGATGGGACATAAGCCACCAATCCC

TGAAAGATTAAGCCCTGAAGGAAAGGACTTCCTTTCTCACTGCCTTGAGA

GTGACCCAAAGATGAGATGGACCGCCAGCCAGCTCCTCGACCATTCGTTT

GTCAAGGTTTGCACAGATGAAGAATG

Human MEKK 6 CDS (SEQ ID NO: 23)

ATGGCGGGGCCGTGTCCCCGGTCCGGGGCGGAGCGCGCCGGCAGCTGCTG

GCAGGACCCGCTGGCCGTGGCGCTGAGCCGGGGCCGGCAGCTCGCGGCGC

CCCCGGGCCGGGGCTGCGCGCGGAGCCGGCCGCTCAGCGTGGTCTACGTG

CTGACCCGGGAGCCGCAGCCCGGGCTCGAGCCTCGGGAGGGAACCGAGGC

GGAGCCGCTGCCCCTGCGCTGCCTGCGCGAGGCTTGCGCGCAGGTCCCCC

GGCCGCGGCCGCCCCCGCAGCTGCGCAGCCTGCCCTTCGGGACGCTGGAG

CTAGGCGACACCGCGGCTCTGGATGCCTTCTACAACGCGGATGTGGTGGT

GCTGGAGGTGAGCAGCTCGCTGGTACAGCCCTCCCTGTTCTACCACCTTG

GTGTGCGTGAGAGCTTCAGCATGACCAACAATGTGCTCCTCTGCTCCCAG

GCCGACCTCCCTGACCTGCAGGCCCTGCGGGAGGATGTTTTCCAGAAGAA

CTCGGATTGCGTTGGCAGCTACACACTGATCCCCTATGTGGTGACGGCCA

CTGGTCGGGTGCTGTGTGGTGATGCAGGCCTTCTGCGGGGCCTGGCTGAT

GGGCTGGTACAGGCTGGAGTGGGGACCGAGGCCCTGCTCACTCCCCTGGT

GGGCCGGCTTGCCCGCCTGCTGGAGGCCACACCCACAGACTCTTGTGGCT

ATTTCCGGGAGACCATTCGGCGGGACATCCGGCAGGCGCGGGAGCGGTTC

AGTGGGCCACAGCTGCGGCAGGAGCTGGCTCGCCTGCAGCGGAGACTGGA

CAGCGTGGAGCTGCTGAGCCCCGACATCATCATGAACTTGCTGCTCTCCT

ACCGCGATGTGCAGGACTACTCGGCCATCATTGAGCTGGTGGAGACGCTG

CAGGCCTTGCCCACCTGTGATGTGGCCGAGCAGCATAATGTCTGCTTCCA

CTACACTTTTGCCCTCAACCGGAGGAACAGGCCTGGGGACCGGGCGAAGG

CCCTGTCTGTGCTGCTGCCGCTGGTACAGCTTGAGGGCTCTGTGGCGCCC

GATCTGTACTGCATGTGTGGCCGTATCTACAAGGACATGTTCTTCAGCTC

GGGTTTCCAGGATGCTGGGCACCGGGAGCAGGCCTATCACTGGTATCGCA

AGGCTTTTGACGTAGAGCCCAGCCTTCACTCAGGCATCAATGCAGCTGTG

CTCCTCATTGCTGCCGGGCAGCACTTTGAGGATTCCAAAGAGCTCCGGCT

AATAGGCATGAAGCTGGGCTGCCTGCTGGCCCGCAAAGGCTGCGTGGAGA

AGATGCAGTATTACTGGGATGTGGGTTTCTACCTGGGAGCCCAGATCCTC

GCCAATGACCCCACCCAGGTGGTGCTGGCTGCAGAGCAGCTGTATAAGCT

CAATGCCCCCATATGGTACCTGGTGTCCGTGATGGAGACCTTCCTGCTCT

ACCAGCACTTCAGGCCCACGCCAGAGCCCCCTGGAGGGCCACCACGCCGT

GCCCACTTCTGGCTCCACTTCTTGCTACAGTCCTGCCAACCATTCAAGAC

AGCCTGTGCCCAGGGCGACCAGTGCTTGGTGCTGGTCCTGGAGATGAACA

AGGTGCTGCTGCCTGCAAAGCTCGAGGTTCGGGGTACTGACCCAGTAAGC

ACAGTGACCCTGAGCCTGCTGGAGCCTGAGACCCAGGACATTCCCTCCAG

CTGGACCTTCCCAGTCGCCTCCATATGCGGAGTCAGCGCCTCAAAGCGCG

ACGAGCGCTGCTGCTTCCTCTATGCACTCCCCCCGGCTCAGGACGTCCAG

-continued

CTGTGCTTCCCCAGCGTAGGGCACTGCCAGTGGTTCTGCGGCCTGATCCA

GGCCTGGGTGACGAACCCGGATTCCACGGCGCCCGCGGAGGAGGCGGAGG

GCGCGGGGGAGATGTTGGAGTTTGATTATGAGTACACGGAGACGGGCGAG

CGGCTGGTGCTGGGCAAGGGCACGTATGGGGTGGTGTACGCGGGCCGCGA

TCGCCACACGAGGGTGCGCATCGCCATCAAGGAGATCCCGGAGCGGGACA

GCAGGTTCTCTCAGCCCCTGCATGAAGAGATCGCTCTTCACAGACGCCTG

CGCCACAAGAACATAGTGCGCTATCTGGGCTCAGCTAGCCAGGGCGGCTA

CCTTAAGATCTTCATGGAGGAAGTGCCTGGAGGCAGCCTGTCCTCCTTGC

TGCGGTCGGTGTGGGGACCCCTGAAGGACAACGAGAGCACCATCAGTTTC

TACACCCGCCAGATCCTGCAGGGACTTGGCTACTTGCACGACAACCACAT

CGTGCACAGGGACATAAAAGGGGACAATGTGCTGATCAACACCTTCAGTG

GGCTGCTCAAGATTTCTGACTTCGGCACCTCCAAGCGGCTGGCAGGCATC

ACACCTTGCACTGAGACCTTCACAGGAACTCTGCAGTATATGGCCCCAGA

AATCATTGACCAGGGCCCACGCGGGTATGGGAAAGCAGCTGACATCTGGT

CACTGGGCTGCACTGTCATTGAGATGGCCACAGGTCGCCCCCCCTTCCAC

GAGCTCGGGAGCCCACAGGCTGCCATGTTTCAGGTGGGTATGTACAAGGT

CCATCCGCCAATGCCCAGCTCTCTGTCGGCCGAGGCCCAAGCCTTTCTCC

TCCGAACTTTTGAGCCAGACCCCCGCCTCCGAGCCAGCGCCCAGACACTG

CTGGGGGACCCCTTCCTGCAGCCTGGGAAAAGGAGCCGCAGCCCCAGCTC

CCCACGACATGCTCCACGGCCCTCAGATGCCCCTTCTGCCAGTCCCACTC

CTTCAGCCAACTCAACCACCCAGTCTCAGACATTCCCGTGCCCTCAGGCA

CCCTCTCAGCACCCACCCAGCCCCCCGAAGCGCTGCCTCAGTTATGGGGG

CACCAGCCAGCTCCGGGTGCCCGAGGAGCCTGCGGCCGAGGAGCCTGCGT

CTCCGGAGGAGAGTTCGGGGCTGAGCCTGCTGCACCAGGAGAGCAAGCGT

CGGGCCATGCTGGCCGCAGTATTGGAGCAGGAGCTGCCAGCGCTGGCGGA

GAATCTGCACCAGGAGCAGAAGCAAGAGCAGGGGGCCCGTCTGGGCAGAA

ACCATGTGGAAGAGCTGCTGCGCTGCCTCGGGGCACACATCCACACTCCC

AACCGCCGGCAGCTCGCCCAGGAGCTGCGGGCGCTGCAAGGACGGCTGAG

GGCCCAGGGCCTTGGGCCTGCGCTTCTGCACAGACCGCTGTTTGCCTTCC

CGGATGCGGTGAAGCAGATCCTCCGCAAGCGCCAGATCCGTCCACACTGG

ATGTTCGTTCTGGACTCACTGCTCAGCCGTGCTGTGCGGGCAGCCCTGGG

TGTGCTAGGACCGGAGGTGGAGAAGGAGGCGGTCTCACCGAGGTCAGAGG

AGCTGAGTAATGAAGGGGACTCCCAGCAGAGCCCAGGCCAGCAGAGCCCG

CTTCCGGTGGAGCCCGAGCAGGGCCCCGCTCCTCTGATGGTGCAGCTGAG

CCTCTTGAGGGCAGAGACTGATCGGCTGCGCGAAATCCTGGCGGGGAAGG

AACGGGAGTACCAGGCCCTGGTGCAGCGGGCTCTACAGCGGCTGAATGAG

GAAGCCCGGACCTATGTCCTGGCCCCAGAGCCTCCAACTGCTCTTTCAAC

GGACCAGGGCCTGGTGCAGTGGCTACAGGAACTGAATGTGGATTCAGGCA

CCATCCAAATGCTGTTGAACCATAGCTTCACCCTCCACACTCTGCTCACC

TATGCCACTCGAGATGACCTCATCTACACCCGCATCAGGGGAGGGATGGT

-continued

ATGCCGCATCTGGAGGGCCATCTTGGCACAGCGAGCAGGATCCACACCAG

TCACCTCTGGACCCTGA

Human MEKK7 CDS (SEQ ID NO: 24)

ATGTCTACAGCCTCTGCCGCCTCCTCCTCCTCCTCGTCTTCGGCCGGTGA

GATGATCGAAGCCCCTTCCCAGGTCCTCAACTTTGAAGAGATCGACTACA

AGGAGATCGAGGTGGAAGAGGTTGTTGGAAGAGGAGCCTTTGGAGTTGTT

TGCAAAGCTAAGTGGAGAGCAAAAGATGTTGCTATTAAACAAATAGAAAG

TGAATCTGAGAGGAAAGCGTTTATTGTAGAGCTTCGGCAGTTATCCCGTG

TGAACCATCCTAATATTGTAAAGCTTTATGGAGCCTGCTTGAATCCAGTG

TGTCTTGTGATGGAATATGCTGAAGGGGGCTCTTTATATAATGTGCTGCA

TGGTGCTGAACCATTGCCATATTATACTGCTGCCCACGCAATGAGTTGGT

GTTTACAGTGTTCCCAAGGAGTGGCTTATCTTCACAGCATGCAACCCAAA

GCGCTAATTCACAGGGACCTGAAACCACCAAACTTACTGCTGGTTGCAGG

GGGGACAGTTCTAAAAATTTGTGATTTTGGTACAGCCTGTGACATTCAGA

CACACATGACCAATAACAAGGGGAGTGCTGCTTGGATGGCACCTGAAGTT

TTTGAAGGTAGTAATTACAGTGAAAAATGTGACGTCTTCAGCTGGGGTAT

TATTCTTTGGGAAGTGATAACGCGTCGGAAACCCTTTGATGAGATTGGTG

GCCCAGCTTTCCGAATCATGTGGGCTGTTCATAATGGTACTCGACCACCA

CTGATAAAAAATTTACCTAAGCCCATTGAGAGCCTGATGACTCGTTGTTG

GTCTAAAGATCCTTCCCAGCGCCCTTCAATGGAGGAAATTGTGAAAATAA

TGACTCACTTGATGCGGTACTTTCCAGGAGCAGATGAGCCATTACAGTAT

CCTTGTCAGTATTCAGATGAAGGACAGAGCAACTCTGCCACCAGTACAGG

CTCATTCATGGACATTGCTTCTACAAATACGAGTAACAAAAGTGACACTA

ATATGGAGCAAGTTCCTGCCACAAATGATACTATTAAGCGCTTAGAATCA

AAATTGTTGAAAAATCAGGCAAAGCAACAGAGTGAATCTGGACGTTTAAG

CTTGGGAGCCTCCCGTGGGAGCAGTGTGGAGAGCTTGCCCCCAACCTCTG

AGGGCAAGAGGATGAGTGCTGACATGTCTGAAATAGAAGCTAGGATCGCC

GCAACCACAGGCAACGGACAGCCAAGACGTAGATCCATCCAAGACTTGAC

TGTAACTGGAACAGAACCTGGTCAGGTGAGCAGTAGGTCATCCAGTCCCA

GTGTCAGAATGATTACTACCTCAGGACCAACCTCAGAAAAGCCAACTCGA

AGTCATCCATGGACCCCTGATGATTCCACAGATACCAATGGATCAGATAA

CTCCATCCCAATGGCTTATCTTACACTGGATCACCAACTACAGCCTCTAG

CACCGTGCCCAAACTCCAAAGAATCTATGGCAGTGTTTGAACAGCATTGT

AAAATGGCACAAGAATATATGAAAGTTCAAACAGAAATTGCATTGTTATT

ACAGAGAAAGCAAGAACTAGTTGCAGAACTGGACCAGGATGAAAAGGACC

AGCAAAATACATCTCGCCTGGTACAGGAACATAAAAAGCTTTTAGATGAA

AACAAAAGCCTTTCTACTTACTACCAGCAATGCAAAAAACAACTAGAGGT

CATCAGAAGTCAGCAGCAGAAACGACAAGGCACTTCATGA

Human MK2 CDS (SEQ ID NO: 25)

ATGCTGTCCAACTCCCAGGGCCAGAGCCCGCCGGTGCCGTTCCCCGCCCC

GGCCCCGCCGCCGCAGCCCCCCACCCCTGCCCTGCCGCACCCCCCGGCGC

-continued

AGCCGCCGCCGCCGCCCCCGCAGCAGTTCCCGCAGTTCCACGTCAAGTCC
GGCCTGCAGATCAAGAAGAACGCCATCATCGATGACTACAAGGTCACCAG
CCAGGTCCTGGGGCTGGGCATCAACGGCAAAGTTTTGCAGATCTTCAACA
AGAGGACCCAGGAGAAATTCGCCCTCAAAATGCTTCAGGACTGCCCCAAG
GCCCGCAGGGAGGTGGAGCTGCACTGGCGGGCCTCCCAGTGCCCGCACAT
CGTACGGATCGTGGATGTGTACGAGAATCTGTACGCAGGGAGGAAGTGCC
TGCTGATTGTCATGGAATGTTTGGACGGTGGAGAACTCTTTAGCCGAATC
CAGGATCGAGGAGACCAGGCATTCACAGAAAGAGAAGCATCCGAAATCAT
GAAGAGCATCGGTGAGGCCATCCAGTATCTGCATTCAATCAACATTGCCC
ATCGGGATGTCAAGCCTGAGAATCTCTTATACACCTCCAAAAGGCCCAAC
GCCATCCTGAAACTCACTGACTTTGGCTTTGCCAAGGAAACCACCAGCCA
CAACTCTTTGACCACTCCTTGTTATACACCGTACTATGTGGCTCCAGAAG
TGCTGGGTCCAGAGAAGTATGACAAGTCCTGTGACATGTGGTCCCTGGGT
GTCATCATGTACATCCTGCTGTGTGGGTATCCCCCCTTCTACTCCAACCA
CGGCCTTGCCATCTCTCCGGGCATGAAGACTCGCATCCGAATGGGCCAGT
ATGAATTTCCCAACCCAGAATGGTCAGAAGTATCAGAGGAAGTGAAGATG
CTCATTCGGAATCTGCTGAAAACAGAGCCCACCCAGAGAATGACCATCAC
CGAGTTTATGAACCACCCTTGGATCATGCAATCAACAAAGGTCCCTCAAA
CCCCACTGCACACCAGCCGGGTCCTGAAGGAGGACAAGGAGCGGTGGGAG
GATGTCAAGGGGTGTCTTCATGACAAGAACAGCGACCAGGCCACTTGGCT
GACCAGGTTGTGA

Human MyD88 CDS (SEQ ID NO: 26)

ATGCGACCCGACCGCGCTGAGGCTCCAGGACCGCCCGCCATGGCTGCAGG
AGGTCCCGGCGCGGGGTCTGCGGCCCCGGTCTCCTCCACATCCTCCCTTC
CCCTGGCTGCTCTCAACATGCGAGTGCGGCGCCGCCTGTCTCTGTTCTTG
AACGTGCGGACACAGGTGGCGGCCGACTGGACCGCGCTGGCGGAGGAGAT
GGACTTTGAGTACTTGGAGATCCGGCAACTGGAGACACAAGCGGACCCCA
CTGGCAGGCTGCTGGACGCCTGGCAGGGACGCCCTGGCGCCTCTGTAGGC
CGACTGCTCGAGCTGCTTACCAAGCTGGGCCGCGACGACGTGCTGCTGGA
GCTGGGACCCAGCATTGAGGAGGATTGCCAAAAGTATATCTTGAAGCAGC
AGCAGGAGGAGGCTGAGAAGCCTTTACAGGTGGCCGCTGTAGACAGCAGT
GTCCCACGGACAGCAGAGCTGGCGGGCATCACCACACTTGATGACCCCCT
GGGGCATATGCCTGAGCGTTTCGATGCCTTCATCTGCTATTGCCCCAGCG
ACATCCAGTTTGTGCAGGAGATGATCCGGCAACTGGAACAGACAAACTAT
CGACTGAAGTTGTGTGTGTCTGACCGCGATGTCCTGCCTGGCACCTGTGT
CTGGTCTATTGCTAGTGAGCTCATCGAAAAGAGGTTGGCTAGAAGGCCAC
GGGGTGGGTGCCGCCGGATGGTGGTGGTTGTCTCTGATGATTACCTGCAG
AGCAAGGAATGTGACTTCCAGACCAAATTTGCACTCAGCCTCTCTCCAGG
TGCCCATCAGAAGCGACTGATCCCCATCAAGTACAAGGCAATGAAGAAAG
AGTTCCCCAGCATCCTGAGGTTCATCACTGTCTGCGACTACACCAACCCC
TGCACCAAATCTTGGTTCTGGACTCGCCTTGCCAAGGCCTTGTCCCTGCC
CTGA

Human NF-κB CDS (SEQ ID NO: 27)

ATGGCAGAAGATGATCCATATTTGGGAAGGCCTGAACAAATGTTTCATTT
GGATCCTTCTTTGACTCATACAATATTTAATCCAGAAGTATTTCAACCAC
AGATGGCACTGCCAACAGATGGCCCATACCTTCAAATATTAGAGCAACCT
AAACAGAGAGGATTTCGTTTCCGTTATGTATGTGAAGGCCCATCCCATGG
TGGACTACCTGGTGCCTCTAGTGAAAAGAACAAGAAGTCTTACCCTCAGG
TCAAAATCTGCAACTATGTGGGACCAGCAAAGGTTATTGTTCAGTTGGTC
ACAAATGGAAAAAATATCCACCTGCATGCCCACAGCCTGGTGGGAAAACA
CTGTGAGGATGGGATCTGCACTGTAACTGCTGGACCCAAGGACATGGTGG
TCGGCTTCGCAAACCTGGGTATACTTCATGTGACAAAGAAAAAAGTATTT
GAAACACTGGAAGCACGAATGACAGAGGCGTGTATAAGGGGCTATAATCC
TGGACTCTTGGTGCACCCTGACCTTGCCTATTTGCAAGCAGAAGGTGGAG
GGGACCGGCAGCTGGGAGATCGGGAAAAAGAGCTAATCCGCCAAGCAGCT
CTGCAGCAGACCAAGGAGATGGACCTCAGCGTGGTGCGGCTCATGTTTAC
AGCTTTTCTTCCGGATAGCACTGGCAGCTTCACAAGGCGCCTGGAACCCG
TGGTATCAGACGCCATCTATGACAGTAAAGCCCCCAATGCATCCAACTTG
AAAATTGTAAGAATGGACAGGACAGCTGGATGTGTGACTGGAGGGGAGGA
AATTTATCTTCTTTGTGACAAAGTTCAGAAAGATGACATCCAGATTCGAT
TTTATGAAGAGGAAGAAAATGGTGGAGTCTGGGAAGGATTTGGAGATTTT
TCCCCCACAGATGTTCATAGACAATTTGCCATTGTCTTCAAAACTCCAAA
GTATAAAGATATTAATATTACAAAACCAGCCTCTGTGTTTGTCCAGCTTC
GGAGGAAATCTGACTTGGAAACTAGTGAACCAAAACCTTTCCTCTACTAT
CCTGAAATCAAAGATAAAGAAGAAGTGCAGAGGAAACGTCAGAAGCTCAT
GCCCAATTTTTCGGATAGTTTCGGCGGTGGTAGTGGTGCTGGAGCTGGAG
GCGGAGGCATGTTTGGTAGTGGCGGTGGAGGAGGGGGCACTGGAAGTACA
GGTCCAGGGTATAGCTTCCCACACTATGGATTTCCTACTTATGGTGGGAT
TACTTTCCATCCTGGAACTACTAAATCTAATGCTGGGATGAAGCATGGAA
CCATGGACACTGAATCTAAAAAGGACCCTGAAGGTTGTGACAAAAGTGAT
GACAAAAACACTGTAAACCTCTTTGGGAAAGTTATTGAAACCACAGAGCA
AGATCAGGAGCCCAGCGAGGCCACCGTTGGGAATGGTGAGGTCACTCTAA
CGTATGCAACAGGAACAAAAGAAGAGAGTGCTGGAGTTCAGGATAACCTC
TTTCTAGAGAAGGCTATGCAGCTTGCAAAGAGGCATGCCAATGCCCTTTT
CGACTACGCGGTGACAGGAGACGTGAAGATGCTGCTGGCCGTCCAGCGCC
ATCTCACTGCTGTGCAGGATGAGAATGGGGACAGTGTCTTACACTTAGCA
ATCATCCACCTTCATTCTCAACTTGTGAGGGATCTACTAGAAGTCACATC
TGGTTTGATTTCTGATGACATTATCAACATGAGAAATGATCTGTACCAGA
CGCCCTTGCACTTGGCAGTGATCACTAAGCAGGAAGATGTGGTGGAGGAT

-continued

TTGCTGAGGGCTGGGGCCGACCTGAGCCTTCTGGACCGCTTGGGTAACTC

TGTTTTGCACCTAGCTGCCAAAGAAGGACATGATAAAGTTCTCAGTATCT

TACTCAAGCACAAAAAGGCAGCACTACTTCTTGACCACCCCAACGGGGAC

GGTCTGAATGCCATTCATCTAGCCATGATGAGCAATAGCCTGCCATGTTT

GCTGCTGCTGGTGGCCGCTGGGGCTGACGTCAATGCTCAGGAGCAGAAGT

CCGGGCGCACAGCACTGCACCTGGCTGTGGAGCACGACAACATCTCATTG

GCAGGCTGCCTGCTCCTGGAGGGTGATGCCCATGTGGACAGTACTACCTA

CGATGGAACCACACCCCTGCATATAGCAGCTGGGAGAGGGTCCACCAGGC

TGGCAGCTCTTCTCAAAGCAGCAGGAGCAGATCCCCTGGTGGAGAACTTT

GAGCCTCTCTATGACCTGGATGACTCTTGGGAAAATGCAGGAGAGGATGA

AGGAGTTGTGCCTGGAACCACGCCTCTAGATATGGCCACCAGCTGGCAGG

TATTTGACATATTAAATGGGAAACCATATGAGCCAGAGTTTACATCTGAT

GATTTACTAGCACAAGGAGACATGAAACAGCTGGCTGAAGATGTGAAGCT

GCAGCTGTATAAGTTACTAGAAATTCCTGATCCAGACAAAAACTGGGCTA

CTCTGGCGCAGAAATTAGGTCTGGGGATACTTAATAATGCCTTCCGGCTG

AGTCCTGCTCCTTCCAAAACACTTATGGACAACTATGAGGTCTCTGGGGG

TACAGTCAGAGAGCTGGTGGAGGCCCTGAGACAAATGGGCTACACCGAAG

CAATTGAAGTGATCCAGGCAGCCTCCAGCCCAGTGAAGACCACCTCTCAG

GCCCACTCGCTGCCTCTCTCGCCTGCCTCCACAAGGCAGCAAATAGACGA

GCTCCGAGACAGTGACAGTGTCTGCGACAGCGGCGTGGAGACATCCTTCC

GCAAACTCAGCTTTACCGAGTCTCTGACCAGTGGTGCCTCACTGCTAACT

CTCAACAAAATGCCCCATGATTATGGGCAGGAAGGACCTCTAGAAGGCAA

AATTTAG

Human NIK CDS (SEQ ID NO: 28)

ATGGCAGTGATGGAAATGGCCTGCCCAGGTGCCCCTGGCTCAGCAGTGGG

GCAGCAGAAGGAACTCCCCAAAGCCAAGGAGAAGACGCCGCCACTGGGGA

AGAAACAGAGCTCCGTCTACAAGCTTGAGGCCGTGGAGAAGAGCCCTGTG

TTCTGCGGAAAGTGGGAGATCCTGAATGACGTGATTACCAAGGGCACAGC

CAAGGAAGGCTCCGAGGCAGGGCCAGCTGCCATCTCTATCATCGCCCAGG

CTGAGTGTGAGAATAGCCAAGAGTTCAGCCCCACCTTTTCAGAACGCATT

TTCATCGCTGGGTCCAAACAGTACAGCCAGTCCGAGAGTCTTGATCAGAT

CCCCAACAATGTGGCCCATGCTACAGAGGGCAAAATGGCCCGTGTGTGTT

GGAAGGGAAAGCGTCGCAGCAAAGCCCGGAAGAAACGGAAGAAGAAGAGC

TCAAAGTCCCTGGCTCATGCAGGAGTGGCCTTGGCCAAACCCCTCCCCAG

GACCCCTGAGCAGGAGAGCTGCACCATCCCAGTGCAGGAGGATGAGTCTC

CACTCGGCGCCCCATATGTTAGAAACACCCCGCAGTTCACCAAGCCTCTG

AAGGAACCAGGCCTTGGGCAACTCTGTTTTAAGCAGCTTGGCGAGGGCCT

ACGGCCGGCTCTGCCTCGATCAGAACTCCACAAACTGATCAGCCCCTTGC

AATGTCTGAACCACGTGTGGAAACTGCACCACCCCCAGGACGGAGGCCCC

CTGCCCCTGCCCACGCACCCCTTCCCCTATAGCAGACTGCCTCATCCCTT

CCCATTCCACCCTCTCCAGCCCTGGAAACCTCACCCTCTGGAGTCCTTCC

-continued

TGGGCAAACTGGCCTGTGTAGACAGCCAGAAACCCTTGCCTGACCCACAC

CTGAGCAAACTGGCCTGTGTAGACAGTCCAAAGCCCCTGCCTGGCCCACA

CCTGGAGCCCAGCTGCCTGTCTCGTGGTGCCCATGAGAAGTTTTCTGTGG

AGGAATACCTAGTGCATGCTCTGCAAGGCAGCGTGAGCTCAGGCCAGGCC

CACAGCCTGACCAGCCTGGCCAAGACCTGGGCAGCAAGGGGCTCCAGATC

CCGGGAGCCCAGCCCCAAAACTGAGGACAACGAGGGTGTCCTGCTCACTG

AGAAACTCAAGCCAGTGGATTATGAGTACCGAGAAGAAGTCCACTGGGCC

ACGCACCAGCTCCGCCTGGGCAGAGGCTCCTTCGGAGAGGTGCACAGGAT

GGAGGACAAGCAGACTGGCTTCCAGTGCGCTGTCAAAAAGGTGCGGCTGG

AAGTATTTCGGGCAGAGGAGCTGATGGCATGTGCAGGATTGACCTCACCC

AGAATTGTCCCTTTGTATGGAGCTGTGAGAGAAGGGCCTTGGGTCAACAT

CTTCATGGAGCTGCTGGAAGGTGGCTCCCTGGGCCAGCTGGTCAAGGAGC

AGGGCTGTCTCCCAGAGGACCGGGCCCTGTACTACCTGGGCCAGGCCCTG

GAGGGTCTGGAATACCTCCACTCACGAAGGATTCTGCATGGGGACGTCAA

AGCTGACAACGTGCTCCTGTCCAGCGATGGGAGCCACGCAGCCCTCTGTG

ACTTTGGCCATGCTGTGTGTCTTCAACCTGATGGCCTGGGAAAGTCCTTG

CTCACAGGGGACTACATCCCTGGCACAGAGACCCACATGGCTCCGGAGGT

GGTGCTGGGCAGGAGCTGCGACGCCAAGGTGGATGTCTGGAGCAGCTGCT

GTATGATGCTGCACATGCTCAACGGCTGCCACCCCTGGACTCAGTTCTTC

CGAGGGCCGCTCTGCCTCAAGATTGCCAGCGAGCCTCCGCCTGTGAGGGA

GATCCCACCCTCCTGCGCCCCTCTCACAGCCCAGGCCATCCAAGAGGGGC

TGAGGAAAGAGCCCATCCACCGCGTGTCTGCAGCGGAGCTGGGAGGGAAG

GTGAACCGGGCACTACAGCAAGTGGGAGGTCTGAAGAGCCCTTGGAGGGG

AGAATATAAAGAACCAAGACATCCACCGCCAAATCAAGCCAATTACCACC

AGACCCTCCATGCCCAGCCGAGAGAGCTTTCGCCAAGGGCCCCAGGGCCC

CGGCCAGCTGAGGAGACAACAGGCAGAGCCCCTAAGCTCCAGCCTCCTCT

CCCACCAGAGCCCCCAGAGCCAAACAAGTCTCCTCCCTTGACTTTGAGCA

AGGAGGAGTCTGGGATGTGGGAACCCTTACCTCTGTCCTCCCTGGAGCCA

GCCCCTGCCAGAAACCCCAGCTCACCAGAGCGGAAAGCAACCGTCCCGGA

GCAGGAACTGCAGCAGCTGGAAATAGAATTATTCCTCAACAGCCTGTCCC

AGCCATTTTCTCTGGAGGAGCAGGAGCAAATTCTCTCGTGCCTCAGCATC

GACAGCCTCTCCCTGTCGGATGACAGTGAGAAGAACCCATCAAAGGCCTC

TCAAAGCTCGCGGGACACCCTGAGCTCAGGCGTACACTCCTGGAGCAGCC

AGGCCGAGGCTCGAAGCTCCAGCTGGAACATGGTGCTGGCCCGGGGGCGG

CCCACCGACACCCCAAGCTATTTCAATGGTGTGAAAGTCCAAATACAGTC

TCTTAATGGTGAACACCTGCACATCCGGGAGTTCCACCGGGTCAAAGTGG

GAGACATCGCCACTGGCATCAGCAGCCAGATCCCAGCTGCAGCCTTCAGC

TTGGTCACCAAAGACGGGCAGCCTGTTCGCTACGACATGGAGGTGCCAGA

CTCGGGCATCGACCTGCAGTGCACACTGGCCCCTGATGGCAGCTTCGCCT

GGAGCTGGAGGGTCAAGCATGGCCAGCTGGAGAACAGGCCCTAA

-continued

Human p38 CDS (SEQ ID NO: 29)

ATGTCTCAGGAGAGGCCCACGTTCTACCGGCAGGAGCTGAACAAGACAAT
CTGGGAGGTGCCCGAGCGTTACCAGAACCTGTCTCCAGTGGGCTCTGGCG
CCTATGGCTCTGTGTGTGCTGCTTTTGACACAAAAACGGGGTTACGTGTG
GCAGTGAAGAAGCTCTCCAGACCATTTCAGTCCATCATTCATGCGAAAAG
AACCTACAGAGAACTGCGGTTACTTAAACATATGAAACATGAAAATGTGA
TTGGTCTGTTGGACGTTTTTACACCTGCAAGGTCTCTGGAGGAATTCAAT
GATGTGTATCTGGTGACCCATCTCATGGGGGCAGATCTGAACAACATTGT
GAAATGTCAGAAGCTTACAGATGACCATGTTCAGTTCCTTATCTACCAAA
TTCTCCGAGGTCTAAAGTATATACATTCAGCTGACATAATTCACAGGGAC
CTAAAACCTAGTAATCTAGCTGTGAATGAAGACTGTGAGCTGAAGATTCT
GGATTTTGGACTGGCTCGGCACACAGATGATGAAATGACAGGCTACGTGG
CCACTAGGTGGTACAGGGCTCCTGAGATCATGCTGAACTGGATGCATTAC
AACCAGACAGTTGATATTTGGTCAGTGGGATGCATAATGGCCGAGCTGTT
GACTGGAAGAACATTGTTTCCTGGTACAGACCATATTAACCAGCTTCAGC
AGATTATGCGTCTGACAGGAACACCCCCCGCTTATCTCATTAACAGGATG
CCAAGCCATGAGGCAAGAAACTATATTCAGTCTTTGACTCAGATGCCGAA
GATGAACTTTGCGAATGTATTTATTGGTGCCAATCCCCTGGCTGTCGACT
TGCTGGAGAAGATGCTTGTATTGGACTCAGATAAGAGAATTACAGCGGCC
CAAGCCCTTGCACATGCCTACTTTGCTCAGTACCACGATCCTGATGATGA
ACCAGTGGCCGATCCTTATGATCAGTCCTTTGAAAGCAGGGACCTCCTTA
TAGATGAGTGGAAAAGCCTGACCTATGATGAAGTCATCAGCTTTGTGCCA
CCACCCCTTGACCAAGAAGAGATGGAGTCCTGA

Human PKR CDS (SEQ ID NO: 30)

ATGGCTGGTGATCTTTCAGCAGGTTTCTTCATGGAGGAACTTAATACATA
CCGTCAGAAGCAGGGAGTAGTACTTAAATATCAAGAACTGCCTAATTCAG
GACCTCCACATGATAGGAGGTTTACATTTCAAGTTATAATAGATGGAAGA
GAATTTCCAGAAGGTGAAGGTAGATCAAAGAAGGAAGCAAAAAATGCCGC
AGCCAAATTAGCTGTTGAGATACTTAATAAGGAAAAGAAGGCAGTTAGTC
CTTTATTATTGACAACAACGAATTCTTCAGAAGGATTATCCATGGGGAAT
TACATAGGCCTTATCAATAGAATTGCCCAGAAGAAAAGACTAACTGTAAA
TTATGAACAGTGTGCATCGGGGGTGCATGGGCCAGAAGGATTTCATTATA
AATGCAAAATGGGACAGAAAGAATATAGTATTGGTACAGGTTCTACTAAA
CAGGAAGCAAAACAATTGGCCGCTAAACTTGCATATCTTCAGATATTATC
AGAAGAAACCTCAGTGAAATCTGACTACCTGTCCTCTGGTTCTTTTGCTA
CTACGTGTGAGTCCCAAAGCAACTCTTTAGTGACCAGCACACTCGCTTCT
GAATCATCATCTGAAGGTGACTTCTCAGCAGATACATCAGAGATAAATTC
TAACAGTGACAGTTTAAACAGTTCTTCGTTGCTTATGAATGGTCTCAGAA
ATAATCAAAGGAAGGCAAAAAGATCTTTGGCACCCAGATTTGACCTTCCT
GACATGAAAGAAACAAAGTATACTGTGGACAAGAGGTTTGGCATGGATTT
TAAAGAAATAGAATTAATTGGCTCAGGTGGATTTGGCCAAGTTTTCAAAG

-continued

CAAAACACAGAATTGACGGAAAGACTTACGTTATTAAACGTGTTAAATAT
AATAACGAGAAGGCGGAGCGTGAAGTAAAAGCATTGGCAAAACTTGATCA
TGTAAATATTGTTCACTACAATGGCTGTTGGGATGGATTTGATTATGATC
CTGAGACCAGTGATGATTCTCTTGAGAGCAGTGATTATGATCCTGAGAAC
AGCAAAAATAGTTCAAGGTCAAAGACTAAGTGCCTTTTCATCCAAATGGA
ATTCTGTGATAAAGGGACCTTGGAACAATGGATTGAAAAAAGAAGAGGCG
AGAAACTAGACAAAGTTTTGGCTTTGGAACTCTTTGAACAAATAACAAAA
GGGGTGGATTATATACATTCAAAAAAATTAATTCATAGAGATCTTAAGCC
AAGTAATATATTCTTAGTAGATACAAAACAAGTAAAGATTGGAGACTTTG
GACTTGTAACATCTCTGAAAAATGATGGAAAGCGAACAAGGAGTAAGGGA
ACTTTGCGATACATGAGCCCAGAACAGATTTCTTCGCAAGACTATGGAAA
GGAAGTGGACCTCTACGCTTTGGGGCTAATTCTTGCTGAACTTCTTCATG
TATGTGACACTGCTTTTGAAACATCAAAGTTTTTCACAGACCTACGGGAT
GGCATCATCTCAGATATATTTGATAAAAAAGAAAAAACTCTTCTACAGAA
ATTACTCTCAAAGAAACCTGAGGATCGACCTAACACATCTGAAATACTAA
GGACCTTGACTGTGTGGAAGAAAAGCCCAGAGAAAAATGAACGACACACA
TGTTAG

Human Rac CDS (SEQ ID NO: 31)

ATGAGCGACGTGGCTATTGTGAAGGAGGGTTGGCTGCACAAACGAGGGGA
GTACATCAAGACCTGGCGGCCACGCTACTTCCTCCTCAAGAATGATGGCA
CCTTCATTGGCTACAAGGAGCGGCCGCAGGATGTGGACCAACGTGAGGCT
CCCCTCAACAACTTCTCTGTGGCGCAGTGCCAGCTGATGAAGACGGAGCG
GCCCCGGCCCAACACCTTCATCATCCGCTGCCTGCAGTGGACCACTGTCA
TCGAACGCACCTTCCATGTGGAGACTCCTGAGGAGCGGGAGGAGTGGACA
ACCGCCATCCAGACTGTGGCTGACGGCCTCAAGAAGCAGGAGGAGGAGGA
GATGGACTTCCGGTCGGGCTCACCCAGTGACAACTCAGGGGCTGAAGAGA
TGGAGGTGTCCCTGGCCAAGCCCAAGCACCGCGTGACCATGAACGAGTTT
GAGTACCTGAAGCTGCTGGGCAAGGGCACTTTCGGCAAGGTGATCCTGGT
GAAGGAGAAGGCCACAGGCCGCTACTACGCCATGAAGATCCTCAAGAAGG
AAGTCATCGTGGCCAAGGACGAGGTGGCCCACACACTCACCGAGAACCGC
GTCCTGCAGAACTCCAGGCACCCCTTCCTCACAGCCCTGAAGTACTCTTT
CCAGACCCACGACCGCCTCTGCTTTGTCATGGAGTACGCCAACGGGGGCG
AGCTGTTCTTCCACCTGTCCCGGGAGCGTGTGTTCTCCGAGGACCGGGCC
CGCTTCTATGGCGCTGAGATTGTGTCAGCCCTGGACTACCTGCACTCGGA
GAAGAACGTGGTGTACCGGGACCTCAAGCTGGAGAACCTCATGCTGGACA
AGGACGGGCACATTAAGATCACAGACTTCGGGCTGTGCAAGGAGGGGATC
AAGGACGGTGCCACCATGAAGACCTTTTGCGGCACACCTGAGTACCTGGC
CCCCGAGGTGCTGGAGGACAATGACTACGGCCGTGCAGTGGACTGGTGGG
GGCTGGGCGTGGTCATGTACGAGATGATGTGCGGTCGCCTGCCCTTCTAC
AACCAGGACCATGAGAAGCTTTTTGAGCTCATCCTCATGGAGGAGATCCG

-continued

CTTCCCGCGCACGCTTGGTCCCGAGGCCAAGTCCTTGCTTTCAGGGCTGC

TCAAGAAGGACCCCAAGCAGAGGCTTGGCGGGGGCTCCGAGGACGCCAAG

GAGATCATGCAGCATCGCTTCTTTGCCGGTATCGTGTGGCAGCACGTGTA

CGAGAAGAAGCTCAGCCCACCCTTCAAGCCCCAGGTCACGTCGGAGACTG

ACACCAGGTATTTTGATGAGGAGTTCACGGCCCAGATGATCACCATCACA

CCACCTGACCAAGATGACAGCATGGAGTGTGTGGACAGCGAGCGCAGGCC

CCACTTCCCCCAGTTCTCCTACTCGGCCAGCGGCACGGCCTGA

Human Raf CDS (SEQ ID NO: 32)

ATGGCTAGCAAACGAAAATCTACAACTCCATGCATGGTTCGGACATCACA

AGTAGTAGAACAAGATGTGCCCGAGGAAGTAGACAGGGCCAAAGAGAAAG

GAATCGGCACACCACAGCCTGACGTGGCCAAGGACAGTTGGGCAGCAGAA

CTTGAAAACTCTTCCAAAGAAAACGAAGTGATAGAGGTGAAATCTATGGG

GGAAAGCCAGTCCAAAAAACTCCAAGGTGGTTATGAGTGCAAATACTGCC

CCTACTCCACGCAAAACCTGAACGAGTTCACGGAGCATGTCGACATGCAG

CATCCCAACGTGATTCTCAACCCCCTCTACGTGTGTGCAGAATGTAACTT

CACAACCAAAAAGTACGACTCCCTATCCGACCACAACTCCAAGTTCCATC

CCGGGGAGGCCAACTTCAAGCTGAAGTTAATTAAACGCAATAATCAAACT

GTCTTGGAACAGTCCATCGAAACCACCAACCATGTCGTGTCCATCACCAC

CAGTGGCCCTGGAACTGGTGACAGTGATTCTGGGATCTCGGTGAGTAAAA

CCCCCATCATGAAGCCTGGAAAACCAAAAGCGGATGCCAAGAAGGTGCCC

AAGAAGCCCGAGGAGATCACCCCCGAGAACCACGTGGAAGGGACCGCCCG

CCTGGTGACAGACACAGCTGAGATCCTCTCGAGACTCGGCGGGGTGGAGC

TCCTCCAAGACACATTAGGACACGTCATGCCTTCTGTACAGCTGCCACCA

AATATCAACCTTGTGCCCAAGGTCCCTGTCCCACTAAATACTACCAAATA

CAACTCTGCCCTGGATACAAATGCCACGATGATCAACTCTTTCAACAAGT

TTCCTTACCCGACCCAGGCTGAGTTGTCCTGGCTGACAGCTGCCTCCAAA

CACCCAGAGGAGCACATCAGAATCTGGTTTGCCACCCAGCGCTTAAAGCA

TGGCATCAGCTGGTCCCCAGAAGAGGTGGAGGAGGCCCGGAAGAAGATGT

TCAACGGCACCATCCAGTCAGTACCCCCGACCATCACTGTGCTGCCCGCC

CAGTTGGCCCCCACAAAGGTGACGCAGCCCATCCTCCAGACGGCTCTACC

GTGCCAGATCCTCGGCCAGACTAGCCTGGTGCTGACTCAGGTGACCAGCG

GGTCAACAACCGTCTCTTGCTCCCCCATCACACTTGCCGTGGCAGGAGTC

ACCAACCATGGCCAGAAGAGACCCTTGGTGACTCCCCAAGCTGCCCCCGA

ACCCAAGCGTCCACACATCGCTCAGGTGCCAGAGCCCCCACCCAAGGTGG

CCAACCCCCCGCTCACACCAGCCAGTGACCGCAAGAAGACAAAGGAGCAG

ATAGCACATCTCAAGGCCAGCTTTCTCCAGAGCCAGTTCCCTGACGATGC

CGAGGTTTACCGGCTCATCGAGGTGACTGGCCTTGCCAGGAGCGAGATCA

AGAAGTGGTTCAGTGACCACCGATATCGGTGTCAAAGGGGCATCGTCCAC

ATCACCAGCGAATCCCTTGCCAAAGACCAGTTGGCCATCGCGGCCTCCCG

ACACGGTCGCACGTATCATGCGTACCCAGACTTTGCCCCCCAGAAGTTCA

AAGAGAAAACACAGGGTCAGGTTAAAATCTTGGAAGACAGCTTTTTGAAA

-continued

AGTTCTTTTCCTACCCAAGCAGAACTGGATCGGCTAAGGGTGGAGACCAA

GCTGAGCAGGAGAGAGATCGACTCCTGGTTCTCGGAGAGGCGGAAGCTTC

GAGACAGCATGGAACAAGCTGTCTTGGATTCCATGGGGTCTGGCAAAAAA

GGCCAAGATGTGGGAGCCCCCAATGGTGCTCTGTCTCGACTCGACCAGCT

CTCCGGTGCCCAGTTAACAAGTTCTCTGCCCAGCCCTTCGCCAGCAATTG

CAAAAAGTCAAGAACAGGTTCATCTCCTGAGGAGCACGTTTGCAAGAACC

CAGTGGCCTACTCCCCAGGAGTACGACCAGTTAGCGGCCAAGACTGGCCT

GGTCCGAACTGAGATTGTGCGTTGGTTCAAGGAGAACAGATGCTTGCTGA

AAACGGGAACCGTGAAGTGGATGGAGCAGTACCAGCACCAGCCCATGGCA

GATGATCACGGCTACGATGCCGTAGCAAGGAAAGCAACAAAACCCATGGC

CGAGAGCCCAAAGAACGGGGGTGATGTGGTTCCACAATATTACAAGGACC

CCAAAAAGCTCTGCGAAGAGGACTTGGAGAAGTTGGTGACCAGGGTAAAA

GTAGGCAGCGAGCCAGCAAAAGACTGTTTGCCAGCAAAGCCCTCAGAGGC

CACCTCAGACCGGTCAGAGGGCAGCAGCCGGGACGGCCAGGGTAGCGACG

AGAACGAGGAGTCGAGCGTTGTGGATTACGTGGAGGTGACGGTCGGGGAG

GAGGATGCGATCTCAGATAGATCAGATAGCTGGAGTCAGGCTGCGGCAGA

AGGTGTGTCGGAACTGGCTGAATCAGACTCCGACTGCGTCCCTGCAGAGG

CTGGCCAGGCCTAG

Human K-Ras CDS (SEQ ID NO: 33)

ATGACTGAATATAAACTTGTGGTAGTTGGAGCTGGTGGCGTAGGCAAGAG

TGCCTTGACGATACAGCTAATTCAGAATCATTTTGTGGACGAATATGATC

CAACAATAGAGGATTCCTACAGGAAGCAAGTAGTAATTGATGGAGAAACC

TGTCTCTTGGATATTCTCGACACAGCAGGTCAAGAGGAGTACAGTGCAAT

GAGGGACCAGTACATGAGGACTGGGGAGGGCTTTCTTTGTGTATTTGCCA

TAAATAATACTAAATCATTTGAAGATATTCACCATTATAGAGAACAAATT

AAAAGAGTTAAGGACTCTGAAGATGTACCTATGGTCCTAGTAGGAAATAA

ATGTGATTTGCCTTCTAGAACAGTAGACACAAAACAGGCTCAGGACTTAG

CAAGAAGTTATGGAATTCCTTTTATTGAAACATCAGCAAAGACAAGACAG

GGTGTTGATGATGCCTTCTATACATTAGTTCGAGAAATTCGAAAACATAA

AGAAAAGATGAGCAAAGATGGTAAAAAGAAGAAAAAGAAGTCAAAGACAA

AGTGTGTAATTATGTAA

Human N-Ras CDS (SEQ ID NO: 34)

ATGACTGAGTACAAACTGGTGGTGGTTGGAGCAGGTGGTGTTGGGAAAAG

CGCACTGACAATCCAGCTAATCCAGAACCACTTTGTAGATGAATATGATC

CCACCATAGAGGATTCTTACAGAAAACAAGTGGTTATAGATGGTGAAACC

TGTTTGTTGGACATACTGGATACAGCTGGACAAGAAGAGTACAGTGCCAT

GAGAGACCAATACATGAGGACAGGCGAAGGCTTCCTCTGTGTATTTGCCA

TCAATAATAGCAAGTCATTTGCGGATATTAACCTCTACAGGGAGCAGATT

AAGCGAGTAAAAGACTCGGATGATGTACCTATGGTGCTAGTGGGAAACAA

GTGTGATTTGCCAACAAGGACAGTTGATACAAAACAAGCCCACGAACTGG

-continued

CCAAGAGTTACGGGATTCCATTCATTGAAACCTCAGCCAAGACCAGACAG
GGTGTTGAAGATGCTTTTTACACACTGGTAAGAGAAATACGCCAGTACCG
AATGAAAAAACTCAACAGCAGTGATGATGGGACTCAGGGTTGTATGGGAT
TGCCATGTGTGGTGATGTAA

Human RIP CDS (SEQ ID NO: 35)

ATGCAACCAGACATGTCCTTGAATGTCATTAAGATGAAATCCAGTGACTT
CCTGGAGAGTGCAGAACTGGACAGCGGAGGCTTTGGGAAGGTGTCTCTGT
GTTTCCACAGAACCCAGGGACTCATGATCATGAAAACAGTGTACAAGGGG
CCCAACTGCATTGAGCACAACGAGGCCCTCTTGGAGGAGGCGAAGATGAT
GAACAGACTGAGACACAGCCGGGTGGTGAAGCTCCTGGGCGTCATCATAG
AGGAAGGGAAGTACTCCCTGGTGATGGAGTACATGGAGAAGGGCAACCTG
ATGCACGTGCTGAAAGCCGAGATGAGTACTCCGCTTTCTGTAAAAGGAAG
GATAATTTTGGAAATCATTGAAGGAATGTGCTACTTACATGGAAAAGGCG
TGATACACAAGGACCTGAAGCCTGAAAATATCCTTGTTGATAATGACTTC
CACATTAAGATCGCAGACCTCGGCCTTGCCTCCTTTAAGATGTGGAGCAA
ACTGAATAATGAAGAGCACAATGAGCTGAGGGAAGTGGACGGCACCGCTA
AGAAGAATGGCGGCACCCTCTACTACATGGCGCCCGAGCACCTGAATGAC
GTCAACGCAAAGCCCACAGAGAAGTCGGATGTGTACAGCTTTGCTGTAGT
ACTCTGGGCGATATTTGCAAATAAGGAGCCATATGAAAATGCTATCTGTG
AGCAGCAGTTGATAATGTGCATAAAATCTGGGAACAGGCCAGATGTGGAT
GACATCACTGAGTACTGCCCAAGAGAAATTATCAGTCTCATGAAGCTCTG
CTGGGAAGCGAATCCGGAAGCTCGGCCGACATTTCCTGGCATTGAAGAAA
AATTTAGGCCTTTTTATTTAAGTCAATTAGAAGAAAGTGTAGAAGAGGAC
GTGAAGAGTTTAAAGAAAGAGTATTCAAACGAAAATGCAGTTGTGAAGAG
AATGCAGTCTCTTCAACTTGATTGTGTGGCAGTACCTTCAAGCCGGTCAA
ATTCAGCCACAGAACAGCCTGGTTCACTGCACAGTTCCCAGGGACTTGGG
ATGGGTCCTGTGGAGGAGTCCTGGTTTGCTCCTTCCCTGGAGCACCCACA
AGAAGAGAATGAGCCCAGCCTGCAGAGTAAACTCCAAGACGAAGCCAACT
ACCATCTTTATGGCAGCCGCATGGACAGGCAGACGAAACAGCAGCCCAGA
CAGAATGTGGCTTACAACAGAGAGGAGGAAAGGAGACGCAGGGTCTCCCA
TGACCCTTTTGCACAGCAAAGACCTTACGAGAATTTTCAGAATACAGAGG
GAAAAGGCACTGCTTATTCCAGTGCAGCCAGTCATGGTAATGCAGTGCAC
CAGCCCTCAGGGCTCACCAGCCAACCTCAAGTACTGTATCAGAACAATGG
ATTATATAGCTCACATGGCTTTGGAACAAGACCACTGGATCCAGGAACAG
CAGGTCCCAGAGTTTGGTACAGGCCAATTCCAAGTCATATGCCTAGTCTG
CATAATATCCCAGTGCCTGAGACCAACTATCTAGGAAATACACCCACCAT
GCCATTCAGCTCCTTGCCACCAACAGATGAATCTATAAAATATACCATAT
ACAATAGTACTGGCATTCAGATTGGAGCCTACAATTATATGGAGATTGGT
GGGACGAGTTCATCACTACTAGACAGCACAAATACGAACTTCAAAGAAGA
GCCAGCTGCTAAGTACCAAGCTATCTTTGATAATACCACTAGTCTGACGG
ATAAACACCTGGACCCAATCAGGGAAAATCTGGGAAAGCACTGGAAAAAC

-continued

TGTGCCCGTAAACTGGGCTTCACACAGTCTCAGATTGATGAAATTGACCA
TGACTATGAGCGAGATGGACTGAAAGAAAAGGTTTACCAGATGCTCCAAA
AGTGGGTGATGAGGGAAGGCATAAAGGGAGCCACGGTGGGGAAGCTGGCC
CAGGCGCTCCACCAGTGTTCCAGGATCGACCTTCTGAGCAGCTTGATTTA
CGTCAGCCAGAACTAA

Human TRAF6 CDS (SEQ ID NO: 36)

ATGAGTCTGCTAAACTGTGAAAACAGCTGTGGATCCAGCCAGTCTGAAAG
TGACTGCTGTGTGGCCATGGCCAGCTCCTGTAGCGCTGTAACAAAAGATG
ATAGTGTGGGTGGAACTGCCAGCACGGGGAACCTCTCCAGCTCATTTATG
GAGGAGATCCAGGGATATGATGTAGAGTTTGACCCACCCCTGGAAAGCAA
GTATGAATGCCCCATCTGCTTGATGGCATTACGAGAAGCAGTGCAAACGC
CATGCGGCCATAGGTTCTGCAAAGCCTGCATCATAAAATCAATAAGGGAT
GCAGGTCACAAATGTCCAGTTGACAATGAAATACTGCTGGAAAATCAACT
ATTTCCAGACAATTTTGCAAAACGTGAGATTCTTTCTCTGATGGTGAAAT
GTCCAAATGAAGGTTGTTTGCACAAGATGGAACTGAGACATCTTGAGGAT
CATCAAGCACATTGTGAGTTTGCTCTTATGGATTGTCCCCAATGCCAGCG
TCCCTTCCAAAAATTCCATATTAATATTCACATTCTGAAGGATTGTCCAA
GGAGACAGGTTTCTTGTGACAACTGTGCTGCATCAATGGCATTTGAAGAT
AAAGAGATCCATGACCAGAACTGTCCTTTGGCAAATGTCATCTGTGAATA
CTGCAATACTATACTCATCAGAGAACAGATGCCTAATCATTATGATCTAG
ACTGCCCTACAGCCCCAATTCCATGCACATTCAGTACTTTTGGTTGCCAT
GAAAAGATGCAGAGGAATCACTTGGCACGCCACCTACAAGAGAACACCCA
GTCACACATGAGAATGTTGGCCCAGGCTGTTCATAGTTTGAGCGTTATAC
CCGACTCTGGGTATATCTCAGAGGTCCGGAATTTCCAGGAAACTATTCAC
CAGTTAGAGGGTCGCCTTGTAAGACAAGACCATCAAATCCGGGAGCTGAC
TGCTAAAATGGAAACTCAGAGTATGTATGTAAGTGAGCTCAAACGAACCA
TTCGAACCCTTGAGGACAAAGTTGCTGAAATCGAAGCACAGCAGTGCAAT
GGAATTTATATTTGGAAGATTGGCAACTTTGGAATGCATTTGAAATGTCA
AGAAGAGGAGAAACCTGTTGTGATTCATAGCCCTGGATTCTACACTGGCA
AACCCGGGTACAAACTGTGCATGCGCTTGCACCTTCAGTTACCGACTGCT
CAGCGCTGTGCAAACTATATATCCCTTTTTGTCCACACAATGCAAGGAGA
ATATGACAGCCACCTCCCTTGGCCCTTCCAGGGTACAATACGCCTTACAA
TTCTTGATCAGTCTGAAGCACCTGTAAGGCAAAACCACGAAGAGATAATG
GATGCCAAACCAGAGCTGCTTGCTTTCCAGCGACCCCACAATCCCACGGAA
CCCAAAAGGTTTTGGCTATGTAACTTTTATGCATCTGGAAGCCCTAAGAC
AAAGAACTTTCATTAAGGATGACACATTATTAGTGCGCTGTGAGGTCTCC
ACCCGCTTTGACATGGGTAGCCTTCGGAGGGAGGGTTTTCAGCCACGAAG
TACTGATGCAGGGGTATAG

-continued

Human TTP CDS (SEQ ID NO: 37)

```
ATGGCCAACCGTTACACCATGGATCTGACTGCCATCTACGAGAGCCTCCT

GTCGCTGAGCCCTGACGTGCCCGTGCCATCCGACCATGGAGGGACTGAGT

CCAGCCCAGGCTGGGGCTCCTCGGGACCCTGGAGCCTGAGCCCCTCCGAC

TCCAGCCCGTCTGGGGTCACCTCCCGCCTGCCTGGCCGCTCCACCAGCCT

AGTGGAGGGCCGCAGCTGTGGCTGGGTGCCCCCACCCCCTGGCTTCGCAC

CGCTGGCTCCCCGCCTGGGCCCTGAGCTGTCACCCTCACCCACTTCGCCC

ACTGCAACCTCCACCACCCCCTCGCGCTACAAGACTGAGCTATGTCGGAC

CTTCTCAGAGAGTGGGCGCTGCCGCTACGGGGCCAAGTGCCAGTTTGCCC

ATGGCCTGGGCGAGCTGCGCCAGGCCAATCGCCACCCCAAATACAAGACG

GAACTCTGTCACAAGTTCTACCTCCAGGGCCGCTGCCCCTACGGCTCTCG

CTGCCACTTCATCCACAACCCTAGCGAAGACCTGGCGGCCCCGGGCCACC

CTCCTGTGCTTCGCCAGAGCATCAGCTTCTCCGGCCTGCCCTCTGGCCGC

CGGACCTCACCACCACCACCAGGCCTGGCCGGCCCTTCCCTGTCCTCCAG

CTCCTTCTCGCCCTCCAGCTCCCCACCACCACCTGGGGACCTTCCACTGT

CACCCTCTGCCTTCTCTGCTGCCCCTGGCACCCCCCTGGCTCGAAGAGAC

CCCACCCCAGTCTGTTGCCCCTCCTGCCGAAGGGCCACTCCTATCAGCGT

CTGGGGGCCCTTGGGTGGCCTGGTTCGGACCCCCTCTGTACAGTCCCTGG

GATCCGACCCTGATGAATATGCCAGCAGCGGCAGCAGCCTGGGGGGCTCT

GACTCTCCCGTCTTCGAGGCGGGAGTTTTTGCACCACCCCAGCCCGTGGC

AGCCCCCCGGCGACTCCCCATCTTCAATCGCATCTCTGTTTCTGAGTGA
```

An antisense nucleic acid molecule can be complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein described herein. Antisense nucleic acids targeting a nucleic acid encoding an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP-MEKK1 protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, 0-units, the strands run parallel to each other (Gaultier et al., *Nucleic Acids Res.* 15:6625-6641, 1987). The antisense nucleic acid can also comprise a chimeric RNA-DNA analog (Inoue et al., *FEBS Lett.* 215:327-330, 1987) or a 2'-O-methylribonucleotide (Inoue et al., *Nucleic Acids Res.* 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of SEQ ID NOs: 1-37). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., *Science* 261:1411-1418, 1993.

Alternatively, a ribozyme having specificity for an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein. For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, INK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, *Bioassays* 14(12):807-15, 1992; Helene, *Anticancer Drug Des.* 6(6):569-84, 1991; and Helene, *Ann. N.Y. Acad. Sci.* 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, INK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, RO5126766 (CH5126766), PLX7904, and MLN2480).

In some examples, the anti-TNFα agent TNFα inhibitor is a small molecule that inhibits the activity of one of MK2 (PF 3644022 and PHA 767491), INK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799 (10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl) amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 15 nucleotides to about 16 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

The following abbreviations have the indicated meanings:

ACN=acetonitrile
BTC=trichloromethyl chloroformate
Boc=t-butyloxy carbonyl
Davephos=2-Dicyclohexylphosphino-2'-(N,N-dimethylamino)biphenyl
DCM=dichloromethane
DEA=diethylamine
DMF=N,N-dimethylformamide
DMSO=dimethyl sulfoxide
DIEA=N,N-diisopropylethylamine
DPPA=diphenylphosphoryl azide
dppf=1,1'-Bis(diphenylphosphino)ferrocene
EtOH=ethanol
HATU=1-[Bis(dimethylamino)methylene]-1H-1,2,3-triazolo[4,5-b]pyridinium 3-oxid hexafluorophosphate
Hex=hexane
HPLC=high performance liquid chromatography
LC-MS=liquid chromatography-mass spectrometry
LiHMDS=lithium bis(trimethylsilyl)amide
LDA=lithium diisopropylamide M=mol/L
Me=methyl
MeOH=methanol
MSA=methanesulfonic acid
NBS=N-bromosuccinimide
NCS=N-chlorosuccinimide
NMR=nuclear magnetic resonance
Pd(dppf)$Cl_2$=dichloro[1,1'-bis(diphenylphosphino)ferrocene]palladium
Ph=phenyl
$PPh_3Cl_2$=dichlorotriphenylphosphorane
Py=pyridine
RT=room temperature
Rt=Retention time
$R_f$=Retardation factor
Sat.=saturated
TBAF=tetrabutylammonium fluoride
TBS=tert-butyldimethylsilyl
TBSCl=tert-butyldimethylsilyl chloride
TBDPSCl=tert-butyldiphenylsilyl chloride
TEA=triethylamine
TFA=trifluoroacetic acid
THF=tetrahydrofuran
TLC=thin layer chromatography
TsOH=4-methylbenzenesulfonic acid
UV=ultraviolet

General

The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% $NH_4HCO_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% $NH_4HCO_3$), 3 minute total run time.

Method F: Phenomenex, CHO-7644, Onyx Monolithic C18, 50×4.6 mm, 10.0 uL injection, 1.5 mL/min flow rate, 100-1500 amu scan range, 220 and 254 nm UV detection, 5% with ACN (0.1% TFA) to 100% water (0.1% TFA) over 9.5 min, with a stay at 100% (ACN, 0.1% TFA) for 1 min, then equilibration to 5% (ACN, 0.1% TFA) over 1.5 min.

The final targets were purified by Prep-HPLC. The Prep-HPLC was carried out using the following method.

Method E: Prep-HPLC: Column, XBridge Shield RP18 OBD (19×250 mm, 10 um); mobile phase, Water (10 mmol/L $NH_4HCO_3$) and ACN, UV detection 254/210 nm.

Method G: Prep-HPLC: Higgins Analytical Proto 200, C18 Column, 250×20 mm, 10 um; mobile phase, Water (0.1% TFA) and ACN (0.1% TFA), UV detection 254/210 nm.

NMR was recorded on BRUKER NMR 300.03 MHz, DUL-C-H, ULTRASHIELD™300, AVANCE II 300 B-ACS™120 or BRUKER NMR 400.13 MHz, BBFO, ULTRASHIELD™400, AVANCE III 400, B-ACS™120 or BRUKER AC 250 NMR instrument with TMS as reference measured in ppm (part per million).

Racemic compounds of this invention can be resolved to give individual enantiomers using a variety of known methods. For example, chiral stationary phases can used and the elution conditions can include normal phase or super-critical fluid with or without acidic or basic additives. Enantiomerically pure acids or bases can be used to form diatereomeric salts with the racemic compounds whereby pure enantiomers can be obtained by fractional crystallization. The racemates can also be derivatized with enantiomerically pure auxiliary reagents to form diastereomeric mixtures that can be separated. The auxiliary is then removed to give pure enantiomers.

Schemes for the Preparation of Final Targets:

Schemes 1-3 below illustrate several conditions used for coupling of sulfonimidamide 1 or 5 and isocyanate 2 to afford aminocarbonyl sulfonimidamide 4 via 3 or 6 after deprotection. As used in the schemes, rings "A" and "B" may be substituted as disclosed herein.

Scheme 1

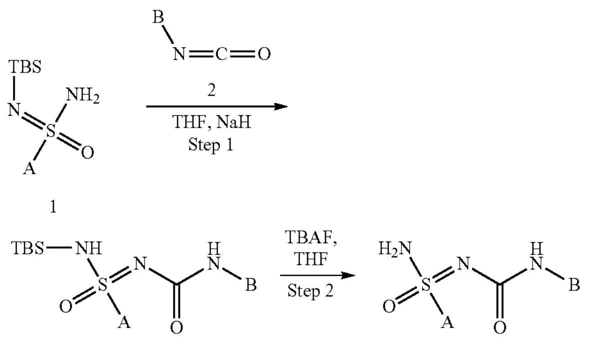

1

3 4

Scheme 2

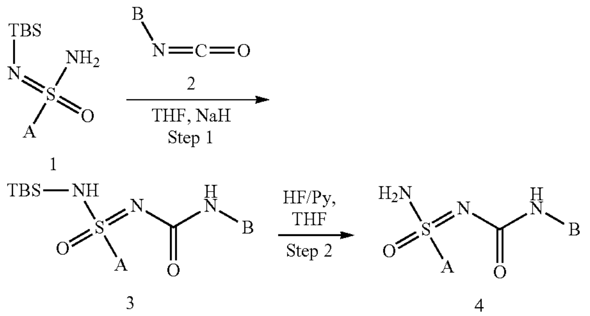

1

3 4

Scheme 3

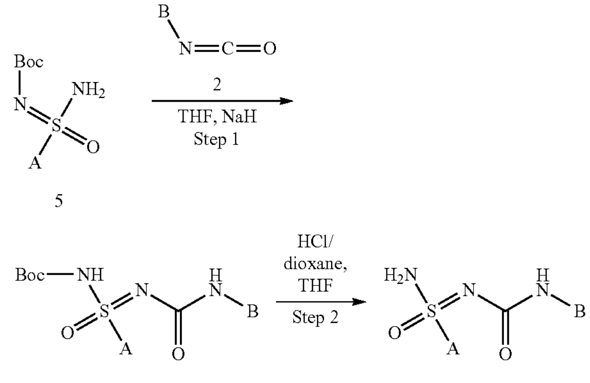

5 6 4

Scheme 3A

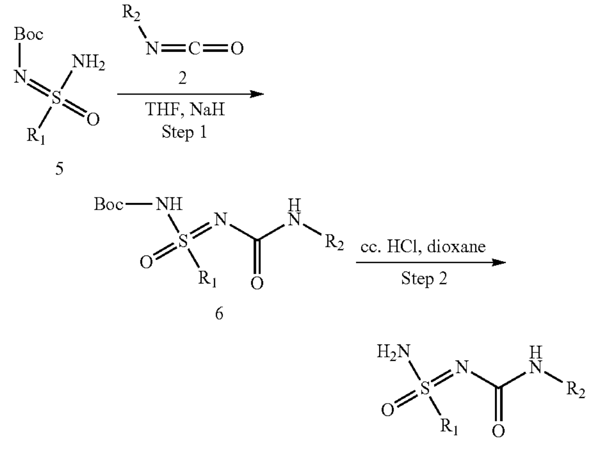

5 6 4

Scheme 3B

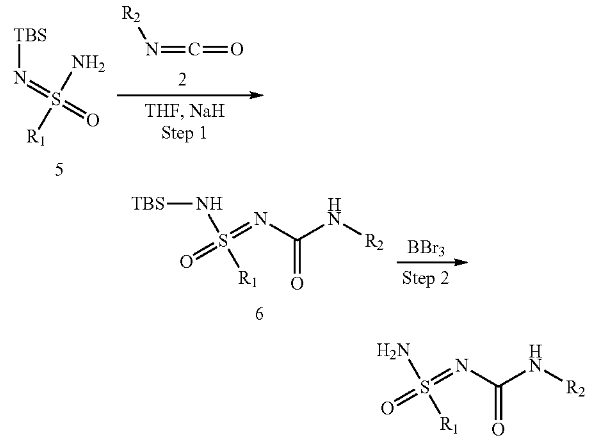

5 6 4

Scheme 4 below illustrates the coupling between sulfonimidamide 7 and isocyanate 2 to provide sulfonimidamide 8.

Scheme 4

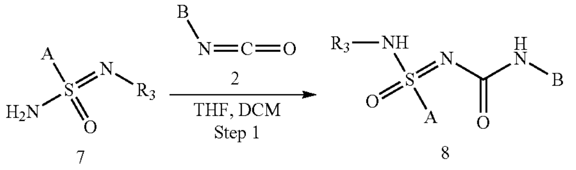

7 8

Scheme 4A

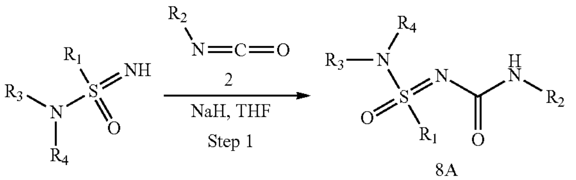

7A 8A

Scheme 5 below illustrates the conversion of carboxylic acid 9 through Curtius rearrangement to isocyanate 2 via acyl azide 10, whereupon coupling between 2 and sulfonimidamide 5 affords aminocarbonyl sulfonimidamide 4.

Scheme 5

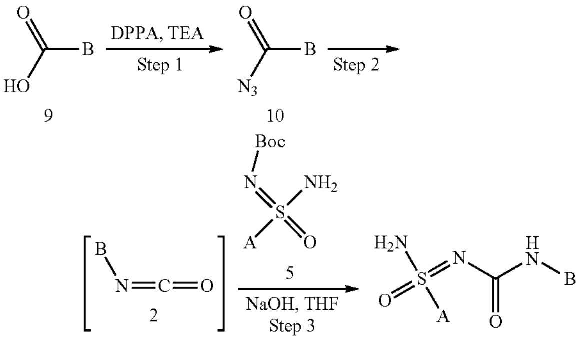

9 10 2 5 4

Schemes for the Preparation of Sulfonimidamide Intermediates 1-29:

Schemes below illustrate the preparation of sulfonamide intermediates.

Scheme 6

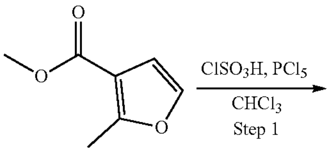

11

-continued

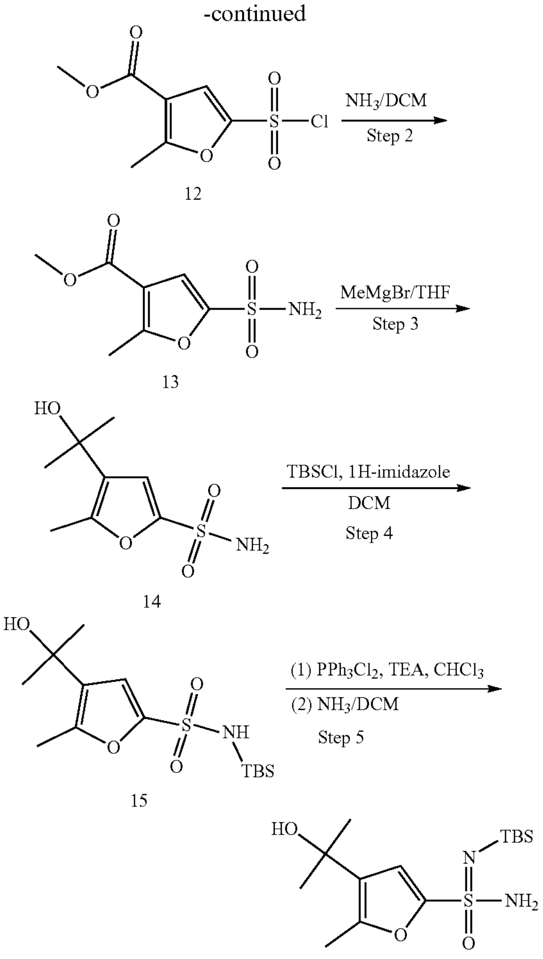

12

13

14

15

Intermediate 1

Intermediate 1

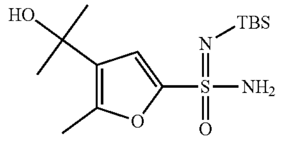

N'-(tert-butyldimethylsilyl)-4-(2-hydroxypropan-2-yl)-5-methylfuran-2-sulfonimidamide Step 1: Methyl 5-(chlorosulfonyl)-2-methylfuran-3-carboxylate Into a 500-mL 3-necked round-bottom flask was placed methyl 2-methylfuran-3-carboxylate (7 g, 50 mmol) in $CHCl_3$ (200 mL). This was followed by the addition of chlorosulfonic acid (11.6 g, 100 mmol) dropwise with stirring at −10° C. The reaction mixture was stirred for 48 h at RT, after which the system was cooled to −10° C. Then to the above was added phosphorus pentachloride (22.9 g, 110 mmol). The resulting solution was stirred for 0.5 h at 50° C. and then was quenched by pouring onto 200 mL of water/ice. The resulting mixture was extracted with 3×200 mL of DCM. The organic layers were combined and dried over anhydrous $Na_2SO_4$, and then concentrated under vacuum. This resulted in 7.5 g (crude, 63%) of the title compound as light brown oil. The crude product was used in the next step.

Step 2: Methyl 2-methyl-5-sulfamoylfuran-3-carboxylate

Into a 250-mL round-bottom flask was placed a solution of methyl 5-(chlorosulfonyl)-2-methylfuran-3-carboxylate (7.5 g, crude) in DCM (75 mL). To the above was added a saturated solution of ammonia in DCM (50 mL). The resulting solution was stirred for 3 h at RT and then was concentrated under vacuum. The residue was applied onto a silica gel column and eluted with a gradient of ethyl acetate/petroleum ether (1:4 to 1:2). This resulted in 5.0 g (46% over two steps) of the title compound as a light yellow solid. MS-ESI: 218.0 (M−1).

Step 3: 4-(2-Hydroxypropan-2-yl)-5-methylfuran-2-sulfonamide

Into a 250-mL 3-necked round-bottom flask purged with and maintained under nitrogen was placed a solution of methyl 2-methyl-5-sulfamoylfuran-3-carboxylate (3.7 g, 16.9 mmol) in THF (100 mL). This was followed by the addition of MeMgBr (3 M in THF, 25 mL) dropwise with stirring at −10° C. The resulting mixture was stirred for 10 h at RT and then was quenched by the addition of 50 mL of $NH_4Cl$ (sat.). The resulting solution was extracted with 3×50 mL of ethyl acetate. The organic layers were combined and dried over anhydrous $Na_2SO_4$, then concentrated under vacuum. The residue was applied onto a silica gel column and eluted with a gradient of ethyl acetate/petroleum ether (1:3 to 1:1). This resulted in 2.6 g (75%) of the title compound as a light yellow solid. MS-ESI: 218.0 (M−1).

Step 4: N-(tert-butyldimethylsilyl)-4-(2-hydroxypropan-2-yl)-5-methylfuran-2-sulfonamide Into a 250-mL round-bottom flask purged with and maintained under nitrogen was placed 4-(2-hydroxypropan-2-yl)-5-methylfuran-2-sulfonamide (1.0 g, 4.56 mmol), DCM (100 mL), 1H-imidazole (612 mg, 9.12 mmol), and TBSCl (3.4 g, 22.6 mmol). The resulting solution was stirred for 14 h at RT and then was diluted with 100 mL of water. The resulting mixture was extracted with 3×50 mL of DCM and the organic layers were combined and concentrated under vacuum. The residue was applied onto a silica gel column and eluted with a gradient of ethyl acetate/petroleum ether (1:10 to 1:3). This resulted in 1.4 g (92%) of the title compound as a white solid. MS-ESI: 332.0 (M−1).

Step 5: N'-(tert-butyldimethylsilyl)-4-(2-hydroxypropan-2-yl)-5-methylfuran-2-sulfonimidamide Into a 250-mL 3-necked round-bottom flask purged with and maintained under nitrogen was placed $PPh_3Cl_2$ (3.0 g, 10.2 mmol) in $CHCl_3$ (100 mL). This was followed by the addition of TEA (2.06 g, 20.4 mmol) dropwise with stirring at RT. After stirred at 0° C. for 10 min, to the above was added a solution of N-(tert-butyldimethylsilyl)-4-(2-hydroxypropan-2-yl)-5-methylfuran-2-sulfonamide (2.3 g, 6.8 mmol) in $CHCl_3$ (10 mL) dropwise with stirring at 0° C. The resulting solution was allowed to react for 30 min at 0° C. To the mixture was added a saturated solution of ammonia in DCM (10 mL) at 0° C. The resulting solution was stirred for 2 h at RT. The reaction was then quenched by the addition of 100 mL of water. The resulting solution was extracted with 3×50 mL of DCM and the organic layers combined and concentrated under vacuum. The residue was applied onto a silica gel column and eluted with a gradient of ethyl acetate/petroleum ether (1:10 to 1:3). This resulted in 0.80 g (52.8%) of the title compound as a light yellow solid. MS-ESI: 333.0 (M+1).

Scheme 7A

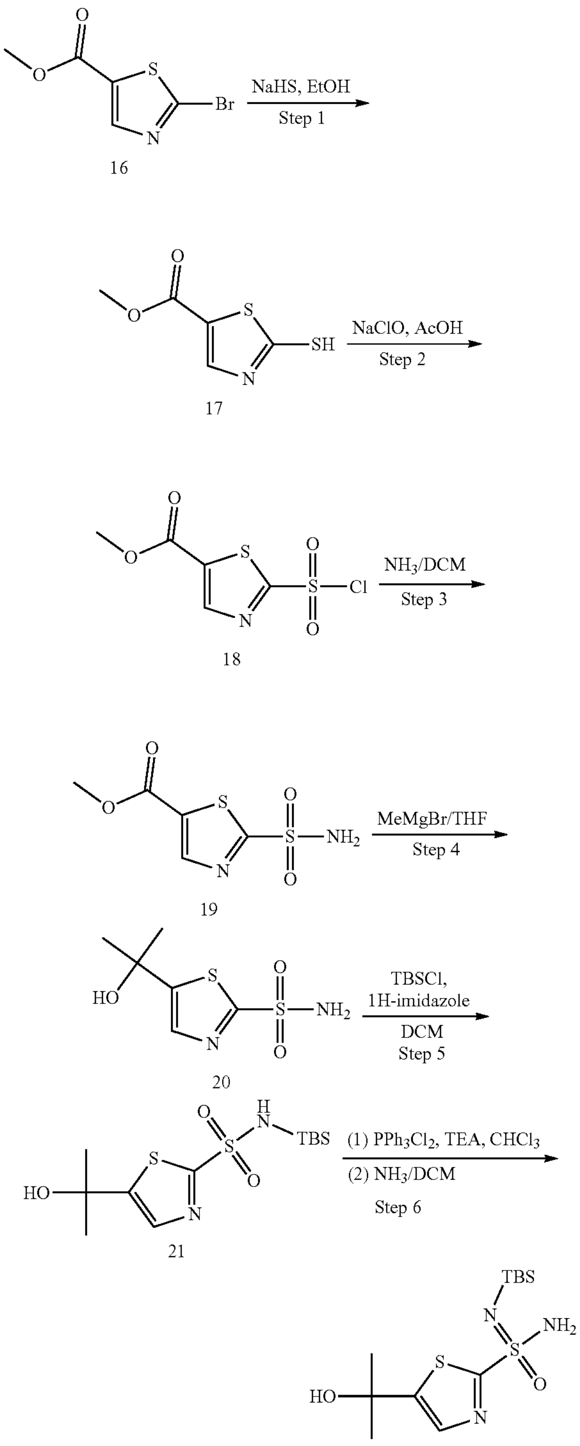

16

17

18

19

20

21

Intermediate 2

Intermediate 2

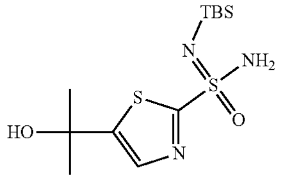

N'-(tert-butyldimethylsilyl)-5-(2-hydroxypropan-2-yl)thiazole-2-sulfonimidamide

Step 1: Methyl 2-mercaptothiazole-5-carboxylate

Into a 250-mL round-bottom flask was placed methyl 2-bromothiazole-5-carboxylate (10 g, 45 mmol), EtOH (100 mL), and sodium hydrogensulfide (5 g, 89 mmol). The resulting solution was stirred for 2 h at 80° C. and then was cooled to 0° C. with a water/ice bath. The pH value of the solution was adjusted to 3 with aq. HCl (1 N). The solids were collected by filtration. This resulted in 6 g (76%) of the title compound as a light yellow solid. MS-ESI: 176.0 (M+1).

Step 2: Methyl 2-(chlorosulfonyl)thiazole-5-carboxylate

Into a 250-mL round-bottom flask was placed methyl 2-mercaptothiazole-5-carboxylate (6 g, 34 mmol) and acetic acid (60 mL). This was followed by the addition of sodium hypochlorite (60 mL, 8%-10% wt.) in portions at 0° C. The resulting solution was stirred for 1 h at RT and then was diluted with 100 mL of water. The solution was extracted with 3×50 mL of DCM. The organic layers were combined and dried over anhydrous $Na_2SO_4$, then concentrated under vacuum. This resulted in 5 g (crude, 60%) of the title compound as yellow oil. The crude product was used in the next step.

Step 3-6 used similar procedure for converting compound 12 to Intermediate 1 shown in Scheme 6 to afford Intermediate 2. MS-ESI: 336.1 (M+1).

Scheme 7B

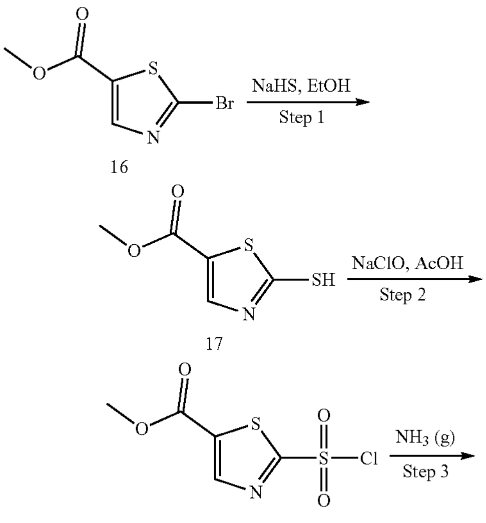

16

17

18

-continued

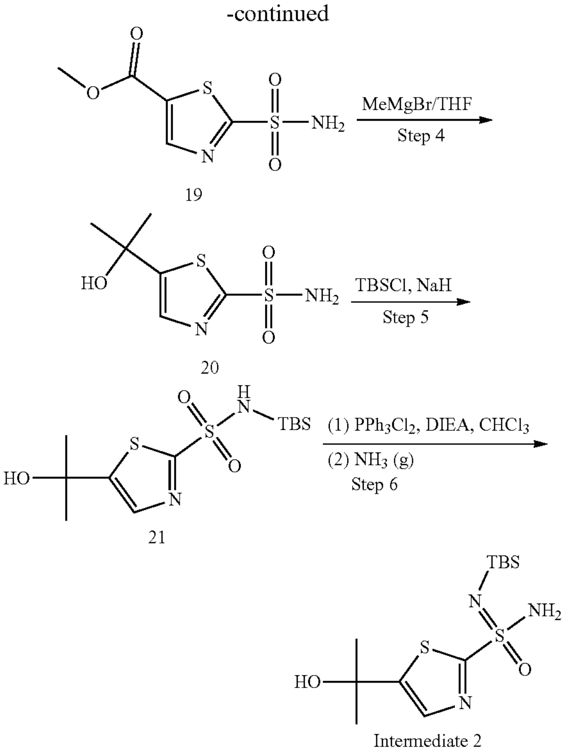

19

20

21

Intermediate 2

Intermediate 2

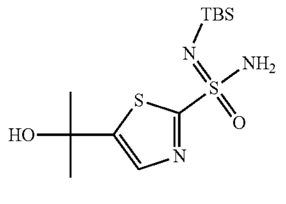

N'-(tert-butyldimethylsilyl)-5-(2-hydroxypropan-2-yl)thiazole-2-sulfonimidamide

Step 1: Methyl 2-mercaptothiazole-5-carboxylate

Into a 2-L round-bottom flask was placed methyl 2-bromothiazole-5-carboxylate (100 g, 450 mmol), EtOH (1000 mL), sodium hydrogensulfide (50 g, 890 mmol). The resulting solution was stirred for 2 h at 80° C. and then was cooled to 0° C. with a water/ice bath. The pH value of the solution was adjusted to 3 with hydrogen chloride (1 N). The solids were collected by filtration. This resulted in 63.2 g (80%) of the title compound as a light yellow solid. MS-ESI: 176.0 (M+1).

Step 2: Methyl 2-(chlorosulfonyl)thiazole-5-carboxylate

Into a 1-L round-bottom flask was placed methyl 2-mercaptothiazole-5-carboxylate (30 g, 170 mmol) and acetic acid (300 mL). This was followed by the addition of sodium hypochlorite (300 mL, 8%-10% wt.) in portions at 0° C. The resulting solution was stirred for 2 h at RT and then was diluted with 500 mL of water. The solution was extracted with 3x300 mL of DCM and the combined organic layers were washed with 2x300 mL of brine and dried over anhydrous $Na_2SO_4$. The crude product as a yellow solution in DCM was used in the next step.

Step 3: Methyl 2-sulfamoylthiazole-5-carboxylate

Into a 2-L round-bottom flask was placed methyl 2-(chlorosulfonyl)thiazole-5-carboxylate as a crude solution in DCM (900 mL). To the solution was introduced $NH_3$ (g) below 0° C. for 20 minutes. The resulting solution was stirred for 1 h at RT and then concentrated under vacuum. The residue was applied onto a silica gel column and eluted with ethyl acetate/petroleum ether (1:5 to 1:3). This resulted in 23 g (75%, 2 steps) of the title compound as a white solid. MS-ESI: 223.0 (M+1).

Step 4: 5-(2-Hydroxypropan-2-yl)thiazole-2-sulfonamide

Into a 500-mL round-bottom flask purged with and maintained under nitrogen was placed a solution of methyl 2-sulfamoylthiazole-5-carboxylate (15 g, 67.5 mmol) in THF (150 mL). This was followed by the addition of MeMgBr/THF (3 M, 90 mL) dropwise with stirring at 0° C. The resulting solution was stirred for 14 h at RT and then was quenched by the addition of 100 mL of $NH_4Cl$ (sat.). The resulting solution was extracted with 3x150 mL of DCM. The organic layers were combined and dried over anhydrous $Na_2SO_4$, then concentrated under vacuum. The residue was applied onto a silica gel column and eluted with ethyl acetate/petroleum ether (1:5 to 1:3). This resulted in 11.5 g (78%) of the title compound as a white solid. MS-ESI: 223.0 (M+1), 221.0 (M−1) in positive and negative ion mode, respectively.

Step 5: N-(tert-butyldimethylsilyl)-5-(2-hydroxypropan-2-yl)thiazole-2-sulfonamide Into a 250-mL 3-necked round-bottom flask purged with and maintained under nitrogen was placed a solution of 5-(2-hydroxypropan-2-yl)thiazole-2-sulfonamide (5 g, 22.5 mmol) in THF (100 mL). Then to the above was added NaH (60% wt, 1.8 g, 45.0 mmol) in portions in an ice/water bath. After stirring for 20 minutes in a water/ice bath, this was followed by the addition of a solution of TBSCl (4.1 g, 27.2 mmol) in THF (10 mL) dropwise with stirring at 0° C. The resulting solution was stirred for 4 h at RT. The reaction was quenched with sat. $NH_4Cl$ (100 mL). The resulting solution was extracted with 3x100 mL of ethyl acetate and the combined organic layers were dried over $Na_2SO_4$ and concentrated under vacuum. The crude solid was washed with ethyl acetate/hexane (1:5) (2x100 mL). This resulted in 6.81 g (90%) of the title compound as a yellow solid. MS-ESI: 337.1 (M+1), 335.1 (M−1) in positive and negative ion mode, respectively.

Step 6: N'-(tert-butyldimethylsilyl)-5-(2-hydroxypropan-2-yl)thiazole-2-sulfonimidamide Into a 100-mL 3-necked round-bottom flask purged with and maintained under nitrogen was placed a solution of $PPh_3Cl_2$ (3 g, 9.0 mmol) in $CHCl_3$ (100 mL). This was followed by the addition of DIEA (1.54 g, 11.9 mmol) dropwise with stirring at RT. The resulting solution was stirred for 10 min at RT. This was followed by the addition of a solution of N-(tert-butyldimethylsilyl)-5-(2-hydroxypropan-2-yl)thiazole-2-sulfonamide (2.0 g, 5.9 mmol) in $CHCl_3$ (30 mL) dropwise with stirring in an ice/water bath. The resulting solution was stirred for 30 min in an ice/water bath. To the above was introduced $NH_3$ (g) below 0° C. for 15 minutes. The resulting solution was stirred for 20 minutes at RT. The solids were filtered out and the filtrate was concentrated and the residue was dissolved in 300 mL of ethyl acetate. The solution was washed with brine (2×100 mL), dried over $Na_2SO_4$ and concentrated under vacuum. The crude solid was washed with $CHCl_3$ (100 mL). Then the filtrate was concentrated under vacuum and the residue was further purified by a silica gel column with ethyl acetate/petroleum ether (1:10 to 1:3). The original washed solid and solid from silica gel purification were combined. This resulted in 1.2 g (60%) of the title compound as a white solid. MS-ESI: 336.1 (M+1). $^1$H-NMR (300 MHz, DMSO-$d_6$) δ 7.66 (s, 1H), 7.12 (s, 2H), 5.78 (s, 1H), 1.51 (s, 6H), 0.86 (s, 9H), 0.02 (s, 3H), 0.01 (s, 3H).

-continued

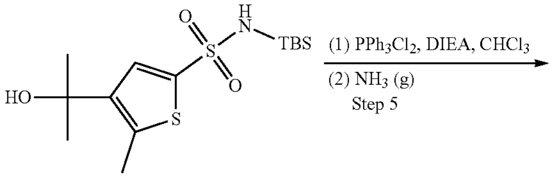

26

TABLE 2

The Intermediate in the following Table was prepared using the similar procedures for converting compound 16 to Intermediate 2 shown in Scheme 7B starting from ethyl 5-bromo-4-methylthiazole-2-carboxylate.

| Intermediate # | Structure | IUPAC Name | Exact Mass[M + H]$^+$ |
|---|---|---|---|
| Intermediate 3 | 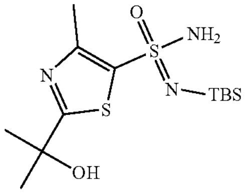 | N'-(tert-butyldimethylsilyl)-2-(2-hydroxypropan-2-yl)-4-methylthiazole-5-sulfonimidamide | 350.2 |

Scheme 8

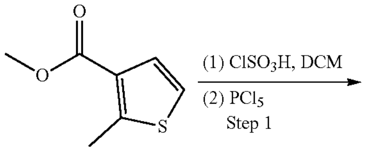

22

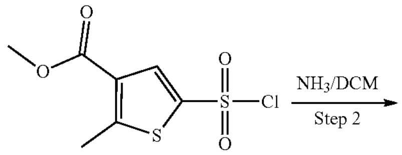

23

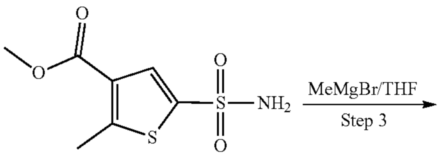

24

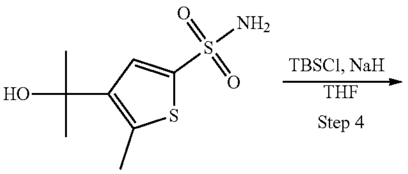

25

-continued

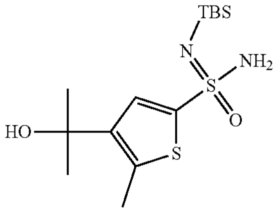

Intermediate 4

Intermediate 4

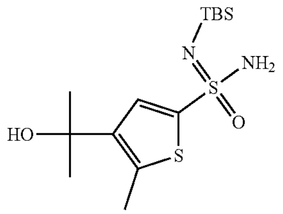

N'-(tert-butyldimethylsilyl)-4-(2-hydroxypropan-2-yl)-5-methylthiophene-2-sulfonimidamide Steps 1-3 used similar procedures for converting compound 11 to compound 14 shown in Scheme 6 to afford compound 25 from compound 22. MS-ESI: 234.0 (M−1).

Steps 4-5 used similar procedure for converting compound 20 to Intermediate 2 shown in Scheme 7B to afford Intermediate 4 from compound 25. MS-ESI: 349.1 (M+1).

TABLE 3

The Intermediate in the following Table was prepared using similar procedure as shown in Scheme 8 above for converting compound 22 to Intermediate 4 starting from the appropriate materials.

| Intermediate # | Structure | IUPAC Name | Exact Mass[M + H]$^+$ |
|---|---|---|---|
| Intermediate 5 | 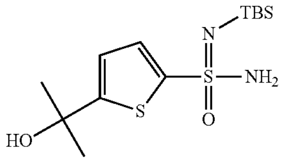 | N'-(tert-butyldimethylsilyl)-5-(2-hydroxypropan-2-yl)thiophene-2-sulfonimidamide | 335.1 |
| Intermediate 6 | 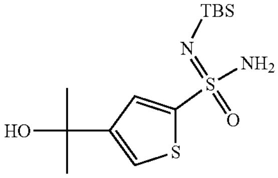 | N'-(tert-butyldimethylsilyl)-4-(2-hydroxypropan-2-yl)thiophene-2-sulfonimidamide | 335.1 |
| Intermediate 7 | 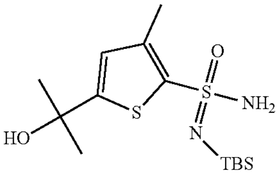 | N'-(tert-butyldimethylsilyl)-5-(2-hydroxypropan-2-yl)-3-methylthiophene-2-sulfonimidamide | 349.1 |
| Intermediate 8 | 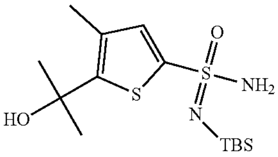 | N'-(tert-butyldimethylsilyl)-5-(2-hydroxypropan-2-yl)-4-methylthiophene-2-sulfonimidamide | 349.1 |
| Intermediate 9 | 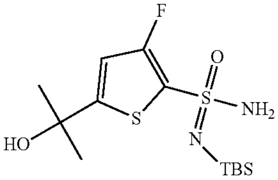 | N'-(tert-butyldimethylsilyl)-3-fluoro-5-(2-hydroxypropan-2-yl)thiophene-2-sulfonimidamide | 353.1 |
| Intermediate 10 | 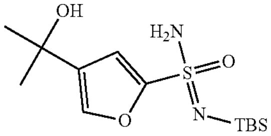 | N'-(tert-butyldimethylsilyl)-4-(2-hydroxypropan-2-yl)furan-2-sulfonimidamide | 319.1 |

Scheme 9

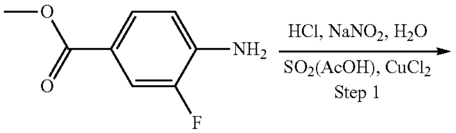

27

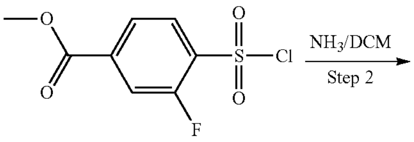

28

-continued

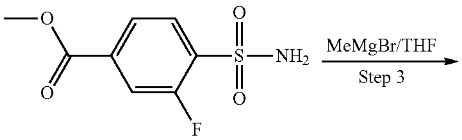

29

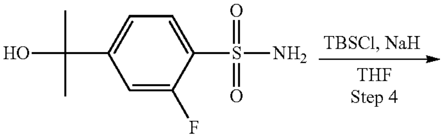

30

-continued

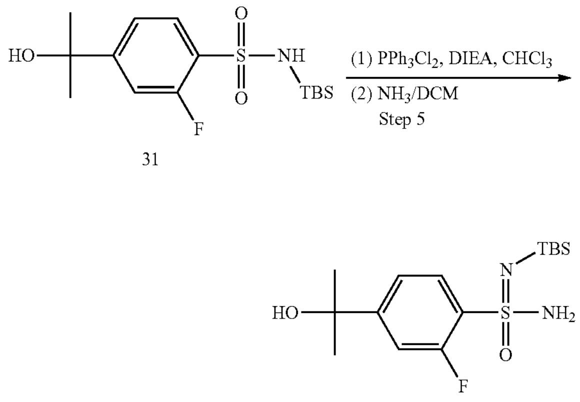

31

Intermediate 11

Intermediate 11

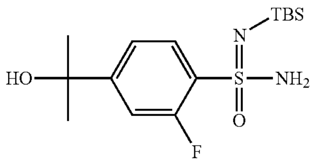

N'-(tert-butyldimethylsilyl)-2-fluoro-4-(2-hydroxy-propan-2-yl)benzenesulfonimidamide Step 1: Methyl 4-(chlorosulfonyl)-3-fluorobenzoate Into a 1 L round-bottom flask was placed a solution of methyl 4-amino-3-fluorobenzoate (10 g, 59.1 mmol) in aq. HCl (6 N, 200 mL). This was followed by the addition of a solution of $NaNO_2$ (6.1 g, 88.8 mmol) in water (20 mL) dropwise with stirring at 0° C. The resulting solution was stirred for 30 min at 0° C. The above mixture was added to a saturated solution of $SO_2$ in AcOH (200 mL) dropwise with stirring at 0° C. Then to the above was added $CuCl_2$ (8.0 g, 59.6 mmol). The resulting solution was stirred for 1 h at RT and was then quenched by the addition of 200 mL of water. The resulting solution was extracted with 3×200 mL of DCM. The organic layers were combined, dried over anhydrous $Na_2SO_4$ and concentrated under vacuum. This resulted in 10 g (67%) of the title compound as yellow oil. The product was used in the next step without further purification.

Step 2: Methyl 3-fluoro-4-sulfamoylbenzoate

Into a 1000 mL round bottom flask was placed a solution of methyl 4-(chlorosulfonyl)-3-fluorobenzoate solution (10 g, 39.5 mmol) in DCM (50 mL). This was followed by the addition of a saturated solution of ammonia in DCM (500 mL) in portions with stirring at 0° C. The resulting solution was stirred for 1 h at 0° C. The resulting solution was concentrated and the residue was purified with $SiO_2$-gel column and diluted with ethyl acetate/petroleum ether (1:2 to 1:1). This resulted in 8.28 g (90%) of the title compound as yellow solid. MS-ESI: 232.1 (M−1).

Step 3: 2-Fluoro-4-(2-hydroxypropan-2-yl)benzene-sulfonamide

Into a 1 L 3-necked round-bottom flask was placed a solution of methyl 3-fluoro-4-sulfamoylbenzoate (8.28 g 35.5 mmol) in THF (500 mL). This was followed by the addition of MeMgBr/THF (3 M, 60 mL) dropwise with stirring at 0° C. The resulting solution was stirred overnight at RT and then was quenched by the addition of 100 mL of sat. $NH_4Cl$. The resulting solution was extracted with 3×200 mL of ethyl acetate and the combined organic layers were concentrated under vacuum. The residue was applied onto a silica gel column and eluted with ethyl acetate/petroleum ether (1:2 to 1:1). This resulted 7.45 g (89.9%) of the title compound as a white solid. MS-ESI: 233.1 (M+1).

Step 4: N-(tert-butyldimethylsilyl)-2-fluoro-4-(2-hydroxypropan-2-yl)benzenesulfonamide Into a 500 mL round bottom flask was placed a solution of 2-fluoro-4-(2-hydroxypropan-2-yl)benzenesulfonamide (7.45 g 31.9 mmol) in THF (200 mL). This was followed by the addition of NaH (60% wt, 1.91 g, 79.6 mmol). The mixture was stirred at 0° C. for 0.5 h. This was followed by the addition of the solution of TBSCl (7.19 g, 47.9 mmol) in THF (50 mL) dropwise. The resulting solution was stirred at RT overnight. The reaction was quenched with ice-water (100 mL); the resulting solution was extracted with EtOAc (3×200 mL). The combined organic layers were dried over anhydrous $Na_2SO_4$ and concentrated under vacuum. The residue was purified with $SiO_2$-gel column and eluted with ethyl acetate/petroleum ether (1:5 to 1:2). This resulted 10 g (90%) of the title compound as a white solid. MS-ESI: 348.1 (M+1).

Step 5: N'-(tert-butyldimethylsilyl)-2-fluoro-4-(2-hydroxypropan-2-yl)benzenesulfonimidamide Into a 1 L 3-necked round-bottom flask purged with and maintained under nitrogen was placed a solution of $PPh_3Cl_2$ (19.2 g, 57.6 mmol) in $CHCl_3$ (100 mL). This was followed by the addition of DIEA (7.4 g, 57.6 mmol) dropwise with stirring at 0° C. After stirred at 0° C. for 10 min, to the above was added a solution of N'-(tert-butyldimethylsilyl)-2-fluoro-4-(2-hydroxypropan-2-yl)benzenesulfonimidamide (10 g, 28.8 mmol) in $CHCl_3$ (100 mL) dropwise with stirring at 0° C. The resulting solution was allowed to react for 30 min at 0° C. To the mixture was added a saturated solution of ammonia in DCM (500 mL) at 0° C. The resulting solution was stirred for 2 h at RT. The solids were filtered out, and the filtrate was dilute with 100 mL of water. The resulting solution was extracted with 3×200 mL of DCM and the combined organic layers were dried over anhydrous $Na_2SO_4$ concentrated under vacuum. The residue was applied onto a silica gel column and eluted with a gradient of ethyl acetate/petroleum ether (1:10 to 1:3). This resulted in 5 g (50%) of the title compound as a light yellow solid. MS-ESI: 347.2 (M+1).

TABLE 4

The Intermediates in the following Table were prepared using similar procedure as shown in Scheme 9 above for converting compound 27 to Intermediate 11 starting from the appropriate materials.

| Intermediate # | Structure | IUPAC Name | Exact Mass[M + H]$^+$ |
|---|---|---|---|
| Intermediate 12 | 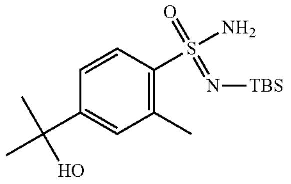 | N'-(tert-butyldimethylsilyl)-4-(2-hydroxypropan-2-yl)-2-methylbenzenesulfonimidamide | 343.2 |
| Intermediate 13 | 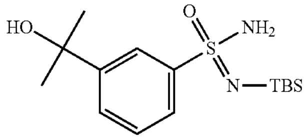 | N'-(tert-butyldimethylsilyl)-3-(2-hydroxypropan-2-yl) benzenesulfonimidamide | 329.1 |
| Intermediate 14 | 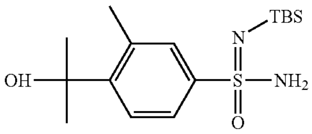 | N'-(tert-butyldimethylsilyl)-4-(2-hydroxypropan-2-yl)-3-methylbenzenesulfonimidamide | 343.2 |
| Intermediate 15 | 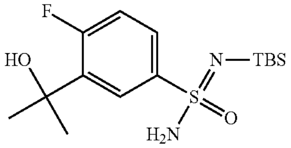 | N'-(tert-butyldimethylsilyl)-4-fluoro-3-(2-hydroxypropan-2-yl)benzenesulfonimidamide | 347.2 |
| Intermediate 16 | 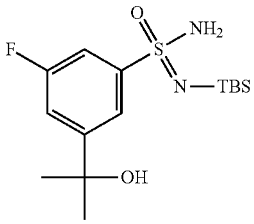 | N'-(tert-butyldimethylsilyl)-3-fluoro-5-(2-hydroxypropan-2-yl)benzenesulfonimidamide | 347.2 |
| Intermediate 17 | 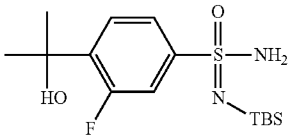 | N'-(tert-butyldimethylsilyl)-3-fluoro-4-(2-hydroxypropan-2-yl)benzenesulfonimidamide | 347.2 |
| Intermediate 18 | 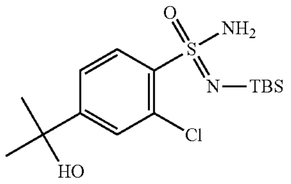 | N'-(tert-butyldimethylsilyl)-2-chloro-4-(2-hydroxypropan-2-yl)benzenesulfonimidamide | 363.1 |

TABLE 5

| The Intermediate in the following Table was prepared using similar procedure as shown in Scheme 9 above for converting compound 28 to Intermediate 11 starting from methyl 4-(chlorosulfonyl)benzoate. | | | |
|---|---|---|---|
| Intermediate # | Structure | IUPAC Name | Exact Mass[M + H]$^+$ |
| Intermediate 19 | 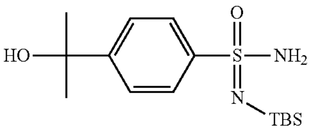 | N'-(tert-butyldimethylsilyl)-4-(2-hydroxypropan-2-yl) benzenesulfonimidamide | 329.2 |

Scheme 10

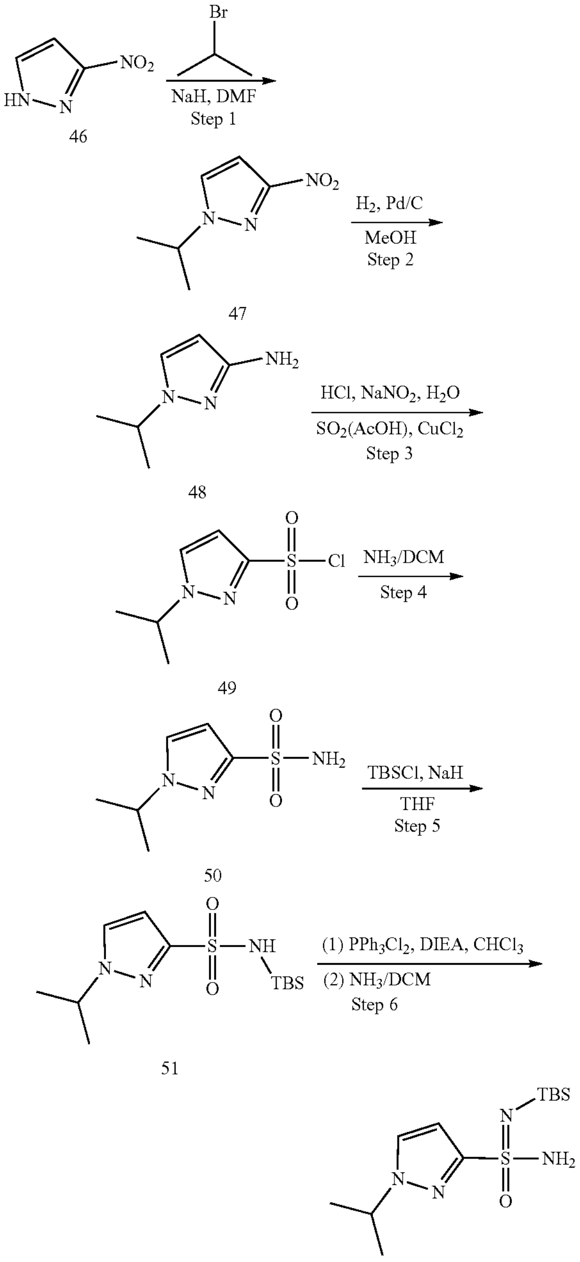

46

47

48

49

50

51

Intermediate 18

Intermediate 18

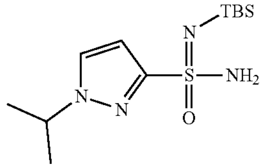

N'-(tert-butyldimethylsilyl)-1-isopropyl-1H-pyrazole-3-sulfonimidamide

Step 1: 1-Isopropyl-3-nitro-1H-pyrazole

Into a 250-mL round-bottom flask was placed a solution of 3-nitro-1H-pyrazole (10 g, 88.4 mmol) in DMF (100 mL). This was followed by the addition of NaH (60% wt., 3.9 g, 97.5 mmol) in portions at 0° C. The resulting solution was stirred for 0.5 h at 0° C. This was followed by the addition of 2-bromopropane (14.1 g, 114.6 mmol) dropwise with stirring at 0° C. in 10 min. The resulting solution was stirred for 16 h at RT and then was quenched by the addition of 100 mL of water. The resulting solution was extracted with 3×100 mL of ethyl acetate. The organic layers were combined and dried over anhydrous $Na_2SO_4$, then concentrated under vacuum. The residue was applied onto a silica gel column and eluted with a gradient of ethyl acetate/petroleum ether (1:5 to 1:3). This resulted in 11.8 g (86%) of the title compound as yellow oil. MS-ESI: 156.1 (M+1).

Step 2: 3-Amino-1-(propan-2-yl)-1H-pyrazole

Into a 250-mL round-bottom flask was placed a solution of 1-isopropyl-3-nitro-1H-pyrazole (10.8 g, 69.6 mmol) in MeOH (100 mL). Then Pd/C (10% wt., 1.5 g) was added. The flask was evacuated and flushed three times with hydrogen. The mixture was stirred for 24 h at RT under an atmosphere of hydrogen. The solids were filtered out. The resulting filtrate was concentrated under vacuum. This resulted in 7.27 g (83%) of the title compound as yellow oil. MS-ESI: 126.1 (M+1).

Steps 3-4 used similar procedures for converting compound 27 to compound 29 shown in Scheme 9 to afford compound 50 from compound 48. MS-ESI: 188.0 (M−1).

Steps 5-6 were using the similar procedures for converting compound 30 to Intermediate 11 shown in Scheme 9 to afford Intermediate 18 from compound 50. MS-ESI: 303.2 (M+1).

TABLE 6

The Intermediate in the following Table was prepared using similar procedure as shown in Scheme 10 above for converting compound 48 to Intermediate 18 starting from the appropriate materials.

| Intermediate # | Structure | IUPAC Name | Exact Mass[M + H]+ |
|---|---|---|---|
| Intermediate 21 | 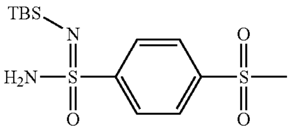 | N'-(tert-butyldimethylsilyl)-4-(methylsulfonyl) benzenesulfonimidamide | 349.1 |
| Intermediate 22 | 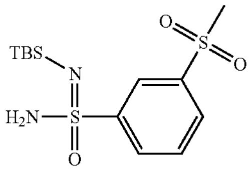 | N'-(tert-butyldimethylsilyl)-3-(methylsulfonyl) benzenesulfonimidamide | 349.1 |

Scheme 11

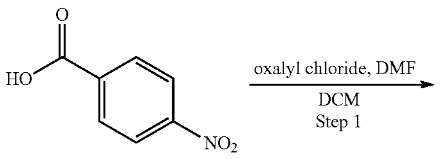

38

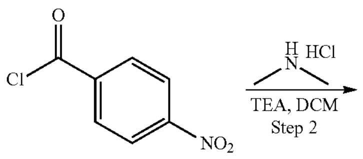

39

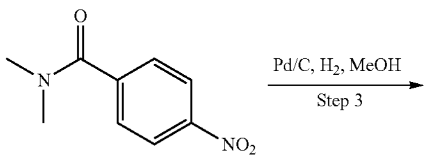

40

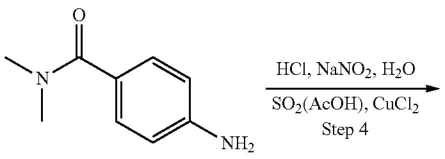

41

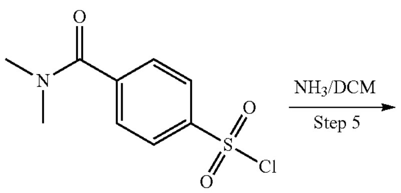

42

-continued

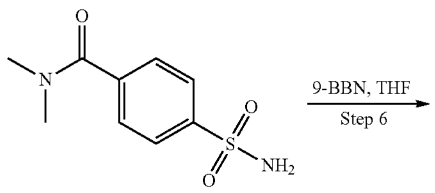

43

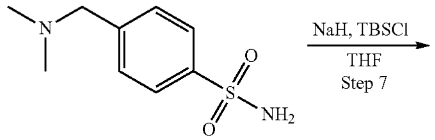

44

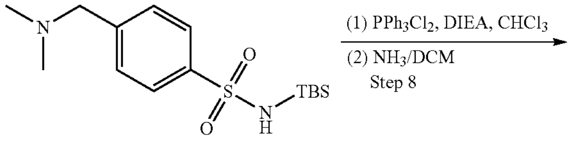

45

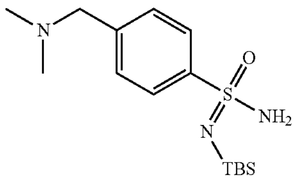

Intermediate 23

Intermediate 23

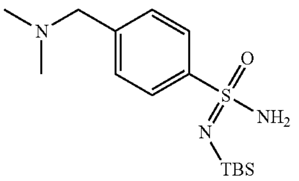

N'-(tert-butyldimethylsily) (dimethylamino)methyl)benzenesulfonimidamide

Step 1: 4-Nitrobenzoyl Chloride

Into a 500-mL round-bottom flask was placed 4-nitrobenzoic acid (20 g, 120 mmol), DCM (200 mL), and DMF (0.2 mL). This was followed by the addition of oxalyl chloride (15 mL, 177.1 mmol) dropwise with stirring at 0° C. The resulting solution was stirred for 4 h at RT and then was concentrated under vacuum. This resulted in 22 g (crude) of the title compound as yellow oil. The crude product was used in the next step.

Step 2: N,N-dimethyl-4-nitrobenzamide

Into a 500-mL round-bottom flask was placed dimethylamine hydrochloride (6.5 g, 79.7 mmol), DCM (200 mL), and TEA (50 mL). This was followed by the addition of 4-nitrobenzoyl chloride (22 g, 119 mmol) dropwise with stirring at 0° C. The resulting solution was stirred for 6 h at RT and then was concentrated under vacuum. The resulting mixture was washed with 2×50 mL of water. The solids were collected by filtration. This resulted in 16 g (69% over two steps) of the title compound as a white solid. MS-ESI. 195.1 (M+1).

Step 3: 4-Amino-N,N-dimethylbenzamide

Into a 250-mL round-bottom flask was placed N,N-dimethyl-4-nitrobenzamide (16 g, 82.4 mmol), MeOH (100 mL). Then Pd/C (10% wt., 1 g) was added. The flask was evacuated and flushed three times with hydrogen. The resulting solution was stirred for 12 h at RT under an atmosphere of hydrogen. The solids were filtered out. The resulting filtrate was concentrated under vacuum. This resulted in 13 g (96%) of the title compound as a white solid. MS-ESI: 165.1 (M+1). Steps 4-5 used similar procedures for converting compound 27 to compound 29 shown in Scheme 9 to afford compound 43 from compound 41. MS-ESI: 229.1 (M+1).

Step 6: 4-((Dimethylamino)methyl)benzenesulfonamide

Into a 100-mL round-bottom flask purged with and maintained under nitrogen was placed a solution of N,N-dimethyl-4-sulfamoylbenzamide (1.8 g, 7.9 mmol) in THF (50 mL). This was followed by the addition of 9-BBN (5.8 g) in portions at 0° C. The resulting solution was stirred for 12 h at 70° C. and then was quenched by the addition of 20 mL of water/ice. The resulting solution was extracted with 3×100 mL of ethyl acetate and the organic layers were combined. The resulting mixture was washed with 200 mL of water and then the organic layer was concentrated under vacuum. The residue was applied onto a silica gel column and eluted with a gradient of DCM/MeOH (20:1 to 15:1). This resulted in 1 g (59%) of the title compound as a white solid. MS-ESI: 215.1 (M+1).

Steps 7-8 were using the similar procedures for converting compound 30 to Intermediate 11 shown in Scheme 9 to afford Intermediate 23 from compound 44. MS-ESI: 328.2 (M+1).

Scheme 12

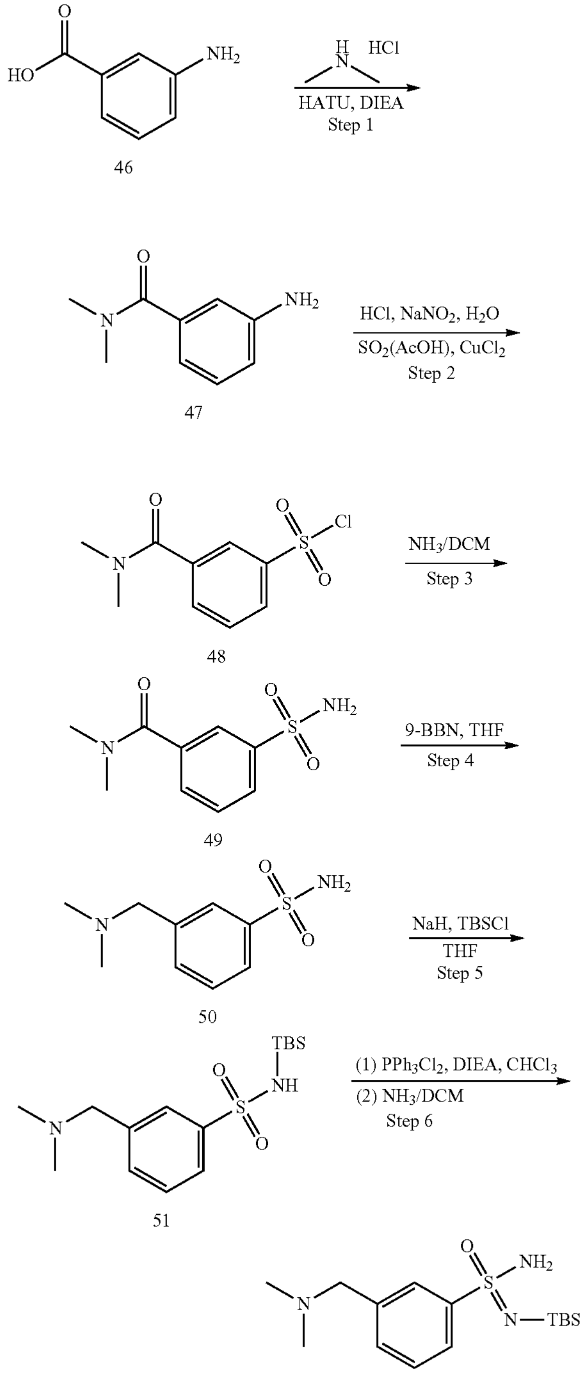

46

47

48

49

50

51

Intermediate 24

Intermediate 24

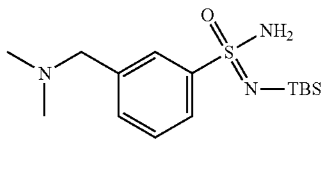

N'-(tert-butyldimethylsilyl)-3-((dimethylamino) methyl)benzenesulfonimidamide

Step 1: 3-amino-N,N-dimethylbenzamide

Into a 1000-mL round-bottom flask was placed dimethylamine as a hydrochloride salt (16.3 g, 200 mmol) in DCM (500 mL), DIEA (25.83 mg, 200 mmol). To the above was added 3-aminobenzoic acid (13.7 g, 100 mmol), HATU (57 g, 150 mmol). The resulting solution was stirred for 1 h at RT. The reaction was then quenched by the addition of 500 mL of $NH_4Cl$ (aq.). The resulting solution was extracted with 3×500 ml of ethyl acetate and the organic layers combined and dried over anhydrous sodium sulfate and concentrated. The residue was applied onto a silica gel column and eluted with a gradient of DCM/methanol (50:1 to 20:1). This resulted in 13.14 g (80%) of the title compound as a yellow solid. MS-ESI: 165.1 (M+1).

Steps 2-6 used the similar procedures for converting compound 41 to Intermediate 23 shown in Scheme 11 to afford Intermediate 24 from compound 47. MS-ESI: 328.2 (M+1).

Scheme 13

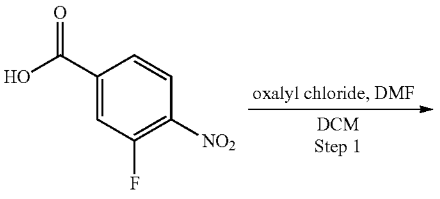

52

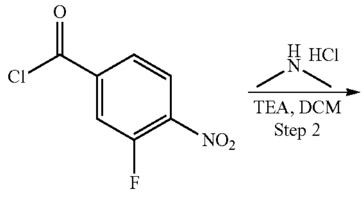

53

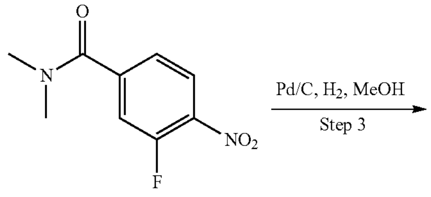

54

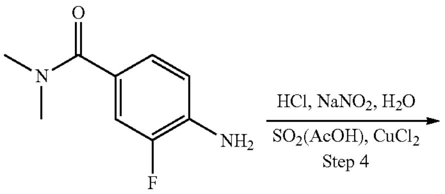

55

-continued

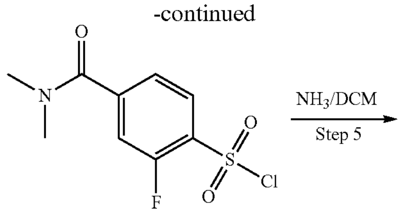

56

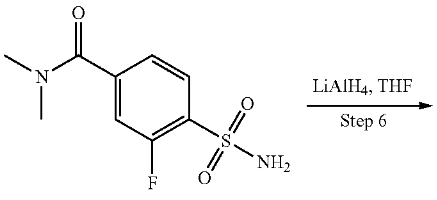

57

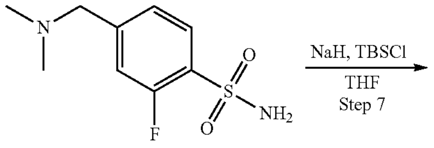

58

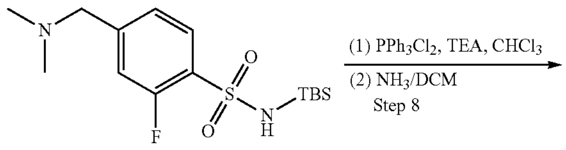

59

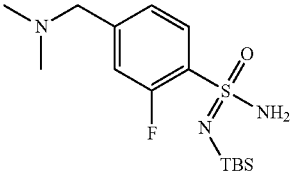

Intermediate 25

Intermediate 25

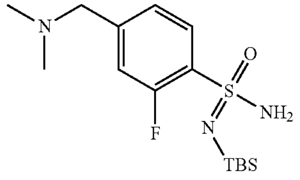

N'-(tert-butyldimethylsilyl)-4-((dimethylamino) methyl)-2-fluorobenzenesulfonimidamide Steps 1-5 used similar procedures for converting compound 38 to compound 43 shown in Scheme 11 to afford compound 57. MS-ESI: 247.0 (M+1).

Step 6: 4-((Dimethylamino)methyl)-2-fluorobenzenesulfonamide

Into a 1-L round-bottom flask was placed a solution of 3-fluoro-N,N-dimethyl-4-sulfamoylbenzamide (19.3 g, 78.4 mmol) in THF (200 mL). This was followed by the addition of $LiAlH_4$ (8.8 g, 231.9 mmol) in portions at 0° C. The resulting solution was stirred for 12 h at RT and then was quenched by the addition of 10 mL of water. The resulting mixture was concentrated under vacuum. The residue was applied onto a silica gel column and eluted with a gradient of ethyl acetate/petroleum ether (6:1 to 8:1). This resulted in 7.0 g (38%) of the title compound as a white solid. MS-ESI: 233.1 (M+1).

Steps 7-8 used similar procedures for converting compound 44 to Intermediate 23 shown in Scheme 11 to afford Intermediate 25. MS-ESI: 346.2 (M+1).

Scheme 14

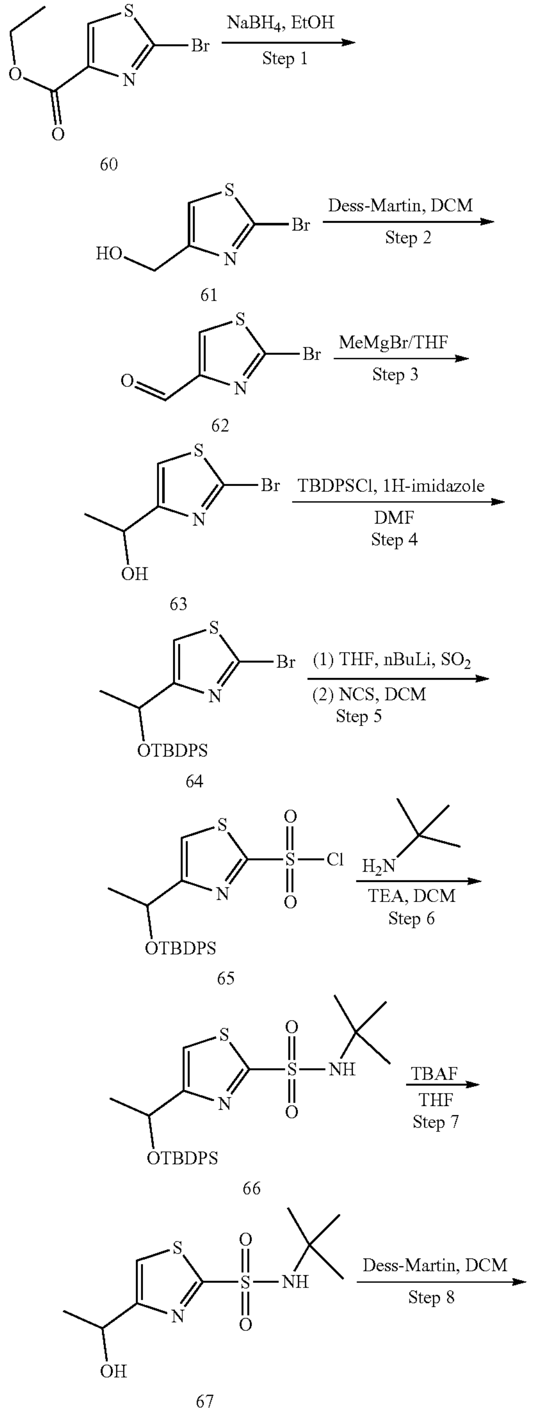

60

61

62

63

64

65

66

67

-continued

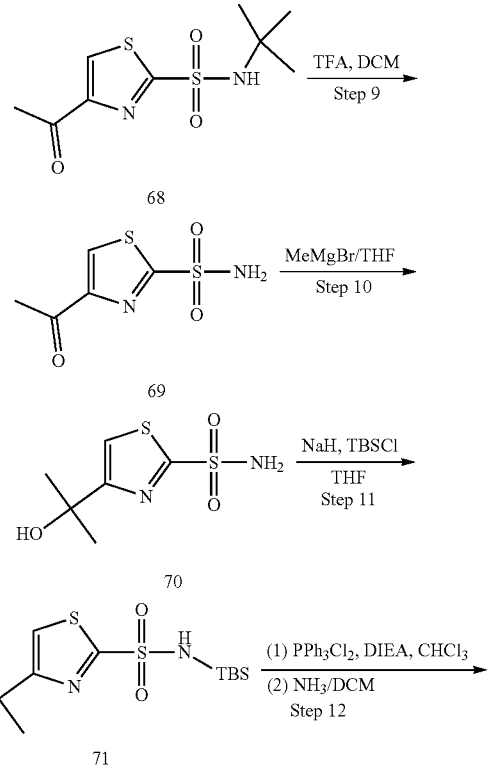

68

69

70

71

Intermediate 26

Intermediate 26

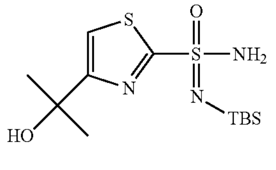

N'-(tert-butyldimethylsilyl)-4-(2-hydroxypropan-2-yl)thiazole-2-sulfonimidamide

Step 1: (2-Bromothiazol-4-yl)methanol

Into a 500-mL round-bottom flask was placed a solution of ethyl 2-bromothiazole-4-carboxylate (14 g, 59.3 mmol), EtOH (200 mL). This was followed by the addition of $NaBH_4$ (2.3 g, 60.5 mmol) in portions at 0° C. The resulting solution was stirred for 3 h at RT and then was quenched by the addition of 100 mL of water. The resulting solution was extracted with 2×200 mL of DCM. The organic layers were combined, dried over anhydrous $Na_2SO_4$ and then concentrated under vacuum. This resulted in 10.0 g (87%) of the title compound as colorless oil. MS-ESI. 195.9, 193.9 (M+1).

Step 2: 2-Bromothiazole-4-carbaldehyde

Into a 250-mL round-bottom flask was placed a solution of (2-bromothiazol-4-yl)methanol (10.0 g, 51.5 mmol) in DCM (100 mL). To the solution was added Dess-Martin reagent (24.0 g, 56.6 mmol). The resulting solution was stirred for 2 h at RT and then was concentrated under vacuum. The residue was applied onto a silica gel column and eluted with a gradient of ethyl acetate/petroleum ether (1:50 to 1:20). This resulted in 8.0 g (81%) of the title compound as yellow oil. MS-ESI: 193.9, 191.9 (M+1).

Step 3: 1-(2-Bromothiazol-4-yl)ethanol

Into a 250-mL 3-necked round-bottom flask purged with and maintained under nitrogen was placed a solution of 2-bromothiazole-4-carbaldehyde (8 g, 41.7 mmol) in THF (100 mL). This was followed by the addition of MeMgBr (3 M in THF, 15 mL) dropwise with stirring at 0° C. The resulting solution was stirred for 2 h at RT and then was quenched by the addition of 100 mL of $NH_4Cl$ (sat.). The resulting solution was extracted with 3×100 mL of DCM and the combined organic layers were concentrated under vacuum. The residue was applied onto a silica gel column and eluted with a gradient of ethyl acetate/petroleum ether (1:10 to 1:5). This resulted in 6.0 g (69%) of the title compound as brown oil. MS-ESI: 209.9, 207.9 (M+1).

Step 4: 2-Bromo-4-(1-(tert-butyldiphenylsilyloxy)ethyl)thiazole

Into a 250-mL round-bottom flask was placed a solution of 1-(2-bromothiazol-4-yl)ethanol (6.0 g, 28.8 mmol) and 1H-imidazole (4.0 g, 58.8 mmol) in DMF (50 mL). To the solution was added TBDPSCl (8.7 g, 31.6 mmol). The resulting solution was stirred for 12 h at RT and then was diluted with 100 mL of water. The resulting solution was extracted with 3×100 mL of DCM and the combined organic layers were concentrated under vacuum. The residue was applied onto a silica gel column and eluted with a gradient of ethyl acetate/petroleum ether (1:100 to 1:50). This resulted in 10.0 g (78%) of the title compound as light yellow oil. MS-ESI: 448.1, 446.1 (M+1).

Step 5: 4-(1-(Tert-butyldiphenylsilyloxy)ethyl)thiazole-2-sulfonyl Chloride

Into a 250-mL 3-necked round-bottom flask purged with and maintained under nitrogen was placed a solution of 2-bromo-4-(1-(tert-butyldiphenylsilyloxy)ethyl)thiazole (10.0 g, 22.4 mmol) in THF (100 mL). This was followed by the addition of n-BuLi (2.5 M in THF, 11 mL) dropwise with stirring at −78° C. The resulting solution was stirred for 30 min at −78° C. To the above $SO_2$ gas was introduced. The reaction was warmed to RT and stirred for 30 min and then was concentrated under vacuum. The residue was dissolved in DCM (100 mL) and then NCS (3.6 g, 26.9 mmol) was added. The resulting solution was stirred for 30 min at RT and then was concentrated under vacuum. This resulted in 8.0 g (crude, 77%) of the title compound as a white solid. The crude product was used in the next step.

Step 6: N-tert-butyl-4-(1-(tert-butyldiphenylsilyloxy)ethyl)thiazole-2-sulfonamide Into a 100-mL round-bottom flask purged with and maintained under nitrogen was placed a solution of 4-(1-(tert-butyldiphenylsilyloxy)ethyl)thiazole-2-sulfonyl chloride (8.0 g, 17.2 mmol) in DCM (50 mL). To the solution were added TEA (3.5 g, 34.6 mmol) and 2-methylpropan-2-amine (1.9 g, 26.0 mmol). The resulting solution was stirred for 2 h at RT and then was concentrated under vacuum. The residue was applied onto a silica gel column and eluted with a gradient of ethyl acetate/petroleum ether (1:15 to 1:5). This resulted in 8.0 g (71%, 2 steps) of the title compound as brown oil. MS-ESI: 503.2 (M+1).

Step 7: N-tert-butyl-4-(1-hydroxyethyl)thiazole-2-sulfonamide

Into a 250-mL round-bottom flask was placed a solution of N-tert-butyl-4-(1-(tert-butyldiphenylsilyloxy)ethyl)thiazole-2-sulfonamide (8.0 g, 15.9 mmol) in THF (100 mL). To the solution was added TBAF (9.6 g, 292.5 mmol). The resulting solution was stirred for 2 h at RT and then was diluted with 100 mL of water. The resulting solution was extracted with 3×100 mL of DCM and the combined organic layers were concentrated under vacuum. The residue was applied onto a silica gel column and eluted with a gradient of ethyl acetate/petroleum ether (1:10 to 1:3). This resulted in 4.0 g (95%) of the title compound as light yellow oil. MS-ESI: 265.1 (M+1).

Step 8: 4-Acetyl-N-tert-butylthiazole-2-sulfonamide

Into a 100-mL round-bottom flask was placed a solution of N-tert-butyl-4-(1-hydroxyethyl)thiazole-2-sulfonamide (4.0 g, 15.1 mmol) in DCM (50 mL). To the solution was added Dess-Martin reagent (7.1 g, 16.6 mmol). The resulting solution was stirred for 2 h at RT and then was concentrated under vacuum. The residue was applied onto a silica gel column and eluted with a gradient of ethyl acetate/petroleum ether (1:10 to 1:3). This resulted in 3.5 g (88%) of the title compound as light yellow oil. MS-ESI: 363.0 (M+1).

Step 9: 4-Acetylthiazole-2-sulfonamide

Into a 100-mL round-bottom flask was placed a solution of 4-acetyl-N-tert-butylthiazole-2-sulfonamide (3.5 g, 13.3 mmol) in DCM (5 mL). To the solution was added TFA (20 mL). The resulting solution was stirred for 14 h at 40° C. and then was concentrated under vacuum. The residue was applied onto a silica gel column and eluted with a gradient of ethyl acetate/petroleum ether (1:10 to 1:3). This resulted in 2.5 g (91%) of the title compound as a gray solid. MS-ESI: 207.0 (M+1).

Steps 10-12 used similar procedures for converting compound 29 to Intermediate 11 shown in Scheme 9 to afford Intermediate 26 from compound 69. MS-ESI: 336.1 (M+1).

Scheme 15A

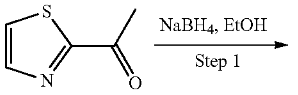

72

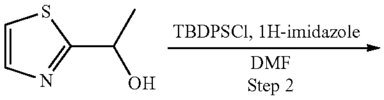

73

-continued

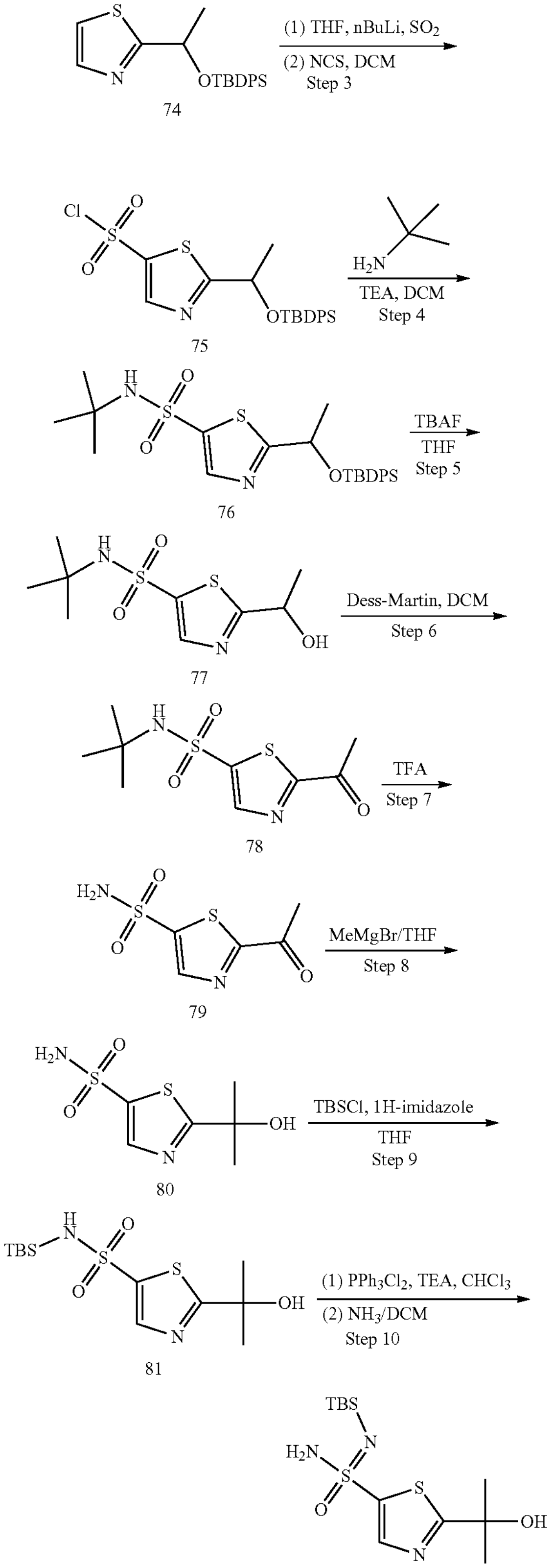

74, 75, 76, 77, 78, 79, 80, 81

Intermediate 27

Intermediate 27

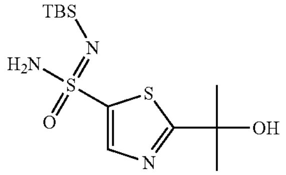

N'-(tert-butyldimethylsilyl)-2-(2-hydroxypropan-2-yl)thiazole-5-sulfonimidamide

Step 1: 1-(Thiazol-2-yl)ethanol

Into a 500-mL round-bottom flask was placed 1-(thiazol-2-yl)ethanone (20 g, 157 mmol), EtOH (200 mL). This was followed by the addition of $NaBH_4$ (3 g, 81.3 mmol) in portions at 0° C. The resulting solution was stirred for 2 h at RT and then was quenched by the addition of 10 mL of $NH_4Cl$ (sat.). The resulting solution was diluted with 200 mL of water and extracted with 2×200 mL of DCM. The organic layers were combined and dried over anhydrous $Na_2SO_4$, then concentrated under vacuum. This resulted in 20 g (98%) of the title compound as light yellow oil. MS-ESI. 130.0 (M+1).

Step 2: 2-(1-(Tert-butyldiphenylsilyloxy)ethyl)thiazole

Into a 500-mL round-bottom flask was placed 1-(thiazol-2-yl)ethanol (20 g, 154.8 mmol), DMF (150 mL), 1H-imidazole (20.5 g, 301 mmol). This was followed by the addition of TBDPSCl (46 g, 167 mmol) dropwise with stirring at 0° C. The resulting solution was stirred for 2 h at RT and then was diluted with 300 mL of water. The resulting solution was extracted with 3×200 mL of DCM. The organic layers were combined and concentrated under vacuum. The residue was applied onto a silica gel column and eluted with a gradient of ethyl acetate/petroleum ether (1:100 to 1:80). This resulted in 55 g (97%) of the title compound as colorless oil. MS-ESI: 368.1 (M+1).

Step 3: 2-(1-(Tert-butyldiphenylsilyloxy)ethyl)thiazole-5-sulfonyl Chloride

Into a 500-mL 3-necked round-bottom flask purged with and maintained under nitrogen was placed a solution of 2-(1-(tert-butyldiphenylsilyloxy)ethyl)thiazole (30 g, 81.6 mmol) in THF (200 mL). This was followed by the addition of n-BuLi (2.5 M in THF, 35.2 mL) dropwise with stirring at −78° C. The resulting solution was stirred for 0.5 h at −78° C. and then $SO_2$ was introduced into the above reaction mixture. The reaction was slowly warmed to RT and then NCS (12.8 g, 95.86 mmol) was added. The resulting solution was stirred for 1 h at RT. The solids were filtered out. The resulting filtrate was concentrated under vacuum. This resulted in 30 g (crude, 79%) of the title compound as brown oil. The crude product was used in the next step.

Step 4: N-tert-butyl-2-(1-(tert-butyldiphenylsilyloxy)ethyl)thiazole-5-sulfonamide Into a 500-mL round-bottom flask was placed 2-(1-(tert-butyldiphenylsilyloxy)ethyl)thiazole-5-sulfonyl chloride (crude, 30 g, 64.37 mmol), DCM (200 mL), TEA (13 g, 128.47 mmol). This was followed by the addition of 2-methylpropan-2-amine (5.6 g, 76.6 mmol) dropwise with stirring at 0° C. The resulting solution was stirred for 2 h at RT and then was concentrated under vacuum. The residue was applied onto a silica gel column and eluted with a gradient of ethyl acetate/petroleum ether (1:30 to 1:20). This resulted in 25 g (61% over two steps) of the title compound as brown oil. MS-ESI: 503.2 (M+1).

Step 5: N-tert-butyl-2-(1-hydroxyethyl)thiazole-5-sulfonamide

Into a 500-mL round-bottom flask was placed N-tert-butyl-2-(1-(tert-butyldiphenylsilyloxy)ethyl)thiazole-5-sulfonamide (25 g, 49.7 mmol), THF (200 mL), TBAF (30 g, 99.67 mmol). The resulting solution was stirred for 2 h at RT and then was diluted with 200 mL of water. The resulting solution was extracted with 3×200 mL of DCM. The organic layers were combined and concentrated under vacuum. The residue was applied onto a silica gel column and eluted with a gradient of ethyl acetate/petroleum ether (1:20 to 1:10). This resulted in 12 g (91%) of the title compound as light yellow oil. MS-ESI: 265.1 (M+1).

Step 6: 2-Acetyl-N-tert-butylthiazole-5-sulfonamide

Into a 500-mL round-bottom flask was placed N-tert-butyl-2-(1-hydroxyethyl)thiazole-5-sulfonamide (12 g, 45.4 mmol), DCM (200 mL). To this solution was added Dess-Martin reagent (20 g, 47.2 mmol) in portions at RT. The resulting solution was stirred for 2 h at RT and then was concentrated under vacuum. The residue was applied onto a silica gel column and eluted with a gradient of ethyl acetate/petroleum ether (1:20 to 1:10). This resulted in 9 g (76%) of the title compound as a light yellow solid. MS-ESI: 263.0 (M+1).

Step 7: 2-Acetylthiazole-5-sulfonamide

Into a 100-mL round-bottom flask was placed 2-acetyl-N-tert-butylthiazole-5-sulfonamide (7 g, 26.7 mmol), TFA (20 mL). The resulting solution was stirred for 14 h at 70° C. and then was concentrated under vacuum. The residue was applied onto a silica gel column and eluted with a gradient of ethyl acetate/petroleum ether (1:5 to 1:3). This resulted in 5 g (91%) of the title compound as a yellow solid. MS-ESI: 207.0 (M+1).

Step 8: 2-(2-Hydroxypropan-2-yl)thiazole-5-sulfonamide

Into a 500-mL 3-necked round-bottom flask purged with and maintained under nitrogen was placed 2-acetylthiazole-5-sulfonamide (5 g, 24.3 mmol), THF (100 mL). This was followed by the addition of MeMgBr (3 M in THF, 8.1 mL, 24.3 mmol) dropwise with stirring at 0° C. The resulting solution was stirred for 14 h at RT and then was quenched by the addition of 100 mL of $NH_4Cl$ (sat.). The resulting solution was extracted with 2×150 mL of DCM. The organic layers were combined and concentrated under vacuum. The residue was applied onto a silica gel column and eluted with a gradient of ethyl acetate/petroleum ether (1:5 to 1:3). This resulted in 2.9 g (54%) of the title compound as a light yellow solid. MS-ESI: 223.0 (M+1).

Steps 9-10 used similar procedures for converting compound 14 to Intermediate 1 shown in Scheme 6 to afford Intermediate 27 from compound 80. MS-ESI: 336.1 (M+1).

Scheme 15B

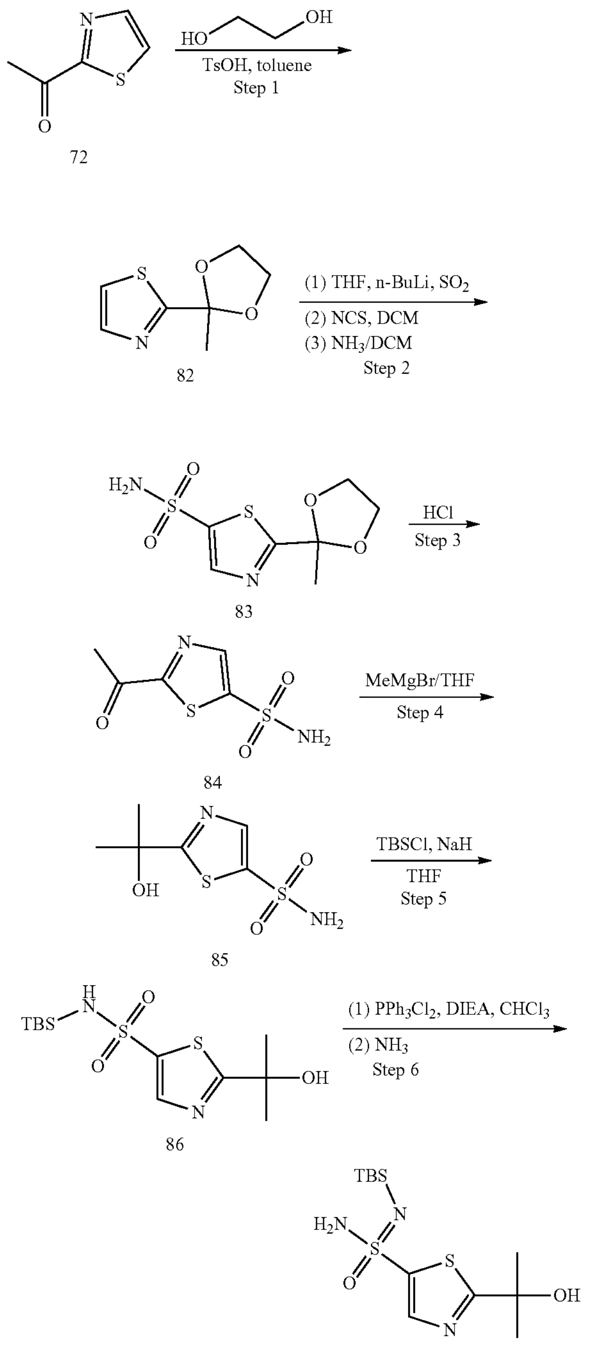

Intermediate 27

Intermediate 27

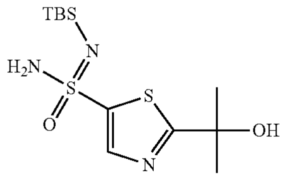

N'-(tert-butyldimethylsilyl)-2-(2-hydroxypropan-2-yl)thiazole-5-sulfonimidamide

Step 1: 2-(2-Methyl-1,3-dioxolan-2-yl)thiazole

Into a 500-mL round-bottom flask was placed a solution of 1-(thiazol-2-yl)ethanone (20 g, 157.0 mmol) in toluene (300 mL) and ethane-1,2-diol (19.5 g, 314 mmol). To the solution was added TsOH (2.7 g, 15.7 mmol). The resulting solution was refluxed overnight and water was separated from the solution during the reflux. The resulting solution was diluted with 200 mL of water and extracted with 2×100 mL of ethyl acetate. The organic layers were combined, dried over anhydrous $Na_2SO_4$, and then concentrated under vacuum. This resulted in 26.6 g (99%) of the title compound as light yellow oil. MS-ESI: 172.0 (M+1).

Step 2: 2-(2-Methyl-1,3-dioxolan-2-yl)thiazole-5-sulfonamide

Into a 500-mL 3-necked round-bottom flask purged with and maintained under nitrogen was placed a solution of 2-(2-methyl-1,3-dioxolan-2-yl)thiazole (14 g, 81.6 mmol) in THF (200 mL). This was followed by the addition of n-BuLi (2.5 M in THF, 35.2 mL, 88.0 mmol) dropwise with stirring at −78° C. The resulting solution was stirred for 0.5 h at −78° C. and then $SO_2$ was introduced into the above reaction mixture. The reaction was slowly warmed to RT and then NCS (12.8 g, 95.86 mmol) was added. The resulting solution was stirred for 1 h at RT. The solids were filtered out. The resulting filtrate was concentrated under vacuum and then was diluted in DCM (160 mL). To the above was added a saturated solution of ammonia in DCM (300 mL). The resulting solution was stirred for 3 h at RT and then was concentrated under vacuum. The residue was applied onto a silica gel column and eluted with a gradient of ethyl acetate/petroleum ether (1:20 to 1:5). This resulted in 12.5 g (61%) of the title compound as a yellow solid. MS-ESI: 251.0 (M+1).

Step 3: 2-Acetylthiazole-5-sulfonamide

Into a 250-mL round-bottom flask was placed a solution of 2-(2-methyl-1,3-dioxolan-2-yl)thiazole-5-sulfonamide (12.5 g, 50.0 mmol) in THF (125 mL). To the above was added aq. HCl (4 N, 50.0 mL). The resulting solution was stirred for 6 h at 70° C. The resulting solution was diluted with 100 mL of water and extracted with 2×200 mL of ethyl acetate. The organic layers were combined, dried over anhydrous $Na_2SO_4$, then concentrated under vacuum. The residue was applied onto a silica gel column and eluted with a gradient of ethyl acetate/petroleum ether (1:2 to 1:1). This resulted in 9.3 g (90%) of the title compound as a yellow solid. MS-ESI: 207.0 (M+1). Steps 4-6 used the same procedures for converting compound 19 to Intermediate 2 shown in Scheme 7B to afford Intermediate 27 from compound 84. MS-ESI: 336.1 (M+1).

Scheme 16

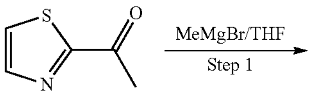

72

-continued

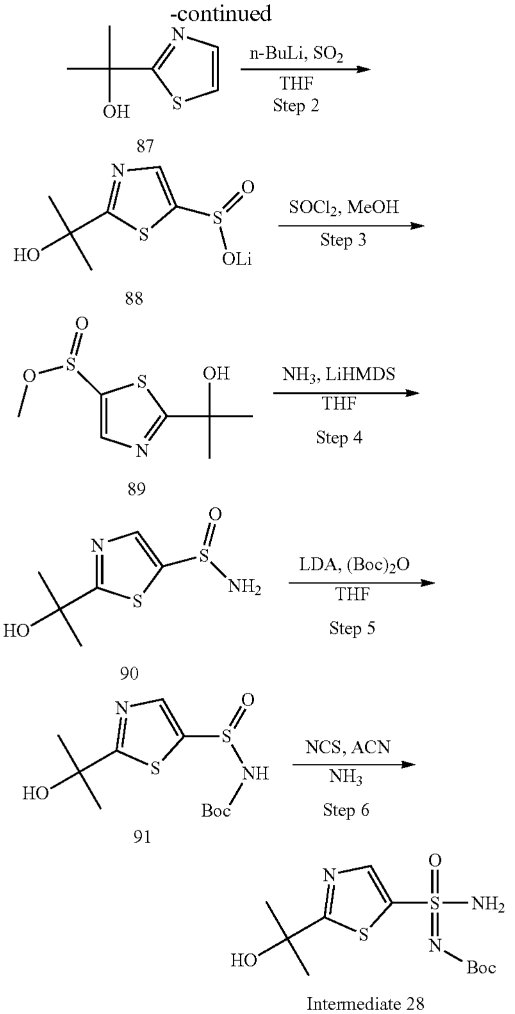

87, 88, 89, 90, 91, Intermediate 28

Intermediate 28

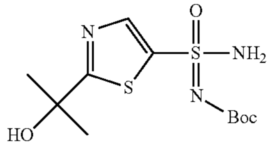

N'-(tert-butoxycarbonyl)-2-(2-hydroxypropan-2-yl)thiazole-5-sulfonimidamide

Step 1: 2-(Thiazol-2-yl)propan-2-ol

Into a 10-L 4-necked round-bottom flask purged with and maintained under nitrogen was placed a solution of 1-(thiazol-2-yl)ethanone (200 g, 1.6 mol) in THF (4 L). This was followed by the addition of MeMgBr (3 M in THF, 942 mL) dropwise with stirring at 0° C. The mixture was stirred at 0° C. for 2 h. After warmed the mixture to RT, the solution was stirred for an additional 16 h. Then the reaction was quenched by the addition of 3 L of $NH_4Cl$ (sat.). The resulting solution was extracted with 3×1 L of ethyl acetate. The organic layers were combined, dried over anhydrous $Na_2SO_4$, then concentrated under vacuum. The residue was applied onto a silica gel column and eluted with a gradient of ethyl acetate/petroleum ether (1:3 to 1:1). This resulted in 210 g (93%) of the title compound as a brown oil. MS-ESI: 144.0 (M+1).

Step 2: Lithium 2-(2-hydroxypropan-2-yl)thiazole-5-sulfinate

Into a 10-L 4-necked round-bottom flask purged with and maintained under nitrogen was placed a solution of 2-(thiazol-2-yl)propan-2-ol (50 g, 349.0 mmol) in THF (1.5 L). This was followed by the addition of n-BuLi (2.5 M in hexane, 350 mL) dropwise with stirring at −78° C. The mixture was stirred at −78° C. for 1 h. Then $SO_2$ was bubbled into the mixture for 15 min below −30° C. The mixture was stirred for an additional 1 h at RT and then was concentrated under vacuum. This resulted in 87 g (crude) of the title compound as a light yellow solid. The crude product was used directly in the next step.

Step 3: Methyl 2-(2-hydroxypropan-2-yl)thiazole-5-sulfinate

Into a 2-L 3-necked round-bottom flask, lithium 2-(2-hydroxypropan-2-yl)thiazole-5-sulfinate (87 g, crude) was dissolved in anhydrous MeOH (500 mL). Then $SOCl_2$ (43 g, 360 mmol) was added to the mixture dropwise with stirring at 0° C. The mixture was stirred overnight at RT and then was concentrated under vacuum. The residue was diluted with 500 mL of ethyl acetate. The resulting solution was washed with 2×200 mL of water and 2×200 mL of brine. The solution was dried over anhydrous $Na_2SO_4$, then concentrated under vacuum. This resulted in 72 g (crude) of the title compound as light yellow oil. The crude product was used directly in the next step.

Step 4: 2-(2-Hydroxypropan-2-yl)thiazole-5-sulfinamide

Into a 10-L 4-necked round-bottom flask purged with and maintained under nitrogen was placed a solution of methyl 2-(2-hydroxypropan-2-yl)thiazole-5-sulfinate (72 g, 326 mmol) in THF (500 mL). Then to the above $NH_3$ (0.5 M in THF, 2.0 L) was added. After cooling to −78° C., LiHMDS (1 M in THF, 2.0 L) was added to the mixture dropwise with stirring. Then the mixture was stirred at −78° C. for 2 h. The reaction was quenched by the addition of 500 mL of $NH_4Cl$ (sat.). The resulting solution was extracted with 3×300 mL of ethyl acetate. The organic layers were combined, dried over anhydrous $Na_2SO_4$, then concentrated under vacuum. This resulted in 32 g (crude) of the title compound as brown oil. The crude product was used directly in the next step.

Step 5: Tert-butyl 2-(2-hydroxypropan-2-yl)thiazol-5-ylsulfinylcarbamate

Into a 1-L 3-necked round-bottom flask purged with and maintained under nitrogen was placed a solution of 2-(2-hydroxypropan-2-yl)thiazole-5-sulfinamide (32 g, crude) in THF (300 mL). This was followed by the addition of LDA (2 M in THF, 116 mL) dropwise with string at 0° C. The mixture was stirred at 0° C. for 1 h, then $(Boc)_2O$ (33.8 g, 155 mmol) was added in portions at 0° C. The mixture was warmed to RT and stirred for an additional 2 h. The reaction was quenched with 200 mL of ice-water (200 mL), and the pH value of the solution was adjusted to 6 with HCOOH. The resulting solution was extracted with 3×200 mL of ethyl acetate. The organic layers were combined, dried over anhydrous $Na_2SO_4$, then concentrated under vacuum. The residue was applied onto a silica gel column and eluted with a gradient of ethyl acetate/petroleum ether (1:2 to 1:1). This resulted in 19 g (18%, 4 steps) of the title compound as a white solid.

Step 6: N-(tert-butyldimethylsilyl)-2-(2-hydroxypropan-2-yl)thiazole-5-sulfonimidamide Into a 1-L 3-necked round-bottom flask purged with and maintained under nitrogen, tert-butyl 2-(2-hydroxypropan-2-yl)thiazol-5-ylsulfinylcarbamate (19 g, 62 mmol) was dissolved in fresh distilled ACN (200 mL). Then to the above solution was added NCS (9.8 g, 74 mmol) in portions. The mixture was stirred for 1 h at RT and then $NH_3$ was bubbled in the mixture for 15 min. The mixture was stirred at RT for 2 h and then was concentrated under vacuum. The residue was applied onto a silica gel column and eluted with a gradient of ethyl acetate/petroleum ether (1:2 to 1:1). This resulted in 13 g (65%) of the title compound as a white solid.

Scheme 17

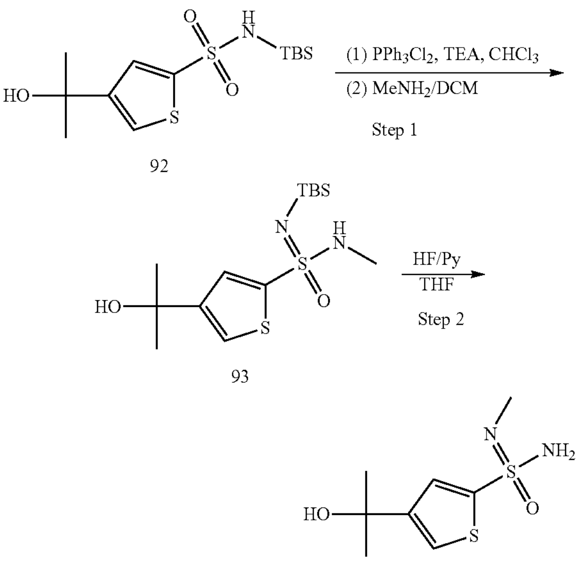

92

93

Intermediate 29

Intermediate 29

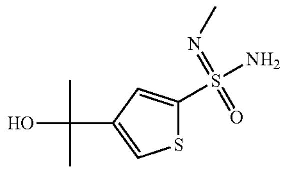

4-(2-Hydroxypropan-2-yl)-N'-methylthiophene-2-sulfonimidamide

Step 1 used the procedures for converting compound 15 to Intermediate 1 shown in Scheme 6 to 10 afford compound 93 by substituting ammonia with methylamine. MS-ESI: 349.1 (M+1).

Step 2: 4-(2-Hydroxypropan-2-yl)-N'-methylthiophene-2-sulfonimidamide Into a 25-mL round-bottom flask purged with under nitrogen was placed a solution of N'-(tert-butyldimethylsilyl)-4-(2-hydroxypropan-2-yl)-N-methylthiophene-2-sulfonimidamide (500 mg, 1.43 mmol) in DCM (10 mL). To the solution was added HF/Py (70% wt., 200 mg). The resulting solution was stirred for 2 h at RT. The pH value of the solution was adjusted to 8 with aq. $Na_2CO_3$ (5% wt.). The resulting solution was extracted with 3×10 mL of ethyl acetate. The organic layers were combined, dried over anhydrous $Na_2SO_4$, then concentrated under vacuum. This resulted in 300 mg (89%) of the title compound as brown oil. MS-ESI: 235.0 (M+1).

Schemes for the Preparation of Isocyanate Intermediates 30-58:

Schemes below illustrate the synthesis of isocyanates.

Scheme 18

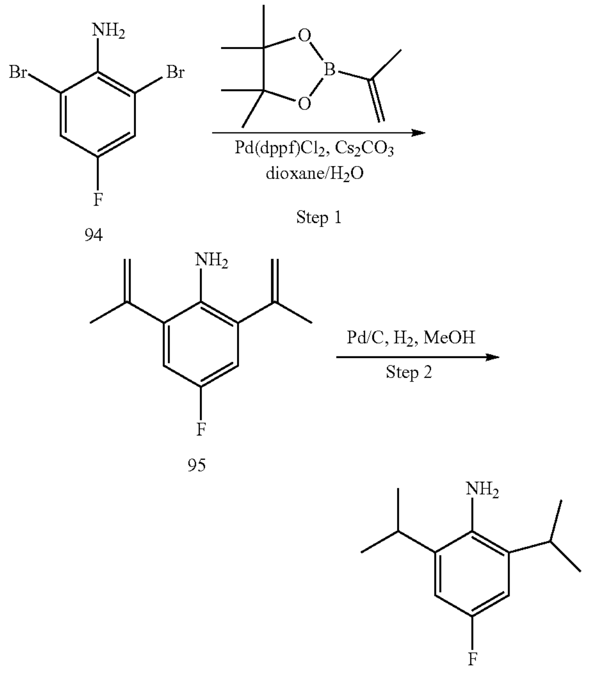

94

95

Intermediate 30

Intermediate 30

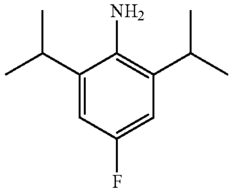

4-Fluoro-2,6-diisopropylbenzenamine

Step 1: 4-Fluoro-2,6-bis(prop-1-en-2-yl)aniline

Into a 500-mL round-bottom flask purged with and maintained under nitrogen was placed 2,6-dibromo-4-fluoroaniline (15 g, 55.8 mmol), dioxane (150 mL), water (15 mL), $Cs_2CO_3$ (55 g, 169 mmol), 4,4,5,5-tetramethyl-2-(prop-1-en-2-yl)-1,3,2-dioxaborolane (25 g, 149 mmol), and $Pd(dppf)Cl_2$ (4 g, 5.47 mmol). The resulting solution was stirred for 15 h at 100° C. and then was concentrated under vacuum. The residue was applied onto a silica gel column and eluted with a gradient of ethyl acetate/petroleum ether (1:10 to 1:8). This resulted in 9.2 g (86%) of the title compound as brown oil. MS-ESI: 192.1 (M+1).

Step 2: 4-Fluoro-2,6-bis(propan-2-yl)aniline

Into a 500-mL round-bottom flask was placed 4-fluoro-2,6-bis(prop-1-en-2-yl)aniline (9.2 g, 48.1 mmol), and MeOH (200 mL). Then Pd/C (10% wt., 900 mg) was added. The flask was evacuated and flushed three times with hydrogen. The resulting solution was stirred for 12 h at RT under an atmosphere of hydrogen. The solids were filtered out. The resulting filtrate was concentrated under vacuum. The residue was applied onto a silica gel column and eluted with a gradient of ethyl acetate/petroleum ether (1:10 to 1:8). This resulted in 7.2 g (77%) of the title compound as brown oil. MS-ESI: 196.1 (M+1).

Scheme 19

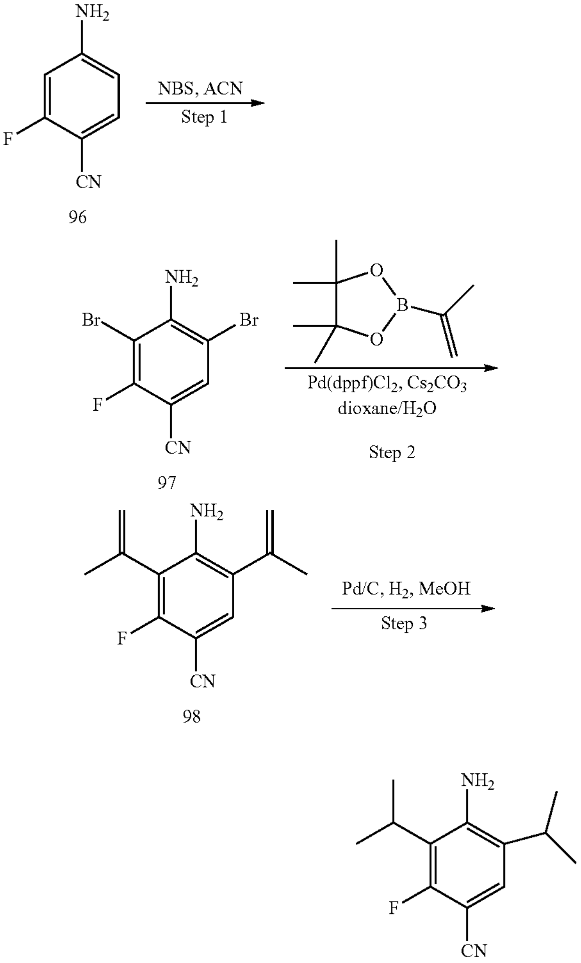

96

97

98

Intermediate 31

Intermediate 31

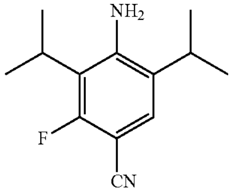

4-Amino-2-fluoro-3,5-diisopropylbenzonitrile

Step 1: 4-Amino-3,5-dibromo-2-fluorobenzonitrile

Into a 1-L round-bottom flask was placed 4-amino-2-fluorobenzonitrile (25 g, 184 mmol), ACN (500 mL), and NBS (81.7 g, 459 mmol). The resulting solution was stirred overnight at 75° C. and then was concentrated under vacuum. The residue was applied onto a silica gel column and eluted with a gradient of ethyl acetate/petroleum ether (1:100 to 1:98). This resulted in 50 g (93%) of the title compound as brown oil. MS-ESI: 294.9/292.9/296.9 (M+1).

Steps 2-3 used similar procedures for converting compound 94 to Intermediate 30 shown in Scheme 18 to afford Intermediate 31 from compound 97. MS-ESI: 221.1 (M+1).

Scheme 20

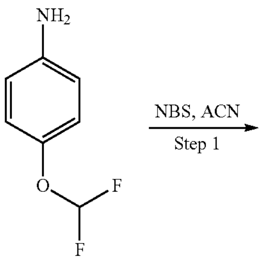

99

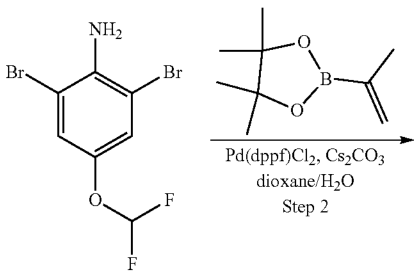

100″

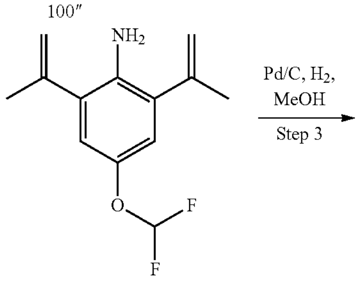

101″

-continued

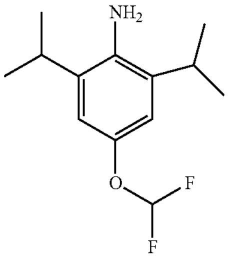

Intermediate 32

Intermediate 32

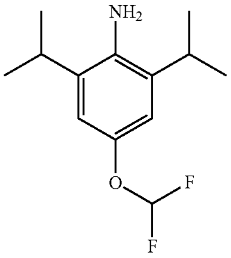

4-(Difluoromethoxy)-2,6-diisopropylbenzenamine

Step 1: 2,6-Dibromo-4-(difluoromethoxy)benzenamine

Into a 100-mL round-bottom flask was placed 4-(difluoromethoxy)benzenamine (3 g, 18.9 mmol), ACN (30 mL), and NBS (7.7 g, 43.3 mmol). The resulting solution was stirred overnight at RT and then was concentrated under vacuum. The residue was applied onto a silica gel column and eluted with a gradient of ethyl acetate/petroleum ether (1:30 to 1:20). This resulted in 2.9 g (48%) of the title compound as brown oil. MS-ESI: 317.9/315.9/319.9 (M+1).

Steps 2-3 used similar procedures for converting compound 94 to Intermediate 30 shown in Scheme 18 to afford Intermediate 32 from compound 100". MS-ESI: 244.1 (M+1).

Scheme 21

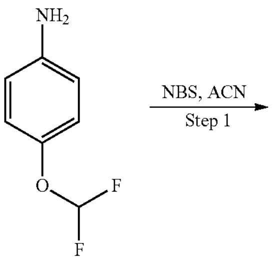

99

-continued

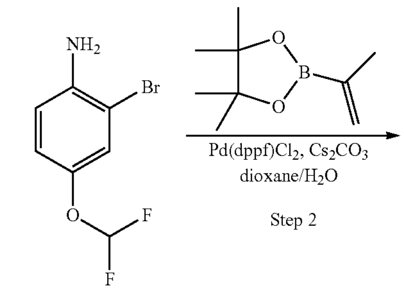

102″

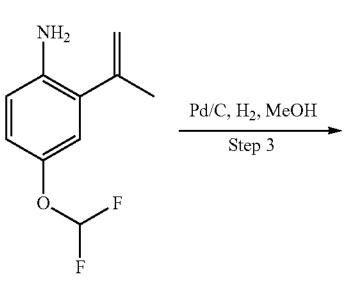

103″

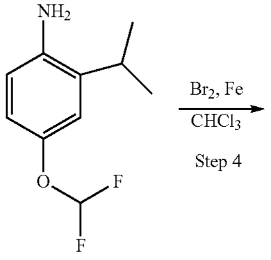

104″

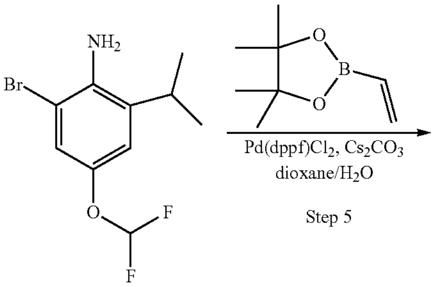

105″

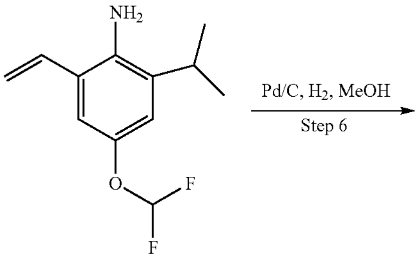

106″

-continued

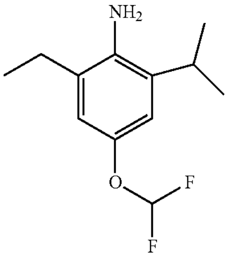

Intermediate 33

Intermediate 33

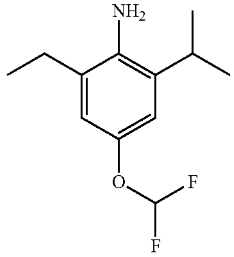

4-(Difluoromethoxy)-2-ethyl-6-isopropylbenzenamine

Step 1: 2-Bromo-4-(difluoromethoxy)benzenamine

Into a 250-mL round-bottom flask purged with and maintained under nitrogen was placed 4-(difluoromethoxy)benzenamine (10 g, 62.8 mmol), ACN (100 mL), and NBS (5.59 g, 31.4 mmol). The resulting solution was stirred for 1 h RT and then was concentrated under vacuum. The residue was applied onto a silica gel column and eluted with a gradient of ethyl acetate/petroleum ether (1:20 to 1:10). This resulted in 7.9 g (53%) of the title compound as red oil. MS-ESI: 238.0/240.0 (M+1).

Step 2: 4-(Difluoromethoxy)-2-(prop-1-en-2-yl) benzenamine

Into a 250-mL round-bottom flask purged with and maintained under nitrogen was placed 2-bromo-4-(difluoromethoxy)benzenamine (7.9 g, 33.2 mmol), dioxane (100 mL), water (10 mL), $Cs_2CO_3$ (32.46 g, 99.63 mmol), 4,4,5,5-tetramethyl-2-(prop-1-en-2-yl)-1,3,2-dioxaborolane (8.36 g, 49.8 mmol), and Pd(dppf)$Cl_2$ (1.21 g, 1.65 mmol). The resulting solution was stirred overnight at 90° C. The solids were filtered out. The filtrate was concentrated under vacuum. The residue was applied onto a silica gel column and eluted with a gradient of ethyl acetate/petroleum ether (1:30 to 1:20). This resulted in 5.3 g (80%) of the title compound as a yellow solid. MS-ESI: 200.1 (M+1).

Step 3: 4-(Difluoromethoxy)-2-isopropylbenzenamine

Into a 250-mL round-bottom flask was placed 4-(difluoromethoxy)-2-(prop-1-en-2-yl)benzenamine (5.3 g, 26.6 mmol) in MeOH (100 mL). Then Pd/C (10% wt., 500 mg) was added. The flask was evacuated and filled three times with hydrogen. The resulting solution was stirred for 3 h at RT under hydrogen. The solids were filtered out. The resulting filtrate was concentrated under vacuum. This resulted in 5.15 g (96%) of the title compound as red oil. MS-ESI: 202.1 (M+1).

Step 4: 2-Bromo-4-(difluoromethoxy)-6-isopropylbenzenamine

Into a 500-mL round-bottom flask was placed 4-(difluoromethoxy)-2-isopropylbenzenamine (5.15 g, 25.6 mmol), $CHCl_3$ (200 mL), Fe turnings (500 mg), and $Br_2$ (4.45 g, 27.9 mmol). The resulting mixture was stirred overnight at 70° C. and then was quenched by the addition of 200 mL of water. The resulting solution was extracted with 3×100 mL of DCM and the organic layers combined and concentrated under vacuum. The residue was applied onto a silica gel column and eluted with a gradient of ethyl acetate/petroleum ether (1:30 to 1:20). This resulted in 6.98 g (97%) of the title compound as dark red oil. MS-ESI: 280.0/282.0 (M+1).

Step 5: 4-(Difluoromethoxy)-2-isopropyl-6-vinylbenzenamine

Into a 250-mL round-bottom flask purged with and maintained under nitrogen was placed 2-bromo-4-(difluoromethoxy)-6-isopropylbenzenamine (3 g, 10.7 mmol), dioxane (100 mL), water (10 mL), $Cs_2CO_3$ (10.47 g, 32.13 mmol), 4,4,5,5-tetramethyl-2-vinyl-1,3,2-dioxaborolane (2.47 g, 16.0 mmol), and $Pd(dppf)Cl_2$ (784 mg, 1.07 mmol). The resulting solution was stirred overnight at 90° C. and then was concentrated under vacuum. The residue was applied onto a silica gel column and eluted with a gradient of ethyl acetate/petroleum ether (1:30 to 1:20). This resulted in 2.3 g (94%) of the title compound as dark green oil. MS-ESI: 228.1 (M+1).

Step 6: 4-(Difluoromethoxy)-2-ethyl-6-isopropylbenzenamine

Into a 250-mL round-bottom flask was placed 4-(difluoromethoxy)-2-isopropyl-6-vinylbenzenamine (2.3 g, 10.1 mmol), MeOH (100 mL). Then Pd/C (10% wt., 200 mg) was added. The flask was evacuated and filled three times with hydrogen. The resulting solution was stirred overnight at RT under hydrogen. The solids were filtered out. The filtrate was concentrated under vacuum. This resulted in 2.2 g (95%) of the title compound as red oil. MS-ESI: 230.1 (M+1).

Scheme 22

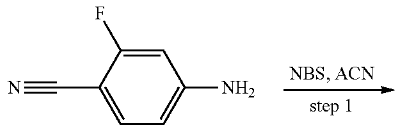

96

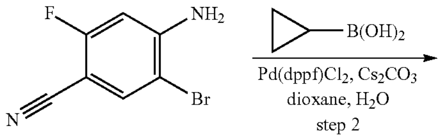

107″

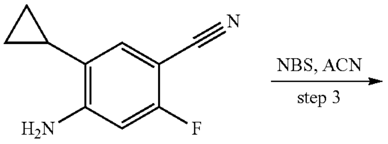

108″

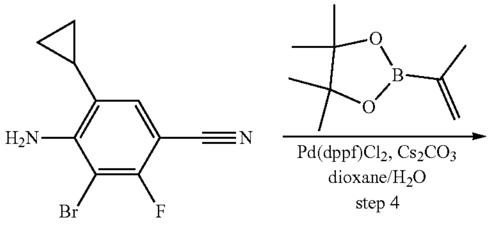

109″

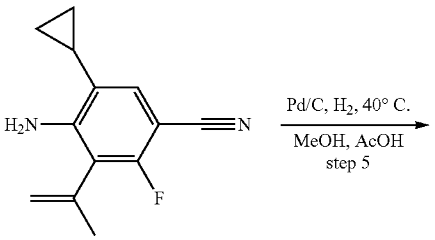

110″

TABLE 7

The Intermediate 34 in the following Table was prepared from compound 105" using similar procedure as shown in Scheme 21 above for converting compound 105" to 106".

| Intermediate # | Structure | IUPAC Name | Exact Mass$[M + H]^+$ |
|---|---|---|---|
| Intermediate 34 | 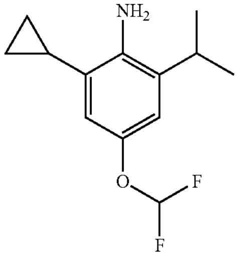 [SMILES: CC(C)c1cc(OC(F)F)cc(C2CC2)c1N] | 2-Cyclopropyl-4-(difluoromethoxy)-6-isopropylbenzenamine | 242.1 |

-continued

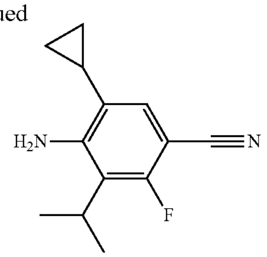

Intermediate 35

Intermediate 35

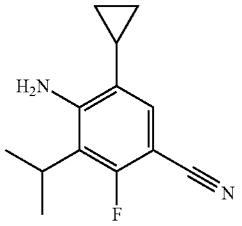

4-Amino-5-cyclopropyl-2-fluoro-3-isopropylbenzonitrile

Step 1: 4-Amino-5-bromo-2-fluorobenzonitrile

Into a 250-mL round-bottom flask was placed a solution of 4-amino-2-fluorobenzonitrile (9 g, 66.1 mmol) in ACN (120 mL). Then NBS (12.4 g, 69.7 mmol) was added. The resulting solution was stirred overnight at 80° C. and then was concentrated under vacuum. The residue was applied onto a silica gel column and eluted with a gradient of ethyl acetate/petroleum ether (1:20 to 1:10). This resulted in 10.9 g (77%) of the title compound as a yellow solid. MS-ESI: 215.0/217.0 (M+1). $^1$H NMR (300 MHz, DMSO-$d_6$) δ 7.89 (d, J=6.0 Hz, 1H), 6.69 (br s, 2H), 6.63 (d, J=12.0 Hz, 1H).

Step 2: 4-Amino-5-cyclopropyl-2-fluorobenzonitrile

Into a 250-mL round-bottom flask purged with and maintained under nitrogen was placed a solution of 4-amino-5-bromo-2-fluorobenzonitrile (6.37 g, 29.6 mmol) in dioxane (70 mL) and water (10 mL). To the solution were added $Cs_2CO_3$ (9.7 g, 29.8 mmol), cyclopropylboronic acid (3.8 g, 44.2 mmol) and Pd(dppf)$Cl_2$ (1.08 g, 1.48 mmol). The resulting solution was stirred overnight at 90° C. and then was concentrated under vacuum. The residue was applied onto a silica gel column and eluted with a gradient of ethyl acetate/petroleum ether (1:10 to 1:5). This resulted in 5.03 g (96%) of the title compound as a yellow solid. MS-ESI: 177.1 (M+1).

Step 3: 4-Amino-3-bromo-5-cyclopropyl-2-fluorobenzonitrile

Into a 250-mL round-bottom flask was placed a solution of 4-amino-5-cyclopropyl-2-fluorobenzonitrile (5.03 g, 28.7 mmol) in ACN (50 mL). To the solution was added NBS (5.6 g, 31.5 mmol). The resulting solution was stirred overnight at 80° C. and then was concentrated under vacuum. The residue was applied onto a silica gel column and eluted with a gradient of ethyl acetate/petroleum ether (1:10 to 1:5). This resulted in 6.972 g (96%) of the title compound as a yellow solid. MS-ESI: 255.0/257.0 (M+1).

Step 4: 4-Amino-5-cyclopropyl-2-fluoro-3-(prop-1-en-2-yl)benzonitrile

Into a 250-mL round-bottom flask purged with and maintained under nitrogen was placed a solution of 4-amino-3-bromo-5-cyclopropyl-2-fluorobenzonitrile (6.972 g, 27.33 mmol) in dioxane (120 mL) and water (20 mL). To the solution were added 4,4,5,5-tetramethyl-2-(prop-1-en-2-yl)-1,3,2-dioxaborolane (6.9 g, 41.00 mmol), $Cs_2CO_3$ (13.4 g, 41.00 mmol) and Pd(dppf)$Cl_2$ (0.4 g, 0.55 mmol). The resulting solution was stirred overnight at 80° C. and then was concentrated under vacuum. The residue was applied onto a silica gel column and eluted with a gradient of ethyl acetate/petroleum ether (1:10 to 1:5). This resulted in 4.73 g (80%) of the title compound as a yellow solid. MS-ESI: 217.1 (M+1).

Step 5: 4-Amino-5-cyclopropyl-2-fluoro-3-isopropylbenzonitrile

Into a 250-mL round-bottom flask was placed a solution of 4-amino-5-cyclopropyl-2-fluoro-3-(prop-1-en-2-yl)benzonitrile (4.73 g, 21.97 mmol), MeOH (100 mL). To the solution was added AcOH (0.5 mL). Then Pd/C (10% wt., 500 mg) was added. The flask was evacuated and filled three times with hydrogen. The resulting solution was stirred for 4 h at 40° C. under an atmosphere of hydrogen. The solids were filtered out. The filtrate was concentrated under vacuum. This resulted in 4.71 g (99%) of the title compound as a light yellow solid. MS-ESI: 219.1 (M+1).

Scheme 23

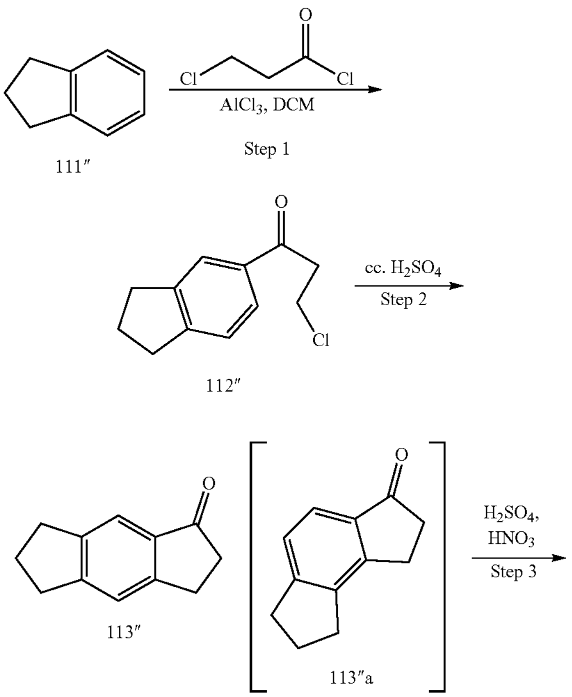

111″

112″

113″

113″a

-continued

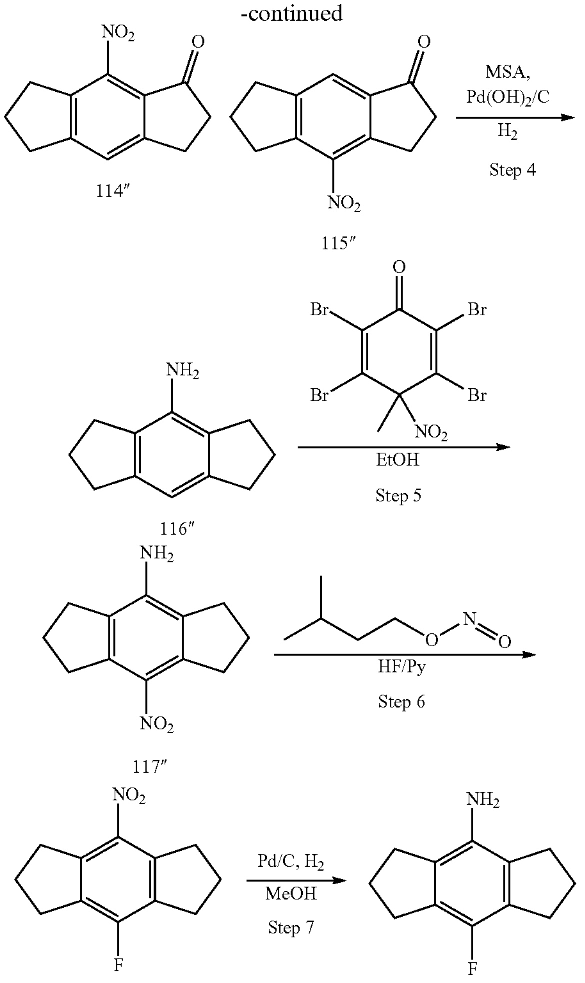

114″ 115″ 116″ 117″ 118″ Intermediate 36

Intermediate 36

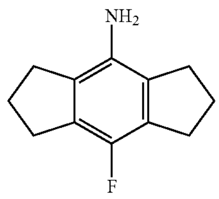

8-Fluoro-1,2,3,5,6,7-hexahydro-s-indacen-4-amine

Step 1: 3-Chloro-1-(2,3-dihydro-1H-inden-5-yl) propan-1-one

Into a 3-L round-bottom flask was placed a solution of $AlCl_3$ (111 g, 834 mmol) in DCM (1200 mL). This was followed by the addition of a solution of 2,3-dihydro-1H-indene (90 g, 762 mmol) and 3-chloropropanoyl chloride (96.3 g, 759 mmol) in DCM (300 mL) dropwise with stirring at −10° C. in 30 min. The resulting solution was stirred for 16 h at RT. Then the reaction mixture was added dropwise to cold HCl (3 N, 1200 mL) over 45 min at −10° C. The resulting solution was extracted with 3×600 mL of DCM and the organic layers were combined, dried over anhydrous $Na_2SO_4$, then concentrated under vacuum. This resulted in 160.5 g (crude) of the title compound as a yellow solid. The crude product was used in the next step.

Step 2: 1,2,3,5,6,7-Hexahydro-s-indacen-1-one

Into a 1-L round-bottom flask was placed a solution of 3-chloro-1-(2,3-dihydro-1H-inden-5-yl)propan-1-one (160.5 g, 759 mmol) in conc. $H_2SO_4$ (900 mL). The resulting solution was stirred for 16 h at 55° C. and then was quenched by adding the reaction mixture carefully to 4500 mL of water/ice. The solids were collected by filtration and dried over infrared lamp for 24 h. The crude mixture was purified by chromatography and eluted with ethyl acetate/petroleum ether (1:100). This resulted in 10 g (7.6%) of 1,6,7,8-tetrahydro-as-indacen-3 (2H)-one (compound 113"a) and 112.2 g (85%) of the title compound (compound 113") as a yellow solid. $^1$H NMR (400 MHz, DMSO-$d_6$) δ 7.44 (s, 1H), 7.39 (s, 1H), 3.13-2.79 (m, 8H), 2.70-2.55 (m, 2H), 2.20-1.90 (m, 2H). $^1$H NMR (400 MHz, DMSO-$d_6$) δ 7.49 (d, J=7.7 Hz, 1H), 7.31 (d, J=7.7 Hz, 1H), 3.19-2.98 (m, 4H), 2.93-2.80 (m, 3H), 2.68-2.54 (m, 2H), 2.15-1.95 (m, 2H).

Step 3: 4-nitro-2,3,6,7-tetrahydro-s-indacen-1 (5H)-one (114) (Major) and 8-nitro-2,3,6,7-tetrahydro-s-indacen-1 (5H)-one (115) (Minor)

Into a 1-L round-bottom flask was placed a solution of 1,2,3,5,6,7-hexahydro-s-indacen-1-one (80 g, 464.5 mmol) in $H_2SO_4$ (500 mL). Then $HNO_3$ (58.5 g, 929 mmol) was added dropwise over 1 h at 0° C. The resulting solution was stirred for 1 hr at 0° C. The reaction mixture was slowly added to a mixture of water/ice (1000 mL) and DCM (500 mL) with ice bath cooling. The organic layer was collected, dried over $Na_2SO_4$ and concentrated under vacuum. This resulted in 90 g (90%) of the mixture of 4-nitro-2,3,6,7-hexahydro-s-indacen-1-one and 8-nitro-2,3,6,7-tetrahydro-s-indacen-1 (5H)-one as a yellow solid.

Step 4: 1,2,3,5,6,7-hexahydro-s-indacen-4-amine

Into a 1-L round-bottom flask was placed a solution of the mixture of 4-nitro-1,2,3,5,6,7-hexahydro-s-indacen-1-one and 8-nitro-2,3,6,7-tetrahydro-s-indacen-1 (5H)-one (21.7 g, 100 mmol) in MeOH (300 mL). To the solution was added MSA (11.5 g, 120 mmol). Then $Pd(OH)_2/C$ (20% wt, 5.5 g) was added. The flask was evacuated and filled three times with hydrogen. The resulting mixture was stirred for 16 h at RT under hydrogen (50 psi). The solids were filtered out and washed with methanol. The methanol filtrate and wash was diluted with water (500 mL) and the pH was adjusted to 10.6 with 2N NaOH. The resulting slurry was filtered and the crude solids were recrystallized from methanol/water (9:1) with heating. This resulted in 13.7 g (79%) of the title compound as an off-white solid.

Step 5: 8-Nitro-1,2,3,5,6,7-hexahydro-s-indacen-4-amine

Into a 500-mL round-bottom flask was placed 1,2,3,5,6,7-hexahydro-s-indacen-4-amine (8 g, 46.2 mmol), EtOH (200 mL), and 2,3,5,6-tetrabromo-4-methyl-4-nitrocyclohexa-2,5-dienone (21.6 g, 46.1 mmol). The resulting solution was stirred for 12 h at RT and then was concentrated under vacuum. The residue was applied onto a silica gel column and eluted with a gradient of ethyl acetate/petroleum ether (1:50 to 1:30). This resulted in 5 g (50%) of the title compound as a yellow solid. MS-ESI: 219.1 (M+1).

Step 6:
4-Fluoro-8-nitro-1,2,3,5,6,7-hexahydro-s-indacene

Into a 100-mL round-bottom flask was placed 8-nitro-1,2,3,5,6,7-hexahydro-s-indacen-4-amine (5 g, 22.9 mmol) and HF/Py (70% wt., 20 mL). This was followed by the addition of 3-methylbutyl nitrite (3 g, 25.6 mmol) dropwise with stirring at 0° C. The resulting solution was stirred for 2 h at RT and then was diluted with 50 mL of water. The resulting solution was extracted with 3x50 mL of DCM. The organic layers were combined and dried over anhydrous $Na_2SO_4$, then concentrated under vacuum. This resulted in 4 g (crude, 79%) of the title compound as brown oil.

Step 7:
8-Fluoro-1,2,3,5,6,7-hexahydro-s-indacen-4-amine

Into a 100-mL round-bottom flask was placed 4-fluoro-8-nitro-1,2,3,5,6,7-hexahydro-s-indacene (4 g, 18.1 mmol) in MeOH (50 mL). Then Pd/C (10% wt., 0.5 g) was added. The flask was evacuated and filled three times with hydrogen. The resulting mixture was stirred for 12 h at RT under an atmosphere of hydrogen. The solids were filtered out and the filtrate was concentrated under vacuum. The residue was applied onto a silica gel column and eluted with a gradient of ethyl acetate/petroleum ether (1:10 to 1:5). This resulted in 2 g (46%, 2 steps) of the title compound as a white solid. MS-ESI: 192.1 (M+1).

Scheme 24

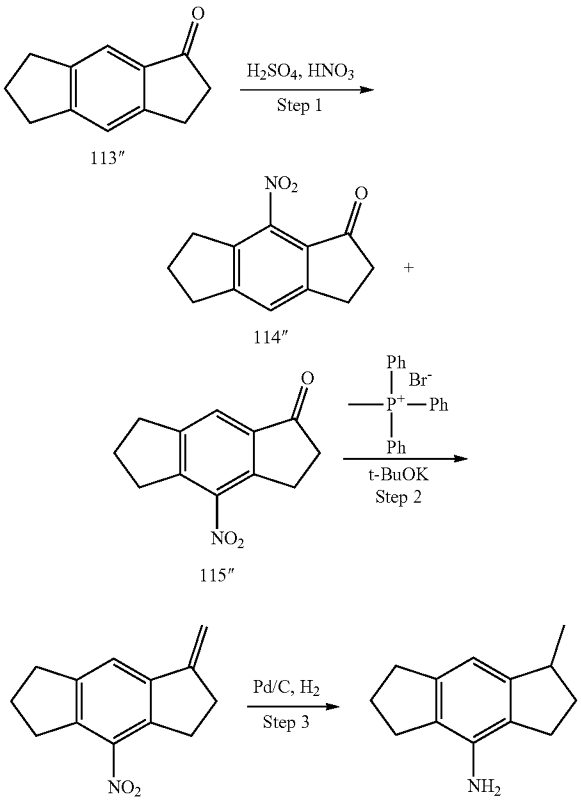

113″

114″

115″

119″

Intermediate 37

Intermediate 37

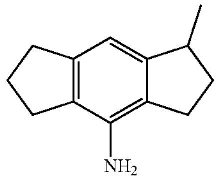

1-methyl-1,2,3,5,6,7-hexahydro-s-indacen-4-amine

Step 1: 4-nitro-2,3,6,7-tetrahydro-s-indacen-1 (5H)-one

Into a 1-L round-bottom flask was placed a solution of 1,2,3,5,6,7-hexahydro-s-indacen-1-one (40 g, 232 mmol) in $H_2SO_4$ (250 mL). Then $HNO_3$ (29 g, 464 mmol) was added dropwise over 1 h at 0° C. The resulting solution was stirred for 1 hr at 0° C. The reaction mixture was slowly added to a mixture of water/ice (500 mL) and DCM (250 mL) with ice bath cooling. The organic layer was collected, dried over anhydrous $Na_2SO_4$ and concentrated under vacuum. The crude product was purified by silica gel column with a gradient of ethyl acetate and petroleum ether (1:50 to 1:1). This resulted in minor product 5 g (10%) of the title compound and major product 30 g (60%) of 8-nitro-2,3,6,7-tetrahydro-s-indacen-1 (5H)-one both as a yellow solid.

Step 2: 1-methylene-4-nitro-1,2,3,5,6,7-hexahydro-s-indacene

Into a 250-mL round-bottom flask was placed a solution of methyltriphenylphosphanium bromide (16.4 g, 46.04 mmol) and t-BuOK (5.2 g, 46.0 mmol) in THF (150 mL) at 0° C. The resulting solution was stirred for 30 min at 0° C. Then the solution of 4-nitro-1,2,3,5,6,7-hexahydro-s-indacen-1-one (5 g, 23.0 mmol) in THF (10 mL) was added dropwise to the reaction mixture at 0° C. The resulting solution was stirred overnight at RT. The resulting mixture was concentrated. The residue was applied onto a silica gel column with ethyl acetate/petroleum ether (1:10). This resulted in 2.6 g (52%) of the title compound as a green solid.

Step 3:
1-methyl-1,2,3,5,6,7-hexahydro-s-indacen-4-amine

Into a 100-mL round-bottom flask was placed a solution of 1-methylidene-4-nitro-1,2,3,5,6,7-hexahydro-s-indacene (2.6 g, 12.1 mmol) in MeOH (20 mL), Pd/C (10% wt, 300 mg) was added. The flask was evacuated and filled three times with hydrogen. then $H_2$ (g) was introduced in with a balloon. The resulting solution was stirred for 2 h at RT. The Pd/C catalyst was filtered out. The filtrate was concentrated. This resulted in 2 g of the title compound as red oil.

TABLE 8

Intermediate 38 in the following Table was prepared from Compound 114" using similar procedure as shown in Scheme 24 above for converting compound 115" to intermediate 37.

| Intermediate # | Structure | IUPAC Name | Exact Mass[M + H]$^+$ |
|---|---|---|---|
| Intermediate 38 | 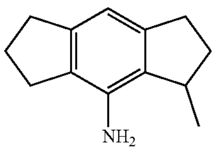 | 3-methyl-1,2,3,5,6,7-hexahydro-s-indacen-4-amine | 188.1 |

Scheme 25

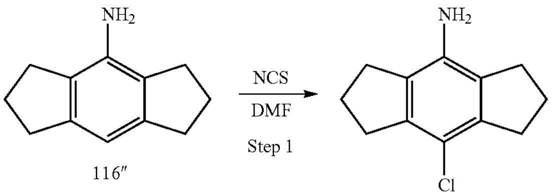

116″

Intermediate 39

Intermediate 39

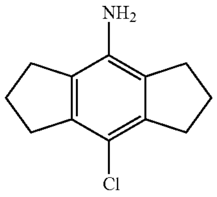

8-Chloro-1,2,3,5,6,7-hexahydro-s-indacen-4-amine

Step 1: 8-Chloro-1,2,3,5,6,7-hexahydro-s-indacen-4-amine

Into a 50-mL round-bottom flask was placed a solution of 1,2,3,5,6,7-hexahydro-s-indacen-4-amine (1.73 g, 9.99 mmol) in DMF (10 mL). To the solution was added NCS (1.47 g, 11.0 mmol). The resulting solution was stirred overnight at RT and then was diluted with 30 mL of DCM. The resulting mixture was washed with 3×10 mL of water and the organic layer was concentrated under vacuum. The residue was applied onto a silica gel column and eluted with a gradient of ethyl acetate/petroleum ether (1:20 to 1:10). This resulted in 1.88 g (91%) of the title compound as a yellow solid. MS-ESI: 208.1/210.1 (M+1).

Scheme 26

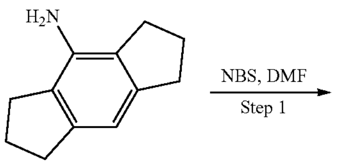

116″

-continued

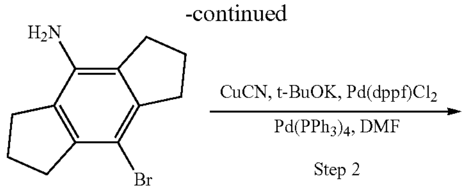

120″

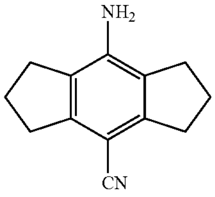

Intermediate 40

Intermediate 40

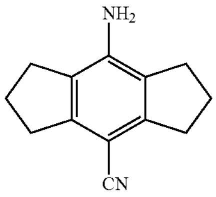

8-Amino-1,2,3,5,6,7-hexahydro-s-indacene-4-carbonitrile

Step 1: 8-Bromo-1,2,3,5,6,7-hexahydro-s-indacen-4-amine

Into a 100-mL round-bottom flask was placed a solution of 1,2,3,5,6,7-hexahydro-s-indacen-4-amine (2.6 g, 15.0 mmol) in DMF (30 mL). To the solution was added NBS (2.9 g, 16.3 mmol). The resulting solution was stirred for 12 h at RT and then was diluted with 80 mL of ethyl acetate. The resulting mixture was washed with 3×20 mL of water and concentrated under vacuum. The residue was applied onto a silica gel column and eluted with a gradient of ethyl acetate/petroleum ether (1:30 to 1:20). This resulted in 3.0 g (79%) of the title compound as a brown solid. MS-ESI: 252.0, 254.0 (M+1).

Step 2: 8-Amino-1,2,3,5,6,7-hexahydro-s-indacene-4-carbonitrile

Into a 50-mL round-bottom flask purged with and maintained under nitrogen was placed a solution of 8-bromo-1, 2,3,5,6,7-hexahydro-s-indacen-4-amine (725 mg, 2.88 mmol) in DMF (10 mL). To the solution were added t-BuOK (330 mg, 2.90 mmol), CuCN (386 mg, 4.32 mmol), and $Pd(dppf)Cl_2$ (424 mg, 0.58 mmol). The resulting solution was stirred for 12 h at 120° C. and then was diluted with 20 mL of water. The resulting solution was extracted with 3×20 mL ethyl acetate. The organic layers were combined, dried over anhydrous $Na_2SO_4$, then concentrated under vacuum. The residue was applied onto a silica gel column and eluted with a gradient of ethyl acetate/petroleum ether (1:60 to 1:40). This resulted in 192 mg (34%) of the title compound as a yellow solid. MS-ESI: 199.1 (M+1).

Scheme 27

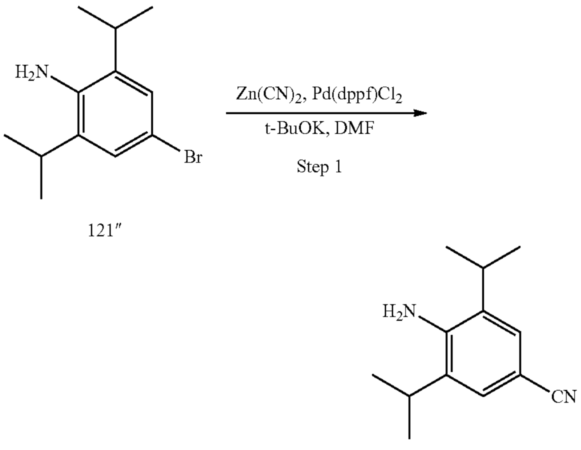

121″

Intermediate 41

Intermediate 41

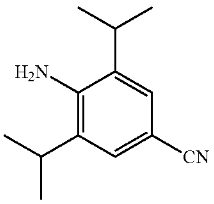

4-Amino-3,5-diisopropylbenzonitrile

Step 1: 4-Amino-3,5-diisopropylbenzonitrile

Into a 100-mL round-bottom flask purged with and maintained under nitrogen was placed a solution of 4-bromo-2,6-diisopropylbenzenamine (5.1 g, 19.9 mmol) in DMF (30 mL). To the solution were added $Zn(CN)_2$ (2.80 g, 23.9 mmol), $Pd(dppf)Cl_2$ (732 mg, 1.00 mmol) and t-BuOK (3.36 g, 29.9 mmol). The resulting mixture was stirred for 16 h at 120° C. and then was diluted with 30 mL of water. The solution was extracted with 3×30 mL of ethyl acetate and the combined organic layers were concentrated under vacuum. The residue was applied onto a silica gel column and eluted with a gradiente of ethyl acetate/petroleum ether (1:30 to 1:20). This resulted in 3.2 g (80%) of the title compound as a yellow solid. MS-ESI: 203.1 (M+1).

Scheme 28

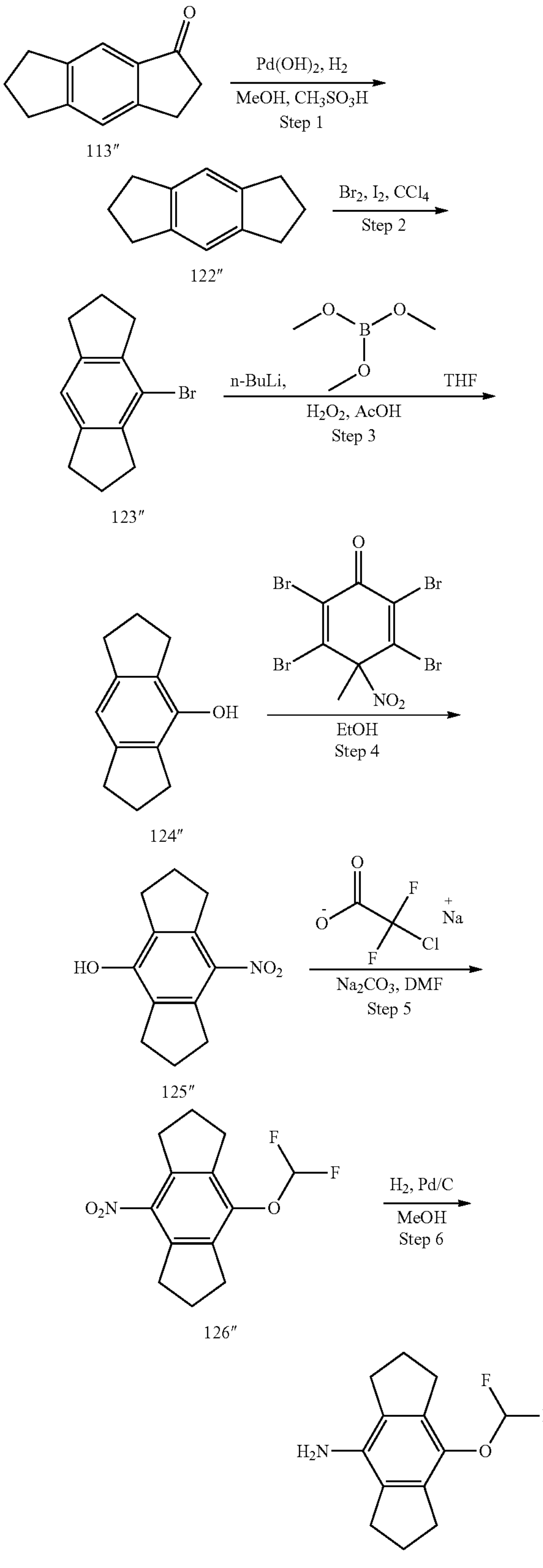

113″

122″

123″

124″

125″

126″

Intermediate 42

Intermediate 42

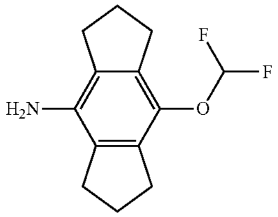

8-(Difluoromethoxy)-1,2,3,5,6,7-hexahydro-s-indacen-4-amine

Step 1: 1,2,3,5,6,7-Hexahydro-s-indacene

Into a 1-L round-bottom flask was placed a solution of 1,2,3,5,6,7-hexahydro-s-indacen-1-one (37.2 g, 216 mmol) and MSA (42 g, 437.5 mmol) in MeOH (300 mL). Then $Pd(OH)_2/C$ (20% wt, 8 g) was added. The flask was evacuated and filled three times with hydrogen. The resulting solution was stirred for 16 h at RT under an atmosphere of hydrogen. The solids were filtered out. The resulting mixture was concentrated under vacuum. The residue was applied onto a silica gel column and eluted with a gradient of ethyl acetate/petroleum ether (1:150 to 1:100). This resulted in 27.1 g (79%) of the title compound as a white solid.

Step 2: 4-Bromo-1,2,3,5,6,7-hexahydro-s-indacene

Into a 500-mL 3-necked round-bottom flask purged with and maintained under nitrogen was placed a solution of 1,2,3,5,6,7-hexahydro-s-indacene (15 g, 94.8 mmol) in $CCl_4$ (200 mL). Then $I_2$ (1.2 g, 4.72 mmol) was added. This was followed by the addition of a solution of $Br_2$ (16 g, 100 mmol) in $CCl_4$ (50 mL) dropwise with stirring at 0° C. in 10 min. The resulting solution was stirred for 2 h at 0° C. The reaction was then quenched by the addition of 150 mL of $NH_4Cl$ (sat.). The resulting solution was extracted with 3×150 mL of DCM and the combined organic layers were dried over anhydrous $Na_2SO_4$ and concentrated under vacuum. The crude product was purified by silica gel column with a gradient of ethyl acetate/hexane (1:500 to 1:100). This resulted in 19 g (85%) of the title compound as yellow oil. $^1H$ NMR (300 MHz, DMSO-$d_6$) δ 7.02 (s, 1H), 2.95-2.75 (m, 8H), 2.03-2.01 (m, 4H)

Step 3: 1,2,3,5,6,7-Hexahydro-s-indacen-4-ol

Into a 500-mL 3-necked round-bottom flask purged with and maintained under nitrogen was placed a solution of 4-bromo-1,2,3,5,6,7-hexahydro-s-indacene (5 g, 21.08 mmol) in THF (150 mL). This was followed by the addition of n-BuLi (2.5 M in hexane, 10 mL) dropwise with stirring at −78° C. The resulting solution was stirred for 30 min at −78° C. Then to the above was added trimethyl borate (2.6 g, 25.30 mmol) dropwise with stirring at −78° C. The reaction was warmed to RT slowly and then was stirred for 1 h at RT. Then to the mixture was added AcOH (2.0 mL, 33.20 mmol) and $H_2O_2$ (1.0 mL, 28.88 mmol) dropwise with stirring at RT. The resulting solution was stirred for 2 h at RT and then was quenched by the addition of 200 mL of $NH_4Cl$ (sat.). The resulting solution was extracted with 3×200 mL of DCM. The organic layers were combined and dried over anhydrous $Na_2SO_4$, then concentrated under vacuum. The residue was applied onto a silica gel column and eluted with a gradient of ethyl acetate/petroleum ether (1:7 to 1:5). This resulted in 1.9 g (52%) of the title compound as an off-white solid. MS-ESI: 175.1 (M+1).

Step 4: 8-Nitro-1,2,3,5,6,7-hexahydro-s-indacen-4-ol

Into a 250-mL round-bottom flask purged with and maintained under nitrogen was placed a solution of 1,2,3,5,6,7-hexahydro-s-indacen-4-ol (1.9 g, 10.9 mmol) in EtOH (100 mL). To the solution was added 2,3,5,6-tetrabromo-4-methyl-4-nitrocyclohexa-2,5-dienone (6.1 g, 13.1 mmol). The resulting solution was stirred overnight at RT and then was concentrated under vacuum. The residue was applied onto a silica gel column and eluted with a gradient of ethyl acetate/petroleum ether (1:5 to 1:3). This resulted in 1.1 g (46%) of the title compound as a light yellow solid. MS-ESI: 218.1 (M−1).

Step 5: 4-(Difluoromethoxy)-8-nitro-1,2,3,5,6,7-hexahydro-s-indacene

Into a 100-mL round-bottom flask purged with and maintained under nitrogen was placed a solution of 8-nitro-1,2,3,5,6,7-hexahydro-s-indacen-4-ol (1.1 g, 5.0 mmol) in DMF (20 mL) and water (2 mL). To the solution were added $K_2CO_3$ (1.4 g, 10.0 mmol) and sodium 2-chloro-2,2-difluoroacetate (1.5 g, 10.0 mmol). The resulting solution was stirred for 1 h at 120° C. and then was diluted with 20 mL of water. The pH value of the solution was adjusted to 7 with aq. HCl (1 N). The resulting solution was extracted with 3×20 mL of DCM. The organic layers were combined and dried over anhydrous $Na_2SO_4$, then concentrated under vacuum. The residue was applied onto a silica gel column and eluted with a gradient of ethyl acetate/petroleum ether (1:2 to 1:3). This resulted in 0.55 g (41%) of the title compound as a light yellow solid. MS-ESI: 270.1 (M+1).

Step 6: 8-(Difluoromethoxy)-1,2,3,5,6,7-hexahydro-s-indacen-4-amine

Into a 100-mL round-bottom flask was placed a solution of 4-(difluoromethoxy)-8-nitro-1,2,3,5,6,7-hexahydro-s-indacene (550 mg, 2.0 mmol) in MeOH (10 mL). Then Pd/C (10% wt., 100 mg) was added. The flask was evacuated and filled three times with hydrogen. The resulting solution was stirred for 12 h at RT under an atmosphere of hydrogen. The solids were filtered out. The resulting filtrate was concentrated under vacuum. This resulted in 460 mg (94%) of the title compound as a light yellow solid. MS-ESI: 240.1 (M+1).

Scheme 29

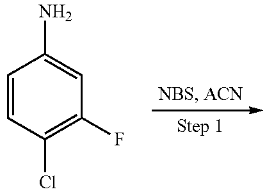

127″

-continued

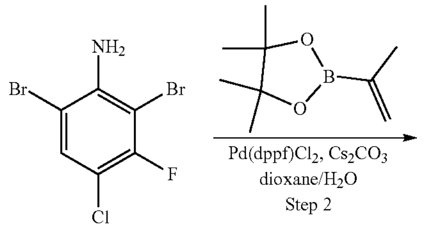

128″

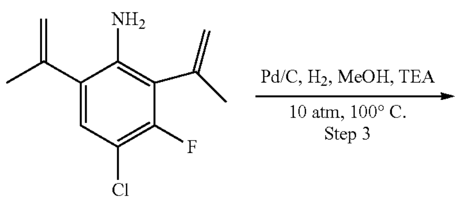

129″

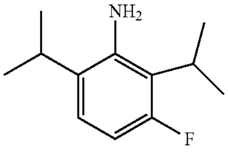

Intermediate 43

Intermediate 43

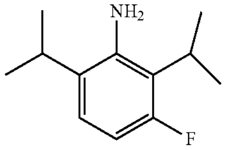

3-Fluoro-2,6-diisopropylbenzenamine

Step 1: 2,6-Dibromo-4-chloro-3-fluoroaniline

Into a 500-mL round-bottom flask was placed 4-chloro-3-fluoroaniline (5.08 g, 34.9 mmol), ACN (200 mL), and NBS (18.69 g, 105.0 mmol). The resulting solution was stirred for 12 h at RT and then was concentrated under vacuum. The residue was applied onto a silica gel column and eluted with a gradient of ethyl acetate/petroleum ether (1:200 to 1:100). This resulted in 9.7 g (92%) of the title compound as a light yellow solid. MS-ESI: 303.8/305.8/301.8 (M+1).

Step 2: 4-Chloro-3-fluoro-2,6-bis(prop-1-en-2-yl) aniline

Into a 500-mL round-bottom flask purged with and maintained under nitrogen was placed a solution of 2,6-dibromo-4-chloro-3-fluoroaniline (9.03 g, 29.8 mmol) in 1,4-dioxane (200 mL) and water (20 mL). To the solution were added 4,4,5,5-tetramethyl-2-(prop-1-en-2-yl)-1,3,2-dioxaborolane (15.12 g, 89.98 mmol), $Cs_2CO_3$ (29.34 g, 90.1 mmol) and $Pd(dppf)Cl_2$ (2.20 g, 3.0 mmol). The resulting solution was stirred for 12 h at 90° C. and then was concentrated under vacuum. The residue was applied onto a silica gel column and eluted with a gradient of ethyl acetate/petroleum ether (1:30 to 1:20). This resulted in 4.3 g (64%) of the title compound as yellow oil. MS-ESI: 226.1, 228.1 (M+1).

Step 3: 3-Fluoro-2,6-bis(propan-2-yl)aniline

Into a 100-mL round-bottom flask was placed a solution of 4-chloro-3-fluoro-2,6-bis(prop-1-en-2-yl)aniline (1 g, 4.4 mmol) in MeOH (15 mL). Then Pd/C (10% wt., 100 mg) was added. The flask was evacuated and filled three times with hydrogen. The resulting solution was stirred for 3 h at RT under an atmosphere of hydrogen. The solids were filtered out. The resulting filtrate was concentrated under vacuum. The residue was applied onto a silica gel column and eluted with a gradient of ethyl acetate/petroleum ether (1:5 to 1:3). This resulted in 700 mg (81%) of the title compound as light yellow oil. MS-ESI: 196.1 (M+1).

Scheme 30

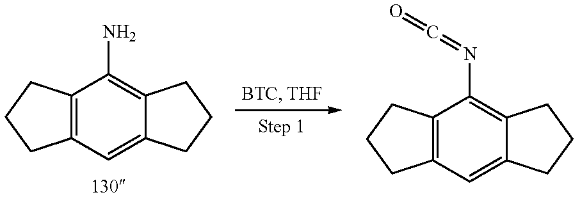

130″

Intermediate 44

Intermediate 44

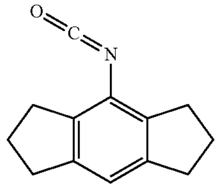

4-Isocyanato-1,2,3,5,6,7-hexahydro-s-indacene

Step 1: 4-Isocyanato-1,2,3,5,6,7-hexahydro-s-indacene

Into a 50-mL round-bottom flask purged with and maintained under nitrogen was placed 1,2,3,5,6,7-hexahydro-s-indacen-4-amine (64 mg, 0.4 mmol), THF (5 mL) and BTC (37 mg, 0.1 mmol). The resulting solution was stirred for 2 h at 65° C. and then was concentrated under vacuum. This resulted in 75 mg (crude) of the title compound as light brown oil. The crude product was used directly in the next step.

TABLE 9

The Intermediates in the following Table were prepared using similar procedure as shown in Scheme 30 above for converting compound 130" to Intermediate 44.

| Intermediate # | Structure | IUPAC Name |
|---|---|---|
| Intermediate 45 | 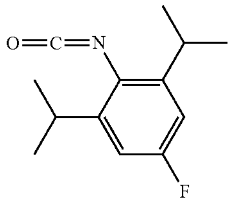 [SMILES: CC(C)c1cc(F)cc(C(C)C)c1N=C=O] | 5-Fluoro-2-isocyanato-1,3-diisopropylbenzene |
| Intermediate 46 | 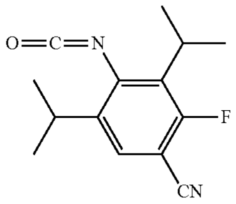 [SMILES: CC(C)c1cc(C#N)c(F)c(C(C)C)c1N=C=O] | 2-Fluoro-4-isocyanato-3,5-diisopropylbenzonitrile |
| Intermediate 47 | 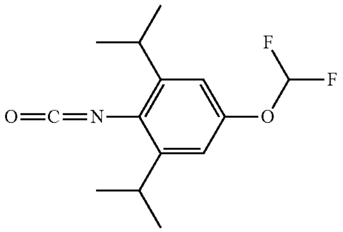 [SMILES: CC(C)c1cc(OC(F)F)cc(C(C)C)c1N=C=O] | 5-(Difluoromethoxy)-2-isocyanato-1,3-diisopropylbenzene |
| Intermediate 48 | 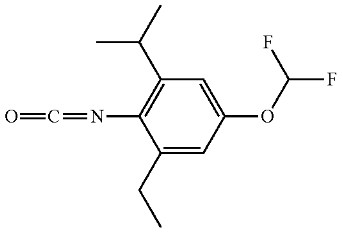 [SMILES: CCc1cc(OC(F)F)cc(C(C)C)c1N=C=O] | 5-(Difluoromethoxy)-1-ethyl-2-isocyanato-3-isopropylbenzene |
| Intermediate 49 | 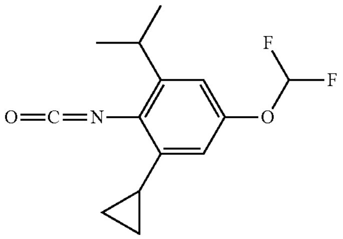 [SMILES: CC(C)c1cc(OC(F)F)cc(C2CC2)c1N=C=O] | 1-Cyclopropyl-5-(difluoromethoxy)-2-isocyanato-3-isopropylbenzene |
| Intermediate 50 | 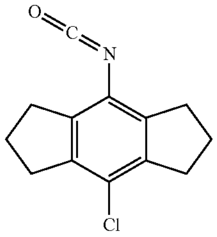 | 4-Chloro-8-isocyanato-1,2,3,5,6,7-hexahydro-s-indacene |

TABLE 9-continued

The Intermediates in the following Table were prepared using similar procedure as shown in Scheme 30 above for converting compound 130" to Intermediate 44.

| Intermediate # | Structure | IUPAC Name |
|---|---|---|
| Intermediate 51 | 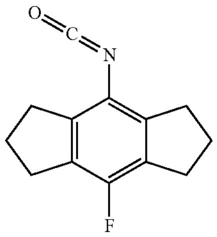 [SMILES: O=C=Nc1c2c(c(F)c3c1CCC3)CCC2] | 4-Fluoro-8-isocyanato-1,2,3,5,6,7-hexahydro-s-indacene |
| Intermediate 52 | 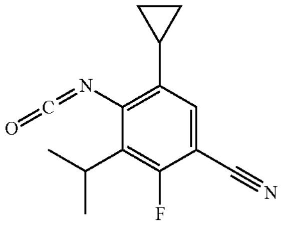 [SMILES: CC(C)c1c(F)c(C#N)cc(C2CC2)c1N=C=O] | 5-Cyclopropyl-2-fluoro-4-isocyanato-3-isopropylbenzonitrile |
| Intermediate 53 | 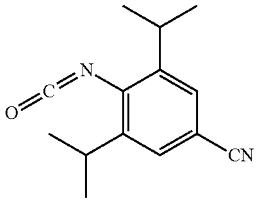 [SMILES: CC(C)c1cc(C#N)cc(C(C)C)c1N=C=O] | 4-Isocyanato-3,5-diisopropylbenzonitrile |
| Intermediate 54 | 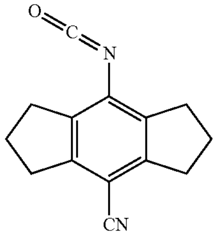 [SMILES: N#Cc1c2c(c(N=C=O)c3c1CCC3)CCC2] | 1,2,3,5,6,7-Hexahydro-8-isocyanato-s-indacene-4-carbonitrile |
| Intermediate 55 | 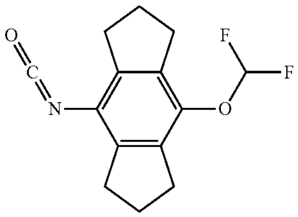 [SMILES: O=C=Nc1c2c(c(OC(F)F)c3c1CCC3)CCC2] | 4-(Difluoromethoxy)-1,2,3,5,6,7-hexahydro-8-isocyanato-s-indacene |
| Intermediate 56 | 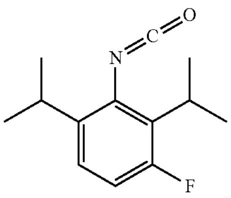 [SMILES: CC(C)c1ccc(F)c(C(C)C)c1N=C=O] | 1-Fluoro-3-isocyanato-2,4-diisopropylbenzene |

TABLE 9-continued

| The Intermediates in the following Table were prepared using similar procedure as shown in Scheme 30 above for converting compound 130" to Intermediate 44. | | |
|---|---|---|
| Intermediate # | Structure | IUPAC Name |
| Intermediate 57 | 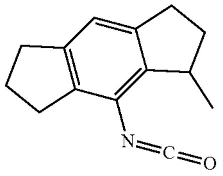 [SMILES: CC1CCc2cc3c(c(N=C=O)c21)CCC3] | 1,2,3,5,6,7-Hexahydro-8-isocyanato-1-methyl-s-indacene |
| Intermediate 58 | 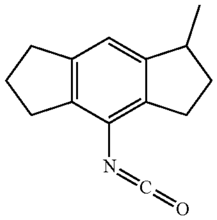 [SMILES: CC1CCc2c1cc1c(c2N=C=O)CCC1] | 1,2,3,5,6,7-Hexahydro-4-isocyanato-1-methyl-s-indacene |

The following schemes illustrate additional general methods for the synthesis of compounds of Formula AA:

Scheme 31

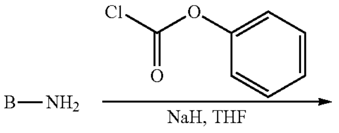

131"

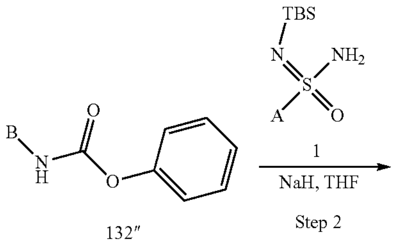

132"

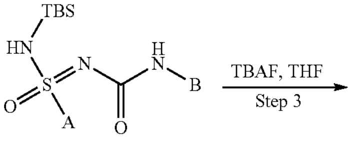

3

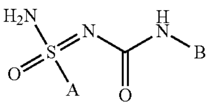

4

Scheme 32

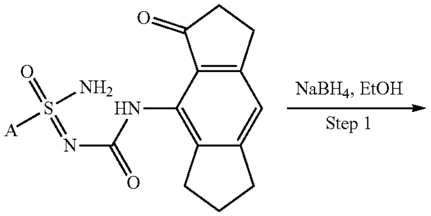

133"

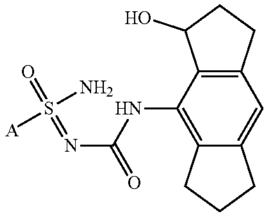

134"

Scheme 33A

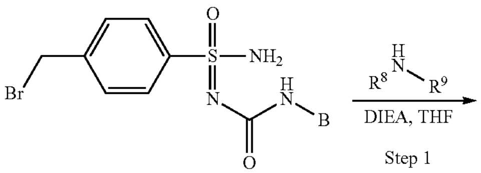

135"

-continued
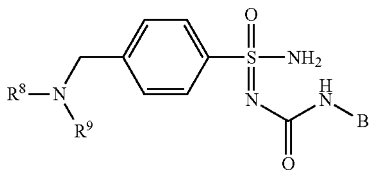
136″
Scheme 33B
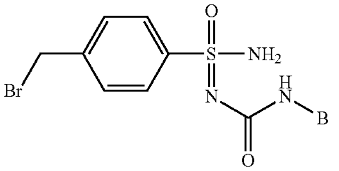
135″
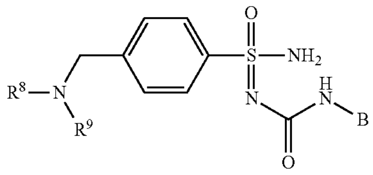
136″
Scheme 34
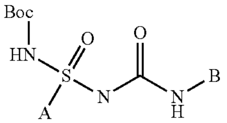
6
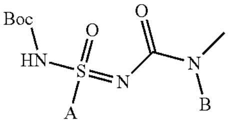
138″
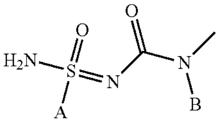
139″
Scheme 35
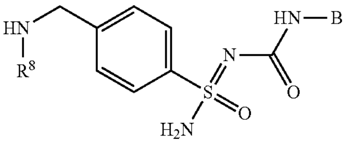
140″
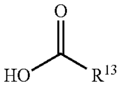
141″
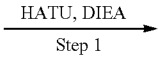
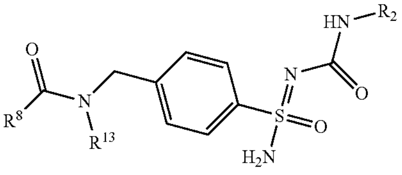
142″
Scheme 35A
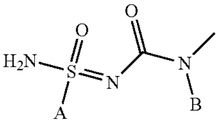
140″A
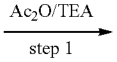
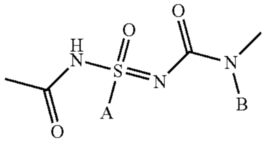
142″B
Scheme for the preparation of Sulfonimidamide Intermediates: Schemes below illustrate the preparation of sulfonimidamide intermediates 59-88 and 112-113.
Scheme 36
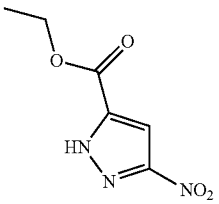
143″
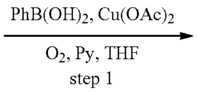
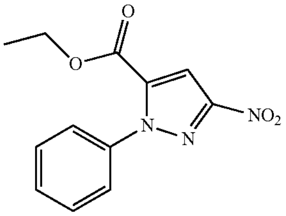
144″
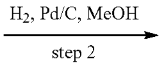

-continued

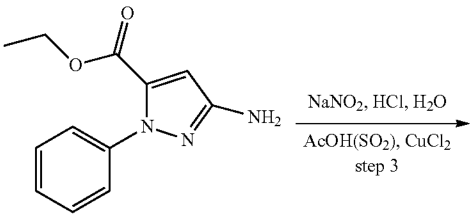

145″

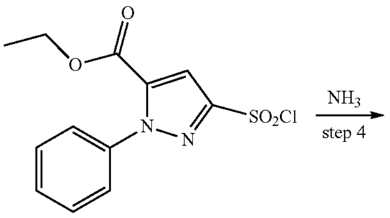

146″

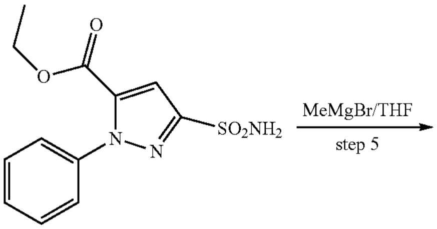

147″

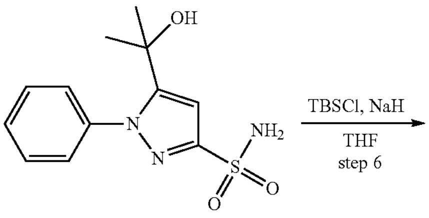

148″

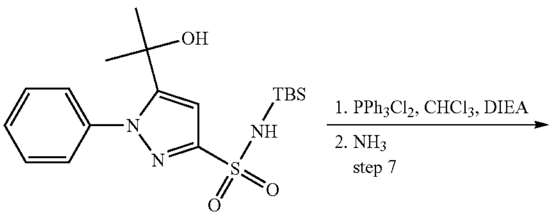

149″

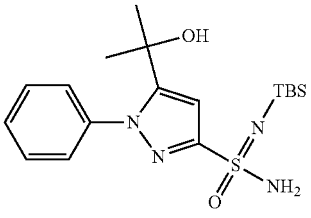

Intermediate 59

Intermediate 59

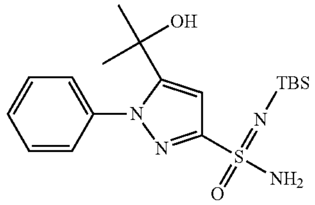

N'-(tert-butyldimethylsilyl)-5-(2-hydroxypropan-2-yl)-1-phenyl-1H-pyrazole-3-sulfonimidamide

Step 1: Ethyl 3-nitro-1-phenyl-1H-pyrazole-5-carboxylate

Into a 250-mL round-bottom flask purged and maintained with an inert atmosphere of nitrogen, was placed ethyl 3-nitro-1H-pyrazole-5-carboxylate (5.0 g, 27.0 mmol), THF (150 mL), phenylboronic acid (6.6 g, 54.1 mmol), $Cu(OAc)_2$ (7.38 g, 40.6 mmol), and pyridine (8.54 g, 108 mmol). The resulting solution was stirred overnight at RT. The resulting mixture was concentrated under vacuum. The residue was eluted from a silica gel column with ethyl acetate/petroleum ether (1:1). This resulted in 3.1 g (44%) of the title compound as an off-white solid. MS-ESI: 262 (M+1).

Step 2: Ethyl 3-amino-1-phenyl-1H-pyrazole-5-carboxylate

Into a 100-mL round-bottom flask, was placed ethyl 3-nitro-1-phenyl-1H-pyrazole-5-carboxylate (3.92 g, 15.0 mmol), MeOH (50 mL), and Pd/C (wet 10% wt., 400 mg). The flask was evacuated and filled three times with hydrogen. The resulting solution was stirred overnight at RT. The solids were filtered out. The resulting mixture was concentrated under vacuum. This resulted in 2.8 g (81%) of the title compound as a light yellow solid. MS-ESI: 232 (M+1).

Step 3: Ethyl 3-(chlorosulfonyl)-1-phenyl-1H-pyrazole-5-carboxylate

Into a 100-mL round-bottom flask, was placed ethyl 3-amino-1-phenyl-1H-pyrazole-5-carboxylate (1.8 g, 7.78 mmol), HCl (cc. 6.0 mol/L, 15 mL). This was followed by the addition of a solution of $NaNO_2$ (646 mg, 9.36 mmol) in water (2.0 mL) dropwise with stirring at −10° C. The resulting solution was stirred for 30 min at −10° C. The above mixture was added to a saturated solution of $SO_2$ in AcOH (20 mL) dropwise with stirring at 0° C. Then to the above was added $CuCl_2$ (1.05 g, 7.81 mmol). The resulting solution was stirred for 1 h at RT. The reaction was then quenched by the addition of 30 mL of water. The resulting solution was extracted with 3x30 mL of DCM and the organic layers combined and dried over anhydrous sodium sulfate and concentrated under vacuum. This resulted in 2.2 g (90%) of the title compound as a light yellow solid.

Step 4: Ethyl 1-phenyl-3-sulfamoyl-1H-pyrazole-5-carboxylate

Into a 100-mL round-bottom flask, was placed a solution of ethyl 3-(chlorosulfonyl)-1-phenyl-1H-pyrazole-5-carboxylate (2.2 g, 6.99 mmol) in DCM (10 mL). Then to the above was introduced $NH_3$ gas bubbled at 0° C. for 10 min.

The resulting solution was stirred for 2 h at RT. The resulting mixture was concentrated under vacuum. The residue was eluted from a silica gel column with ethyl acetate/petroleum ether (1:1). This resulted in 1.07 g (52%) of the title compound as a light yellow solid. MS-ESI: 296 (M+1).

Step 5: 5-(2-Hydroxypropan-2-yl)-1-phenyl-1H-pyrazole-3-sulfonamide

Into a 100-mL 3-necked round-bottom flask purged and maintained with an inert atmosphere of nitrogen, was placed a solution of ethyl 1-phenyl-3-sulfamoyl-1H-pyrazole-5-carboxylate (1.65 g, 5.59 mmol) in THF (30 mL). This was followed by the addition of MeMgBr/THF (3.0 M, 18.6 mL) dropwise with stirring at 0° C. The resulting solution was stirred overnight at RT. The reaction was then quenched by the addition of 30 mL of $NH_4Cl$ (sat.). The resulting solution was extracted with 3x30 mL of DCM and the organic layers combined and dried over anhydrous sodium sulfate and concentrated under vacuum. The residue was eluted from a silica gel column with ethyl acetate/petroleum ether (2:1). This resulted in 1.35 g (86%) of the title compound as a yellow solid. MS-ESI: 282 (M+1).

Step 6: N-(tert-butyldimethylsilyl)-5-(2-hydroxypropan-2-yl)-1-phenyl-1H-pyrazole-3-sulfonamide Into a 100-mL round-bottom flask, was placed 5-(2-hydroxypropan-2-yl)-1-phenyl-1H-pyrazole-3-sulfonamide (500 mg, 1.78 mmol), THF (10 mL). This was followed by the addition of sodium hydride (60% wt. oil dispersion, 86 mg, 3.58 mmol) in portions at 0° C. Then to the above was added TBSCl (538 mg, 3.57 mmol). The resulting solution was stirred for 2 h at RT. The reaction was then quenched by the addition of 10 mL of water. The resulting solution was extracted with 3x10 mL of DCM. The organic layers were combined, dried over anhydrous sodium sulfate, and concentrated under vacuum. The residue was eluted from a silica gel column with ethyl acetate/petroleum ether (1:2). This resulted in 660 mg (94%) of the title compound as a light yellow solid. MS-ESI: 396 (M+1).

Step 7: N'-(tert-butyldimethylsilyl)-5-(2-hydroxypropan-2-yl)-1-phenyl-1H-pyrazole-3-sulfonimidamide Into a 100-mL 3-necked round-bottom flask purged and maintained with an inert atmosphere of nitrogen, was placed the solution of $PPh_3Cl_2$ (1.67 g, 5.01 mmol) in chloroform (30 mL). This was followed by the addition of DIEA (1.29 g, 9.98 mmol) dropwise with stirring at RT. The resulting solution was stirred for 10 min at RT and the reaction system was cooled to 0° C. To this was added a solution of N-(tert-butyldimethylsilyl)-5-(2-hydroxypropan-2-yl)-1-phenyl-1H-pyrazole-3-sulfonamide (660 mg, 1.67 mmol) in chloroform (3.0 mL) dropwise with stirring at 0° C. The resulting solution was stirred for 30 min at 0° C. To the mixture was added introduced $NH_3$ gas bubble for 15 min at 0° C. The resulting solution was stirred for 2 h at RT. The resulting solution was diluted with 30 mL of water. The resulting solution was extracted with 3x30 mL of DCM and the organic layers combined and dried over anhydrous sodium sulfate and concentrated under vacuum. The residue was eluted from a silica gel column with ethyl acetate/petroleum ether (1:1). This resulted in 530 mg (81%) of the title compound as a light yellow solid. MS-ESI: 395 (M+1).

Scheme 37

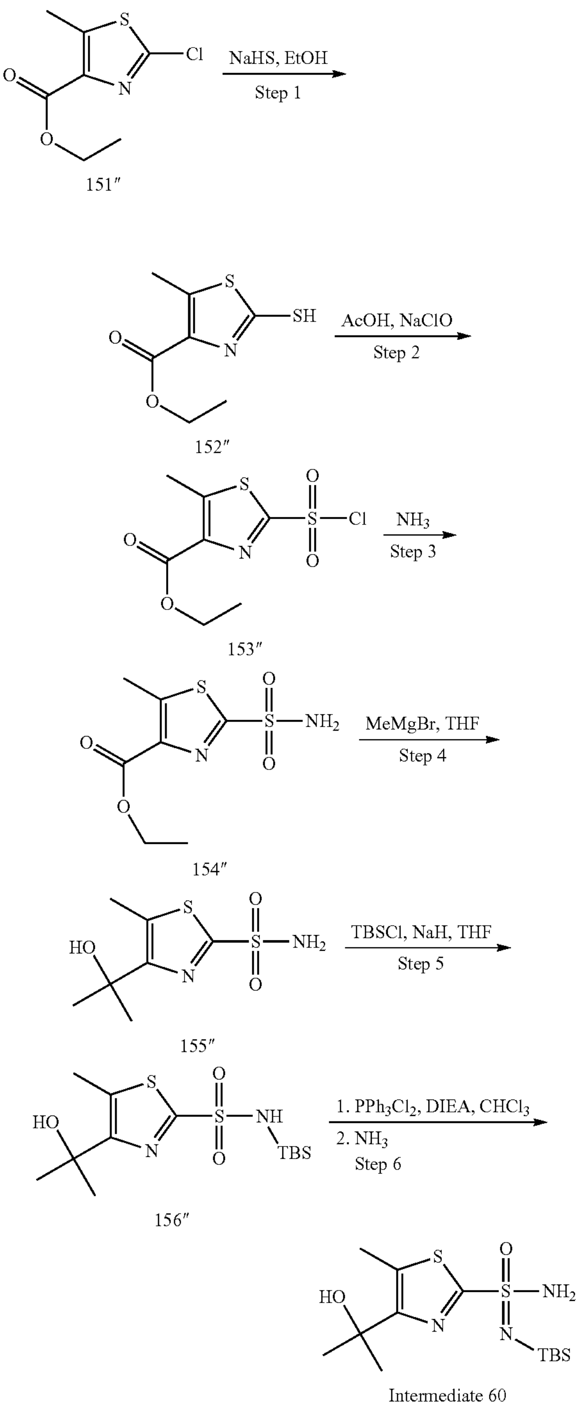

Intermediate 60

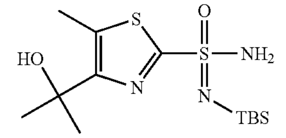

N'-(tert-butyldimethylsilyl)-4-(2-hydroxypropan-2-yl)-5-methylthiazole-2-sulfonimidamide Steps 1-6 used similar procedures for converting compound 16 to intermediate 2 shown in Scheme 7B to afford intermediate 60 from compound 151". MS-ESL: 350 (M+1).

Scheme 38

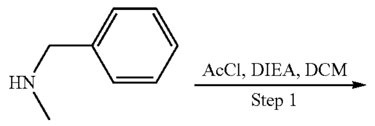

157″

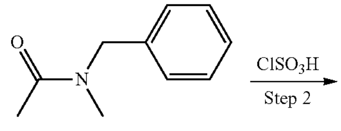

158″

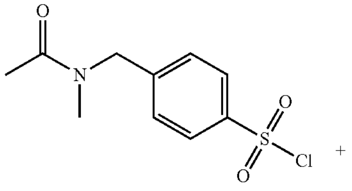

159″

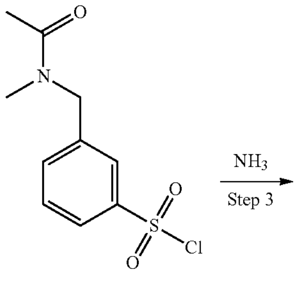

159″A

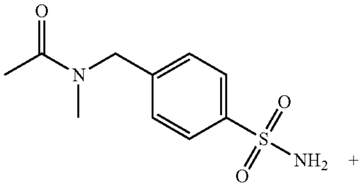

intermediate 61
major

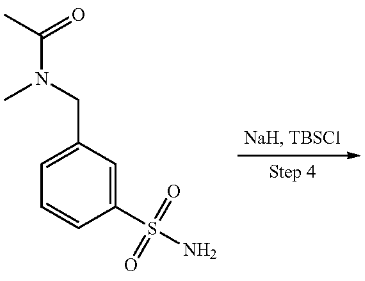

159″B
minor

-continued

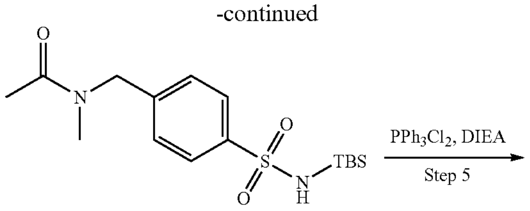

160″

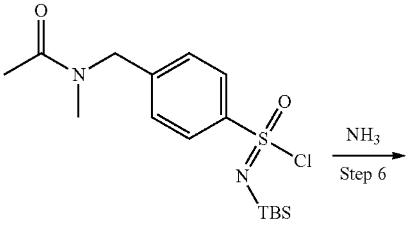

161″

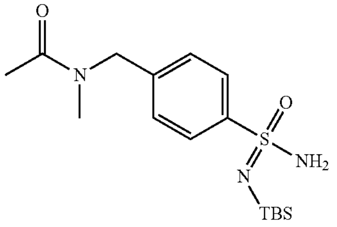

Intermediate 62

Intermediate 61

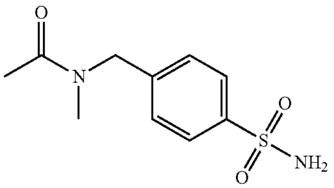

N-methyl-N-(4-sulfamoylbenzyl)acetamide

Intermediate 62

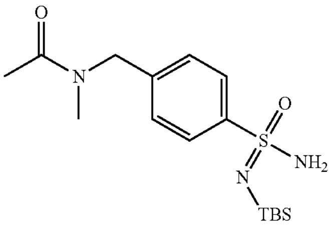

N-(4-(N'-(tert-butyldimethylsilyl)sulfamidimidoyl)benzyl)-N-methylacetamide

Step 1: N-benzyl-N-methylacetamide

Into a 1.0 L round-bottom flask were added benzyl (methyl)amine (10 g, 82.5 mmol) and DCM (500 mL) at 0° C. To this stirred solution were added DIEA (21.3 g, 165 mmol) and acetyl chloride (9.72 g, 124 mmol) in portions at 0° C. The resulting mixture was stirred for 4 h at RT. The resulting mixture was concentrated under reduced pressure. The residue was eluted from a silica gel column with ethyl acetate/petroleum ether (1:1) to afford the title compound (13 g, 96.5%) as a yellow oil. MS-ESI: 164 (M+1).

Step 2: 4-((N-methylacetamido)methyl)benzenesulfonyl Chloride

Into a 250 mL round-bottom flask were added N-benzyl-N-methylacetamide (3.0 g, 18.4 mmol,) and DCM (6.0 mL) at 0° C. To this stirred solution were added $ClSO_2OH$ (6.0 mL) in one portion at 0° C. The resulting mixture was stirred for 3 h at RT. The reaction was quenched by the addition of water/ice (150 mL) at 0° C. The resulting solution was extracted with 3×150 mL of DCM and the organic layers combined and dried over anhydrous sodium sulfate and concentrated under vacuum. The crude product of the title compound (2.2 g, 45.7%)) was used in the next step directly without further purification.

Step 3: N-methyl-N-(4-sulfamoylbenzyl)acetamide

Into a 250 mL round-bottom flask were added 4-[(N-methylacetamido)methyl]benzene-1-sulfonyl chloride (2.2 g, 8.41 mmol) and DCM (3.0 mL) at 0° C. To this stirred solution were added $NH_3$ (g) in DCM (40 mL) dropwise at 0° C. The resulting mixture was stirred overnight at RT. The resulting mixture was concentrated under reduced pressure. The residue was eluted from a silica gel column with ethyl acetate/petroleum ether (1:1) to afford the minor compound 159B (122 mg, 6.1%) and the title compound (1.9 g, 93.3%) both as white solids. MS-ESI: 243 (M+1).

Step 4-6 used similar procedures for converting compound 148" to intermediate 59 shown in Scheme 36 to afford intermediate 62 from intermediate 61. MS-ESI. 356 (M+1).

Scheme 39

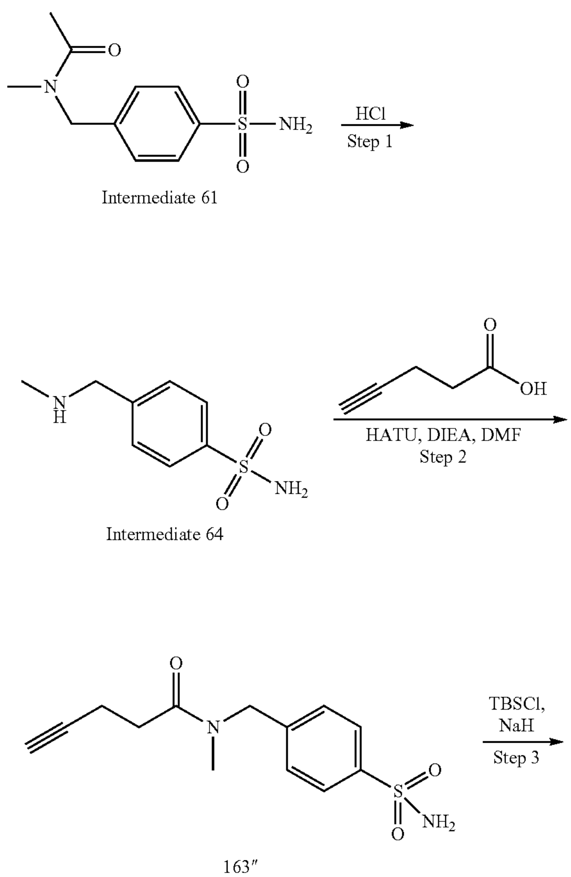

Intermediate 61

Intermediate 64

163″

TABLE 10

Intermediate 62B in the following Table was prepared using the similar procedures for converting compound 157" to Intermediate 62 shown in Scheme 38 from compound 159"B which 5 was separated from step 3 in Scheme 38. The Intermediate 63 was prepared using similar procedures for converting compound 157" to Intermediate 62 shown in Scheme 38 from appropriate starting materials.

| Intermediate # | Structure | IUPAC Name | Exact Mass[M + H]$^+$ |
|---|---|---|---|
| Intermediate 62B | 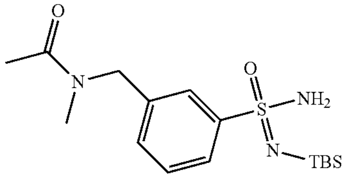 | N-(3-(N'-(tert-butyldimethylsilyl) sulfamimidoyl)benzyl)-N-methylacetamide | 356 |
| Intermediate 63 | 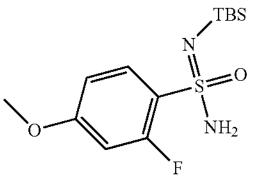 | N'-(tert-butyldimethylsilyl)-2-fluoro-4-methoxybenzenesulfonimidamide | 319 |

-continued

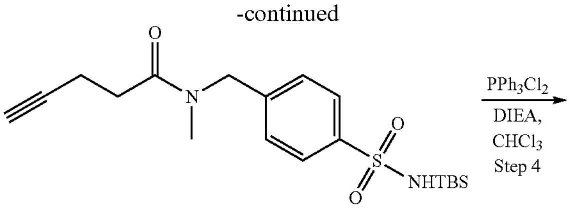

164″

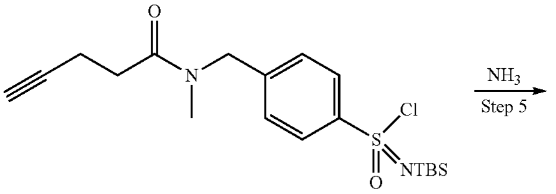

165″

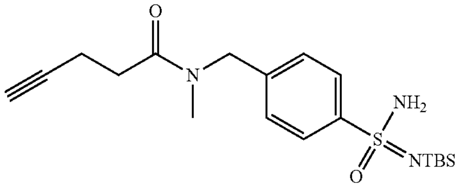

Intermediate 65

Intermediate 64

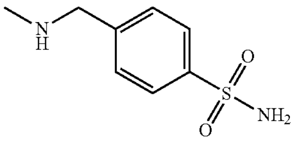

4-((Methylamino)methyl)benzenesulfonamide

Intermediate 65

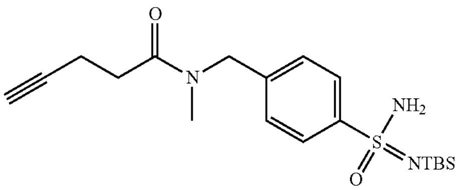

N-(4-(N'-(tert-butyldimethylsilyl)sulfamimidoyl)benzyl)-N-methylpent-4-ynamide

Step 1: 4-((Methylamino)methyl)benzenesulfonamide

Into a 500-mL sealed tube, was placed N-methyl-N-[(4-sulfamoylphenyl)methyl]acetamide (5.0 g), hydrogen chloride (200 mL, 12 M). The resulting solution was stirred for 16 h at 100° C. in an oil bath. The resulting mixture was concentrated. This resulted in 5.0 g of the title compound as an off-white crude solid. MS-ESI: 201 (M+1)

Step 2: N-methyl-N-(4-sulfamoylbenzyl)pent-4-ynamide

Into a 250 mL round-bottom flask was placed 4-((methylamino)methyl)benzenesulfonamide (4.0 g, 20 mmol) in DMF (40 mL). To this stirred solution was added HATU (6.33 g, 16.7 mmol), DIEA (5.16 g, 40 mmol) and pent-4-ynoic acid (2.16 g, 22 mmol). Then the mixture was stirred overnight RT. The resulting solution was diluted with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (1:1). This resulted in 2.97 g (53%) of the title compound as a light yellow solid. MS-ESI: 281 (M+1).

Steps 3-5 used similar procedures for converting Intermediate 61 to Intermediate 62 shown in Scheme 38 to afford Intermediate 65 from compound 163". MS-ESI: 394 (M+1).

Scheme 40A

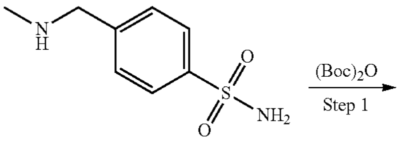

Intermediate 64

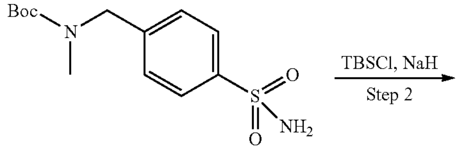

166″

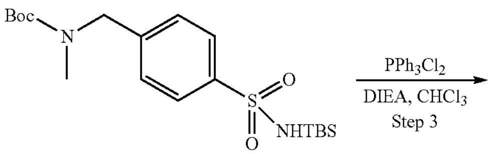

167″

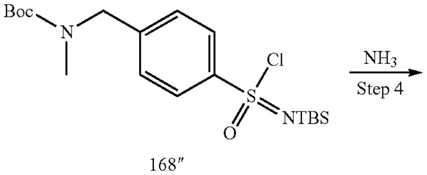

168″

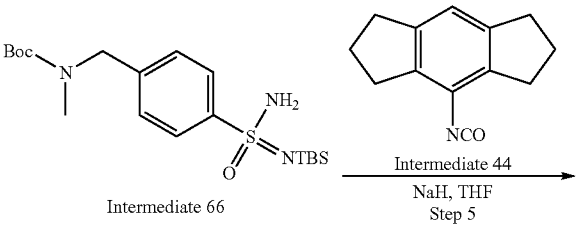

Intermediate 66

-continued

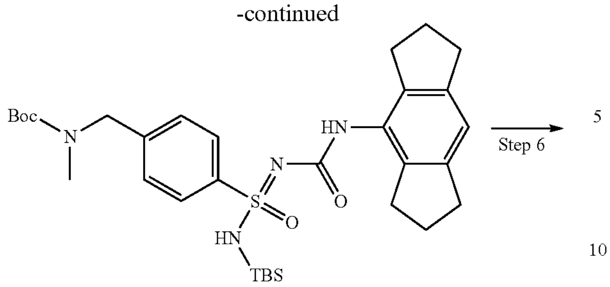

169″

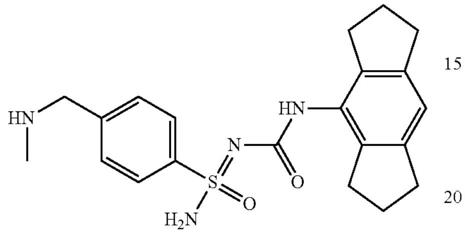

Intermediate 67

Intermediate 66

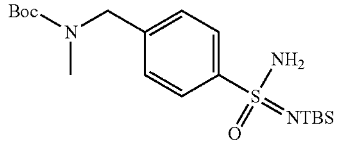

Tert-butyl 4-(N'-(tert-butyldimethylsilyl)sulfamimidoyl)benzyl(methyl)carbamate

Intermediate 67

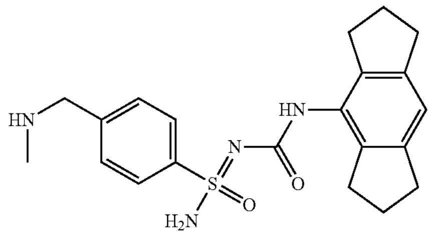

N'-((1,2,3,5,6,7-hexahydro-s-indacen-4-yl)carbamoyl)-4-((methylamino)methyl)benzenesulfonimidamide Step 1: Tert-butyl methyl(4-sulfamoylbenzyl)carbamate Into a 250-mL round-bottom flask, was placed 4-[(methylamino)methyl]benzene-1-sulfonamide (5.0 g, 25 mmol) in DCM (100 mL). To this stirred solution was added di-tert-butyl dicarbonate (6.0 g, 27.5 mmol). The resulting solution was stirred for 5 h at RT. The resulting mixture was concentrated. The residue was eluted from a silica gel column with ethyl acetate/petroleum ether (1:1). This resulted in 5.0 g (66.7%) of the title compound as a light yellow solid. MS-ESI: 301 (M+1).

Steps 2-4 used similar procedures for converting compound 148" to intermediate 59 shown in Scheme 36 to afford Intermediate 66 from compound 166". MS-ESI: 414 (M+1).

Step 5: Tert-butyl(4-(N-(tert-butyldimethylsilyl)-N'-((1,2,3,5,6,7-hexahydro-s-indacen-4-yl)carbamoyl)-sulfamidimidoyl)benzyl)(methyl)carbamate Into a 50-mL round-bottom flask, was placed tert-butyl (4-(N'-(tert-butyldimethylsilyl)sulfamidimidoyl)benzyl)(methyl)carbamate (500 mg, 1.21 mmol) in THF (15 mL). To this stirred solution was added 4-isocyanato-1,2,3,5,6,7-hexahydro-s-indacene (343 mg, 1.81 mmol) and NaH (60% wt. oil dispersion, 96.8 mg, 2.42 mmol). The resulting solution was stirred for 3 h at RT. The reaction was quenched by the addition of MeOH (10 mL). This resulted in 500 mg (67.5%) of the title compound as a white crude solid. MS-ESI: 613 (M+1).

Step 6: N'-(1,2,3,5,6,7-hexahydro-s-indacen-4-ylcarbamoyl)-4-((methylamino)methyl)benzenesulfonimidamide Into a 50-mL round-bottom flask was placed tert-butyl N-[(4-[[(tert-butyldimethylsilyl)amino]([[(1,2,3,5,6,7-hexahydro-s-indacen-4-yl)carbamoyl]imino])oxo-$\lambda^6$-sulfanyl]phenyl)methyl]-N-methylcarbamate (90 mg) and HCl in dioxane (4 M, 5.0 mL). The resulting solution was stirred for 16 h at RT. The resulting mixture was concentrated. The crude product was purified by Prep-HPLC with the following conditions: Column, Sunfire Prep C18 OBD, 10 um, 19*250 mm; mobile phase A: water (0.05% TFA) and B: ACN (20% to 50% gradient of B over 17 min); Detector, UV 220/254 nm. This resulted in 30 mg of the title compound as a white solid. MS-ESI: 399 (M+1).

Scheme 42

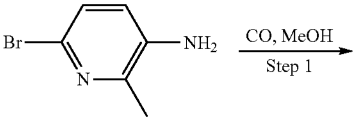

172″

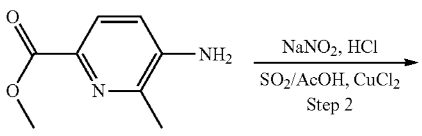

173″

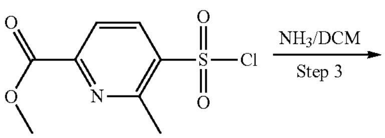

174″

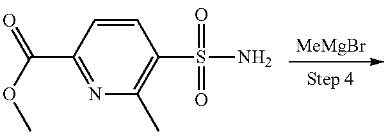

175″

-continued

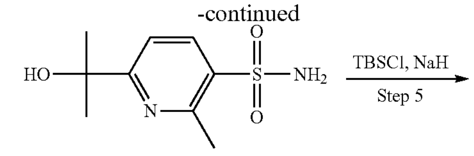

176″

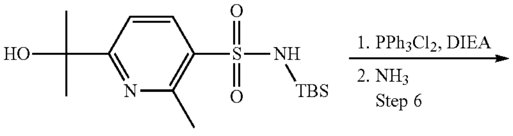

177″

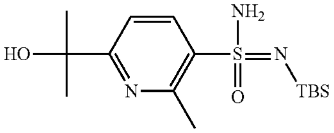

Intermediate 70

Intermediate 70

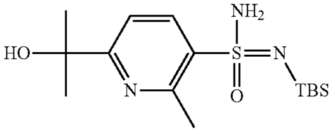

N'-(tert-butyldimethylsilyl)-6-(2-hydroxypropan-2-yl)-2-methylpyridine-3-sulfonimidamide Step 1: Methyl 5-amino-6-methylpicolinate Into a 50-mL seal tube was placed methyl 6-bromo-2-methylpyridin-3-amine (500 mg, 2.67 mmol) in MeOH (15 mL) and $Pd(OAc)_2$ (120 mg, 0.53 mmol), dppf (444 mg, 0.80 mmol), TEA (809 mg, 8.01 mmol). The seal tube was evacuated and flushed three times with CO. The resulting solution was stirred for 5 h at 100° C. under 10 atm of CO. Then the solution was concentrated under vacuum. The residue was eluted from a silica gel column with ethyl acetate/petroleum ether (1:1). This resulted in 351 mg (79.2%) of the title compound as a light yellow solid. MS-ESI: 167 (M+1).

Steps 2-4 used similar procedures for converting compound 27 to Intermediate 30 shown in Scheme 9 to afford compound 176" from compound 173". MS-ESI: 231 (M+1).

Steps 5-6 used similar procedures for converting compound 148" to intermediate 59 shown in Scheme 36 to afford Intermediate 70 from compound 176". MS-ESI: 344 (M+1).

Scheme 43

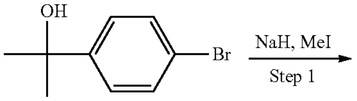

178″

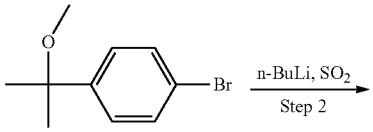

179″

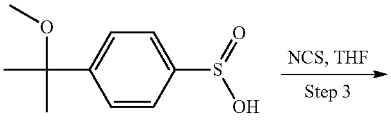

180″

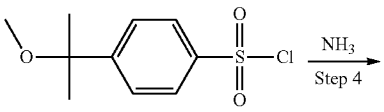

181″

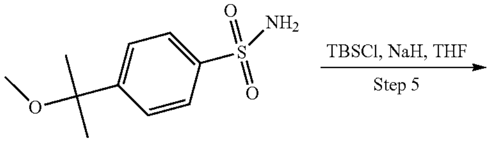

182″

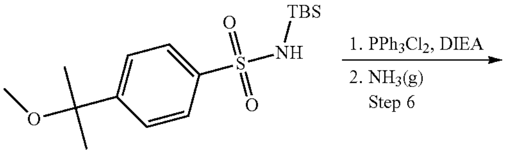

183″

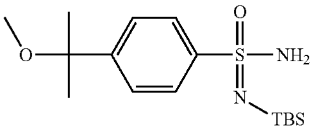

Intermediate 72

TABLE 11

The Intermediates in the following Table were prepared using the similar procedures for converting compound 172" to Intermediate 70 shown in Scheme 42 from appropriate starting materials.

| Intermediate # | Structure | IUPAC Name | Exact Mass[M + H]$^+$ |
|---|---|---|---|
| Intermediate 71 | 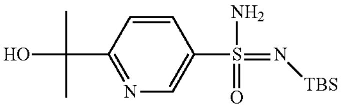 | N'-(tert-butyldimethylsilyl)-6-(2-hydroxypropan-2-yl)pyridine-3-sulfonimidamide | 330 |

Intermediate 72

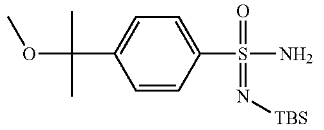

N'-(tert-butyldimethylsilyl)-4-(2-methoxypropan-2-yl)benzenesulfonimidamide

Step 1: 1-Bromo-4-(2-methoxypropan-2-yl)benzene

Into a 250-mL round-bottom flask, was placed a solution of 2-(4-bromophenyl)propan-2-ol (10 g, 46.5 mmol) in THF (50 mL). To this stirred solution was added NaH (60% wt. oil dispersion, 5.19 g, 93 mmol) at 0° C. The resulting solution was stirred for 30 min at 0° C. To this stirred solution was added MeI (6.60 g, 46.5 mmol) dropwise with stirring at 0° C. The resulting solution was allowed to react for an additional 15 h at RT. The resulting solution was quenched with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (15/85). This resulted in 8.5 g (50.3%) of the title compound as a yellow solid.

Step 2: 4-(2-Methoxypropan-2-yl)benzenesulfinic Acid

Into a 250-mL 3-necked round-bottom flask purged and maintained with an inert atmosphere of nitrogen, was placed a solution of 1-bromo-4-(2-methoxypropan-2-yl)benzene (5.0 g, 21.8 mmol) in THF (50 mL). To this stirred solution was added n-BuLi (13 mL, 32.7 mmol, 2.5 M) dropwise with stirring at −78° C. The resulting solution was stirred for 30 min at −78° C. $SO_2$ (g) was introduced into the stirring solution at −78° C. The resulting solution was allowed to react for an additional 60 min at RT. The resulting mixture was concentrated. This resulted in 6.0 g (crude) of the title compound as a yellow solid. MS-ESI: 213 (M−1)

Step 3: 4-(2-Methoxypropan-2-yl)benzenesulfonyl Chloride

Into a 50-mL round-bottom flask, was placed 4-(2-methoxypropan-2-yl)benzene-1-sulfinic acid (4.9 g, 22.9 mmol) in THF (50 mL). To this stirred solution was added NCS (4.58 g, 34.3 mmol). The resulting solution was stirred for 30 min at 0° C. The mixture was allowed to react for an additional 60 min at RT. $NH_3$ (g) was introduced into the reaction solution. The resulting solution was allowed to react for an additional 120 min at RT. The resulting mixture was concentrated. The residue was eluted from a silica gel column with ethyl acetate/petroleum ether (1/4). This resulted in 4.3 g (82%) of the title compound as a yellow solid.

Step 4: 4-(2-Methoxypropan-2-yl)benzenesulfonamide

Into a 250-mL round-bottom flask was placed 4-(2-methoxypropan-2-yl)benzene-1-sulfonyl chloride (4.3 g, 17.3 mmol) in DCM (50 mL). $NH_3$ (g) was introduced into the reaction solution at 0° C. The resulting solution was stirred for 180 min at RT. The resulting mixture was concentrated. The residue was eluted from a silica gel column with ethyl acetate/petroleum ether (1/3). This resulted in 3.9 g (98.5%) of the title compound as a yellow solid. MS-ESI: 230 (M+1).

Step 5: N-(tert-butyldimethylsilyl)-4-(2-methoxypropan-2-yl)benzenesulfonamide

Into a 100-mL round-bottom flask, was placed a solution of 4-(2-methoxypropan-2-yl)benzene-1-sulfonamide (4.0 g, 17.5 mmol) in THF (40 mL). To this stirred solution was added NaH (1.4 g, 34.9 mmol, 60% wt. oil dispersion) and TBSCl (3.16 g, 21 mmol) at 0° C. The resulting solution was allowed to react with stirring for 15 h at RT. The resulting solution was quenched with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (30/70). This resulted in 2.3 g (38.4%) of the title compound as a yellow solid. MS-ESI: 344 (M+1)

Step 6: N'-(tert-butyldimethylsilyl)-4-(2-methoxypropan-2-yl)benzenesulfonimidamide Into a 500-mL 3-necked round-bottom flask purged and maintained with an inert atmosphere of nitrogen, was placed the solution of $PPh_3Cl_2$ (12.4 g, 37.3 mmol) in chloroform (150 mL). This was followed by the addition of DIEA (9.63 g, 74.5 mmol) dropwise with stirring at RT. The resulting solution was stirred for 10 min at RT and the reaction system was cooled to 0° C. To this was added a solution of N-(tert-butyldimethylsilyl)-4-(2-methoxypropan-2-yl)benzene-1-sulfonamide (3.2 g, 9.31 mmol) in chloroform (30 mL) dropwise with stirring at 0° C. The resulting solution was stirred for 30 min at 0° C. To the mixture was introduced $NH_3$ gas bubble for 15 min at 0° C. The resulting solution was stirred for 2 h at RT. The resulting solution was diluted with 100 mL of water. The resulting solution was extracted with 3×200 mL of DCM and the organic layers combined and dried over anhydrous sodium sulfate and concentrated under vacuum. The residue was eluted from a silica gel column with ethyl acetate/petroleum ether (36/64). This resulted in 1.4 g (36.5%) of the title compound as a yellow solid. MS-ESI. 343 (M+1)

Scheme 44

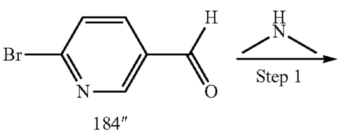

184″

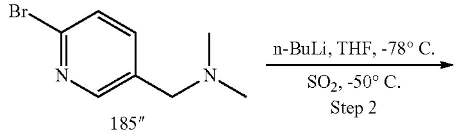

185″

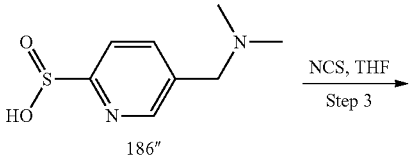

186″

-continued

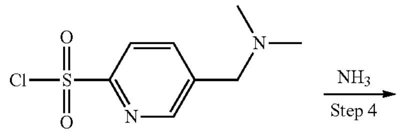

187″

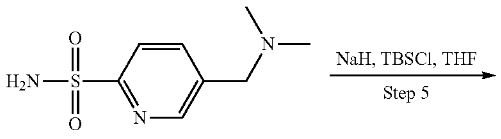

188″

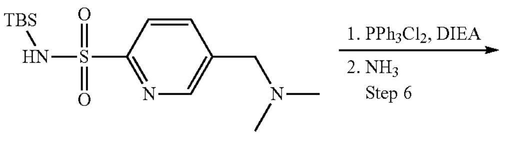

189″

-continued

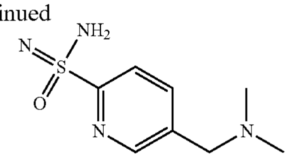

Intermediate 73

Intermediate 73

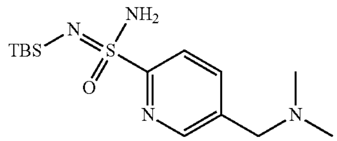

N'-(tert-butyldimethylsilyl)-5-((dimethylamino) methyl)pyridine-2-sulfonimidamide Step 1: (6-Bromopyridin-3-yl)-N,N-dimethylmethanamine Into a 500-mL 3-necked round-bottom flask purged and maintained with an inert atmosphere of nitrogen, were placed $Ti(OEt)_4$ (12.3 g, 53.8 mmol) and dimethylamine (4.85 g, 108 mmol) in Me OH (50 mL) at RT. To a stirred solution was added 6-bromopyridine-3-carbaldehyde (5.0 g, 26. 9 mmol) in MeOH (30 mL) dropwise at 0° C. Then the reaction solution was stirred at RT for 3 h. $NaBH_4$ (1.02 g, 26.9 mmol) was added to the mixture and the resulting solution was stirred over night at RT. The reaction was quenched by the addition of water/ice (30 mL) at 0° C. The result in g mixture was concentrated under reduced pressure. Then the resulting mixture extracted with ethyl acetate (3×50 mL) and the organic layers combined and dried over anhydrous sodium sulfate and concentrated under vacuum. The residue was eluted from a silica gel column with ethyl acetate/petroleum ether (5:1) to afford the title compound (3.5 g, 60.5%) as a yellow oil. MS-ESI: 216/218 (M+1).

Steps 2-6 used similar procedures for converting compound 179" to Intermediate 72 shown in Scheme 43 to afford Intermediate 73 from compound 185. MS-ESI: 329 (M+1).

TABLE 12

The Intermediates in the following Table were prepared using the similar procedures for converting compound 184" to Intermediate 73 shown in Scheme 44 from appropriate starting materials.

| Intermediate # | Structure | IUPAC Name | Exact Mass[M + H]$^+$ |
|---|---|---|---|
| Intermediate 74 | 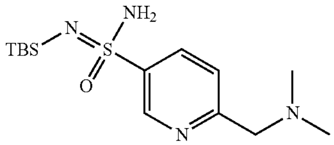 | N'-(tert-butyldimethylsilyl)-6-((dimethylamino)methyl)pyridine-3-sulfonimidamide | 329 |

Scheme 45

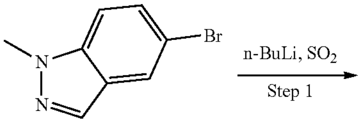

190″

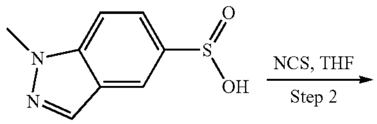

191″

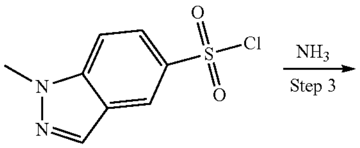

192″

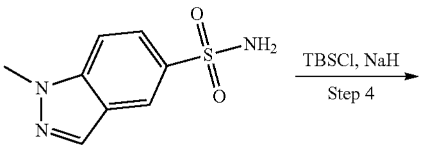

193″

-continued

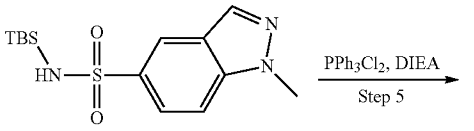

194″

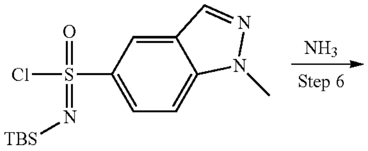

195″

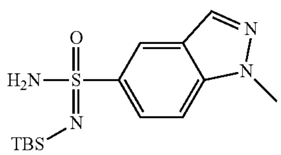

Intermediate 75

Intermediate 75

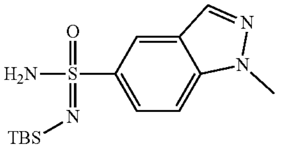

N'-(tert-butyldimethylsilyl)-1-methyl-1H-indazole-5-sulfonimidamide

Steps 1-6 used similar procedures for converting compound 179" to Intermediate 72 shown in Scheme 43 to afford Intermediate 75 from compound 190". MS-ESI: 325 (M+1).

Scheme 46

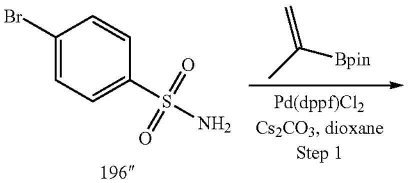

196″

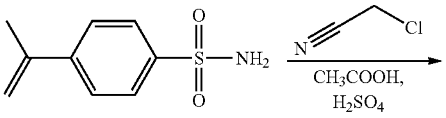

197″

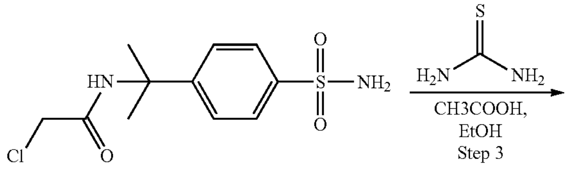

198″

-continued

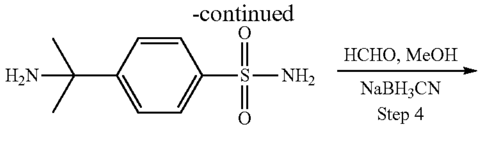

199″

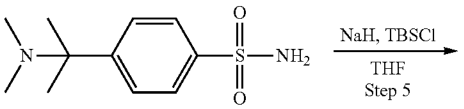

200″

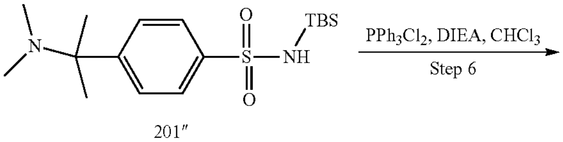

201″

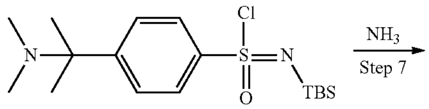

202″

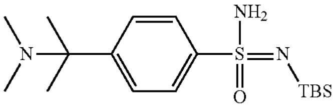

Intermediate 76

Intermediate 76

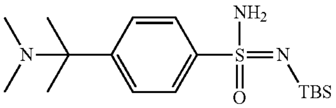

N'-(tert-butyldimethylsilyl)-4-(2-(dimethylamino)propan-2-yl)benzenesulfonimidamide Step 1: 4-(Prop-1-en-2-yl)benzenesulfonamide Into a 250-mL round-bottom flask purged and maintained with an inert atmosphere of nitrogen, was placed 4-bromobenzene-1-sulfonamide (5.0 g, 21.2 mmol) in dioxane (100 mL) and $H_2O$ (15 mL). To this stirred solution was added 4,4,5,5-tetramethyl-2-(prop-1-en-2-yl)-1,3,2-dioxaborolane (14.2 g, 84.7 mmol), $Pd(dppf)Cl_2$ (4.65 g, 6.35 mmol) and $Cs_2CO_3$ (13.8 g, 42.4 mmol). The resulting solution was stirred for 15 h at 100° C.

The resulting mixture was concentrated under reduced pressure. The residue was eluted from a silica gel column with ethyl acetate/petroleum ether (40/60). This resulted in 3.6 g (86.2%) of the title compound as a yellow solid. MS-ESI: 198 (M+1).

Step 2: 2-Chloro-N-(2-(4-sulfamoylphenyl)propan-2-yl)acetamide

Into a 1.0-L round-bottom flask, was placed 4-(prop-1-en-2-yl)benzene-1-sulfonamide (5.0 g, 25.4 mmol) in $H_2SO_4$ (50 mL) and AcOH (250 mL). To the stirred solution was added 2-chloroacetonitrile (38.3 g, 507 mmol). The resulting solution was stirred for 30 min at 0° C. The resulting solution was allowed to react for an additional 15 h at RT. The pH value of the solution was adjusted to 7 with $Na_2CO_3$ (5.0 M). Then the resulting mixture was extracted with ethyl acetate (3×200 mL) and the organic layers combined and dried over anhydrous sodium sulfate and concentrated under vacuum. The residue was eluted from a silica gel column with ethyl acetate/petroleum ether (2/3). This resulted in 4.2 g (57%) of the title compound as yellow oil. MS-ESI: 291 (M+1).

Step 3: 4-(2-Aminopropan-2-yl)benzenesulfonamide

Into a 250-mL round-bottom flask, was placed 2-chloro-N-[2-(4-sulfamoylphenyl)propan-2-yl]acetamide (4.2 g, 14.5 mmol) in $CH_3COOH$ (15 mL) and ethanol (75 mL). To this stirred solution was added thiourea (1.32 g, 17.3 mmol). The resulting solution was stirred for 16 h at 85° C. The resulting mixture was washed with 100 ml of $H_2O$ and extracted with 3×250 mL of ethyl acetate and the organic layers combined and dried over anhydrous sodium sulfate and concentrated under vacuum. This resulted in 2.3 g (54.3%) of the title compound as a yellow solid. MS-ESI: 215 (M+1).

Step 4: 4-(2-(Dimethylamino)propan-2-yl)benzenesulfonamide

Into a 250-mL round-bottom flask, was placed 4-(2-aminopropan-2-yl)benzene-1-sulfonamide (2.14 g, 9.99 mmol) in MeOH (50 mL). To this stirred solution was added HCHO (37% wt., 599 mg, 20 mmol) and $NaBH_3CN$ (1.86 g, 30 mmol). The resulting solution was stirred for 120 min at RT. The resulting mixture was diluted with 100 mL of water and extracted with 3×250 mL of ethyl acetate and the organic layers combined and dried over anhydrous sodium sulfate and concentrated under vacuum The residue was eluted from a silica gel column with ethyl acetate/petroleum ether (30/70). This resulted in 1.0 g (41.3%) of the title compound as a yellow solid. MS-ESI: 243 (M+1).

Steps 5-7 used similar procedures for converting compound 148" to intermediate 59 shown in Scheme 36 to afford Intermediate 76 from compound 200. MS-ESI: 356 (M+1).

Scheme 47

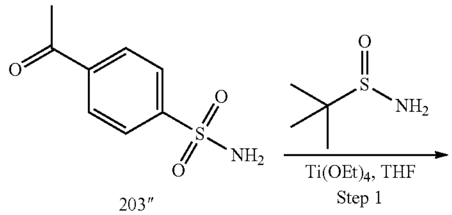

203″

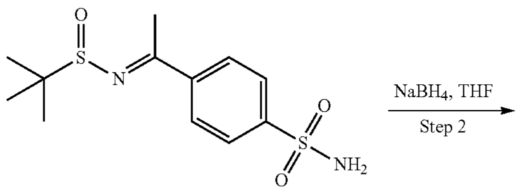

204″

-continued

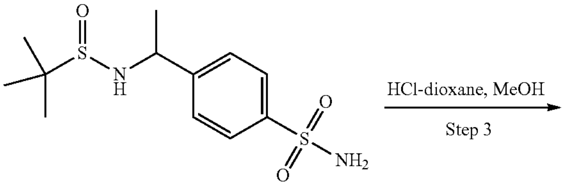

205″

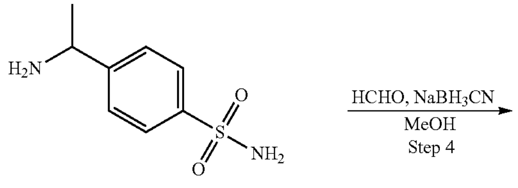

206″

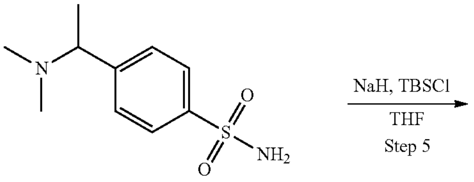

207″

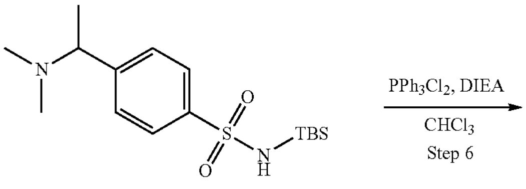

208″

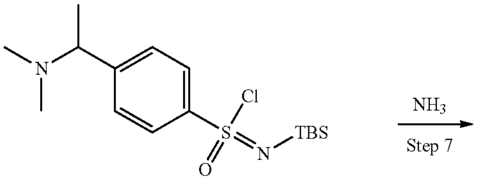

209″

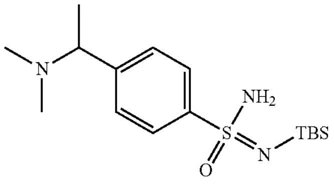

Intermediate 77

Intermediate 77

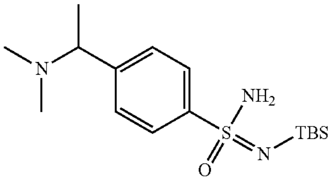

N'-(tert-butyldimethylsilyl)-4-(1-(dimethylamino)ethyl)benzenesulfonimidamide

Step 1: (E)-4-(1-((tert-butylsulfinyl)imino)ethyl)benzenesulfonamide

Into a 250-mL 3-necked round-bottom flask purged and maintained with an inert atmosphere of nitrogen was added 2-methylpropane-2-sulfinamide (3.04 g, 25.1 mmol) in THF (50 mL). To this stirred solution was added $Ti(OEt)_4$ (11.5 g, 50.2 mmol) and 4-acetylbenzene-1-sulfonamide (5.0 g, 25.1 mmol) in portions at RT. The resulting mixture was stirred for overnight at 70° C. under nitrogen atmosphere. The reaction was quenched with Water (20 mL) at 0° C. The resulting mixture was extracted with ethyl acetate (3x30 mL). The combined organic layers were dried over anhydrous $Na_2SO_4$. After filtration, the filtrate was concentrated under reduced pressure. The residue was purified by silica gel column chromatography, eluted with ethyl acetate/petroleum ether (1:1) to afford the title compound (5.0 g, 75.8%) as a yellow solid. MS-ESI: 303 (M+1).

Step 2: 4-(1-((Tert-butylsulfinyl)amino)ethyl)benzenesulfonamide

Into a 500 mL round-bottom flask were added 4-[(1E)-1-[(2-methylpropane-2-sulfinyl)imino]ethyl]benzene-1-sulfonamide (4.65 g, 15.4 mmol) in THF (200 mL) at RT. To this stirred solution was added $NaBH_4$ (1.16 g, 30.8 mmol) in portions at 0° C. under nitrogen atmosphere. The resulting mixture was stirred for 4 h at RT under nitrogen atmosphere. The reaction was quenched by the addition of HCl (2M 50 mL) at 0° C. The resulting mixture was extracted with ethyl acetate (3x50 mL). The combined organic layers were dried over anhydrous $Na_2SO_4$. After filtration, the filtrate was concentrated under reduced pressure to afford the title compound (4.5 g, 96.1%) as a white solid. MS-ESI: 305 (M+1).

Step 3: 4-(1-Aminoethyl)benzenesulfonamide

Into a 250 mL round-bottom flask were added 4-[1-[(2-methylpropane-2-sulfinyl)amino]ethyl]benzene-1-sulfonamide (4.4 g, 14.5 mmol) and MeOH (50 mL) at room temperature. To this stirred solution was added HCl (gas) in 1,4-dioxane (8.0 mL, 26.3 mmol) in one portions at RT. The resulting mixture was stirred overnight at RT. The resulting mixture was concentrated under reduced pressure. The residue was purified by reverse flash chromatography with the following conditions (column, C18 silica gel; mobile phase, MeCN in water, 10% to 50% gradient in 10 min; detector, UV 254 nm.) to afford the title compound (2.6 g, 89.7%) as a white solid. MS-ESI: 201 (M+1).

Step 4: 4-(1-(Dimethylamino)ethyl)benzenesulfonamide

Into a 250 mL round-bottom flask was added 4-(1-aminoethyl)benzene-1-sulfonamide (2.0 g, 9.99 mmol) and MeOH (60 mL) at RT. To this stirred solution was added HCHO (37% wt., 1.61 g, 53.6 mmol) and $NaBH_3CN$ (1.25 g, 20 mmol) in portions at RT. The resulting mixture was stirred overnight at RT. The reaction solution was diluted with 100 mL of water and extracted with 3x100 mL of ethyl acetate and the organic layers combined and dried over anhydrous sodium sulfate and concentrated under vacuum. The residue was eluted from a silica gel column with ethyl acetate/petroleum ether. The residue was purified by silica gel column chromatography, eluted with ethyl acetate/petroleum ether (1:2) to afford the title compound (1.5 g, 65.8%) as a white solid. MS-ESI: 229 (M+1).

Steps 5-7 used similar procedures for converting compound 148" to intermediate 59 shown in Scheme 36 to afford Intermediate 77 from compound 207". MS-ESI: 342 (M+1).

Scheme 48

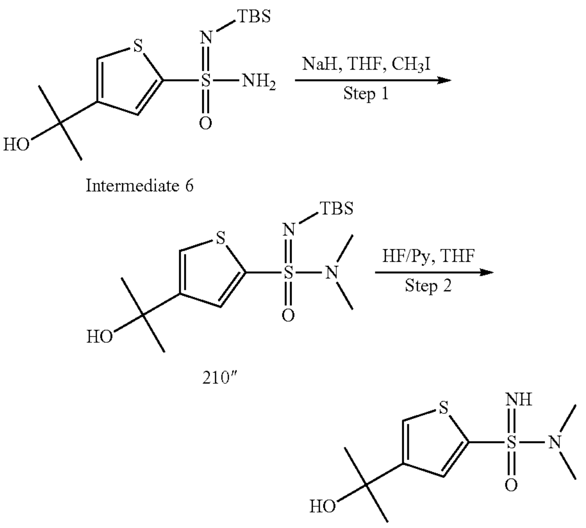

Intermediate 6

210"

Intermediate 78

Intermediate 78

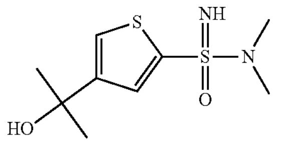

4-(2-Hydroxypropan-2-yl)-N,N-dimethylthiophene-2-sulfonimidamide

Step 1: N'-(tert-butyldimethylsilyl)-4-(2-hydroxypropan-2-yl)-N,N-dimethylthiophene-2-sulfonimidamide Into a 50-mL 3-necked round-bottom flask, was placed N-(tert-butyldimethylsilyl)-4-(2-hydroxypropan-2-yl) thiophene-2-sulfonoimidamide (300 mg, 0.90 mmol) in THF (3.0 mL). To the solution were added NaH (60% wt. oil dispersion, 53.8 mg, 1.35 mmol) at −10° C. in ethanol/ice bath. To the solution were added iodomethane (0.50 mL) dropwise with stirring at 0° C. in 30 min. The resulting solution was stirred for 30 min at RT. The reaction was then quenched by the addition of $NH_4Cl$(aq.). The resulting solution was extracted with 3x20 mL of ethyl acetate and the organic layers combined, dried over anhydrous sodium sulfate and concentrated under vacuum. The residue was eluted from a silica gel column with ethyl acetate/petroleum ether (1:5). This resulted in 252 mg (77.5%) of the title compound as a white solid. MS-ESI: 363 (M+1).

Step 2: N'-(tert-butyldimethylsilyl)-4-(2-hydroxy-propan-2-yl)-N,N-dimethylthiophene-2-sulfonimid-amide Into a 50-mL round-bottom flask, was placed N-(tert-butyldimethylsilyl)-4-(2-hydroxypropan-2-yl)-N,N-dimethylthiophene-2-sulfonoimidamide (200 mg, 0.55 mmol) in THF (10 mL). To the solution was added HF/Py (70% wt., 0.10 mL) dropwise with stirring at RT. The resulting solution was stirred for 60 min at RT. The resulting mixture was concentrated under vacuum. The resulting solution was extracted with ethyl acetate (3×10 mL), the organic layers combined and dried over anhydrous sodium sulfate. The residue was eluted from a silica gel column with ethyl acetate. This resulted in 127 mg (92.7%) of the title compound as a white solid. MS-ESI: 249 (M+1).

Scheme 49

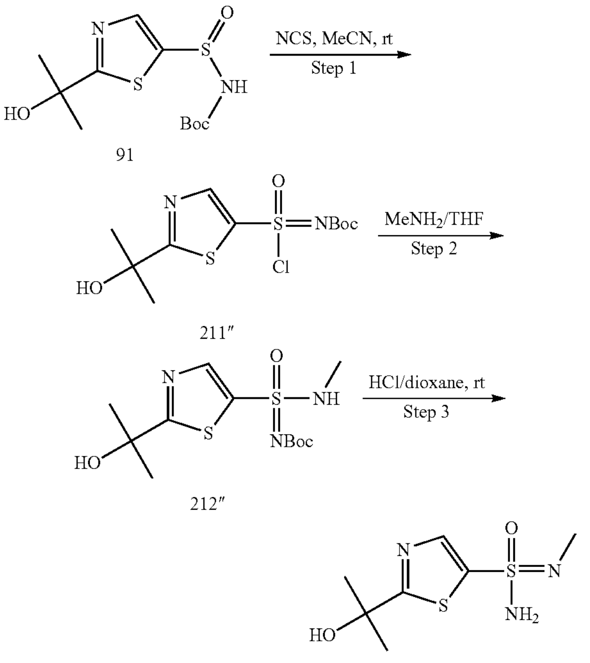

91
211″
212″

Intermediate 79

Intermediate 79

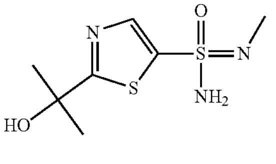

2-(2-Hydroxypropan-2-yl)-N-methylthiazole-5-sulfonimidamide

Step 1: Tert-butyl (chloro(2-(2-hydroxypropan-2-yl)thiazol-5-yl)(oxo)-λ$^6$-sulfaneylidene)carbamate Into a 1.0-L round-bottom flask, was placed tert-butyl N-[[2-(2-hydroxypropan-2-yl)-1,3-thiazol-5-yl] sulfinyl] carbamate (100 g, 326 mmol) in ACN (500 mL). To the stirred solution was added NCS (65.4 g, 490 mmol). The resulting solution was stirred for 2 h at RT. The resulted solution was concentrated. This resulted in 120 g (crude) of the title compound as yellow oil. MS-ESI. 341/343 (M+1).

Step 2: Tert-butyl((2-(2-hydroxypropan-2-yl)thiazol-5-yl)(methylamino)(oxo)-λ$^6$-sulfaneylidene) carbamate Into a 250-mL round-bottom flask, was placed tert-butyl (chloro(2-(2-hydroxypropan-2-yl)thiazol-5-yl)(oxo)-λ$^6$-sulfaneylidene)carbamate (10 g, 29.3 mmol) in THF (100 mL). To the stirred solution was added $CH_3NH_2$ (1.82 g, 58.6 mmol). The resulting solution was stirred for 2 h at RT. The resulted solution was concentrated. The residue was eluted from a silica gel column with ethyl acetate/petroleum ether (1:1). This resulted in 6.1 g (62%) of the title compound as a yellow solid. MS-ESI: 336 (M+1).

Step 3: 2-(2-Hydroxypropan-2-yl)-N'-methylthiazole-5-sulfonimidamide

Into a 100-mL round-bottom flask, was placed tert-butyl ((2-(2-hydroxypropan-2-yl)thiazol-5-yl)(methylamino)(oxo)-λ$^6$-sulfaneylidene) carbamate (3.0 g, 8.94 mmol) in HCl (gas) in 1,4-dioxane (8 mL, 26.3 mmol) in one portion at RT. The resulting solution was stirred for 60 min at RT. The resulting mixture was concentrated under vacuum. This resulted in 2.10 g (crude) of the title compound as a yellow solid. MS-ESI: 236 (M+1).

Scheme 50A

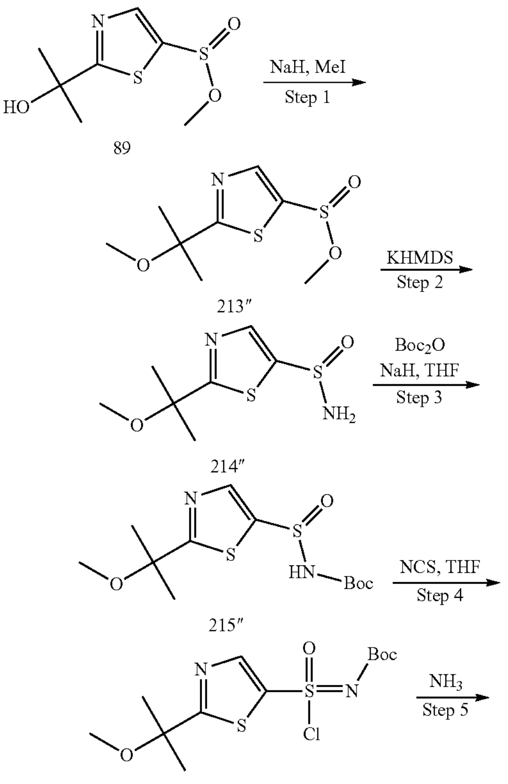

89
213″
214″
215″
216″

-continued

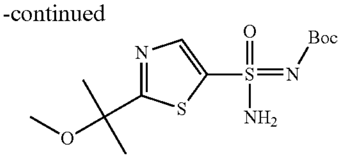

Intermediate 80

Intermediate 80

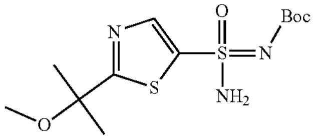

Tert-butyl (amino(2-(2-methoxypropan-2-yl)thiazol-5-yl)(oxo)-$\lambda^6$-sulfaneylidene)carbamate Step 1: Methyl 2-(2-methoxypropan-2-yl)thiazole-5-sulfinate Into a 1-L round-bottom flask, was placed a solution of methyl 2-(2-hydroxypropan-2-yl)-1,3-thiazole-5-sulfinate (40 g, 181 mmol) in THF (500 mL). To this stirred solution was added NaH (60% wt. oil dispersion, 7.95 g, 199 mmol) in three portions at 0° C. in an ice/ethanol bath. To this reaction solution was added MeI (51.3 g, 362 mmol) dropwise with stirring at 0° C. in an ice/ethanol bath. The resulting solution was stirred for 3 h at RT. The reaction was then quenched by the addition of water (50 mL) at 0° C. The resulting solution was extracted with 3x300 mL of ethyl acetate and the organic layers combined and dried over anhydrous sodium sulfate and concentrated under vacuum. This resulted in 32 g (75.3%) of the title compound as a white solid. MS-ESI: 236 (M+1).

Step 2: 2-(2-Methoxypropan-2-yl)thiazole-5-sulfinamide

Into a 1-L 3-necked round-bottom flask purged and maintained with an inert atmosphere of nitrogen, was placed a solution of methyl 2-(2-methoxypropan-2-yl)-1,3-thiazole-5-sulfinate (20 g, 85 mmol) in THF (500 mL). This was followed by the addition of KHMDS (500 mL, 1.0 mole, 2 M) dropwise with stirring at −78° C. in a liquid nitrogen/ethanol bath. The resulting solution was stirred for 3 h at −78° C. in a liquid nitrogen/ethanol bath. The reaction was quenched by the addition of water (50 mL). The resulting solution was extracted with 3x300 mL of ethyl acetate dried over anhydrous sodium sulfate and concentrated under vacuum. The residue was eluted from a silica gel column with ethyl acetate/petroleum ether (1:3). This resulted in 14 g (74.8%) of the title compound as a white solid. MS-ESI: 221.0 (M+1).

Step 3: Tert-butyl ((2-(2-methoxypropan-2-yl)thiazol-5-yl)sulfinyl)carbamate

Into a 500-mL round-bottom flask purged and maintained with an inert atmosphere of nitrogen, was placed a solution of 2-(2-methoxypropan-2-yl)-1,3-thiazole-5-sulfinamide (10 g, 45.4 mmol) in THF (250 mL). To this stirred solution was added NaH (60% wt. oil dispersion, 3.63 g, 90.8 mmol) in three times at 0° C. in an ice/ethanol bath. To this solution was added $Boc_2O$ (9.91 g, 45.4 mmol) in portions at 0° C. in an ice/ethanol bath. The resulting solution was stirred for 3 h at RT. The reaction was then quenched by the addition of water (50 mL). The resulting solution was extracted with 3x300 mL of ethyl acetate concentrated under vacuum. This resulted in 12 g (82.5%) of the title compound as a white solid. MS-ESI: 321.1 (M+1).

Step 4: Tert-butyl (chloro(2-(2-methoxypropan-2-yl)thiazol-5-yl)(oxo)-$\lambda^6$-sulfaneylidene)carbamate Into a 500-mL round-bottom flask purged and maintained with an inert atmosphere of nitrogen, was placed a solution of tert-butyl N-[[2-(2-methoxypropan-2-yl)-1,3-thiazol-5-yl]sulfinyl]carbamate (11 g, 34.3 mmol) in THF (200 mL). NCS (13.8 g, 103 mmol) was added to the reaction solution in one portion at RT. The resulting solution was stirred for 3 h at RT. This reaction solution was used to the next step directly without further purification.

Step 5: Tert-butyl (amino(2-(2-methoxypropan-2-yl)thiazol-5-yl)(oxo)-$\lambda^6$-sulfaneylidene)carbamate Into a 500-mL round-bottom flask purged and maintained with an inert atmosphere of nitrogen, was placed a solution of tert-butyl N-[[2-(2-methoxypropan-2-yl)-1,3-thiazol-5-yl]sulfinyl]carbamate (9.0 g, 28.9 mmol) in THF (200 mL). To the mixture was added introduced $NH_3$ gas bubble for 15 min at 0° C. The resulting solution was stirred for 1 h at RT. The resulting mixture was concentrated. The residue was eluted from a silica gel column with ethyl acetate/petroleum ether (1:1). This resulted in 7 g (72.3%) of the title compound as a white solid. MS-ESI: 336.1 (M+1).

Scheme 51

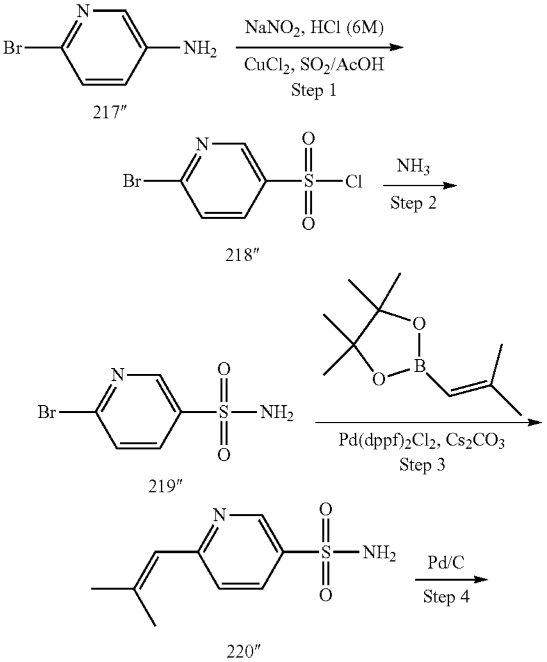

217″

218″

219″

220″

-continued

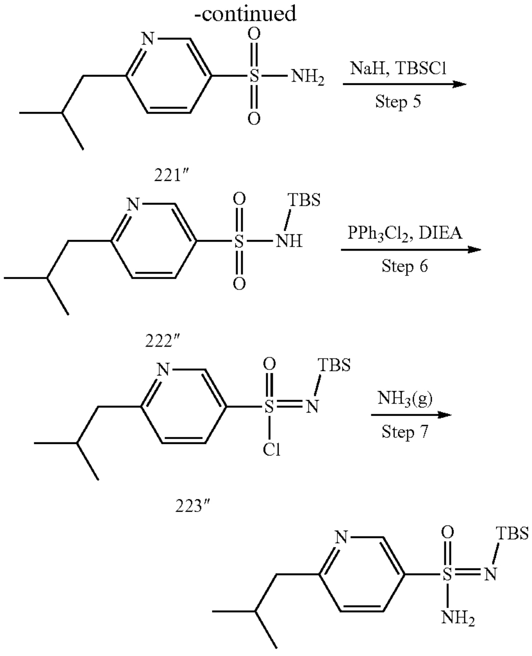

221″

222″

223″

Intermediate 81

Intermediate 81

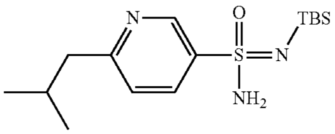

N'-(tert-butyldimethylsilyl)-6-isobutylpyridine-3-sulfonimidamide

Steps 1-2 used similar procedures for converting compound 27 to Intermediate 29 shown in Scheme 9 to afford compound 219" from compound 217". MS-ESI: 238 (M+1).

Step 3: 6-(2-Methylprop-1-enyl)pyridine-3-sulfonamide

Into a 500 mL round-bottom flash were added 6-bromopyridine-3-sulfonamide (5.5 g, 23.2 mmol) and dioxane (150 mL) and water (15 mL) at RT. To this solution was added Pd(dppf)$Cl_2$ (1.7 g, 2.32 mmol), $Cs_2CO_3$ (15.1 g, 46.4 mmol) and 4,4,5,5-tetramethyl-2-(2-methylprop-1-en-1-yl)-1,3,2-dioxaborolane (8.45 g, 46.4 mmol) in one portion at RT under nitrogen atmosphere. The resulting mixture was stirred overnight at 100° C. under nitrogen atmosphere. The resulting mixture was concentrated under reduced pressure. The residue was purified by silica gel column chromatography with ethyl acetate/petroleum ether (1:1) to afford title compound (4.0 g, 81.2%) as a light yellow oil. MS-ESI: 213 (M+1).

Step 4: 6-Isobutylpyridine-3-sulfonamide

Into a 250 mL 3-necked round-bottom flask was added 6-(2-methylprop-1-en-1-yl)pyridine-3-sulfonamide (4 g, 18.8 mmol) and MeOH (100 mL) at RT under nitrogen atmosphere. To this stirred solution was added Pd/C (wet 10% wt., 900 mg). The flask was evacuated and filled three times with hydrogen. The resulting mixture was stirred overnight at RT under hydrogen atmosphere. The resulting mixture was filtered; the filter cake was washed with MeOH (3x20 mL). The filtrate was concentrated under reduced pressure. The crude product of the title compound (3.8 g) was used to the next step directly without further purification. MS-ESI: 215 (M+1).

Steps 5-7 used similar procedures for converting compound 148" to intermediate 59 shown in Scheme 36 to afford intermediate 81 from compound 221". MS-ESI: 328 (M+1).

TABLE 13

The Intermediates in the following Table were prepared using the similar procedures for converting compound 217" to Intermediate 81 shown in Scheme 51 from appropriate starting materials.

| Intermediate # | Structure | IUPAC Name | Exact Mass $[M + H]^+$ |
|---|---|---|---|
| Intermediate 82 | 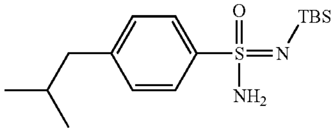 | N'-(tert-butyldimethylsilyl)-4-isobutylbenzenesulfonimidamide | 327 |

Scheme 52

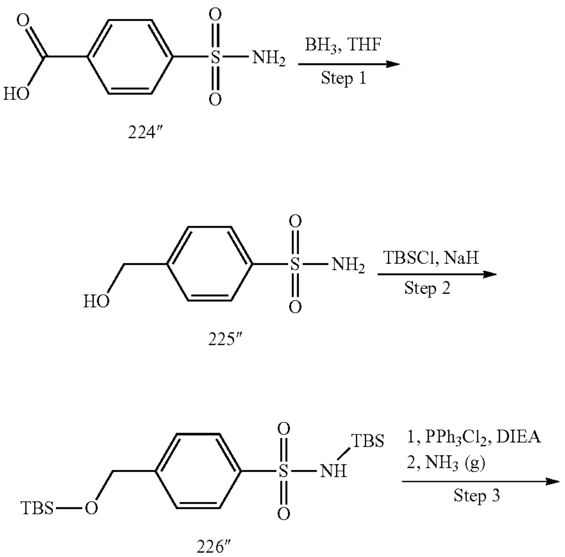

224″

225″

226″

-continued

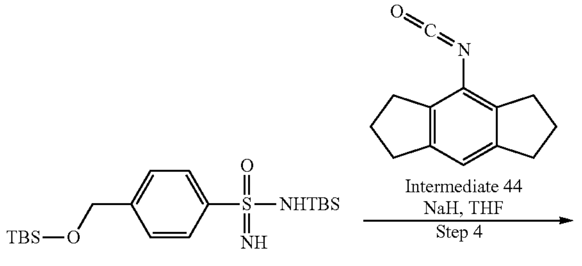

Intermediate 83

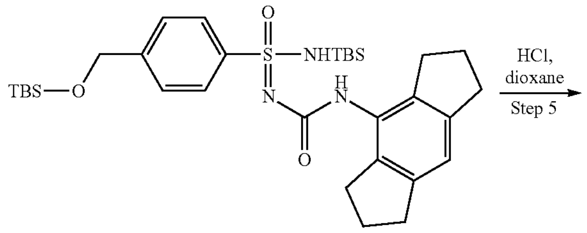

227″

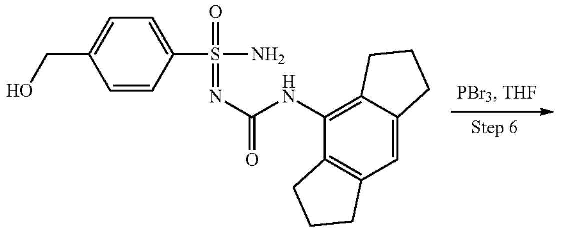

Example 233

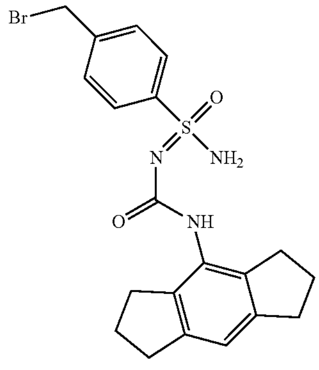

Intermediate 84

Intermediate 83

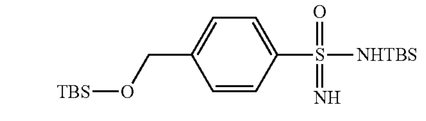

N-(tert-butyldimethylsilyl)-4-((tert-butyldimethylsilyloxy)methyl)benzenesulfonimidamide Example 233 (Compound 342)

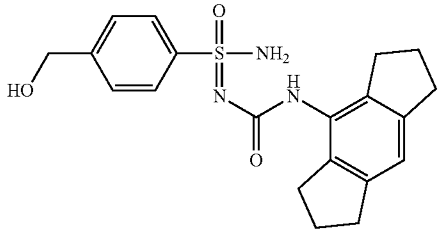 [SMILES: NS(=O)(=NC(=O)Nc1c2c(cc3c1CCC3)CCC2)c1ccc(CO)cc1]

N'-((1,2,3,5,6,7-hexahydro-s-indacen-4-yl)carbamoyl)-4-(hydroxymethyl)benzenesulfonimidamide Step 1: 4-(Hydroxymethyl)benzenesulfonamide Into a 100-mL round-bottom flask, was placed 4-sulfamoylbenzoic acid (1.0 g, 4.97 mmol) in THF (15 mL). This was followed by the addition of $BH_3$-THF (14.3 mL, 149 mmol) dropwise with stirring at 0° C. in an ice/ethanol bath. The resulting solution was stirred for 12 h at RT. The reaction was then quenched by the addition of HCl (50 mL, 2 M) dropwise in an ice bath and stirred for 1 h at RT. The mixture was extracted with 8×50 mL of ethyl acetate. The organic layers were combined and concentrated. This resulted in 800 mg (860%) of the title compound as a yellow solid. MS-ESI: 188 (M+1).

Steps 2-3 used similar procedures for converting compound 148" to Intermediate 59 shown in Scheme 36 to afford Intermediate 83 from compound 225". MS-ESI: 415 (M+1). Steps 4-5 used similar procedures for converting compound 166" to Intermediate 67 shown in Scheme 40A to afford compound Example 233 from Intermediate 83. MS-ESI: 386 (M+1).

Intermediate 84

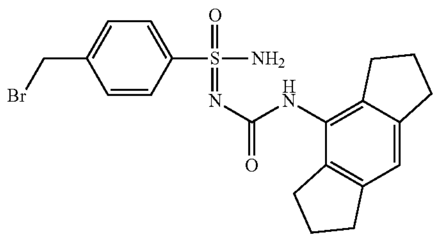

4-(Bromomethyl)-N'-(1,2,3,5,6,7-hexahydro-s-indacen-4-ylcarbamoyl)benzenesulfonimidamide Step 6: 4-(Bromomethyl)-N'-(1,2,3,5,6,7-hexahydro-s-indacen-4-ylcarbamoyl)benzenesulfonimidamide Into a 250-mL round-bottom flask purged and maintained with an inert atmosphere of nitrogen, was placed 1-[amino[4-(hydroxymethyl)phenyl]oxo-λ$^6$-sulfanylidene]-3-(1,2,3,5,6,7-hexahydro-s-indacen-4-yl)urea (1.0 g, 2.59 mmol) in THF (50 mL). To the stirred solution was added $PBr_3$ (702 mg, 2.59 mmol) in portions. The resulting solution was stirred for 3 h at RT. The solids were collected by filtration. This resulted in 500 mg (43%) of the title compound as a white solid. MS-ESI: 449/411 (M+1).

Scheme 53

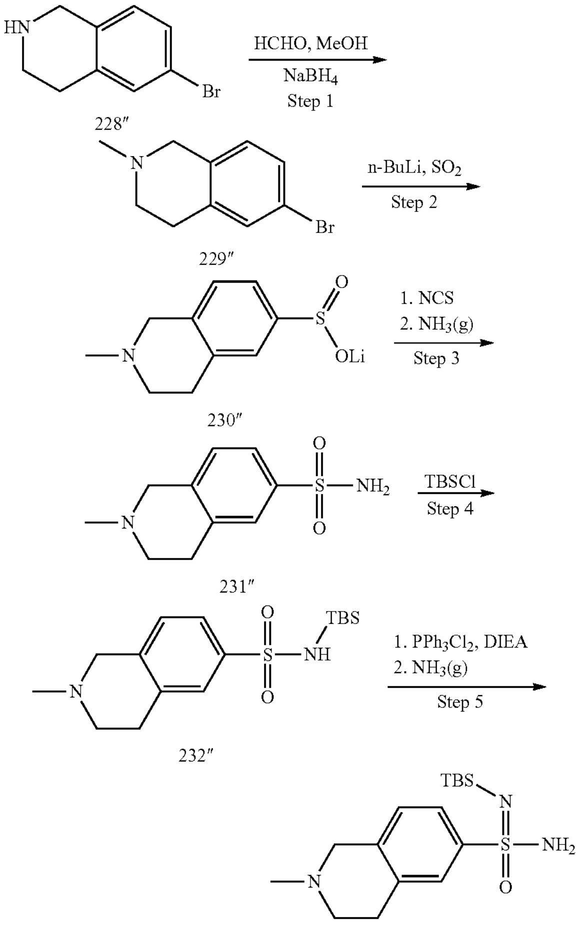

Intermediate 85

Intermediate 85

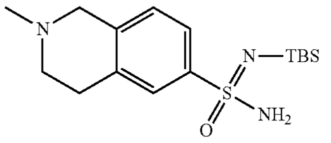

N'-(tert-butyldimethylsilyl)-2-methyl-1,2,3,4-tetrahydroisoquinoline-6-sulfonimidamide Step 1: 6-Bromo-2-methyl-1,2,3,4-tetrahydroisoquinoline Into a 250-mL round-bottom flask, was placed 6-bromo-1,2,3,4-tetrahydroisoquinoline (6.0 g, 28.3 mmol) in MeOH (100 mL) under $N_2$. To the stirred solution was added HCHO (1.02 g, 34 mmol) in portions at RT. The resulting solution was stirred for 4 h, then $NaBH_3CN$ (3.56 g, 56.6 mmol) was added in portions at RT. The resulting solution was stirred overnight at RT. The reaction was then quenched by the addition of water (100 mL) and extracted with 3×150 mL ethyl acetate. The organic layers were combined and dried over anhydrous sodium sulfate and concentrated under vacuum. The crude product was eluted from a silica gel column with acetate/petroleum ether (1:1). This resulted in 5 g (78.2%) of the title compound as a white solid. MS-ESI: 226/228 (M+1).

Steps 2-5 used similar procedures for converting compound 185" to Intermediate 173" shown in Scheme 44 to afford Intermediate 85 from compound 229. MS-ESI: 238 (M+1).

Scheme 54

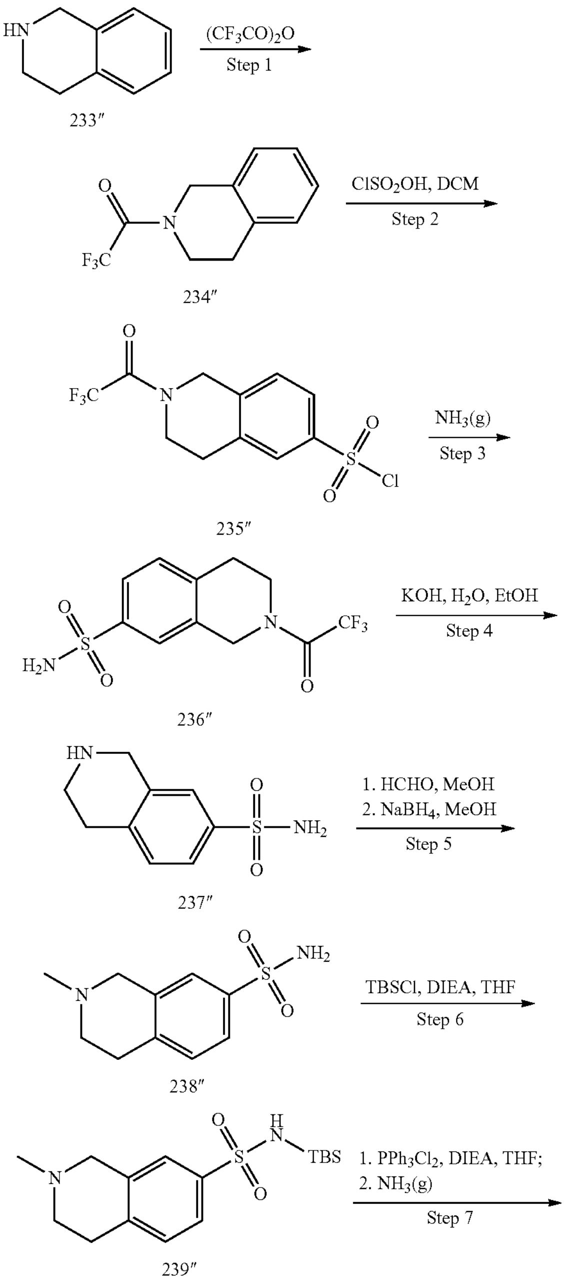

-continued

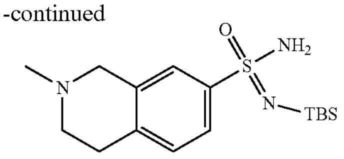

Intermediate 86

Intermediate 86

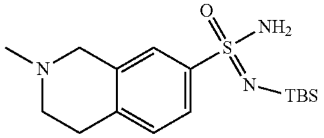

N'-(tert-butyldimethylsilyl)-2-methyl-1,2,3,4-tetrahydroisoquinoline-7-sulfonimidamide Step 1: 1-(3,4-Dihydroisoquinolin-2(1H)-yl)-2,2,2-trifluoroethanone Into a 250-mL round-bottom flask purged and maintained with an inert atmosphere of nitrogen, was placed 1,2,3,4-tetrahydroisoquinoline (8.0 g, 60.1 mmol) and 2,2,2-trifluoroacetic anhydride (25.2 g, 120 mmol). The resulting solution was stirred for 12 h at RT. The reaction was then quenched by the addition of 100 mL of water/ice. The resulting solution was extracted with 3×100 mL of ethyl acetate and the organic layers were combined and dried over anhydrous sodium sulfate and concentrated under vacuum. This resulted in 10 g (72.6%) of the title compound as a yellow solid. MS-ESI: 230 (M+1).

Steps 2-3 used similar procedures for converting compound 158" to Intermediate 61 shown in Scheme 38 to afford compound 236" from compound 234". MS-ESI: 309 (M+1).

Step 4: 1,2,3,4-Tetrahydroisoquinoline-7-sulfonamide

Into a 100-mL round-bottom flask, was placed 2-(2,2,2-trifluoroacetyl)-1,2,3,4-tetrahydroisoquinoline-7-sulfonamide (8.0 g, 26 mmol) in ethanol (12 mL) and $H_2O$ (60 mL). To the stirred solution was added KOH (7.28 g, 123 mmol) in one portion at RT. The resulting solution was stirred for 12 h at RT. The resulting mixture was concentrated. The crude product was applied onto a silica gel column with DCM/MeOH (10:1). This resulted in 5.0 g (90.8%) of the title compound as a light yellow solid.

Step 5 used similar procedures for converting compound 228" to compound 229" shown in Scheme 53 to afford compound 238" from compound 237". MS-ESI: 227 (M+1).

Steps 6-7 used similar procedures for converting compound 148" to intermediate 59 shown in Scheme 36 to afford intermediate 86 from compound 238". MS-ESI: 340 (M+1).

Scheme 55

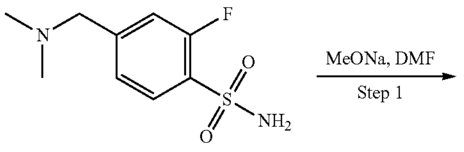

Cpd 58

-continued

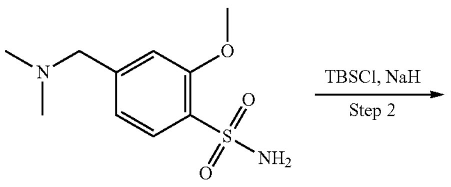

240"

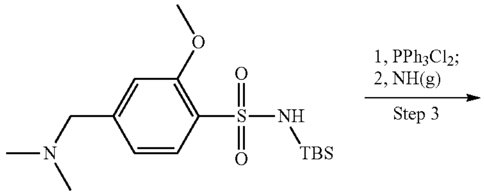

241"

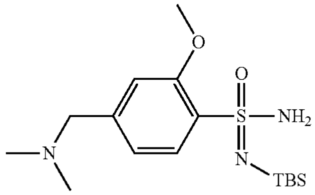

Intermediate 87

Intermediate 87

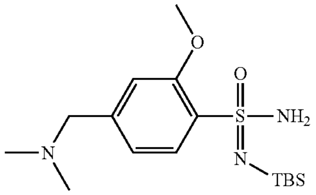

N'-(tert-butyldimethylsilyl)-2-methyl-1,2,3,4-tetrahydroisoquinoline-7-sulfonimidamide Step 1: 4-((Dimethylamino)methyl)-2-methoxybenzenesulfonamide Into a 50-mL round-bottom flask, was placed 4-[(dimethylamino)methyl]-2-fluorobenzene-1-sulfonamide (1 g, 4.31 mmol) and DMF (10 mL, 0.14 mmol). Then to the above was added sodium methoxide (2.16 g, 40 mmol). The resulting solution was stirred for 12 h at RT. The reaction was then quenched by the addition of 5.0 mL of water. The residue was eluted from a C18 column with ACN:$H_2O$ (3:7). This resulted in 800 mg (76.1%) of the title compound as a yellow solid. MS-ESI: 245 (M+1).

Steps 2-3 used similar procedures for converting compound 148" to intermediate 59 shown in Scheme 36 to afford intermediate 87 from compound 240". MS-ESI: 358 (M+1).

Scheme 56

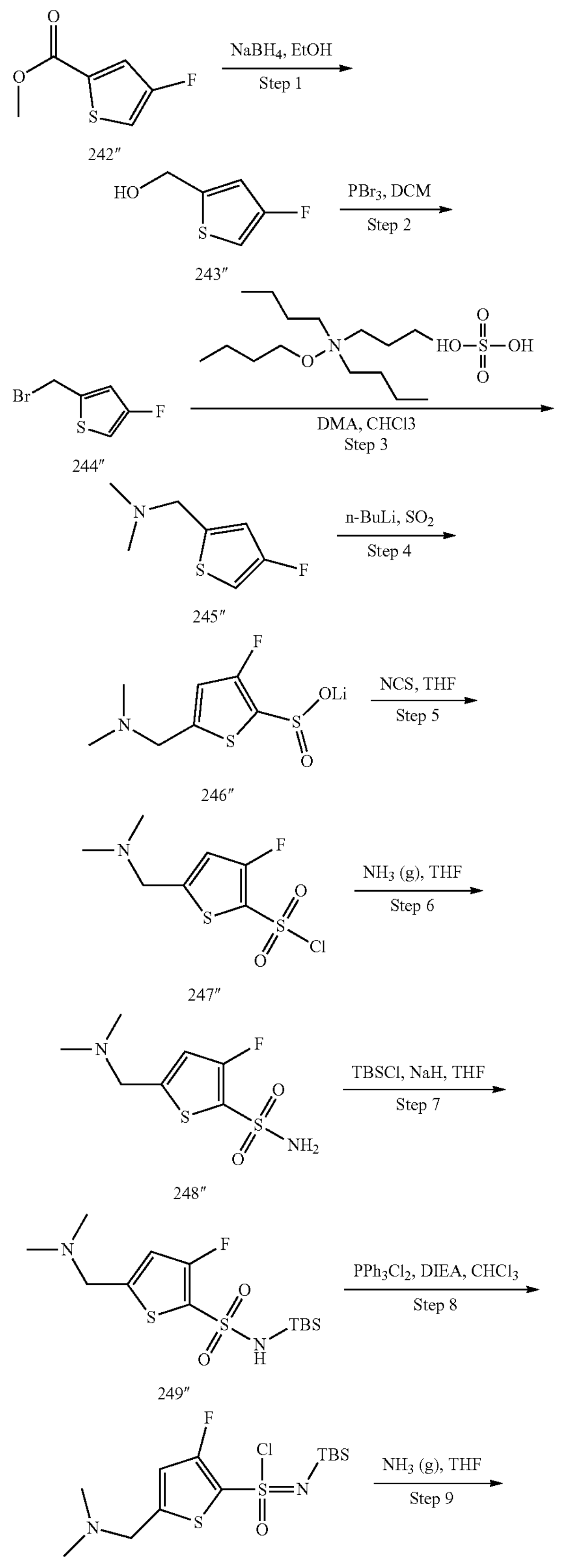

242″ 243″ 244″ 245″ 246″ 247″ 248″ 249″ 250″

-continued

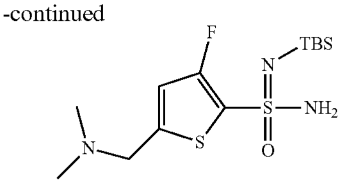

Intermediate 88

Intermediate 88

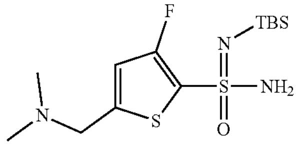

N'-(tert-butyldimethylsilyl)-5-((dimethylamino)methyl)-3-fluorothiophene-2-sulfonimidamide Step 1: (4-Fluorothiophen-2-yl)methanol Into a 1000-mL round-bottom flask, was placed methyl 4-fluorothiophene-2-carboxylate (10 g, 62.4 mmol) in ethanol (300 mL). Then to the above solution was added NaBH$_4$ (4.62 g, 125 mmol) in portions at 0° C. in an ice/ethanol bath. The resulting solution was stirred for 30 min at 0° C. and then the reaction solution was allowed to react for an additional 16 h at RT. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. This resulted in 6.4 g (77.6%) of the title compound as white oil. MS-ESI. 133 (M+1)

Step 2: 2-(Bromomethyl)-4-fluorothiophene

Into a 250-mL round-bottom flask, was placed (4-fluorothiophen-2-yl)methanol (8.5 g, 64.3 mmol) in DCM (70 mL). To the stirred solution was added PBr$_3$ (19.2 g, 70.8 mmol) dropwise at 0° C. in an ice/ethanol bath. The resulting solution was stirred for 30 min at 0° C. The resulting solution was allowed to react for an additional 12 h at RT. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (15/85). This resulted in 7.0 g (55.8%) of the title compound as yellow oil. MS-ESI: 194/196 (M+1).

Step 3: 1-(4-Fluorothiophen-2-yl)-N,N-dimethylmethanamine

Into a 250-mL round-bottom flask, was placed 2-(bromomethyl)-4-fluorothiophene (7.4 g, 37.9 mmol) in CHCl$_3$ (50 mL). To the above solution was added butoxytributyl-14-azane sulfate (6.76 g, 19 mmol) and DMA (37 mL, 425 mmol) with stirring at RT. The resulting solution was stirred for 2 h at 60° C. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (17/83). This resulted in 6.0 g (99.5%) of the title compound as a yellow solid. MS-ESI: 160 (M+1).

Step 4: Lithium 5-((dimethylamino)methyl)-3-fluorothiophene-2-sulfinate

Into a 500-mL 3-necked round-bottom flask purged with and maintained under nitrogen, was placed a solution of [(4-fluorothiophen-2-yl)methyl]dimethylamine (6.2 g, 38.9 mmol) in THF (60 mL). This was followed by the addition of n-BuLi/THF (18.7 mL, 2.5 M) dropwise with stirring at −78° C. in a liquid nitrogen/ethanol bath. The resulting solution was stirred for 30 min at −78° C. To the above $SO_2$ (g) was introduced into the reaction solution at −78° C. The resulting solution was allowed to react for an additional 2 h at RT. The resulting mixture was concentrated. This resulted in 10 g (crude) of the title compound as a yellow solid. MS-ESI: 222 (M−1).

Step 5: 5-((Dimethylamino)methyl)-3-fluorothiophene-2-sulfonyl Chloride

Into a 500-mL round-bottom flask, was placed a solution of 5-[(dimethylamino)methyl]-3-fluorothiophene-2-sulfinic acid (10 g, 44.8 mmol) in THF (100 mL). To the above solution was added NCS (7.18 g, 53.8 mmol). The resulting solution was stirred for 30 min at 0° C. and then allowed to react for an additional 2 h at RT. This reaction was used for next step without purification.

Step 6: 5-((Dimethylamino)methyl)-3-fluorothiophene-2-sulfonamide

Into a 500-mL round-bottom flask, was placed a solution of 5-[(dimethylamino)methyl]-3-fluorothiophene-2-sulfonyl chloride (10 g, 38.8 mmol) in THF (100 mL). To the above $NH_3$ (g) was introduced at RT. The resulting solution was stirred for 30 min at RT. The resulting mixture was concentrated. The residue was eluted from a silica gel column with ethyl acetate/petroleum ether (60/40). This resulted in 2.1 g (22.7%) of the title compound as yellow oil. MS-ESI: 239 (M+1).

Step 7: N-(tert-butyldimethylsilyl)-5-((dimethylamino)methyl)-3-fluorothiophene-2-sulfonamide Into a 100-mL round-bottom flask, was placed a solution of 5-[(dimethylamino)methyl]-3-fluorothiophene-2-sulfonamide (1.8 g, 7.55 mmol) in THF (30 mL) under $N_2$. To the above solution was added NaH (60% wt. oil dispersion, 640 mg, 15 mmol) with stirring at 0° C. The resulting solution was stirred for 5 min at 0° C. This was followed by the addition of TBSCl (1.37 g, 9.09 mmol) at 0° C. The resulting solution was allowed to react for an additional 15 h at RT. The reaction was then quenched by the addition of 20 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (1:1). This resulted in 2.0 g (75.2%) of the title compound as yellow oil. MS-ESI: 353 (M+1).

Step 8: N-(tert-butyldimethylsilyl)-5-((dimethylamino)methyl)-3-fluorothiophene-2-sulfonimidoyl Chloride Into a 500-mL round-bottom flask purged and maintained with an inert atmosphere of nitrogen was placed a solution of $PPh_3Cl_2$ (29.5 g, 88.7 mmol) in $CHCl_3$ (50 mL). To the above solution was added DIEA (17.2 g, 133 mmol) dropwise in an ice/water bath. The solution was stirred at RT for 20 minutes. This was followed by the addition of N-(tert-butyldimethylsilyl)-5-[(dimethylamino)methyl]-3-fluorothiophene-2-sulfonamide (15.7 g, 44.4 mmol) in $CHCl_3$ (30 mL) at 0° C. The resulting solution was allowed to react for an additional 30 min at 0° C. Then the reaction solution was used for next step without purification.

Step 9: N'-(tert-butyldimethylsilyl)-5-((dimethylamino)methyl)-3-fluorothiophene-2-sulfonimidamide Into a 500-mL round-bottom flask purged and maintained with an inert atmosphere of nitrogen, was placed [(tert-butyldimethylsilyl)imino](chloro)[5-[(dimethylamino)methyl]-3-fluorothiophen-2-yl]-$\lambda^6$-sulfanone (16.5 g, 44.4 mmol) in $CHCl_3$ (80 mL). To the above $NH_3$ (g) was introduced at 0° C. for 15 min. The resulting solution was stirred for 15 min at 0° C. and then allowed to react for an additional 15 h at RT. The resulting mixture was concentrated. The residue was eluted from a silica gel column with ethyl acetate/petroleum ether (60/40). This resulted in 5.8 g (37.2%) of the title compound as a yellow solid. MS-ESI: 352 (M+1).

Scheme 68

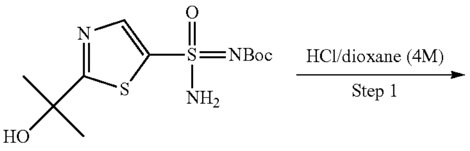

Intermediate 28

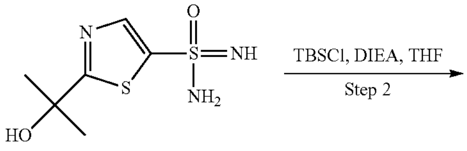

295″

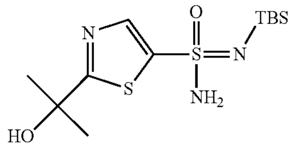

Intermediate 112

Intermediate 112

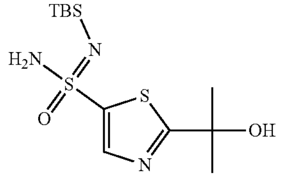

N'-(tert-butyldimethylsilyl)-2-(2-hydroxypropan-2-yl)thiazole-5-sulfonimidamide

Step 1: 2-(2-Hydroxypropan-2-yl)thiazole-5-sulfonimidamide

Into a 250-mL round-bottom flask, was placed a solution of tert-butyl 2-(2-hydroxypropan-2-yl)thiazole-5-sulfonimidoylcarbamate (3.21 g, 10 mmol) in HCl/dioxane (4 M, 50 mL). The resulting solution was stirred for 1 h at RT. The solution was concentrated to give the title compound (3.2 g, crude, yellow oil). MS-ESI: 222 (M+1).

Step 2: N'-(tert-butyldimethylsilyl)-2-(2-hydroxypropan-2-yl)thiazole-5-sulfonimidamide Into a 250-mL round-bottom flask, was placed 2-(2-hydroxypropan-2-yl)thiazole-5-sulfonimidamide (3.2 g crude, 10 mmol) in THF (100 mL), DIEA (3.87 g, 30 mmol) was added in at RT. Then TBSCl (3.0 g, 20 mmol) was added to the solution in portions. The resulting solution was stirred for 16 h at RT. The solution was concentrated and the crude product was purified by silica gel column with ethyl acetate/petroleum ether (1:1) to give the title compound (2.3 g, yield 70%, yellow solid). MS-ESI: 336 (M+1).

Scheme 69

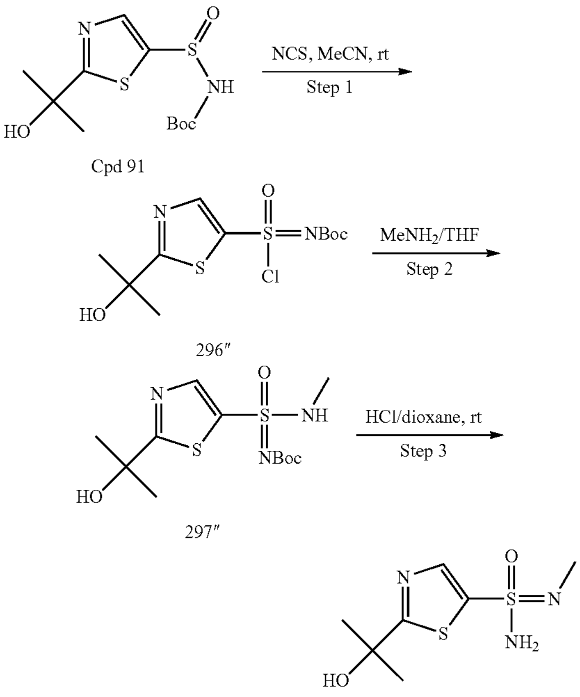

Cpd 91

296"

297"

Intermediate 113

Intermediate 113

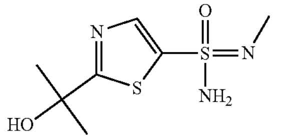

2-(2-Hydroxypropan-2-yl)-N-methylthiazole-5-sulfonimidamide

Step 1: Tert-butyl (chloro(2-(2-hydroxypropan-2-yl)thiazol-5-yl)(oxo)-$\lambda^6$-sulfaneylidene)carbamate Into a 1-L round-bottom flask, was placed tert-butyl N-[[2-(2-hydroxypropan-2-yl)-1,3-thiazol-5-yl]sulfinyl]carbamate (100 g, 326 mmol) in ACN (500 mL). To the stirred solution was added NCS (65.4 g, 49 mmol). The resulting solution was stirred for 2 h at RT. The resulted solution was concentrated. This resulted in 120 g crude title compound as yellow oil.

Step 2: Tert-((2-(2-hydroxypropan-2-yl)thiazol-5-yl)(methylamino)(oxo)-$\lambda^6$-sulfaneylidene)carbamate Into a 250-mL round-bottom flask, was placed tert-butyl N-[chloro[2-(2-hydroxypropan-2-yl)-1,3-thiazol-5-yl]oxo-$\lambda^6$-sulfanylidene]carbamate (10 g, 29.3 mmol) in THF (100 mL). To the stirred solution was added $CH_3NH_2$ (1.82 g, 58.6 mmol). The resulting solution was stirred for 2 h at RT. The resulted solution was concentrated. The residue was eluted from silica gel with ethyl acetate/petroleum ether (1:1). This resulted in 6.1 g (62%) of the title compound as a yellow solid. MS-ESI: 336 (M+1).

Step 3: 2-(2-Hydroxypropan-2-yl)-N'-methylthiazole-5-sulfonimidamide

Into a 100-mL round-bottom flask, was placed tert-butyl ((2-(2-hydroxypropan-2-yl)thiazol-5-yl) (methylamino)(oxo)-$\lambda^6$-sulfaneylidene)carbamate (3.0 g, 8.94 mmol) in HCl (gas) in 1,4-dioxane (8.0 mL, 26.3 mmol) in one portion at RT. The resulting solution was stirred for 60 min at RT. The resulting mixture was concentrated under vacuum. This resulted in 2.10 g crude title compound as a yellow solid. MS-ESI: 236 (M+1).

The schemes below illustrate the synthesis of Intermediates 89-96, 101-104, 114-117A, and 118"-126", which are isocyanate and precursors thereof as well as other intermediates:

Scheme 57

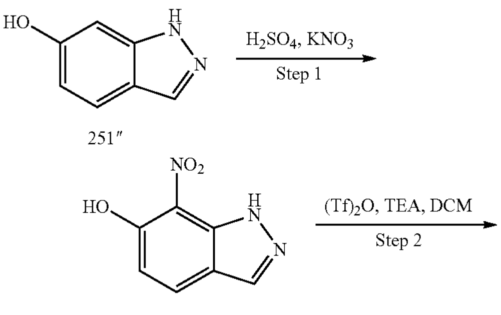

251"

252"

-continued

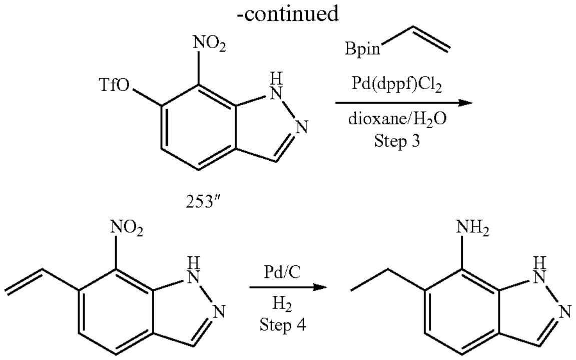

253″

Intermediate 89

Intermediate 90

Intermediate 89

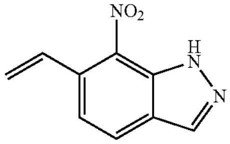

7-Nitro-6-vinyl-1H-indazole

Step 1: 7-Nitro-1H-indazol-6-ol

Into a 25-mL round-bottom flask, was placed 1H-indazol-6-ol (500 mg, 3.73 mmol). This was followed by the addition of $H_2SO_4$ (5.0 mL) in several batches at 0° C. To this was added $KNO_3$ (377 mg, 3.73 mmol) in portions at 0° C. The resulting solution was stirred for 30 min at 0° C. in a water/ice bath. The reaction was then quenched by the addition of 50 mL of water/ice. The solids were collected by filtration. This resulted in 350 mg (52.4%) of the title compound as a brown solid. MS-ESI: 180 (M+1).

Step 2: 7-Nitro-1H-indazol-6-yl trifluoromethanesulfonate

Into a 50-mL round-bottom flask, was placed 7-nitro-1H-indazol-6-ol (350 mg, 1.95 mmol) in DCM (10 mL), TEA (593 mg, 5.86 mmol), $Tf_2O$ (717 mg, 2.54 mmol). The resulting solution was stirred for 16 h at RT. The resulting solution was diluted with 20 mL of $H_2O$. The resulting solution was extracted with 3×20 mL of ethyl acetate dried over anhydrous sodium sulfate and concentrated. The residue was eluted from a silica gel column with ethyl acetate/petroleum ether (1:3). This resulted in 80 mg (13.2%) of the title compound as a yellow solid. MS-ESI: 312 (M+1).

Step 3: 7-Nitro-6-vinyl-1H-indazole

Into a 50-mL round-bottom flask purged and maintained with an inert atmosphere of nitrogen, was placed 7-nitro-1H-indazol-6-yl trifluoromethanesulfonate (100 mg, 0.32 mmol) in dioxane (10 mL) and $H_2O$ (2.0 mL), $Cs_2CO_3$ (209 mg, 0.64 mmol), 2-ethenyl-4,4,5,5-tetramethyl-1,3,2-dioxaborolane (59.4 mg, 0.39 mmol), $Pd(dppf)Cl_2$ (23.5 mg, 0.030 mmol). The resulting solution was stirred for 16 h at 90° C. in an oil bath. Then the mixture was concentrated under vacuum. The residue was eluted from a silica gel column with ethyl acetate/petroleum ether (1:3). This resulted in 50 mg (82.6%) of the title compound as a yellow solid. MS-ESI: 190 (M+1).

Intermediate 90

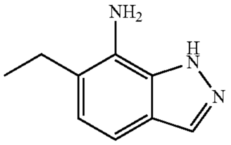

6-Ethyl-1H-indazol-7-amine

Step 4: 6-Ethyl-1H-indazol-7-amine

Into a 50-mL round-bottom flask, was placed 6-ethenyl-7-nitro-1H-indazole (50 mg) in MeOH (10 mL), and Pd/C (10% wt., 5.0 mg). The flask was evacuated and flushed three times with hydrogen. The resulting solution was stirred for 12 h at RT under an atmosphere of hydrogen. The Pd/C catalysts were filtered out, the filtrate was concentrated under vacuum. This resulted in 44 mg of the title compound as a yellow solid. MS-ESI: 162 (M+1).

Scheme 58

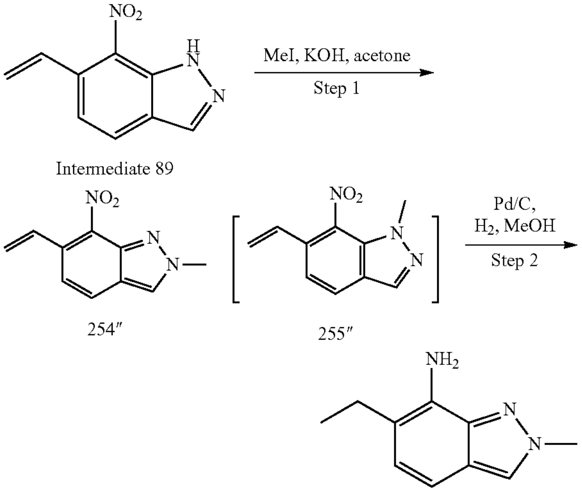

Intermediate 89

254″

255″

Intermediate 91

Intermediate 91

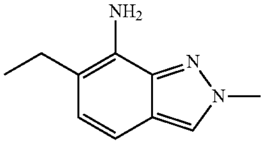

6-Ethyl-2-methyl-2H-indazol-7-amine

Step 1: 2-Methyl-7-nitro-6-vinyl-2H-indazole

Into a 50-mL round-bottom flask, was placed 6-ethenyl-7-nitro-1H-indazole (380 mg, 2.01 mmol) in acetone (20 mL), KOH (225 mg, 4.02 mmol). This was followed by the addition of MeI (342 mg, 2.41 mmol) dropwise with stirring. The resulting solution was stirred for 1 h at 0° C. in a water/ice bath. The resulting solution was diluted with 20 mL of $H_2O$. The resulting solution was extracted with 3×30 ml of ethyl acetate dried over anhydrous sodium sulfate and concentrated. The residue was eluted from a silica gel column with ethyl acetate/petroleum ether (1:1). This resulted in 210 mg (51.5%) of 254" as a yellow solid and 180 mg (44%) of 255" as a yellow solid. MS-ESI: 208 (M+1).

Step 2: 6-Ethyl-2-methyl-2H-indazol-7-amine

Into a 50-mL round-bottom flask purged and maintained with an inert atmosphere of $N_2$, was placed 6-ethenyl-1-methyl-7-nitro-1H-indazole (210 mg, 1.03 mmol) in MeOH (15 mL) and Pd/C (10% wt., 50 mg). The flask was evacuated and flushed three times with hydrogen. The resulting solution was stirred for 12 h at RT under an atmosphere of hydrogen. The Pd/C catalysts were filtered out, and the filtrate was concentrated under vacuum. This resulted in 160 mg (88.4%) of the title compound as a yellow solid. MS-ESI: 176 (M+1).

TABLE 14

The Intermediates in the following Table were prepared using the similar procedures for converting compound 254" to Intermediate 91 shown in Scheme 58 from 255".

| Intermediate # | Structure | IUPAC Name | Exact Mass [M + H]$^+$ |
|---|---|---|---|
| Intermediate 92 | 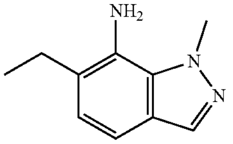 | 6-Ethyl-1-methyl-1H-indazol-7-amine | 176 |

Scheme 59

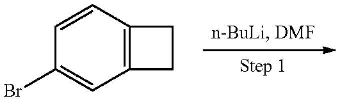

256"

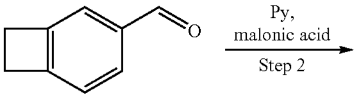

257"

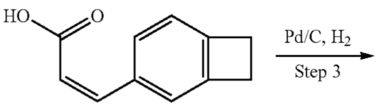

258"

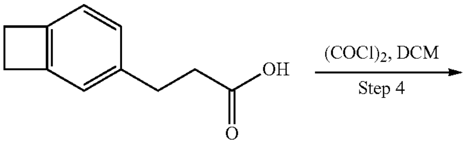

259"

-continued

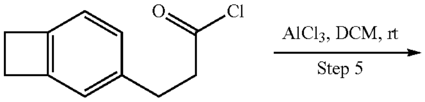

260"

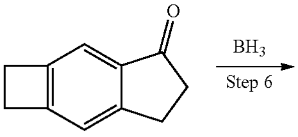

261"

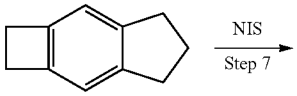

262"

-continued

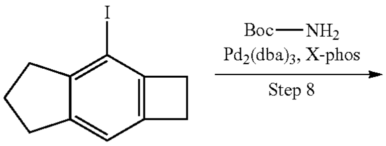

263"

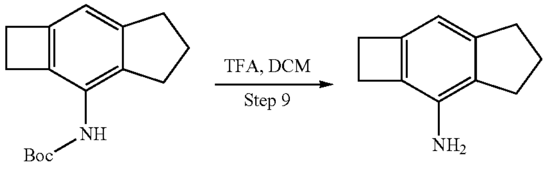

264"

Intermediate 93

Intermediate 93

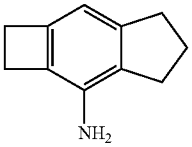

2,4,5,6-Tetrahydro-1H-cyclobuta[f]inden-3-amine

Step 1: Bicyclo[4.2.0]octa-1 (6),2,4-triene-3-carbaldehyde

Into a 500-mL round-bottom flask purged and maintained with an inert atmosphere of nitrogen, was placed 3-bromo-bicyclo[4.2.0]octa-1 (6),2,4-triene (70 g, 382 mmol) in THF (300 mL). This was followed by the addition of n-BuLi (184 mL, 459 mmol) dropwise with stirring at about −70° C. After addition, the reaction mixture was stirred at this temperature for 30 min. To this solution was added DMF (36.3 g, 497 mmol) dropwise with stirring at −70° C. The resulting solution was stirred for 30 min at −70° C. in a liquid nitrogen bath. The reaction was slowly warmed to RT and then quenched by the addition of 100 mL of water. The resulting solution was extracted with 3×200 ml of DCM. The organic layers combined and dried over anhydrous $Na_2SO_4$, and then the organic layers was concentrated. This resulted in 50 g (98.9%) of the title compound as light yellow oil. MS-ESI: 133 (M+1).

Step 2: (Z)-3-(bicyclo[4.2.0]octa-1 (6),2,4-trien-3-yl)acrylic Acid

Into a 250-mL round-bottom flask purged and maintained with an inert atmosphere of nitrogen, was placed bicyclo[4.2.0]octa-1 (6),2,4-triene-3-carbaldehyde (1.7 g, 12.9 mmol) in pyridine (20 mL), propanedioic acid (1.99 g, 19.2 mmol) and piperidine (110 mg, 1.29 mmol). The resulting solution was stirred for overnight at 90° C. in an oil bath. The resulting mixture was concentrated. This resulted in 2.1 g (93.7%) of the title compound as a solid. MS-ESI: 173 (M−1).

Step 3: 3-(Bicyclo[4.2.0]octa-1 (6),2,4-trien-3-yl) propanoic acid

Into a 250-mL round-bottom flask, was placed 2-(Z or E)-3-[bicyclo[4.2.0]octa-1 (6),2,4-trien-3-yl]prop-2-enoic acid (2.1 g, 12.1 mmol) and Pd/C (10% wt., 200 mg). The flask was evacuated and flushed three times with hydrogen. The resulting solution was stirred for 12 h at RT under an atmosphere of hydrogen. The Pd/C catalysts were filtered out, the filtrate was concentrated under vacuum. This resulted in 2.1 g (98.9%) of the title compound as a solid. MS-ESI: 175 (M−1).

Step 4: 3-(Bicyclo[4.2.0]octa-1 (6),2,4-trien-3-yl) propanoyl Chloride

Into a 250-mL round-bottom flask purged and maintained with an inert atmosphere of nitrogen, was placed 3-[bicyclo[4.2.0]octa-1 (6),2,4-trien-3-yl]propanoic acid (10 g, 56.8 mmol) in DCM (100 mL). This was followed by the addition of oxalyl chloride (7.2 g, 56.8 mmol) dropwise with stirring at 0° C. The resulting solution was stirred for 2 h at 0° C. in a water/ice bath. The resulting mixture was concentrated. This resulted in 10 g (90.5%) of the title compound as light yellow oil.

Step 5: 1,2,5,6-Tetrahydro-4H-cyclobuta[f]inden-4-one

Into a 100-mL round-bottom flask, was placed 3-[bicyclo[4.2.0]octa-1 (6),2,4-trien-3-yl]propanoyl chloride (5.0 g, 25.7 mmol) in DCM (50 mL). This was followed by the addition of $AlCl_3$ (3.4 g, 25.7 mmol) in portions at 0° C. for 10 min. The resulting solution was stirred for 1 h at 0° C. in a water/ice bath. The reaction was then quenched by the addition of 100 mL of water. The resulting solution was extracted with 2×50 mL of DCM. The organic layers combined and dried over anhydrous $Na_2SO_4$, then concentrated. The residue was eluted from a silica gel column with ethyl acetate/petroleum ether (1:20 to 1:15). This resulted in 3.5 g (86.1%) of the title compound as a white solid. $^1H$ NMR (300 MHz, $CDCl_3$) δ 7.45 (s, 1H), 7.17 (s, 1H), 3.22 (m, 4H), 3.18-3.00 (m, 2H), 2.73-2.63 (m, 2H).

Step 6: 2,4,5,6-Tetrahydro-1H-cyclobuta[f]indene

Into a 500-mL round-bottom flask purged and maintained with an inert atmosphere of nitrogen, was placed 1,2,5,6-tetrahydrocyclobuta[f]inden-4-one (20 g, 126 mmol) in THF (200 mL). This was followed by the addition of $BH_3$-$Me_2S$ (25.3 mL, 253 mmol, 10 M) dropwise at 0° C. in an ice bath. The resulting solution was stirred for 14 h at 70° C. in an oil bath. The reaction was then quenched by the addition of 20 mL of MeOH. The resulting mixture was concentrated. The residue was eluted from a silica gel column with ethyl acetate/petroleum ether (1:100 to 1:50). This resulted in 15 g (82.3%) of the title compound as colorless oil. $^1H$ NMR (300 MHz, $CDCl_3$) δ 6.95 (s, 2H), 3.10 (s, 4H), 2.88 (t, J=7.4 Hz, 4H), 2.03 (p, J=7.4 Hz, 2H).

Step 7: 3-Iodo-2,4,5,6-tetrahydro-1H-cyclobuta[f]indene

Into a 500-mL round-bottom flask, was placed acetic acid (100 mL), 2,4,5,6-tetrahydro-1H-cyclobuta[f]indene (15 g, 104 mmol) and NIS (35.1 g, 156 mmol). The resulting solution was stirred for 3 h at 50° C. in an oil bath. The resulting solution was diluted with 200 mL of water. The mixture was extracted with 3×100 mL of DCM. The organic layers combined and dried over anhydrous $Na_2SO_4$, then concentrated. The residue was eluted from a silica gel column with ethyl acetate/petroleum ether (1:100 to 1:80). This resulted in 5.0 g (17.8%) of the title compound as yellow oil.

Step 8: Tert-butyl (2,4,5,6-tetrahydro-1H-cyclobuta[f]inden-3-yl)carbamate

Into a 250-mL round-bottom flask purged and maintained with an inert atmosphere of nitrogen, was placed 3-iodo-2,4,5,6-tetrahydro-1H-cyclobuta[f]indene (5.0 g, 18.5 mmol) in toluene (100 mL), tert-butyl carbamate (6.5 g, 55.5 mmol), X-phos (900 mg, 1.85 mmol), $Pd_2(dba)_3$ (800 mg, 0.93 mmol), t-BuOK (6.2 g, 55.5 mmol). The resulting solution was stirred for 14 h at 100° C. in an oil bath. The resulting mixture was concentrated. The residue was eluted from a silica gel column with ethyl acetate/petroleum ether (1:50 to 1:20). This resulted in 3.0 g (83.3%) of the title compound as a white solid. MS-ESI: 260 (M+1).

$^1H$ NMR (300 MHz, $CDCl_3$) δ 6.72 (s, 1H), 6.13 (br, 1H), 3.26 (d, J=4.5 Hz, 2H), 3.01 (d, J=4.5 Hz, 2H), 2.90 (t, J=7.4 Hz, 2H), 2.75 (t, J=7.4 Hz, 2H), 2.06 (p, J=7.4 Hz, 2H), 1.52 (s, 9H).

Step 9: 2,4,5,6-Tetrahydro-1H-cyclobuta[f]inden-3-amine

Into a 100-mL round-bottom flask, was placed tert-butyl2,4,5,6-tetrahydro-1H-cyclobuta[f]inden-3-ylcarbamate (3.0 g, 11.6 mmol) in DCM (20 mL), 2,2,2-trifluoroacetic acid (5.0 mL). The resulting solution was stirred for 2 h at RT. The resulting solution was diluted with 50 mL of water. The pH value of the solution was adjusted to 10 with sat. aqueous $Na_2CO_3$. The resulting solution was extracted with 3×20 mL of DCM. The organic layers combined and dried over anhydrous $Na_2SO_4$, then concentrated. This resulted in 1.5 g (81.4%) of the title compound as a yellow solid. MS-ESI: 160 (M+1).

Scheme 60

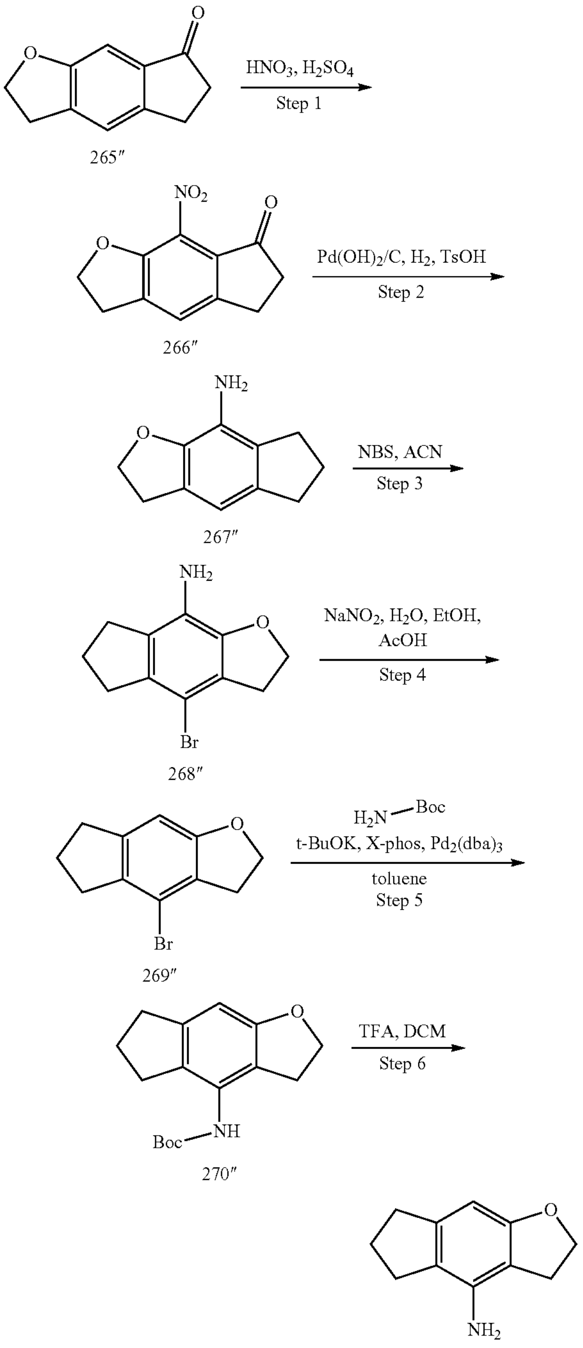

265″

266″

267″

268″

269″

270″ intermediate 94

Intermediate 94

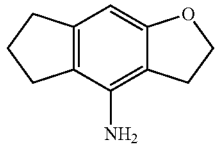

3,5,6,7-tetrahydro-2H-indeno[5,6-b]furan-4-amine

Step 1: 8-Nitro-2,3,5,6-tetrahydro-7H-indeno[5,6-b]furan-7-one

Into a 100-mL round-bottom flask, was placed 2H,3H,5H,6H,7H-indeno[5,6-b]furan-7-one (4 g, 23 mmol,) in $H_2SO_4$ (20 mL). This was followed by the addition of $HNO_3$ (2.13 g, 23 mmol, 68%) dropwise with stirring at 0° C. in an ice/ethanol bath. The resulting solution was stirred for 1 h at 0° C. The reaction was then quenched by the addition of 200 mL of water/ice. The solids were collected by filtration. This resulted in 4.0 g (79.5%) of the title compound as a light brown solid. MS-ESI: 220 (M+1).

Step 2: 3,5,6,7-Tetrahydro-2H-indeno[5,6-b]furan-8-amine

Into a 100-mL round-bottom flask purged and maintained with an inert atmosphere of nitrogen, was placed 8-nitro-2H,3H,5H,6H,7H-indeno[5,6-b]furan-7-one (4.0 g, 18.3 mmol) in MeOH (50 mL), TsOH (1.0 mL), $Pd(OH)_2/C$ (20% wt., 1 g). The flask was evacuated and flushed three times with hydrogen. The resulting solution was stirred for 16 h at RT under an atmosphere of hydrogen. The solids were filtered out. The resulting mixture was concentrated. The residue was dissolved in 50 mL of EA. The resulting mixture was washed with 2×50 ml of $NaHCO_3$ and 3×40 ml of $H_2O$. The mixture was dried over anhydrous sodium sulfate. The residue was eluted from a silica gel column with ethyl acetate/petroleum ether (1:9). This resulted in 1.1 g (34.4%) of the title compound as a yellow solid. MS-ESI: 176 (M+1).

Step 3: 4-Bromo-3,5,6,7-tetrahydro-2H-indeno[5,6-b]furan-8-amine

Into a 50-mL round-bottom flask, was placed 2H,3H,5H,6H,7H-indeno[5,6-b]furan-8-amine (1.1 g, 6.28 mmol) in ACN (30 mL) and NBS (1.34 g, 7.53 mmol). The resulting solution was stirred for 2 h at RT. The resulting mixture was concentrated. The residue was eluted from a silica gel column with ethyl acetate/petroleum ether (1:8). This resulted in 83 mg (52%) of the title compound as a yellow solid. MS-ESI: 254 (M+1).

Step 4: 4-Bromo-3,5,6,7-tetrahydro-2H-indeno[5,6-b]furan

Into a 50-mL round-bottom flask, was placed 4-bromo-2H,3H,5H,6H,7H-indeno[5,6-b]furan-8-amine (500 mg, 1.97 mmol) in ethanol (15 mL) and acetic acid (3.0 mL, 0.050 mmol). To the above solution was added $NaNO_2$ (1.36 g, 19.7 mmol) in $H_2O$ (3 mL) dropwise at 0° C. The resulting solution was stirred for 2 h at RT. The resulting solution was diluted with 30 mL of $H_2O$. The resulting solution was extracted with 3×30 ml of ethyl acetate dried over anhydrous sodium sulfate and concentrated. The residue was eluted from a silica gel column with ethyl acetate/petroleum ether (1:10). This resulted in 100 mg (21.3%) of the title compound as a yellow solid. MS-ESI: 239 (M+1).

Step 5: Tert-butyl (3,5,6,7-tetrahydro-2H-indeno[5,6-b]furan-4-yl)carbamate

Into a 50-mL round-bottom flask purged and maintained with an inert atmosphere of nitrogen, was placed 4-bromo-2H,3H,5H,6H,7H-indeno[5,6-b]furan (120 mg, 0.50 mmol) in toluene (15 mL), t-BuOK (282 mg, 2.51 mmol), tert-butyl carbamate (588 mg, 5.02 mmol), Xphos (47.8 mg, 0.10 mmol), and $Pd_2(dba)_3CHCl_3$ (104 mg, 0.10 mmol). The resulting solution was stirred for 16 h at 100° C. in an oil bath. The resulting mixture was concentrated. The residue was eluted from a silica gel column with ethyl acetate/petroleum ether (1:5). This resulted in 80 mg (57.9%) of the title compound as a yellow solid. MS-ESI: 276 (M+1).

Step 6: 3,5,6,7-Tetrahydro-2H-indeno[5,6-b]furan-4-amine

Into a 50-mL round-bottom flask, was placed tert-butyl N-[2H,3H,5H,6H,7H-indeno[5,6-b]furan-4-yl] carbamate (80 mg, 0.29 mmol) in DCM (8 mL) and TFA (3.0 mL, 0.030 mmol). The resulting solution was stirred for 2 h at room temperature. The resulting mixture was concentrated. The residue was dissolved in 15 mL of DCM. The resulting mixture was washed with 2×15 ml of NaOH (aq.). The organic layer was dried with $Na_2SO_4$ and then concentrated. This resulted in 50 mg (98.2%) of the title compound as a yellow solid. MS-ESI: 176 (M+1).

Scheme 61

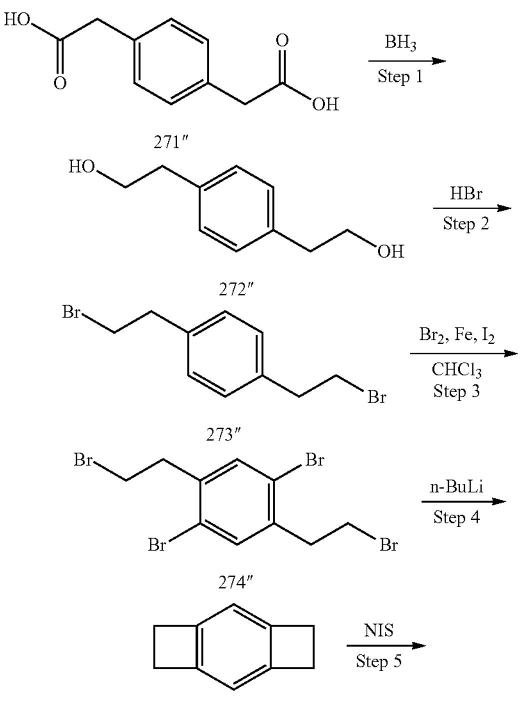

271″ 272″ 273″ 274″ 275″

-continued

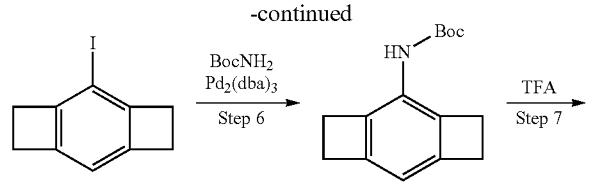

276″ 277″ intermediate 95

Intermediate 95

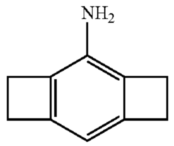

Tricyclo[6.2.0.0$^{3,6}$]deca-1,3(6),7-trien-2-amine

Step 1: 2,2'-(1,4-Phenylene)bis(ethan-1-ol)

Into a 1.0-L round-bottom flask purged and maintained with an inert atmosphere of nitrogen, was placed 2-[4-(carboxymethyl)phenyl]acetic acid (40 g, 200 mmol) in THF (500 mL). This was followed by the addition of $BH_3$-$Me_2S$ (60 mL, 600 mmol, 10 M) dropwise with stirring at 0° C. The resulting solution was stirred for 24 h at RT. The reaction was then quenched by the addition of 200 mL of water. The resulting solution was extracted with 2×150 mL of ethyl acetate. The organic layers combined and dried over anhydrous $Na_2SO_4$, then concentrated. The residue was eluted from a silica gel column with ethyl acetate/petroleum ether (1:10 to 1:3). This resulted in 28 g (81.8%) of the title compound as brown oil. MS-ESI: 167 (M+1).

Step 2: 1,4-Bis(2-bromoethyl)benzene

Into a 50-mL round-bottom flask purged and maintained with an inert atmosphere of nitrogen, was placed 2-[4-(2-hydroxyethyl)phenyl]ethan-1-ol (28 g, 168 mmol) in aq. HBr (300 mL, 40% wt.). The resulting solution was stirred for 5 h at 100° C. in an oil bath. The resulting solution was diluted with 500 mL of water. The resulting solution was extracted with 3×200 mL of DCM. The organic layers combined, then concentrated. This resulted in 40 g (81.4%) of the title compound as a white solid. MS-ESI: 291, 293, 295 (M+1).

Step 3: 1,4-Dibromo-2,5-bis(2-bromoethyl)benzene

Into a 500-mL round-bottom flask, was placed 1,4-bis(2-bromoethyl)benzene (30 g, 103 mmol) in trichloromethane (200 mL). To the above solution was added $I_2$ (0.78 g, 3.08 mmol), iron powder (0.75 g, 13.4 mmol), $Br_2$ (41 g, 257 mmol). The resulting solution was stirred for 24 h at RT. The reaction was then quenched by the addition of aqueous $Na_2SO_3$. The resulting solution was extracted with 3×200 mL DCM and the organic layers was combined and dried over anhydrous $Na_2SO_4$ then concentrated. This resulted in 40 g (86.6%) of the title compound as a white solid. MS-ESI: 449/451/453 (M+1).

Step 4: Tricyclo[6.2.0.0$^{3,6}$]deca-1,3(6),7-triene

Into a 1000-mL round-bottom flask purged and maintained with an inert atmosphere of nitrogen, was placed 1,4-dibromo-2,5-bis(2-bromoethyl)benzene (40 g, 88.9 mmol) in THF (400 mL). This was followed by the addition of n-BuLi (74.7 mL, 187 mmol, 2.5 M) dropwise with stirring at −78° C. in a liquid nitrogen bath. The resulting solution was stirred for 30 min at −78° C. The reaction was then quenched by the addition of aqueous $NH_4Cl$ (300 ml) and extracted with 2×200 mL of DCMDCM and the organic layers was combined and dried over anhydrous $Na_2SO_4$ then concentrated. This resulted in 8.0 g (69.1%) of the title compound as a light yellow solid.

Step 5: 2-Iodotricyclo[6.2.0.0$^{3,6}$]deca-1,3(6),7-triene

Into a 250-mL round-bottom flask purged and maintained with an inert atmosphere of nitrogen, was placed tricyclo [6.2.0.0$^{3,6}$]deca-1,3(6),7-triene (8 g, 61.45 mmol) in acetic acid (50 mL) and NIS (20.7 g, 92.2 mmol). The resulting solution was stirred for 3 h at 50° C. in an oil bath. The resulting solution was diluted with 100 mL of water. The reaction was then quenched by the addition of aqueous $Na_2SO_3$. The resulting solution was extracted with 3×50 mL of DCM and the organic layers was combined and dried over anhydrous $Na_2SO_4$ then concentrated. The residue was eluted from a silica gel column with ethyl acetate/petroleum ether (1:100). This resulted in 2.5 g (18.2%) of the title compound as a white solid.

Step 6: Tert-butyl tricyclo[6.2.0.0$^3$,6]deca-1,3(6),7-trien-2-ylcarbamate

Into a 250-mL round-bottom flask purged and maintained with an inert atmosphere of nitrogen, was placed 2-iodotricyclo[6.2.0.0$^3$,6]deca-1,3(6),7-triene (2.5 g, 9.76 mmol) in toluene (50 mL). To the stirred solution was added tert-butyl carbamate (3.43 g, 29.3 mmol), $Pd_2(dba)_3$ (447 mg, 0.49 mmol), Xphos (466 mg, 0.98 mmol), and t-BuOK (3.29 g, 29.3 mmol). The resulting solution was stirred for 14 h at 100° C. in an oil bath. The resulting mixture was concentrated. The residue was eluted from a silica gel column with ethyl acetate/petroleum ether (1:50 to 1:30). This resulted in 1.5 g (62.6%) of the title compound as a light yellow solid. MS-ESI: 246 (M+1).

Step 7: Tricyclo[6.2.0.0$^{3,6}$]deca-1,3(6),7-trien-2-amine

Into a 50-mL round-bottom flask purged and maintained with an inert atmosphere of nitrogen, was placed tert-butyl N-[tricyclo[6.2.0.0$^3$,6]deca-1,3(6),7-trien-2-yl]carbamate (1.5 g, 6.1 mmol) in DCM (20 mL) and 2,2,2-trifluoroacetic acid (4.0 mL). The resulting solution was stirred for 2 h at RT. The resulting mixture was concentrated. This resulted in 800 mg (90.10%) of the title compound as a brown solid. MS-ESI: 146 (M+1).

Scheme 62A

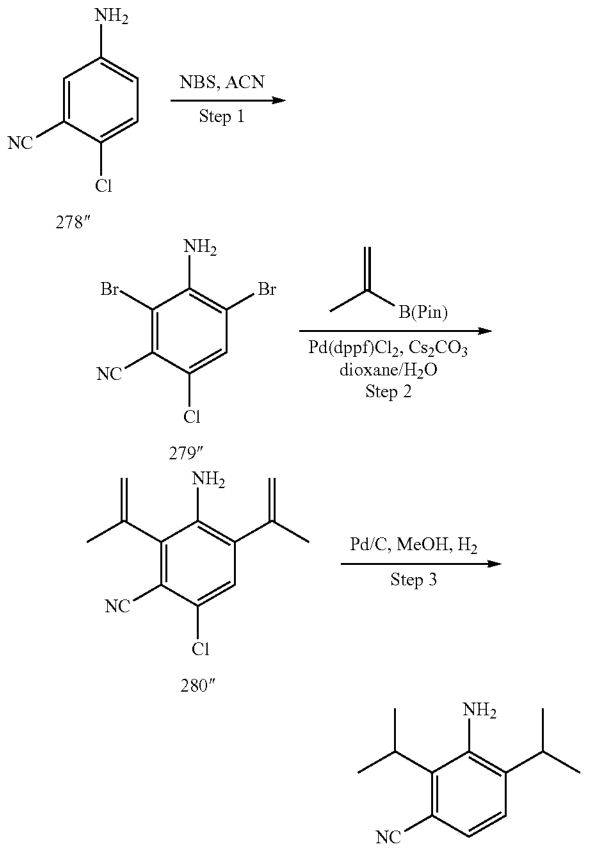

278″

279″

280″

Intermediate 96

Intermediate 96

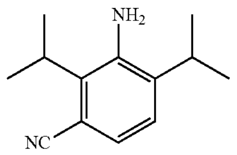

3-Amino-2,4-diisopropylbenzonitrile

Step 1: 3-Amino-2,4-dibromo-6-chlorobenzonitrile

Into a 500-mL round-bottom flask, was placed 5-amino-2-chlorobenzonitrile (10 g, 65.8 mmol), ACN (200 mL) and NBS (17.6 g, 98.7 mmol). The resulting solution was stirred for 14 h at RT. The resulting mixture was concentrated. The residue was eluted from a silica gel column with ethyl acetate/petroleum ether (1:15 to 1:5). This resulted in 18 g of the title compound as a yellow solid. MS-ESI: 310, 312 (M+1).

Step 2: 3-Amino-6-chloro-2,4-di(prop-1-en-2-yl) benzonitrile

Into a 500-mL round-bottom flask purged and maintained with an inert atmosphere of nitrogen, was placed 3-amino-2,4-dibromo-6-chlorobenzonitrile (15 g, 48 mmol) in dioxane (200 mL) and $H_2O$ (20 mL), 2-(tetramethyl-1,3,2-dioxaborolan-2-yl)prop-2-en-1-ylium (17.6 g, 106 mmol), $Cs_2CO_3$ (47 g, 144 mmol), and Pd(dppf)$Cl_2$ (1.5 g, 4.8 mmol). The resulting solution was stirred for 14 h at 100° C. in an oil bath. The resulting mixture was concentrated. The residue was eluted from a silica gel column with ethyl acetate/petroleum ether (1:0 to 1:25). This resulted in 10 g of the title compound as brown oil. MS-ESI: 233 (M+1).

Step 3: 3-Amino-2,4-diisopropylbenzonitrile

Into a 500-mL round-bottom flask purged and maintained with an inert atmosphere of nitrogen, was placed 3-amino-6-chloro-2,4-bis(prop-1-en-2-yl)benzonitrile (10 g, 43 mmol) in MeOH (50 mL). Then Pd/C (10% wt., 2.0 g) was added. The flask was evacuated and flushed three times with hydrogen. The resulting solution was stirred for 16 h at RT under an atmosphere of hydrogen. The solids were filtered out. The resulting filtrate was concentrated under vacuum. This resulted in 8.0 g of the title compound as brown oil. MS-ESI: 203 (M+1).

Scheme 65

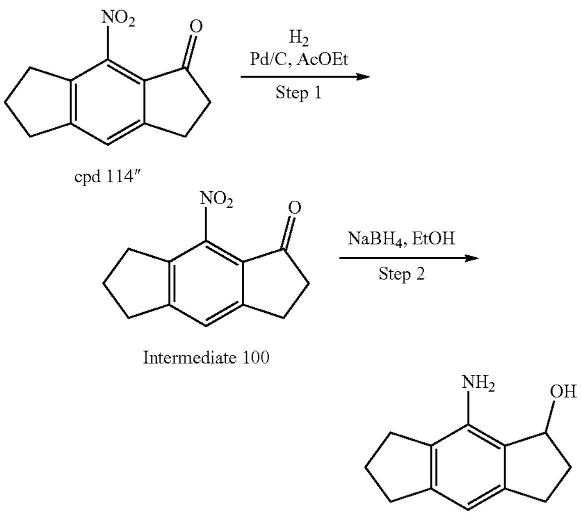

cpd 114″

Intermediate 100

Intermediate 101

Intermediate 101

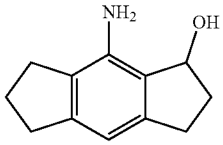

8-Amino-1,2,3,5,6,7-hexahydro-s-indacen-1-ol

Step 1: 8-Amino-3,5,6,7-tetrahydro-s-indacen-1 (2H)-one

Into a 250-mL round-bottom flask purged and maintained with an inert atmosphere of hydrogen, was placed a solution of 8-nitro-1,2,3,5,6,7-hexahydro-s-indacen-1-one (700 mg, 3.22 mmol) in MeOH (10 mL), and Pd/C (10% wt., 100 mg). The flask was evacuated and flushed three times with hydrogen. The resulting solution was stirred for 2 h at RT under an atmosphere of hydrogen. The Pd/C catalysts were filtered out, and the filtrate was concentrated under vacuum. This resulted in 550 mg (91.2%) of the title compound as a yellow oil. MS-ESI: 188 (M+1).

Step 2: 8-Amino-1,2,3,5,6,7-hexahydro-s-indacen-1-ol

Into a 100 mL round-bottom flask, was placed a solution of 8-amino-3,5,6,7-tetrahydro-s-indacen-1 (2H)-one (2.0 g, 10.7 mmol) in ethanol. To this solution was added $NaBH_4$ (1.9 g, 50 mmol) with stirring in portions at 0° C. in an ice bath. The resulting solution was stirred for 16 h at RT. The reaction was quenched by water (10 mL). The resulting solution was extracted with 3×50 mL of ethyl acetate and the organic layers combined and dried over anhydrous sodium sulfate, and then concentrated under vacuum. This resulted in 1.5 g of the title compound as a yellow solid. MS-ESI: 189 (M+1).

Scheme 66

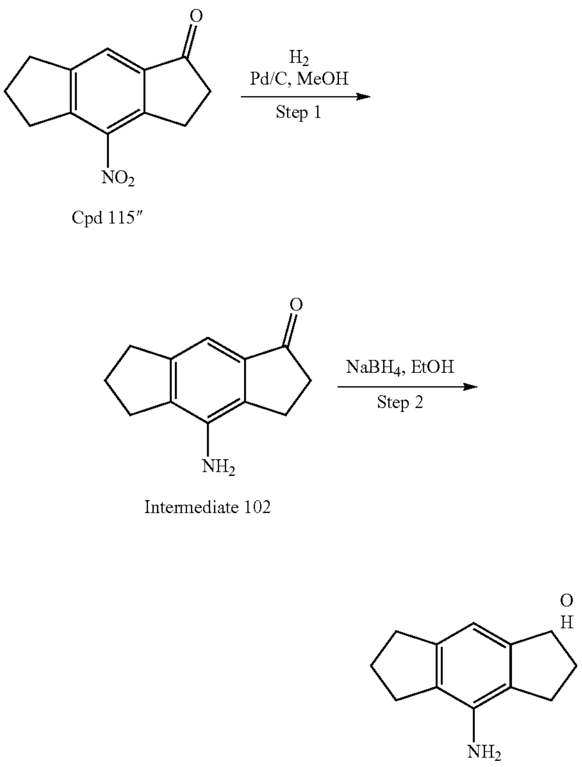

Cpd 115″

Intermediate 102

Intermediate 103

Intermediate 103

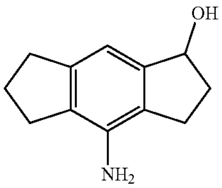

4-Amino-1,2,3,5,6,7-hexahydro-s-indacen-1-ol

Step 1: 4-Amino-3,5,6,7-tetrahydro-s-indacen-1 (2H)-one

Into a 250-mL round-bottom flask purged and maintained with an inert atmosphere of hydrogen, was placed a solution of 4-nitro-1,2,3,5,6,7-hexahydro-s-indacen-1-one (3.0 g, 13.8 mmol) in MeOH (30 mL), and Pd/C (10% wt., 500 mg). The flask was evacuated and flushed three times with hydrogen. The resulting solution was stirred for 4 h at RT under an atmosphere of hydrogen. The Pd/C catalysts were filtered out, the filtrate was concentrated under vacuum. The residue was eluted from a silica gel column with DCM/MeOH (10:1). This resulted in 2.2 g (85.1%) of the title compound as a white solid. MS-ESI: 187 (M+1).

Step 2: 4-Amino-1,2,3,5,6,7-hexahydro-s-indacen-1-ol

Into a 100-mL round-bottom flask, was placed a solution of 8-amino-3,5,6,7-tetrahydro-s-indacen-1 (2H)-one (2.0 g, 10.7 mmol) in ethanol (20 mL) and $NaBH_4$ (1.9 g, 50 mmol). The resulting solution was stirred for 16 h at RT. The reaction was quenched with water. The resulting solution was extracted with 3×50 mL of ethyl acetate and the organic layers combined and dried over anhydrous sodium sulfate. The mixture was concentrated under vacuum. This resulted in 1.36 g of the title compound as a yellow solid. MS-ESI: 190 (M+1).

Scheme 67

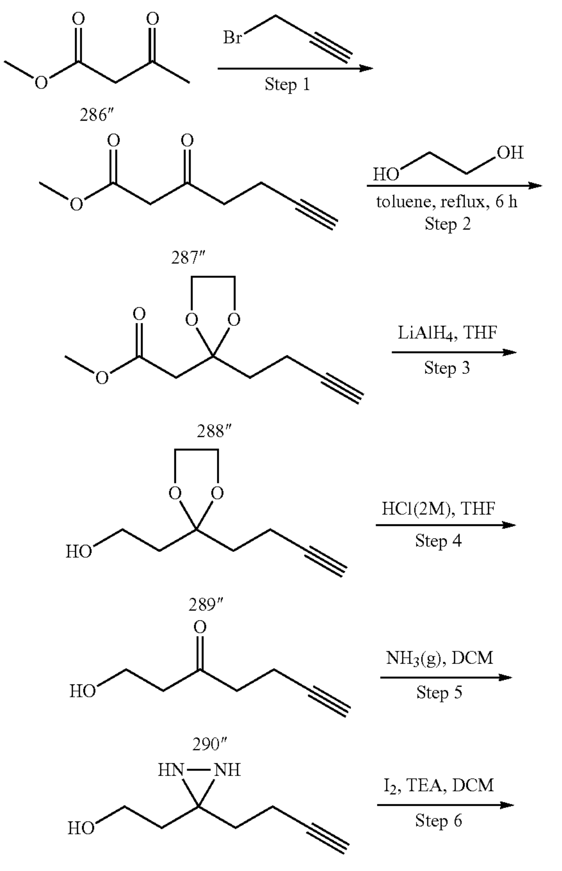

-continued

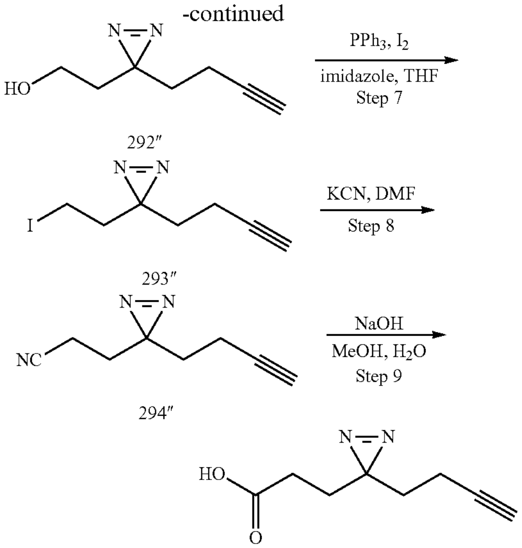

Intermediate 104

Intermediate 104

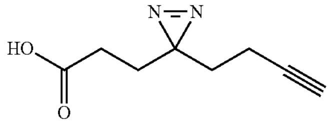

3-(3-(But-3-ynyl)-3H-diazirin-3-yl)propanoic Acid

Step 1: Methyl 3-oxohept-6-ynoate

Into a 2000-mL 3-neck round-bottom flask purged with and maintained under nitrogen, was placed methyl 3-oxobutanoate (20 g, 172 mmol) in THF (200 mL). To the above solution was added LDA (200 mL, 400 mmol, 2 M) dropwise at −20° C. in a dry ice bath. Then reaction was allowed to react at −20° C. for 30 min. Then 3-bromoprop-1-yne (20.5 g, 172 mmol) was added to the reaction solution in portions at −20° C. The resulting solution was stirred for 3 h at −20° C. in a dry ice bath. The reaction was then quenched by the addition of 500 mL of $NH_4Cl$ solution. The pH value of the solution was adjusted to 3 with HCl (aq). The resulting solution was extracted with 3×200 ml of ethyl acetate and the organic layers was combined and dried over anhydrous $Na_2SO_4$, then concentrated. This resulted in the title compound (2.0 g, 7.53%) as white oil.

Step 2: Methyl 2-(2-(but-3-ynyl)-1,3-dioxolan-2-yl) acetate

Into a 500-mL round-bottom flask, was placed methyl 3-oxohept-6-ynoate (20 g, 130 mmol) in toluene (200 mL), ethane-1,2-diol (40.2 g, 649 mmol) and TsOH (2.23 g, 13 mmol). The resulting solution was stirred for 6 h at 120° C. in an oil bath. The resulting solution was diluted with 200 mL of $Et_2O$. The resulting mixture was washed with 3×100 ml of $NaHCO_3$ and 3×100 ml of saturated NaCl solution. The mixture was dried over anhydrous sodium sulfate and concentrated. This resulted in the title compound (20 g, 77.9%) as yellow oil.

Step 3: 2-(2-(But-3-ynyl)-1,3-dioxolan-2-yl)ethanol

Into a 1.0-L 3-necked round-bottom flask purged and maintained with an inert atmosphere of nitrogen, was placed methyl 2-[2-(but-3-yn-1-yl)-1,3-dioxolan-2-yl]acetate (90 g, 454 mmol) in THF (300 mL). To this above solution was added $LiAlH_4$ (17.9 g, 472 mmol) in portions with stirring at 0° C. in an ice/ethanol bath. The resulting solution was stirred for 6 h at RT. The reaction was then quenched by the addition of water/ice. The solids were filtered out. The resulting filtrate was concentrated under vacuum. This resulted in the title compound (80 g crude) and used in the next step directly. MS-ESI. 169 (M−1).

Step 4: 1-Hydroxyhept-6-yn-3-one

Into a 3.0-L 3-necked round-bottom flask purged and maintained with an inert atmosphere of nitrogen, was placed 2-[2-(but-3-yn-1-yl)-1,3-dioxolan-2-yl]ethan-1-ol (80 g, 470 mmol) in THF (1.0 L) and HCl (500 mL). The resulting solution was stirred for 16 h at RT. The resulting solution was diluted with 1.0 L of water. The mixture was extracted with 3×1.0 L of ethyl acetate and the organic layer was combined and dried over anhydrous sodium sulfate. The solids were filtered out. The resulting filtrate was concentrated under vacuum. The residue was eluted from a silica gel column with DCM/petroleum ether (1:1). This resulted in 20 g of the title compound as a white solid. MS-ESI: 125 (M−1).

Step 5: 2-(3-(But-3-ynyl)diaziridin-3-yl)ethanol

Into a 500-mL round-bottom flask purged and maintained with an inert atmosphere of nitrogen, was placed 1-hydroxy-hept-6-yn-3-one (20 g, 159 mmol) in DCM (250 mL). To the above solution was introduced $NH_3$ (g) for 15 min at −40° C. in a liquid nitrogen/ethanol bath. The resulting solution was stirred for 1 h at −40° C. and then allowed to react for 16 h at RT. The resulting mixture was concentrated. This resulted in 18 g (crude) of the title compound as a white solid. MS-ESI: 141 (M+1).

Step 6: 2-(3-(But-3-ynyl)-3H-diazirin-3-yl)ethanol

Into a 500-mL 3-necked round-bottom flask purged and maintained with an inert atmosphere of nitrogen, was placed 2-[3-(but-3-yn-1-yl)diaziridin-3-yl]ethan-1-ol (14.4 g, 114 mmol) in DCM (200 mL), TEA (34.6 g, 342 mmol), $I_2$ (58 g, 228 mmol). The resulting solution was stirred for 4 h at RT. The reaction was then quenched by the addition of $Na_2S_2O_3$. The resulting mixture was quenched with 100 mL of water. The resulting solution was extracted with 3×300 mL of DCM and the organic layers combined and dried over anhydrous sodium sulfate. The solids were filtered out. The resulting mixture was concentrated. This resulted in 6.0 g (38%) of the title compound as a white solid. MS-ESI: 139 (M+1).

Step 7: 3-(But-3-ynyl)-3-(2-iodoethyl)-3H-diazirine

Into a 250-mL round-bottom flask purged and maintained with an inert atmosphere of nitrogen, was placed 2-[3-(but-3-yn-1-yl)-3H-diazirin-3-yl]ethan-1-ol (5.0 g, 36.2 mmol) in THF (20 mL), imidazole (3.7 g, 54.3 mmol), $I_2$ (9.18 g, 36.2 mmol), $PPh_3$ (14.2 g, 54.3 mmol). The resulting solution was stirred for 16 h at RT. The reaction was then quenched by the addition of 20 mL of saturated $Na_2S_2O_3$ solution. The resulting solution was extracted with 3×50 mL of DCM dried over anhydrous sodium sulfate. The solids were filtered out. The resulting mixture was concentrated. This resulted in 5.0 g (crude) of the title compound as a yellow solid. MS-ESI: 248 (M+1).

Step 8: 3-(3-(But-3-ynyl)-3H-diazirin-3-yl)propanenitrile

Into a 500-mL round-bottom flask purged and maintained with an inert atmosphere of nitrogen, was placed 3-(but-3-yn-1-yl)-3-(2-iodoethyl)-3H-diazirine (5.0 g, 20.2 mmol) in DMF (250 mL), KCN (2.62 g, 40.3 mmol). The resulting solution was stirred for 16 h at 60° C. in an oil bath. The reaction was then quenched by the addition of 20 mL of $FeSO_4$ solution. The resulting solution was extracted with 3×50 ml of ethyl acetate dried over anhydrous sodium sulfate. The solids were filtered out. The resulting mixture was concentrated. This resulted in 2.0 g (crude) of the title compound as a solid. MS-ESI: 148 (M+1).

Step 9: 3-(3-(But-3-ynyl)-3H-diazirin-3-yl)propanoic Acid

Into a 100-mL round-bottom flask purged and maintained with an inert atmosphere of nitrogen, was placed 3-[3-(but-3-yn-1-yl)-3H-diazirin-3-yl]propanenitrile (1.0 g, 3.40 mmol) in MeOH (40 mL), NaOH (272 mg, 6.79 mmol). The resulting solution was stirred for 16 h at 90° C. in an oil bath. The resulting solution was concentrated. The residue was eluted from a silica gel column with ethyl acetate/petroleum ether (1:1). This resulted in 400 mg crude (26.6%) of the title compound as yellow oil. MS-ESI: 167 (M+1).

Scheme 70

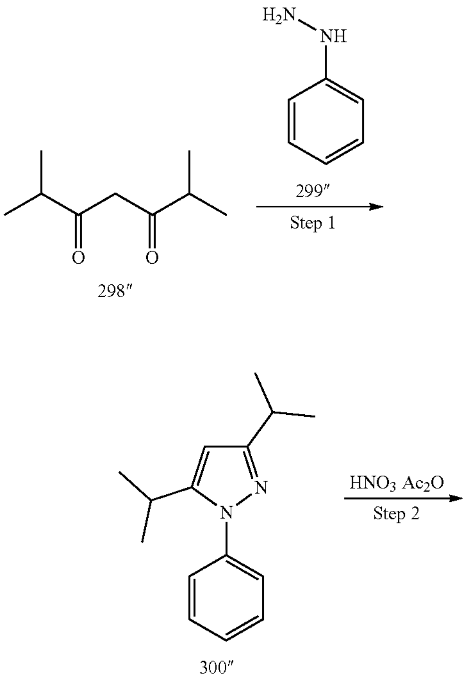

298″

300″

-continued

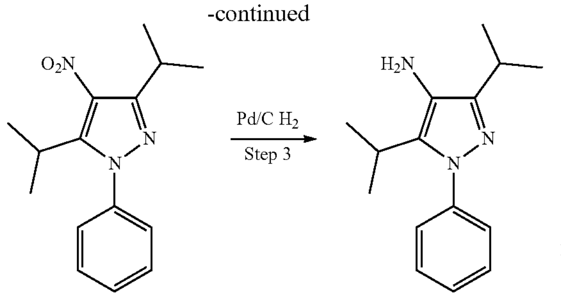

301″

Intermediate 114

Intermediate 114

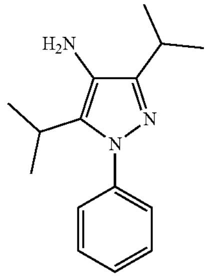

3,5-Diisopropyl-1-phenyl-1H-pyrazol-4-amine

Step 1: 3,5-Diisopropyl-1-phenyl-1H-pyrazole

Into a 100-mL round-bottom flask, was placed 2-propanol (50 mL), phenylhydrazine (3.81 g, 35.2 mmol) and 2,6-dimethylheptane-3,5-dione (5.0 g, 32.0 mmol). The resulting solution was stirred overnight at 85° C. in an oil bath. The resulting mixture was concentrated. The residue was dissolved in 100 mL of ethyl acetate. The resulting mixture was washed with 50 mL of $H_2O$. The mixture was dried over anhydrous sodium sulfate and then concentrated. This resulted in 6.9 g (94%) of the title compound as a light yellow oil. MS-ESI: 229 (M+1).

Step 2: 3,5-Diisopropyl-4-nitro-1-phenyl-1H-pyrazole

Into a 100-mL round-bottom flask, was placed 1-phenyl-3,5-bis(propan-2-yl)-1H-pyrazole (6.9 g, 30 mmol) in $Ac_2O$ (50 mL). This was followed by the addition of $HNO_3$ (4.07 mL, 91 mmol) dropwise with stirring at 0° C. in 10 min. The resulting solution was stirred for overnight at RT. The residue was dissolved in 150 mL of ethyl acetate. The resulting mixture was washed with 2×100 mL of $H_2O$. The mixture was dried over anhydrous sodium sulfate and then concentrated. This resulted in 3.7 g (44.8%) of the title compound as yellow oil. MS-ESI: 274 (M+1).

Step 3: 3,5-Diisopropyl-1-phenyl-1H-pyrazol-4-amine

Into a 250-mL round-bottom flask, was placed 4-nitro-1-phenyl-3,5-bis(propan-2-yl)-1H-pyrazole (3.7 g, 13.5 mmol) in MeOH (100 mL), to the stirred solution was added Pd/C (10% wt., 400 mg). The flask was evacuated and flushed three times with hydrogen. The resulting solution was stirred overnight at RT under an atmosphere of hydrogen. The Pd/C catalysts were filtered out, the filtrate was concentrated under vacuum. This resulted in 2.7 g (82%) of the title compound as a light yellow oil. MS-ESI: 244 (M+1).

Scheme 72

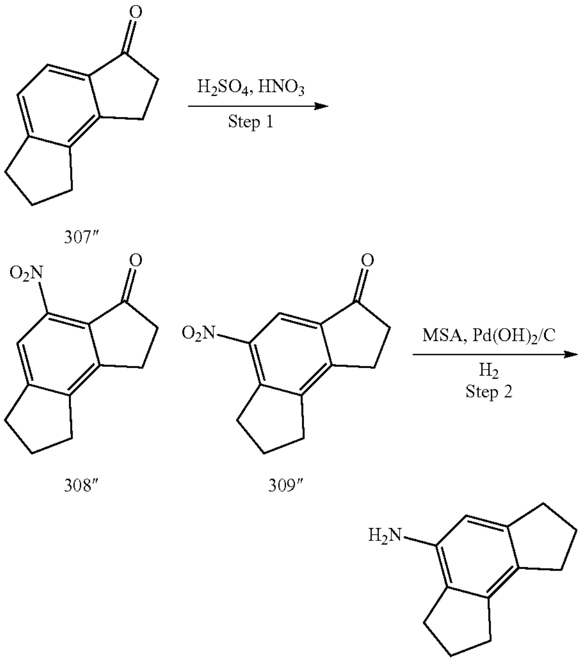

307″

308″

309″

Intermediate 116

Intermediate 116

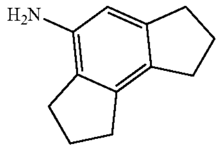

1,2,3,6,7,8-Hexahydro-as-indacen-4-amine

Step 1: 4-Nitro-1,6,7,8-tetrahydro-as-indacen-3 (2H)-one (308) and 5-nitro-1,6,7,8-tetrahydro-as-indacen-3 (2H)-one (309")

Into a 250-mL round-bottom flask was placed a solution of 1,6,7,8-tetrahydro-as-indacen-3 (2H)-one (Cpd 307" was isolated from 113" in Scheme 23 by chromatography) (9.8 g, 46.5 mmol) in $H_2SO_4$ (50 mL). Then $HNO_3$ (5.85 g, 92.9 mmol) was added dropwise over 10 min at 0° C. The resulting solution was stirred for 1 h at 0° C. The reaction mixture was slowly added to a mixture of water/ice (100 mL) and DCM (50 mL) with ice bath cooling. The organic layer was collected, dried over $Na_2SO_4$ and concentrated under vacuum. This resulted in 11 g (89%) of a mixture of cpd 308" and cpd 309" as a yellow solid. The mixture was monitored by TLC (ethyl acetate/petroleum ether=1/10, $R_f$=0.4), Step 2: 1,2,3,6,7,8-hexahydro-as-indacen-4-amine (116)

Into a 100-mL round-bottom flask was placed a solution of the mixture of 4-nitro-1,6,7,8-tetrahydro-as-indacen-3 (2H)-one and 5-nitro-1,6,7,8-tetrahydro-as-indacen-3 (2H)-one (2.17 g, 10 mmol) in MeOH (30 mL). To the solution was added MSA (1.15 g, 12 mmol). Then $Pd(OH)_2/C$ (20% wt., 550 mg) was added. The flask was evacuated and filled three times with hydrogen. The resulting mixture was stirred for 16 h at RT under hydrogen (50 psi). The solids were filtered out and washed with MeOH. The MeOH filtrate and wash was diluted with water (50 mL) and the pH was adjusted to 10.6 with 2 N NaOH. The resulting mixture was filtered and the crude solids were recrystallized from MeOH/water (9:1) with heating. This resulted in 1.38 g (80%) of the title compound as an off-white solid. MS-ESI: 174 (M+1).

Scheme 73

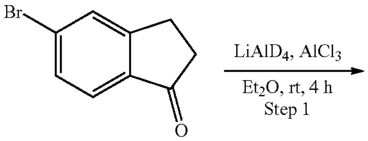

310″

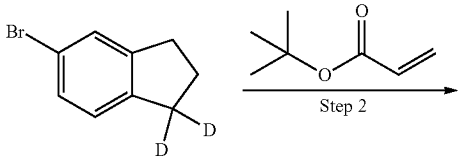

311″

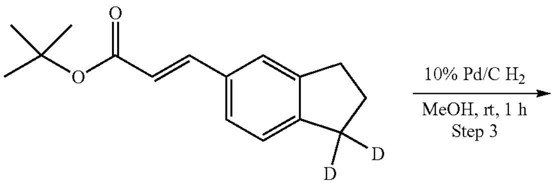

312″

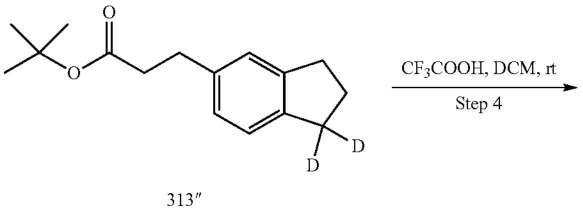

313″

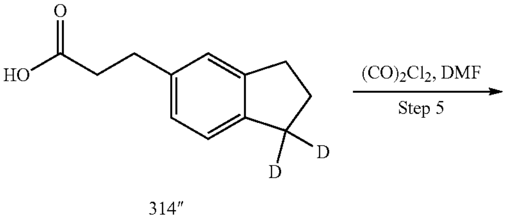

314″

-continued

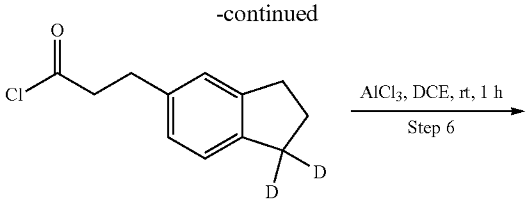

315″

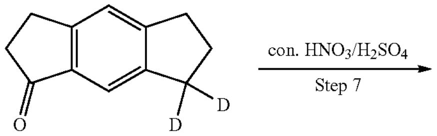

316″

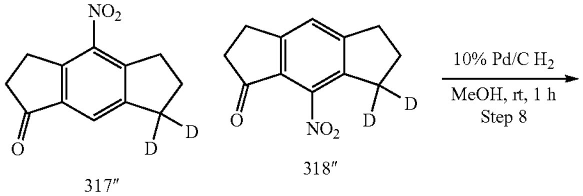

317″ 318″

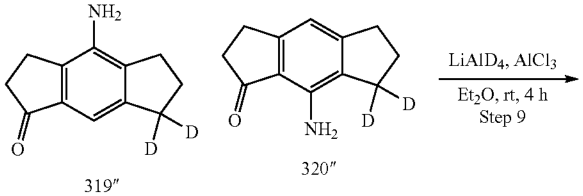

319″ 320″

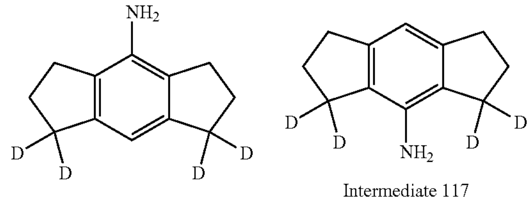

Intermediate 117A Intermediate 117

Intermediate 117

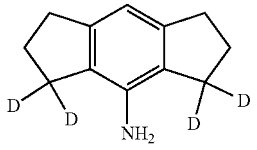

1,2,3,5,6,7-Hexahydro-s-indacen-3,3,5,5-$d_4$-4-amine

Step 1: 5-Bromo-2,3-dihydro-1H-indene-1,1-$d_2$

Into a 250-mL 3-necked round-bottom flask purged and maintained with an inert atmosphere of nitrogen, was placed a solution of $LiAlD_4$ (1.57 g, 37 mmol) in $Et_2O$ (150 mL). This was followed by the addition of $AlCl_3$ (10.1 g, 76 mmol) in portions at 0° C. in 5 min. To this was added 5-bromo-2,3-dihydro-1H-inden-1-one (4.0 g, 19 mmol) in portions at 0° C. in 5 min. The resulting solution was stirred for 4 h at RT. The reaction mixture was cooled to 0° C. with a water/ice bath. The reaction was then quenched by careful addition of 10 mL of water. The solids were filtered out. The resulting solution was extracted with 3×100 mL of ethyl acetate and concentrated under vacuum. This resulted in 3.5 g (93%) of the title compound as brown oil. MS-ESI: 199/201 (M+1).

Step 2: Tert-butyl (E)-3-(2,3-dihydro-1H-inden-5-yl-1,1-$d_2$)acrylate

Into a 250-mL round-bottom flask purged and maintained with an inert atmosphere of nitrogen, was placed a solution of 5-bromo-2,3-dihydro-1H-indene-1,1-$d_2$ (7.0 g, 35 mmol) in DMF (80 mL), to the stirred solution was added tris(4-methylphenyl)phosphane (1.07 g, 3.52 mmol), tert-butyl prop-2-enoate (4.0 mL), triethylamine (5.0 mL) and $Pd(OAc)_2$ (395 mg, 1.76 mmol). The resulting solution was stirred overnight at 100° C. in an oil bath. The resulting mixture was concentrated under vacuum. The resulting solution was extracted with 3×50 mL of ethyl acetate and the organic layers combined and dried over anhydrous sodium sulfate. The residue was eluted from a silica gel column with DCM/petroleum ether (1:1). This resulted in 5.7 g (66%) of the title compound as light yellow oil. MS-ESI: 247 (M+1).

Step 3: Tert-butyl 3-(2,3-dihydro-1H-inden-5-yl-1,1-$d_2$)propanoate

Into a 100-mL round-bottom flask purged and maintained with an inert atmosphere of nitrogen, was placed a solution of tert-butyl (E)-3-(2,3-dihydro-1H-inden-5-yl-1,1-$d_2$)acrylate (5.8 g, 24 mmol) in MeOH (40 mL), to the stirred solution was added Pd/C (580 mg, 10% wt.). The flask was evacuated and flushed three times with hydrogen. The resulting solution was stirred for 1 h at RT under an atmosphere of hydrogen. The Pd/C catalysts were filtered out, the filtrate was concentrated under vacuum. This resulted in 5.7 g (98%) of the title compound as colorless oil. MS-ESI: 249 (M+1).

Step 4: 3-(2,3-Dihydro-1H-inden-5-yl-1,1-$d_2$)propanoic Acid

Into a 100-mL round-bottom flask, was placed a solution of tert-butyl 3-(2,3-dihydro-1H-inden-5-yl-1,1-$d_2$)propanoate (4.3 g, 17.3 mmol) in DCM (50 mL), to the stirred solution was added $CF_3COOH$ (5.5 mL, 74 mmol). The resulting solution was stirred for overnight at RT. The resulting mixture was concentrated under vacuum. This resulted in 3.1 g (93%) of the title compound as an off-white solid. MS-ESI: 191 (M−1).

Step 5: 3-(2,3-Dihydro-1H-inden-5-yl-1,1-$d_2$)propanoyl Chloride

Into a 100-mL round-bottom flask purged and maintained with an inert atmosphere of nitrogen, was placed a solution of 3-(2,3-dihydro-1H-inden-5-yl-1,1-$d_2$)propanoic acid (9.0 g, 41.7 mmol) in DCM (40 mL). This was followed by the addition of oxalic dichloride (8.0 mL) at 0° C. To this was added DMF (0.5 mL) at 0° C. The resulting solution was stirred for 3 h at RT. The resulting mixture was concentrated under vacuum. This resulted in 4.0 g (41%) of the title compound as brown oil.

Step 6: 3,5,6,7-Tetrahydro-s-indacen-1 (2H)-one-7,7-$d_2$

Into a 100-mL round-bottom flask purged and maintained with an inert atmosphere of nitrogen, was placed a solution of 3-(2,3-dihydro-1H-inden-5-yl-1,1-$d_2$)propanoyl chloride (3.9 g, 18 mmol) in DCE (40 mL). This was followed by the addition of $AlCl_3$ (3.3 g, 25 mmol) in portions at 0° C. in 2 min. The resulting solution was stirred for 1 h at RT. The reaction was then quenched by the addition of 200 mL of water/ice. The resulting solution was extracted with 3×50 mL of DCM and the organic layers combined and dried over anhydrous sodium sulfate. The residue was eluted from a silica gel column with ethyl acetate/petroleum ether (2:100). This resulted in 1.5 g (46%) of the title compound as an off-white solid. MS-ESI: 175 (M+1).

Step 7: 8-Nitro-3,5,6,7-tetrahydro-s-indacen-1 (2H)-one-7,7-$d_2$ (Cpd 318", major) and 4-Nitro-3,5,6,7-tetrahydro-s-indacen-1 (2H)-one-7,7-$d_2$ (Cpd 317", Minor)

Into a 25-mL round-bottom flask, was placed 3,5,6,7-tetrahydro-s-indacen-1 (2H)-one-7,7-$d_2$ (120 g). This was followed by the addition of $H_2SO_4$ (8.0 mL) at 0° C. To this was added $HNO_3$ (2.0 mL) at 0° C. in 2 min. To the mixture was added $H_2SO_4$ (2.0 mL) at 0° C. in 2 min. The resulting solution was stirred for 1 h at 0° C. The reaction was then quenched by the addition of water/ice. The resulting solution was extracted with 3×50 mL of ethyl acetate dried in an oven under reduced pressure. The residue was separated on silica gel eluted with ethyl acetate/petroleum ether (3:100). This resulted in 870 mg of cpd 318" and 290 mg of cpd 317", both as yellow solids. Cpd 317": $^1$H NMR (300 MHz, $CDCl_3$) δ 7.83 (s, 1H), 3.55-3.45 (m, 2H), 3.42 (t, J=7.6 Hz, 2H), 2.84-2.74 (m, 2H), 2.22 (t, J=7.6 Hz, 2H). Cpd 318": $^1$H NMR (300 MHz, $CDCl_3$) δ 7.46 (s, 1H), 3.20-3.00 (m, 4H), 2.83-2.73 (m, 2H), 2.20 (t, J=7.5 Hz, 2H).

Step 8: 8-Amino-3,5,6,7-tetrahydro-s-indacen-1 (2H)-one-7,7-$d_2$

Into a 250-mL round-bottom flask purged and maintained with an inert atmosphere of nitrogen, was placed a solution of 8-nitro-3,5,6,7-tetrahydro-s-indacen-1 (2H)-one-7,7-$d_2$ (870 mg) in MeOH (100 mL), to the stirred solution was added Pd/C (87 mg, 10% wt.). The flask was evacuated and flushed three times with hydrogen. The resulting solution was stirred for 1 h at RT under an atmosphere of hydrogen. The Pd/C catalysts were filtered out, the filtrate was concentrated under vacuum. This resulted in 700 mg of the title compound as a yellow solid. MS-ESI: 190 (M+1).

Step 9: 1,2,3,5,6,7-Hexahydro-s-indacen-3,3,5,5-$d_4$-4-amine

Into a 250-mL round-bottom flask purged and maintained with an inert atmosphere of nitrogen, was placed a solution of $LiAlD_4$ (160 mg, 3.8 mmol) in $Et_2O$ (40 mL). This was followed by the addition of $AlCl_3$ (634 mg, 4.8 mmol) in portions at 0° C. in 2 min. To this solution was added 8-amino-3,5,6,7-tetrahydro-s-indacen-1 (2H)-one-7,7-$d_2$ (600 mg, 3.17 mmol) at 0° C. The resulting solution was stirred for 4 h at RT. The reaction was then quenched by the addition of 10 mL of water. The resulting solution was diluted with 20 mL of EtOAc. The solids were filtered out. The resulting solution was extracted with 3×50 mL of ethyl acetate dried over anhydrous sodium sulfate and concentrated under vacuum. The residue was eluted from a silica gel column with ethyl acetate/petroleum ether (5:1). This resulted in 470 mg (78%) of the Intermediate 117 as a yellow solid. MS-ESI: 178 (M+1).

Intermediate 117A

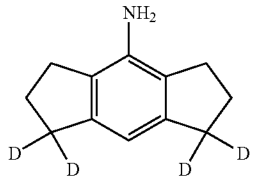

1,2,3,5,6,7-hexahydro-s-indacen-1,1,7,7-$d_4$-4-amine

Intermediate 117A was prepared starting from compound 317" and using the same procedure as shown in scheme 73 above for converting compound 318" to intermediate 117. MS-ESI: 178 (M+1).

TABLE 15

The Intermediates in the following Table were prepared using similar procedure as shown in Scheme 30 above for converting compound 130" to Intermediate 44.

| Intermediate # | Structure | IUPAC Name |
|---|---|---|
| Intermediate 118" | 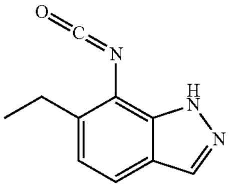 | 6-Ethyl-7-isocyanato-1H-indazole |
| Intermediate 119" | 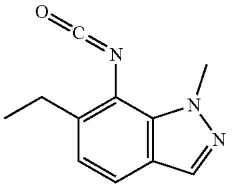 | 6-Ethyl-7-isocyanato-1-methyl-1H-indazole |
| Intermediate 120" | 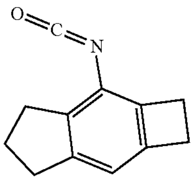 [SMILES: O=C=Nc1c2c(cc3c1CC3)CCC2] | 3-Isocyanato-2,4,5,6-tetrahydro-1H-cyclobuta[f]indene |
| Intermediate 121" | 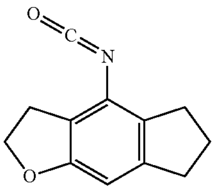 [SMILES: O=C=Nc1c2c(cc3c1CCO3)CCC2] | 4-Isocyanato-3,5,6,7-tetrahydro-2H-indeno[5,6-b]furan |
| Intermediate 122" | 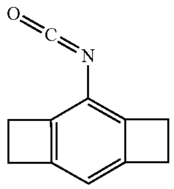 [SMILES: O=C=Nc1c2c(cc3c1CC3)CC2] | 2-Isocyanato-tricyclo[6.2.0.03,6]deca-1,3(6),7-triene |

TABLE 15-continued

The Intermediates in the following Table were prepared using similar procedure as shown in Scheme 30 above for converting compound 130" to Intermediate 44.

| Intermediate # | Structure | IUPAC Name |
|---|---|---|
| Intermediate 123" | 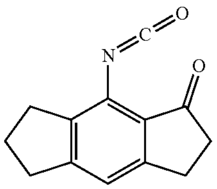 [SMILES: O=C=Nc1c2c(cc3c1C(=O)CC3)CCC2] | 8-Isocyanato-2,3,6,7-tetrahydros-indacen-1(5H)-one |
| Intermediate 124" | 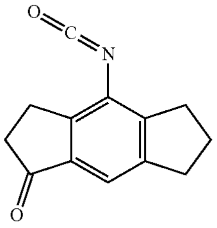 [SMILES: O=C=Nc1c2c(cc3c1CCC3=O)CCC2] | 4-Isocyanato-2,3,6,7-tetrahydros-indacen-1(5H)-one |
| Intermediate 125" | 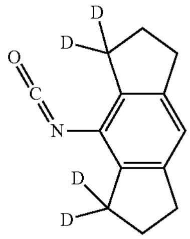 [SMILES: [2H]C1([2H])CCc2cc3c(c(N=C=O)c21)C([2H])([2H])CC3] | 4-isocyanato-1,2,3,5,6,7-hexahydro-s-indacene-3,3,5,5-$d_4$ |
| Intermediate 126" | 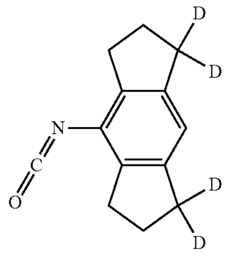 [SMILES: [2H]C1([2H])CCc2c1cc1c(c2N=C=O)CCC1([2H])[2H]] | 4-isocyanato-1,2,3,5,6,7-hexahydro-s-indacene-1,1,7,7-$d_4$ |

Schemes below the synthesis of sulfonimidamide Intermediates 118-123.

Scheme 74

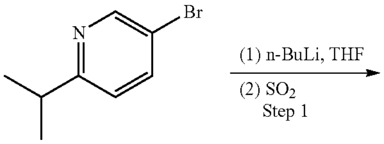

322"

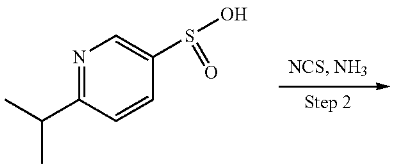

323"

-continued
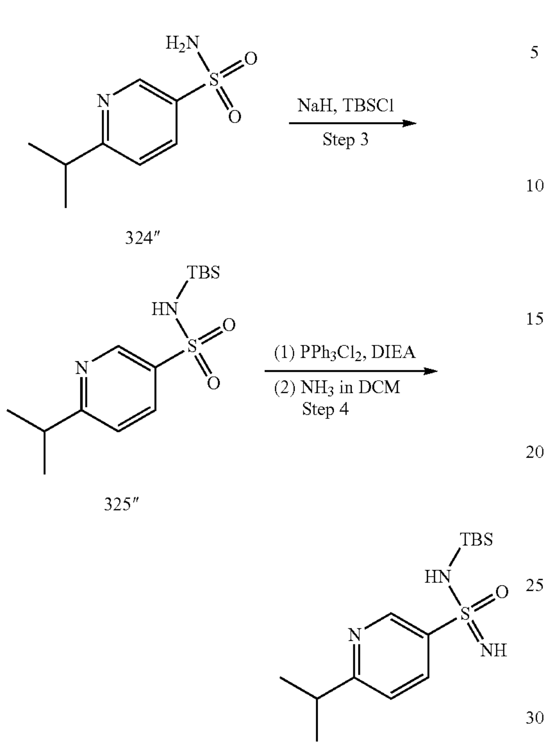
324″
325″
Intermediate 118
Intermediate 118
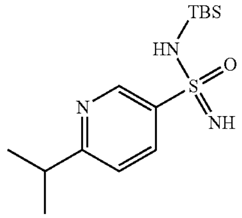
N-(tert-butyldimethylsilyl)-6-isopropylpyridine-3-sulfonimidamide
Steps 1-4 used similar procedures for converting compound 245" to Intermediate 88 shown in Scheme 56 to afford Intermediate 118 from compound 322". MS-ESI. 314 (M+1).
Scheme 75
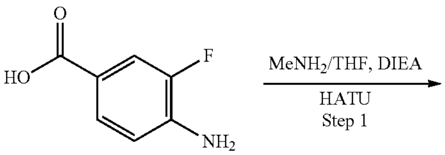
326″
-continued
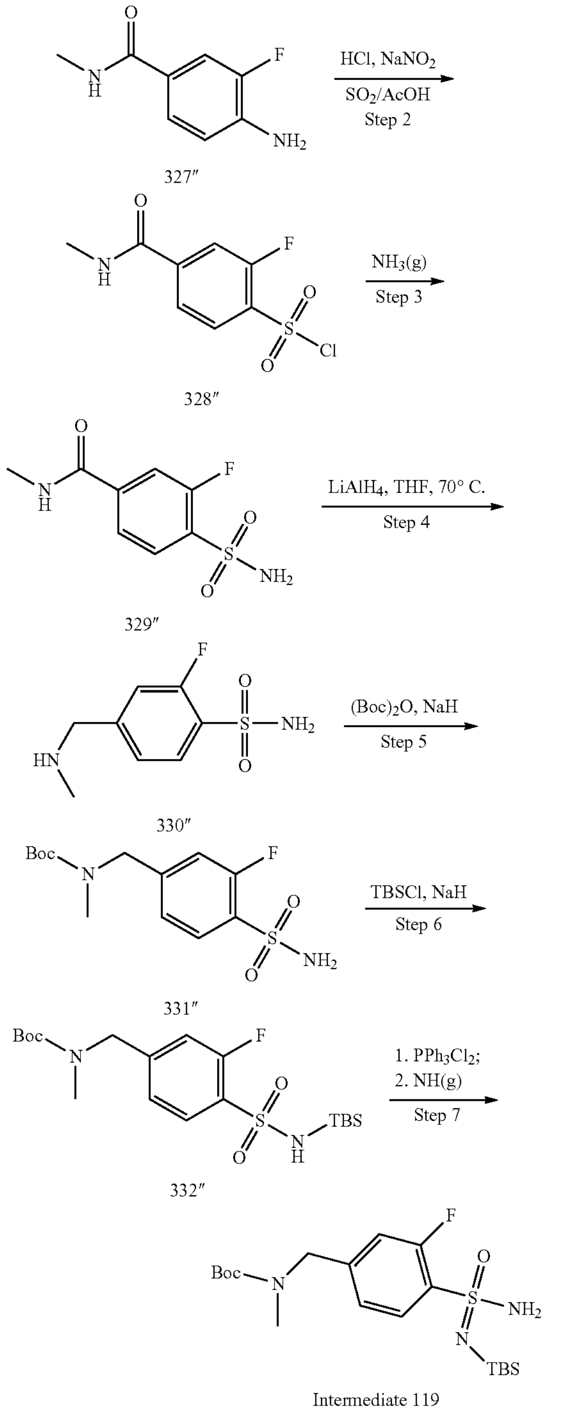
327″
328″
329″
330″
331″
332″
Intermediate 119
Intermediate 119
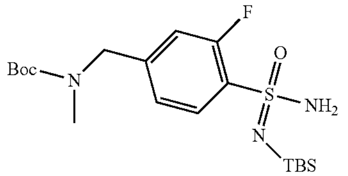

Step 1: 4-Amino-3-fluoro-N-methylbenzamide

Into a 500 mL round-bottom flask were added 4-amino-3-fluorobenzoic acid (15 g, 97 mmol) and DMF (100 mL) at RT. To the stirred solution was added HATU (74 mg, 0.19 mmol) and DIEA (25 mg, 0.19 mmol) at 0° C. To the above mixture was added $MeNH_2$/THF (2 M 97 mL, 194 mmol) in one portion at 0° C. The resulting mixture was stirred for additional 2 h at RT. The resulting mixture was extracted with EtOAc (3×100 mL). The combined organic layers were dried over anhydrous $Na_2SO_4$. After filtration, the filtrate was concentrated under reduced pressure. The residue was eluted from silica gel column with petroleum ether/EtOAc (1:1) to afford the title compound (16 g, 98%) as yellow oil. MS-ESI: 169 (M+1).

Steps 2-3 used similar procedures for converting compound 27 to Intermediate 29 shown in Scheme 9 to afford compound 329" from compound 327". MS-ESI: 233 (M+1).

Step 4: 2-Fluoro-4-((methylamino)methyl)benzenesulfonamide

Into a 250-mL round-bottom flask were placed 3-fluoro-N-methyl-4-sulfamoylbenzamide (1.2 g) in THF (40 mL) at 0° C. To the stirred solution was added $LiAlH_4$ (543 mg, 14 mmol) in portions at 0° C. under nitrogen atmosphere. The resulting mixture was stirred overnight at 70° C. The reaction was quenched with water (2 mL). The resulting mixture was filtered, the filter cake was washed with EtOAc (3×10 mL). The filtrate was concentrated under reduced pressure. The residue was purified by Prep-TLC (EtOAc/MeOH=25:1) to afford the title compound (800 mg, 77%) as a white solid. MS-ESI: 219 (M+1).

Step 5: Tert-butyl (3-fluoro-4-sulfamoylbenzyl)(methyl)carbamate

Into a 100-mL round-bottom flask were placed 2-fluoro-4-[(methylamino)methyl]benzene-1-sulfonamide (800 mg, 3.7 mmol) in THF (20 mL) at 0° C. To a stirred solution was added $(Boc)_{2}O$ (1.5 g, 6.89 mmol) in portions at 0° C. The resulting mixture was stirred for 2 h at RT and concentrated under reduced pressure. The residue was purified by Prep-TLC (PE/EtOAc 1:1) to afford the title compound (900 mg, 77%) as a white solid. MS-ESI: 319 (M+1).

Steps 6-7 used similar procedures for converting compound 248" to Intermediate 88 shown in Scheme 56 to afford Intermediate 119 from compound 331". MS-ESI: 432 (M+1).

Scheme 76

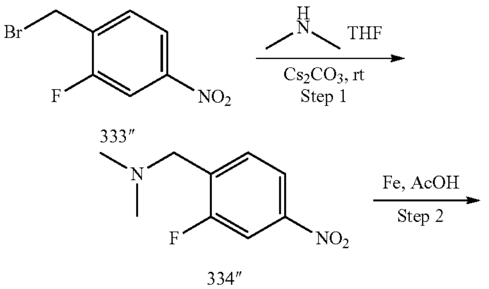

333″

334″

-continued

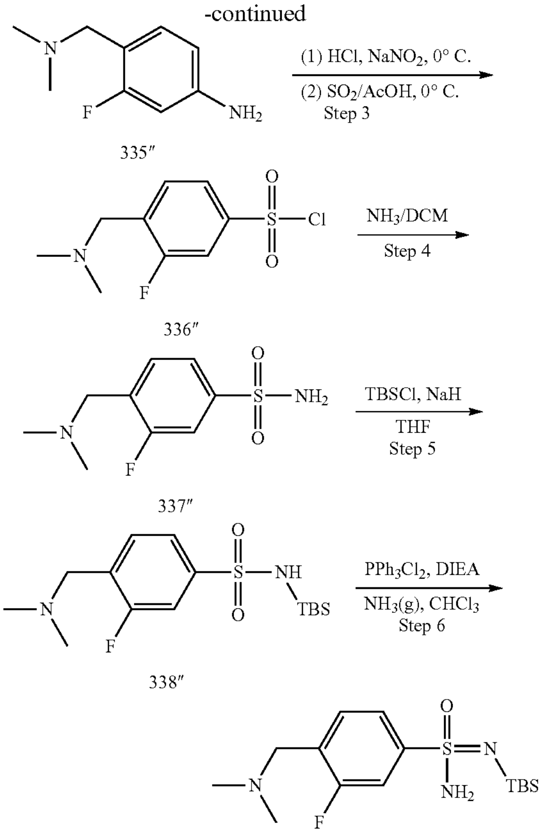

335″

336″

337″

338″

Intermediate 120

Intermediate 120

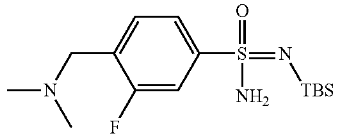

N'-(tert-butyldimethylsilyl)-4-((dimethylamino)methyl)-3-fluorobenzenesulfonimidamide Step 1: 1-(2-Fluoro-4-nitrophenyl)-N,N-dimethylmethanamine Into a 250-mL round-bottom flask, was placed a solution of 1-(bromomethyl)-2-fluoro-4-nitrobenzene (8.0 g, 34 mmol) in MeOH (50 mL). This was followed by the addition of dimethylamine (2 M, 21 mL) dropwise with stirring at 0° C. in 5 min. The resulting solution was stirred for 4 h at RT. The resulting mixture was concentrated under vacuum. This resulted in 7.0 g crude title compound as yellow oil. MS-ESI: 199 (M+1).

Step 2: 4-((Dimethylamino)methyl)-3-fluoroaniline

Into a 100-mL round-bottom flask, was placed the solution of [(2-fluoro-4-nitrophenyl)methyl]dimethylamine (7.0 g, 35 mmol) in AcOH (20 mL), to the stirred solution was added iron powder (10 g, 179 mmol). The resulting solution was stirred for 16 h at RT. The solids were filtered out. The resulting filtrate was concentrated under vacuum. The residue was eluted from a silica gel column with DCM/MeOH (9:1). This resulted in 6.5 g crude title compound as yellow oil. MS-ESI: 169 (M+1).

Steps 3-4 used similar procedures for converting compound 145" to compound 147" shown in Scheme 36 to afford compound 337" from compound 335". MS-ESI: 233 (M+1).

Steps 5-6 used similar procedures for converting compound 148" to Intermediate 59 shown in Scheme 36 to afford Intermediate 120 from compound 337". MS-ESI: 233 (M+1).

Scheme 77

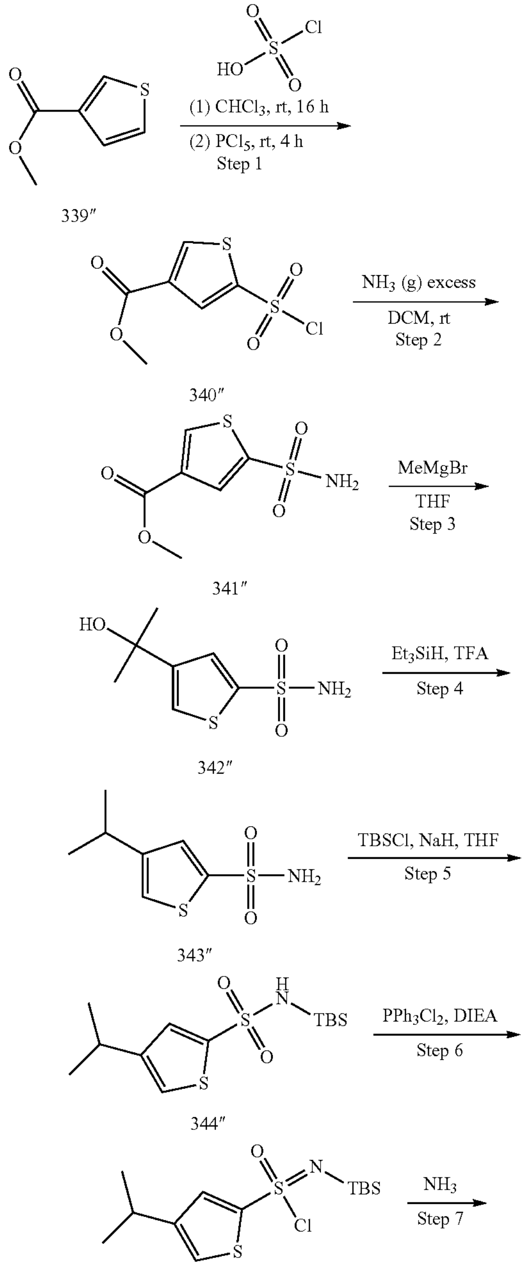

339"

340"

341"

342"

343"

344"

345"

-continued

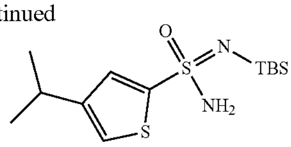

Intermediate 121

Intermediate 121

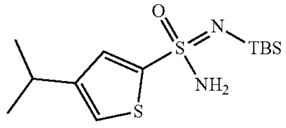

N'-(tert-butyldimethylsilyl)-4-isopropylthiophene-2-sulfonimidamide

Steps 1-2 used similar procedures for converting compound 158" to intermediate 61 shown in Scheme 38 to afford compound 341" from compound 339". MS-ESI: 221 (M+1).

Step 3 used similar procedures for converting compound 147" to compound 148" shown in Scheme 36 to afford compound 342" from compound 341". MS-ESI: 221 (M+1).

Step 4: 4-Isopropylthiophene-2-sulfonamide

Into a 250-mL round-bottom flask, was placed the solution of 4-(2-hydroxypropan-2-yl)thiophene-2-sulfonamide (1.5 g, 6.79 mmol) in DCM (20 mL). To the stirred solution was added TFA (3.9 g, 34 mmol) and $Et_3SiH$ (2.32 g, 20 mmol). The result solution was stirred overnight at RT. The mixture was concentrated under vacuum. The residue was eluted from silica gel column with a gradient of ethyl acetate/petroleum ether (1:5 to 1:3). This resulted in 1.1 g (79%) of the title compound as a light yellow solid. MS-ESI: 206 (M+1).

Steps 5-6 used similar procedures for converting compound 148" to Intermediate 59 shown in Scheme 36 to afford Intermediate 121 from compound 344". MS-ESI: 319 (M+1).

Scheme 78

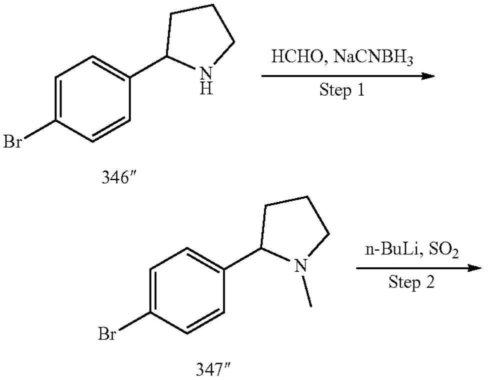

346"

347"

-continued

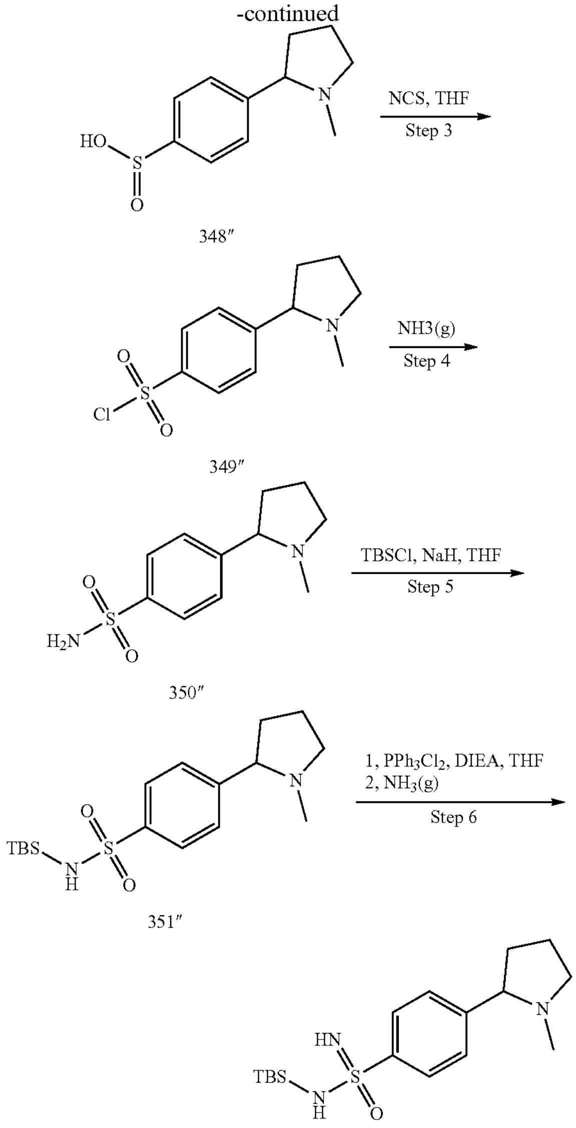

348″ 349″ 350″ 351″

Intermediate 122

Intermediate 122

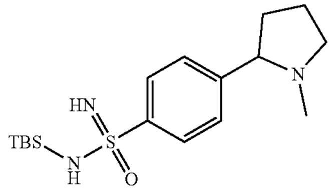

N-(tert-butyldimethylsilyl)-4-(1-methylpyrrolidin-2-yl)benzenesulfonimidamide

Step 1: 2-(4-Bromophenyl)-1-methylpyrrolidine

Into a 100-mL round-bottom flask, was placed 2-(4-bromophenyl)pyrrolidine (3.0 g, 13.3 mmol) in HCHO (3.23 g, 37% wt.), to the stirred solution was added $NaBH_3CN$ (2.5 g, 40 mmol). The resulting solution was stirred for 12 h at RT and concentrated under vacuum. The residue was eluted from a silica gel column with ethyl acetate/petroleum ether (1:1). This resulted in 2.8 g (88%) of the title compound as a light yellow solid. MS-ESI: 240/242 (M+1).

Steps 2-6 used similar procedures for converting compound 245" to Intermediate 88 shown in Scheme 56 to afford Intermediate 122" from compound 347". MS-ESI: 354 (M+1).

Scheme 79

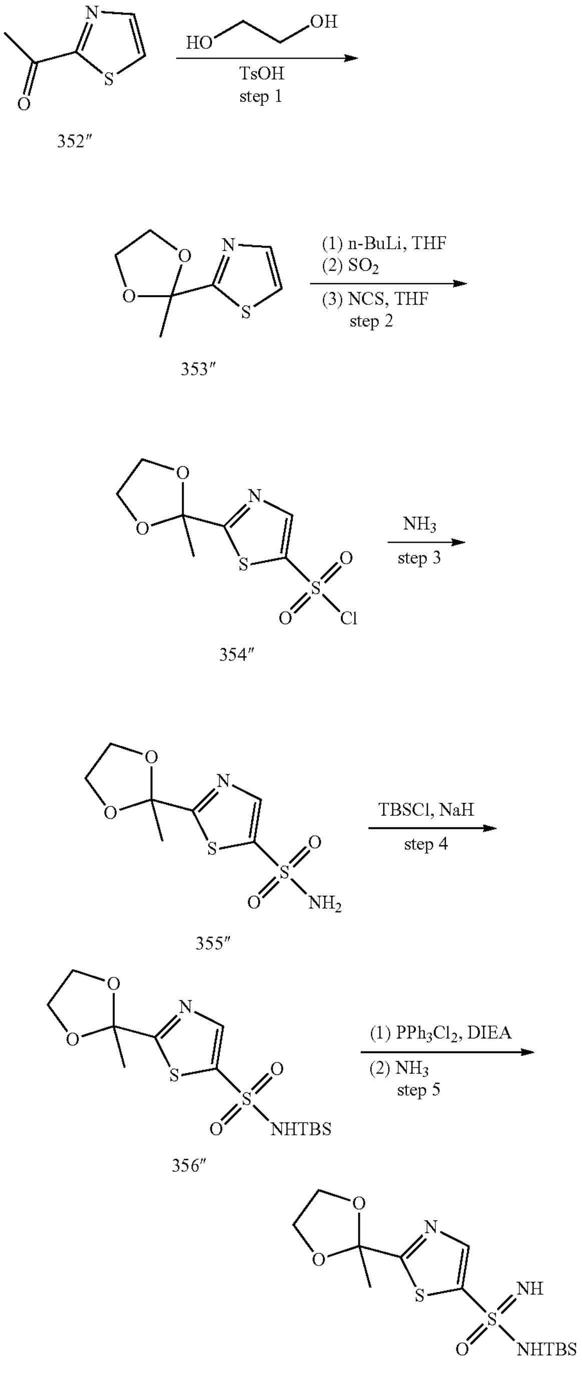

352″ 353″ 354″ 355″ 356″

Intermediate 123

Intermediate 123

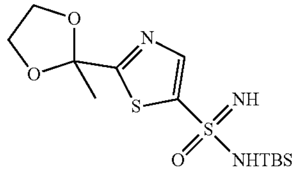

N-(tert-butyldimethylsilyl)-2-(2-methyl-1,3-dioxolan-2-yl)thiazole-5-sulfonimidamide Step 1: 2-(2-Methyl-1,3-dioxolan-2-yl)thiazole Into a 50-mL round-bottom flask purged and maintained with an inert atmosphere of nitrogen, was placed 1-(1,3-thiazol-2-yl)ethan-1-one (27 g, 212 mmol) in toluene (300 mL), to the stirred solution was added TsOH (2.0 g, 11.6 mmol) and ethane-1,2-diol (40 g, 644 mmol). The resulting solution was stirred for 14 h at 110° C. in an oil bath. The resulting mixture was concentrated under vacuum. The residue was eluted from a silica gel column with ethyl acetate/petroleum ether (1:20 to 1:10). This resulted in 36 g (99%) of the title compound as brown oil. MS-ESI: 172 (M+1).

Steps 2-5 used similar procedures for converting compound 245" to Intermediate 88 shown in Scheme 56 to afford Intermediate 123 from compound 353". MS-ESI: 363 (M+1).

Reagent 1

Dichlorotriphenylphosphorane

This reagent was either purchased or prepared using the following procedure:

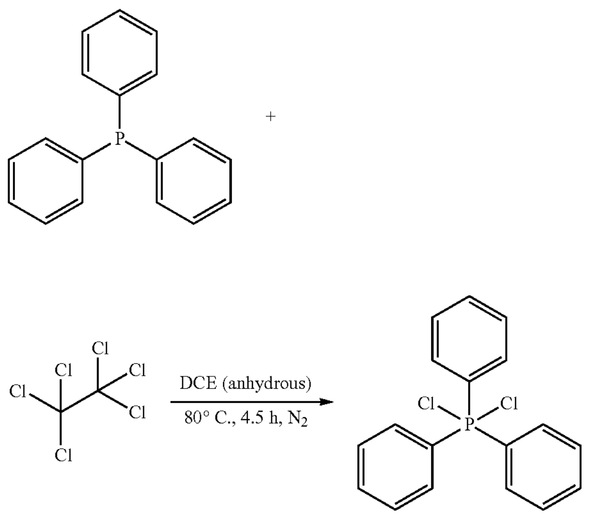

An oven dried 40 mL vial equipped with a stir bar was capped with a rubber septum and flushed with nitrogen. At room temperature, a solution of $PPh_3$ (0.85 g, 3.2 mmol) in anhydrous 1,2-dichloroethane (5 mL) was introduced via syringe. The reaction vessel was immersed in an ice/water bath and cooled for 5 min. A solution of hexachloroethane (0.76 g, 3.2 mmol) in anhydrous 1,2-dichloroethane (5 mL) was introduced dropwise via syringe. After the addition was complete the reaction mixture was stirred at the same temperature for an additional 5 min and then placed into a preheated block set at 80° C. Heating was continued for 4.5 h, at which time the reaction was assumed to be complete. The light golden clear solution was cooled to ambient temperature. The reagent thus prepared was transferred via syringe in subsequent reactions without any work up or purification. The total volume of the reaction mixture was 11 mL for the molar calculations for next steps. This solution containing $PPh_3Cl_2$ was stored under nitrogen at room temperature until used.

Reagent 2

Polymer-bound dichlorotriphenylphosphorane

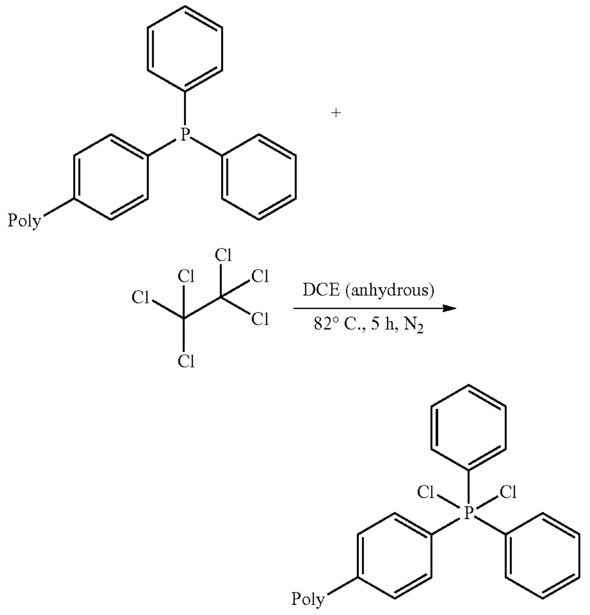

A

Polystyrene bound $PPh_3$ (0.32 g, 0.32 mmol) was suspended in anhydrous dichloroethane (6 mL) and shaked on a shaker for 5 mins. It was then filtered and the process was repeated again to swell the polymer. Filtered resin was suspended in anhydrous dichloroethane (6 mL) a third time and the whole suspension was transferred into an oven dried 40 mL vial with a stir bar via pipette. The vial was capped with a rubber septum and connected to a steady flow of nitrogen. The reaction vessel was immersed in an ice/water bath and cooled down for 10 min. A solution of hexachloroethane (0.076 g, 0.32 mmol) in anhydrous 1,2-dichloroethane (2 mL) was introduced drop wise via syringe. After the addition was complete the reaction mixture was placed in an already heated block set at 82° C. for 5 h. At this point the reaction is assumed to be completed. It was gradually brought to room temperature and used in the next step as is.

This reagent was used at 1.5 equiv. with respect to sulfonamide in the next step.

SYNTHETIC EXAMPLES

Example 1

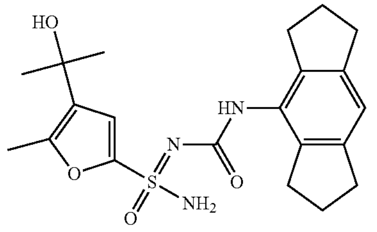 [SMILES: Cc1oc(S(N)(=O)=NC(=O)Nc2c3c(cc4c2CCC4)CCC3)cc1C(C)(C)O]

Example 1 (181): N'-(1,2,3,5,6,7-hexahydro-s-indacen-4-ylcarbamoyl)-4-(2-hydroxypropan-2-yl)-5-methylfuran-2-sulfonimidamide Example 1 was synthesized according to the general method shown in Scheme 1, as illustrated below.

Examples 2 and 3

Examples 2 and 3

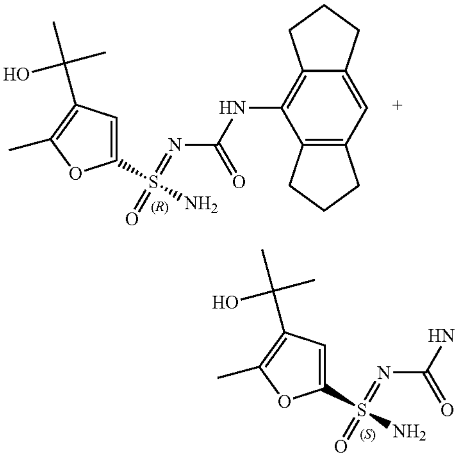

Examples 2 (181a) and 3 (181b): (S)- and (R)—N'-(1,2,3,5,6,7-hexahydro-s-indacen-4-ylcarbamoyl)-4-(2-hydroxypropan-2-yl)-5-methylfuran-2-sulfonimidamide Examples 2 and 3 were prepared through chiral separation of Example 1 as illustrated below.

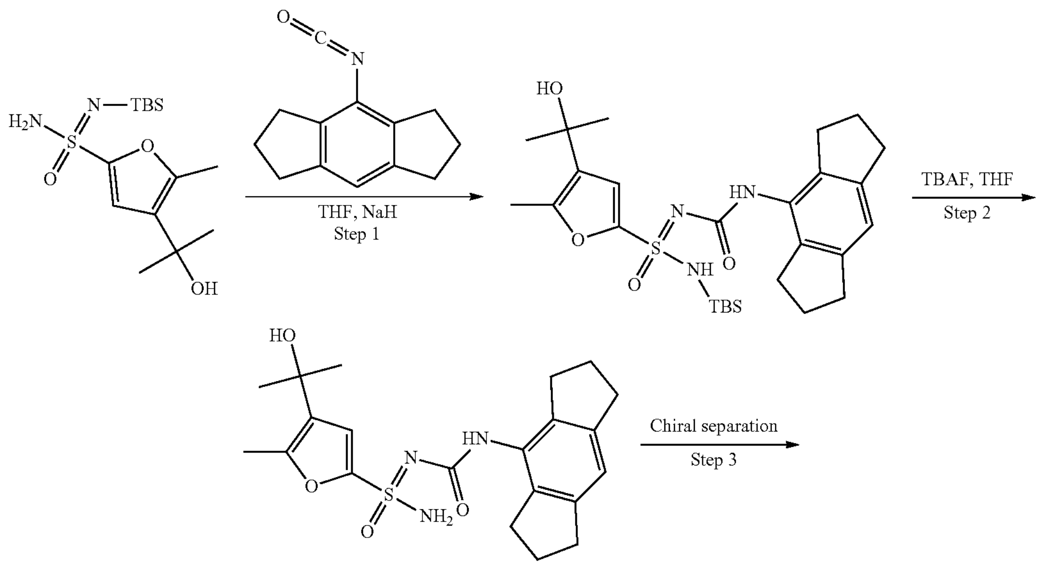

Example 1

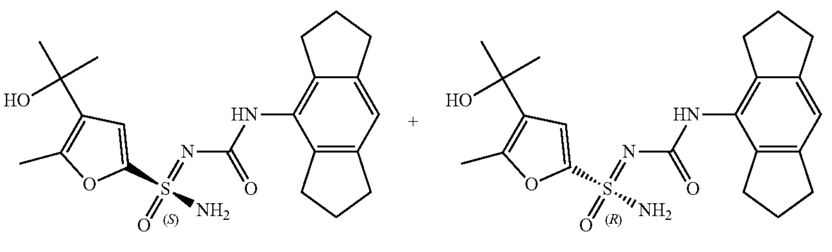

Examples 2 and 3

Step 1: N'-(tert-butyldimethylsilyl)-N-(1,2,3,5,6,7-hexahydro-s-indacen-4-ylcarbamoyl)-4-(2-hydroxy-propan-2-yl)-5-methylfuran-2-sulfonimidamide Into a 50-mL round-bottom flask was placed N'-(tert-butyldimethylsilyl)-4-(2-hydroxypropan-2-yl)-5-methyl-furan-2-sulfonimidamide (200 mg, 0.6 mmol), THF (10 mL), NaH (60% wt, 48 mg, 1.2 mmol). This was followed by the addition of a solution of 4-isocyanato-1,2,3,5,6,7-hexahydro-s-indacene (120 mg, 0.6 mmol) in THF (1 mL) dropwise with stirring at RT. The resulting solution was stirred for 12 h at RT. The reaction was then quenched by the addition of 10 mL of $NH_4Cl$ (sat.). The resulting solution was extracted with 3×10 mL of DCM and the organic layers combined and concentrated under vacuum. The residue was applied onto a silica gel column and eluted with ethyl acetate/petroleum ether (1:10 to 1:3). This resulted in 140 mg (43.8%) of the title compound as brown oil. MS-ESI: 532.0 (M−1).

Step 2: N'-(1,2,3,5,6,7-hexahydro-s-indacen-4-ylcarbamoyl)-4-(2-hydroxypropan-2-yl)-5-methylfuran-2-sulfonimidamide Into a 50-mL round-bottom flask was placed N'-(tert-butyldimethylsilyl)-N-(1,2,3,5,6,7-hexahydro-s-indacen-4-ylcarbamoyl)-4-(2-hydroxypropan-2-yl)-5-methylfuran-2-sulfonimidamide (130 g, 0.2 mmol), THF (10 mL), and TBAF (300 mg, 0.5 mmol). The resulting solution was stirred for 2 h at RT and then concentrated under vacuum. The crude product was purified by Prep-HPLC using method E eluted with a gradient of 30~60% ACN. This resulted in 82 mg (80.3%) of Example 1 as a white solid.

Example 1: MS-ESI: 418.0 (M+1). $^1H$ NMR (400 MHz, DMSO-$d_6$) δ 8.39 (s, 1H), 7.57 (s, 2H), 6.87 (s, 1H), 6.85 (s, 1H), 5.04 (s, 1H), 2.79 (t, J=7.4 Hz, 4H), 2.71-2.63 (m, 4H), 2.42 (s, 3H), 1.94 (tt, J=7.4 and 7.4 Hz, 4H), 1.40 (s, 6H).

Step 3: Chiral Separation

The product obtained as described in the previous step (70 mg) was resolved by Chiral-Prep-HPLC using the following conditions: Column, ChiralPak ID, 2*25 cm, 5 um; mobile phase, Hex and EtOH (hold 20% EtOH over 18 min); Flow rate, 20 mL/min; Detector, UV 254/220 nm. This resulted in 26.8 mg of Example 2 (front peak, 99% ee) as a white solid and 27.7 mg (second peak, 99.3% ee) of Example 3 as a white solid.

Example 2: MS-ESI: 418.0 (M+1). $^1H$ NMR (400 MHz, DMSO-$d_6$) δ 8.36 (s, 1H), 7.57 (s, 2H), 6.87 (s, 1H), 6.85 (s, 1H), 5.03 (s, 1H), 2.78 (t, J=7.2 Hz, 4H), 2.73-2.60 (m, 4H), 2.41 (s, 3H), 1.93 (tt, J=7.2 and 7.2 Hz, 4H), 1.39 (s, 6H).

Example 3: MS-ESI: 418.0 (M+1). $^1H$ NMR (400 MHz, DMSO-$d_6$) δ 8.39 (s, 1H), 7.58 (s, 2H), 6.87 (s, 1H), 6.85 (s, 1H), 5.03 (s, 1H), 2.78 (t, J=7.2 Hz, 4H), 2.73-2.60 (m, 4H), 2.41 (s, 3H), 1.93 (tt, J=7.2 and 7.2 Hz, 4H), 1.39 (s, 6H).

Single crystal X-ray crystallographic analysis was performed on compound 181a. FIG. 1 shows ball and stick models of the asymmetrical unit containing two crystallographically independent molecules of compound 181a, with hydrogen atoms omitted for clarity. Table M below shows fractional atomic coordinates of compound 181a.

TABLE M

Fractional Atomic Coordinates (×$10^4$) and Equivalent Isotropic Displacement Parameters (Å$^2$ × $10^3$) for Example 2. $U_{eq}$ is defined as ⅓ of the trace of the orthogonalised $U_{IJ}$ tensor.

| Atom | x | y | z | U(eq) |
|---|---|---|---|---|
| S1 | 722.5(7) | 5368.3(5) | 6903.3(4) | 14.52(18) |
| S2 | 4304.8(7) | 505.4(5) | 3262.9(4) | 16.15(18) |
| O1 | 2143(2) | 6680.8(16) | 8220.2(13) | 16.1(4) |
| O2 | −195(2) | 4624.4(17) | 6478.0(14) | 21.9(5) |
| O5 | 2874(2) | 1624.4(17) | 1805.2(15) | 22.8(5) |
| O6 | 5238(2) | −141.6(18) | 3795.4(15) | 25.6(5) |
| O3 | 1492(3) | 5769.7(18) | 5397.8(14) | 25.5(5) |
| O7 | 2974(2) | 2151.0(17) | 3638.1(14) | 24.6(5) |
| N1 | 51(2) | 7218.5(19) | 8513.8(16) | 14.6(5) |
| N2 | 59(3) | 5986.0(18) | 7536.5(16) | 15.3(5) |
| O4 | 2422(3) | 8513(2) | 4297.8(17) | 34.3(6) |
| N4 | 4956(2) | 2247(2) | 1576.1(16) | 16.9(5) |
| O8 | 2771(3) | 3430(2) | 6070.3(18) | 36.7(6) |
| N5 | 4980(3) | 1071.7(19) | 2602.6(17) | 16.6(5) |
| N3 | 2120(3) | 4817(2) | 7347.5(17) | 16.3(5) |
| C13 | 854(3) | 6633(2) | 8105.0(18) | 12.9(6) |
| C1 | 605(3) | 7947(2) | 9133.7(19) | 14.4(6) |
| N6 | 2978(3) | −121(2) | 2801.8(19) | 20.2(6) |
| C22 | 4388(3) | 2952(2) | 936.5(19) | 16.2(6) |
| C24 | 5733(3) | 2203(2) | −207(2) | 18.3(6) |
| C34 | 4164(3) | 1656(2) | 1979(2) | 16.6(6) |
| C11 | −695(3) | 7200(2) | 10304.5(19) | 17.2(6) |
| C12 | 267(3) | 7915(2) | 9953.6(19) | 14.2(6) |
| C23 | 4754(3) | 2918(2) | 127(2) | 17.0(6) |
| C27 | 4221(3) | 3614(2) | −494(2) | 18.1(6) |
| C8 | 800(3) | 8626(2) | 10566(2) | 17.0(6) |
| C28 | 3315(3) | 4357(2) | −324(2) | 18.6(6) |
| C4 | 2436(4) | 10034(2) | 8218(2) | 23.3(7) |
| C7 | 1688(3) | 9377(2) | 10382(2) | 16.9(6) |
| C29 | 2969(3) | 4399(2) | 492(2) | 18.0(6) |
| C9 | 237(3) | 8445(2) | 11388(2) | 20.4(6) |
| C38 | 2557(3) | 2633(3) | 4320(2) | 24.9(7) |
| C2 | 1458(3) | 8717(2) | 8931.9(19) | 15.1(6) |
| C6 | 2005(3) | 9409(2) | 9557(2) | 17.2(6) |
| C26 | 4804(3) | 3424(2) | −1310(2) | 21.8(7) |
| C31 | 2476(4) | 5023(2) | 1822(2) | 24.4(7) |
| C5 | 2927(3) | 10137(2) | 9193(2) | 19.6(6) |
| C16 | 2044(3) | 7389(3) | 5427(2) | 22.4(7) |
| C25 | 5416(4) | 2367(3) | −1181(2) | 24.1(7) |
| C15 | 1514(3) | 7144(2) | 6188(2) | 21.6(6) |
| C33 | 3503(3) | 3713(2) | 1124(2) | 16.9(6) |
| C37 | 3005(3) | 2117(3) | 5067(2) | 23.8(7) |
| C30 | 2028(3) | 5128(2) | 844(2) | 20.5(6) |
| C10 | −360(4) | 7379(2) | 11275(2) | 23.9(7) |
| C36 | 3748(3) | 1285(3) | 4821(2) | 24.5(7) |
| C17 | 2020(4) | 6535(3) | 4974(2) | 28.3(7) |
| C14 | 1181(3) | 6178(2) | 6137.8(19) | 19.0(6) |
| C35 | 3710(3) | 1326(2) | 3973(2) | 23.7(7) |
| C19 | 2583(3) | 8401(3) | 5214(2) | 26.0(7) |
| C3 | 1902(3) | 8960(2) | 8090(2) | 19.0(6) |
| C32 | 3002(3) | 3944(2) | 1954(2) | 21.0(6) |
| C40 | 2768(4) | 2390(3) | 5955(2) | 33.7(8) |
| C20 | 1804(4) | 9231(3) | 5566(3) | 34.6(8) |
| C39 | 1810(4) | 3575(3) | 4092(3) | 35.7(8) |
| C42 | 1313(4) | 2062(3) | 6087(3) | 40.3(9) |
| C21 | 4139(4) | 8447(3) | 5541(3) | 40.0(9) |
| C18 | 2406(5) | 6256(3) | 4130(3) | 44.7(10) |
| C41 | 3893(5) | 1934(4) | 6622(3) | 54.3(12) |

Figure 2:
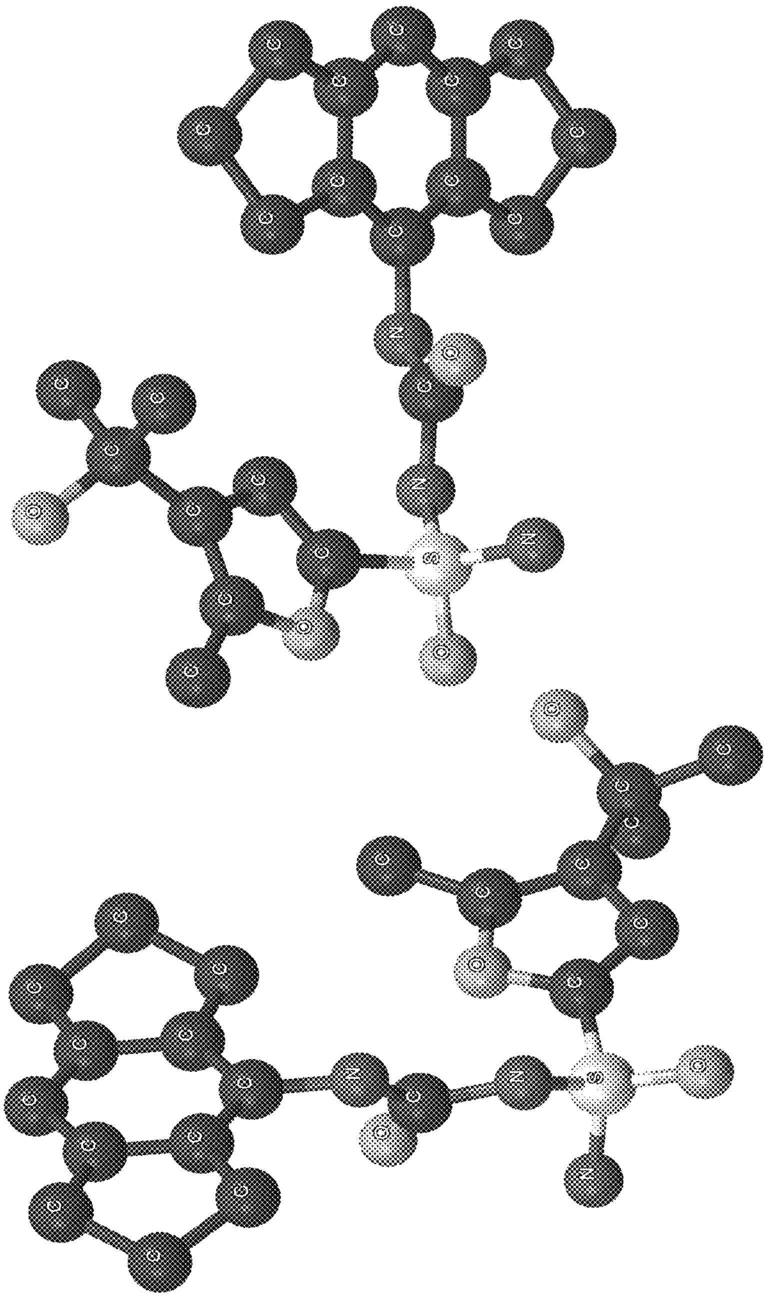
FIG. 2 depicts ball-and-stick representations of two crystallographically independent molecules of compound 181b in the asymmetrical unit.

Single crystal X-ray crystallographic analysis was performed on compound 181b. FIG. 2 shows ball and stick models of the asymmetrical unit containing two crystallographically independent molecules of compound 181b, with hydrogen atoms omitted for clarity. Table N below shows fractional atomic coordinates of compound 181b.

TABLE N

Fractional Atomic Coordinates (×$10^4$) and Equivalent Isotropic Displacement Parameters ($Å^2$ × $10^3$) for Example 3. $U_{eq}$ is defined as ⅓ of the trace of the orthogonalised $U_{IJ}$ tensor.

| Atom | x | y | z | U(eq) |
|---|---|---|---|---|
| S1 | 9264.0(7) | 4621.3(5) | 3094.0(4) | 16.15(17) |
| S2 | 5705.1(7) | 9485.8(5) | 6733.7(4) | 19.00(17) |
| O1 | 7853(2) | 3305.2(16) | 1778.9(13) | 18.6(4) |
| O7 | 7027(2) | 7842.4(18) | 6357.2(15) | 26.4(5) |
| O2 | 10182(2) | 5364.5(17) | 3520.0(14) | 23.6(5) |
| O5 | 7131(2) | 8368.0(19) | 8192.5(15) | 25.5(5) |
| O3 | 8512(3) | 4220.7(18) | 4605.0(14) | 26.6(5) |
| O6 | 4770(2) | 10133.7(19) | 6200.8(15) | 28.4(5) |
| O8 | 7211(3) | 6563(2) | 3921.7(19) | 38.6(7) |
| O4 | 7597(3) | 1484(2) | 5713.0(18) | 37.3(6) |
| N2 | 9933(3) | 4006.4(19) | 2465.8(16) | 17.8(5) |
| N1 | 9943(2) | 2773(2) | 1482.7(16) | 16.3(5) |
| N4 | 5051(3) | 7745(2) | 8421.8(17) | 20.2(5) |
| N3 | 7870(3) | 5173(2) | 2653.4(17) | 18.4(5) |
| N5 | 5031(3) | 8923(2) | 7390.2(17) | 19.9(5) |
| C14 | 9136(3) | 3353(2) | 1894.3(18) | 15.8(6) |
| C1 | 9391(3) | 2043(2) | 864.7(19) | 17.4(6) |
| N6 | 7031(3) | 10109(2) | 7191.6(19) | 23.0(6) |
| C30 | 5618(3) | 7045(2) | 9058(2) | 19.3(6) |
| C6 | 9205(3) | 1370(2) | −570(2) | 20.1(6) |
| C53 | 7446(4) | 7363(3) | 5675(2) | 26.1(7) |
| C32 | 4273(3) | 7792(2) | 10199(2) | 20.6(6) |
| C2 | 9731(3) | 2078(2) | 44.2(19) | 16.8(6) |
| C43 | 5846(3) | 8333(2) | 8016(2) | 20.2(6) |
| C3 | 10685(3) | 2795(2) | −304(2) | 20.3(6) |
| C37 | 7028(3) | 5597(2) | 9506(2) | 21.2(6) |
| C7 | 8316(3) | 620(2) | −386(2) | 20.2(6) |
| C35 | 5773(3) | 6383(2) | 10493(2) | 20.7(6) |
| C10 | 7573(4) | −36(3) | 1780(2) | 27.4(7) |
| C36 | 6681(3) | 5639(2) | 10322(2) | 21.2(6) |
| C22 | 8481(3) | 2845(3) | 3816(2) | 23.0(6) |
| C8 | 8002(3) | 584(2) | 440(2) | 20.3(6) |
| C39 | 7525(4) | 4977(3) | 8177(2) | 28.0(7) |
| C31 | 5248(3) | 7078(2) | 9867(2) | 19.6(6) |
| C52 | 6981(3) | 7875(3) | 4927(2) | 24.2(7) |
| C12 | 8541(3) | 1280(2) | 1066.4(19) | 18.0(6) |
| C34 | 5191(4) | 6574(3) | 11302(2) | 24.8(7) |
| C51 | 6252(4) | 8707(3) | 5170(2) | 26.7(7) |
| C33 | 4585(4) | 7630(3) | 11175(2) | 27.6(7) |
| C24 | 7990(4) | 3461(3) | 5032(2) | 30.5(8) |
| C23 | 7962(3) | 2603(3) | 4580(2) | 24.0(7) |
| C50 | 6302(4) | 8662(3) | 6020(2) | 25.4(7) |
| C9 | 7077(3) | −142(2) | 804(2) | 23.6(7) |
| C38 | 7972(3) | 4873(2) | 9155(2) | 23.5(7) |
| C5 | 9763(4) | 1551(3) | −1391(2) | 24.9(7) |
| C41 | 6502(3) | 6286(2) | 8872(2) | 20.5(6) |
| C21 | 8811(3) | 3816(2) | 3866.6(19) | 20.4(6) |
| C4 | 10356(4) | 2619(3) | −1277(2) | 28.3(7) |
| C11 | 8099(3) | 1036(2) | 1909(2) | 22.6(6) |
| C40 | 7006(3) | 6055(3) | 8044(2) | 24.5(6) |
| C25 | 7419(4) | 1599(3) | 4793(2) | 26.8(7) |
| C58 | 8189(4) | 6425(3) | 5905(3) | 37.6(9) |
| C54 | 7221(4) | 7601(3) | 4036(2) | 34.1(8) |
| C27 | 8195(4) | 774(3) | 4438(3) | 38.1(9) |
| C29 | 7607(6) | 3737(3) | 5874(3) | 46.7(10) |
| C56 | 8674(4) | 7924(3) | 3907(3) | 42.4(10) |
| C28 | 5872(4) | 1551(3) | 4471(3) | 44.2(10) |
| C57 | 6101(6) | 8060(4) | 3369(3) | 58.9(14) |

Example 4

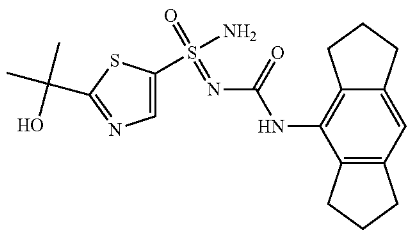 [SMILES: CC(C)(O)c1ncc(S(N)(=O)=NC(=O)Nc2c3c(cc4c2CCC4)CCC3)s1]

Example 4 (101'): N'-(1,2,3,5,6,7-hexahydro-s-indacen-4-ylcarbamoyl)-2-(2-hydroxypropan-2-yl) thiazole-5-sulfonimidamide Example 4 (above) was synthesized according to the general methods in Schemes 2 and 3, as illustrated in Route 1 and Route 2 below.

Examples 5 and 6

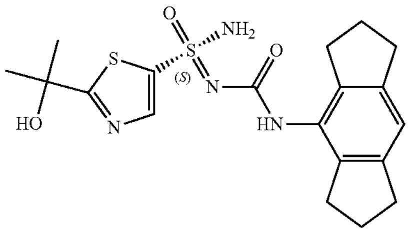

+

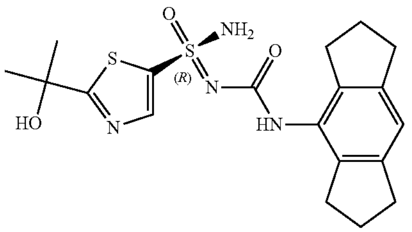

Examples 5 and 6 (stereochemistry not assigned)

Examples 5 (101) and 6 (102): (S)- and (R)—N'-(1,2,3,5,6,7-hexahydro-s-indacen-4-ylcarbamoyl)-2-(2-hydroxypropan-2-ylthiazole-5-sulfonimidamide Examples 5 and 6 (above) were synthesized according to general methods shown in Schemes 2 and 3, as illustrated in Route 1 and Route 2 below.

Example 7

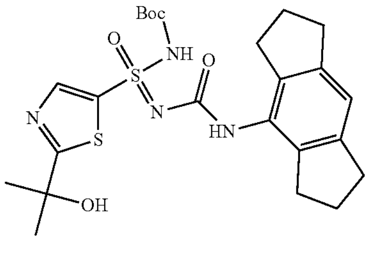 [SMILES: CC(C)(C)OC(=O)NS(=O)(=NC(=O)Nc1c2c(cc3c1CCC3)CCC2)c1cnc(C(C)(C)O)s1]

Example 7 (194): Tert-butyl N-(1,2,3,5,6,7-hexahydro-s-indacen-4-ylcarbamoyl)-2-(2-hydroxypropan-2-yl)thiazole-5-sulfonimidoylcarbamate Example 7 was synthesized according to general method shown in Scheme 3, as illustrated in Route 2 below.

Route 1

To this solution was added NaH (60% wt, 80 mg, 2.0 mmol) in portions at 0° C. The solution was stirred at 0° C. for 15 minutes, and this was followed by the addition of a solution of 4-isocyanato-1,2,3,5,6,7-hexahydro-s-indacene (209 mg, 1.1 mmol) in THF (5 mL) dropwise with stirring at RT. The resulting solution was stirred for 12 h at RT. The reaction was then quenched by the addition of 10 mL of $NH_4Cl$ (sat.). The resulting solution was extracted with 3×10 mL of DCM and the combined organic layers were concentrated under vacuum. This resulted in 535 mg (crude) of the title compound as a brown oil. MS-ESI: 535.0 (M+1).

Step 2: N'-(1,2,3,5,6,7-hexahydro-s-indacen-4-ylcarbamoyl)-2-(2-hydroxypropan-2-yl)thiazole-5-sulfonimidamide Into a 50-mL round-bottom flask was placed a solution of N-(tert-butyldimethylsilyl)-N'-(1,2,3,5,6,7-hexahydro-s-indacen-4-ylcarbamoyl)-2-(2-hydroxypropan-2-yl)thiazole-5-sulfonimidamide (535 mg, crude, 1.0 mmol) in THF (10 mL). To this solution was added HF/Py (70% wt, 143 mg, 5.0 mmol) dropwise at 0° C. The solution was stirred at RT for 4 h. The reaction was then quenched by the addition of 10 mL of water. The resulting solution was extracted with

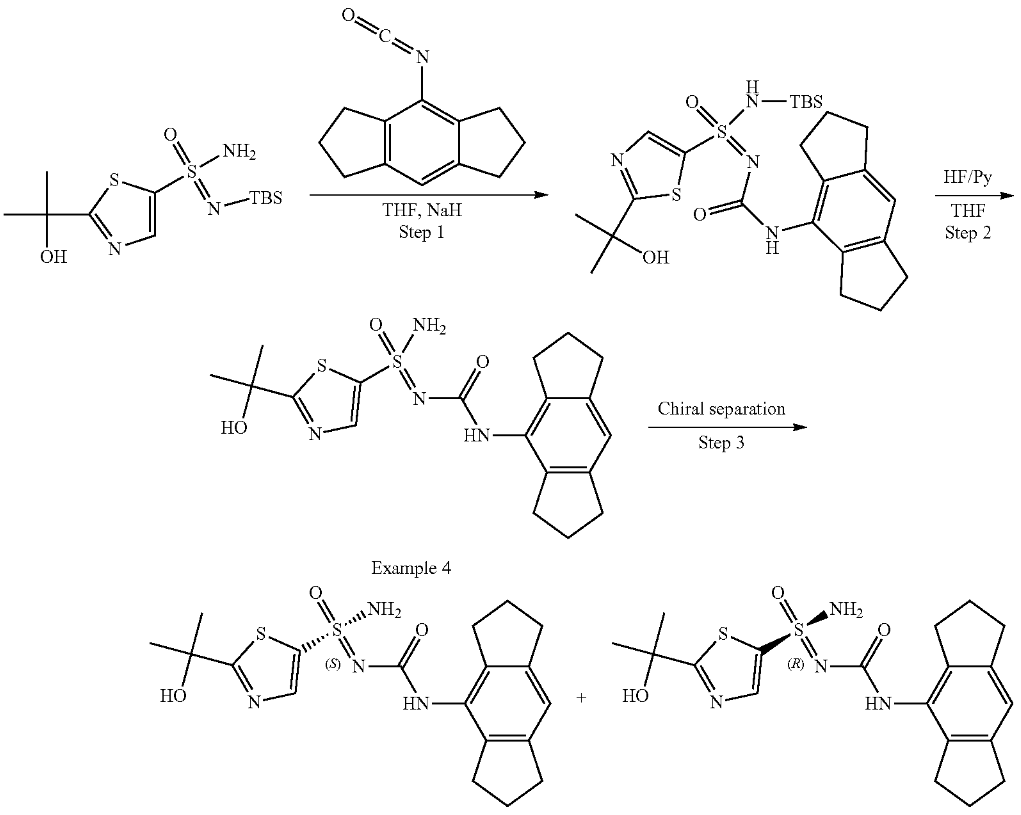

Examples 5 and 6 (stereochemistry not assigned)

Step 1: N-(tert-butyldimethylsilyl)-N'-(1,2,3,5,6,7-hexahydro-s-indacen-4-ylcarbamoyl)-2-(2-hydroxypropan-2-yl)thiazole-5-sulfonimidamide Into a 50-mL round-bottom flask was placed a solution of N'-(tert-butyldimethylsilyl)-2-(2-hydroxypropan-2-yl)thiazole-5-sulfonimidamide (336 mg, 1.0 mmol) in THF (10 mL).

3×10 mL of ethyl acetate and the combined organic layers were concentrated under vacuum. The crude product was purified by Prep-HPLC using Method E with ACN/water (20% to 60% in 10 minutes). This resulted in 189 mg (45%, 2 steps) of Example 4 as a white solid.

Example 4: MS-ESI: 421.0 (M+1). $^1H$ NMR (400 MHz, DMSO-$d_6$) δ 8.46 (br s, 1H), 8.04 (s, 1H), 7.80 (br s, 2H), 6.86 (s, 1H) 6.28 (s, 1H), 2.88-2.71 (m, 4H), 2.71-2.56 (m, 4H), 2.02-1.80 (m, 4H), 1.49 (s, 6H).

Step 2: Chiral Separation

The product obtained as described in the previous step (189 mg) was resolved by Chiral-Prep-HPLC using the following conditions: Column, CHIRAL Cellulose-SB, 2*25 cm, 5 um; mobile phase, Hex (0.1% DEA) and EtOH (hold 20% EtOH over 16 min); Flow rate, 20 mL/min; Detector, UV 254/220 nm. This resulted in 70 mg of Example 5 (front peak, 99% ee 101) as a white solid and 65 mg of Example 6 (second peak, 97.5% ee 102) as a white solid. Absolute stereochemistry of these two isomers has not been assigned.

Example 5: MS-ES: 421.0 (M+1). $^1H$ NMR (400 MHz, DMSO-$d_6$) δ 8.43 (br s, 1H), 8.05 (s, 1H), 7.83 (br s, 2H), 6.87 (s, 1H) 6.29 (s, 1H), 2.82-2.71 (m, 4H), 2.71-2.56 (m, 4H), 2.02-1.80 (m, 4H), 1.50 (s, 6H).

Example 6: MS-ESI: 421.0 (M+1). $^1H$ NMR (400 MHz, DMSO-$d_6$) δ 8.41 (br s, 1H), 8.05 (s, 1H), 7.83 (s, 2H), 6.87 (s, 1H) 6.27 (s, 1H), 2.82-2.71 (m, 4H), 2.71-2.56 (m, 4H), 2.02-1.80 (m, 4H), 1.50 (s, 6H).

Route 2

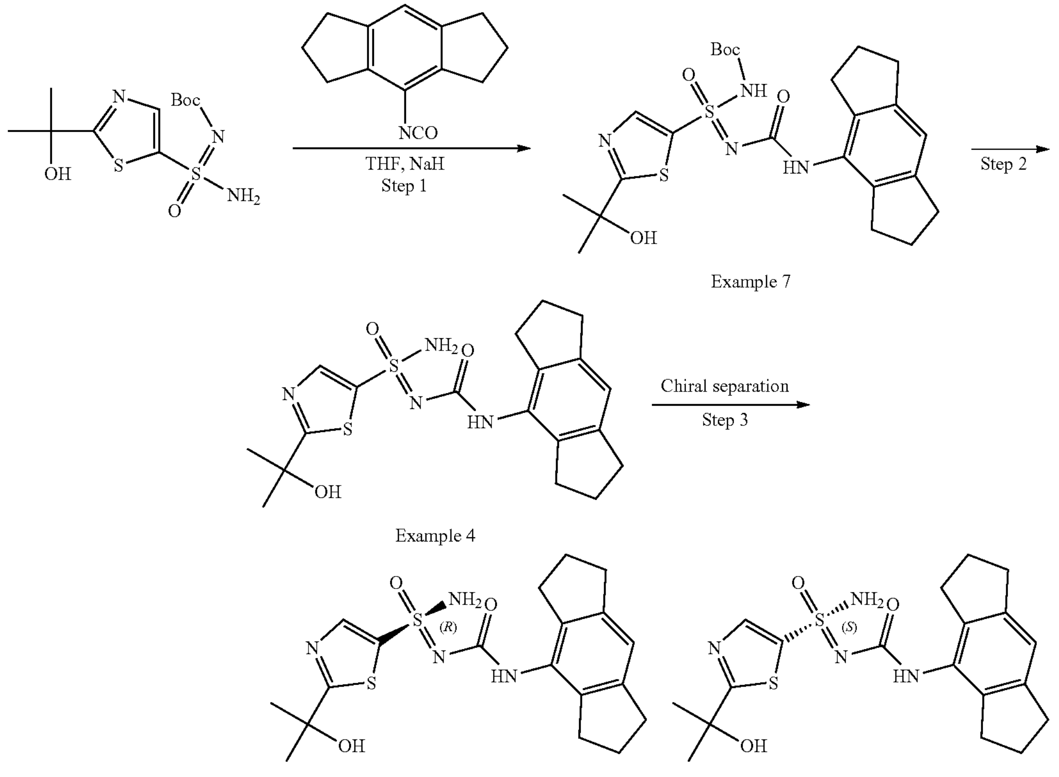

Examples 5 and 6 (stereochemistry not assigned)

Step 1: Tert-butyl N-(1,2,3,5,6,7-hexahydro-s-indacen-4-ylcarbamoyl)-2-(2-hydroxypropan-2-yl) thiazole-5-sulfonimidoylcarbamate Tert-butyl (amino(2-(2-hydroxypropan-2-yl)thiazol-5-yl) (oxo)-$\lambda^6$-sulfaneylidene)carbamate (12 g, 37 mmol) was dissolved in dried THF (200 mL). To the solution was added NaH (17.7 g, 60%, 44 mmol) in portions at 0° C. under nitrogen atmosphere, and then the mixture was stirred at 0° C. for 0.5 h. Freshly prepared 4-isocyanato-1,2,3,5,6,7-hexahydro-s-indacene (7.4 g, 37 mmol) was dissolved in dried THF (50 mL) and the solution was added to the front mixture dropwise at 0° C. The mixture was stirred at RT for 1 h. The reaction was quenched with ice-water (100 mL), and the pH value of the resulting solution was adjusted to 6 with $HCO_2H$. The solution was extracted with EtOAc (3×200 mL) and the combined organic layers were dried over anhydrous $Na_2SO_4$ and concentrated to give 17.5 g of Example 7 as a crude grey solid.

Example 7: MS-ESI. 521.0 (M+1). $^1H$ NMR (300 MHz, MeOD-$d_4$) δ 8.14 (s, 1H), 6.89 (s, 1H), 3.00-2.60 (m, 8H), 2.20-1.90 (m, 4H), 1.51 (s, 6H), 1.37 (s, 9H).

Step 2: N'-(1,2,3,5,6,7-hexahydro-s-indacen-4-ylcarbamoyl)-2-(2-hydroxypropan-2-yl)thiazole-5-sulfonimidamide The crude tert-butyl (N-((1,2,3,5,6,7-hexahydro-s-indacen-4-yl)carbamoyl)-2-(2-hydroxypropan-2-yl)-thiazole-5-sulfonimidoyl)carbamate (crude 17.5 g) was dissolved in THF (200 mL). To the solution was added HCl (200 mL, 4M in 1,4-dioxane) at RT. The mixture was stirred at RT overnight and concentrated. The residue was purified with $SiO_2$-gel column and eluted with MeOH/DCM (5%) and further purified by reverse column with MeOH/water (50% to 80% in 50 minutes) to give 12 g of Example 4 (51%, 2 steps) as a white solid.

Example 4: MS-ESI: 421.0 (M+1). $^1H$ NMR (400 MHz, DMSO-$d_6$) δ 8.46 (br s, 1H), 8.04 (s, 1H), 7.80 (br s, 2H), 6.86 (s, 1H) 6.28 (s, 1H), 2.88-2.71 (m, 4H), 2.71-2.56 (m, 4H), 2.02-1.80 (m, 4H), 1.49 (s, 6H).

Step 3: Chiral Separation

The product obtained as described in the previous step (12 g) was resolved by Chiral-Prep-SFC using the following conditions: Column, CHIRALPAK IF, 2*25 cm, 5 um; Mobile Phase A: $CO_2$: 60, Mobile Phase B: MeOH (2 mM $NH_3$-MeOH): 40; Flow rate: 40 mL/min; Detector, UV 220 nm. This resulted in 3.8 g of Example 6 (front peak, 99% ee 102) as a white solid and 4.6 g of Example 5 (second peak, 97.5% ee 101) as a white solid. Absolute stereochemistry of these two isomers has not been assigned.

Example 5: MS-ESI: 421.0 (M+1). $^1$H NMR (400 MHz, DMSO-$d_6$) δ 8.43 (br s, 1H), 8.05 (s, 1H), 7.83 (br s, 2H), 6.87 (s, 1H) 6.29 (s, 1H), 2.82-2.71 (m, 4H), 2.71-2.56 (m, 4H), 2.02-1.80 (m, 4H), 1.50 (s, 6H).

Example 6: MS-ESI: 421.0 (M+1). $^1$H NMR (400 MHz, DMSO-$d_6$) δ 8.41 (br s, 1H), 8.05 (s, 1H), 7.83 (s, 2H), 6.87 (s, 1H) 6.27 (s, 1H), 2.82-2.71 (m, 4H), 2.71-2.56 (m, 4H), 2.02-1.80 (m, 4H), 1.50 (s, 6H).

Example 8

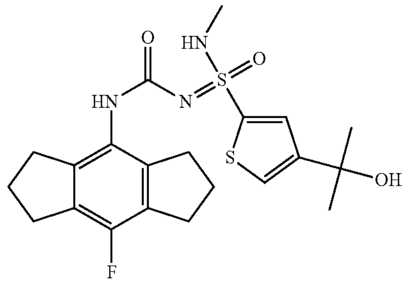 [SMILES: CNS(=O)(=NC(=O)Nc1c2c(c(F)c3c1CCC3)CCC2)c1cc(C(C)(C)O)cs1]

Example 8 (270): N'-(8-fluoro-1,2,3,5,6,7-hexahydro-s-indacen-4-ylcarbamoyl)-4-(2-hydroxypropan-2-yl)-N-methylthiophene-2-sulfonimidamide (Scheme 4)

Example 8 was synthesized according to the general method shown in Scheme 4.

Into a 50-mL round-bottom flask purged with and maintained under nitrogen was placed a solution of 4-fluoro-8-isocyanato-1,2,3,5,6,7-hexahydro-s-indacene (110 mg, 0.51 mmol) in DCM (5 mL). To the solution were added TEA (153 mg, 1.51 mmol) and 4-(2-hydroxypropan-2-yl)-N'-methylthiophene-2-sulfonimidamide (120 mg, 0.51 mmol). The resulting solution was stirred for 14 h at RT and then was concentrated under vacuum. The crude product was purified by Prep-HPLC using method E eluted with a gradient of 30~74% ACN. This resulted in 80 mg (35%) of Example 8 as a white solid.

Example 8: MS-ESI: 450.1 (M−1). $^1$H NMR (400 MHz, DMSO-$d_6$) δ 8.50 (br s, 1H), 7.64 (s, 1H), 7.59-7.50 (m, 2H), 5.23 (s, 1H), 2.84-2.69 (m, 8H), 2.50 (s, 3H), 1.99 (t, J=7.2 Hz, 4H), 1.42 (d, J=2.8 Hz, 6H)

Example 9 (204)

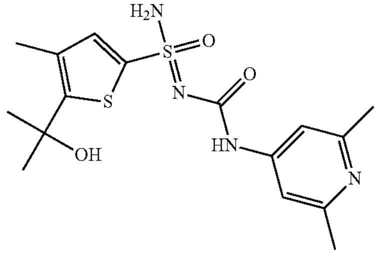 [SMILES: Cc1cc(NC(=O)N=S(N)(=O)c2cc(C)c(C(C)(C)O)s2)cc(C)n1]

N'-((2,6-dimethylpyridin-4-yl)carbamoyl)-4-methyl-5-(2-hydroxypropan-2-yl)thiophene-2-sulfonimidamide (Scheme 5)

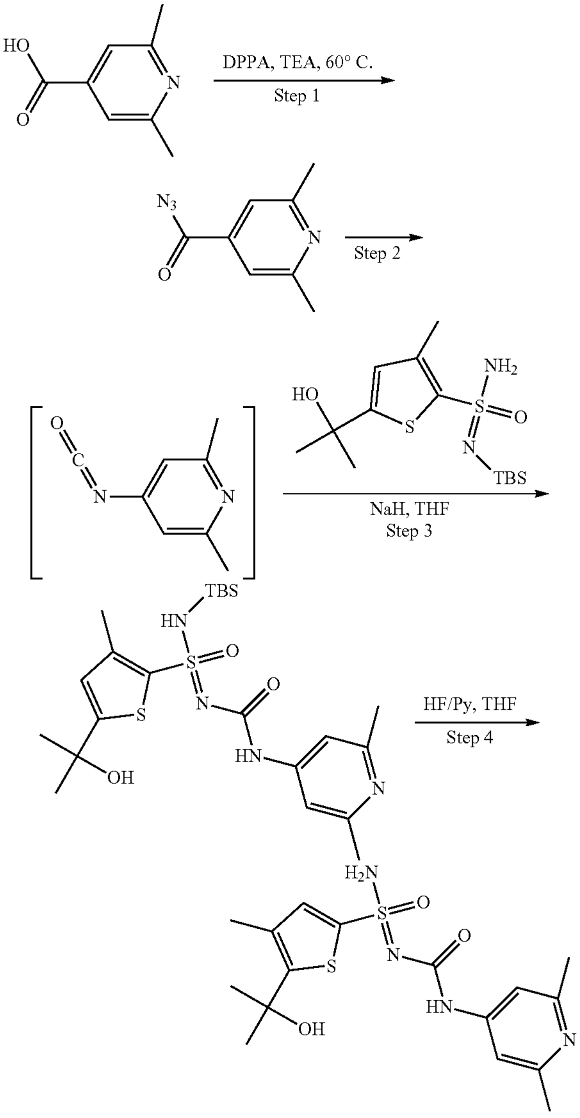

Example 9

Step 1: 4-Azido-2,6-dimethylpyridine

To the solution of 2,6-dimethylpyridine-4-carboxylic acid (151 mg, 1.0 mmol) in dried toluene (15 mL). To the solution was added DPPA (825 mg, 3.0 mmol) and TEA (303 mg, 3.0 mmol). The mixture was stirred at 60° C. for 4 h. The solution was concentrated under vacuum. This gave 900 mg (crude) of the title compound as yellow oil.

Step 2 & 3: N-(tert-butyldimethylsilyl)-N'-((2,6-dimethylpyridin-4-yl)carbamoyl)-5-(2-hydroxypropan-2-yl)-3-methylthiophene-2-sulfonimidamide The 4-azido-2,6-dimethylpyridine (900 mg, crude) was dissolved in THF (20 mL). To the solution was added N'-(tert-butyldimethylsilyl)-5-(2-hydroxypropan-2-yl)-3-methylthiophene-2-sulfonimidamide (349 mg, 1.0 mmol) and NaOH (120 mg, 3.0 mmol). The mixture was stirred at 50° C. for 12 h. The solution was diluted with water 20 mL, then the resulting solution was extracted with 3×20 mL of ethyl acetate. The organic layers were combined, dried over anhydrous $Na_2SO_4$, then concentrated under vacuum. This gave 500 mg (crude) of the title compound as a yellow solid. MS-ESI: 497.0 (M+1).

Step 4: N'-((2,6-dimethylpyridin-4-yl)carbamoyl)-4-methyl-5-(2-hydroxypropan-2-yl)thiophene-2-sulfonimidamide Into a 50-mL round-bottom flask was placed a solution of N-(tert-butyldimethylsilyl)-N'-((2,6-dimethylpyridin-4-yl)carbamoyl)-4-methyl-5-(2-hydroxypropan-2-yl)thiophene-2-sulfonimidamide (500 mg, crude) in THF (10 mL), to this solution was added HF/Py (70% wt, 143 mg, 5.0 mmol) dropwise at 0° C. The solution was stirred at RT for 4 h. The reaction was then quenched by the addition of 10 mL of water. The resulting solution was extracted with 3×10 mL of ethyl acetate and the combined organic layers were concentrated under vacuum. The crude product was purified by Prep-HPLC using method E eluted with a gradient of ACN/water (10% to 30% in 10 minutes). This resulted in 15 mg (4%, 4 steps) of Example 9 as a white solid. MS-ESI: 383.0 (M+1). $^1H$ NMR (300 MHz, DMSO-$d_6$) δ 9.31 (s, 1H), 7.53 (br s, 2H), 7.31 (s, 1H), 7.14 (s, 2H), 5.81 (s, 1H), 2.28 (s, 6H), 2.23 (s, 3H), 1.50 (s, 6H).

TABLE 16

Examples in the following table were prepared using similar conditions as described in Example 1 and Scheme 1 from appropriate starting materials.

| Example # | Final Target Number | Structure | IUPAC Name | Exact Mass $[M + H]^+$ |
|---|---|---|---|---|
| 10 | 180 | 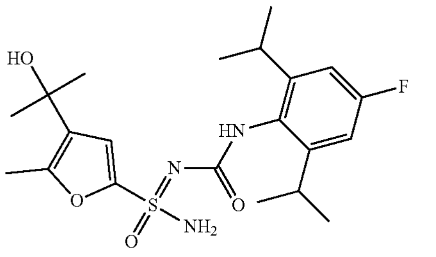 [SMILES: Cc1oc(S(N)(=O)=NC(=O)Nc2c(C(C)C)cc(F)cc2C(C)C)cc1C(C)(C)O] | N'-(4-fluoro-2,6-diisopropylphenylcarbamoyl)-4-(2-hydroxypropan-2-yl)-5-methylfuran-2-sulfonimidamide | 440.2 |
| 11 | 190 | 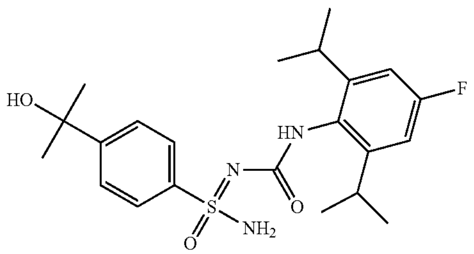 [SMILES: CC(C)c1cc(F)cc(C(C)C)c1NC(=O)N=S(N)(=O)c1ccc(C(C)(C)O)cc1] | N'-(4-fluoro-2,6-diisopropylphenylcarbamoyl)-4-(2-hydroxypropan-2-yl)benzenesulfonimidamide | 436.2 |
| 12 | 182 | 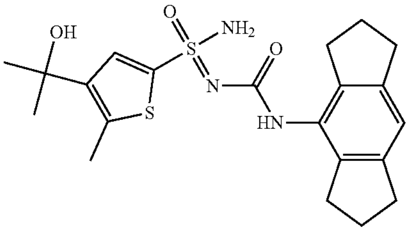 [SMILES: Cc1sc(S(N)(=O)=NC(=O)Nc2c3c(cc4c2CCC4)CCC3)cc1C(C)(C)O] | N'-(1,2,3,5,6,7-hexahydro-s-indacen-4-ylcarbamoyl)-4-(2-hydroxypropan-2-yl)-5-methylthiophene-2-sulfonimidamide | 434.1 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]$^+$ |
|---|---|---|---|---|
| 13 | 191 | 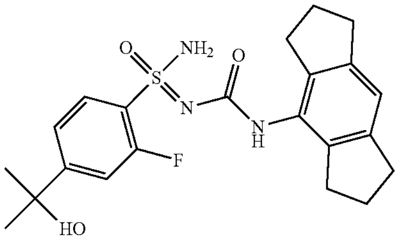 [SMILES: CC(C)(O)c1ccc(S(N)(=O)=NC(=O)Nc2c3c(cc4c2CCC4)CCC3)c(F)c1] | 2-fluoro-N'-(1,2,3,5,6,7-hexahydro-s-indacen-4-ylcarbamoyl)-4-(2-hydroxypropan-2-yl)benzenesulfonimidamide | 432.2 |
| 14 | 177 | 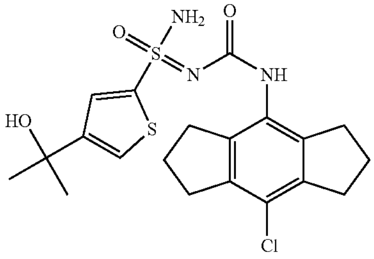 [SMILES: CC(C)(O)c1csc(S(N)(=O)=NC(=O)Nc2c3c(c(Cl)c4c2CCC4)CCC3)c1] | N'-(8-chloro-1,2,3,5,6,7-hexahydro-s-indacen-4-ylcarbamoyl)-4-(2-hydroxypropan-2-yl)thiophene-2-sulfonimidamide | 452.0 (M − 1) |
| 15 | 185 | 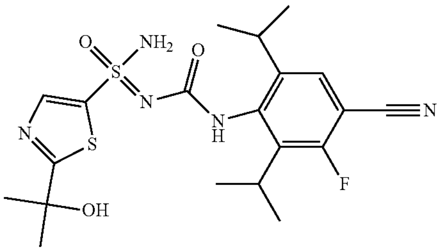 [SMILES: CC(C)c1cc(C#N)c(F)c(C(C)C)c1NC(=O)N=S(N)(=O)c1cnc(C(C)(C)O)s1] | N'-(4-cyano-3-fluoro-2,6-diisopropylphenylcarbamoyl)-2-(2-hydroxypropan-2-yl)thiazole-5-sulfonimidamide | 468.2 |
| 16 | 186 | 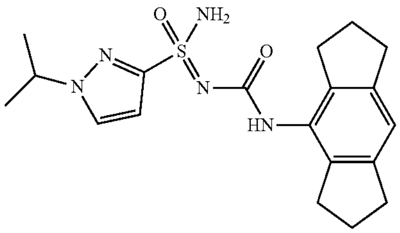 [SMILES: CC(C)n1ccc(S(N)(=O)=NC(=O)Nc2c3c(cc4c2CCC4)CCC3)n1] | N'-(1,2,3,5,6,7-hexahydro-5-indacen-4-ylcarbamoyl)-1-isopropyl-1H-pyrazole-3-sulfonimidamide | 388.1 |
| 17 | 187 | 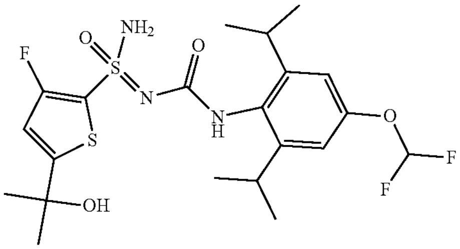 [SMILES: CC(C)c1cc(OC(F)F)cc(C(C)C)c1NC(=O)N=S(N)(=O)c1sc(C(C)(C)O)cc1F] | N'-(4-(difluoromethoxy)-2,6-diisopropylphenylcarbamoyl)-3-fluoro-5-(2-hydroxypropan-2-yl)thiophene-2-sulfonimidamide | 508.2 |
| 18 | 188 | 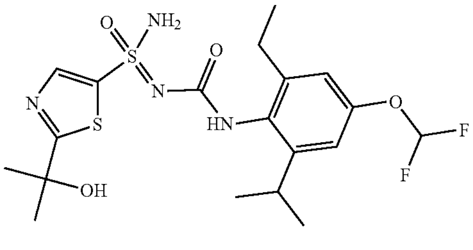 [SMILES: CCc1cc(OC(F)F)cc(C(C)C)c1NC(=O)N=S(N)(=O)c1cnc(C(C)(C)O)s1] | N'-(4-(difluoromethoxy)-2-ethyl-6-isopropylphenylcarbamoyl)-2-(2-hydroxypropan-2-yl)thiazole-5-sulfonimidamide | 477.1 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]$^+$ |
|---|---|---|---|---|
| 19 | 192 | 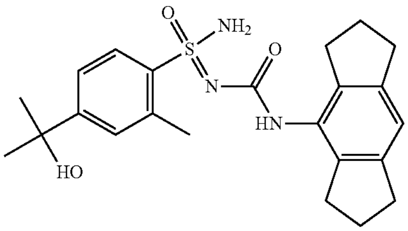 [SMILES: Cc1cc(C(C)(C)O)ccc1S(N)(=O)=NC(=O)Nc1c2c(cc3c1CCC3)CCC2] | N'-(1,2,3,5,6,7-hexahydro-s-indacen-4-ylcarbamoyl)-4-(2-hydroxypropan-2-yl)-2-methylbenzenesulfonimidamide | 426.2 (M − 1) |
| 20 | 189 | 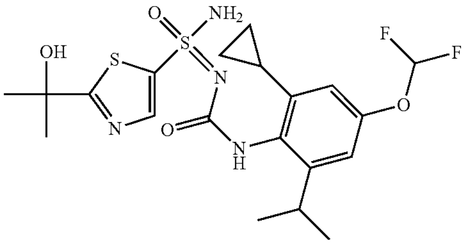 [SMILES: CC(C)c1cc(OC(F)F)cc(C2CC2)c1NC(=O)N=S(N)(=O)c1cnc(C(C)(C)O)s1] | N'-(2-cyclopropyl-4-(difluoromethoxy)-6-isopropylphenylcarbamoyl)-2-(2-hydroxypropan-2-yl)thiazole-5-sulfonimidamide | 487.1 (M − 1) |
| 21 | 178 | 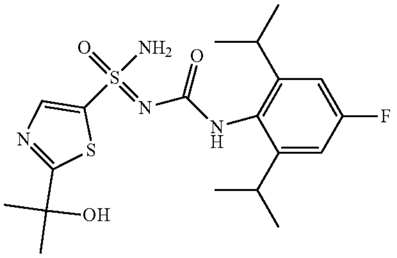 [SMILES: CC(C)c1cc(F)cc(C(C)C)c1NC(=O)N=S(N)(=O)c1cnc(C(C)(C)O)s1] | N'-(4-fluoro-2,6-diisopropylphenylcarbamoyl)-2-(2-hydroxypropan-2-yl)thiazole-5-sulfonimidamide | 441.1 (M − 1) |
| 22 | 193 | 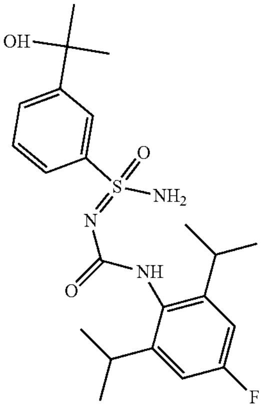 [SMILES: CC(C)c1cc(F)cc(C(C)C)c1NC(=O)N=S(N)(=O)c1cccc(C(C)(C)O)c1] | N'-(4-fluoro-2,6-diisopropylphenylcarbamoyl)-3-(2-hydroxypropan-2-yl)benzenesulfonimidamide | 436.1 |
| 23 | 170 | 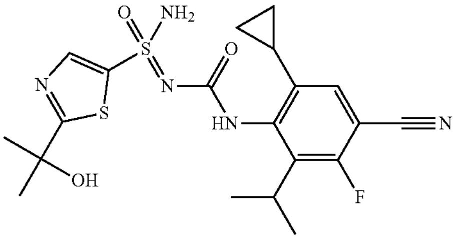 [SMILES: CC(C)c1c(F)c(C#N)cc(C2CC2)c1NC(=O)N=S(N)(=O)c1cnc(C(C)(C)O)s1] | N'-(4-cyano-6-cyclopropyl-3-fluoro-2-isopropylphenylcarbamoyl)-2-(2-hydroxypropan-2-yl)thiazole-5-sulfonimidamide | 466.1 |

TABLE 16-continued

Examples in the following table were prepared using similar conditions as described in Example 1 and Scheme 1 from appropriate starting materials.

| Example # | Final Target Number | Structure | IUPAC Name | Exact Mass $[M + H]^+$ |
|---|---|---|---|---|
| 24 | 168 | 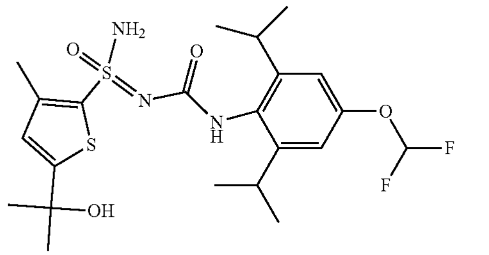 [SMILES: Cc1cc(C(C)(C)O)sc1S(N)(=O)=NC(=O)Nc1c(C(C)C)cc(OC(F)F)cc1C(C)C] | N'-(4-(difluoromethoxy)-2,6-diisopropylphenylcarbamoyl)-5-(2-hydroxypropan-2-yl)-3-methylthiophene-2-sulfonimidamide | 504.3 |
| 25 | 171 | 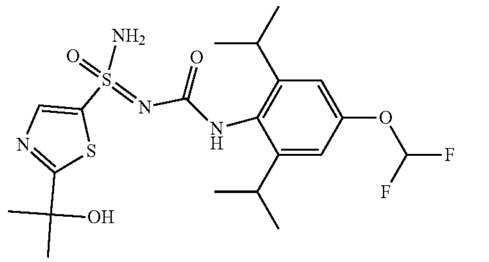 [SMILES: CC(C)c1cc(OC(F)F)cc(C(C)C)c1NC(=O)N=S(N)(=O)c1cnc(C(C)(C)O)s1] | N'-(4-(difluoromethoxy)-2,6-diisopropylphenylcarbamoyl)-2-(2-hydroxypropan-2-yl)thiazole-5-sulfonimidamide | 491.1 |
| 26 | 122 | 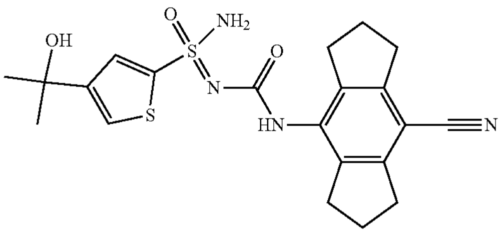 [SMILES: CC(C)(O)c1csc(S(N)(=O)=NC(=O)Nc2c3c(c(C#N)c4c2CCC4)CCC3)c1] | N'-(8-cyano-1,2,3,5,6,7-hexahydro-s-indacen-4-ylcarbamoyl)-4-(2-hydroxypropan-2-yl)thiophene-2-sulfonimidamide | 443.1 (M − 1) |
| 27 | 120 | 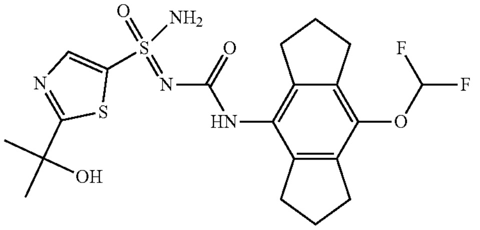 [SMILES: CC(C)(O)c1ncc(S(N)(=O)=NC(=O)Nc2c3c(c(OC(F)F)c4c2CCC4)CCC3)s1] | N'-(8-(difluoromethoxy)-1,2,3,5,6,7-hexahydro-s-indacen-4-ylcarbamoyl)-2-(2-hydroxypropan-2-yl)thiazole-5-sulfonimidamide | 487.1 |
| 28 | 125 | 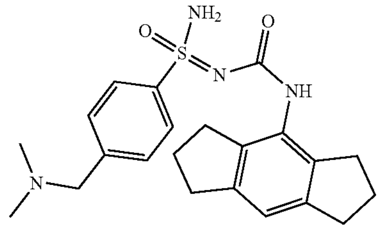 [SMILES: CN(C)Cc1ccc(S(N)(=O)=NC(=O)Nc2c3c(cc4c2CCC4)CCC3)cc1] | 4-((dimethylamino)methyl)-N'-(1,2,3,5,6,7-hexahydro-s-indacen-4-ylcarbamoyl)benzenesulfonimidamide | 413.3 |
| 29 | 129 | 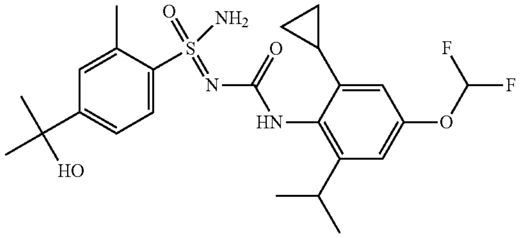 [SMILES: Cc1cc(C(C)(C)O)ccc1S(N)(=O)=NC(=O)Nc1c(C(C)C)cc(OC(F)F)cc1C1CC1] | N'-(2-cyclopropyl-4-(difluoromethoxy)-6-isopropylphenylcarbamoyl)-4-(2-hydroxypropan-2-yl)-2-methylbenzenesulfonimidamide | 496.2 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]+ |
|---|---|---|---|---|
| 30 | 213 | 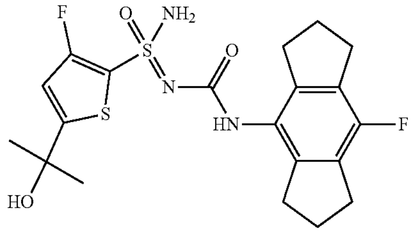 [SMILES: CC(C)(O)c1cc(F)c(S(N)(=O)=NC(=O)Nc2c3c(c(F)c4c2CCC4)CCC3)s1] | 3-fluoro-N'-(8-fluoro-1,2,3,5,6,7-hexahydro-s-indacen-4-ylcarbamoyl)-5-(2-hydroxypropan-2-yl)thiophene-2-sulfonimidamide | 456.1 |
| 31 | 207 | 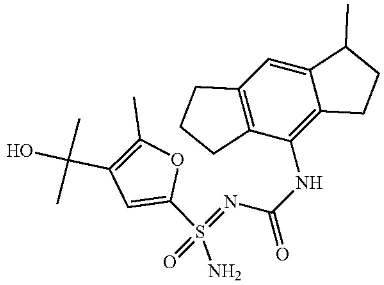 [SMILES: Cc1oc(S(N)(=O)=NC(=O)Nc2c3c(cc4c2CCC4C)CCC3)cc1C(C)(C)O] | 4-(2-hydroxypropan-2-yl)-5-methyl-N'-((3-methyl-1,2,3,5,6,7-hexahydro-s-indacen-4-yl)carbamoyl)furan-2-sulfonimidamide | 432.2 |
| 32 | 195 | 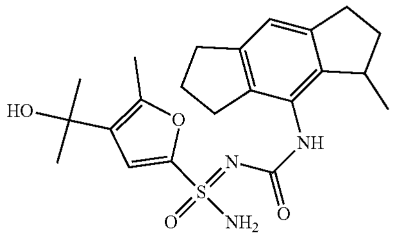 [SMILES: Cc1oc(S(N)(=O)=NC(=O)Nc2c3c(cc4c2C(C)CC4)CCC3)cc1C(C)(C)O] | 4-(2-hydroxypropan-2-yl)-5-methyl-N'-((1-methyl-1,2,3,5,6,7-hexahydro-s-indacen-4-yl)carbamoyl)furan-2-sulfonimidamide | 432.2 |

TABLE 17

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 33 | 179 | 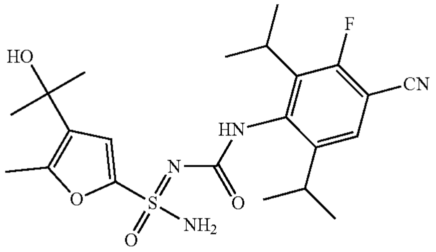 [SMILES: Cc1oc(S(N)(=O)=NC(=O)Nc2c(C(C)C)cc(C#N)c(F)c2C(C)C)cc1C(C)(C)O] | N'-(4-cyano-3-fluoro-2,6-diisopropylphenylcarbamoyl)-4-(2-hydroxypropan-2-yl)-5-methylfuran-2-sulfonimidamide | 465.2 |
| 34 | 105 | 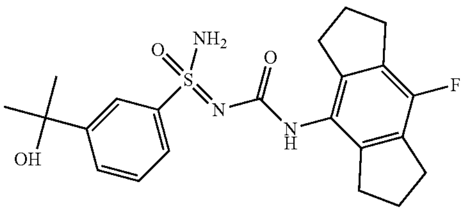 [SMILES: CC(C)(O)c1cccc(S(N)(=O)=NC(=O)Nc2c3c(c(F)c4c2CCC4)CCC3)c1] | N'-(8-fluoro-1,2,3,5,6,7-hexahydro-s-indacen-4-ylcarbamoyl)-3-(2-hydroxypropan-2-yl)benzenesulfonimidamide | 432.2 |

TABLE 17-continued

| Examples in the following table were prepared using similar conditions as described in Example 4 - route 1 and Scheme 2 from appropriate starting materials. | | | | |
|---|---|---|---|---|
| Example # | Final Target Number | Structure | IUPAC Name | Exact Mass [M + H]+ |
| 35 | 121 | 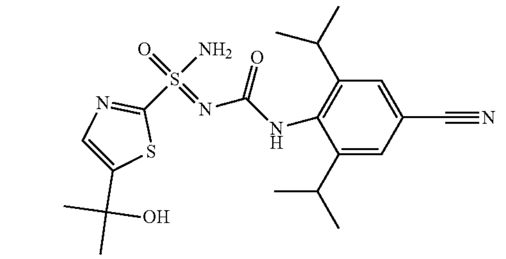 [SMILES: CC(C)c1cc(C#N)cc(C(C)C)c1NC(=O)N=S(N)(=O)c1ncc(C(C)(C)O)s1] | N'-(4-cyano-2,6-diisopropylphenylcarbamoyl)-5-(2-hydroxypropan-2-yl)thiazole-2-sulfonimidamide | 448.1 (M − 1) |
| 36 | 145 | 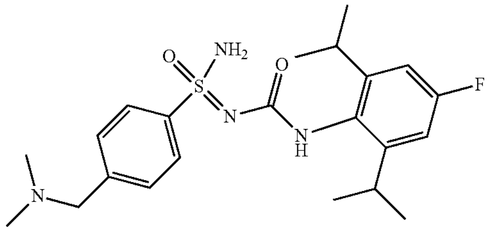 [SMILES: CC(C)c1cc(F)cc(C(C)C)c1NC(=O)N=S(N)(=O)c1ccc(CN(C)C)cc1] | 4-((dimethylamino)methyl)-N'-(4-fluoro-2,6-diisopropylphenylcarbamoyl) benzenesulfonimidamide | 435.2 |
| 37 | 131 | 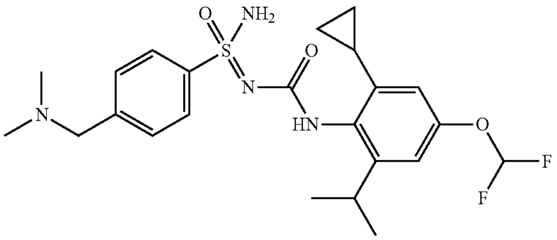 [SMILES: CC(C)c1cc(OC(F)F)cc(C2CC2)c1NC(=O)N=S(N)(=O)c1ccc(CN(C)C)cc1] | N'-(2-cyclopropyl-4-(difluoromethoxy)-6-isopropylphenylcarbamoyl)-4-((dimethylamino)methyl)benzene-sulfonimidamide | 481.3 |
| 38 | 132 | 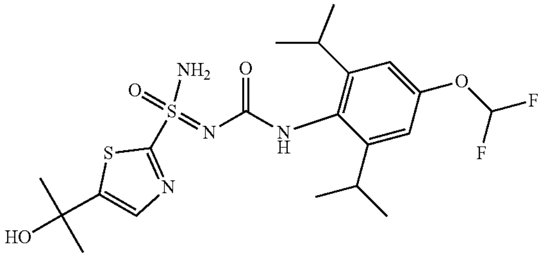 [SMILES: CC(C)c1cc(OC(F)F)cc(C(C)C)c1NC(=O)N=S(N)(=O)c1ncc(C(C)(C)O)s1] | N'-(4-(difluoromethoxy)-2,6-diisopropylphenylcarbamoyl)-5-(2-hydroxypropan-2-yl)thiazole-2-sulfonimidamide | 489.1 (M − 1) |
| 39 | 144 | 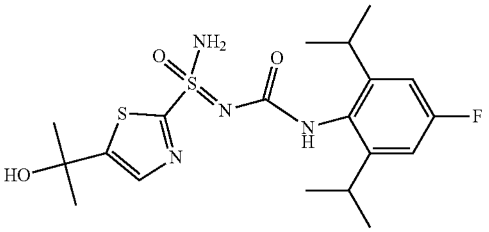 [SMILES: CC(C)c1cc(F)cc(C(C)C)c1NC(=O)N=S(N)(=O)c1ncc(C(C)(C)O)s1] | N'-(4-fluoro-2,6-diisopropylphenylcarbamoyl)-5-(2-hydroxypropan-2-yl)thiazole-2-sulfonimidamide | 441.1 (M − 1) |
| 40 | 149 | 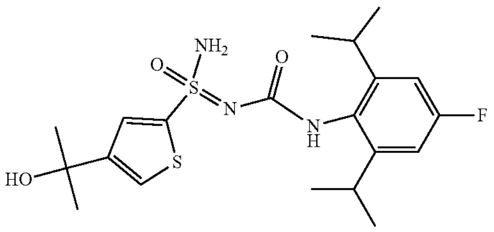 [SMILES: CC(C)c1cc(F)cc(C(C)C)c1NC(=O)N=S(N)(=O)c1cc(C(C)(C)O)cs1] | N'-(4-fluoro-2,6-diisopropylphenylcarbamoyl)-4-(2-hydroxypropan-2-yl)thiophene-2-sulfonimidamide | 440.1 (M − 1) |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 41 | 152 | 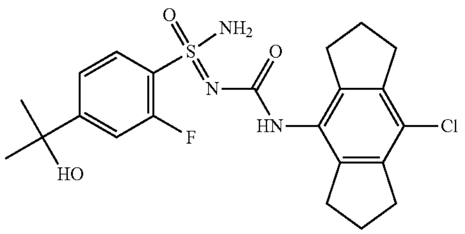 [SMILES: CC(C)(O)c1ccc(S(N)(=O)=NC(=O)Nc2c3c(c(Cl)c4c2CCC4)CCC3)c(F)c1] | N'-(8-chloro-1,2,3,5,6,7-hexahydro-s-indacen-4-ylcarbamoyl)-2-fluoro-4-(2-hydroxypropan-2-yl)benzenesulfonimidamide | 466.2 |
| 42 | 150 | 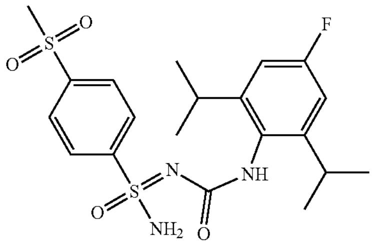 [SMILES: CC(C)c1cc(F)cc(C(C)C)c1NC(=O)N=S(N)(=O)c1ccc(S(C)(=O)=O)cc1] | N'-(4-fluoro-2,6-diisopropylphenylcarbamoyl)-4-(methylsulfonyl)benzene-sulfonimidamide | 454.1 (M − 1) |
| 43 | 167 | 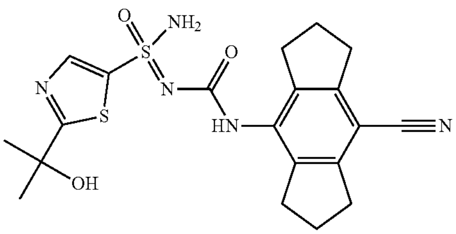 [SMILES: CC(C)(O)c1ncc(S(N)(=O)=NC(=O)Nc2c3c(c(C#N)c4c2CCC4)CCC3)s1] | N'-(8-cyano-1,2,3,5,6,7-hexahydro-s-indacen-4-ylcarbamoyl)-2-(2-hydroxypropan-2-yl)thiazole-5-sulfonimidamide | 444.2 (M − 1) |
| 44 | 106 | 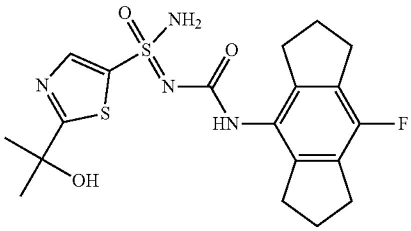 [SMILES: CC(C)(O)c1ncc(S(N)(=O)=NC(=O)Nc2c3c(c(F)c4c2CCC4)CCC3)s1] | N'-(8-fluoro-1,2,3,5,6,7-hexahydro-s-indacen-4-ylcarbamoyl)-2-(2-hydroxypropan-2-yl)thiazole-5-sulfonimidamide | 437.1 (M − 1) |
| 45 | 107 | 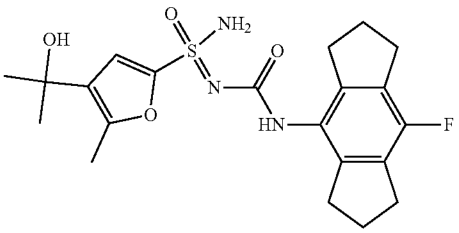 [SMILES: Cc1oc(S(N)(=O)=NC(=O)Nc2c3c(c(F)c4c2CCC4)CCC3)cc1C(C)(C)O] | N'-(8-fluoro-1,2,3,5,6,7-hexahydro-s-indacen-4-ylcarbamoyl)-4-(2-hydroxypropan-2-yl)-5-methylfuran-2-sulfonimidamide | 436.2 |
| 46 | 110 | 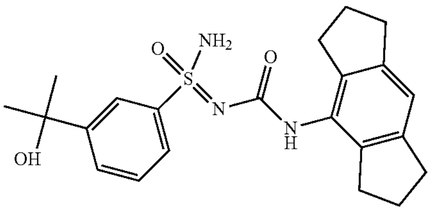 [SMILES: CC(C)(O)c1cccc(S(N)(=O)=NC(=O)Nc2c3c(cc4c2CCC4)CCC3)c1] | N'-(1,2,3,5,6,7-hexahydro-s-indacen-4-ylcarbamoyl)-3-(2-hydroxypropan-2-yl)benzenesulfonimidamide | 414.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass $[M + H]^+$ |
|---|---|---|---|---|
| 47 | 151 | 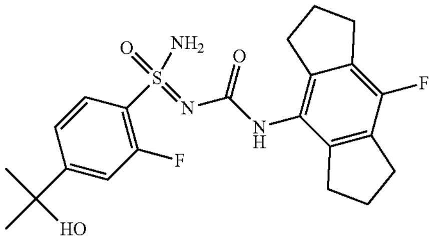 [SMILES: CC(C)(O)c1ccc(S(N)(=O)=NC(=O)Nc2c3c(c(F)c4c2CCC4)CCC3)c(F)c1] | 2-fluoro-N'-(8-fluoro-1,2,3,5,6,7-hexahydro-s-indacen-4-ylcarbamoyl)-4-(2-hydroxypropan-2-yl)benzenesulfonimidamide | 448.1 (M − 1) |
| 48 | 154 | 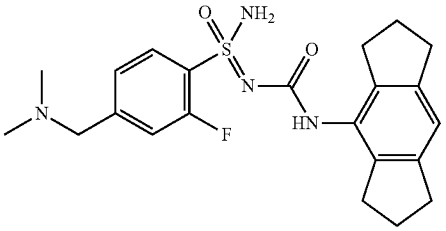 [SMILES: CN(C)Cc1ccc(S(N)(=O)=NC(=O)Nc2c3c(cc4c2CCC4)CCC3)c(F)c1] | 4-((dimethylamino)methyl)-2-fluoro-N'-(1,2,3,5,6,7-hexahydro-s-indacen-4-ylcarbamoyl)benzene-sulfonimidamide | 431.2 |
| 49 | 148 | 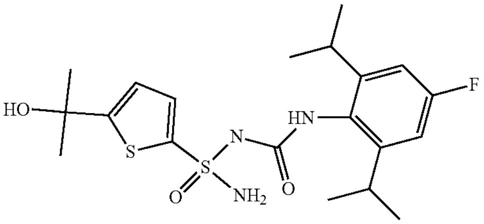 | N'-(4-fluoro-2,6-diisopropylphenylcarbamoyl)-5-(2-hydroxypropan-2-yl)thiophene-2-sulfonimidamide | 442.2 |
| 50 | 153 | 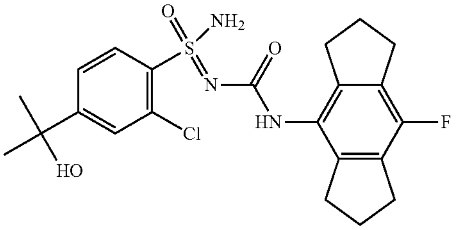 [SMILES: CC(C)(O)c1ccc(S(N)(=O)=NC(=O)Nc2c3c(c(F)c4c2CCC4)CCC3)c(Cl)c1] | 2-chloro-N'-(8-fluoro-1,2,3,5,6,7-hexahydro-s-indacen-4-ylcarbamoyl)-4-(2-hydroxypropan-2-yl)benzenesulfonimidamide | 464.1 (M − 1) |
| 51 | 109 | 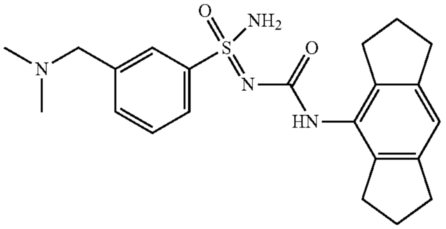 [SMILES: CN(C)Cc1cccc(S(N)(=O)=NC(=O)Nc2c3c(cc4c2CCC4)CCC3)c1] | 3-((dimethylamino)methyl)-N'-(1,2,3,5,6,7-hexahydro-s-indacen-4-ylcarbamoyl)benzene-sulfonimidamide | 411.1 (M − 1) |
| 52 | 135 | 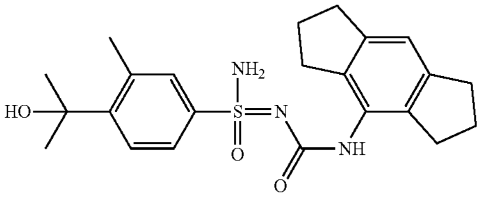 [SMILES: Cc1cc(S(N)(=O)=NC(=O)Nc2c3c(cc4c2CCC4)CCC3)ccc1C(C)(C)O] | N'-((1,2,3,5,6,7-hexahydro-s-indacen-4-yl)carbamoyl)-4-(2-hydroxypropan-2-yl)-3-methylbenzenesulfonimidamide | 428.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 53 | 134 | 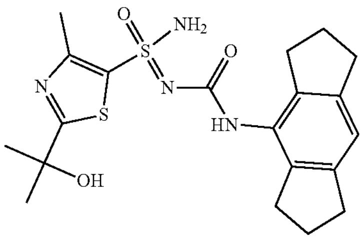 [SMILES: Cc1nc(C(C)(C)O)sc1S(N)(=O)=NC(=O)Nc1c2c(cc3c1CCC3)CCC2] | N'-((1,2,3,5,6,7-hexahydro-s-indacen-4-yl)carbamoyl)-2-(2-hydroxypropan-2-yl)-4-methylthiazole-5-sulfonimidamide | 435.1 |
| 54 | 130 | 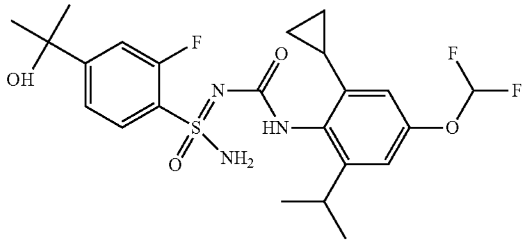 [SMILES: CC(C)c1cc(OC(F)F)cc(C2CC2)c1NC(=O)N=S(N)(=O)c1ccc(C(C)(C)O)cc1F] | N'-((2-cyclopropyl-4-(difluoromethoxy)-6-isopropylphenyl)carbamoyl)-2-fluoro-4-(2-hydroxypropan-2-yl)benzenesulfonimidamide | 500.2 |
| 55 | 212 | 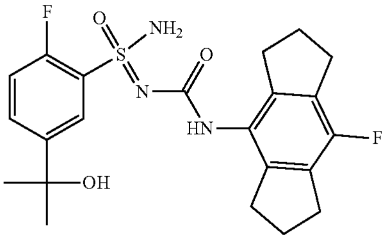 [SMILES: CC(C)(O)c1ccc(F)c(S(N)(=O)=NC(=O)Nc2c3c(c(F)c4c2CCC4)CCC3)c1] | 2-fluoro-N'-((8-fluoro-1,2,3,5,6,7-hexahydro-s-indacen-4-yl)carbamoyl)-5-(2-hydroxypropan-2-yl)benzenesulfonimidamide | 450.2 |
| 56 | 205 | 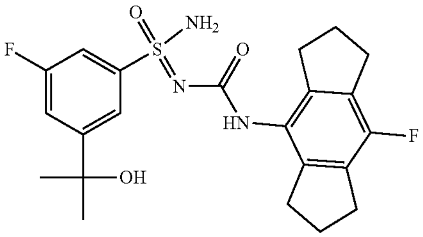 [SMILES: CC(C)(O)c1cc(F)cc(S(N)(=O)=NC(=O)Nc2c3c(c(F)c4c2CCC4)CCC3)c1] | 3-fluoro-N'-((8-fluoro-1,2,3,5,6,7-hexahydro-s-indacen-4-yl)carbamoyl)-5-(2-hydroxypropan-2-yl)benzenesulfonimidamide | 450.2 |
| 57 | 143 | 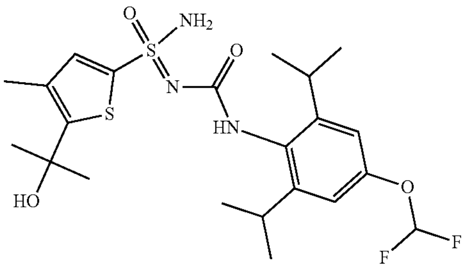 [SMILES: Cc1cc(S(N)(=O)=NC(=O)Nc2c(C(C)C)cc(OC(F)F)cc2C(C)C)sc1C(C)(C)O] | N'-((4-(difluoromethoxy)-2,6-diisopropylphenyl)carbamoyl)-5-(2-hydroxypropan-2-yl)-4-methylthiophene-2-sulfonimidamide | 504.2 |
| 58 | 206 | 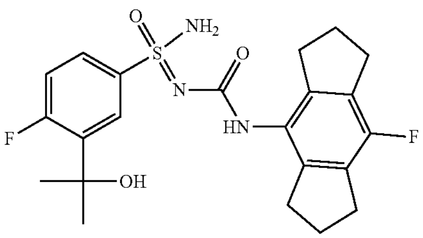 [SMILES: CC(C)(O)c1cc(S(N)(=O)=NC(=O)Nc2c3c(c(F)c4c2CCC4)CCC3)ccc1F] | 4-fluoro-N'-((8-fluoro-1,2,3,5,6,7-hexahydro-s-indacen-4-yl)carbamoyl)-3-(2-hydroxypropan-2-yl)benzenesulfonimidamide | 450.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 59 | 108 | 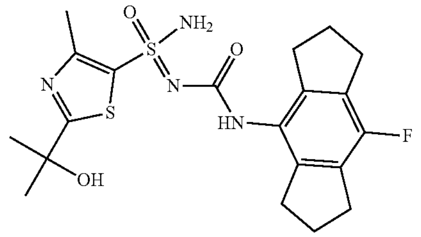 [SMILES: Cc1nc(C(C)(C)O)sc1S(N)(=O)=NC(=O)Nc1c2c(c(F)c3c1CCC3)CCC2] | N'-((8-fluoro-1,2,3,5,6,7-hexahydro-s-indacen-4-yl)carbamoyl)-2-(2-hydroxypropan-2-yl)-4-methylthiazole-5-sulfonimidamide | 453.1 |
| 60 | 202 | 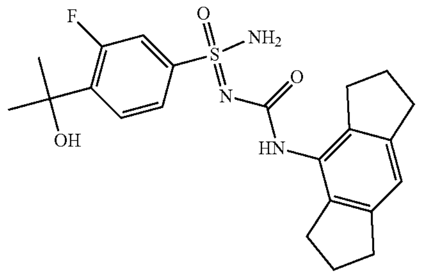 [SMILES: CC(C)(O)c1ccc(S(N)(=O)=NC(=O)Nc2c3c(cc4c2CCC4)CCC3)cc1F] | 3-fluoro-N'-((1,2,3,5,6,7-hexahydro-s-indacen-4-yl)carbamoyl)-4-(2-hydroxypropan-2-yl)benzenesulfonimidamide | 432.2 |
| 61 | 208 | 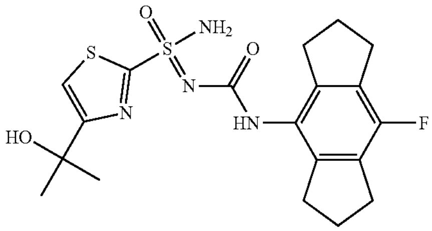 [SMILES: CC(C)(O)c1csc(S(N)(=O)=NC(=O)Nc2c3c(c(F)c4c2CCC4)CCC3)n1] | N'-((8-fluoro-1,2,3,5,6,7-hexahydro-s-indacen-4-yl)carbamoyl)-4-(2-hydroxypropan-2-yl)thiazole-2-sulfonimidamide | 439.1 |
| 62 | 197 | 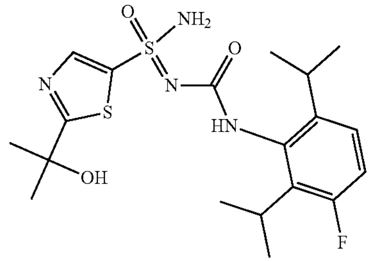 [SMILES: CC(C)c1ccc(F)c(C(C)C)c1NC(=O)N=S(N)(=O)c1cnc(C(C)(C)O)s1] | N'-((3-fluoro-2,6-diisopropylphenyl)carbamoyl)-2-(2-hydroxypropan-2-yl)thiazole-5-sulfonimidamide | 443.2 |
| 63 | 196 | 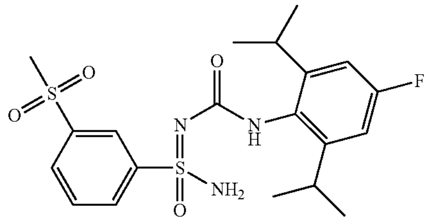 [SMILES: CC(C)c1cc(F)cc(C(C)C)c1NC(=O)N=S(N)(=O)c1cccc(S(C)(=O)=O)c1] | N'-((4-fluoro-2,6-diisopropylphenyl)carbamoyl)-3-(methylsulfonyl)benzene-sulfonimidamide | 456.1 |
| 64 | 124 | 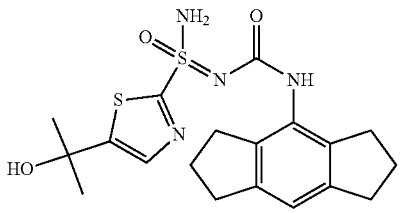 [SMILES: CC(C)(O)c1cnc(S(N)(=O)=NC(=O)Nc2c3c(cc4c2CCC4)CCC3)s1] | N'-((1,2,3,5,6,7-hexahydro-s-indacen-4-yl)carbamoyl)-5-(2-hydroxypropan-2-yl)thiazole-2-sulfonimidamide | 421.1 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass $[M + H]^+$ |
|---|---|---|---|---|
| 65 | 173 | 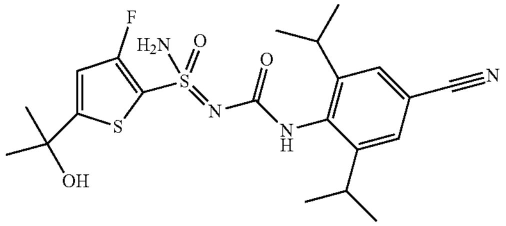 [SMILES: CC(C)c1cc(C#N)cc(C(C)C)c1NC(=O)N=S(N)(=O)c1sc(C(C)(C)O)cc1F] | N'-((4-cyano-2,6-diisopropylphenyl)carbamoyl)-3-fluoro-5-(2-hydroxypropan-2-yl)thiophene-2-sulfonimidamide | 467.2 |
| 66 | 172 | 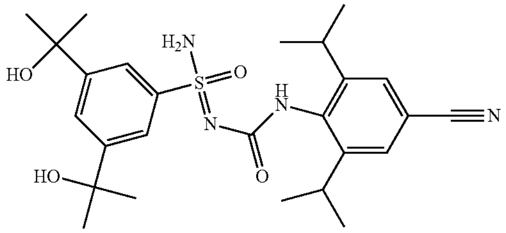 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | 501.2 |
| 67 | 174 | 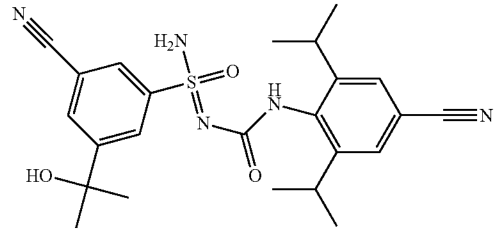 [SMILES: CC(C)c1cc(C#N)cc(C(C)C)c1NC(=O)N=S(N)(=O)c1cc(C#N)cc(C(C)(C)O)c1] | 3-cyano-N'-((4-cyano-2,6-diisopropylphenyl)carbamoyl)-5-(2-hydroxypropan-2-yl)benzenesulfonimidamide | 468.2 |
| 68 | 158 | 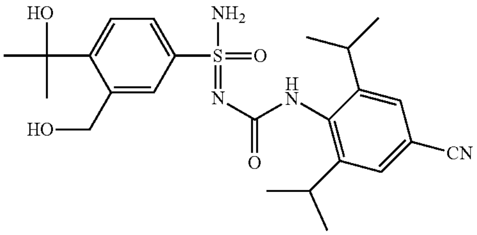 [SMILES: CC(C)c1cc(C#N)cc(C(C)C)c1NC(=O)N=S(N)(=O)c1ccc(C(C)(C)O)c(CO)c1] | N'-((4-cyano-2,6-diisopropylphenyl)carbamoyl)-3-(hydroxymethyl)-4-(2-hydroxypropan-2-yl)benzenesulfonimidamide | 473.2 |
| 69 | 220 | 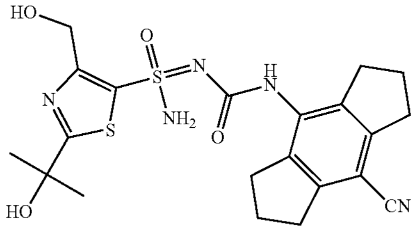 [SMILES: CC(C)(O)c1nc(CO)c(S(N)(=O)=NC(=O)Nc2c3c(c(C#N)c4c2CCC4)CCC3)s1] | N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | 476.1 |
| 70 | 157 | 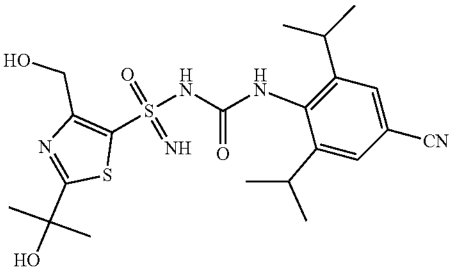 [SMILES: CC(C)c1cc(C#N)cc(C(C)C)c1NC(=O)NS(=N)(=O)c1sc(C(C)(C)O)nc1CO] | N-((4-cyano-2,6-diisopropylphenyl)carbamoyl)-4-(hydroxymethyl)-2-(2-hydroxypropan-2-yl)thiazole-5-sulfonimidamide | 480.2 |

TABLE 17-continued

| Example # | Final Target Number | Structure | IUPAC Name | Exact Mass $[M + H]^+$ |
|---|---|---|---|---|
| Examples in the following table were prepared using similar conditions as described in Example 4 - route 1 and Scheme 2 from appropriate starting materials. | | | | |
| 71 | 161 | 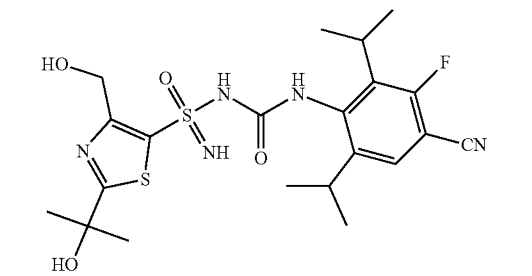 [SMILES: CC(C)c1cc(C#N)c(F)c(C(C)C)c1NC(=O)NS(=N)(=O)c1sc(C(C)(C)O)nc1CO] | N-((4-cyano-3-fluoro-2,6-diisopropylphenyl)carbamoyl)-4-(hydroxymethyl)-2-(2-hydroxypropan-2-yl)thiazole-5-sulfonimidamide | 498.2 |
| 72 | 159 | 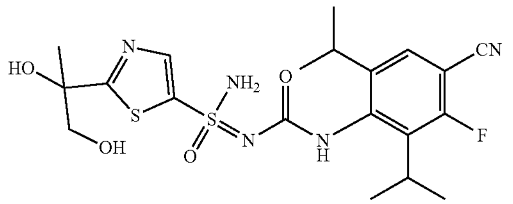 [SMILES: CC(C)c1cc(C#N)c(F)c(C(C)C)c1NC(=O)N=S(N)(=O)c1cnc(C(C)(O)CO)s1] | N'-((4-cyano-3-fluoro-2,6-diisopropylphenyl)carbamoyl)-2-(1,2-dihydroxypropan-2-yl)thiazole-5-sulfonimidamide | 484.1 |
| 73 | 165 | 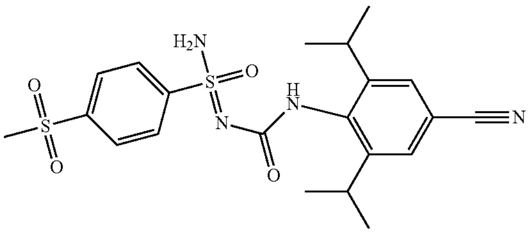 [SMILES: CC(C)c1cc(C#N)cc(C(C)C)c1NC(=O)N=S(N)(=O)c1ccc(S(C)(=O)=O)cc1] | N'-((4-cyano-2,6-diisopropylphenyl)carbamoyl)-4-(methylsulfonyl)benzene-sulfonimidamide | 463.1 |
| 74 | 183 | 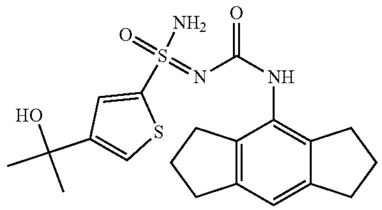 [SMILES: CC(C)(O)c1csc(S(N)(=O)=NC(=O)Nc2c3c(cc4c2CCC4)CCC3)c1] | N'-(1,2,3,5,6,7-hexahydro-s-indacen-4-ylcarbamoyl)-4-(2-hydroxypropan-2-yl)thiophene-2-sulfonimidamide | 418.1 (M − 1) |
| 75 | 176 | 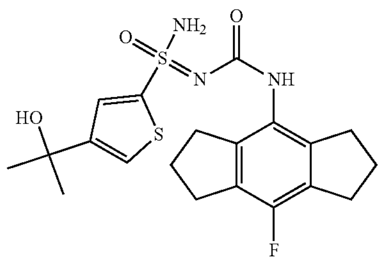 [SMILES: CC(C)(O)c1csc(S(N)(=O)=NC(=O)Nc2c3c(c(F)c4c2CCC4)CCC3)c1] | N'-(8-fluoro-1,2,3,5,6,7-hexahydro-s-indacen-4-ylcarbamoyl)-4-(2-hydroxypropan-2-yl)thiophene-2-sulfonimidamide | 438.0 |
| 76 | 136 | 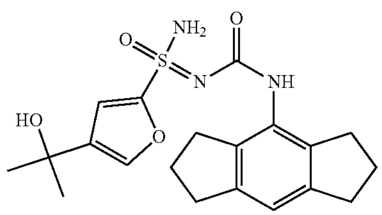 [SMILES: CC(C)(O)c1coc(S(N)(=O)=NC(=O)Nc2c3c(cc4c2CCC4)CCC3)c1] | N'-(1,2,3,5,6,7-hexahydro-s-indacen-4-ylcarbamoyl)-4-(2-hydroxypropan-2-yl)furan-2-sulfonimidamide | 404.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
| --- | --- | --- | --- | --- |
| 77 | 209 | 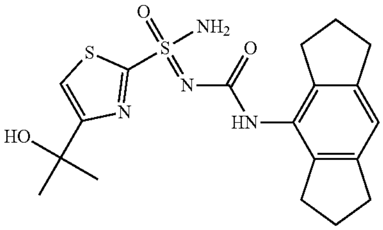 [SMILES: CC(C)(O)c1csc(S(N)(=O)=NC(=O)Nc2c3c(cc4c2CCC4)CCC3)n1] | N'-(1,2,3,5,6,7-hexahydro-s-indacen-4-ylcarbamoyl)-4-(2-hydroxypropan-2-yl)thiazole-2-sulfonimidamide | 421.1 |

TABLE 18

Examples in the following table were prepared using similar conditions as described in Example 9 and Scheme 5 from appropriate materials.

| Example # | Final Target Number | Structure | IUPAC Name | Exact Mass [M + H]+ |
| --- | --- | --- | --- | --- |
| 78 | 203 | 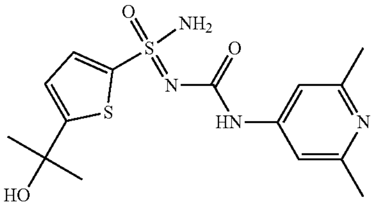 [SMILES: Cc1cc(NC(=O)N=S(N)(=O)c2ccc(C(C)(C)O)s2)cc(C)n1] | N-((2,6-dimethylpyridin-4-yl)carbamoyl)-5-(2-hydroxypropan-2-yl)thiophene-2-sulfonimidamide | 369.1 |

TABLE 19

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
| --- | --- | --- | --- | --- | --- | --- |
| 79 | 180a or 180b | 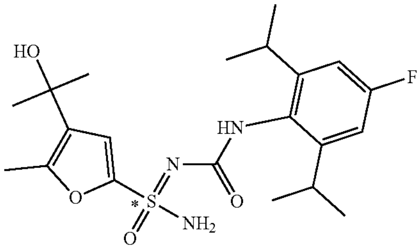 [SMILES: Cc1oc(S(N)(=O)=NC(=O)Nc2c(C(C)C)cc(F)cc2C(C)C)cc1C(C)(C)O] | (S)-or (R)-N'-(4-fluoro-2,6-diisopropylphenylcarbamoyl)-4-(2-hydroxypropan-2-yl)-5-methylfuran-2-sulfonimidamide | ChiralPak ID, 2*25 cm, 5 um | 20% EtOH in Hex | 440.3 |
| 80 | 180b or 180a | 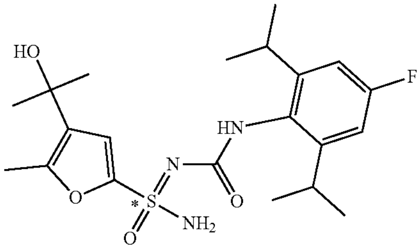 [SMILES: Cc1oc(S(N)(=O)=NC(=O)Nc2c(C(C)C)cc(F)cc2C(C)C)cc1C(C)(C)O] | (R)-or (S)-N'-(4-fluoro-2,6-diisopropylphenylcarbamoyl)-4-(2-hydroxypropan-2-yl)-5-methylfuran-2-sulfonimidamide | ChiralPak ID, 2*25 cm, 5 um | 20% EtOH in Hex | 440.3 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 81 | 179a or 179b | 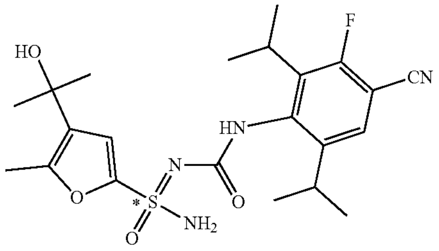 [SMILES: Cc1oc(S(N)(=O)=NC(=O)Nc2c(C(C)C)cc(C#N)c(F)c2C(C)C)cc1C(C)(C)O] | (S)-or (R)-N'-(4-cyano-3-fluoro-2,6-diisopropylphenylcarbamoyl)-4-(2-hydroxypropan-2-yl)-5-methylfuran-2-sulfonimidamide | ChiralPak ID, 2*25 cm, 5 um | 23% EtOH in Hex | 465.3 |
| 82 | 179b or 179a | 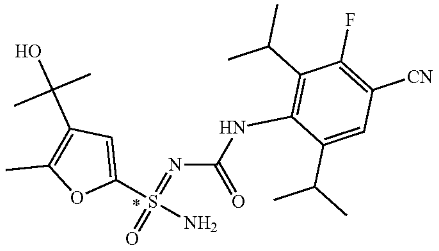 [SMILES: Cc1oc(S(N)(=O)=NC(=O)Nc2c(C(C)C)cc(C#N)c(F)c2C(C)C)cc1C(C)(C)O] | (R)-or (S)-N'-(4-cyano-3-fluoro-2,6-diisopropylphenylcarbamoyl)-4-(2-hydroxypropan-2-yl)-5-methylfuran-2-sulfonimidamide | ChiralPak ID, 2*25 cm, 5 um | 23% EtOH in Hex | 465.3 |
| 83 | 190a or 190b | 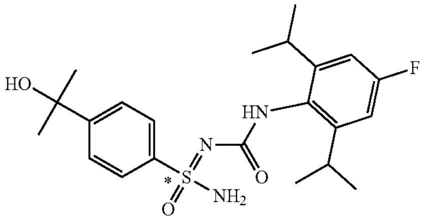 [SMILES: CC(C)c1cc(F)cc(C(C)C)c1NC(=O)N=S(N)(=O)c1ccc(C(C)(C)O)cc1] | (S)-or (R)-N'-(4-fluoro-2,6-diisopropylphenylcarbamoyl)-4-(2-hydroxypropan-2-yl)benzenesulfonimidamide | ChiralPak ID, 2*25 cm, 5 um | 20% EtOH in Hex | 436.2 |
| 84 | 190b or 190a | 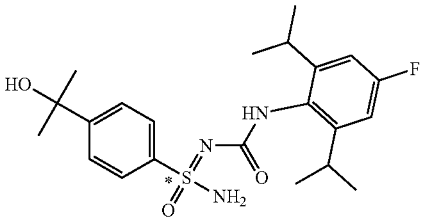 [SMILES: CC(C)c1cc(F)cc(C(C)C)c1NC(=O)N=S(N)(=O)c1ccc(C(C)(C)O)cc1] | (R)-or (S)-N'-(4-fluoro-2,6-diisopropylphenylcarbamoyl)-4-(2-hydroxypropan-2-yl)benzenesulfonimidamide | ChiralPak ID, 2*25 cm, 5 um | 20% EtOH in Hex | 436.2 |
| 85 | 182a or 182b | 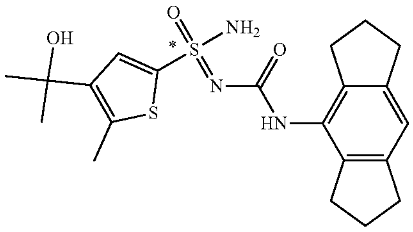 [SMILES: Cc1sc(S(N)(=O)=NC(=O)Nc2c3c(cc4c2CCC4)CCC3)cc1C(C)(C)O] | (S)-or (R)-N'-(1,2,3,5,6,7-hexahydro-s-indacen-4-ylcarbamoyl)-4-(2-hydroxypropan-2-yl)-5-methylthiophene-2-sulfonimidamide | ChiralPak IC, 2*25 cm, 5 um | 20% EtOH in Hex | 434.1 |
| 86 | 182b or 182a | 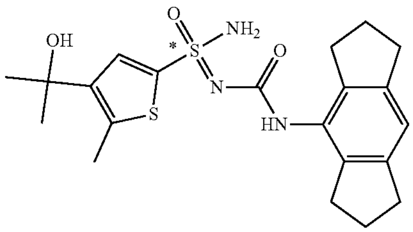 [SMILES: Cc1sc(S(N)(=O)=NC(=O)Nc2c3c(cc4c2CCC4)CCC3)cc1C(C)(C)O] | (R)-or (S)-N'-(1,2,3,5,6,7-hexahydro-s-indacen-4-ylcarbamoyl)-4-(2-hydroxypropan-2-yl)-5-methylthiophene-2-sulfonimidamide | ChiralPak IC, 2*25 cm, 5 um | 20% EtOH in Hex | 434.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 87 | 191a or 191b | 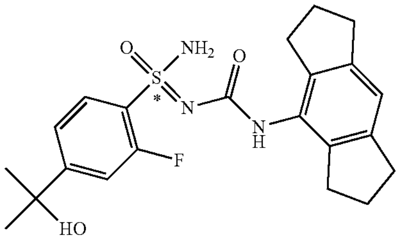 [SMILES: CC(C)(O)c1ccc(S(N)(=O)=NC(=O)Nc2c3c(cc4c2CCC4)CCC3)c(F)c1] | (S)-or (R)-2-fluoro-N'-(1,2,3,5,6,7-hexahydro-s-indacen-4-ylcarbamoyl)-4-(2-hydroxypropan-2-yl)benzenesulfonimidamide | ChiralPak IG, 2*25 cm, 5 um | 30% IPA in Hex (0.1% DEA) | 430.1 (M − 1) |
| 88 | 191b or 191a | 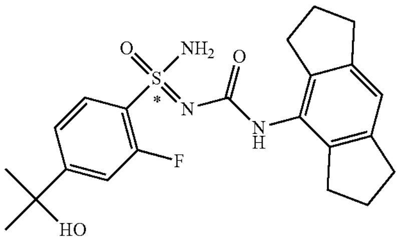 [SMILES: CC(C)(O)c1ccc(S(N)(=O)=NC(=O)Nc2c3c(cc4c2CCC4)CCC3)c(F)c1] | (R)-or (S)-2-fluoro-N'-(1,2,3,5,6,7-hexahydro-s-indacen-4-ylcarbamoyl)-4-(2-hydroxypropan-2-yl)benzenesulfonimidamide | ChiralPak IG, 2*25 cm, 5 um | 30% IPA in Hex (0.1% DEA) | 430.1 (M − 1) |
| 89 | 177a or 177b | 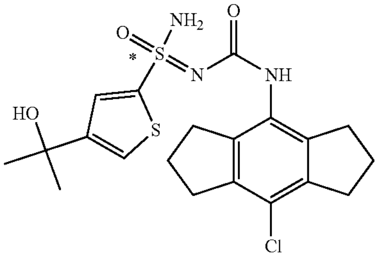 [SMILES: CC(C)(O)c1csc(S(N)(=O)=NC(=O)Nc2c3c(c(Cl)c4c2CCC4)CCC3)c1] | (S)-or (R)-N'-(8-chloro-1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 20% EtOH in Hex (0.1% DEA) | 452.0 (M − 1) |
| 90 | 177b or 177a | 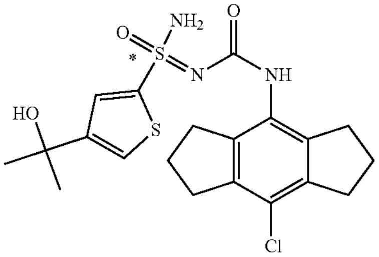 [SMILES: CC(C)(O)c1csc(S(N)(=O)=NC(=O)Nc2c3c(c(Cl)c4c2CCC4)CCC3)c1] | (R)-or (S)-N'-(8-chloro-1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 20% EtOH in Hex (0.1% DEA) | 452.0 (M − 1) |
| 91 | 185a or 185b | 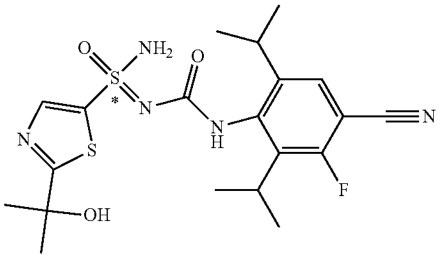 [SMILES: CC(C)c1cc(C#N)c(F)c(C(C)C)c1NC(=O)N=S(N)(=O)c1cnc(C(C)(C)O)s1] | (S)-or (R)-N'-(4-cyano-3-fluoro-2,6-diisopropylphenylcarbamoyl)-2-(2-hydroxypropan-2-yl)thiazole-5-sulfonimidamide | ChiralPak ID, 2*25 cm, 5 um | 30% EtOH in Hex (0.1% DEA) | 466.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 92 | 185b or 185a | 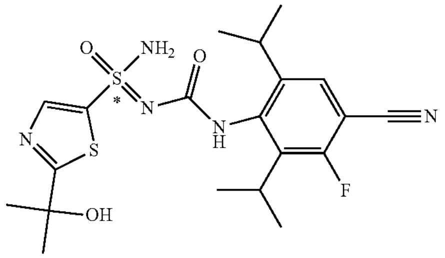 [SMILES: CC(C)c1cc(C#N)c(F)c(C(C)C)c1NC(=O)N=S(N)(=O)c1cnc(C(C)(C)O)s1] | (R)-or (S)-N'-(4-cyano-3-fluoro-2,6-diisopropylphenylcarbamoyl)-2-(2-hydroxypropan-2-yl)thiazole-5-sulfonimidamide | ChiralPak ID, 2*25 cm, 5 um | 30% EtOH in Hex (0.1% DEA) | 466.1 (M − 1) |
| 93 | 186a or 186b | 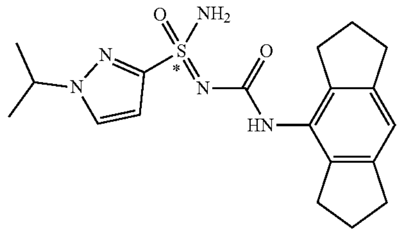 [SMILES: CC(C)n1ccc(S(N)(=O)=NC(=O)Nc2c3c(cc4c2CCC4)CCC3)n1] | (S)-or (R)-N'-(1,2,3,5,6,7-hexahydro-s-indacen-4-ylcarbamoyl)-1-isopropyl-1H-pyrazole-3-sulfonimidamide | ChiralPak IG, 2*25 cm, 5 um | 30% EtOH in Hex (0.1% DEA) | 388.1 |
| 94 | 186b or 186a | 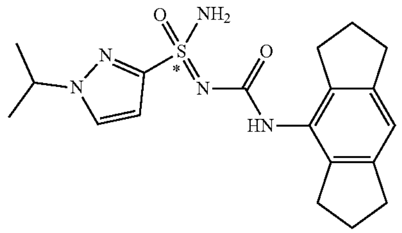 [SMILES: CC(C)n1ccc(S(N)(=O)=NC(=O)Nc2c3c(cc4c2CCC4)CCC3)n1] | (R)-or (S)-N'-(1,2,3,5,6,7-hexahydro-s-indacen-4-ylcarbamoyl)-1-isopropyl-1H-pyrazole-3-sulfonimidamide | ChiralPak IG, 2*25 cm, 5 um | 30% EtOH in Hex (0.1% DEA) | 388.1 |
| 95 | 187a or 187b | 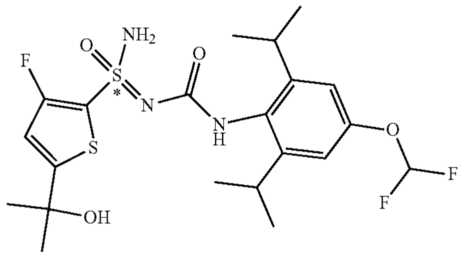 [SMILES: CC(C)c1cc(OC(F)F)cc(C(C)C)c1NC(=O)N=S(N)(=O)c1sc(C(C)(C)O)cc1F] | (S)-or (R)-N'-(4-(difluoromethoxy)-2,6-diisopropylphenylcarbamoyl)-3-fluoro-5-(2-hydroxypropan-2-yl)thiophene-2-sulfonimidamide | ChiralPak ID, 2*25 cm, 5 um | 20% EtOH in Hex (0.1% DEA) | 508.2 |
| 96 | 187b or 187a | 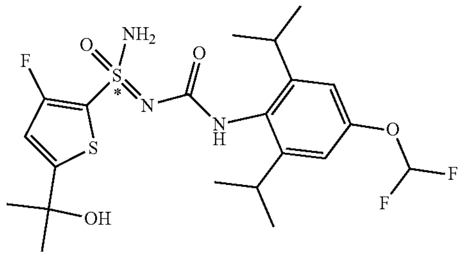 [SMILES: CC(C)c1cc(OC(F)F)cc(C(C)C)c1NC(=O)N=S(N)(=O)c1sc(C(C)(C)O)cc1F] | (R)-or (S)-N'-(4-(difluoromethoxy)-2,6-diisopropylphenylcarbamoyl)-3-fluoro-5-(2-hydroxypropan-2-yl)thiophene-2-sulfonimidamide | ChiralPak ID, 2*25 cm, 5 um | 20% EtOH in Hex (0.1% DEA) | 508.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 97 | 188a or 188b | 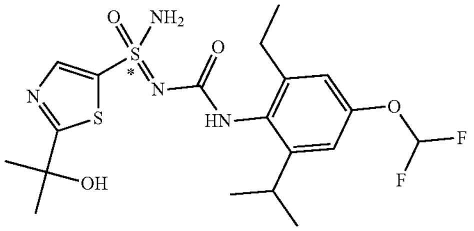 [SMILES: CCc1cc(OC(F)F)cc(C(C)C)c1NC(=O)N=S(N)(=O)c1cnc(C(C)(C)O)s1] | (S)-or (R)-N'-(4-(difluoromethoxy)-2-ethyl-6-isopropylphenylcarbamoyl)-2-(2-hydroxypropan-2-yl)thiazole-5-sulfonimidamide | ChiralPak ID, 2*25 cm, 5 um | 30% IPA in Hex (0.1% DEA) | 477.2 |
| 98 | 188b or 188a | 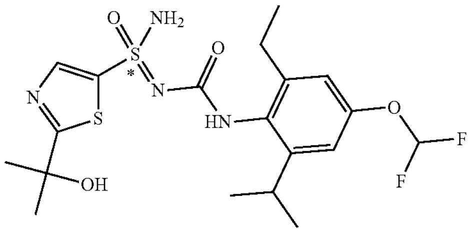 [SMILES: CCc1cc(OC(F)F)cc(C(C)C)c1NC(=O)N=S(N)(=O)c1cnc(C(C)(C)O)s1] | (R)-or (S)-N'-(4-(difluoromethoxy)-2-ethyl-6-isopropylphenylcarbamoyl)-2-(2-hydroxypropan-2-yl)thiazole-5-sulfonimidamide | ChiralPak ID, 2*25 cm, 5 um | 30% IPA in Hex (0.1% DEA) | 477.2 |
| 99 | 192a or 192b | 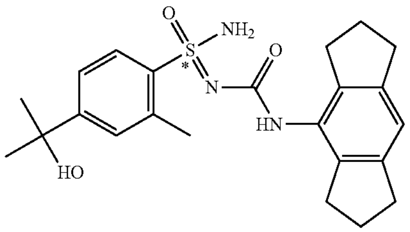 [SMILES: Cc1cc(C(C)(C)O)ccc1S(N)(=O)=NC(=O)Nc1c2c(cc3c1CCC3)CCC2] | (S)-or (R)-N'-(1,2,3,5,6,7-hexahydro-s-indacen-4-ylcarbamoyl)-4-(2-hydroxypropan-2-yl)-2-methylbenzenesulfonimidamide | ChiralPak ID, 2*25 cm, 5 um | 30% EtOH in Hex (0.1% DEA) | 428.2 |
| 100 | 192b or 192a | 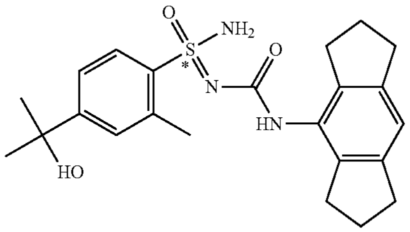 [SMILES: Cc1cc(C(C)(C)O)ccc1S(N)(=O)=NC(=O)Nc1c2c(cc3c1CCC3)CCC2] | (R)-or (S)-N'-(1,2,3,5,6,7-hexahydro-s-indacen-4-ylcarbamoyl)-4-(2-hydroxypropan-2-yl)-2-methylbenzenesulfonimidamide | ChiralPak ID, 2*25 cm, 5 um | 30% EtOH in Hex (0.1% DEA) | 428.2 |
| 101 | 189a or 189b | 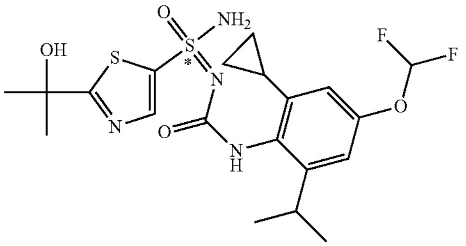 [SMILES: CC(C)c1cc(OC(F)F)cc(C2CC2)c1NC(=O)N=S(N)(=O)c1cnc(C(C)(C)O)s1] | (S)-or (R)-N'-(2-cyclopropyl-4-(difluoromethoxy)-6-isopropylphenylcarbamoyl)-2-(2-hydroxypropan-2-yl)thiazole-5-sulfonimidamide | ChiralPak ID, 2*25 cm, 5 um | 50% IPA in Hex (0.1% DEA) | 489.3 |
| 102 | 189b or 189a | 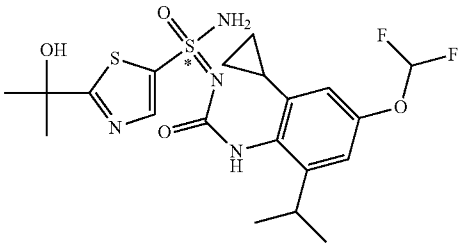 [SMILES: CC(C)c1cc(OC(F)F)cc(C2CC2)c1NC(=O)N=S(N)(=O)c1cnc(C(C)(C)O)s1] | (R)-or (S)-N'-(2-cyclopropyl-4-(difluoromethoxy)-6-isopropylphenylcarbamoyl)-2-(2-hydroxypropan-2-yl)thiazole-5-sulfonimidamide | ChiralPak ID, 2*25 cm, 5 um | 50% IPA in Hex (0.1% DEA) | 489.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 103 | 178a or 178b | 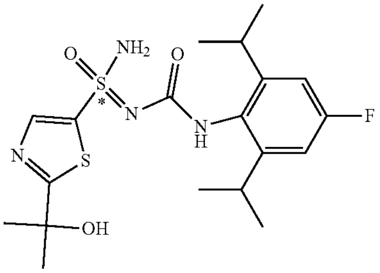 [SMILES: CC(C)c1cc(F)cc(C(C)C)c1NC(=O)N=S(N)(=O)c1cnc(C(C)(C)O)s1] | (S)-or (R)-N'-(4-fluoro-2,6-diisopropylphenylcarbamoyl)-2-(2-hydroxypropan-2-yl)thiazole-5-sulfonimidamide | ChiralPak ID, 2*25 cm, 5 um | 30% IPA (0.1% DEA) in Hex:DCM = 3:1 | 443.2 |
| 104 | 178b or 178a | 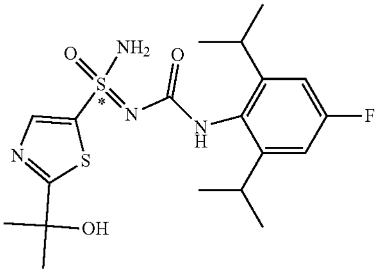 [SMILES: CC(C)c1cc(F)cc(C(C)C)c1NC(=O)N=S(N)(=O)c1cnc(C(C)(C)O)s1] | (R)-or (S)-N'-(4-fluoro-2,6-diisopropylphenylcarbamoyl)-2-(2-hydroxypropan-2-yl)thiazole-5-sulfonimidamide | ChiralPak ID, 2*25 cm, 5 um | 30% IPA (0.1% DEA) in Hex:DCM = 3:1 | 443.1 |
| 105 | 193a or 193b | 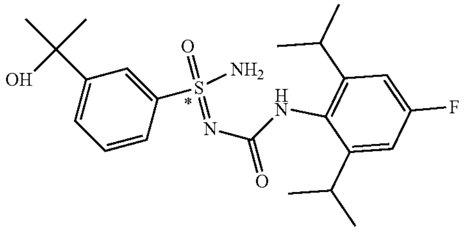 [SMILES: CC(C)c1cc(F)cc(C(C)C)c1NC(=O)N=S(N)(=O)c1cccc(C(C)(C)O)c1] | (S)-or (R)-N'-(4-fluoro-2,6-diisopropylphenylcarbamoyl)-3-(2-hydroxypropan-2-yl)benzenesulfonimidamide | ChiralPak IG, 2*25 cm, 5 um | 20% IPA in Hex (0.1% DEA) | 436.2 |
| 106 | 193b or 193a | 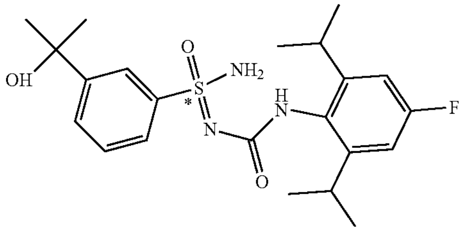 [SMILES: CC(C)c1cc(F)cc(C(C)C)c1NC(=O)N=S(N)(=O)c1cccc(C(C)(C)O)c1] | (R)-or (S)-N'-(4-fluoro-2,6-diisopropylphenylcarbamoyl)-3-(2-hydroxypropan-2-yl)benzenesulfonimidamide | ChiralPak IG, 2*25 cm, 5 um | 20% IPA in Hex (0.1% DEA) | 436.2 |
| 107 | 170a or 170b | 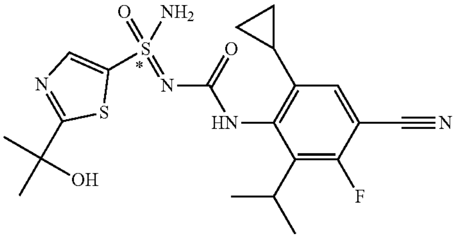 [SMILES: CC(C)c1c(F)c(C#N)cc(C2CC2)c1NC(=O)N=S(N)(=O)c1cnc(C(C)(C)O)s1] | (S)-or (R)-N'-(4-cyano-6-cyclopropyl-3-fluoro-2-isopropylphenylcarbamoyl)-2-(2-hydroxypropan-2-yl)thiazole-5-sulfonimidamide | ChiralPak IG, 2*25 cm, 5 um | 15% EtOH in Hex (0.1% DEA) | 466.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 108 | 170b or 170a | 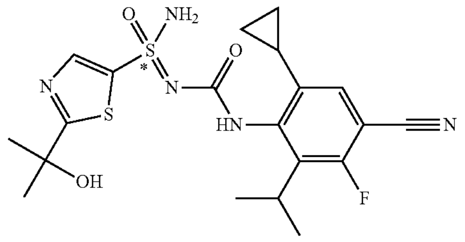 [SMILES: CC(C)c1c(F)c(C#N)cc(C2CC2)c1NC(=O)N=S(N)(=O)c1cnc(C(C)(C)O)s1] | (R)-or (S)-N'-(4-cyano-6-cyclopropyl-3-fluoro-2-isopropylphenylcarbamoyl)-2-(2-hydroxypropan-2-yl)thiazole-5-sulfonimidamide | ChiralPak IG, 2*25 cm, 5 um | 15% EtOH in Hex (0.1% DEA) | 466.1 |
| 109 | 168a or 168b | 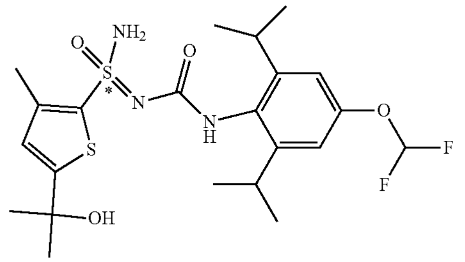 [SMILES: Cc1cc(C(C)(C)O)sc1S(N)(=O)=NC(=O)Nc1c(C(C)C)cc(OC(F)F)cc1C(C)C] | (S)-or (R)-N'-(4-(difluoromethoxy)-2,6-diisopropylphenylcarbamoyl)-5-(2-hydroxypropan-2-yl)-3-methylthiophene-2-sulfonimidamide | ChiralPak ID, 2*25 cm, 5 um | 30% IPA in Hex (0.1% DEA) | 504.2 |
| 110 | 168b or 168a | 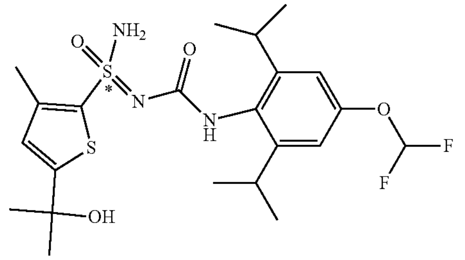 [SMILES: Cc1cc(C(C)(C)O)sc1S(N)(=O)=NC(=O)Nc1c(C(C)C)cc(OC(F)F)cc1C(C)C] | (R)-or (S)-N'-(4-(difluoromethoxy)-2,6-diisopropylphenylcarbamoyl)-5-(2-hydroxypropan-2-yl)-3-methylthiophene-2-sulfonimidamide | ChiralPak ID, 2*25 cm, 5 um | 30% IPA in Hex (0.1% DEA) | 504.2 |
| 111 | 171a or 171b | 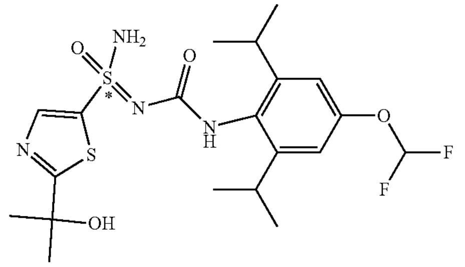 [SMILES: CC(C)c1cc(OC(F)F)cc(C(C)C)c1NC(=O)N=S(N)(=O)c1cnc(C(C)(C)O)s1] | (S)-or (R)-N'-(4-(difluoromethoxy)-2,6-diisopropylphenylcarbamoyl)-2-(2-hydroxypropan-2-yl)thiazole-5-sulfonimidamide | ChiralPak ID, 2*25 cm, 5 um | 50% IPA in Hex:DCM = 1:1 | 489.1 (M − 1) |
| 112 | 171b or 171a | 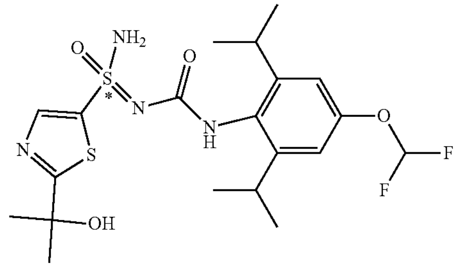 [SMILES: CC(C)c1cc(OC(F)F)cc(C(C)C)c1NC(=O)N=S(N)(=O)c1cnc(C(C)(C)O)s1] | (R)-or (S)-N'-(4-(difluoromethoxy)-2,6-diisopropylphenylcarbamoyl)-2-(2-hydroxypropan-2-yl)thiazole-5-sulfonimidamide | ChiralPak ID, 2*25 cm, 5 um | 50% IPA in Hex:DCM = 1:1 | 489.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 113 | 122a or 122b | 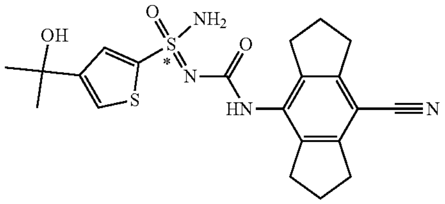 [SMILES: CC(C)(O)c1csc(S(N)(=O)=NC(=O)Nc2c3c(c(C#N)c4c2CCC4)CCC3)c1] | (S)-or (R)-N'-(8-cyano-1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 30% IPA in Hex | 443.1 (M − 1) |
| 114 | 122b or 122a | 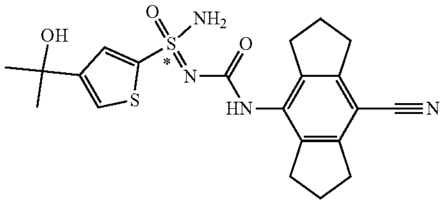 [SMILES: CC(C)(O)c1csc(S(N)(=O)=NC(=O)Nc2c3c(c(C#N)c4c2CCC4)CCC3)c1] | (R)-or (S)-N'-(8-cyano-1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 30% IPA in Hex | 443.1 (M − 1) |
| 115 | 120a or 120b | 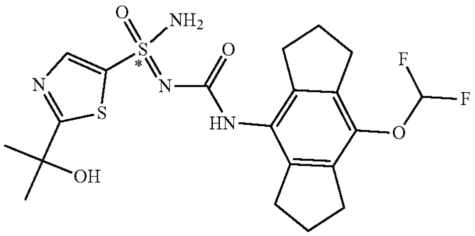 [SMILES: CC(C)(O)c1ncc(S(N)(=O)=NC(=O)Nc2c3c(c(OC(F)F)c4c2CCC4)CCC3)s1] | (S)-or (R)-N'-(8-(difluoromethoxy)-1,2,3,5,6,7-hexahydro-s-indacen-4-ylcarbamoyl)-2-(2-hydroxypropan-2-yl)thiazole-5-sulfonimidamide | Chiral ART Cellulose-SB 2*25 cm, 5 um | 20% EtOH in Hex (0.1% DEA) | 485.1 (M − 1) |
| 116 | 120b or 120a | 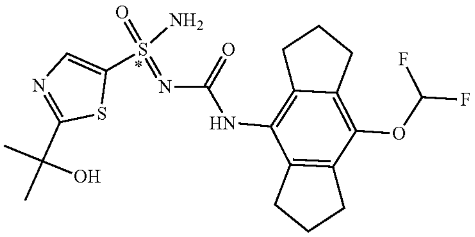 [SMILES: CC(C)(O)c1ncc(S(N)(=O)=NC(=O)Nc2c3c(c(OC(F)F)c4c2CCC4)CCC3)s1] | (R)-or (S)-N'-(8-(difluoromethoxy)-1,2,3,5,6,7-hexahydro-s-indacen-4-ylcarbamoyl)-2-(2-hydroxypropan-2-yl)thiazole-5-sulfonimidamide | Chiral ART Cellulose-SB 2*25 cm, 5 um | 20% EtOH in Hex (0.1% DEA) | 485.1 (M − 1) |
| 117 | 125a or 125b | 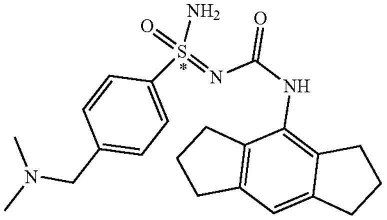 [SMILES: CN(C)Cc1ccc(S(N)(=O)=NC(=O)Nc2c3c(cc4c2CCC4)CCC3)cc1] | (S)-or (R)-4-((dimethylamino)methyl)-N'-(1,2,3,5,6,7-hexahydro-s-indacen-4-ylcarbamoyl)benzene-sulfonimidamide | ChiralPak ID, 2*25 cm, 5 um | 50% IPA in Hex:DCM = 3:1 | 413.2 |
| 118 | 125b or 125a | 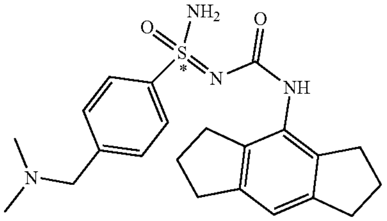 [SMILES: CN(C)Cc1ccc(S(N)(=O)=NC(=O)Nc2c3c(cc4c2CCC4)CCC3)cc1] | (R)-or (S)-4-((dimethylamino)methyl)-N'-(1,2,3,5,6,7-hexahydro-s-indacen-4-ylcarbamoyl)benzene-sulfonimidamide | ChiralPak ID, 2*25 cm, 5 um | 50% IPA in Hex:DCM = 3:1 | 413.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 119 | 129a or 129b | 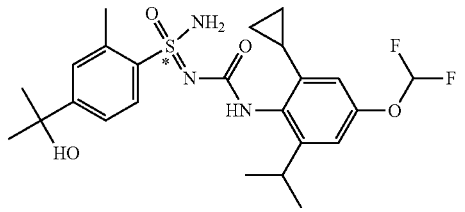 [SMILES: Cc1cc(C(C)(C)O)ccc1S(N)(=O)=NC(=O)Nc1c(C(C)C)cc(OC(F)F)cc1C1CC1] | (S)-or (R)-N'-(2-cyclopropyl-4-(difluoromethoxy)-6-isopropylphenylcarbamoyl)-4-(2-hydroxypropan-2-yl)-2-methylbenzenesulfonimidamide | ChiralPak ID, 2*25 cm, 5 um | 50% IPA in Hex:DCM = 3:1 | 496.2 |
| 120 | 129b or 129a | 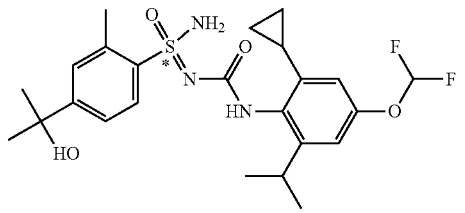 [SMILES: Cc1cc(C(C)(C)O)ccc1S(N)(=O)=NC(=O)Nc1c(C(C)C)cc(OC(F)F)cc1C1CC1] | (R)-or (S)-N'-(2-cyclopropyl-4-(difluoromethoxy)-6-isopropylphenylcarbamoyl)-4-(2-hydroxypropan-2-yl)-2-methylbenzenesulfonimidamide | ChiralPak ID, 2*25 cm, 5 um | 50% IPA in Hex:DCM = 3:1 | 496.2 |
| 121 | 112a or 112b | 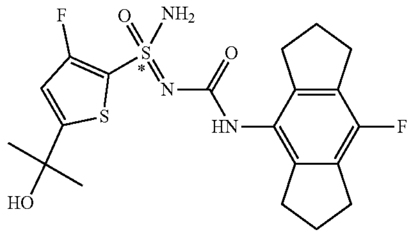 [SMILES: CC(C)(O)c1cc(F)c(S(N)(=O)=NC(=O)Nc2c3c(c(F)c4c2CCC4)CCC3)s1] | (S)-or (R)-3-fluoro-N'-(8-fluoro-1,2,3,5,6,7-hexahydro-s-indacen-4-ylcarbamoyl)-5-(2-hydroxypropan-2-yl)thiophene-2-sulfonimidamide | ChiralPak IG, 2*25 cm, 5 um | 15% EtOH in Hex (0.1% DEA) | 456.1 |
| 122 | 112b or 112a | 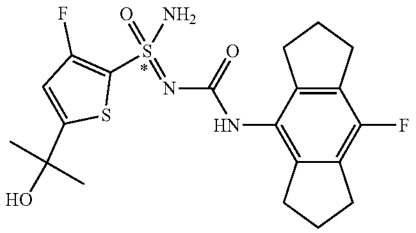 [SMILES: CC(C)(O)c1cc(F)c(S(N)(=O)=NC(=O)Nc2c3c(c(F)c4c2CCC4)CCC3)s1] | (R)-or (S)-3-fluoro-N'-(8-fluoro-1,2,3,5,6,7-hexahydro-s-indacen-4-ylcarbamoyl)-5-(2-hydroxypropan-2-yl)thiophene-2-sulfonimidamide | ChiralPak IG, 2*25 cm, 5 um | 15% EtOH in Hex (0.1% DEA) | 456.1 |
| 128 | 105a or 105b | 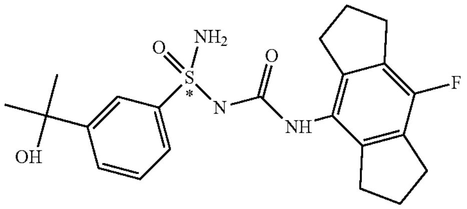 | (S)-or (R)-N'-(8-fluoro-1,2,3,5,6,7-hexahydro-s-indacen-4-ylcarbamoyl)-3-(2-hydroxypropan-2-yl)benzenesulfonimidamide | ChiralPak ID, 2*25 cm, 5 um | 40% EtOH in Hex | 432.1 |
| 129 | 105b or 105a | 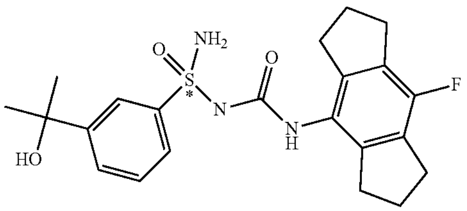 | (R)-or (S)-N'-(8-fluoro-1,2,3,5,6,7-hexahydro-s-indacen-4-ylcarbamoyl)-3-(2-hydroxypropan-2-yl)benzenesulfonimidamide | ChiralPak ID, 2*25 cm, 5 um | 40% EtOH in Hex | 432.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 130 | 121a or 121b | 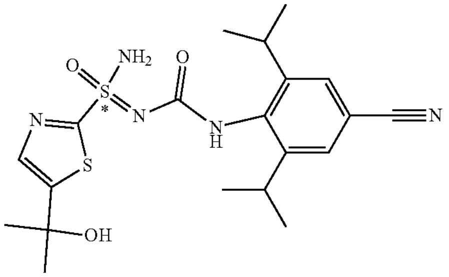 [SMILES: CC(C)c1cc(C#N)cc(C(C)C)c1NC(=O)N=S(N)(=O)c1ncc(C(C)(C)O)s1] | (S)-or (R)-N'-(4-cyano-2,6-diisopropylphenylcarbamoyl)-5-(2-hydroxypropan-2-yl)thiazole-2-sulfonimidamide | ChiralPak ID, 2*25 cm, 5 um | 40% EtOH in Hex | 448.1 (M − 1) |
| 131 | 121b or 121a | 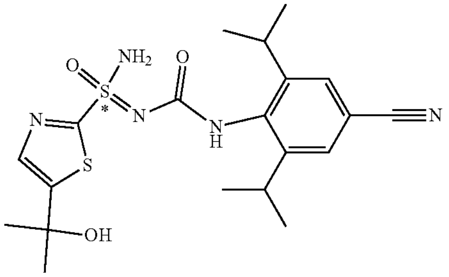 [SMILES: CC(C)c1cc(C#N)cc(C(C)C)c1NC(=O)N=S(N)(=O)c1ncc(C(C)(C)O)s1] | (R)-or (S)-N'-(4-cyano-2,6-diisopropylphenylcarbamoyl)-5-(2-hydroxypropan-2-yl)thiazole-2-sulfonimidamide | ChiralPak ID, 2*25 cm, 5 um | 40% EtOH in Hex | 448.1 (M − 1) |
| 132 | 145a or 145b | 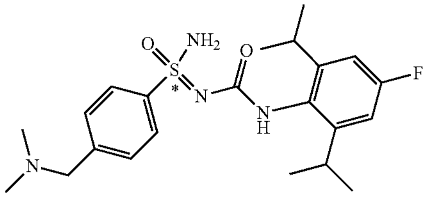 [SMILES: CC(C)c1cc(F)cc(C(C)C)c1NC(=O)N=S(N)(=O)c1ccc(CN(C)C)cc1] | (S)-or (R)-4-((dimethylamino)methyl)-N'-(4-fluoro-2,6-diisopropyl-phenylcarbamoyl)benzene-sulfonimidamide | ChiralPak IG, 2*25 cm, 5 um | 30% EtOH in Hex | 435.2 |
| 133 | 145b or 145a | 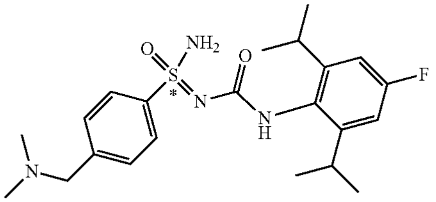 [SMILES: CC(C)c1cc(F)cc(C(C)C)c1NC(=O)N=S(N)(=O)c1ccc(CN(C)C)cc1] | (R)-or (S)-4-((dimethylamino)methyl)-N'-(4-fluoro-2,6-diisopropyl-phenylcarbamoyl)benzene-sulfonimidamide | ChiralPak IG, 2*25 cm, 5 um | 30% EtOH in Hex | 435.2 |
| 134 | 131a or 131b | 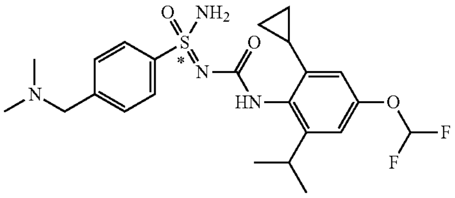 [SMILES: CC(C)c1cc(OC(F)F)cc(C2CC2)c1NC(=O)N=S(N)(=O)c1ccc(CN(C)C)cc1] | (S)-or (R)-N'-(2-cyclopropyl-4-(difluoromethoxy)-6-isopropylphenylcarbamoyl)-4-((dimethylamino)methyl)benzene-sulfonimidamide | ChiralPak IG, 2*25 cm, 5 um | 50% EtOH in Hex | 481.2 |
| 135 | 131b or 131a | 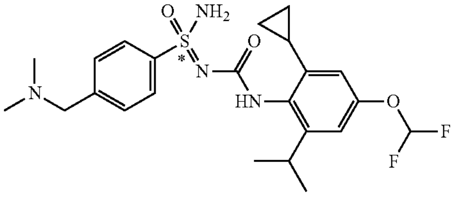 [SMILES: CC(C)c1cc(OC(F)F)cc(C2CC2)c1NC(=O)N=S(N)(=O)c1ccc(CN(C)C)cc1] | (R)-or (S)-N'-(2-cyclopropyl-4-(difluoromethoxy)-6-isopropylphenylcarbamoyl)-4-((dimethylamino)methyl)benzene-sulfonimidamide | ChiralPak IG, 2*25 cm, 5 um | 50% EtOH in Hex | 481.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 136 | 225a or 225b | 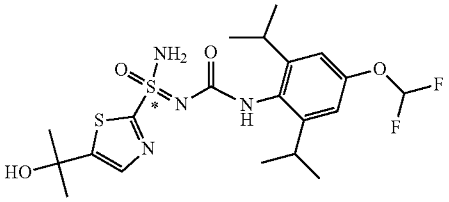 [SMILES: CC(C)c1cc(OC(F)F)cc(C(C)C)c1NC(=O)N=S(N)(=O)c1ncc(C(C)(C)O)s1] | (S)-or (R)-N'-(4-(difluoromethoxy)-2,6-diisopropylphenylcarbamoyl)-5-(2-hydroxypropan-2-yl)thiazole-2-sulfonimidamide | ChiralPak IF, 2*25 cm, 5 um | 20% MeOH (0.1% TFA) in $CO_2$ | 489.1 (M − 1) |
| 137 | 225b or 225a | 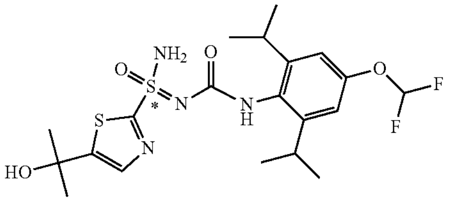 [SMILES: CC(C)c1cc(OC(F)F)cc(C(C)C)c1NC(=O)N=S(N)(=O)c1ncc(C(C)(C)O)s1] | (R)-or (S)-N'-(4-(difluoromethoxy)-2,6-diisopropylphenylcarbamoyl)-5-(2-hydroxypropan-2-yl)thiazole-2-sulfonimidamide | ChiralPak IF, 2*25 cm, 5 um | 20% MeOH (0.1% TFA) in $CO_2$ | 489.1 (M − 1) |
| 138 | 144a or 144b | 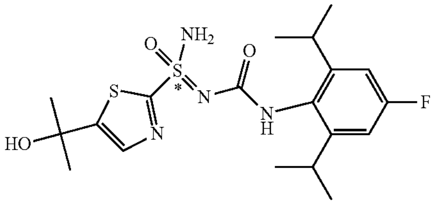 [SMILES: CC(C)c1cc(F)cc(C(C)C)c1NC(=O)N=S(N)(=O)c1ncc(C(C)(C)O)s1] | (S)-or (R)-N'-(4-fluoro-2,6-diisopropylphenylcarbamoyl)-5-(2-hydroxypropan-2-yl)thiazole-2-sulfonimidamide | ChiralPak IF, 2*25 cm, 5 um | 20% MeOH (0.1% TFA) in $CO_2$ | 443.2 |
| 139 | 144b or 144a | 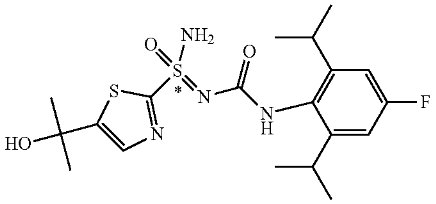 [SMILES: CC(C)c1cc(F)cc(C(C)C)c1NC(=O)N=S(N)(=O)c1ncc(C(C)(C)O)s1] | (R)-or (S)-N'-(4-fluoro-2,6-diisopropylphenylcarbamoyl)-5-(2-hydroxypropan-2-yl)thiazole-2-sulfonimidamide | ChiralPak IF, 2*25 cm, 5 um | 20% MeOH (0.1% TFA) in $CO_2$ | 443.1 |
| 140 | 149a or 149b | 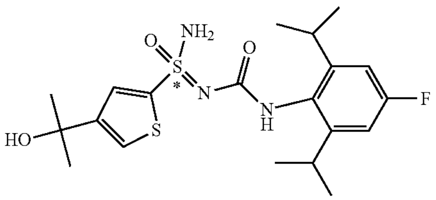 [SMILES: CC(C)c1cc(F)cc(C(C)C)c1NC(=O)N=S(N)(=O)c1cc(C(C)(C)O)cs1] | (S)-or (R)-N'-(4-fluoro-2,6-diisopropylphenylcarbamoyl)-4-(2-hydroxypropan-2-yl)thiophene-2-sulfonimidamide | ChiralPak ID, 2*25 cm, 5 um | 30% EtOH in Hex | 440.1 (M − 1) |
| 141 | 149b or 149a | 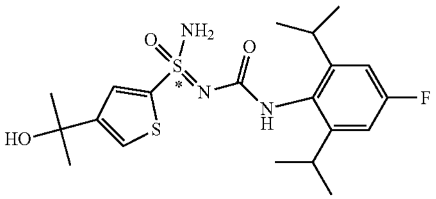 [SMILES: CC(C)c1cc(F)cc(C(C)C)c1NC(=O)N=S(N)(=O)c1cc(C(C)(C)O)cs1] | (R)-or (S)-N'-(4-fluoro-2,6-diisopropylphenylcarbamoyl)-4-(2-hydroxypropan-2-yl)thiophene-2-sulfonimidamide | ChiralPak ID, 2*25 cm, 5 um | 30% EtOH in Hex | 440.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 142 | 152a or 152b | 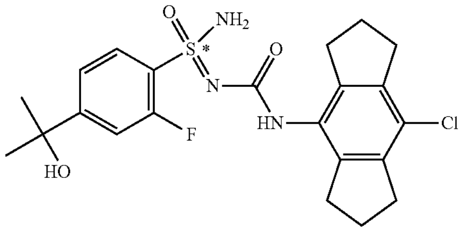 [SMILES: CC(C)(O)c1ccc(S(N)(=O)=NC(=O)Nc2c3c(c(Cl)c4c2CCC4)CCC3)c(F)c1] | (S)-or (R)-N'-(4-fluoro-2,6-diisopropylphenylcarbamoyl)-4-(2-hydroxypropan-2-yl)thiophene-2-sulfonimidamide | ChiralPak IG, 2*25 cm, 5 um | 30% IPA in Hex | 466.2 |
| 143 | 152b or 152a | 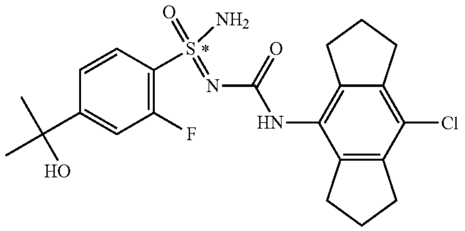 [SMILES: CC(C)(O)c1ccc(S(N)(=O)=NC(=O)Nc2c3c(c(Cl)c4c2CCC4)CCC3)c(F)c1] | (R)-or (S)-N'-(4-fluoro-2,6-diisopropylphenylcarbamoyl)-4-(2-hydroxypropan-2-yl)thiophene-2-sulfonimidamide | ChiralPak IG, 2*25 cm, 5 um | 30% IPA in Hex | 466.2 |
| 144 | 151a' or 151b' | 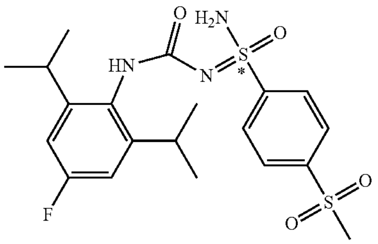 [SMILES: CC(C)c1cc(F)cc(C(C)C)c1NC(=O)N=S(N)(=O)c1ccc(S(C)(=O)=O)cc1] | (S)-or (R)-N'-(4-fluoro-2,6-diisopropylphenylcarbamoyl)-4-(methylsulfonyl)benzene-sulfonimidamide | Lux 5u Cellulose-4, AXIA Packed, 2.12*25 cm, 5 um | 35% MeOH (2 mM $NH_3$) in $CO_2$ | 454.1 (M − 1) |
| 145 | 151b' or 151a' | 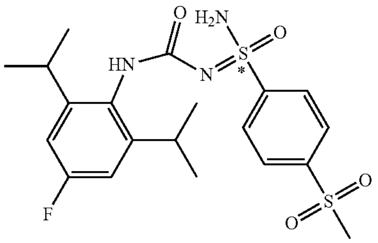 [SMILES: CC(C)c1cc(F)cc(C(C)C)c1NC(=O)N=S(N)(=O)c1ccc(S(C)(=O)=O)cc1] | (R)-or (S)-N'-(4-fluoro-2,6-diisopropylphenylcarbamoyl)-4-(methylsulfonyl)benzene-sulfonimidamide | Lux 5u Cellulose-4, AXIA Packed, 2.12*25 cm, 5 um | 35% MeOH (2 mM $NH_3$) in $CO_2$ | 454.1 (M − 1) |
| 146 | 167a or 167b | 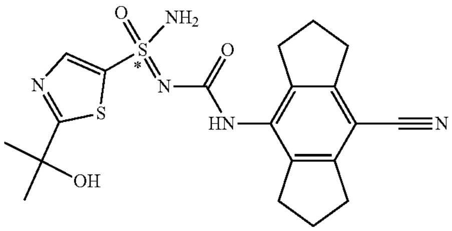 [SMILES: CC(C)(O)c1ncc(S(N)(=O)=NC(=O)Nc2c3c(c(C#N)c4c2CCC4)CCC3)s1] | (S)-or (R)-N'-(8-cyano-1,2,3,5,6,7-hexahydro-s-indacen-4-ylcarbamoyl)-2-(2-hydroxypropan-2-yl)thiazole-5-sulfonimidamide | ChiralPak IC, 2*25 cm, 5 um | 30% EtOH in Hex (0.1% DEA) | 444.1 (M − 1) |
| 147 | 167b or 167a | 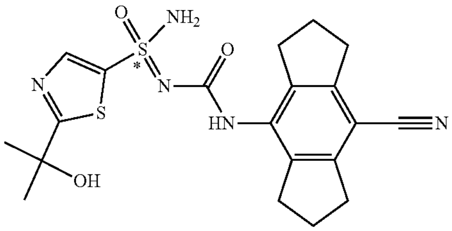 [SMILES: CC(C)(O)c1ncc(S(N)(=O)=NC(=O)Nc2c3c(c(C#N)c4c2CCC4)CCC3)s1] | (R)-or (S)-N'-(8-cyano-1,2,3,5,6,7-hexahydro-s-indacen-4-ylcarbamoyl)-2-(2-hydroxypropan-2-yl)thiazole-5-sulfonimidamide | ChiralPak IC, 2*25 cm, 5 um | 30% EtOH in Hex (0.1% DEA) | 444.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 148 | 107a or 107b | 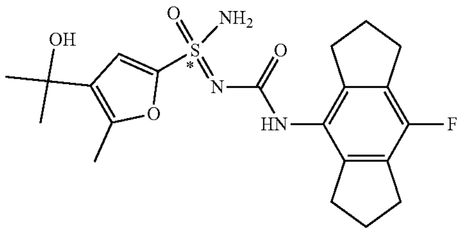 [SMILES: Cc1oc(S(N)(=O)=NC(=O)Nc2c3c(c(F)c4c2CCC4)CCC3)cc1C(C)(C)O] | (S)-or (R)-N'-(8-fluoro-1,2,3,5,6,7-hexahydro-s-indacen-4-ylcarbamoyl)-4-(2-hydroxypropan-2-yl)-5-methylfuran-2-sulfonimidamide | ChiralPak ID, 2*25 cm, 5 um | 50% IPA in Hex | 434.1 (M − 1) |
| 149 | 107b or 107a | 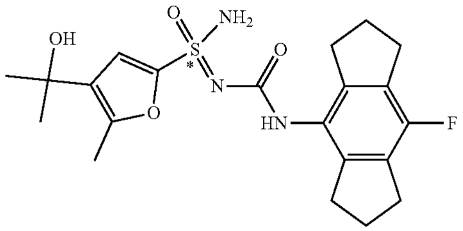 [SMILES: Cc1oc(S(N)(=O)=NC(=O)Nc2c3c(c(F)c4c2CCC4)CCC3)cc1C(C)(C)O] | (R)-or (S)-N'-(8-fluoro-1,2,3,5,6,7-hexahydro-s-indacen-4-ylcarbamoyl)-4-(2-hydroxypropan-2-yl)-5-methylfuran-2-sulfonimidamide | ChiralPak ID, 2*25 cm, 5 um | 50% IPA in Hex | 434.1 (M − 1) |
| 150 | 110a or 110b | 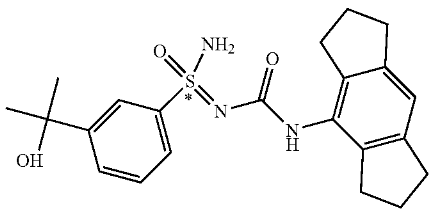 [SMILES: CC(C)(O)c1cccc(S(N)(=O)=NC(=O)Nc2c3c(cc4c2CCC4)CCC3)c1] | (S)-or (R)-N'-(1,2,3,5,6,7-hexahydro-s-indacen-4-ylcarbamoyl)-3-(2-hydroxypropan-2-yl)benzenesulfonimidamide | ChiralPak IF, 2*25 cm, 5 um | 30% EtOH in Hex | 412.1 (M − 1) |
| 151 | 110b or 110a | 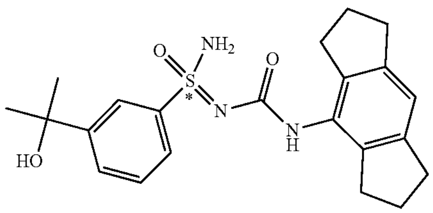 [SMILES: CC(C)(O)c1cccc(S(N)(=O)=NC(=O)Nc2c3c(cc4c2CCC4)CCC3)c1] | (R)-or (S)-N'-(1,2,3,5,6,7-hexahydro-s-indacen-4-ylcarbamoyl)-3-(2-hydroxypropan-2-yl)benzenesulfonimidamide | ChiralPak IF, 2*25 cm, 5 um | 30% EtOH in Hex | 412.1 (M − 1) |
| 152 | 151a or 151b | 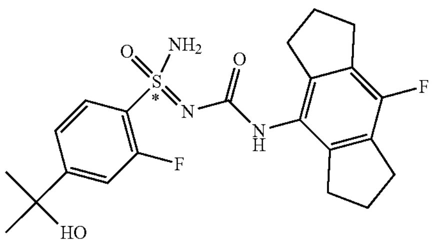 [SMILES: CC(C)(O)c1ccc(S(N)(=O)=NC(=O)Nc2c3c(c(F)c4c2CCC4)CCC3)c(F)c1] | (S)-or (R)-2-fluoro-N'-(8-fluoro-1,2,3,5,6,7-hexahydro-s-indacen-4-ylcarbamoyl)-4-(2-hydroxypropan-2-yl)benzenesulfonimidamide | ChiralPak IG, 2*25 cm, 5 um | 30% IPA in Hex | 448.1 (M − 1) |
| 153 | 151b or 151a | 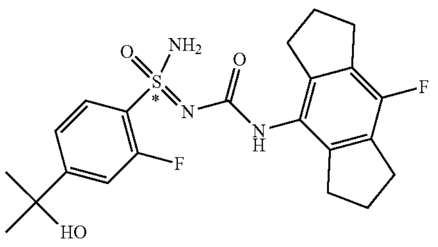 [SMILES: CC(C)(O)c1ccc(S(N)(=O)=NC(=O)Nc2c3c(c(F)c4c2CCC4)CCC3)c(F)c1] | (R)-or (S)-2-fluoro-N'-(8-fluoro-1,2,3,5,6,7-hexahydro-s-indacen-4-ylcarbamoyl)-4-(2-hydroxypropan-2-yl)benzenesulfonimidamide | ChiralPak IG, 2*25 cm, 5 um | 30% IPA in Hex | 448.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 154 | 154a or 154b | 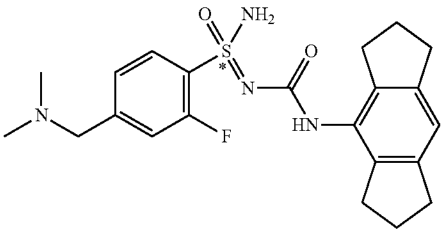 [SMILES: CN(C)Cc1ccc(S(N)(=O)=NC(=O)Nc2c3c(cc4c2CCC4)CCC3)c(F)c1] | (S)-or (R)-4-((dimethylamino)methyl)-2-fluoro-N'-(1,2,3,5,6,7-hexahydro-s-indacen-4-ylcarbamoyl)benzene-sulfonimidamide | ChiralPak IG, 2*25 cm, 5 um | 30% EtOH in Hex | 431.2 |
| 155 | 154b or 154a | 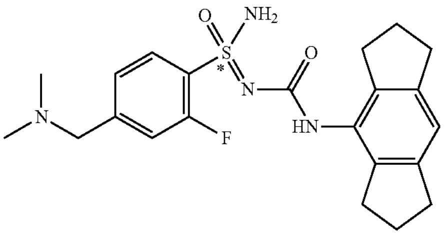 [SMILES: CN(C)Cc1ccc(S(N)(=O)=NC(=O)Nc2c3c(cc4c2CCC4)CCC3)c(F)c1] | (R)-or (S)-4-((dimethylamino)methyl)-2-fluoro-N'-(1,2,3,5,6,7-hexahydro-s-indacen-4-ylcarbamoyl)benzene-sulfonimidamide | ChiralPak IG, 2*25 cm, 5 um | 30% EtOH in Hex | 431.2 |
| 156 | 148a or 148b | 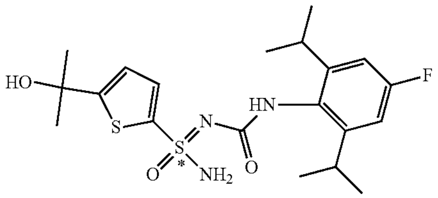 [SMILES: CC(C)c1cc(F)cc(C(C)C)c1NC(=O)N=S(N)(=O)c1ccc(C(C)(C)O)s1] | (S)-or (R)-N'-(4-fluoro-2,6-diisopropylphenylcarbamoyl)-5-(2-hydroxypropan-2-yl)thiophene-2-sulfonimidamide | ChiralPak ID, 2*25 cm, 5 um | 30% EtOH in Hex | 442.1 |
| 157 | 148b or 148a | 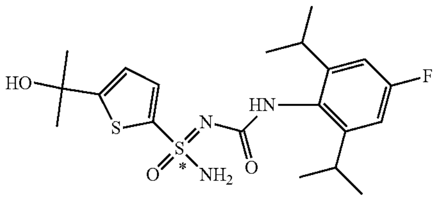 [SMILES: CC(C)c1cc(F)cc(C(C)C)c1NC(=O)N=S(N)(=O)c1ccc(C(C)(C)O)s1] | (R)-or (S)-N'-(4-fluoro-2,6-diisopropylphenylcarbamoyl)-5-(2-hydroxypropan-2-yl)thiophene-2-sulfonimidamide | ChiralPak ID, 2*25 cm, 5 um | 30% EtOH in Hex | 442.1 |
| 158 | 153a or 153b | 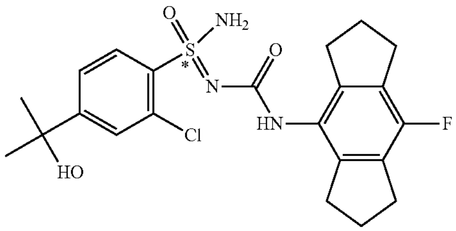 [SMILES: CC(C)(O)c1ccc(S(N)(=O)=NC(=O)Nc2c3c(c(F)c4c2CCC4)CCC3)c(Cl)c1] | (S)-or (R)-2-chloro-N'-(8-fluoro-1,2,3,5,6,7-hexahydro-s-indacen-4-ylcarbamoyl)-4-(2-hydroxypropan-2-yl)benzenesulfonimidamide | ChiralPak IF, 2*25 cm, 5 um | 30% EtOH in Hex | 464.1 (M − 1) |
| 159 | 153a or 153b | 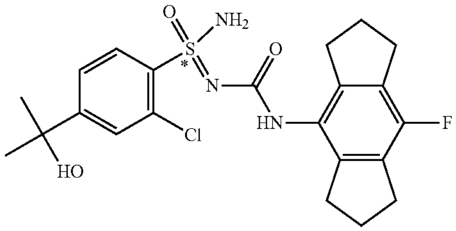 [SMILES: CC(C)(O)c1ccc(S(N)(=O)=NC(=O)Nc2c3c(c(F)c4c2CCC4)CCC3)c(Cl)c1] | (R)-or (S)-2-chloro-N'-(8-fluoro-1,2,3,5,6,7-hexahydro-s-indacen-4-ylcarbamoyl)-4-(2-hydroxypropan-2-yl)benzenesulfonimidamide | ChiralPak IF, 2*25 cm, 5 um | 30% EtOH in Hex | 464.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 160 | 109a or 109b | 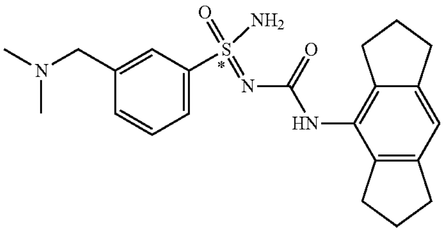 [SMILES: CN(C)Cc1cccc(S(N)(=O)=NC(=O)Nc2c3c(cc4c2CCC4)CCC3)c1] | (S)-or (R)-3-((dimethylamino)methyl)-N'-(1,2,3,5,6,7-hexahydro-s-indacen-4-ylcarbamoyl)benzene-sulfonimidamide | ChiralPak ID, 2*25 cm, 5 um | 50% EtOH in Hex (0.1% DEA) | 413.1 |
| 161 | 109b or 109a | 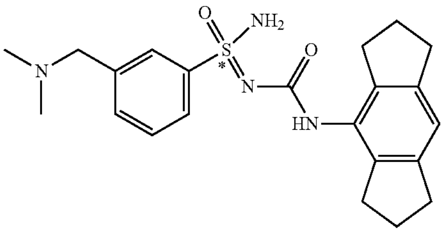 [SMILES: CN(C)Cc1cccc(S(N)(=O)=NC(=O)Nc2c3c(cc4c2CCC4)CCC3)c1] | (R)-or (S)-3-((dimethylamino)methyl)-N'-(1,2,3,5,6,7-hexahydro-s-indacen-4-ylcarbamoyl)benzene-sulfonimidamide | ChiralPak ID, 2*25 cm, 5 um | 50% EtOH in Hex (0.1% DEA) | 413.1 |
| 162 | 135a or 135b | 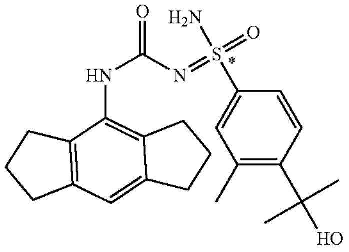 [SMILES: Cc1cc(S(N)(=O)=NC(=O)Nc2c3c(cc4c2CCC4)CCC3)ccc1C(C)(C)O] | (S)-or (R)-N'-((1,2,3,5,6,7-hexahydro-s-indacen-4-yl)carbamoyl)-4-(2-hydroxypropan-2-yl)-3-methylbenzenesulfonimidamide | ChiralPak ID, 2*25 cm, 5 um | 30% IPA in Hex | 428.2 |
| 163 | 135b or 135a | 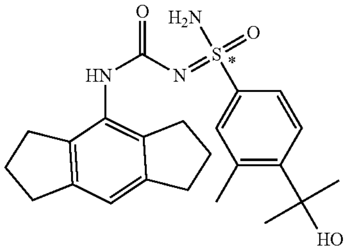 [SMILES: Cc1cc(S(N)(=O)=NC(=O)Nc2c3c(cc4c2CCC4)CCC3)ccc1C(C)(C)O] | (R)-or (S)-N'-((1,2,3,5,6,7-hexahydro-s-indacen-4-yl)carbamoyl)-4-(2-hydroxypropan-2-yl)-3-methylbenzenesulfonimidamide | ChiralPak ID, 2*25 cm, 5 um | 30% IPA in Hex | 428.2 |
| 164 | 134a or 134b | 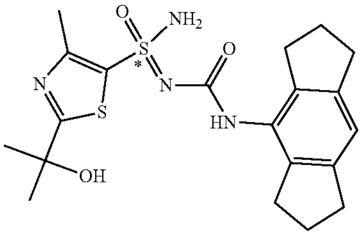 [SMILES: Cc1nc(C(C)(C)O)sc1S(N)(=O)=NC(=O)Nc1c2c(cc3c1CCC3)CCC2] | (S)-or (R)-N'-((1,2,3,5,6,7-hexahydro-s-indacen-4-yl)carbamoyl)-2-(2-hydroxypropan-2-yl)-4-methylthiazole-5-sulfonimidamide | ChiralPak ID, 2*25 cm, 5 um | 30% IPA in Hex | 435.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 165 | 134b or 134a | 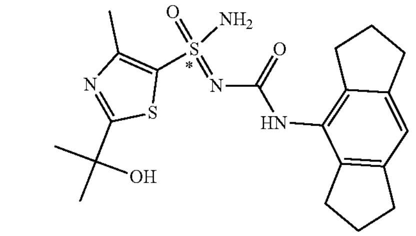 [SMILES: Cc1nc(C(C)(C)O)sc1S(N)(=O)=NC(=O)Nc1c2c(cc3c1CCC3)CCC2] | (R)-or (S)-N'-((1,2,3,5,6,7-hexahydro-s-indacen-4-yl)carbamoyl)-2-(2-hydroxypropan-2-yl)-4-methylthiazole-5-sulfonimidamide | ChiralPak ID, 2*25 cm, 5 um | 30% IPA in Hex | 435.1 |
| 166 | 130a or 130b | 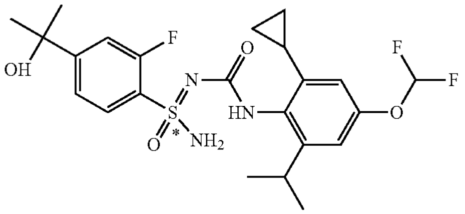 [SMILES: CC(C)c1cc(OC(F)F)cc(C2CC2)c1NC(=O)N=S(N)(=O)c1ccc(C(C)(C)O)cc1F] | (S)-or (R)-N'-((2-cyclopropyl-4-(difluoromethoxy)-6-isopropylphenyl)carbamoyl)-2-fluoro-4-(2-hydroxypropan-2-yl)benzenesulfonimidamide | ChiralPak ID, 2*25 cm, 5 um | 40% IPA in Hex | 500.2 |
| 167 | 130b or 130a | 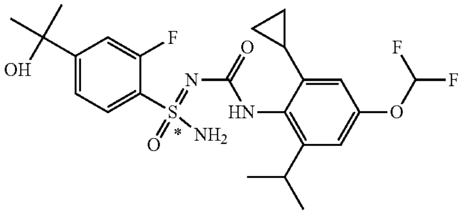 [SMILES: CC(C)c1cc(OC(F)F)cc(C2CC2)c1NC(=O)N=S(N)(=O)c1ccc(C(C)(C)O)cc1F] | (R)-or (S)-N'-((2-cyclopropyl-4-(difluoromethoxy)-6-isopropylphenyl)carbamoyl)-2-fluoro-4-(2-hydroxypropan-2-yl)benzenesulfonimidamide | ChiralPak ID, 2*25 cm, 5 um | 40% IPA in Hex | 500.2 |
| 168 | 212a or 212b | 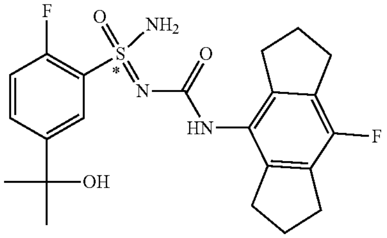 [SMILES: CC(C)(O)c1ccc(F)c(S(N)(=O)=NC(=O)Nc2c3c(c(F)c4c2CCC4)CCC3)c1] | (S)-or (R)-2-fluoro-N'-((8-fluoro-1,2,3,5,6,7-hexahydro-s-indacen-4-yl)carbamoyl)-5-(2-hydroxypropan-2-yl)benzenesulfonimidamide | ChiralPak ID, 2*25 cm, 5 um | 40% EtOH in Hex | 450.2 |
| 169 | 212b or 212a | 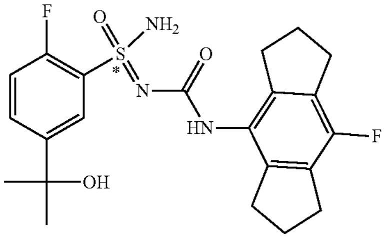 [SMILES: CC(C)(O)c1ccc(F)c(S(N)(=O)=NC(=O)Nc2c3c(c(F)c4c2CCC4)CCC3)c1] | (S)-or (R)-2-fluoro-N'-((8-fluoro-1,2,3,5,6,7-hexahydro-s-indacen-4-yl)carbamoyl)-5-(2-hydroxypropan-2-yl)benzenesulfonimidamide | ChiralPak ID, 2*25 cm, 5 um | 40% EtOH in Hex | 450.2 |
| 170 | 205a or 205b | 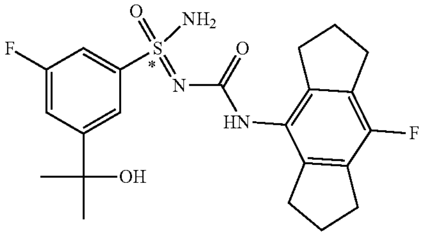 [SMILES: CC(C)(O)c1cc(F)cc(S(N)(=O)=NC(=O)Nc2c3c(c(F)c4c2CCC4)CCC3)c1] | (R)-or (S)-3-fluoro-N'-((8-fluoro-1,2,3,5,6,7-hexahydro-s-indacen-4-yl)carbamoyl)-5-(2-hydroxypropan-2-yl)benzenesulfonimidamide | Chiral ART Cellulose-SB, 2*25 cm, 5 um | 30% EtOH in Hex | 450.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 171 | 205a or 205b | 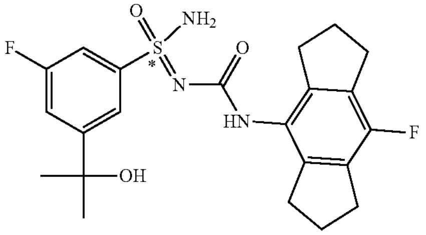 [SMILES: CC(C)(O)c1cc(F)cc(S(N)(=O)=NC(=O)Nc2c3c(c(F)c4c2CCC4)CCC3)c1] | (S)-or (R)-3-fluoro-N'-((8-fluoro-1,2,3,5,6,7-hexahydro-s-indacen-4-yl)carbamoyl)-5-(2-hydroxypropan-2-yl)benzenesulfonimidamide | Chiral ART Cellulose-SB, 2*25 cm, 5 um | 40% EtOH in Hex | 450.2 |
| 172 | 143a or 143b | 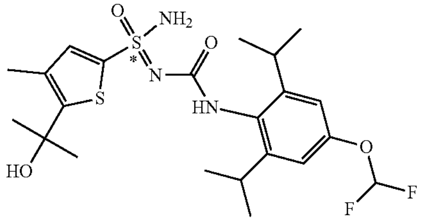 [SMILES: Cc1cc(S(N)(=O)=NC(=O)Nc2c(C(C)C)cc(OC(F)F)cc2C(C)C)sc1C(C)(C)O] | (S)-or (R)-N'-((4-(difluoromethoxy)-2,6-diisopropylphenyl)carbamoyl)-5-(2-hydroxypropan-2-yl)-4-methylthiophene-2-sulfonimidamide | ChiralPak ID, 2*25 cm, 5 um | 30% EtOH in Hex | 504.2 |
| 173 | 143b or 143a | 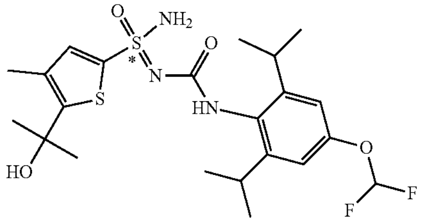 [SMILES: Cc1cc(S(N)(=O)=NC(=O)Nc2c(C(C)C)cc(OC(F)F)cc2C(C)C)sc1C(C)(C)O] | (R)-or (S)-N'-((4-(difluoromethoxy)-2,6-diisopropylphenyl)carbamoyl)-5-(2-hydroxypropan-2-yl)-4-methylthiophene-2-sulfonimidamide | ChiralPak ID, 2*25 cm, 5 um | 30% EtOH in Hex | 504.2 |
| 174 | 206a or 206b | 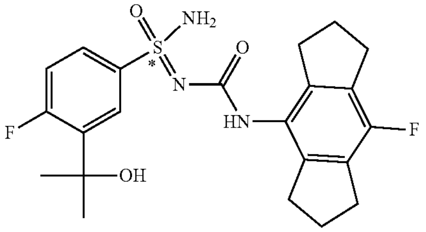 [SMILES: CC(C)(O)c1cc(S(N)(=O)=NC(=O)Nc2c3c(c(F)c4c2CCC4)CCC3)ccc1F] | (S)-or (R)-4-fluoro-N'-((8-fluoro-1,2,3,5,6,7-hexahydro-s-indacen-4-yl)carbamoyl)-3-(2-hydroxypropan-2-yl)benzenesulfonimidamide | ChiralPak ID, 2*25 cm, 5 um | 30% EtOH in Hex (8 mM $NH_3$•MeOH) | 450.2 |
| 175 | 206b or 206a | 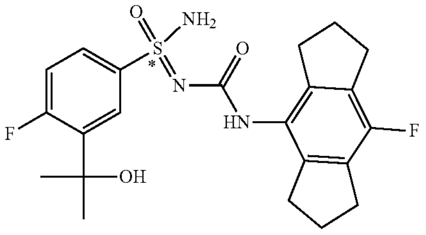 [SMILES: CC(C)(O)c1cc(S(N)(=O)=NC(=O)Nc2c3c(c(F)c4c2CCC4)CCC3)ccc1F] | (R)-or (S)-4-fluoro-N'-((8-fluoro-1,2,3,5,6,7-hexahydro-s-indacen-4-yl)carbamoyl)-3-(2-hydroxypropan-2-yl)benzenesulfonimidamide | ChiralPak ID, 2*25 cm, 5 um | 30% EtOH in Hex (8 mM $NH_3$•MeOH) | 450.2 |
| 176 | 108a or 108b | 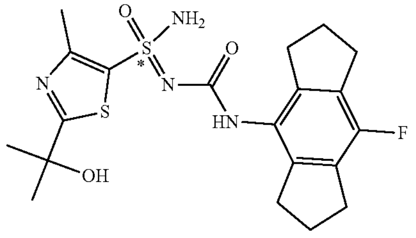 [SMILES: Cc1nc(C(C)(C)O)sc1S(N)(=O)=NC(=O)Nc1c2c(c(F)c3c1CCC3)CCC2] | (S)-or (R)-N'-((8-fluoro-1,2,3,5,6,7-hexahydro-s-indacen-4-yl)carbamoyl)-2-(2-hydroxypropan-2-yl)-4-methylthiazole-5-sulfonimidamide | ChiralPak IG, 2*25 cm, 5 um | 30% IPA in Hex | 453.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 177 | 108b or 108a | 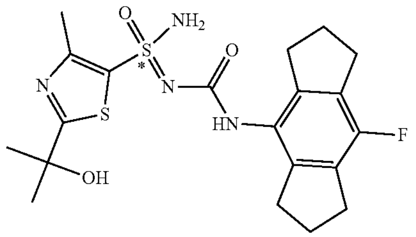 [SMILES: Cc1nc(C(C)(C)O)sc1S(N)(=O)=NC(=O)Nc1c2c(c(F)c3c1CCC3)CCC2] | (R)-or (S)-N'-((8-fluoro-1,2,3,5,6,7-hexahydro-s-indacen-4-yl)carbamoyl)-2-(2-hydroxypropan-2-yl)-4-methylthiazole-5-sulfonimidamide | ChiralPak IG, 2*25 cm, 5 um | 40% IPA in Hex | 453.1 |
| 178 | 202a or 202b | 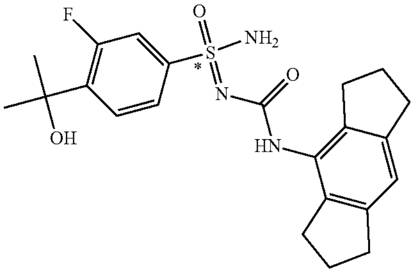 [SMILES: CC(C)(O)c1ccc(S(N)(=O)=NC(=O)Nc2c3c(cc4c2CCC4)CCC3)cc1F] | (S)-or (R)-3-fluoro-N'-((1,2,3,5,6,7-hexahydro-s-indacen-4-yl)carbamoyl)-4-(2-hydroxypropan-2-yl)benzenesulfonimidamide | Chiral ART Cellulose-SB, 2*25 cm, 5 um | 50% EtOH in Hex (8 mM $NH_3$•MeOH) | 432.2 |
| 179 | 202b or 202a | 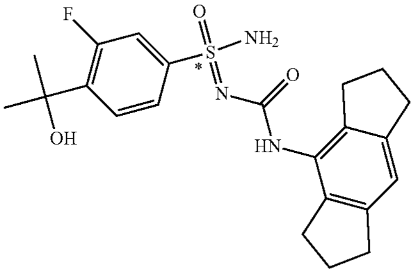 [SMILES: CC(C)(O)c1ccc(S(N)(=O)=NC(=O)Nc2c3c(cc4c2CCC4)CCC3)cc1F] | (R)-or (S)-3-fluoro-N'-((1,2,3,5,6,7-hexahydro-s-indacen-4-yl)carbamoyl)-4-(2-hydroxypropan-2-yl)benzenesulfonimidamide | Chiral ART Cellulose-SB, 2*25 cm, 5 um | 50% EtOH in Hex (8 mM $NH_3$•MeOH) | 432.2 |
| 180 | 116a or 116b | 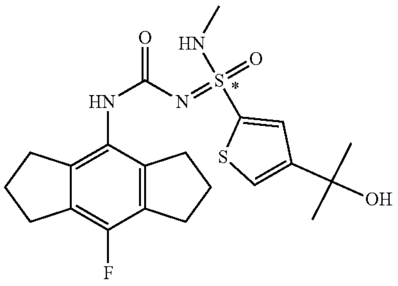 [SMILES: CNS(=O)(=NC(=O)Nc1c2c(c(F)c3c1CCC3)CCC2)c1cc(C(C)(C)O)cs1] | (S)-or (R)-N'-((8-fluoro-1,2,3,5,6,7-hexahydro-s-indacen-4-yl)carbamoyl)-4-(2-hydroxypropan-2-yl)-N-methylthiophene-2-sulfonimidamide | ChiralPak IG, 2*25 cm, 5 um | 30% EtOH in Hex | 452.1 |
| 181 | 116b or 116a | 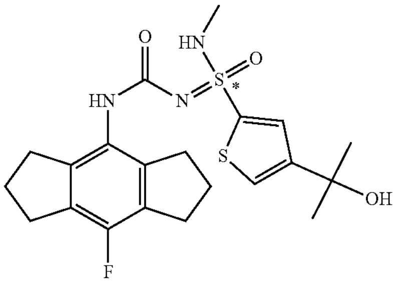 [SMILES: CNS(=O)(=NC(=O)Nc1c2c(c(F)c3c1CCC3)CCC2)c1cc(C(C)(C)O)cs1] | (R)-or (S)-N'-((8-fluoro-1,2,3,5,6,7-hexahydro-s-indacen-4-yl)carbamoyl)-4-(2-hydroxypropan-2-yl)-N-methylthiophene-2-sulfonimidamide | ChiralPak IG, 2*25 cm, 5 um | 30% EtOH in Hex | 452.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 182 | 173a or 173b | 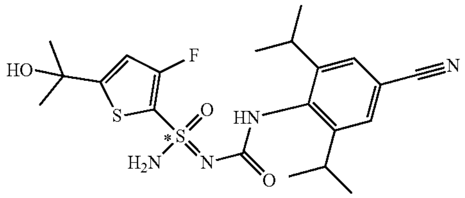 [SMILES: CC(C)c1cc(C#N)cc(C(C)C)c1NC(=O)N=S(N)(=O)c1sc(C(C)(C)O)cc1F] | (S)-or (R)-N'-((4-cyano-2,6-diisopropylphenyl)carbamoyl)-3-fluoro-5-(2-hydroxypropan-2-yl)thiophene-2-sulfonimidamide | ChiralPak ID, 2*25 cm, 5 um | 15% EtOH in Hex (0.1% DEA) | 467.2 |
| 183 | 173b or 173a | 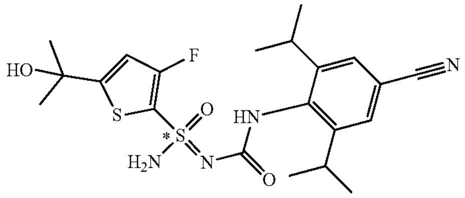 [SMILES: CC(C)c1cc(C#N)cc(C(C)C)c1NC(=O)N=S(N)(=O)c1sc(C(C)(C)O)cc1F] | (R)-or (S)-N'-((4-cyano-2,6-diisopropylphenyl)carbamoyl)-3-fluoro-5-(2-hydroxypropan-2-yl)thiophene-2-sulfonimidamide | ChiralPak ID, 2*25 cm, 5 um | 15% EtOH in Hex (0.1% DEA) | 467.2 |
| 184 | 174a or 174b | 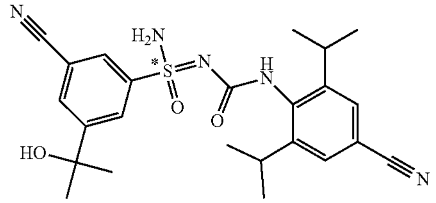 [SMILES: CC(C)c1cc(C#N)cc(C(C)C)c1NC(=O)N=S(N)(=O)c1cc(C#N)cc(C(C)(C)O)c1] | (S)-or (R)-3-cyano-N'-((4-cyano-2,6-diisopropylphenyl)carbamoyl)-5-(2-hydroxypropan-2-yl)benzenesulfonimidamide | ChiralPak IG, 2*25 cm, 5 um | 15% EtOH in Hex (0.1% DEA) | 468.2 |
| 185 | 174b or 174a | 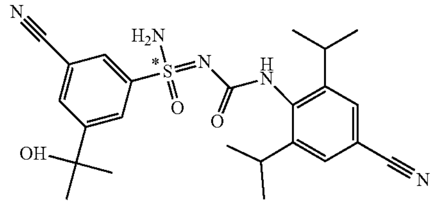 [SMILES: CC(C)c1cc(C#N)cc(C(C)C)c1NC(=O)N=S(N)(=O)c1cc(C#N)cc(C(C)(C)O)c1] | (R)-or (S)-3-cyano-N'-((4-cyano-2,6-diisopropylphenyl)carbamoyl)-5-(2-hydroxypropan-2-yl)benzenesulfonimidamide | ChiralPak IG, 2*25 cm, 5 um | 15% EtOH in Hex (0.1% DEA) | 468.2 |
| 186 | 223a or 223b | 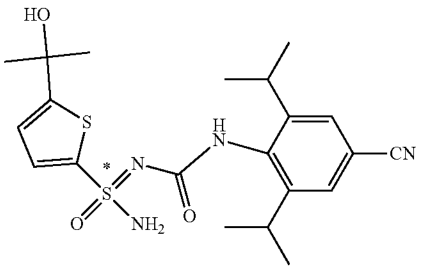 [SMILES: CC(C)c1cc(C#N)cc(C(C)C)c1NC(=O)N=S(N)(=O)c1ccc(C(C)(C)O)s1] | (S)-or (R)-N'-((4-cyano-2,6-diisopropylphenyl)carbamoyl)-5-(2-hydroxypropan-2-yl)thiophene-2-sulfonimidamide | ChiralPak ID, 2*25 cm, 5 um | 30% EtOH in Hex (0.1% DEA) | 449.2 |
| 187 | 223b or 223a | 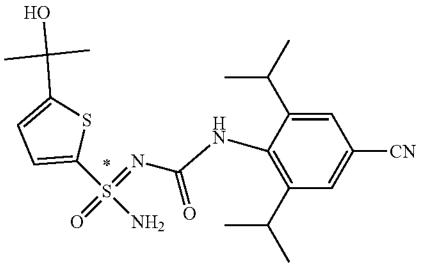 [SMILES: CC(C)c1cc(C#N)cc(C(C)C)c1NC(=O)N=S(N)(=O)c1ccc(C(C)(C)O)s1] | (R)-or (S)-N'-((4-cyano-2,6-diisopropylphenyl)carbamoyl)-5-(2-hydroxypropan-2-yl)thiophene-2-sulfonimidamide | ChiralPak ID, 2*25 cm, 5 um | 30% EtOH in Hex (0.1% DEA) | 449.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 188 | 158a or 158b | 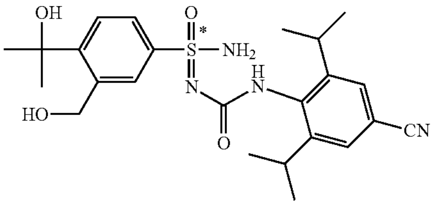 [SMILES: CC(C)c1cc(C#N)cc(C(C)C)c1NC(=O)N=S(N)(=O)c1ccc(C(C)(C)O)c(CO)c1] | (S)-or (R)-N'-((4-cyano-2,6-diisopropylphenyl)carbamoyl)-3-(hydroxymethyl)-4-(2-hydroxypropan-2-yl)benzenesulfonimidamide | ChiralPak ID, 2*25 cm, 5 um | 30% EtOH in Hex (0.1% DEA) | 473.2 |
| 189 | 158b or 158a | 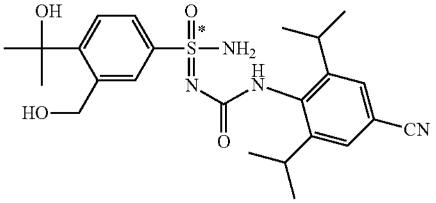 [SMILES: CC(C)c1cc(C#N)cc(C(C)C)c1NC(=O)N=S(N)(=O)c1ccc(C(C)(C)O)c(CO)c1] | (R)-or (S)-N'-((4-cyano-2,6-diisopropylphenyl)carbamoyl)-3-(hydroxymethyl)-4-(2-hydroxypropan-2-yl)benzenesulfonimidamide | ChiralPak ID, 2*25 cm, 5 um | 30% EtOH in Hex (0.1% DEA) | 473.2 |
| 190 | 220a or 220b | 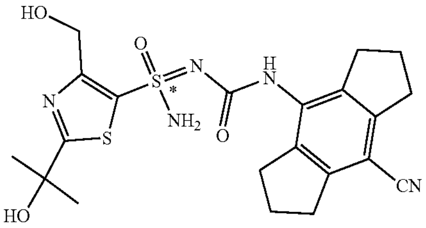 [SMILES: CC(C)(O)c1nc(CO)c(S(N)(=O)=NC(=O)Nc2c3c(c(C#N)c4c2CCC4)CCC3)s1] | (S)-or (R)-N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | ChiralPak IF, 2*25 cm, 5 um | MeOH (0.1% DEA) | 476.1 |
| 191 | 220b or 220a | 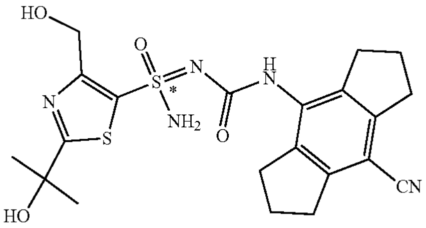 [SMILES: CC(C)(O)c1nc(CO)c(S(N)(=O)=NC(=O)Nc2c3c(c(C#N)c4c2CCC4)CCC3)s1] | (R)-or (S)-N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | ChiralPak IF, 2*25 cm, 5 um | MeOH (0.1% DEA) | 476.1 |
| 192 | 157a or 157b | 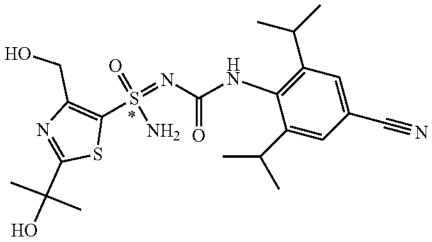 [SMILES: CC(C)c1cc(C#N)cc(C(C)C)c1NC(=O)N=S(N)(=O)c1sc(C(C)(C)O)nc1CO] | (S)-or (R)-N'-((4-cyano-2,6-diisopropylphenyl)carbamoyl)-4-(hydroxymethyl)-2-(2-hydroxypropan-2-yl)thiazole-5-sulfonimidamide | ChiralPak IC, 2*25 cm, 5 um | 15% EtOH in Hex | 480.2 |
| 193 | 157b or 157a | 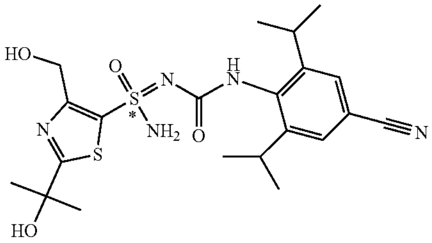 [SMILES: CC(C)c1cc(C#N)cc(C(C)C)c1NC(=O)N=S(N)(=O)c1sc(C(C)(C)O)nc1CO] | (R)-or (S)-N'-((4-cyano-2,6-diisopropylphenyl)carbamoyl)-4-(hydroxymethyl)-2-(2-hydroxypropan-2-yl)thiazole-5-sulfonimidamide | ChiralPak IC, 2*25 cm, 5 um | 15% EtOH in Hex | 480.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 194 | 161a or 161b | 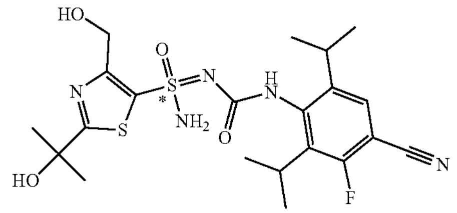 [SMILES: CC(C)c1cc(C#N)c(F)c(C(C)C)c1NC(=O)N=S(N)(=O)c1sc(C(C)(C)O)nc1CO] | (S)-or (R)-N'-((4-cyano-3-fluoro-2,6-diisopropylphenyl)carbamoyl)-4-(hydroxymethyl)-2-(2-hydroxypropan-2-yl)thiazole-5-sulfonimidamide | ChiralPak IC, 2*25 cm, 5 um | 15% EtOH in Hex | 498.2 |
| 195 | 161b or 161a | 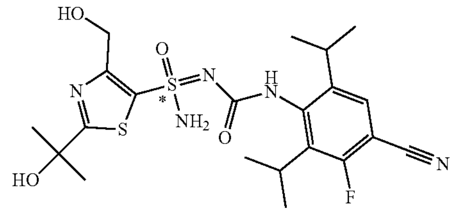 [SMILES: CC(C)c1cc(C#N)c(F)c(C(C)C)c1NC(=O)N=S(N)(=O)c1sc(C(C)(C)O)nc1CO] | (R)-or (S)-N'-((4-cyano-3-fluoro-2,6-diisopropylphenyl)carbamoyl)-4-(hydroxymethyl)-2-(2-hydroxypropan-2-yl)thiazole-5-sulfonimidamide | ChiralPak IC, 2*25 cm, 5 um | 15% EtOH in Hex | 498.2 |
| 196 | 165a or 165b | 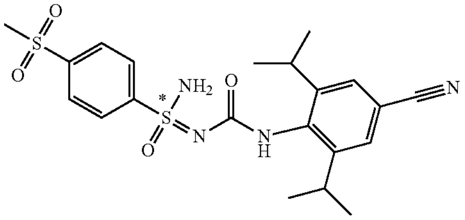 [SMILES: CC(C)c1cc(C#N)cc(C(C)C)c1NC(=O)N=S(N)(=O)c1ccc(S(C)(=O)=O)cc1] | (S)-or (R)-N'-((4-cyano-2,6-diisopropylphenyl)carbamoyl)-4-(methylsulfonyl)benzene-sulfonimidamide | ChiralPak IG, 2*25 cm, 5 um | 30% EtOH in Hex (0.1% DEA) | 463.1 |
| 197 | 165b or 165a | 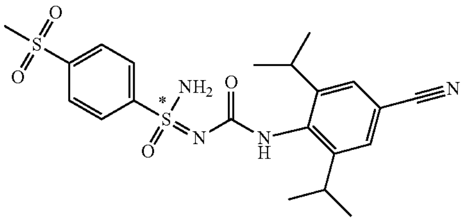 [SMILES: CC(C)c1cc(C#N)cc(C(C)C)c1NC(=O)N=S(N)(=O)c1ccc(S(C)(=O)=O)cc1] | (R)-or (S)-N'-((4-cyano-2,6-diisopropylphenyl)carbamoyl)-4-(methylsulfonyl)benzene-sulfonimidamide | ChiralPak IG, 2*25 cm, 5 um | 30% EtOH in Hex (0.1% DEA) | 463.1 |
| 198 | 172a or 172b | 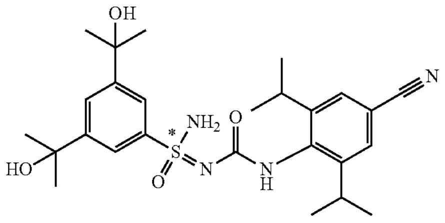 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | ChiralPak IC, 2*25 cm, 5 um | 15% EtOH in Hex (0.1% DEA) | 501.2 |
| 199 | 172b or 172a | 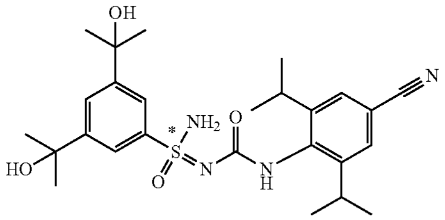 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | ChiralPak IC, 2*25 cm, 5 um | 15% EtOH in Hex (0.1% DEA) | 501.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]$^+$ |
|---|---|---|---|---|---|---|
| 200 | 106a or 106b | 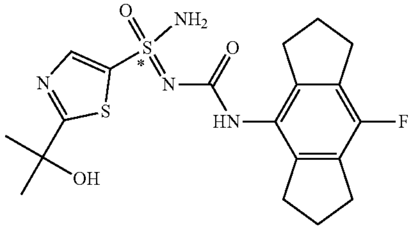 [SMILES: CC(C)(O)c1ncc(S(N)(=O)=NC(=O)Nc2c3c(c(F)c4c2CCC4)CCC3)s1] | (R)-or (S)-N'-(8-fluoro-1,2,3,5,6,7-hexahydro-s-indacen-4-ylcarbamoyl)-2-(2-hydroxypropan-2-yl)thiazole-5-sulfonimidamide | ChiralPak AD-H, 2*25 cm, 5 um | 25% EtOH in CO2 | 439.2 |
| 201 | 106b or 106a | 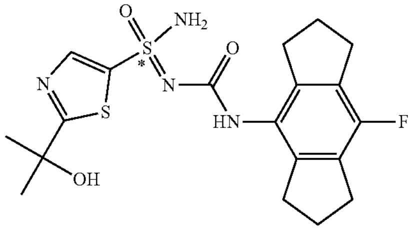 [SMILES: CC(C)(O)c1ncc(S(N)(=O)=NC(=O)Nc2c3c(c(F)c4c2CCC4)CCC3)s1] | (S)-or (R)-N'-(8-fluoro-1,2,3,5,6,7-hexahydro-s-indacen-4-ylcarbamoyl)-2-(2-hydroxypropan-2-yl)thiazole-5-sulfonimidamide | ChiralPak AD-H, 2*25 cm, 5 um | 25% EtOH in $CO_2$ | 439.2 |
| 202 | 136a or 136b | 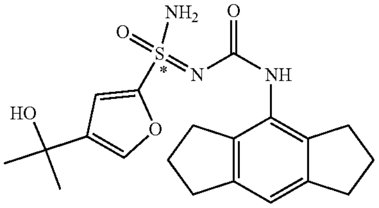 [SMILES: CC(C)(O)c1coc(S(N)(=O)=NC(=O)Nc2c3c(cc4c2CCC4)CCC3)c1] | (S)-or (R)-N'-(1,2,3,5,6,7-hexahydro-s-indacen-4-ylcarbamoyl)-4-(2-hydroxypropan-2-yl)furan-2-sulfonimidamide | Chiral ART Cellulose-SB, 2*25 cm, 5 um | 20% EtOH in Hex (0.2% DEA) | 404.2 |
| 203 | 136b or 136a | 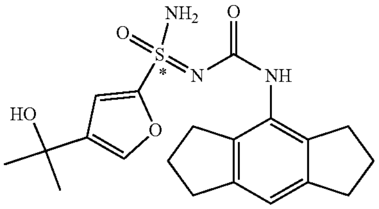 [SMILES: CC(C)(O)c1coc(S(N)(=O)=NC(=O)Nc2c3c(cc4c2CCC4)CCC3)c1] | (R)-or (S)-N'-(1,2,3,5,6,7-hexahydro-s-indacen-4-ylcarbamoyl)-4-(2-hydroxypropan-2-yl)furan-2-sulfonimidamide | Chiral ART Cellulose-SB, 2*25 cm, 5 um | 20% EtOH in Hex (0.2% DEA) | 404.2 |
| 204 | 183a or 183b | 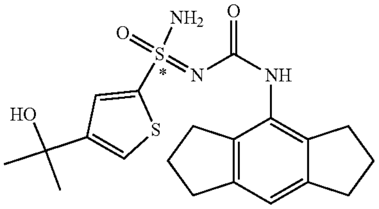 [SMILES: CC(C)(O)c1csc(S(N)(=O)=NC(=O)Nc2c3c(cc4c2CCC4)CCC3)c1] | (R)-or (S)-N'-(1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 20% EtOH in Hex (0.1% DEA) | 418.1 (M − 1) |
| 205 | 183a or 183b | 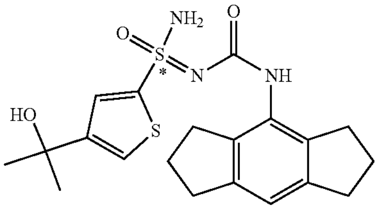 [SMILES: CC(C)(O)c1csc(S(N)(=O)=NC(=O)Nc2c3c(cc4c2CCC4)CCC3)c1] | (S)-or (R)-N'-(1,2,3,5,6,7-hexahydro-s-indacen-4-ylcarbamoyl)-4-(2-hydroxypropan-2-yl)thiophene-2-sulfonimidamide | ChiralPak ID, 2*25 cm, 5 um | 20% EtOH in Hex (0.1% DEA) | 418.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex. # | Final Target Number | Structure | IUPAC Name | Column | Eluents | LC-MS [M + H]+ |
|---|---|---|---|---|---|---|
| 206 | 176a or 176b | 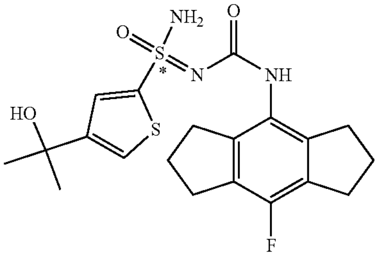 [SMILES: CC(C)(O)c1csc(S(N)(=O)=NC(=O)Nc2c3c(c(F)c4c2CCC4)CCC3)c1] | (S)-or (R)-N'-(8-fluoro-1,2,3,5,6,7-hexahydro-s-indacen-4-ylcarbamoyl)-4-(2-hydroxypropan-2-yl)thiophene-2-sulfonimidamide | ChiralPak IG, 2*25 cm, 5 um | 30% EtOH in Hex | 438.2 |
| 207 | 176b or 176a | 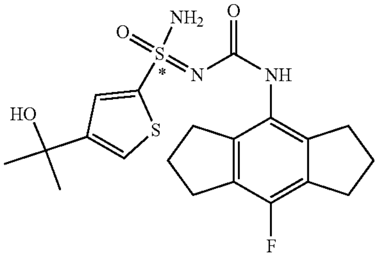 [SMILES: CC(C)(O)c1csc(S(N)(=O)=NC(=O)Nc2c3c(c(F)c4c2CCC4)CCC3)c1] | (R)-or (S)-N'-(8-fluoro-1,2,3,5,6,7-hexahydro-s-indacen-4-ylcarbamoyl)-4-(2-hydroxypropan-2-yl)thiophene-2-sulfonimidamide | ChiralPak IG, 2*25 cm, 5 um | 30% EtOH in Hex | 438.2 |

Example 77: MS-ESI: 421.1 (M+1). $^1$H NMR (400 MHz, DMSO-$d_6$) δ 8.41 (br s, 1H), 7.74 (br s, 2H), 7.68 (s, 1H), 6.87 (s, 1H), 5.36 (s, 1H), 3.02-2.50 (m, 8H), 2.10-1.80 (m, 4H), 1.48 (s, 6H).

Example 200: MS-ESI: 439.2 (M+1). 1H NMR (400 MHz, DMSO-$d_6$) δ 8.38 (br, 1H), 8.02 (s, 1H), 7.75 (br, 1H), 6.27 (s, 1H), 2.81 (t, J=7.6 Hz, 4H), 2.70 (t, J=6.8 Hz, 4H), 2.02-1.95 (m, 4H), 1.50 (s, 6H).

Example 203: MS-ESI: 404.2 (M+1). $^1$H NMR (300 MHz, DMSO-$d_6$) δ 8.42 (br s, 1H), 7.76 (s, 1H), 7.72 (s, 2H), 7.01 (s, 1H), 6.88 (s, 1H), 5.11 (s, 1H), 2.90-2.72 (m, 4H), 2.72-2.60 (m, 4H), 2.10-1.80 (m, 4H), 1.46 (s, 6H).

Example 205: MS-ESI: 418.1 (M−1). $^1$H NMR (400 MHz, DMSO-$d_6$) δ 8.39 (br s, 1H), 7.68 (s, 2H), 7.63 (s, 1H), 7.59 (s, 1H), 6.88 (s, 1H), 5.23 (s, 1H), 2.95-2.75 (m, 4H), 2.75-2.60 (m, 4H), 2.05-1.80 (m, 4H), 1.43 (s, 6H).

Example 206: MS-ESI: 438.2 (M+1). $^1$H NMR (300 MHz, DMSO-$d_6$) δ 8.41 (br s, 1H), 7.65 (s, 2H), 7.59 (s, 1H), 7.55 (s, 1H), 5.20 (s, 1H), 2.90-2.60 (m, 8H), 2.10-1.80 (m, 4H), 1.39 (s, 6H).

Example 208 (Compound 221)

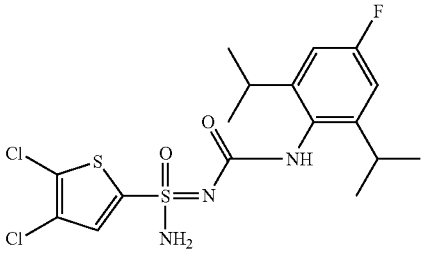 [SMILES: CC(C)c1cc(F)cc(C(C)C)c1NC(=O)N=S(N)(=O)c1cc(Cl)c(Cl)s1]

4,5-Dichloro-N'-((4-fluoro-2,6-diisopropylphenyl) carbamoyl)thiophene-2-sulfonimidamide

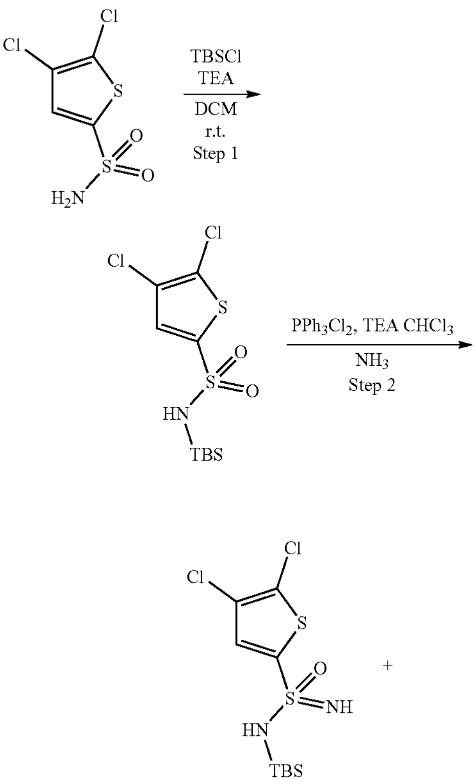

-continued

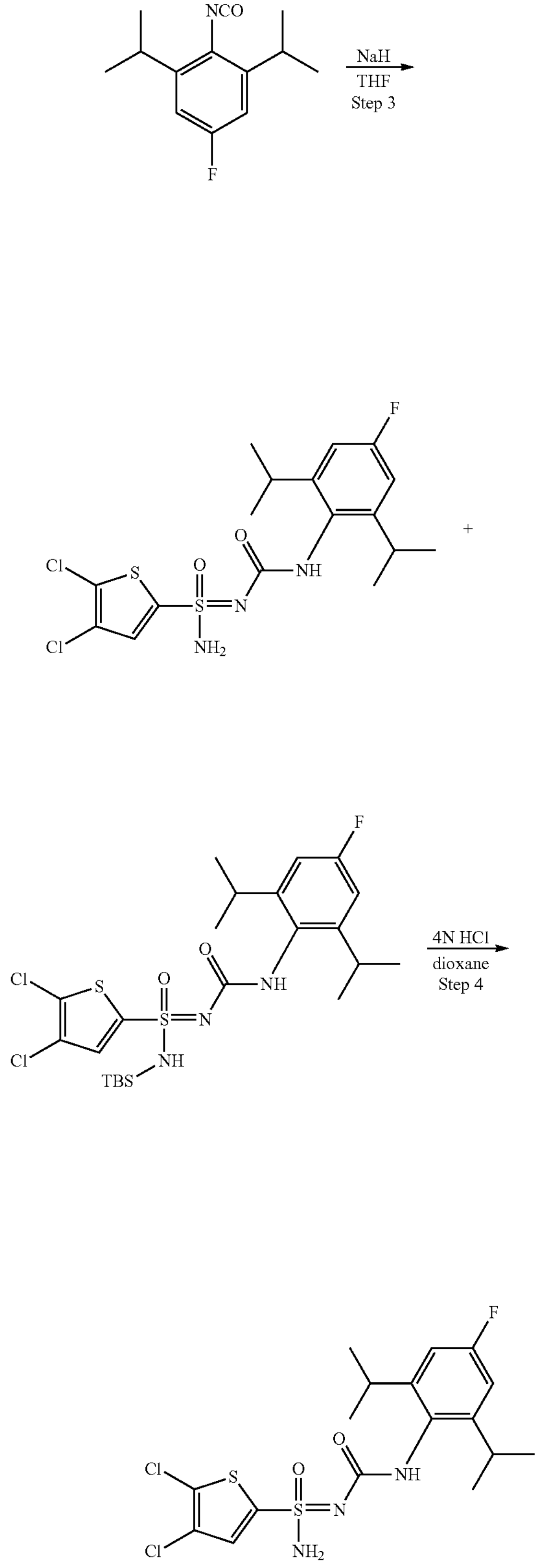

Step 1: N-(tert-butyldimethylsilyl)-4,5-dichlorothiophene-2-sulfonamide 4,5-Dichlorothiophene-2-sulfonamide (50 mg, 0.22 mmol) was dissolved in anhydrous $CH_2Cl_2$ (2 mL). Triethylamine (0.090 mL, 0.65 mmol) and TBSCl (38 mg, 0.25 mmol) were added and the resulting mixture was stirred overnight at room temperature, or until the reaction was complete as indicated by LCMS (Method F: m/Z=424.1 $[M+DMSO+H]^+$, retention time=3.70 min). The reaction mixture was used in the next step as is.

Step 2: N-(tert-butyldimethylsilyl)-4,5-dichlorothiophene-2-sulfonimidamide

In an oven-dried vial under nitrogen, a solution of $PPh_3Cl_2$ (143 mg, 0.44 mmol) was prepared in dichloroethane (1.5 mL). Triethylamine (0.120 mL, 0.86 mmol) was introduced in a steady stream via syringe at 0° C. The reaction mixture was stirred at room temperature for 10 min. The reaction mixture was then cooled in an ice/water bath for 2 min and the reaction mixture of TBS protected sulfonamide (prepared in 2 mL DCM) from step 1 was introduced via syringe rapidly drop by drop (addition time<30 seconds). The resulting mixture was stirred at 0° C. for 30 min, at which time anhydrous ammonia was bubbled into the reaction mixture for 45 seconds. The suspension thus formed was stirred in an ice/water bath for 30 min and then warmed to room temperature and centrifuged to remove solids. The supernatant was concentrated in vacuo and dried under high vacuum for 30 min.

Step 3: 4,5-Dichloro-N'-((4-fluoro-2,6-diisopropylphenyl)carbamoyl)thiophene-2-sulfonimidamide and N-(tert-butyldimethylsilyl)-4,5-dichloro-N'-((4-fluoro-2,6-diisopropyl phenyl)carbamoyl)thiophene-2-sulfonimidamide To the crude reaction mixture from step 2 was added anhydrous THF (1.5 mL) and the resulting solution was stirred in an ice/water bath for 5 min, at which time NaH (17 mg, 0.44 mmol) was added. After 2 min stirring, a solution of 5-fluoro-2-isocyanato-1,3-diisopropylbenzene (36.5 mg, 0.165 mmol) in THF (3 ml) was added dropwise at 0° C. The resulting mixture was brought to room temperature and stirred for 30 min to give a mixture of crude products. LC-MS (Method F): m/Z=451.8 $[M+H]^+$, retention time=6.18 min; for TBS-protected product, 566.4 $[M+H]'''$, retention time=9.25 min.

Step 4: 4,5-Dichloro-N'-((4-fluoro-2,6-diisopropylphenyl)carbamoyl)thiophene-2-sulfonimidamide To the reaction mixture from step 3 was carefully added 4N HCl in dioxane (0.3 mL) and the resulting mixture was stirred at room temperature for approximately 30 min until the completion of reaction, as determined by LCMS analysis (Method F: 451.8 $[M+H]^+$, retention time=6.18 min). The reaction mixture was then concentrated in vaculo. DMSO (0.5 mL) was added to the residue and the resulting solution was purified on a prep-HPLC to afford the title compound. LC-MS: 451 $[M+H]^+$.

TABLE 20

Examples in the following table were prepared using similar procedures as described in Example 208 above starting from appropriate sulfonamides.

| Example # | Final Target Number | Structure | IUPAC Name | Exact Mass $[M + H]^+$ |
|---|---|---|---|---|
| 209 | 219 | 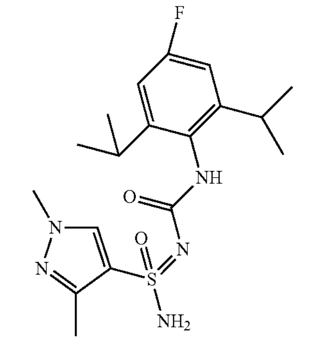 [SMILES: Cc1nn(C)cc1S(N)(=O)=NC(=O)Nc1c(C(C)C)cc(F)cc1C(C)C] | N'-((4-fluoro-2,6-diisopropylphenyl)carbamoyl)-1,3-dimethyl-1H-pyrazole-4-sulfonimidamide | 396.05 |
| 210 | 217 | 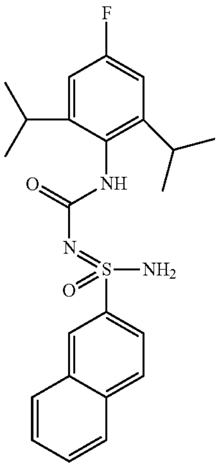 [SMILES: CC(C)c1cc(F)cc(C(C)C)c1NC(=O)N=S(N)(=O)c1ccc2ccccc2c1] | N'-((4-fluoro-2,6-diisopropylphenyl)carbamoyl) naphthalene-2-sulfonimidamide | 428.17 |
| 211 | 216 | 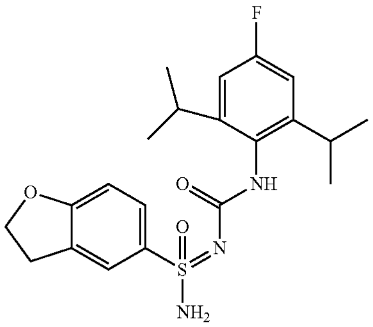 [SMILES: CC(C)c1cc(F)cc(C(C)C)c1NC(=O)N=S(N)(=O)c1ccc2c(c1)CCO2] | N'-((4-fluoro-2,6-diisopropylphenyl)carbamoyl)-2,3-dihydrobenzofuran-5-sulfonimidamide | 420.07 |
| 212 | 215 | 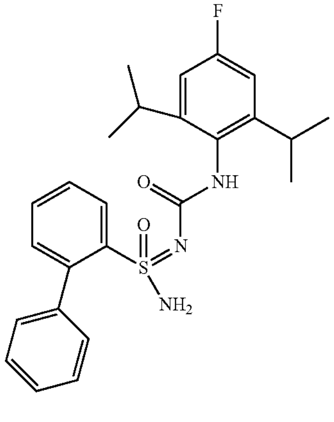 [SMILES: CC(C)c1cc(F)cc(C(C)C)c1NC(=O)N=S(N)(=O)c1ccccc1-c1ccccc1] | N'-((4-fluoro-2,6-diisopropylphenyl)carbamoyl)-[1,1'-biphenyl]-2-sulfonimidamide | 454.28 |

TABLE 20-continued

Examples in the following table were prepared using similar procedures as described in Example 208 above starting from appropriate sulfonamides.

| Example # | Final Target Number | Structure | IUPAC Name | Exact Mass $[M + H]^+$ |
|---|---|---|---|---|
| 213 | 218 | 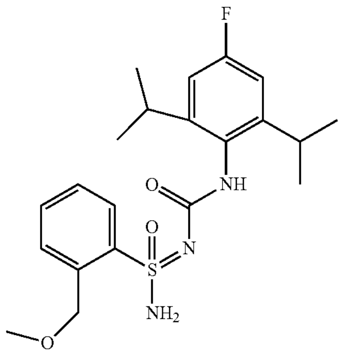 [SMILES: COCc1ccccc1S(N)(=O)=NC(=O)Nc1c(C(C)C)cc(F)cc1C(C)C] | N'-((4-fluoro-2,6-diisopropylphenyl)carbamoyl)-2-(methoxymethyl) benzenesulfonimidamide | 422.17 |
| 214 | 214 | 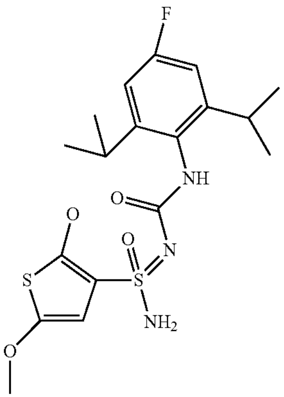 [SMILES: COc1cc(S(N)(=O)=NC(=O)Nc2c(C(C)C)cc(F)cc2C(C)C)c(O)s1] | 2,5-dichloro-N'-((4-fluoro-2,6-diisopropylphenyl) carbamoyl)thiophene-3-sulfonimidamide | 452.18 |
| 215 | 211 | 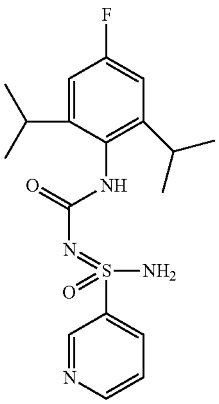 [SMILES: CC(C)c1cc(F)cc(C(C)C)c1NC(=O)N=S(N)(=O)c1cccnc1] | N'-((4-fluoro-2,6-diisopropylphenyl) carbamoyl)pyridine-3-sulfonimidamide | 379.24 |
| 216 | 210 | 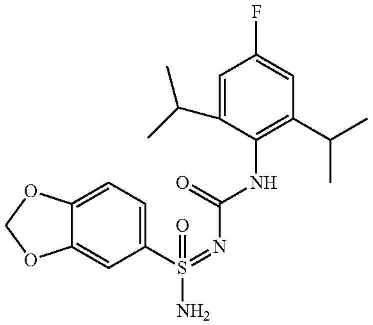 | N'-((4-fluoro-2,6-diisopropylphenyl)carbamoyl) benzo[d][1,3]dioxole-5-sulfonimidamide | 422.17 |

TABLE 20-continued

| Examples in the following table were prepared using similar procedures as described in Example 208 above starting from appropriate sulfonamides. | | | | |
|---|---|---|---|---|
| Example # | Final Target Number | Structure | IUPAC Name | Exact Mass $[M + H]^+$ |
| 217 | 201 | 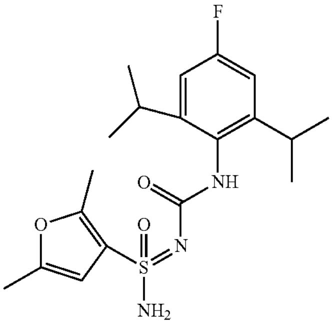 [SMILES: Cc1cc(S(N)(=O)=NC(=O)Nc2c(C(C)C)cc(F)cc2C(C)C)c(C)o1] | N'-((4-fluoro-2,6-diisopropylphenyl) carbamoyl)-2,5-dimethylfuran-3-sulfonimidamide | 396.40 |
| 218 | 200 | 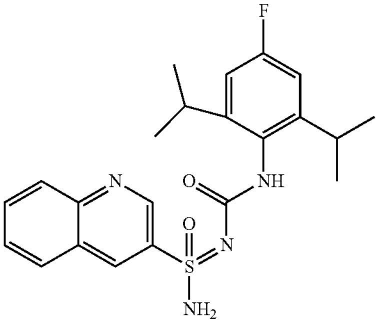 [SMILES: CC(C)c1cc(F)cc(C(C)C)c1NC(=O)N=S(N)(=O)c1cnc2ccccc2c1] | N'-((4-fluoro-2,6-diisopropylphenyl) carbamoyl)quinoline-3-sulfonimidamide | 429.40 |
| 219 | 199 | 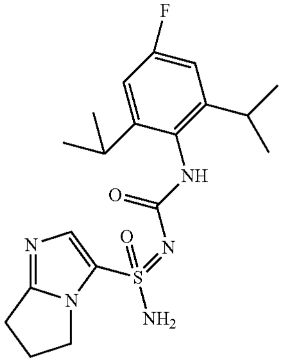 [SMILES: CC(C)c1cc(F)cc(C(C)C)c1NC(=O)N=S(N)(=O)c1cnc2n1CCC2] | N'-((4-fluoro-2,6-diisopropylphenyl)carbamoyl)-6,7-dihydro-5H-pyrrolo[1,2-a]imidazole-3-sulfonimidamide | 408.40 |
| 220 | 198 | 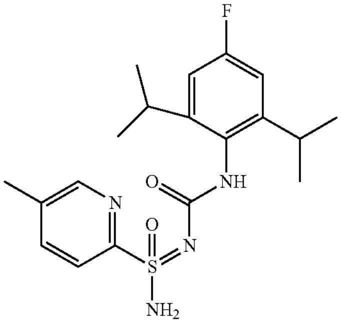 [SMILES: Cc1ccc(S(N)(=O)=NC(=O)Nc2c(C(C)C)cc(F)cc2C(C)C)nc1] | N'-((4-fluoro-2,6-diisopropylphenyl)carbamoyl)-5-methylpyridine-2-sulfonimidamide | 393.40 |

Example 221 (Compound 141)

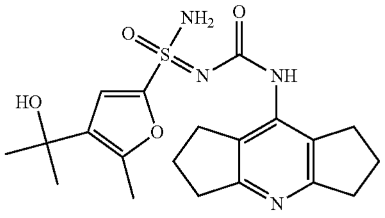 [SMILES: Cc1oc(S(N)(=O)=NC(=O)Nc2c3c(nc4c2CCC4)CCC3)cc1C(C)(C)O]

N'-((1,2,3,5,6,7-hexahydrodicyclopenta[b,e]pyridin-8-yl)carbamoyl)-4-(2-hydroxypropan-2-yl)-5-methylfuran-2-sulfonimidamide (Scheme 31)

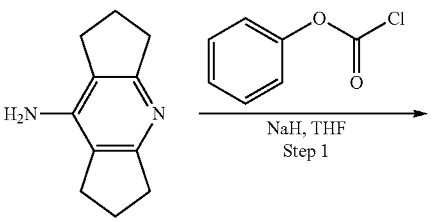

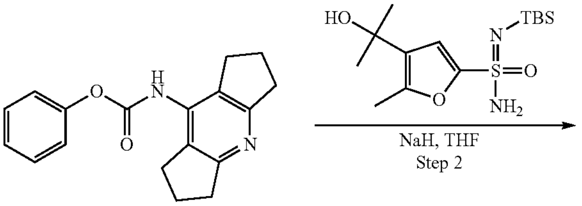

2

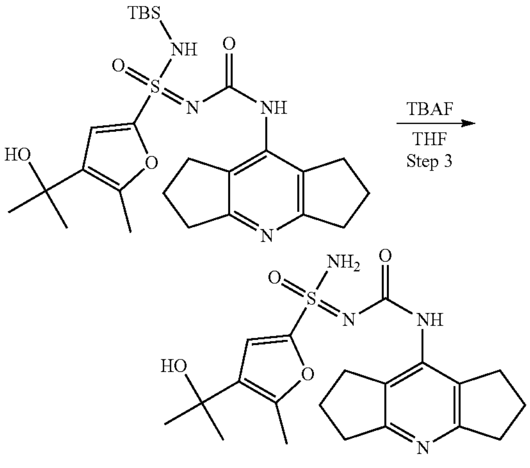

Example 221

Step 1: Phenyl (1,2,3,5,6,7-hexahydrodicyclopenta[b,e]pyridin-8-yl)carbamate

Into a 50-mL 3-necked round-bottom flask purged and maintained with nitrogen, was placed 1,2,3,5,6,7-hexahydrodicyclopenta[b,e]pyridin-8-amine (50 mg, 0.29 mmol) in THF (10 mL), to this was added NaH (60% wt. oil dispersion, 22.8 mg, 0.57 mmol) at 0° C.; and then phenyl chloroformate (67.4 mg, 0.43 mmol,) in THF (2.0 mL) was added dropwise at 0° C. The resulting solution was stirred for 2 h at RT. This reaction solution was used for next step directly without any purification.

Step 2: N-(tert-butyldimethylsilyl)-N'-((1,2,3,5,6,7-hexahydrodicyclopenta[b,e]pyridin-8-yl)carbamoyl)-4-(2-hydroxypropan-2-yl)-5-methylfuran-2-sulfonimidamide Into a 50-mL 3-necked round-bottom flask purged and maintained with nitrogen, was placed N-(tert-butyldimethylsilyl)-4-(2-hydroxypropan-2-yl)-5-methylfuran-2-sulfonoimidamide (96 mg, 0.29 mmol) in THF (10 mL). To this was added NaH (60% wt. oil dispersion, 23.2 mg, 0.58 mmol) at 0° C., followed by phenyl (1,2,3,5,6,7-hexahydrodicyclopenta[b,e]pyridin-8-yl)carbamate (127 mg, 0.43 mmol) crude in THF from via syringe rapidly drop by drop. The resulting mixture was stirred for 16 h at RT. The reaction was then quenched by the addition of 5.0 mL of water. The resulting solution was extracted with 4×10 ml of ethyl acetate. The combined organic layers were dried over anhydrous sodium sulfate and concentrated under vacuum. The residue was eluted from a silica gel column with ethyl acetate/petroleum ether (1;1). This resulted in 50 mg (38.4%) of the title compound as an off-white solid. MS-ESI: 533 (M+1).

Step 3: N'-((1,2,3,5,6,7-hexahydrodicyclopenta[b,e]pyridin-8-yl)carbamoyl)-4-(2-hydroxypropan-2-yl)-5-methylfuran-2-sulfonimidamide Into a 50-mL round-bottom flask, was placed N-(tert-butyldimethylsilyl)-N'-((1,2,3,5,6,7-hexahydrodicyclopenta[b,e]pyridin-8-yl)carbamoyl)-4-(2-hydroxypropan-2-yl)-5-methylfuran-2-sulfonimidamide (58 mg, 0.11 mmol) in THF (10 mL), to this was added TBAF (28.8 mg, 0.11 mmol). The resulting solution was stirred for 1 h at RT. The resulting mixture was concentrated under vacuum. The residue was eluted from a silica gel column with DCM/MeOH (10:1). The crude product was further purified by Prep-HPLC with the following conditions: Column: XBridge Prep OBD C18 Column 19*250 mm, 5 um; Mobile Phase A: water (10 mM $NH_4HCO_3$), Mobile Phase B: ACN; Flow rate: 25 mL/min; Gradient: 11% B to 40% B in 7 min; UV 254/210 nm; Rt: 6 min. This resulted in 25 mg (54.87%) of Example 221 as a white solid. MS-ESI: 419 (M+1). $^1H$ NMR (400 MHz, DMSO-$d_6$, ppm) δ: 8.82 (s, 1H), 7.65 (s, 2H), 6.90 (s, 1H), 5.03 (s, 1H), 2.82-2.78 (m, 4H), 2.76-2.67 (m, 4H), 2.41 (s, 3H), 2.00-1.92 (m, 4H), 1.39 (s, 6H).

TABLE 21

Examples in the following table were prepared using similar conditions as described in Example 221 and Scheme 31 from appropriate starting materials.

| Example # | Final Target Number | Structure | IUPAC Name | Exact Mass [M + H]$^+$ |
|---|---|---|---|---|
| 222 | 140 | 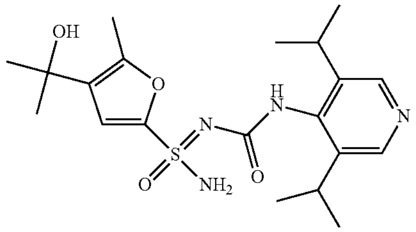 [SMILES: Cc1oc(S(N)(=O)=NC(=O)Nc2c(C(C)C)cncc2C(C)C)cc1C(C)(C)O] | N'-((3,5-diisopropylpyridin-4-yl)carbamoyl)-4-(2-hydroxypropan-2-yl)-5-methylfuran-2-sulfonimidamide | 423 |

Example 223 (Compound 321)

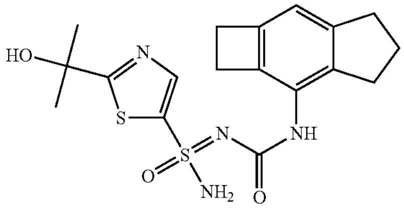 [SMILES: CC(C)(O)c1ncc(S(N)(=O)=NC(=O)Nc2c3c(cc4c2CC4)CCC3)s1]

2-(2-Hydroxypropan-2-yl)-N'-((2,4,5,6-tetrahydro-1H-cyclobuta[f]inden-3-yl)carbamoyl)thiazole-5-sulfonimidamide (Scheme 3A)

Examples 224 and 225 (Compound 321b and 321a)

Examples 224 and 225

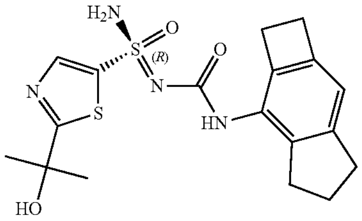

-continued

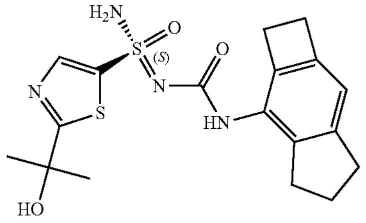

(stereochemistry tentatively assigned)

(R)- and (S)-2-(2-hydroxypropan-2-yl)-N'-((2,4,5,6-tetrahydro-1H-cyclobuta[f]inden-3-yl)carbamoyl) thiazole-5-sulfonimidamide Route 1

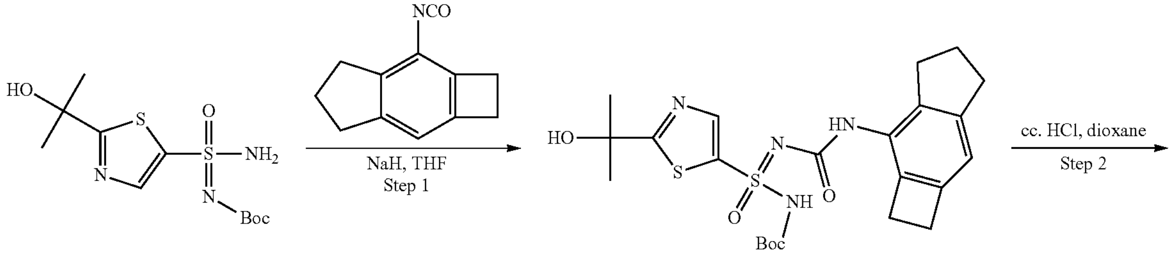

-continued

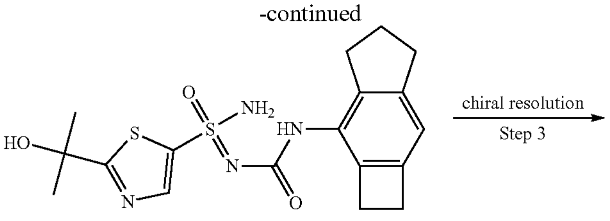

Examples 223

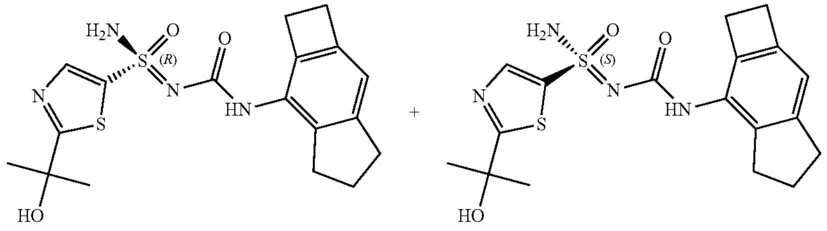

Examples 224 and 225 (stereochemistry tentatively assigned)

Step 1: Tert-butyl(2-(2-hydroxypropan-2-yl)-N-((2,4,5,6-tetrahydro-1H-cyclobuta[f]inden-3-yl) carbamoyl)thiazole-5-sulfonimidoyl)carbamate Into a 100-mL round-bottom flask purged and maintained with an inert atmosphere of nitrogen, was placed tert-butyl N-[amino[2-(2-hydroxypropan-2-yl)-1,3-thiazol-5-yl]oxo-$\lambda^6$-sulfanylidene]carbamate (1.39 g, 4.32 mmol) in THF (50 mL). To this solution was added NaH (60% wt. oil dispersion, 518 mg, 13 mmol) at 0° C., followed by the addition of 3-isocyanato-2,4,5,6-tetrahydro-1H-cyclobuta[f]indene (800 mg, 4.32 mmol) in THF (5.0 mL) dropwise at 0° C. The resulting solution was stirred for 14 h at RT. The reaction was then quenched by the addition of 100 mL of water. The resulting solution was extracted with 3x50 mL of DCM. The organic layers combined and dried over anhydrous $Na_2SO_4$, then concentrated. The residue was eluted from a silica gel column with ethyl acetate/petroleum ether (1:5 to 1:1). This resulted in 2.0 g (91%) of title compound as a light yellow solid. MS-ESI: 507 (M+1).

Step 2: 2-(2-Hydroxypropan-2-yl)-N'-((2,4,5,6-tetrahydro-1H-cyclobuta[f]inden-3-yl)carbamoyl) thiazole-5-sulfonimidamide Into a 100-mL round-bottom flask purged and maintained with an inert atmosphere of nitrogen, was placed tert-butyl (2-(2-hydroxypropan-2-yl)-N-((2,4,5,6-tetrahydro-1H-cyclobuta[f]inden-3-yl)carbamoyl) thiazole-5-sulfonimidoyl) carbamate (2.2 g, 4.34 mmol) in dioxane (40 mL). To this was added conc. HCl (8 mL, 12 M) dropwise at 0° C. The resulting solution was stirred for 14 h at RT. The resulting solution was diluted with 100 mL of water. The resulting solution was extracted with 3x50 mL of DCM. The organic layers combined and dried over anhydrous $Na_2SO_4$, then concentrated. The crude product was purified by HP-Flash with the following conditions: Column, C18 silica gel; mobile phase, ACN:$H_2O$=25:75 increasing to ACN:$H_2O$=55:45 within 25; Detector, UV 254 nm. This resulted in 1.5 g (85%) of Example 223. MS-ESI: 407 (M+1). $^1H$ NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Step 3: Chiral Resolution

Example 223 (1.5 g) was separated with the followed condition: Column: CHIRALPAK IG, 20*250 mm, 5 um; Mobile Phase A: $CO_2$: 60, Mobile Phase B: MeOH—Preparative: 40; Flow rate: 50 mL/min; 220 nm. The resulting solution was stirred for 20 min at 10° C. This resulted in 546 mg (99% ee, 36.4%) of Example 224 ($RT_1$: 3.47 min) as a white solid and 595 mg (99% ee, 39.6%) of Example 225 ($RT_2$: 5.35 min) as a white solid. The absolute stereochemistry was tentatively assigned.

Example 224: MS-ESI: 407.1 (M+1). $^1H$ NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Example 225: MS-ESI: 407.1 (M+1). $^1H$ NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Route 2

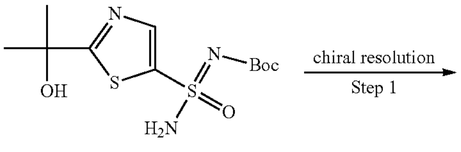

Intermediate 28

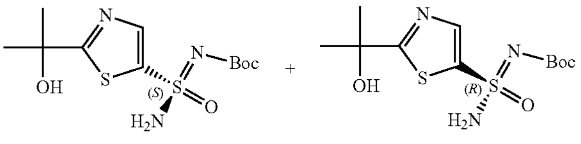

Intermediate 28A or 28B
(stereochemistry arbitrarily assigned)

-continued

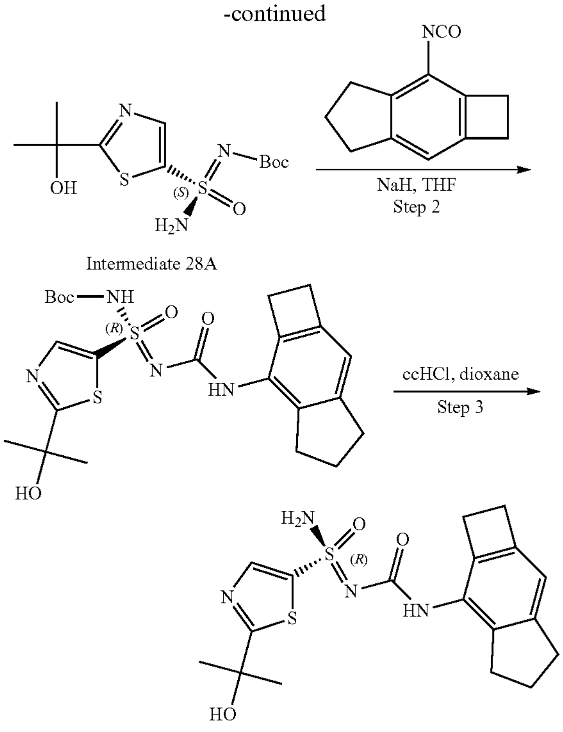

Intermediate 28A

Example 224

Step 1: Chiral Resolution (R) and (S)-tert-butyl (amino(2-(2-hydroxypropan-2-yl)thiazol-5-yl)(oxo)-$\lambda^6$-sulfaneylidene)carbamate The product 10 g of Intermediate 28 was separated with the followed condition: Column: CHIRALPAK IC, 5*25 cm, 5 um; Mobile Phase A: $CO_2$:55, Mobile Phase B: EtOH:HeX=1:1:45; Flow rate: 150 mL/min; UV 220 nm; $Rt_1$: 5.13 (Intermediate 28A); $Rt_2$: 5.65 (Intermediate 28B). This resulted in 3 g (99.5% ee, 60%) of 28A, and 3 g (99.0% ee, 60%) of 28B.

Step 2: Tert-butyl (R)-(2-(2-hydroxypropan-2-yl)-N-((2,4,5,6-tetrahydro-1H-cyclobuta[f]inden-3-yl) carbamoyl)thiazole-5-sulfonimidoyl)carbamate Into a 100-mL round-bottom flask purged and maintained with an inert atmosphere of nitrogen, was placed intermediate 28A (>99% ee, 1.67 g, 5.20 mmol) in THF (50 mL), NaH (60% wt. oil dispersion, 624 mg, 15.6 mmol) was added at 0° C., this was followed by the addition of 3-isocyanato-2,4,5,6-tetrahydro-1H-cyclobuta[f]indene (850 mg, crude) in THF (5 mL) dropwise at 0° C. The resulting solution was stirred for 14 h at RT. The reaction was then quenched by the addition of 100 mL of water. The resulting solution was extracted with 3×100 mL of DCM. The organic layers combined and dried over anhydrous $Na_2SO_4$, then concentrated. This resulted in 2.2 g (83.5%) of title compound as a light yellow solid. MS-ESI: 507 (M+1).

Step 3: (R)-2-(2-hydroxypropan-2-yl)-N'-((2,4,5,6-tetrahydro-1H-cyclobuta[f]inden-3-yl)carbamoyl) thiazole-5-sulfonimidamide Into a 100-mL round-bottom flask purged and maintained with an inert atmosphere of nitrogen, was placed tert-butyl (S)-(2-(2-hydroxypropan-2-yl)-N-((2,4,5,6-tetrahydro-1H-cyclobuta[f]inden-3-yl)carbamoyl) thiazole-5-sulfonimidoyl)carbamate (2.2 g, 4.34 mmol) in dioxane (40 mL), to this was added conc. HCl (8 mL, 12 M) dropwise at 0° C. The resulting solution was stirred for 8 h below 10° C. The resulting solution was diluted with 100 mL of water. The resulting solution was extracted with 3×100 mL of DCM. The organic layers combined and dried over anhydrous $Na_2SO_4$, then concentrated. The crude product was purified by HP-Flash with the following conditions: Column, C18 silica gel; mobile phase, MeCN:water=25:75 increasing to MeCN:water=55:45 within 30 min; Detector, UV 210 nm. This resulted in 1.37 g (77.3%) of Example 224 (99.4% ee) as a white solid. MS-ESI: 407 (M+1).

$^1H$ NMR (300 MHz, DMSO-$d_6$) δ 8.43 (s, 1H), 8.09 (s, 1H), 7.90 (s, 2H), 6.67 (s, 1H), 6.29 (s, 1H), 2.92 (d, J=3.9 Hz, 2H), 2.89 (d, J=3.9 Hz, 2H), 2.90-2.55 (m, 4H), 2.00-1.75 (m, 6H), 1.50 (s, 6H).

TABLE 22

Examples in the following table were prepared using similar conditions as described in Example 223-Route 1 and Scheme 3A from appropriate starting materials.

| Example # | Final Target # | Structure | IUPAC Name | Exact Mass [M + H]$^+$ |
|---|---|---|---|---|
| 226 | 329 | 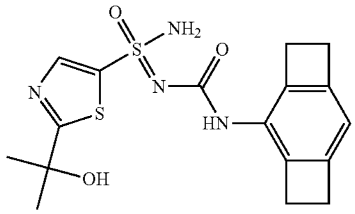 [SMILES: CC(C)(O)c1ncc(S(N)(=O)=NC(=O)Nc2c3c(cc4c2CC4)CC3)s1] | 2-(2-Hydroxypropan-2-yl)-N'-(tricyclo[6.2.0.03,6]deca-1,3(6),7-trien-2-ylcarbamoyl)thiazole-5-sulfonimidamide | 393 |

TABLE 22-continued

Examples in the following table were prepared using similar conditions as described in Example 223-Route 1 and Scheme 3A from appropriate starting materials.

| Example # | Final Target # | Structure | IUPAC Name | Exact Mass $[M + H]^+$ |
|---|---|---|---|---|
| 227 | 375 | 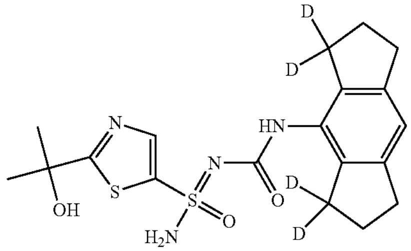 [SMILES: [2H]C1([2H])CCc2cc3c(c(NC(=O)N=S(N)(=O)c4cnc(C(C)(C)O)s4)c21)C([2H])([2H])CC3] | N'-((1,2,3,5,6,7-hexahydro-s-indacen-4-yl-3,3,5,5-$d_4$)carbamoyl)-2-(2-hydroxypropan-2-yl)thiazole-5-sulfonimidamide | 425 |
| 228 | 376 | 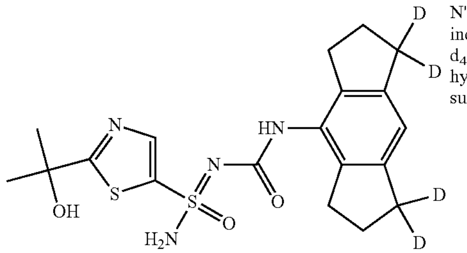 | N'-((1,2,3,5,6,7-hexahydro-s-indacen-4-yl-1,1,7,7-$d_4$)carbamoyl)-2-(2-hydroxypropan-2-yl)thiazole-5-sulfonimidamide | 425 |

Example 229 (Compound 307)

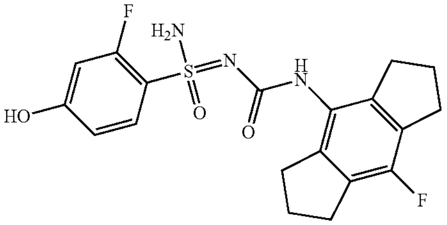 [SMILES: NS(=O)(=NC(=O)Nc1c2c(c(F)c3c1CCC3)CCC2)c1ccc(O)cc1F]

2-Fluoro-N'-((8-fluoro-1,2,3,5,6,7-hexahydro-s-indacen-4-yl)carbamoyl)-4-hydroxybenzenesulfonimidamide (Scheme 3B)

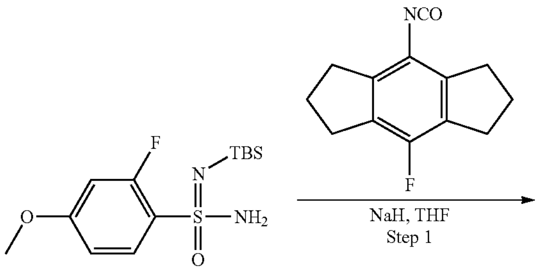

-continued

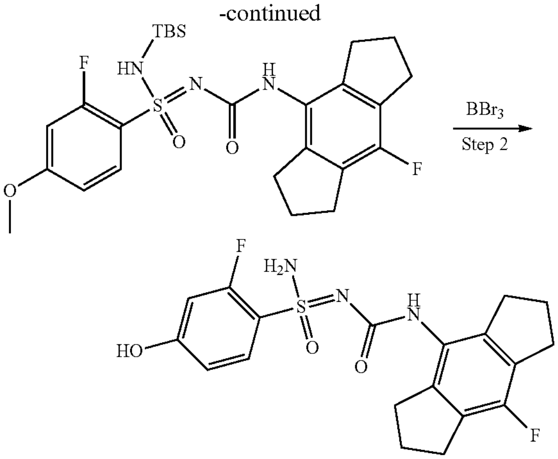

Examples 229

Step 1: N-(tert-butyldimethylsilyl)-2-fluoro-N'-(8-fluoro-1,2,3,5,6,7-hexahydro-s-indacen-4-ylcarbamoyl)-4-methoxybenzenesulfonimidamide Into a 50-mL round-bottom flask, was placed a solution of N-(tert-butyldimethylsilyl)-2-fluoro-4-methoxybenzene-1-sulfonoimidamide (139 mg, 0.44 mmol) in THF (5.0 mL). To this solution was added NaH (60% wt. oil dispersion, 35.2 mg, 0.44 mmol) at 0° C. This was followed by the addition of 4-fluoro-8-isocyanato-1,2,3,5,6,7-hexahydro-s-indacene (95 mg, 0.44 mmol) in THF (5 mL) dropwise at RT. The resulting solution was stirred for 1 h at RT. The reaction was then quenched by the addition of 100 mL of water. The resulting solution was extracted with 3×50 mL of ethyl acetate. The organic layers combined and dried over anhydrous $Na_2SO_4$, and then concentrated. The residue was eluted from a silica gel column with ethyl acetate/petroleum ether (1:5 to 1:1). This resulted in 120 mg (51.2%) of the title compound as yellow oil. MS-ESI: 536 (M+1).

Step 2: 2-Fluoro-N'-(8-fluoro-1,2,3,5,6,7-hexahydro-s-indacen-4-ylcarbamoyl)-4-hydroxybenzenesulfonimidamide Into a 50-mL round-bottom flask, was placed a solution of 1-[[(tert-butyldimethylsilyl)imino](2-fluoro-4-methoxybenzene)sulfinyl]-3-(8-fluoro-1,2,3,5,6,7-hexahydro-s-indacen-4-yl)urea (120 mg, 0.22 mmol) in ACN (5.0 mL), to this solution was added $BBr_3$ (561 mg, 2.24 mmol) dropwise at 0° C. The resulting solution was stirred for 2 h at RT. The reaction was then quenched by the addition of 5 mL of MeOH. The resulting mixture was concentrated. The crude product (100 mg) was purified by Prep-HPLC under the following conditions: Column, XBridge Prep OBD C18, 19*250 mm, 5 um; mobile phase: water (10 mM $NH_4HCO_3$) and ACN (25% to 43% ACN gradient in 7 min); Detector, UV. This resulted in 17.7 mg (19.4%) of Example 229 as a white solid. MS-ESI: 408 (M+1).

Example 230 (Compound 323)

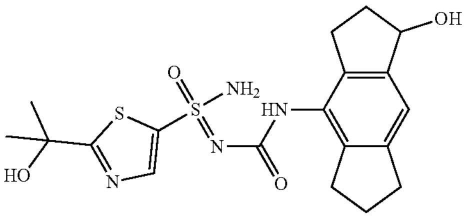 [SMILES: CC(C)(O)c1ncc(S(N)(=O)=NC(=O)Nc2c3c(cc4c2CCC4O)CCC3)s1]

N'-((1-hydroxy-1,2,3,5,6,7-hexahydro-s-indacen-4-yl)carbamoyl)-2-(2-hydroxypropan-2-yl)thiazole-5-sulfonimidamide (Scheme 32)

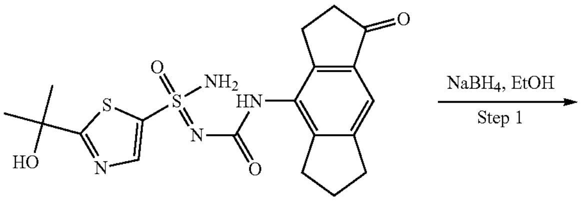

Example 293

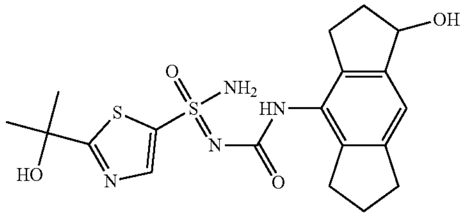

Examples 230

Into a 50-mL round-bottom flask, was placed 2-(2-hydroxypropan-2-yl)-N'-((1-oxo-1,2,3,5,6,7-hexahydro-s-indacen-4-yl)carbamoyl)thiazole-5-sulfonimidamide (100 mg, 0.23 mmol) in ethanol (10 mL). To this solution was added $NaBH_4$ (17.4 mg, 0.46 mmol) in portions at 0° C. The resulting solution was stirred for 2 h at RT. The crude product (5 mL) was purified by Flash-Prep-HPLC with the following conditions: Column: XBridge Prep OBD C18 Column 30×150 mm 5 um; Mobile Phase A: water (10 mM $NH_4HCO_3$), Mobile Phase B: ACN; Flow rate: 60 mL/min; Gradient: 10% 5 to 28% B in 7 min; 210/254 nm; Rt: 6.00 min. This resulted in 180 mg of the title compound (Example 230) as a solid. MS-ESI: 437.1 (M+1).

$^1$H NMR (400 MHz, DMSO-$d_6$) δ 8.51 (br s, 1H), 8.04 (s, 1H), 7.82 (br s, 2H), 6.97 (s, 1H), 6.28 (s, 1H), 5.07 (d, J=5.6 Hz, 1H), 5.05-4.85 (m, 1H), 2.95-2.75 (m, 2H), 2.75-50 (m, 4H), 2.35-2.15 (m, 1H), 2.00-1.80 (m, 2H), 1.80-1.60 (m, 1H), 1.51 (s, 6H).

Example 231 (Compound 338)

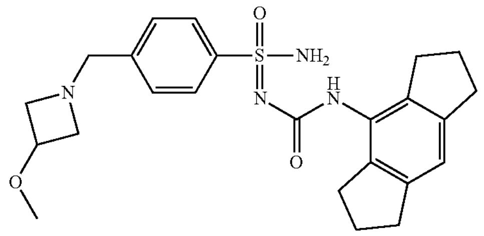 [SMILES: COC1CN(Cc2ccc(S(N)(=O)=NC(=O)Nc3c4c(cc5c3CCC5)CCC4)cc2)C1]

N'-((1,2,3,5,6,7-hexahydro-s-indacen-4-yl)carbamoyl)-4-((3-methoxyazetidin-1-yl)methyl)benzenesulfonimidamide (Scheme 33A)

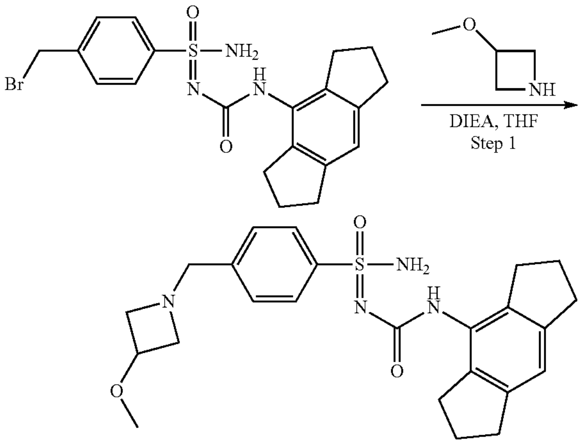

Example 231

Into a 50-mL round-bottom flask purged and maintained with an inert atmosphere of nitrogen, was placed 1-[amino [4-(bromomethyl)phenyl]oxo-λ$^6$-sulfanylidene]-3-(1,2,3,5,6,7-hexahydro-s-indacen-4-yl)urea (50 mg, 0.11 mmol) in THF (5 mL). To this solution was added DIEA (28.4 mg, 0.22 mmol) and 3-methoxyazetidine (10.5 mg, 0.12 mmol) at RT. The resulting solution was stirred for 1 h at 65° C. The resulting mixture was concentrated. The crude product was purified by Prep-HPLC with the following conditions: Column: XBridge Prep C18 OBD Column 19×100 mm 5 um 13 nm; Mobile Phase A: water (10 mM $NH_4HCO_3$ mM+0.1% $NH_3.H_2O$), Mobile Phase B: ACN; Flow rate: 25 mL/min; Gradient: 30% to 37% B in 9.5 min; 254/210 nm; Rt: 9.62 min. This resulted in 5 mg of Example 231 as a white solid. MS-ESL 455 (M+1). $^1$H NMR (300 MHz DMSO-$d_6$) δ: 8.27 (br s, 1H), 7.81 (d, J=8.4 Hz, 2H), 7.45 (d, J=8.4 Hz, 2H), 7.34 (s, 2H), 6.85 (s, 1H), 4.02-3.94 (m, 1H), 3.67 (s, 2H), 3.51-3.46 (m, 2H), 3.14 (s, 3H), 2.95-2.80 (m, 2H), 2.78-2.73 (m, 4H), 2.69-2.63 (m, 4H), 1.96-1.88 (in, 4H).

TABLE 23

Examples in the following table were prepared using similar conditions as described in Example 231 and Scheme 33A from appropriate starting materials.

| Example # | Final Target # | Structure | IUPAC Name | Exact Mass [M + H]$^+$ |
|---|---|---|---|---|
| 232 | 341 | 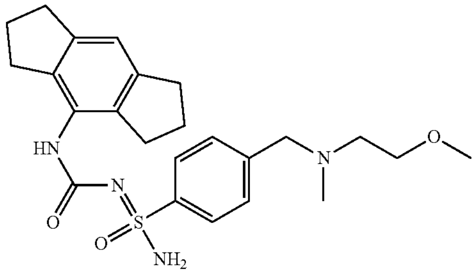 [SMILES: COCCN(C)Cc1ccc(S(N)(=O)=NC(=O)Nc2c3c(cc4c2CCC4)CCC3)cc1] | N'-(1,2,3,5,6,7-hexahydro-A-indacen-4-ylcarbamoyl)-4-(((2-methoxyethyl)(methyl)amino) methyl)benzenesulfonimidamide | 457 |
| 233 | 342 | 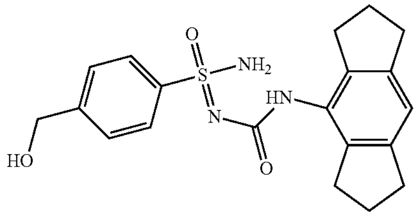 [SMILES: NS(=O)(=NC(=O)Nc1c2c(cc3c1CCC3)CCC2)c1ccc(CO)cc1] | N'-(1,2,3,5,6,7-hexahydro-s-indacen-4-ylcarbamoyl)-4-(hydroxymethyl)benzene-sulfonimidamide | 386 |
| 234 | 345 | 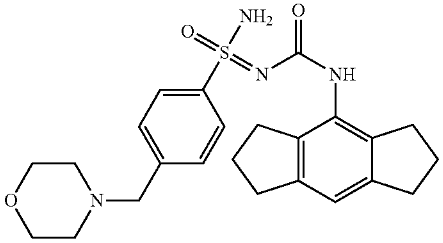 [SMILES: NS(=O)(=NC(=O)Nc1c2c(cc3c1CCC3)CCC2)c1ccc(CN2CCOCC2)cc1] | N'-(1,2,3,5,6,7-hexahydro-s-indacen-4-ylcarbamoyl)-4-(morpholinomethyl)benzene-sulfonimidamide | 455 |
| 235 | 346 | 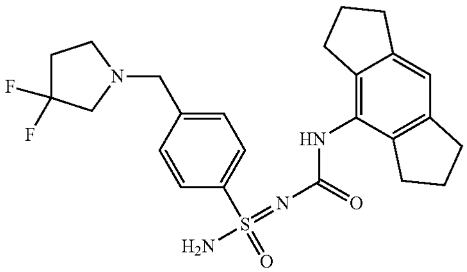 [SMILES: NS(=O)(=NC(=O)Nc1c2c(cc3c1CCC3)CCC2)c1ccc(CN2CCC(F)(F)C2)cc1] | 4-((3,3-Difluoropyrrolidin-1-yl)methyl)-N'-(1,2,3,5,6,7-hexahydro-s-indacen-4-ylcarbamoyl)benzene-sulfonimidamide | 475 |
| 236 | 347 | 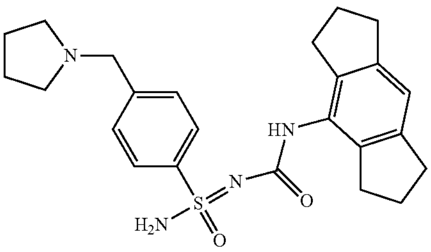 [SMILES: NS(=O)(=NC(=O)Nc1c2c(cc3c1CCC3)CCC2)c1ccc(CN2CCCC2)cc1] | N'-(1,2,3,5,6,7-hexahydro-s-indacen-4-ylcarbamoyl)-4-(pyrrolidin-1-ylmethyl) benzenesulfonimidamide | 439 |

TABLE 23-continued

| Examples in the following table were prepared using similar conditions as described in Example 231 and Scheme 33A from appropriate starting materials. | | | | |
|---|---|---|---|---|
| Example # | Final Target # | Structure | IUPAC Name | Exact Mass [M + H]+ |
| 237 | 348 | 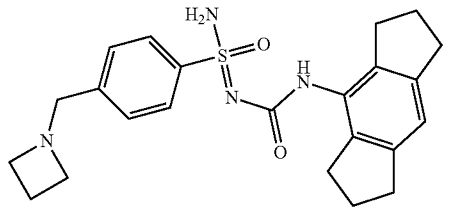 [SMILES: NS(=O)(=NC(=O)Nc1c2c(cc3c1CCC3)CCC2)c1ccc(CN2CCC2)cc1] | 4-(Azetidin-1-ylmethyl)-N'-(1,2,3,5,6,7-hexahydro-s-indacen-4-ylcarbamoyl)benzene-sulfonimidamide | 425 |
| 238 | 403 | 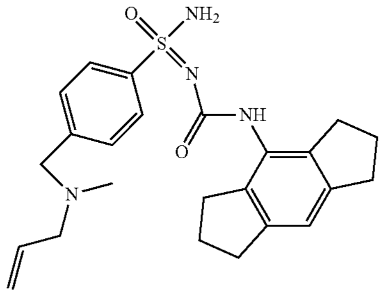 [SMILES: C=CCN(C)Cc1ccc(S(N)(=O)=NC(=O)Nc2c3c(cc4c2CCC4)CCC3)cc1] | 4-((Allyl(methyl)amino)methyl)-N'-(1,2,3,5,6,7-hexahydro-s-indacen-4-ylcarbamoyl)benzene-sulfonimidamide | 439 |
| 239 | 402 | 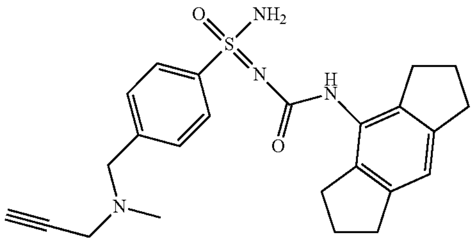 [SMILES: C#CCN(C)Cc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-((methyl(prop-2-ynyl)amino)methyl)benzenesulfonimidamide | 437 |
| 240 | 350 | 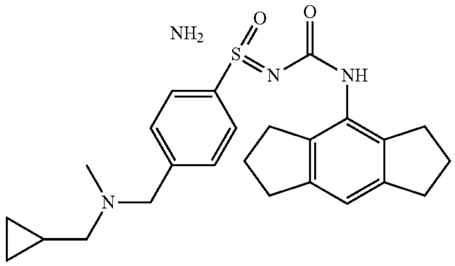 | 4-(((Cyclopropylmethyl)(methyl)amino)methyl)-N'-(1,2,3,5,6,7-hexahydro-s-indacen-4-ylcarbamoyl)benzene-sulfonimidamide | 453 |
| 241 | 322 | 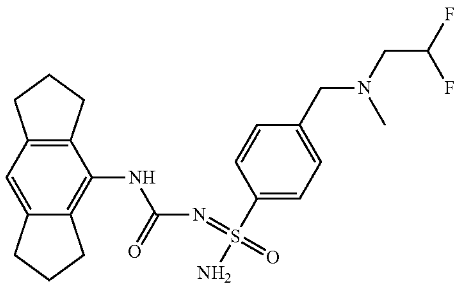 [SMILES: CN(Cc1ccc(S(N)(=O)=NC(=O)Nc2c3c(cc4c2CCC4)CCC3)cc1)CC(F)F] | 4-(((2,2-Difluoroethyl)(methyl)amino)methyl)-N'-(1,2,3,5,6,7-hexahydro-s-indacen-4-ylcarbamoyl)benzenesulfonimidamide | 463 |

TABLE 23-continued

| Example # | Final Target # | Structure | IUPAC Name | Exact Mass [M + H]+ |
|---|---|---|---|---|
| Examples in the following table were prepared using similar conditions as described in Example 231 and Scheme 33A from appropriate starting materials. | | | | |
| 242 | 351 | 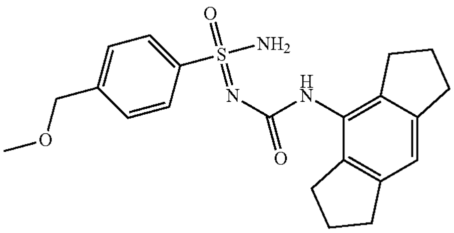 [SMILES: COCc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-(methoxymethyl)benzene-sulfonimidamide | 400 |
| 243 | 358 | 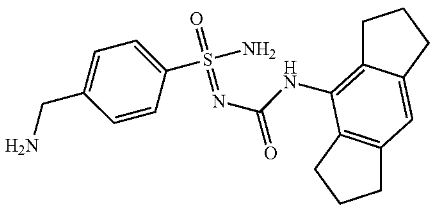 [SMILES: NCc1ccc(S(N)(=O)=NC(=O)Nc2c3c(cc4c2CCC4)CCC3)cc1] | 4-(Aminomethyl)-N'-(1,2,3,5,6,7-hexahydro-s-indacen-4-ylcarbamoyl)benzene-sulfonimidamide | 385 |

Example 244 (Compound 401)

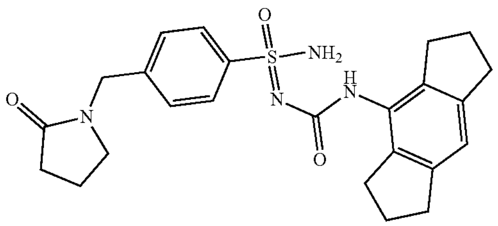 [SMILES: NS(=O)(=NC(=O)Nc1c2c(cc3c1CCC3)CCC2)c1ccc(CN2CCCC2=O)cc1]

N'-((1,2,3,5,6,7-hexahydro-s-indacen-4-yl)carbam-oyl)-4-((2-oxopyrrolidin-1-1 meth 1 benzenesulfo-nimidamide (Scheme 33B

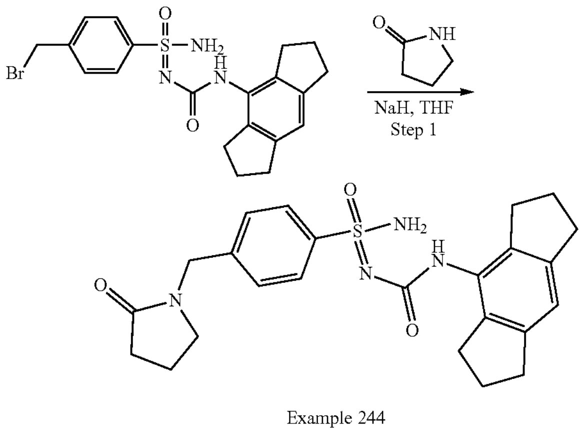

Example 244

Into a 40-mL sealed tube purged and maintained with an inert atmosphere of nitrogen, was placed 1-[amino[4-(bromomethyl)phenyl]oxo-$\lambda^6$-sulfanylidene]-3-(1,2,3,5,6,7-hexahydro-s-indacen-4-yl)urea (200 mg, 0.45 mmol) in THF (10 mL), to this stirred solution was added DIEA (173 mg, 1.34 mmol) and pyrrolidin-2-one (114 mg, 1.34 mmol) at RT. The resulting solution was stirred for 3 h at 60° C. The resulting mixture was concentrated. The crude product was purified by Prep-HPLC with the following conditions: Column, XBridge Prep OBD C18, 30×150 mm 5 um; mobile phase, water (10 mM $NH_4HCO_3$) and ACN (25% to 44% ACN gradient in 7 min); Detector, UV. This resulted in 10 mg (4.95%) of Example 244 as a white solid. MS-ESI: 453 (M+1).

$^1H$ NMR (400 MHz, DMSO-$d_6$) δ: 8.26 (br s, 1H), 7.83 (d, J=8.0 Hz, 2H), 7.40 (d, J=8.0 Hz, 2H), 7.27 (br s, 2H), 6.85 (s, 1H), 4.43 (s, 2H), 3.26-3.22 (m, 2H), 2.78-2.74 (m, 4H), 2.65-2.61 (m, 4H), 2.30 (t, J=8.20 Hz, 2H), 1.98-1.89 (m, 6H).

Example 245 (Compound 404)

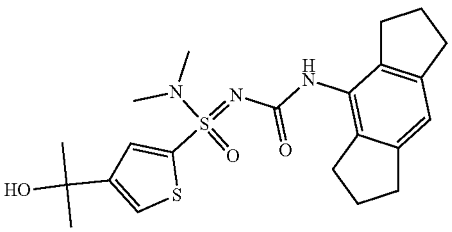 [SMILES: CN(C)S(=O)(=NC(=O)Nc1c2c(cc3c1CCC3)CCC2)c1cc(C(C)(C)O)cs1]

N'-((1,2,3,5,6,7-hexahydro-s-indacen-4-yl)carbamoyl)-4-(2-hydroxypropan-2-yl)-N,N-dimethylthiophene-2-sulfonimidamide (Scheme 4A)

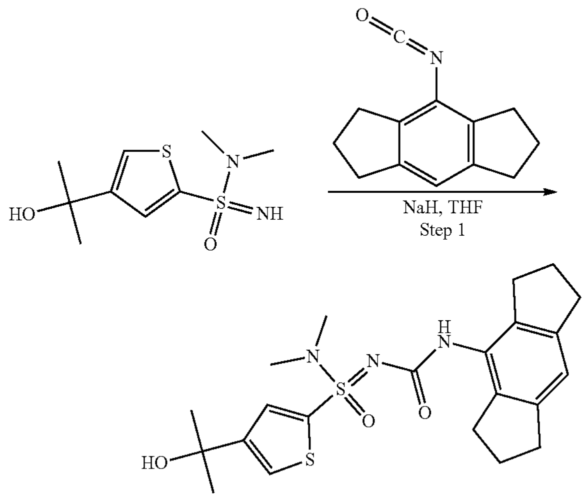

Example 245

Into a 50-mL 3-necked round-bottom flask, was placed a solution of 4-(2-hydroxypropan-2-yl)-N,N-dimethylthiophene-2-sulfonoimidamide (125 mg, 0.50 mmol) in THF (2.0 mL). To this was added NaH (60% wt. oil dispersion, 30.2 mg, 0.75 mmol) in several batches at 0° C. in an ice/water bath. To the mixture was added 4-isocyanato-1,2,3,5,6,7-hexahydro-s-indacene (110 mg, 0.55 mmol) at 0° C. in an ice/water bath. The resulting solution was stirred for 30 min at 0° C. in a water/ice bath. The reaction was then quenched by the addition of $NH_4Cl$ (aq.). The resulting solution was extracted with ethyl acetate and the organic layers combined, the organic layer was dried over anhydrous sodium sulfate and concentrated under vacuum. The crude product was purified by Prep-HPLC with the following conditions: X Bridge Prep Cis OBD, 19*150 mm 5 um; mobile phase, water (10 mM $NH_4HCO_3$) and ACN (10% to 80% in 6 min); Detector, UV 254 nm. This resulted in 90 mg (39.9%) of Example 245 as a white powder. MS-ESI: 448.2 (M+1). $^1$H NMR (DMSO-$d_6$, 300 MHz): δ 8.60 (br s, 1H), 7.71 (s, 1H), 7.58 (br s, 1H), 6.88 (s, 1H), 5.21 (s, 1H), 2.86-2.70 (m, 8H), 2.70 (s, 6H), 1.98-1.90 (m, 4H), 1.3 (s, 6H).

Example 246 (Compound 331)

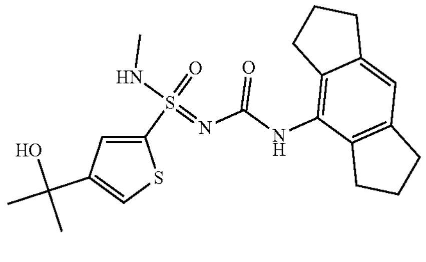 [SMILES: CNS(=O)(=NC(=O)Nc1c2c(cc3c1CCC3)CCC2)c1cc(C(C)(C)O)cs1]

N'-((1,2,3,5,6,7-hexahydro-s-indacen-4-yl)carbamoyl)-4-(2-hydroxypropan-2-yl)-N-methylthiophene-2-sulfonimidamide (Scheme 4)

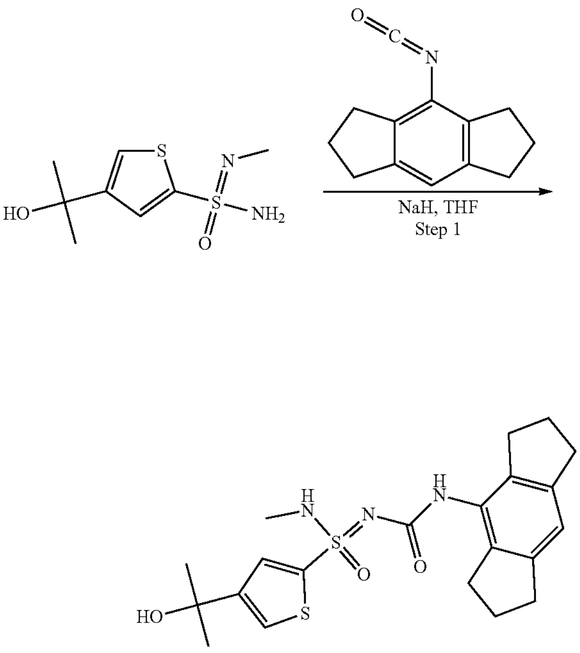

Example 246

Into a 50-mL 3-necked round-bottom flask purged and maintained with an inert atmosphere of nitrogen, was placed 4-(2-hydroxypropan-2-yl)-N-methylthiophene-2-sulfonoimidamide (106 mg, 0.45 mmol) in THF (4.0 mL). This was followed by the addition of NaH (60% wt. oil dispersion, 23.5 mg, 0.59 mmol) in several batches at 0° C. in a water/ice bath. To this was added a solution of 4-isocyanato-1,2,3,5,6,7-hexahydro-s-indacene (99.1 mg, 0.50 mmol) in THF (2.0 mL) dropwise with stirring at 0° C. The resulting solution was stirred for 30 min at 0° C. in a water/ice bath. The reaction was then quenched by the addition of water/ice. The resulting solution was extracted with ethyl acetate and the organic layers combined, the organic layer was dried over anhydrous sodium sulfate and concentrated under vacuum. The crude product was purified by Prep-HPLC with the following conditions: Column, X Bridge Shield RP18 OBD, 19×250 mm, 10 um; mobile phase, water (10 mM $NH_4HCO_3$+0.1% $NH_3.H_2O$) and ACN (43% to 67% ACN gradient in 6 min); Detector, UV 254 nm. This resulted in 80 mg (40.79%) of Example 246 as a white solid. MS-ESI: 434.15 (M+1). $^1$H NMR (DMSO-$d_6$, 300 MHz): δ 8.55 (br s, 1H) 7.65 (s, 1H), 7.59 (s, 1H), 7.53 (s, 1H), 6.89 (s, 1H), 5.22 (s, 1H) 2.63-2.85 (m, 8H) 2.49 (s, 3H) 2.00-1.80 (m, 4H) 1.31 (s, 6H).

TABLE 24

| Examples in the following table were prepared using similar conditions as described in Example 246 and Scheme 4 from appropriate starting materials. | | | | |
|---|---|---|---|---|
| Example # | Final Target Number | Structure | IUPAC Name | Exact Mass [M + H]+ |
| 247 | 339 | 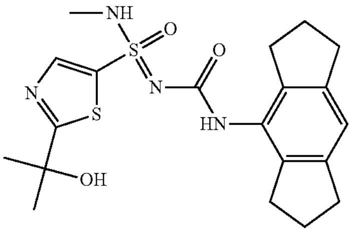 [SMILES: CNS(=O)(=NC(=O)Nc1c2c(cc3c1CCC3)CCC2)c1cnc(C(C)(C)O)s1] | N'-((1,2,3,5,6,7-hexahydro-s-indacen-4-yl)carbamoyl)-2-(2-hydroxypropan-2-yl)-N-methylthiazole-5-sulfonimidamide | 435 |

Example 248 (Compound 405)

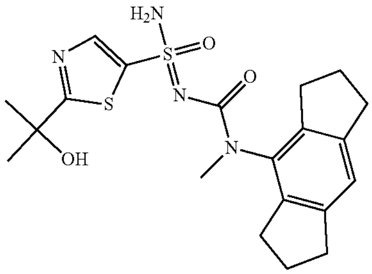 [SMILES: CN(C(=O)N=S(N)(=O)c1cnc(C(C)(C)O)s1)c1c2c(cc3c1CCC3)CCC2]

N'-((1,2,3,5,6,7-hexahydro-s-indacen-4-yl)(methyl)carbamoyl)-2-(2-hydroxypropan-2-yl)thiazole-5-sulfonimidamide (Scheme 34)

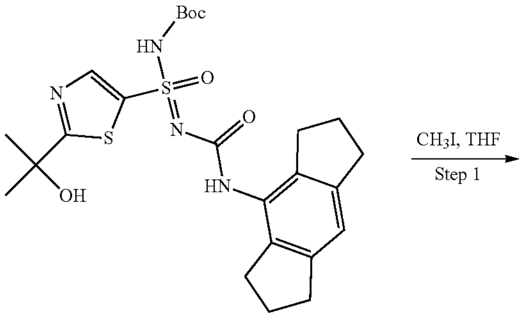

Example 7

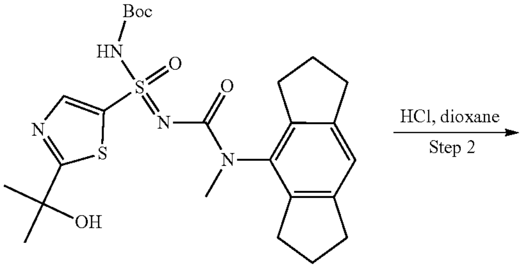

-continued

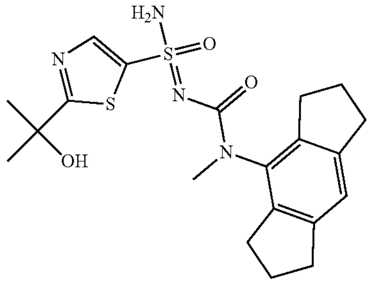

Example 248

Step 1: Tert-butyl(N-((1,2,3,5,6,7-hexahydro-s-indacen-4-yl)(methyl)carbamoyl)-2-(2-hydroxypropan-2-yl)thiazole-5-sulfonimidoyl)carbamate Into a 50-mL round-bottom flask, was placed tert-butyl N-([[(1,2,3,5,6,7-hexahydro-s-indacen-4-yl) carbamoyl] imino][2-(2-hydroxypropan-2-yl)-1,3-thiazol-5-yl]oxo-$\lambda^6$-sulfanyl)carbamate (200 mg, 0.38 mmol) in THF (10 mL), to this stirred solution was added $CH_3I$ (60 mg, 0.42 mmol) dropwise at 0° C. The resulting solution was stirred for 1 d at RT. The resulting mixture was concentrated. This resulted in 100 mg (49%) of the title compound as a solid. MS-ESI. 535 (M+1).

Step 2: N'-((1,2,3,5,6,7-hexahydro-s-indacen-4-yl)(methyl)carbamoyl)-2-(2-hydroxypropan-2-yl) thiazole-5-sulfonimidamide Into a 25-mL round-bottom flask, was placed tert-butyl N-([[(1,2,3,5,6,7-hexahydro-s-indacen-4-yl) (methyl)carbamoyl]imino][2-(2-hydroxypropan-2-yl)-1,3-thiazol-5-yl] oxo-k 6-sulfanyl)carbamate (100 mg) in HCl (4 M 10 mL). The resulting solution was stirred for 5 h at RT. The crude product was purified by Prep-HPLC with the following conditions: Column, XBridge Prep C18 OBD, 5 um, 19*150 mm; mobile phase, water (10 mM $NH_4HCO_3$ mM) and ACN (22% to 53% ACN gradient in 7 min); Detector, UV. This resulted in 15.7 mg of Example 248 as a solid. MS-ESI: 435 (M+1).

TABLE 25

Example 249 was isolated as a side product from the preparation of Example 248.

| Example # | Final Target Number | Structure | IUPAC Name | Exact Mass [M + H]+ |
|---|---|---|---|---|
| 249 | 406 | 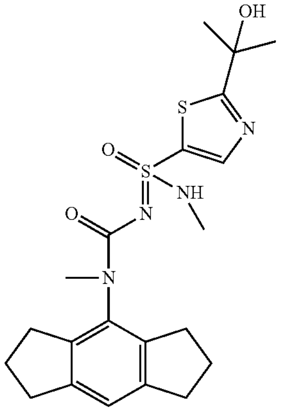 [SMILES: CNS(=O)(=NC(=O)N(C)c1c2c(cc3c1CCC3)CCC2)c1cnc(C(C)(C)O)s1] | N'-((1,2,3,5,6,7-hexahydro-s-indacen-4-yl)(methyl)carbamoyl)-2-(2-hydroxypropan-2-yl)-N-methylthiazole-5-sulfonimidamide | 449 |

Example 250 (Compound 324)

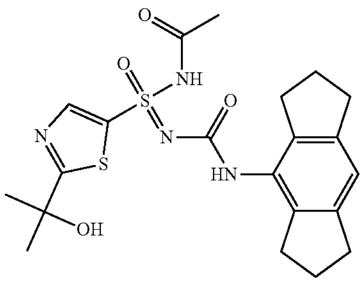 [SMILES: CC(=O)NS(=O)(=NC(=O)Nc1c2c(cc3c1CCC3)CCC2)c1cnc(C(C)(C)O)s1]

N—(N-((1,2,3,5,6,7-hexahydro-s-indacen-4-yl)carbamoyl)-2-(2-hydroxypropan-2-yl)thiazole-5-sulfonimidoyl)acetamide (Scheme 35A)

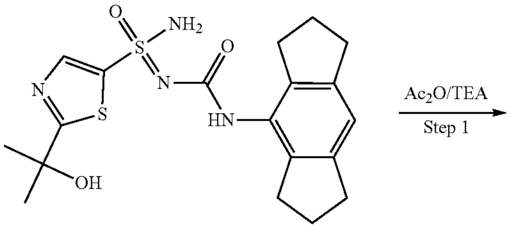

Example 4

-continued

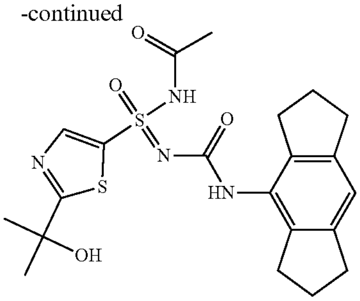

Example 250

Into a 50-mL round-bottom flask purged and maintained with an inert atmosphere of nitrogen, was placed a mixture of N'-((1,2,3,5,6,7-hexahydro-s-indacen-4-yl)carbamoyl)-2-(2-hydroxypropan-2-yl)thiazole-5-sulfonimidamide (200 mg, 0.48 mmol) and TEA (96 mg, 0.96 mmol) in DCM (20 mL). To the stirred solution, $Ac_2O$ (74 mg, 0.72 mmol) was added dropwise at 0° C. The resulting solution was stirred overnight. Then 80 mg of the product was obtained by Prep-HPLC with the following conditions: Column: XBridge Prep C18 OBD Column 19×150 mm 5 um; Mobile Phase A: water (10 mM $NH_4HCO_3$), Mobile Phase B: ACN; Flow rate: 25 mL/min; Gradient: 18% B to 41% B in 7 min; 254/210 nm; Rt: 5.05 min, this resulted in 100 mg of the Example 250 as a white solid. MS-ESI: 462.14 (M+1). $^1H$ NMR (300 MHz, $CD_3OD-d_4$) δ: 8.11 (s, 1H), 6.89 (s, 1H), 2.92-2.69 (m, 8H), 2.09-2.01 (m, 4H), 1.99 (s, 3H), 1.60 (d, J=2.3 Hz, 6H).

Example 251 (Compound 407)

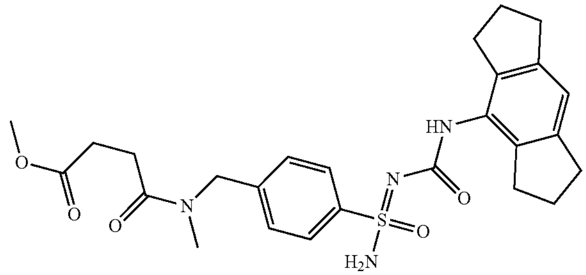 [SMILES: COC(=O)CCC(=O)N(C)Cc1ccc(S(N)(=O)=NC(=O)Nc2c3c(cc4c2CCC4)CCC3)cc1]

methyl 4-((4-(N'-((1,2,3,5,6,7-hexahydro-s-indacen-4-yl)carbamoyl)sulfamidimidoyl)benzyl)(methyl) amino)-4-oxobutanoate (Scheme 35)

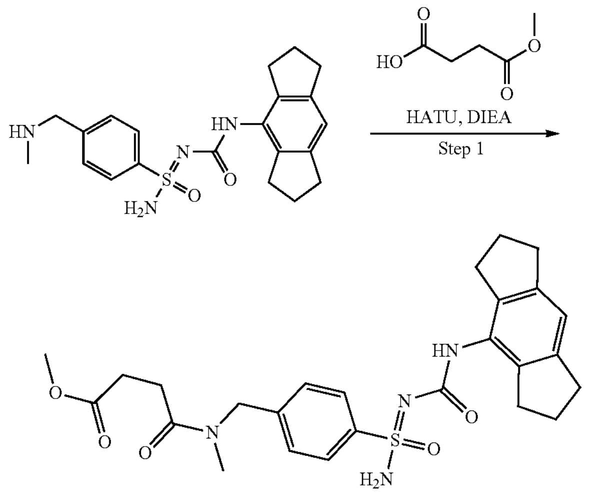

Example 251

Into a 8-mL round-bottom flask, was placed a solution of 1-[amino([4-[(methylamino)methyl]-phenyl])oxo-λ$^6$-sulfanylidene]-3-(1,2,3,5,6,7-hexahydro-s-indacen-4-yl)urea (100 mg, 0.25 mmol), methyl 4-chloro-4-oxobutanoate (37.8 mg, 0.25 mmol) in DMF (10 mL), to this stirred solution was added HATU (191 mg, 0.50 mmol) and DIEA (64.9 mg, 0.50 mmol). The resulting solution was stirred for 20 min at RT. The crude product was purified by Prep-HPLC with the following conditions: Column, XBridge Shield RP18 OBD, 19*250 mm, 10 um; mobile phase, water (10 mM $NH_4HCO_3$) and ACN (15% to 75% ACN gradient in 7 min); Detector, UV 250 nm. This resulted in 4.2 mg (3.27%) of Example 251 as a white solid. MS-ESI: 513 (M+1). $^1$H NMR (300 MHz, $CD_3OD$-$d_4$) δ: 8.02-7.94 (m, 2H), 7.49-7.41 (m, 2H), 6.89 (s, 1H), 4.68 (s, 2H), 3.68 (s, 3H), 3.04 (s, 3H), 2.85-2.80 (m, 4H), 2.75-2.60 (m, 8H), 2.03-1.97 (m, 4H).

Example 252 Compound 10)

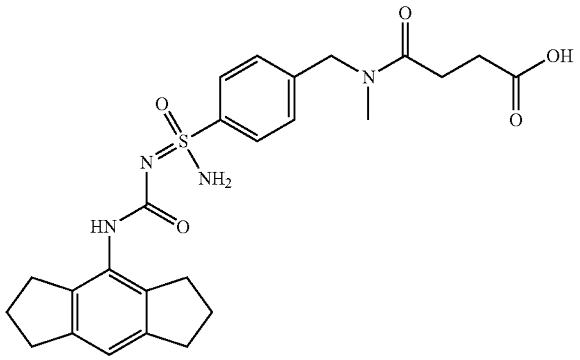 [SMILES: CN(Cc1ccc(S(N)(=O)=NC(=O)Nc2c3c(cc4c2CCC4)CCC3)cc1)C(=O)CCC(=O)O]

4-((4-(N'-(1,2,3,5,6,7-hexahydro-s-indacen-4-ylcarbamoyl)sulfamimidoyl)benzyl)(methyl)amino)-4-oxobutanoic Acid

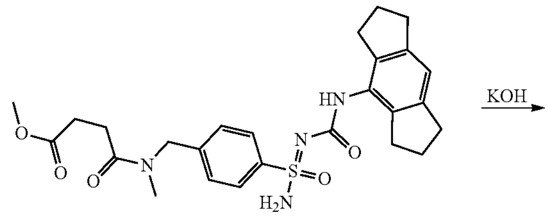

Example 251

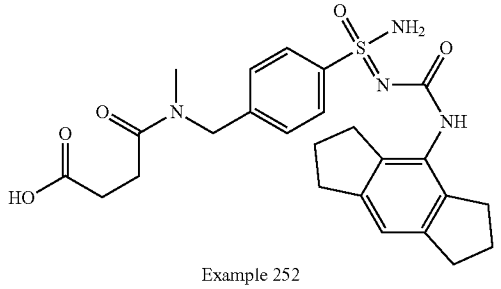

Example 252

Into a 50-mL round-bottom flask, was placed a solution of methyl 3-[([4-[amino([[(1,2,3,5,6,7-hexahydro-s-indacen-4-yl)carbamoyl]imino])oxo-λ$^6$-sulfanyl]phenyl]methyl)(methyl)-carbamoyl]propanoate (80 mg, 0.16 mmol) in THF (3.0 mL) and $H_2O$ (3.0 mL), to the stirred solution was added KOH (17.5 mg, 0.31 mmol). The resulting solution was stirred for 120 min at RT. The crude product was purified by Prep-HPLC with the following conditions: Column, XBridge Shield RP18 OBD, 19*250 mm, 10 um; mobile phase, water (10 mM $NH_4HCO_3$) and ACN (15% to 75% gradient in 7 min); Detector, UV250 nm. This resulted in 39 mg (50%) of Example 252 as a white solid. MS-ESI: 499 (M+1). $^1$H-NMR (300 MHz, $CD_3OD$-$d_4$) δ: 8.10-7.80 (m, 2H), 7.55-7.30 (m, 2H), 6.89 (s, 1H), 4.68 (s, 2H), 3.04 (s, 3H), 2.90-2.60 (m, 12H), 2.10-1.80 (m, 4H).

Example 253 (Compound 408)

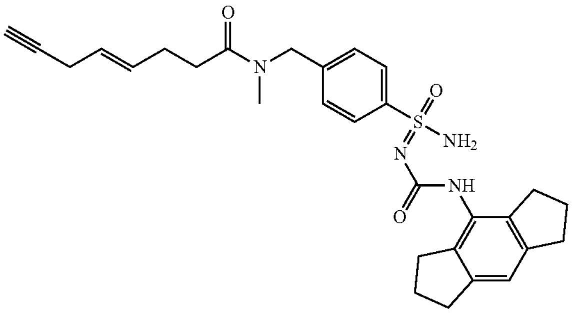 [SMILES: C#CC/C=C/CCC(=O)N(C)Cc1ccc(S(N)(=O)=NC(=O)Nc2c3c(cc4c2CCC4)CCC3)cc1]

(E)-N-(4-(N'-((1,2,3,5,6,7-hexahydro-s-indacen-4-yl) carbamoyl)sulfamidimidoyl)benzyl)-N-methyloct-4-en-7-ynamide (Scheme 35)

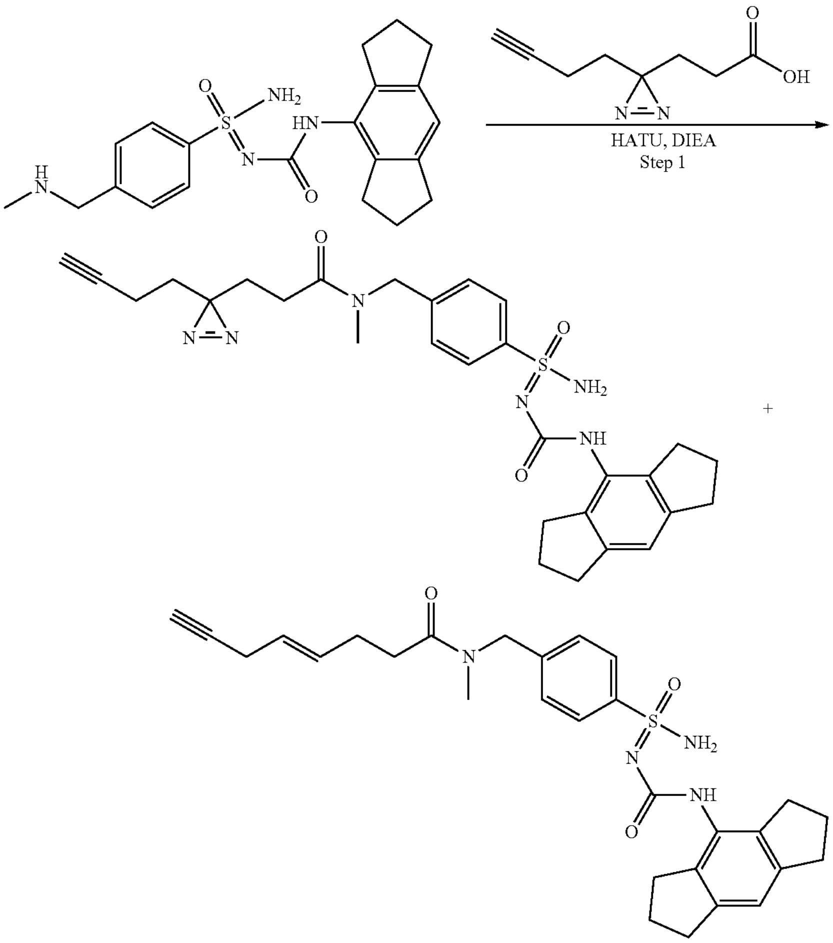

Example 253

Example 253 was prepared using similar conditions as described in Example 251 and Scheme 35 from 3-(3-(but-3-ynyl)-3H-diazirin-3-yl)propanoic acid and Intermediate 67. MS-ESI: 519 (M+1)

TABLE 26

Examples in the following table were prepared using similar conditions as described in Example 4-route 1 and Scheme 2 from appropriate starting materials.

| Example # | Final Target Number | Structure | IUPAC Name | Exact Mass [M + H]$^+$ |
|---|---|---|---|---|
| 254 | 308 | 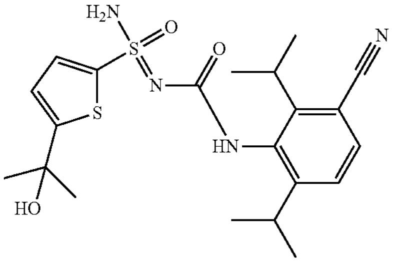 [SMILES: CC(C)c1ccc(C#N)c(C(C)C)c1NC(=O)N=S(N)(=O)c1ccc(C(C)(C)O)s1] | N'-((3-cyano-2,6-diisopropylphenyl)carbamoyl)-5-(2-hydroxypropan-2-yl) thiophene-2-sulfonimidamide | 449 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass $[M + H]^+$ |
|---|---|---|---|---|
| 255 | 311 | 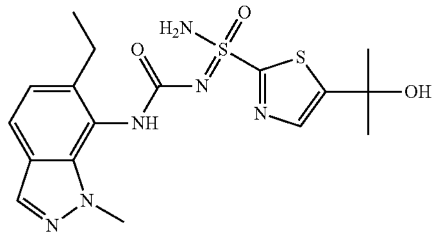 [SMILES: CCc1ccc2cnn(C)c2c1NC(=O)N=S(N)(=O)c1ncc(C(C)(C)O)s1] | N'-((6-ethyl-1-methyl-1H-indazol-7-yl)carbamoyl)-5-(2-hydroxypropan-2-yl)thiazole-2-sulfonimidamide | 423 |
| 256 | 312 | 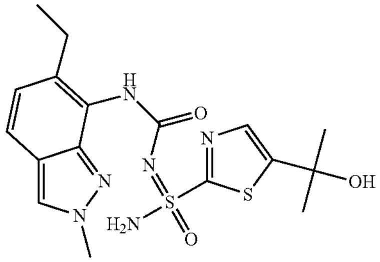 [SMILES: CCc1ccc2cn(C)nc2c1NC(=O)N=S(N)(=O)c1ncc(C(C)(C)O)s1] | N'-((6-ethyl-2-methyl-2H-indazol-7-yl)carbamoyl)-5-(2-hydroxypropan-2-yl)thiazole-2-sulfonimidamide | 423 |
| 257 | 327 | 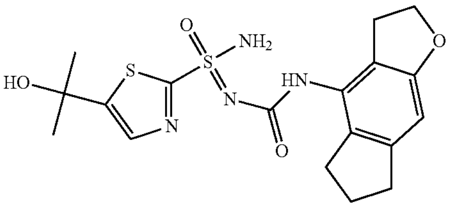 [SMILES: CC(C)(O)c1cnc(S(N)(=O)=NC(=O)Nc2c3c(cc4c2CCO4)CCC3)s1] | 5-(2-hydroxypropan-2-yl)-N'-((3,5,6,7-tetrahydro-2H-indeno[5,6-b]furan-4-yl) carbamoyl)thiazole-2-sulfonimidamide | 423 |
| 258 | 326 | 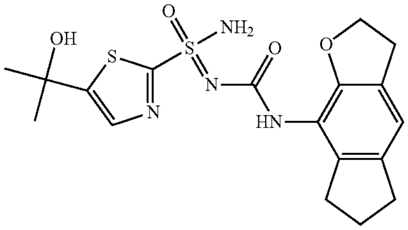 [SMILES: CC(C)(O)c1cnc(S(N)(=O)=NC(=O)Nc2c3c(cc4c2OCC4)CCC3)s1] | 5-(2-Hydroxypropan-2-yl)-N'-((3,5,6,7-tetrahydro-2H-indeno[5,6-b]furan-8-yl) carbamoyl)thiazole-2-sulfonimidamide | 423 |
| 259 | 139 | 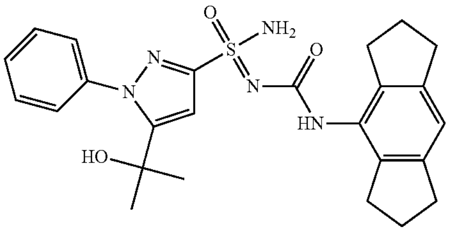 [SMILES: CC(C)(O)c1cc(S(N)(=O)=NC(=O)Nc2c3c(cc4c2CCC4)CCC3)nn1-c1ccccc1] | N'-((1,2,3,5,6,7-hexahydro-s-indacen-4-yl)carbamoyl)-5-(2-hydroxypropan-2-yl)-1-phenyl-1H-pyrazole-3-sulfonimidamide | 480 |
| 260 | 137 | 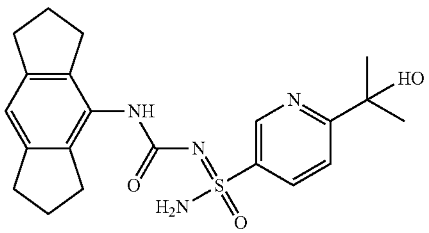 [SMILES: CC(C)(O)c1ccc(S(N)(=O)=NC(=O)Nc2c3c(cc4c2CCC4)CCC3)cn1] | N'-((1,2,3,5,6,7-hexahydro-s-indacen-4-yl)carbamoyl)-6-(2-hydroxypropan-2-yl) pyridine-3-sulfonimidamide | 415 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 261 | 409 | 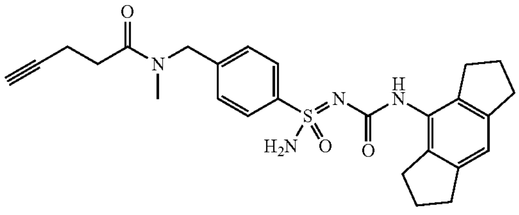 [SMILES: C#CCCC(=O)N(C)Cc1ccc(S(N)(=O)=NC(=O)Nc2c3c(cc4c2CCC4)CCC3)cc1] | N-(4-(N'-((1,2,3,5,6,7-hexahydro-s-indacen-4-yl)carbamoyl)sulfamidimidoyl)benzyl)-N-methylpent-4-ynamide | 479 |
| 262 | 303 | 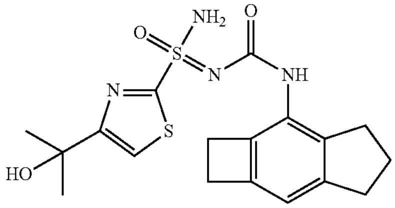 [SMILES: CC(C)(O)c1csc(S(N)(=O)=NC(=O)Nc2c3c(cc4c2CC4)CCC3)n1] | 4-(2-Hydroxypropan-2-yl)-N'-((2,4,5,6-tetrahydro-1H-cyclobuta[f]inden-3-yl) carbamoyl)thiazole-2-sulfonimidamide | 407 |
| 263 | 325 | 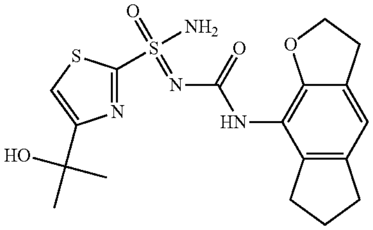 [SMILES: CC(C)(O)c1csc(S(N)(=O)=NC(=O)Nc2c3c(cc4c2OCC4)CCC3)n1] | 4-(2-Hydroxypropan-2-yl)-N'-((3,5,6,7-tetrahydro-2H-indeno[5,6-b]furan-8-yl) carbamoyl)thiazole-2-sulfonimidamide | 423 |
| 264 | 138 | 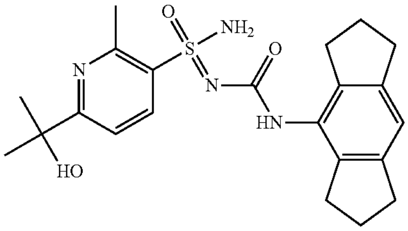 [SMILES: Cc1nc(C(C)(C)O)ccc1S(N)(=O)=NC(=O)Nc1c2c(cc3c1CCC3)CCC2] | N'-((1,2,3,5,6,7-hexahydro-s-indacen-4-yl)carbamoyl)-6-(2-hydroxypropan-2-yl)-2-methylpyridine-3-sulfonimidamide | 429 |
| 265 | 332 | 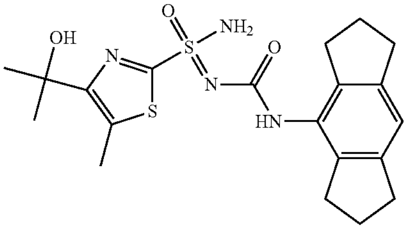 [SMILES: Cc1sc(S(N)(=O)=NC(=O)Nc2c3c(cc4c2CCC4)CCC3)nc1C(C)(C)O] | N'-(1,2,3,5,6,7-hexahydro-s-indacen-4-ylcarbamoyl)-4-(2-hydroxypropan-2-yl)-5-methylthiazole-2-sulfonimidamide | 435 |
| 266 | 334 | 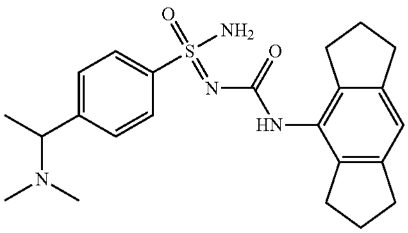 [SMILES: CC(c1ccc(S(N)(=O)=NC(=O)Nc2c3c(cc4c2CCC4)CCC3)cc1)N(C)C] | 4-(1-(Dimethylamino)ethyl)-N'-(1,2,3,5,6,7-hexahydro-s-indacen-4-ylcarbamoyl) benzenesulfonimidamide | 427 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 267 | 335 | 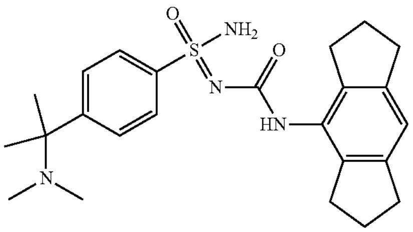 [SMILES: CN(C)C(C)(C)c1ccc(S(N)(=O)=NC(=O)Nc2c3c(cc4c2CCC4)CCC3)cc1] | 4-(2-(Dimethylamino)propan-2-yl)-N'-(1,2,3,5,6,7-hexahydro-s-indacen-4-yl-carbamoyl)benzene-sulfonimidamide | 441 |
| 268 | 337 | 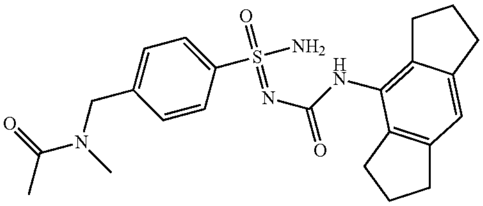 [SMILES: CC(=O)N(C)Cc1ccc(S(N)(=O)=NC(=O)Nc2c3c(cc4c2CCC4)CCC3)cc1] | N-(4-(N'-(1,2,3,5,6,7-hexahydro-s-indacen-4-ylcarbamoyl)sulfamimidoyl) benzyl)-N-methylacetamide | 441 |
| 269 | 113 | 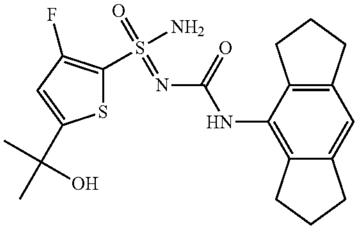 [SMILES: CC(C)(O)c1cc(F)c(S(N)(=O)=NC(=O)Nc2c3c(cc4c2CCC4)CCC3)s1] | 3-Fluoro-N'-(1,2,3,5,6,7-hexahydro-s-indacen-4-ylcarbamoyl)-5-(2-hydroxypropan-2-yl) thiophene-2-sulfonimidamide | 438 |
| 270 | 343 | 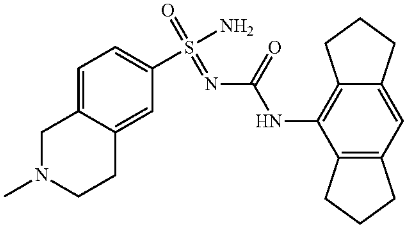 [SMILES: CN1CCc2cc(S(N)(=O)=NC(=O)Nc3c4c(cc5c3CCC5)CCC4)ccc2C1] | N'-((1,2,3,5,6,7-hexahydro-s-indacen-4-yl)carbamoyl)-2-methyl-1,2,3,4-tetrahydroisoquinoline-6-sulfonimidamide | 425 |
| 271 | 349 | 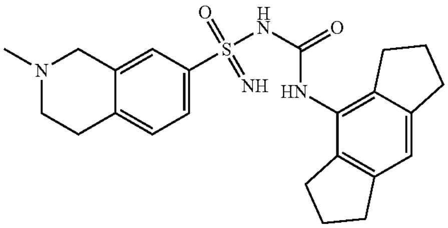 [SMILES: CN1CCc2ccc(S(=N)(=O)NC(=O)Nc3c4c(cc5c3CCC5)CCC4)cc2C1] | N-(1,2,3,5,6,7-hexahydro-s-indacen-4-ylcarbamoyl)-2-methyl-1,2,3,4-tetrahydroisoquinoline-7-sulfonimidamide | 425 |
| 272 | 344 | 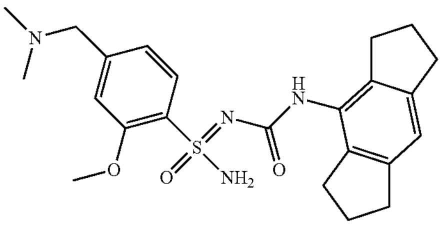 [SMILES: COc1cc(CN(C)C)ccc1S(N)(=O)=NC(=O)Nc1c2c(cc3c1CCC3)CCC2] | 4-((Dimethylamino)methyl)-N'-((1,2,3,5,6,7-hexahydro-s-indacen-4-yl)carbamoyl)-2-methoxybenzene-sulfonimidamide | 443 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 273 | 359 | 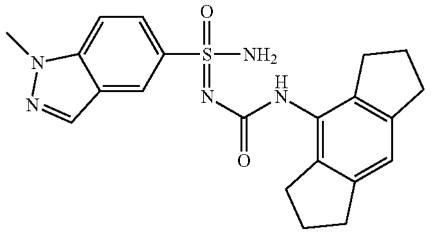 [SMILES: Cn1ncc2cc(S(N)(=O)=NC(=O)Nc3c4c(cc5c3CCC5)CCC4)ccc21] | N'-(1,2,3,5,6,7-hexahydro-s-indacen-4-ylcarbamoyl)-1-methyl-1H-indazole-5-sulfonimidamide | 410 |
| 274 | 352 | 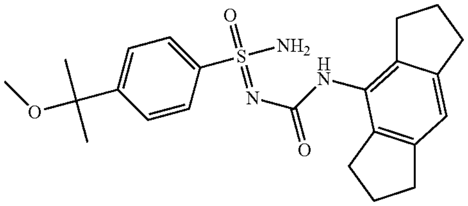 [SMILES: COC(C)(C)c1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-(2-methoxypropan-2-yl) benzenesulfonimidamide | 428 |
| 275 | 354 | 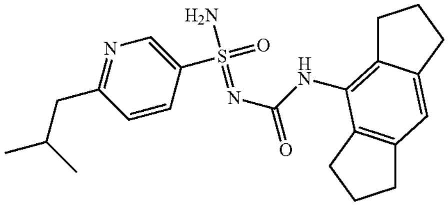 [SMILES: CC(C)Cc1ccc(S(N)(=O)=NC(=O)Nc2c3c(cc4c2CCC4)CCC3)cn1] | N'-(1,2,3,5,6,7-hexahydro-s-indacen-4-ylcarbamoyl)-6-isobutylpyridine-3-sulfonimidamide | 413 |
| 276 | 355 | 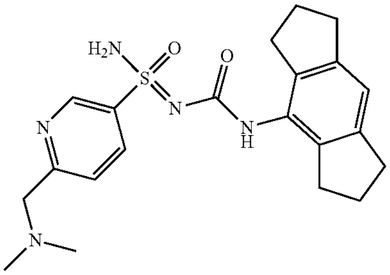 [SMILES: CN(C)Cc1ccc(S(N)(=O)=NC(=O)Nc2c3c(cc4c2CCC4)CCC3)cn1] | 6-((Dimethylamino)methyl)-N'-(1,2,3,5,6,7-hexahydro-5-indacen-4-ylcarbamoyl) pyridine-3-sulfonimidamide | 414 |
| 277 | 356 | 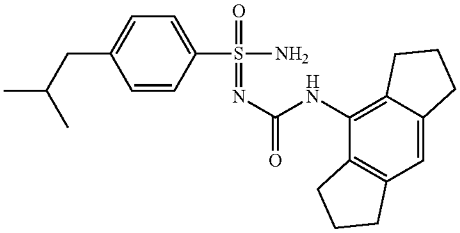 [SMILES: CC(C)Cc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-isobutylbenzene-sulfonimidamide | 412 |
| 278 | 357 | 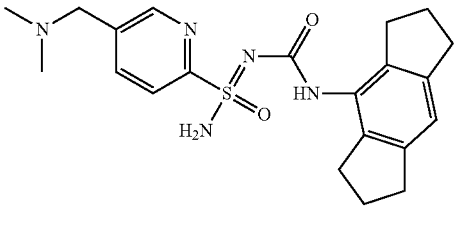 | 5-((Dimethylamino)methyl)-N'-(1,2,3,5,6,7-hexahydro-s-indacen-4-ylcarbamoyl) pyridine-2-sulfonimidamide | 414 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 279 | 340 | 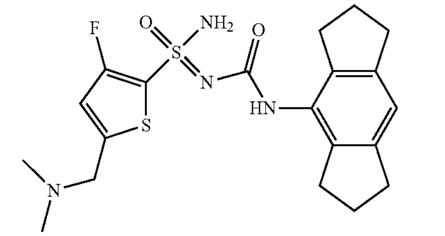 [SMILES: CN(C)Cc1cc(F)c(S(N)(=O)=NC(=O)Nc2c3c(cc4c2CCC4)CCC3)s1] | 5-((Dimethylamino)methyl)-3-fluoro-N'-(1,2,3,5,6,7-hexahydro-s-indacen-4-ylcarbamoyl)thiophene-2-sulfonimidamide | 437 |
| 280 | 377 | 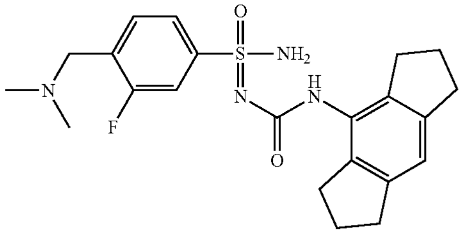 [SMILES: CN(C)Cc1ccc(S(N)(=O)=NC(=O)Nc2c3c(cc4c2CCC4)CCC3)cc1F] | 4-((dimethylmino)methyl)-3-fluoro-N'-((1,2,3,5,6,7-hexahydro-s-indacen-4-yl)carbamoyl) benzenesulfonimidamide | 431 |
| 281 | 378 | 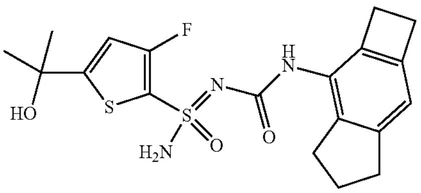 [SMILES: CC(C)(O)c1cc(F)c(S(N)(=O)=NC(=O)Nc2c3c(cc4c2CC4)CCC3)s1] | 3-fluoro-5-(2-hydroxy-propan-2-yl)-N'-((2,4,5,6-tetrahydro-1H-cyclobuta[f]inden-3-yl) carbamoyl)thiophene-2-sulfonimidamide | 424 |
| 282 | 379 | 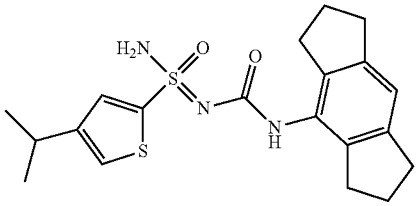 [SMILES: CC(C)c1csc(S(N)(=O)=NC(=O)Nc2c3c(cc4c2CCC4)CCC3)c1] | N'-((1,2,3,5,6,7-hexahydro-s-indacen-4-yl)carbamoyl)-4-isopropylthiophene-2-sulfonimidamide | 404 |
| 283 | 380 | 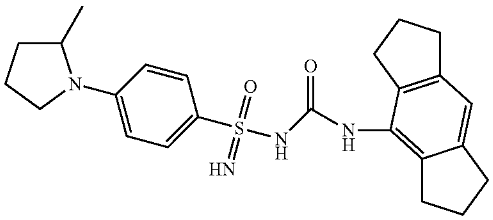 [SMILES: CC1CCCN1c1ccc(S(=N)(=O)NC(=O)Nc2c3c(cc4c2CCC4)CCC3)cc1] | N-((1,2,3,5,6,7-hexahydro-s-indacen-4-yl)carbamoyl)-4-(1-methylpyrrolidin-2-yl)benzenesulfonimidamide | 439 |
| 284 | 353 | 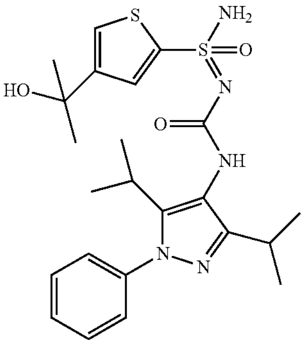 [SMILES: CC(C)c1nn(-c2ccccc2)c(C(C)C)c1NC(=O)N=S(N)(=O)c1cc(C(C)(C)O)cs1] | N'-((3,5-diisopropyl-1-phenyl-1H-pyrazol-4-yl) carbamoyl)-4-(2-hydroxy-propan-2-yl)thiophene-2-sulfonimidamide | 490 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass $[M + H]^+$ |
|---|---|---|---|---|
| 285 | 333 | 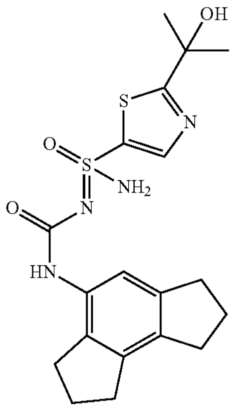 [SMILES: CC(C)(O)c1ncc(S(N)(=O)=NC(=O)Nc2cc3c(c4c2CCC4)CCC3)s1] | N'-((1,2,3,6,7,8-hexahydro-as-indacen-4-yl)carbamoyl)-2-(2-hydroxypropan-2-yl) thiazole-5-sulfonimidamide | 421 |
| 287 | 382 | 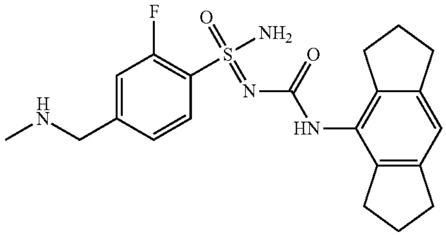 [SMILES: CNCc1ccc(S(N)(=O)=NC(=O)Nc2c3c(cc4c2CCC4)CCC3)c(F)c1] | 2-fluoro-N'-((1,2,3,5,6,7-hexahydro-s-indacen-4-yl) carbamoyl)-4-((methylamino) methyl) benzenesulfonimidamide | 417 |
| 288 | 383 | 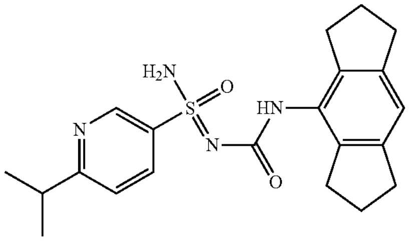 | N'-((1,2,3,5,6,7-hexahydro-s-indacen-4-yl)carbamoyl)-6-isopropylpyridine-3-sulfonimidamide | 399 |

TABLE 27

Examples in the following table were prepared using similar conditions as described in Example 4-route 2 and Scheme 3 from appropriate starting materials.

| Example # | Final Target Number | Structure | IUPAC Name | Exact Mass $[M + H]^+$ |
|---|---|---|---|---|
| 289 | 315 | 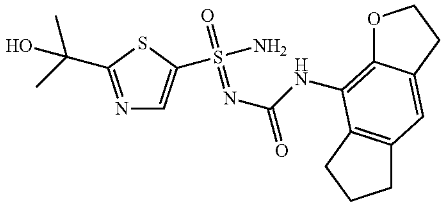 [SMILES: CC(C)(O)c1ncc(S(N)(=O)=NC(=O)Nc2c3c(cc4c2OCC4)CCC3)s1] | 2-(2-Hydroxypropan-2-yl)-N'-((3,5,6,7-tetrahydro-2H-indeno[5,6-b]furan-8-yl)carbamoyl)thiazole-5-sulfonimidamide | 423 |

TABLE 27-continued

| Examples in the following table were prepared using similar conditions as described in Example 4-route 2 and Scheme 3 from appropriate starting materials. | | | | |
|---|---|---|---|---|
| Example # | Final Target Number | Structure | IUPAC Name | Exact Mass [M + H]$^+$ |
| 290 | 316 | 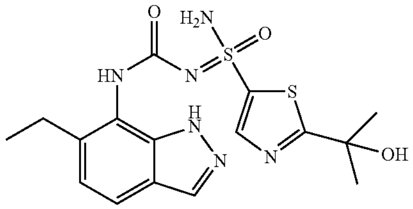 [SMILES: CCc1ccc2cn[nH]c2c1NC(=O)N=S(N)(=O)c1cnc(C(C)(C)O)s1] | N'-((6-ethyl-1H-indazol-7-yl)carbamoyl)-2-(2-hydroxypropan-2-yl)thiazole-5-sulfonimidamide | 409 |
| 291 | 317 | 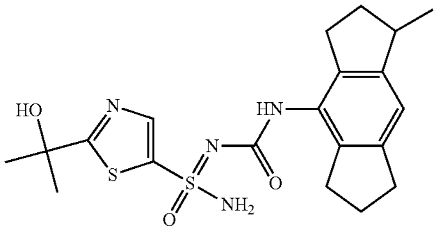 [SMILES: CC1CCc2c1cc1c(c2NC(=O)N=S(N)(=O)c2cnc(C(C)(C)O)s2)CCC1] | 2-(2-Hydroxypropan-2-yl)-N'-((1-methyl-1,2,3,5,6,7-hexahydro-s-indacen-4-yl)carbamoyl)thiazole-5-sulfonimidamide | 435 |
| 292 | 319 | 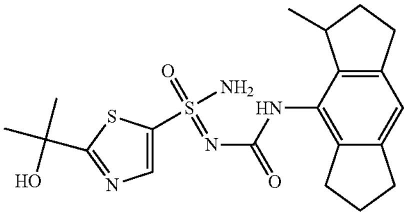 [SMILES: CC1CCc2cc3c(c(NC(=O)N=S(N)(=O)c4cnc(C(C)(C)O)s4)c21)CCC3] | 2-(2-Hydroxypropan-2-yl)-N'-((3-methyl-1,2,3,5,6,7-hexahydro-s-indacen-4-yl)carbamoyl)thiazole-5-sulfonimidamide | 435 |
| 293 | 320 | 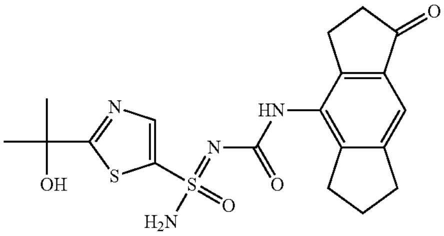 [SMILES: CC(C)(O)c1ncc(S(N)(=O)=NC(=O)Nc2c3c(cc4c2CCC4=O)CCC3)s1] | 2-(2-Hydroxypropan-2-yl)-N'-((1-oxo-1,2,3,5,6,7-hexahydro-s-indacen-4-yl)carbamoyl)thiazole-5-sulfonimidamide | 435 |
| 294 | 336 | 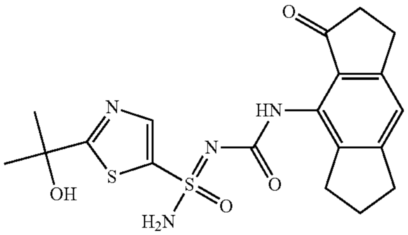 [SMILES: CC(C)(O)c1ncc(S(N)(=O)=NC(=O)Nc2c3c(cc4c2C(=O)CC4)CCC3)s1] | 2-(2-Hydroxypropan-2-yl)-N'-((3-oxo-1,2,3,5,6,7-hexahydro-s-indacen-4-yl)carbamoyl)thiazole-5-sulfonimidamide | 435 |
| 295 | 330 | 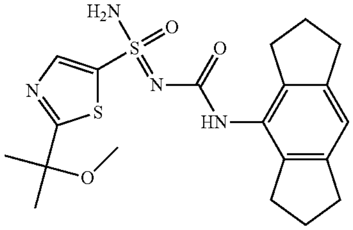 [SMILES: COC(C)(C)c1ncc(S(N)(=O)=NC(=O)Nc2c3c(cc4c2CCC4)CCC3)s1] | N'-((1,2,3,5,6,7-hexahydro-s-indacen-4-yl)carbamoyl)-2-(2-methoxypropan-2-yl) thiazole-5-sulfonimidamide | 435 |

TABLE 28

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 296 | 364a | 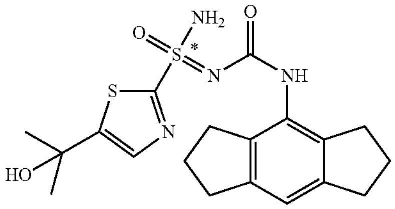 | (R) or (S)-N'-((1,2,3,5,6,7-hexahydro-s-indacen-4-yl) carbamoyl)-5-(2-hydroxy-propan-2-yl) thiazole-2-sulfonimidamide | CHIRALPAK IG 2*25 cm (5 um) | 50% MeOH (8 mM $NH_3$-MeOH) in $CO_2$# | 421 |
| 297 | 364b | 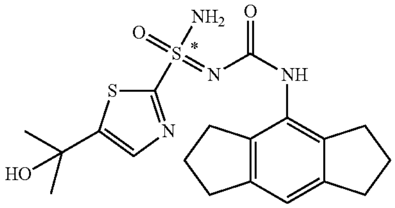 | (S) or (R)-N'-((1,2,3,5,6,7-hexahydro-s-indacen-4-yl) carbamoyl)-5-(2-hydroxy-propan-2-yl) thiazole-2-sulfonimidamide | CHIRALPAK IG 2*25 cm (5 um) | 50% MeOH (8 mM $NH_3$• MeOH) in $CO_2$ | 421 |
| 298 | 365a | 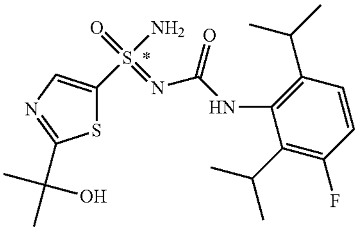 | (R) or (S)-N'-((3-fluoro-2,6-diisopropyl-phenyl)carbamoyl)-2-(2-hydroxy-propan-2-yl) thiazole-5-sulfonimidamide | Chiralpak ID, 2*25 cm, 5 um | IPA in Hex: DCM = 5:1 | 443 |
| 299 | 365b | 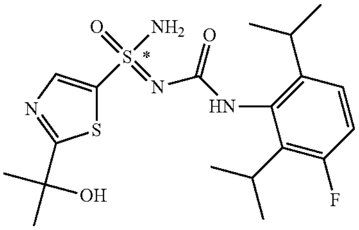 | (S) or (R)-N'-((3-fluoro-2,6-diisopropyl-phenyl)carbamoyl)-2-(2-hydroxy-propan-2-yl) thiazole-5-sulfonimidamide | Chiralpak ID, 2*25 cm, 5 um | IPA in Hex: DCM= 5:1 | 443 |
| 300 | 308a | 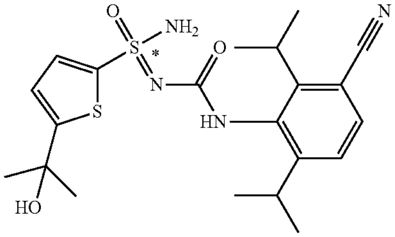 | (R) or (S)-N'-((3-cyano-2,6-diisopropyl-phenyl)carbamoyl)-5-(2-hydroxy-propan-2-yl) thiophene-2-sulfonimidamide | CHIRALPAK IG, 20*250 mm, 5 um | 30% EtOH in Hex (0.1% DEA) | 449 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 301 | 308b | 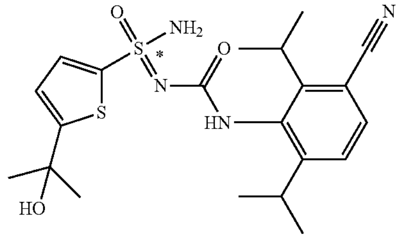 | (S) or (R)-N'-((3-fluoro-2,6-diisopropylphenyl)carbamoyl)-2-(2-hydroxypropan-2-yl)thiazole-5-sulfonimidamide | CHIRALPAK IG, 20*250 mm, 5 um | 30% EtOH in Hex (0.1% DEA) | 449 |
| 126 | 195a | 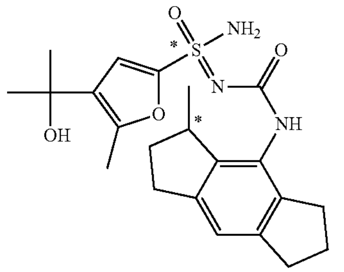 | Two isomers of (S,S)-and (S,R)-or (R,S)-and (R,R) 4-(2-hydroxypropan-2-yl)-5-methyl-N'-((3-methyl-1,2,3,5,6,7-hexahydro-s-indacen-4-yl)carbamoyl)furan-2-sulfonimidamide | CHIRALART Cellulose-SB, 2*25 cm, 5 um | MeOH (0.1% DEA); 1st and 2nd peaks | 432 |
| 127 | 195e | 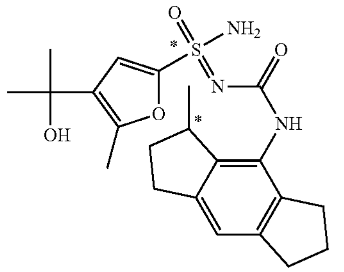 | Two isomers of (R,S)-and (R,R)-or (S,S)-and (S,R) 4-(2-hydroxypropan-2-yl)-5-methyl-N'-((3-methyl-1,2,3,5,6,7-hexahydro-s-indacen-4-yl)carbamoyl)furan-2-sulfonimidamide | | MeOH (0.1% DEA); 3rd peak | 432 |
| 302 | 195ba | 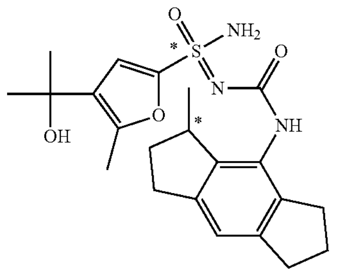 | (R,R) or (R,S) or (S,S) or (S,R)-4-(2-hydroxypropan-2-yl)-5-methyl-N'-((3-methyl-1,2,3,5,6,7-hexahydro-s-indacen-4-yl)carbamoyl)furan-2-sulfonimidamide resolved from example 127 | Phenomenex Lux 5u Cellulose-4, AXIA Packed 2.12*25 cm, 5 um | 40% MeOH in $CO_2$ | 432 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 303 | 195bb | 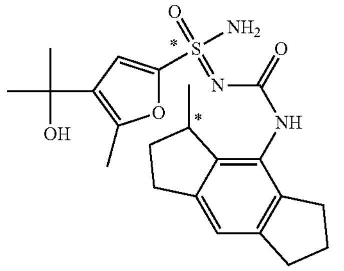 | (R,S) or (R,R) or (S,R) or (S,S)-4-(2-hydroxy-propan-2-yl)-5-methyl-N'-((3-methyl-1,2,3,5,6,7-hexahydro-s-indacen-4-yl) carbamoyl) furan-2-sulfonimi-damide re-solved from example 127 | Pheno-menex Lux 5u Cellu-lose-4, AXIA Packed 2.12*25 cm, 5 um | 40% MeOH in $CO_2$ | 432 |
| 123 | 207c | 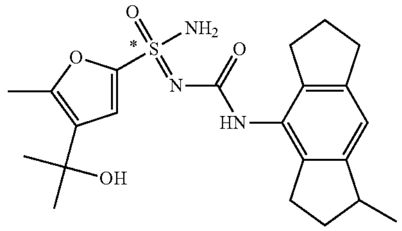 | Two isomers of (R,S)- and (R,R) 4-(2-hydroxy-propan-2-yl)-5-methyl-N'-(1-methyl-1,2,3,5,6,7-hexahydros-indacen-4-yl-carbamoyl) furan-2-sulfonimi-damide | Chiral-Pak IC, 2*25 cm, 5 um | 50% EtOH in MTBE; 1st and 2nd peaks | 432.2 |
| 124 | 207aa | 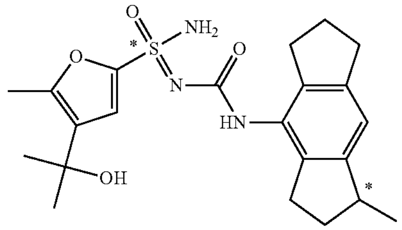 | (S,S)-or (S,R)-4-(2-hydroxy-propan-2-yl)-5-methyl-N'-(1-methyl-1,2,3,5,6,7-hexahydros-indacen-4-yl-carbamoyl) furan-2-sulfonimi-damide | | 50% EtOH in MTBE; 3rd peak | 432.2 |
| 125 | 207b | 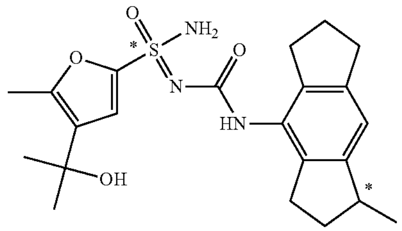 | (S,R)-or (S,S)-4-(2-hydroxy-propan-2-yl)-5-methyl-N'-(1-methyl-1,2,3,5,6,7-hexahydros-indacen-4-yl-carbamoyl) furan-2-sulfonimi-damide | | 50% EtOH in MTBE; 4th peak | 432.2 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 304 | 207a | 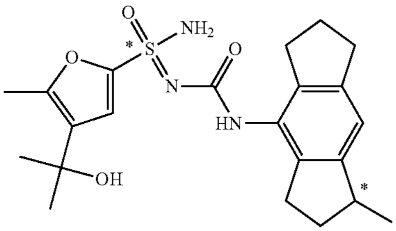 | (R,R) or (R,S)-4-(2-hydroxy-propan-2-yl)-5-methyl-N'-((3-methyl-1,2,3,5,6,7-hexahydro-s-indacen-4-yl) carbamoyl) furan-2-sulfonimi-damide; resolved from example 123 | CHIRAL-PAK IG, 20*250 mm, 5 um | EtOH in Hex (0.1% FA) | 432 |
| 305 | 207bb | 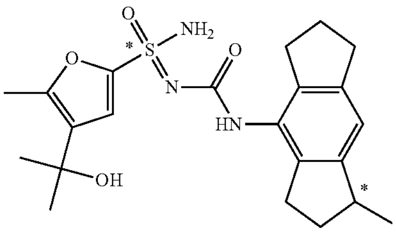 | (R,S) or (R,R)-4-(2-hydroxy-propan-2-yl)-5-methyl-N'-((3-methyl-1,2,3,5,6,7-hexahydro-s-indacen-4-yl) carbamoyl) furan-2-sulfonimi-damide; resolved from example 123 | CHIRAL-PAK IG, 20*250 mm, 5 um | EtOH in Hex (0.1% FA) | 432 |
| 306 | 366a | 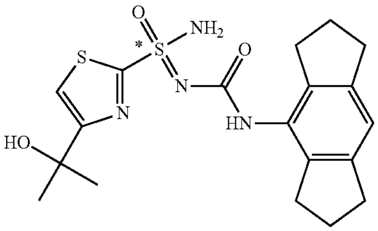 | (R) or (S)-N'-((1,2,3,5,6,7-hexahydro-s-indacen-4-yl) carbamoyl)-4-(2-hydroxy-propan-2-yl) thiazole-2-sulfonimi-damide | CHIRAL-PAK AS-H, 2*25 cm (5 um) | 35% IPA (2 mM $NH_3$-MeOH) in $CO_2$ | 421 |
| 307 | 366b | 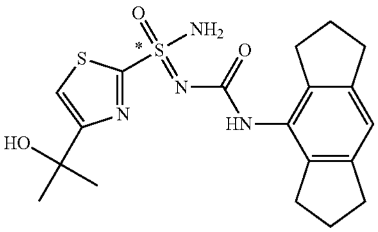 | (S) or (R)-N'-((1,2,3,5,6,7-hexahydro-s-indacen-4-yl) carbamoyl)-4-(2-hydroxy-propan-2-yl) thiazole-2-sulfonimi-damide | CHIRAL-PAK AS-H, 2*25 cm (5 um) | 35% IPA (2 mM $NH_3$-MeOH) in $CO_2$ | 421 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 308 | 139a | 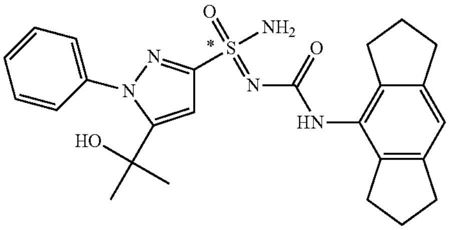 | (S) or (R)-N'-((1,2,3,5,6,7-hexahydro-s-indacen-4-yl) carbamoyl)-5-(2-hydroxy-propan-2-yl)-1-phenyl-1H-pyrazole-3-sulfonimi-damide | CHIRAL-PAK AS-H, 2*25 cm (5 um) | EtOH in Hex (0.1% DEA) | 480 |
| 309 | 139b | 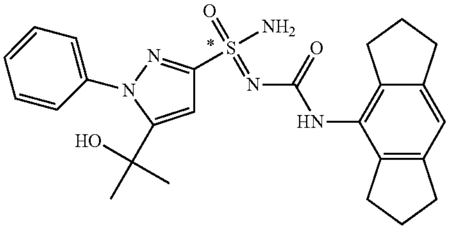 | (R) or (S)-N'-((1,2,3,5,6,7-hexahydro-s-indacen-4-yl) carbamoyl)-5-(2-hydroxy-propan-2-yl)-1-phenyl-1H-pyrazole-3-sulfonimi-damide | CHIRAL-PAK AS-H, 2*25 cm (5 um) | EtOH in Hex (0.1% DEA) | 480 |
| 310 | 367a | 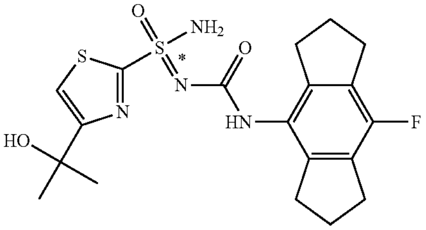 | (R) or (S)-N'-((8-fluoro-1,2,3,5,6,7-hexahydro-s-indacen-4-yl) carbamoyl)-4-(2-hydroxy-propan-2-yl) thiazole-2-sulfonimi-damide | Chiral-pak AS-H 2*25 cm (5 um) | 35% IPA in $CO_2$ | 439 |
| 311 | 367b | 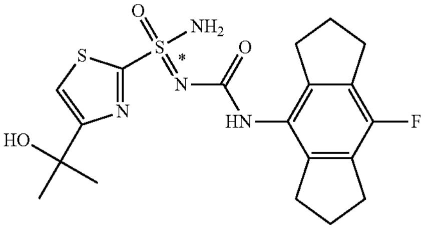 | (S) or (R)-N'-((8-fluoro-1,2,3,5,6,7-hexahydro-s-indacen-4-yl) carbamoyl)-4-(2-hydroxy-propan-2-yl) thiazole-2-sulfonimi-damide | Chiral-pak AS-H 2*25 cm (5 um) | 35% IPA in $CO_2$ | 439 |
| 312 | 409b | 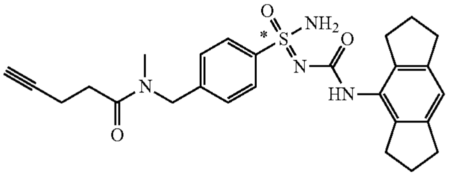 | (S) or (R)-N-(4-(N'-((1,2,3,5,6,7-hexahydro-s-indacen-4-yl) carbamoyl) sulfamidi-midoyl) benzyl)-N-methylpent-4-ynamide | CHIRAL ART Cellu-lose-SB, 2*25 cm, 5 um | EtOH in Hex (8 mM $NH_3$-MeOH) | 479 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 313 | 409a | 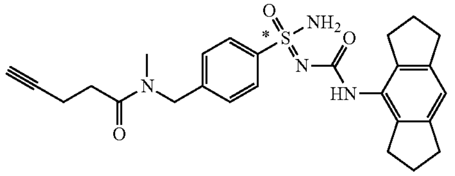 | (R) or (S)-N-(4-(N'-((1,2,3,5,6,7-hexahydro-s-indacen-4-yl) carbamoyl) sulfamidimidoyl) benzyl)-N-methylpent-4-ynamide | CHIRAL ART Cellulose-SB, 2*25 cm, 5 um | EtOH in Hex (8 mM $NH_3$• MeOH) | 479 |
| 314 | 369a | 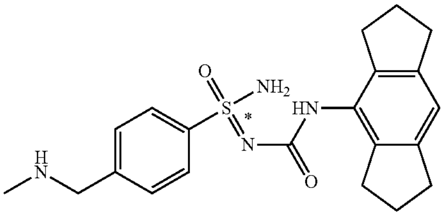 | (S) or (R)-N'-((1,2,3,5,6,7-hexahydro-s-indacen-4-yl) carbamoyl)-4-((methylamino)methyl) benzenesulfonimidamide | Chiralpak ID-2, 2*25 cm, 5 um | EtOH in Hex (8 mM $NH_3$• MeOH) | 399 |
| 315 | 369b | 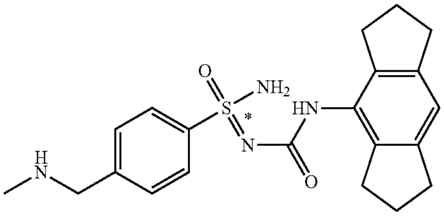 | (R) or (S)-N'-((1,2,3,5,6,7-hexahydro-s-indacen-4-yl) carbamoyl)-4-((methylamino)methyl) benzenesulfonimidamide | Chiralpak ID-2, 2*25 cm, 5 um | EtOH in Hex (8 mM $NH_3$• MeOH) | 399 |
| 316 | 159a | 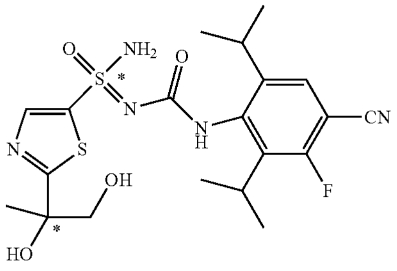 | Two isomers of (R,R) or (R,S) or (S,S) or (S,R)-N'-((4-cyano-3-fluoro-2,6-diisopropylphenyl) carbamoyl)-2-(1,2-dihydroxypropan-2-yl) thiazole-5-sulfonimidamide | CHIRAL ART Cellulose-SB, 2*25 cm, 5 um | EtOH in Hex (0.1% FA) 1st and 2nd peak | 484 |
| 317 | 159ab | 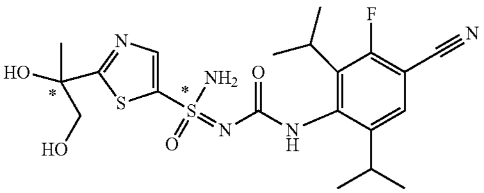 | (R,R) or (R,S) or (S,S) or (S,R)-N-((4-cyano-3-fluoro-2,6-diisopropylphenyl) carbamoyl)-2-(1,2-dihydroxy- | CHIRAL ART Cellulose-SB, 2*25 cm, 5 um | EtOH in Hex (0.1% FA) 3rd peak | 484 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M + H]^+$ |
|---|---|---|---|---|---|---|
| | | | propan-2-yl) thiazole-5-sulfonimidamide | | | |
| 318 | 159ba | 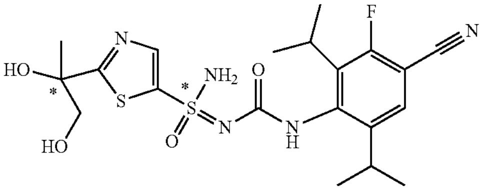 | (S,S) or (S,R) or (R,R) or (R,S)-N-((4-cyano-3-fluoro-2,6-diisopropylphenyl) carbamoyl)-2-(1,2-dihydroxypropan-2-yl) thiazole-5-sulfonimidamide | CHIRAL ART Cellulose-SB, 2*25 cm, 5 um | EtOH in Hex (0.1% FA) $4^{th}$ peak | 484 |
| 319 | 137a | 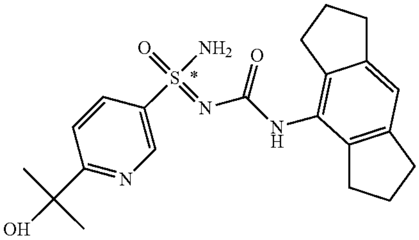 | (S) or (R)-N'-((1,2,3,5,6,7-hexahydro-s-indacen-4-yl) carbamoyl)-6-(2-hydroxypropan-2-yl) pyridine-3-sulfonimidamide | CHIRAL ART Cellulose-SB, 2*25 cm, 5 um | EtOH in Hex (0.1% FA) | 415 |
| 320 | 137b | 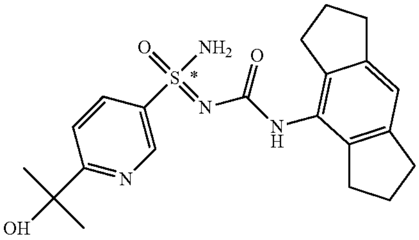 | (R) or (S)-N'-((1,2,3,5,6,7-hexahydro-s-indacen-4-yl) carbamoyl)-6-(2-hydroxypropan-2-yl) pyridine-3-sulfonimidamide | CHIRAL ART Cellulose-SB, 2*25 cm, 5 um | EtOH in Hex (0.1% FA) | 415 |
| 321 | 317ab | 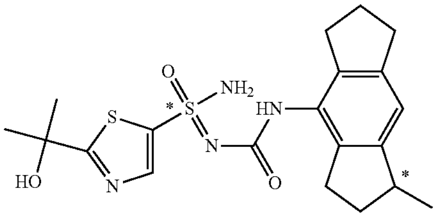 | (S,S) or (S,R)-2-(2-hydroxypropan-2-yl)-N'-((1-methyl-1,2,3,5,6,7-hexahydro-s-indacen-4-yl) carbamoyl) thiazole-5-sulfonimidamide (from Example 291) | $1^{st}$ and $2^{nd}$ peak (two isomers) Faster-eluting on column 1: CHIRAL ART Cellulose-SB, 2*25 cm, 5 um, IPA in Hex (0.1% FA). Separated further on column 2: CHIRALPAK IE, EtOH in MTBE (0.1% FA) to obtain single isomers. | | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 322 | 317aa | 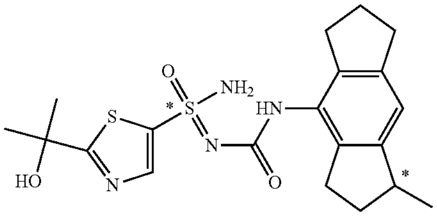 | (S,R) or (S,S)-2-(2-hydroxy-propan-2-yl)-N'-((1-methyl-1,2,3,5,6,7-hexahydro-s-indacen-4-yl) carbamoyl) thiazole-5-sulfonimi-damide (from Example 291) | | | 435 |
| 323 | 317bb | 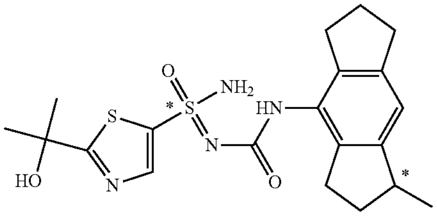 | (R,R) or (R,S)-2-(2-hydroxy-propan-2-yl)-N'-((1-methyl-1,2,3,5,6,7-hexahydro-s-indacen-4-yl) carbamoyl) thiazole-5-sulfonimi-damide (from Example 291) | CHIRAL ART Cellu-lose-SB, 2*25 cm, 5 um | IPA in Hex (0.1% FA) 3rd peak | 435 |
| 324 | 317ba | 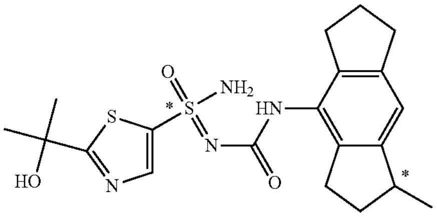 | (R,S) or (R,R)-2-(2-hydroxy-propan-2-yl)-N'-((1-methyl-1,2,3,5,6,7-hexahydro-s-indacen-4-yl) carbamoyl) thiazole-5-sulfonimi-damide (from Example 291) | | IPA in Hex (0.1% FA) 4th peak | 435 |
| 325 | 316a | 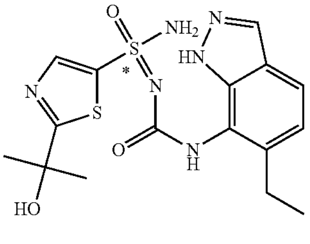 | (S) or (R)-N'-((6-ethyl-1H-indazol-7-yl) carbamoyl)-2-(2-hydroxy-propan-2-yl) thiazole-5-sulfonimi-damide | Chiral-pak ID, 2*25 cm, 5 um | EtOH in Hex (0.1% FA) | 409 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 326 | 316b | 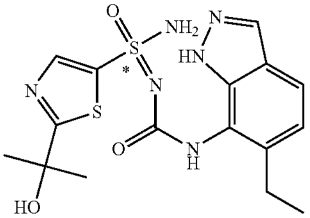 | (R) or (S)-N'-((6-ethyl-1H-indazol-7-yl) carbamoyl)-2-(2-hydroxy-propan-2-yl) thiazole-5-sulfonimidamide | Chiral-pak ID, 2*25 cm, 5 um | EtOH in Hex (0.1% FA) | 409 |
| 327 | 373a | 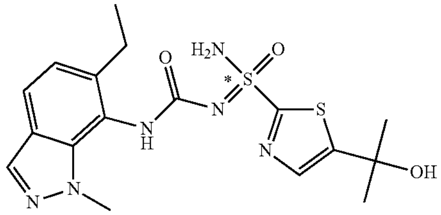 | (S) or (R)-N'-((6-ethyl-1-methyl-1H-indazol-7-yl) carbamoyl)-5-(2-hydroxy-propan-2-yl) thiazole-2-sulfonimidamide | CHIRAL-PAK IG, 20*250 mm, 5 um | EtOH in Hex (0.1% FA) | 423 |
| 328 | 373b | 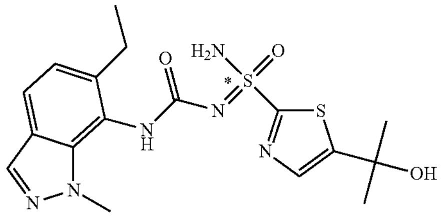 | (R) or (S)-N'-((6-ethyl-1-methyl-1H-indazol-7-yl) carbamoyl)-5-(2-hydroxy-propan-2-yl) thiazole-2-sulfonimidamide | CHIRAL-PAK IG, 20*250 mm, 5 um | EtOH in Hex (0.1% FA) | 423 |
| 329 | 374a | 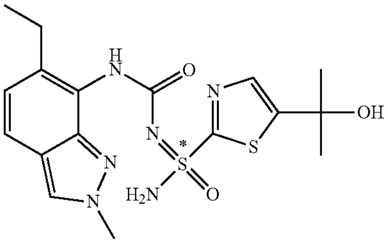 | (S) or (R)-N'-((6-ethyl-2-methyl-2H-indazol-7-yl) carbamoyl)-5-(2-hydroxy-propan-2-yl) thiazole-2-sulfonimidamide | CHIRAL ART Cellu-lose-SB S-5 um, 250*20 mm | EtOH in Hex (0.1% FA) | 423 |
| 330 | 374b | 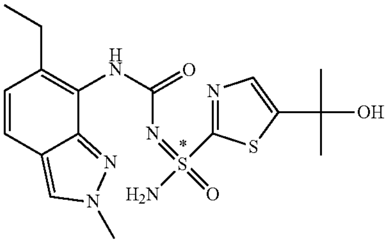 | (R) or (S)-N'-((6-ethyl-2-methyl-2H-indazol-7-yl) carbamoyl)-5-(2-hydroxy-propan-2-yl) thiazole-2-sulfonimidamide | CHIRAL ART Cellu-lose-SB S-5 um, 250*20 mm | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 331 | 319ab | 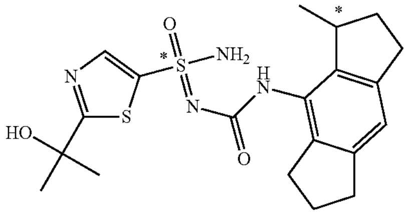 | (S,S) or (S,R)-2-(2-hydroxypropan-2-yl)-N'-((3-methyl-1,2,3,5,6,7-hexahydro-s-indacen-4-yl)carbamoyl)thiazole-5-sulfonimidamide | 1st peak CHIRAL ART Cellulose-SB, 2*25 cm, 5 um | EtOH in Hex (0.1% FA) | 435 |
| 332 | 319aa | 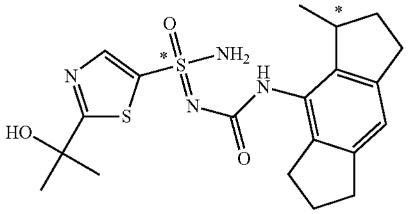 | (R,R) or (R,S)-2-(2-hydroxypropan-2-yl)-N'-((3-methyl-1,2,3,5,6,7-hexahydro-s-indacen-4-yl)carbamoyl)thiazole-5-sulfonimidamide | 2nd peak CHIRAL ART Cellulose-SB, 2*25 cm, 5 um | EtOH in Hex (0.1% FA) | 435 |
| 333 | 319bb | 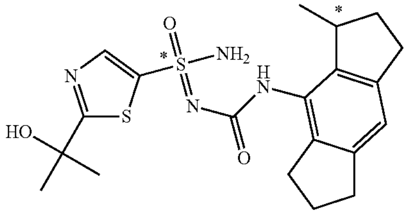 | (S,R) or (S,S)-2-(2-hydroxypropan-2-yl)-N'-((3-methyl-1,2,3,5,6,7-hexahydro-s-indacen-4-yl)carbamoyl)thiazole-5-sulfonimidamide | 3rd peak CHIRAL ART Cellulose-SB, 2*25 cm, 5 um | EtOH in Hex (0.1% FA) | 435 |
| 334 | 319ba | 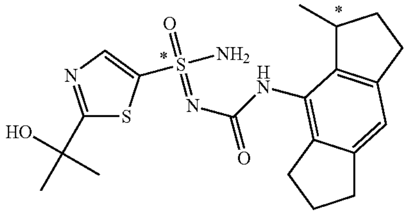 | (R,S) or (R,R)-2-(2-hydroxypropan-2-yl)-N'-((3-methyl-1,2,3,5,6,7-hexahydro-s-indacen-4-yl)carbamoyl)thiazole-5-sulfonimidamide | 4th peak CHIRAL ART Cellulose-SB, 2*25 cm, 5 um | EtOH in Hex (0.1% FA) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M + H]^+$ |
|---|---|---|---|---|---|---|
| 335 | 320a | 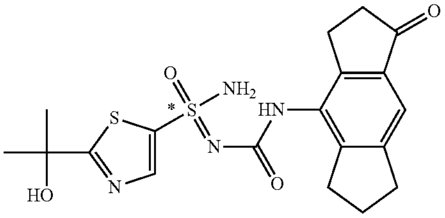 | (S) or (R)-2-(2-Hydroxy-propan-2-yl)-N'-((1-oxo-1,2,3,5,6,7-hexahydro-s-indacen-4-yl) carbamoyl) thiazole-5-sulfonimi-damide from Example 293 | Chiral-pak IA, 2*25 cm, 5 um | EtOH in Hex (0.1% FA) | 435 |
| 336 | 320b | 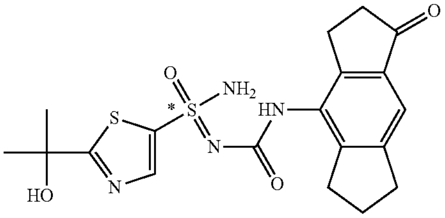 | (R) or (S)-2-(2-Hydroxy-propan-2-yl)-N'-((1-oxo-1,2,3,5,6,7-hexahydro-s-indacen-4-yl) carbamoyl) thiazole-5-sulfonimi-damide from Example 293 | Chiral-pak IA, 2*25 cm, 5 um | EtOH in Hex (0.1% FA) | 435 |
| 337 | 323ab | 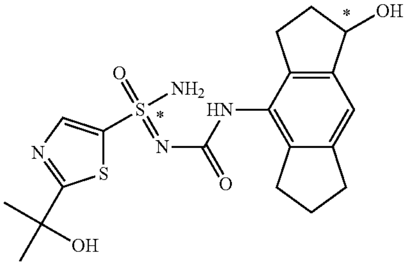 | (R,R) or (R,S)-N'-((1-hydroxy-1,2,3,5,6,7-hexahydro-s-indacen-4-yl) carbamoyl)-2-(2-hydroxy-propan-2-yl) thiazole-5-sulfonimi-damide (from example 336) | CHIRAL-PAK AD, 2*25 cm, 5 um | EtOH (0.1% DEA) in $CO_2$, $1^{st}$ peak | 437 |
| 338 | 323bb | 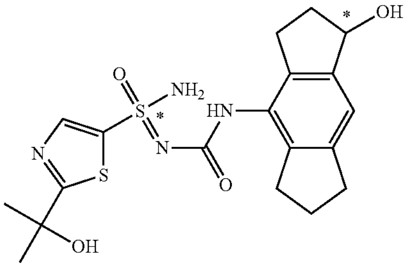 | (R,S) or (R,R)-N'-((1-hydroxy-1,2,3,5,6,7-hexahydro-s-indacen-4-yl) carbamoyl)-2-(2-hydroxy-propan-2-yl) thiazole-5-sulfonimi-damide (from example 336) | | EtOH (0.1% DEA) in $CO_2$, $2^{nd}$ peak | 437 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 339 | 323aa | 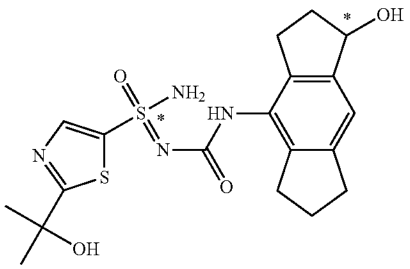 | (S,S) or (S,R)-N'-((1-hydroxy-1,2,3,5,6,7-hexahydro-s-indacen-4-yl) carbamoyl)-2-(2-hydroxy-propan-2-yl) thiazole-5-sulfonimidamide (from example 335) | CHIRALPAK AD, 2*25 cm, 5 um | EtOH (0.1% DEA) in $CO_2$, $1^{st}$ peak | 437 |
| 340 | 323ba | 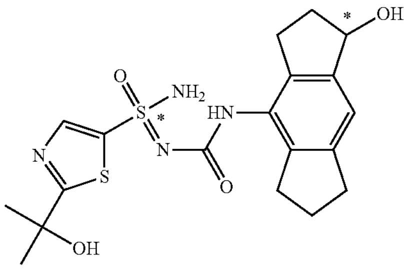 | (S,R) or (S,S)-N'-((1-hydroxy-1,2,3,5,6,7-hexahydro-s-indacen-4-yl) carbamoyl)-2-(2-hydroxy-propan-2-yl) thiazole-5-sulfonimidamide (from example 335) | | EtOH (0.1% DEA) in $CO_2$, $2^{nd}$ peak | 437 |
| 341 | 303a | 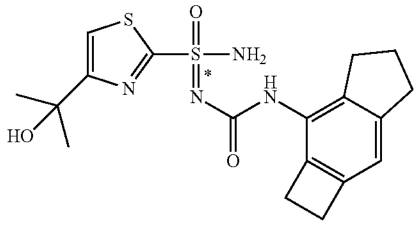 | (R) or (S)-4-(2-hydroxy-propan-2-yl)-N'-((2,4,5,6-tetrahydro-1H-cyclobuta [f]inden-3-yl) carbamoyl) thiazole-2-sulfonimidamide | Chiralpak ID, 2*25 cm, 5 um | EtOH in Hex (0.1% FA) | 407 |
| 342 | 303b | 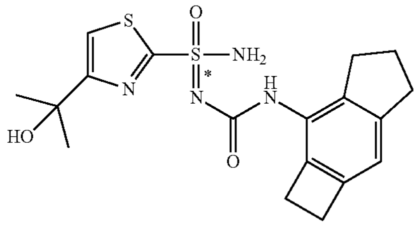 | (R) or (S)-4-(2-hydroxy-propan-2-yl)-N'-((2,4,5,6-tetrahydro-1H-cyclobuta [f]inden-3-yl) carbamoyl) thiazole-2-sulfonimidamide | Chiralpak ID, 2*25 cm, 5 um | EtOH in Hex (0.1% FA) | 407 |
| 343 | 315a | 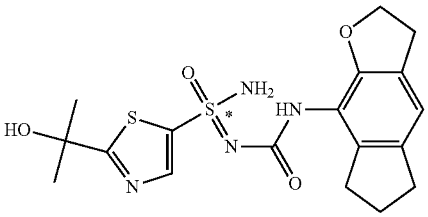 | (R) or (S)-2-(2-hydroxy-propan-2-yl)-N'-((3,5,6,7-tetrahydro-2H-indeno [5,6-b]furan-8-yl) carbamoyl) thiazole-5-sulfonimidamide | Chiralpak ID, 2*25 cm, 5 um | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 344 | 315b | 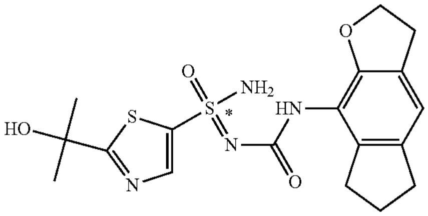 | (R) or (S)-2-(2-hydroxy-propan-2-yl)-N'-((3,5,6,7-tetrahydro-2H-indeno[5,6-b]furan-8-yl)carbamoyl)thiazole-5-sulfonimidamide | Chiral-pak ID, 2*25 cm, 5 um | EtOH in Hex (0.1% FA) | 423 |
| 345 | 138a | 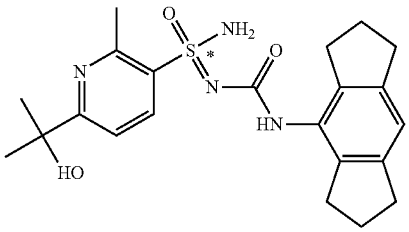 | (R) or (S)-N'-((1,2,3,5,6,7-hexahydro-s-indacen-4-yl)carbamoyl)-6-(2-hydroxy-propan-2-yl)-2-methyl-pyridine-3-sulfonimidamide | CHIRAL-PAK IF, 2*25 cm, 5 um | EtOH in Hex (8 mM $NH_3$-MeOH) | 429 |
| 346 | 138b | 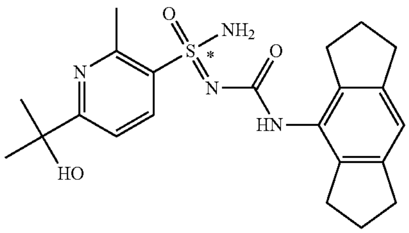 | (R) or (S)-N'-((1,2,3,5,6,7-hexahydro-s-indacen-4-yl)carbamoyl)-6-(2-hydroxy-propan-2-yl)-2-methyl-pyridine-3-sulfonimidamide | CHIRAL-PAK IF, 2*25 cm, 5 um | EtOH in Hex (8 mM $NH_3$• MeOH) | 429 |
| 347 | 328a | 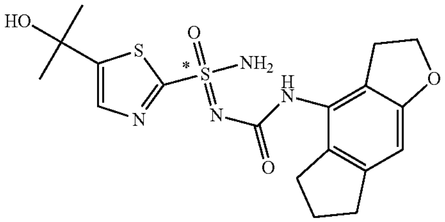 | (R) or (S)-5-(2-hydroxy-propan-2-yl)-N'-((3,5,6,7-tetrahydro-2H-indeno[5,6-b]furan-4-yl)carbamoyl)thiazole-2-sulfonimidamide | CHIRAL-PAK IC, 2*25 cm, 5 um | EtOH in Hex (0.1% FA) | 423 |
| 348 | 328b | 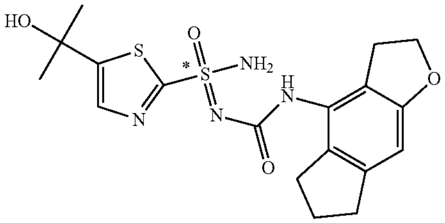 | (S) or (R)-5-(2-hydroxy-propan-2-yl)-N'-((3,5,6,7-tetrahydro-2H-indeno[5,6-b]furan-4-yl)carbamoyl)thiazole-2-sulfonimidamide | CHIRAL-PAK IC, 2*25 cm, 5 um | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 349 | 326b | 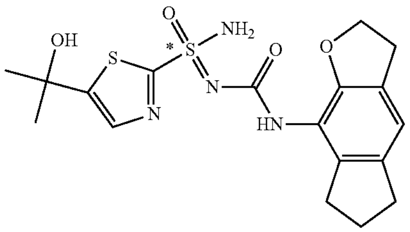 | (S) or (R)-5-(2-hydroxy-propan-2-yl)-N'-((3,5,6,7-tetrahydro-2H-indeno[5,6-b]furan-8-yl)carbamoyl)thiazole-2-sulfonimidamide | CHIRAL-PAK IG, 20*250 mm, 5 um | IPA in Hex: DCM = 5:1 (0.1% FA) | 423 |
| 350 | 326a | 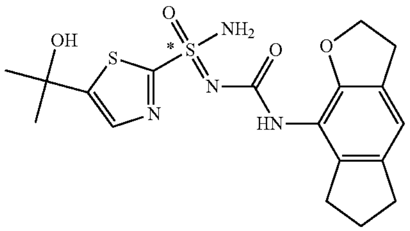 | (R) or (S)-5-(2-hydroxy-propan-2-yl)-N'-((3,5,6,7-tetrahydro-2H-indeno[5,6-b]furan-8-yl)carbamoyl)thiazole-2-sulfonimidamide | CHIRAL-PAK IG, 20*250 mm, 5 um | IPA in Hex: DCM = 5:1 (0.1% FA) | 423 |
| 351 | 318a | 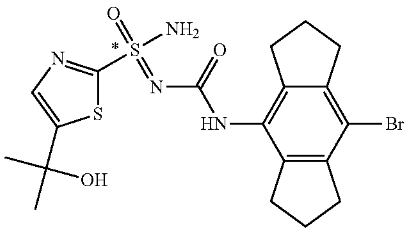 | (S) or (R)-N'-((8-bromo-1,2,3,5,6,7-hexahydro-s-indacen-4-yl)carbamoyl)-5-(2-hydroxy-propan-2-yl)thiazole-2-sulfonimidamide | CHIRAL ART Cellulose-SB S-5 um, 2*25 cm, 5 um | EtOH in Hex (8 mM $NH_3$•MeOH) | 499 |
| 352 | 318b | 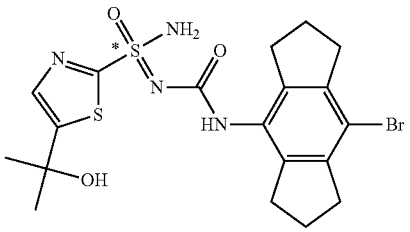 | (R) or (S)-N'-((8-bromo-1,2,3,5,6,7-hexahydro-s-indacen-4-yl)carbamoyl)-5-(2-hydroxy-propan-2-yl)thiazole-2-sulfonimidamide | CHIRAL ART Cellulose-SB S-5 um, 2*25 cm, 5 um | EtOH in Hex (8 mM $NH_3$•MeOH) | 499 |
| 353 | 325a | 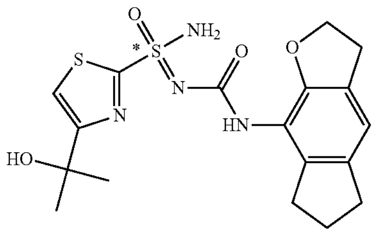 | (S) or (R)-4-(2-hydroxy-propan-2-yl)-N'-((3,5,6,7-tetrahydro-2H-indeno[5,6-b]furan-8-yl)carbamoyl)thiazole-2-sulfonimidamide | CHIRAL ART Cellulose-SB, 2*25 cm, 5 um | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 354 | 325b | 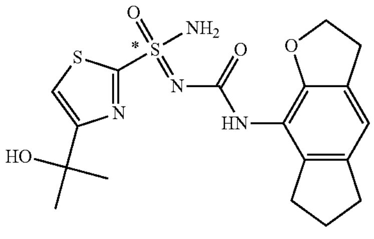 | (R) or (S)-4-(2-hydroxypropan-2-yl)-N'-((3,5,6,7-tetrahydro-2H-indeno[5,6-b]furan-8-yl)carbamoyl)thiazole-2-sulfonimidamide | CHIRAL ART Cellulose-SB, 2*25 cm, 5 um | EtOH in Hex (0.1% FA) | 423 |
| 355 | 329a | 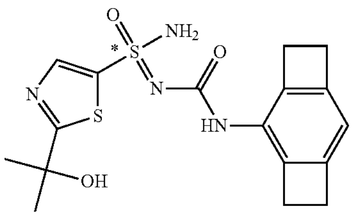 | (R) or (S)-2-(2-hydroxypropan-2-yl)-N'-(tricyclo[6.2.0.03,6]deca-1,3(6),7-trien-2-ylcarbamoyl)thiazole-5-sulfonimidamide | Chiralpak ID, 2*25 cm, 5 um | IPA in Hex (0.1% FA) | 393 |
| 356 | 329b | 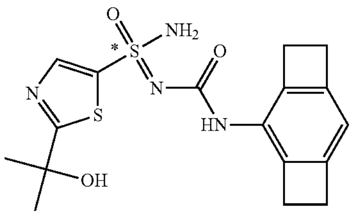 | (S) or (R)-2-(2-hydroxypropan-2-yl)-N'-(tricyclo[6.2.0.03,6]deca-1,3(6),7-trien-2-ylcarbamoyl)thiazole-5-sulfonimidamide | Chiralpak ID, 2*25 cm, 5 um | IPA in Hex (0.1% FA) | 393 |
| 357 | 404b | 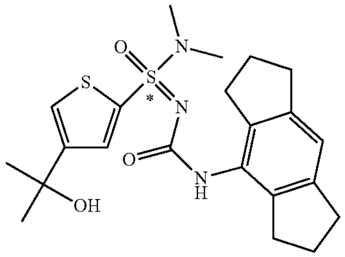 | (R) or (S)-N'-((1,2,3,5,6,7-hexahydro-s-indacen-4-yl)carbamoyl)-4-(2-hydroxypropan-2-yl)-N,N-dimethylthiophene-2-sulfonimidamide | CHIRALPAK IG, 20*250 mm, 5 um | IPA in Hex: DCM = 3:1 (10 mM $NH_3$-MeOH) | 448 |
| 358 | 404a | 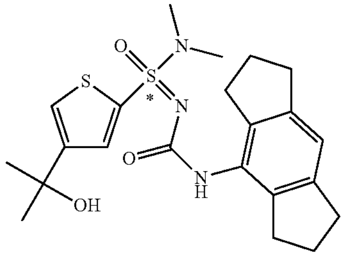 | (S) or (R)-N'-((1,2,3,5,6,7-hexahydro-s-indacen-4-yl)carbamoyl)-4-(2-hydroxypropan-2-yl)-N,N-dimethylthiophene-2-sulfonimidamide | CHIRALPAK IG, 20*250 mm, 5 um | IPA in Hex: DCM = 3:1 (10 mM $NH_3$-MeOH) | 448 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 359 | 332a | 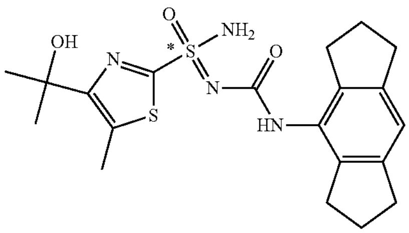 | (R) or (S)-N'-((1,2,3,5,6,7-hexahydro-s-indacen-4-yl) carbamoyl)-4-(2-hydroxy-propan-2-yl)-5-methyl-thiazole-2-sulfonimidamide | Chiralpak ID, 2*25 cm, 5 um | IPA in Hex (0.1% FA) | 435 |
| 360 | 332b | 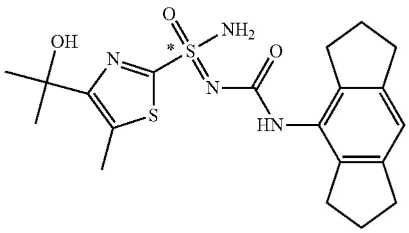 | (S) or (R)-N'-((1,2,3,5,6,7-hexahydro-s-indacen-4-yl) carbamoyl)-4-(2-hydroxy-propan-2-yl)-5-methyl-thiazole-2-sulfonimidamide | Chiralpak ID, 2*25 cm, 5 um | IPA in Hex (0.1% FA) | 435 |
| 361 | 335a | 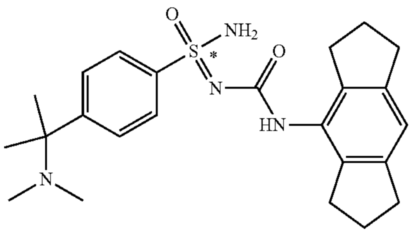 | (R) or (S)-4-(2-(dimethyl-amino) propan-2-yl)-N'-((1,2,3,5,6,7-hexahydro-s-indacen-4-yl) carbamoyl) benzene-sulfonimidamide | CHIRALPAK IG, 2.0*25 cm (5 um) | IPA in Hex (8 mM $NH_3$-MeOH) | 441 |
| 362 | 335b | 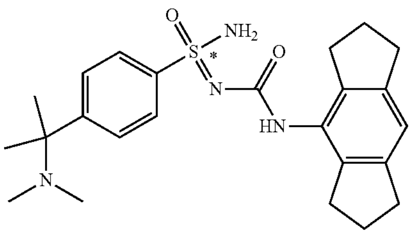 | (S) or (R)-4-(2-(dimethyl-amino) propan-2-yl)-N'-((1,2,3,5,6,7-hexahydro-s-indacen-4-yl) carbamoyl) benzene-sulfonimidamide | CHIRALPAK IG, 2.0*25 cm (5 um) | IPA in Hex (8 mM $NH_3$-MeOH) | 441 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 363 | 336a | 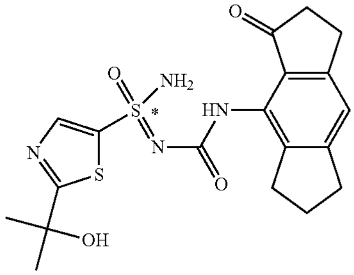 | (S) or (R)-2-(2-Hydroxy-propan-2-yl)-N'-((3-oxo-1,2,3,5,6,7-hexahydro-s-indacen-4-yl) carbamoyl) thiazole-5-sulfonimi-damide | CHIRAL ART Cellu-lose-SB, 2*25 cm, 5 um | EtOH in MTBE (10 mM $NH_3$-MeOH) | 435 |
| 364 | 336b | 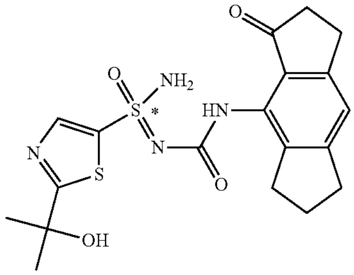 | (R) or (S)-2-(2-Hydroxy-propan-2-yl)-N'-((3-oxo-1,2,3,5,6,7-hexahydro-s-indacen-4-yl) carbamoyl) thiazole-5-sulfonimi-damide | CHIRAL ART Cellu-lose-SB, 2*25 cm, 5 um | EtOH in MTBE (10 mM $NH_3$-MeOH) | 435 |
| 365 | 337a | 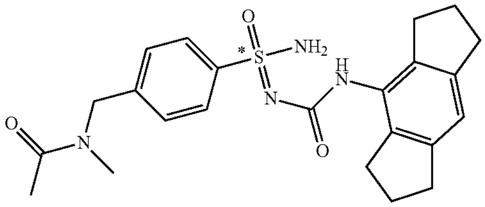 | (S) or (R)-N-(4-(N'-((1,2,3,5,6,7-hexahydro-s-indacen-4-yl) carbamoyl) sulfamidimi-doyl)benzyl)-N-methyl-acetamide | CHIRAL ART Cellu-lose-SB, 2*25 cm, 5 um | EtOH in Hex (8 mM $NH_3$-MeOH) | 441 |
| 366 | 337b | 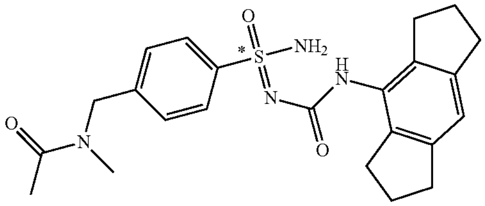 | (R) or (S)-N-(4-(N'-((1,2,3,5,6,7-hexahydro-s-indacen-4-yl) carbamoyl) sulfamidimi-doyl)benzyl)-N-methyl-acetamide | CHIRAL ART Cellu-lose-SB, 2*25 cm, 5 um | EtOH in Hex (8 mM $NH_3$-MeOH) | 441 |
| 367 | 371a | 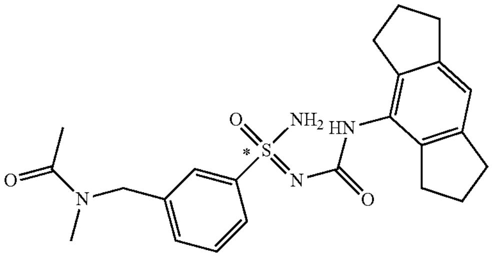 | (S) or (R)-N-(3-(N'-((1,2,3,5,6,7-hexahydro-s-indacen-4-yl) carbamoyl) sulfamidimi-doyl)benzyl)-N-methyl-acetamide | CHIRAL ART Cellu-lose-SB, 2*25 cm, 5 um | EtOH in Hex (8 mM $NH_3$-MeOH) | 441 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 368 | 371b | 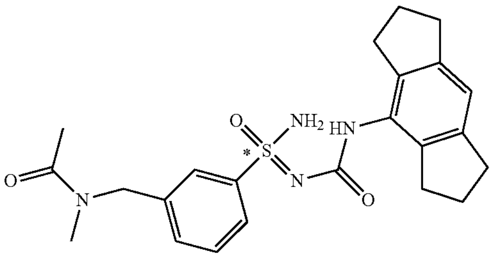 | (R) or (S)-N-(3-(N'-((1,2,3,5,6,7-hexahydro-s-indacen-4-yl)carbamoyl)sulfamidimidoyl)benzyl)-N-methylacetamide | CHIRAL ART Cellulose-SB, 2*25 cm, 5 um | EtOH in Hex (8 mM $NH_3$-MeOH) | 441 |
| 369 | 372a | 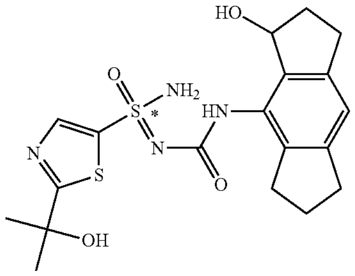 | (S,R/S) or (R,R/S)-N'-((3-hydroxy-1,2,3,5,6,7-hexahydro-s-indacen-4-yl)carbamoyl)-2-(2-hydroxypropan-2-yl)thiazole-5-sulfonimidamide | Obtained from Example 363 | N/A | 435 (M − 1) |
| 370 | 372b | 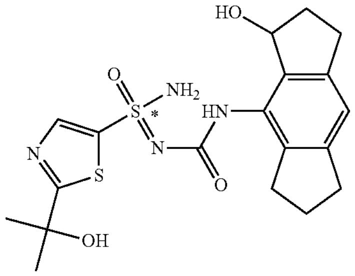 | (R,R/S) or (S,R/S)-N'-((3-hydroxy-1,2,3,5,6,7-hexahydro-s-indacen-4-yl)carbamoyl)-2-(2-hydroxypropan-2-yl)thiazole-5-sulfonimidamide | Obtained from Example 364 | N/A | 435 (M − 1) |
| 371 | 334a | 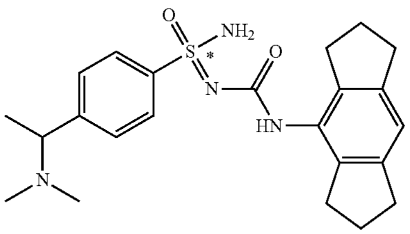 | (S) or (R)-4-(1-(dimethylamino)ethyl)-N'-((1,2,3,5,6,7-hexahydro-s-indacen-4-yl)carbamoyl)benzenesulfonimidamide | CHIRAL ART Cellulose-SB, 2*25 cm, 5 um | IPA in Hex (8 mM $NH_3$-MeOH) | 427 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 372 | 334b | 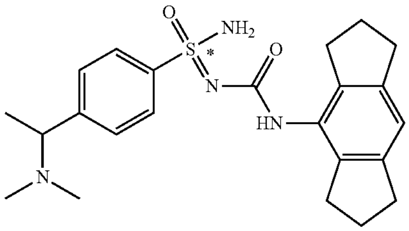 | (R) or (S)-4-(1-(dimethyl-amino) ethyl)-N'-((1,2,3,5,6,7-hexahydro-s-indacen-4-yl) carbamoyl) benzene-sulfonimi-damide | CHIRAL ART Cellu-lose-SB, 2*25 cm, 5 um | IPA in Hex (8 mM $NH_3$-MeOH) | 427 |
| 373 | 339a | 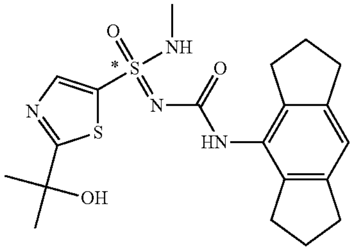 | (R) or (S)-N'-((1,2,3,5,6,7-hexahydro-s-indacen-4-yl) carbamoyl)-2-(2-hydroxy-propan-2-yl)-N-methyl-thiazole-5-sulfonimi-damide | CHIRAL-PAK IE, 2*25 cm, 5 um | IPA in Hex (8 mM $NH_3$-MeOH) | 435 |
| 374 | 339b | 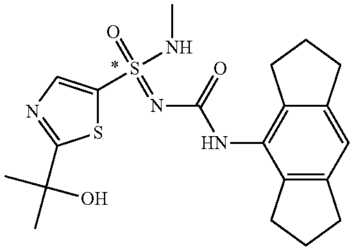 | (S) or (R)-N'-((1,2,3,5,6,7-hexahydro-s-indacen-4-yl) carbamoyl)-2-(2-hydroxy-propan-2-yl)-N-methyl-thiazole-5-sulfonimi-damide | CHIRAL-PAK IE, 2*25 cm, 5 um | IPA in Hex (8 mM $NH_3$-MeOH) | 435 |
| 375 | 334ab | 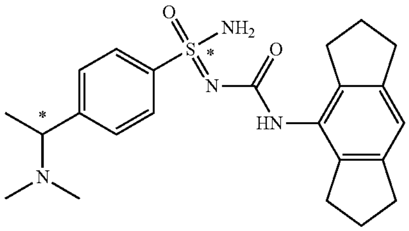 | (S,R) or (S,S) or (R,S) or (R,R)-4-(1-(dimethyl-amino) ethyl)-N'-((1,2,3,5,6,7-hexahydro-s-indacen-4-yl) carbamoyl) benzene-sulfonimi-damide | CHIRAL-PAK IG, 20*250 mm, 5 um | EtOH in Hex (8 mM $NH_3$-MeOH) | 427 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 376 | 334aa | 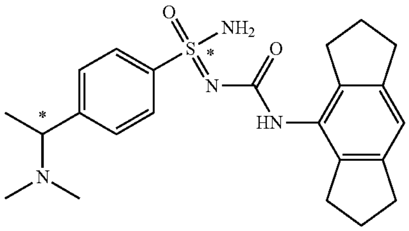 | (S,S) or (S,R) or (R,R) or (R,S)-4-(1-(dimethyl-amino) ethyl)-N'-((1,2,3,5,6,7-hexahydro-s-indacen-4-yl) carbamoyl) benzene-sulfonimi-damide | CHIRAL-PAK IG, 20*250 mm, 5 um | EtOH in Hex (8 mM $NH_3$-MeOH) | 427 |
| 377 | 334bb | 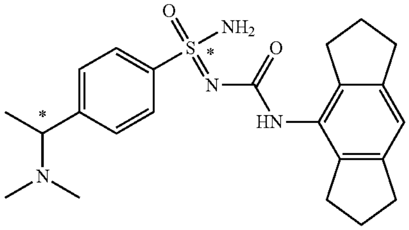 | (R,R) or (R,S) or (S,S) or (S,R)-4-(1-(dimethyl-amino) ethyl)-N'-((1,2,3,5,6,7-hexahydro-s-indacen-4-yl) carbamoyl) benzene-sulfonimi-damide | CHIRAL-PAK IG, 20*250 mm, 5 um | EtOH in Hex (8 mM $NH_3$-MeOH) | 427 |
| 378 | 334ba | 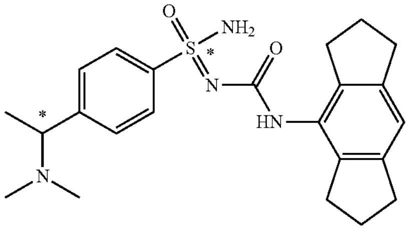 | (R,S) or (R,R) or (S,R) or (S,S)-4-(1-(dimethyl-amino) ethyl)-N'-((1,2,3,5,6,7-hexahydro-s-indacen-4-yl) carbamoyl) benzene-sulfonimi-damide | CHIRAL-PAK IG, 20*250 mm, 5 um | EtOH in Hex (8 mM $NH_3$-MeOH) | 427 |
| 379 | 338a | 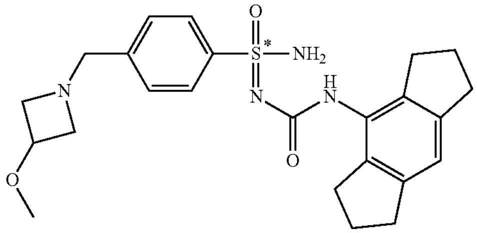 | (R) or (S)-N'-((1,2,3,5,6,7-hexahydro-s-indacen-4-yl) carbamoyl)-4-((3-methoxy-azetidin-1-yl) methyl) benzene-sulfonimi-damide | CHIRAL-PAK IF, 2*25 cm, 5 um | EtOH in Hex (8 mM $NH_3$-MeOH) | 455 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M + H]^+$ |
|---|---|---|---|---|---|---|
| 380 | 338b | 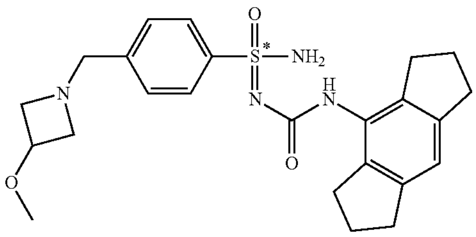 | (S) or (R)-N'-((1,2,3,5,6,7-hexahydro-s-indacen-4-yl) carbamoyl)-4-((3-methoxy-azetidin-1-yl) methyl) benzene-sulfonimi-damide | CHIRAL-PAK IF, 2*25 cm, 5 um | EtOH in Hex (8 mM $NH_3$-MeOH) | 455 |
| 381 | 340a | 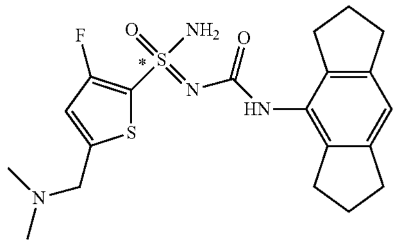 | (R) or (S)-5-((dimethyl-amino) methyl)-3-fluoro-N'-((1,2,3,5,6,7-hexahydro-s-indacen-4-yl) carbamoyl) thiophene-2-sulfonimi-damide | CHIRAL-PAK IG, 20*250 mm, 5 um | Hex (0.1% DEA): EtOH = 50:50 | 437 |
| 382 | 340b | 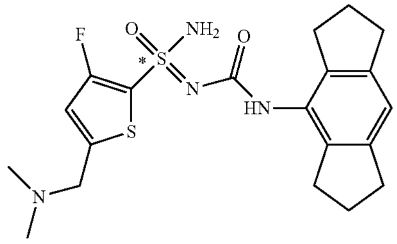 | (S) or (R)-5-((dimethyl-amino) methyl)-3-fluoro-N'-((1,2,3,5,6,7-hexahydro-s-indacen-4-yl) carbamoyl) thiophene-2-sulfonimi-damide | CHIRAL-PAK IG, 20*250 mm, 5 um | Hex (0.1% DEA): EtOH = 50:50 | 437 |
| 383 | 361b | 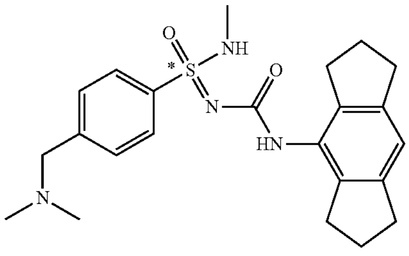 | (R) or (S)-4-((dimethyl-amino) methyl)-N'-((1,2,3,5,6,7-hexahydro-s-indacen-4-yl) carbamoyl)-N-methyl-benzene-sulfonimi-damide | CHIRAL-PAK IE, 2*25 cm, 5 um | EtOH in Hex (8 mM $NH_3$-MeOH) | 427 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 384 | 361a | 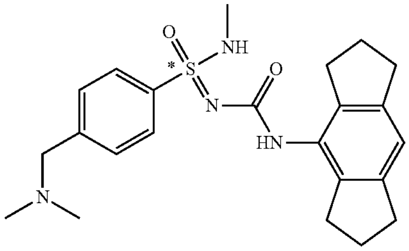 | (S) or (R)-4-((dimethylamino)methyl)-N'-((1,2,3,5,6,7-hexahydro-s-indacen-4-yl)carbamoyl)-N-methylbenzenesulfonimidamide | CHIRALPAK IE, 2*25 cm, 5 um | EtOH in Hex (8 mM $NH_3$-MeOH) | 427 |
| 385 | 113a | 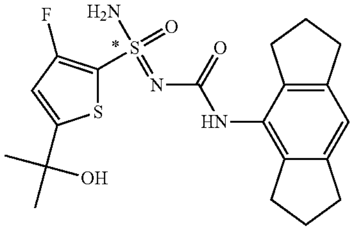 | (R) or (S)-3-fluoro-N'-((1,2,3,5,6,7-hexahydro-s-indacen-4-yl)carbamoyl)-5-(2-hydroxypropan-2-yl)thiophene-2-sulfonimidamide | CHIRALPAK IG, 20*250 mm, 5 um | IPA in Hex (8 mM $NH_3$-MeOH) | 438 |
| 386 | 113b | 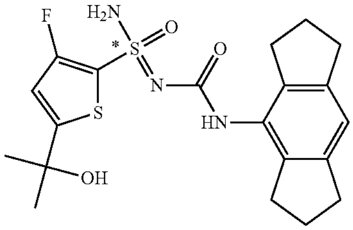 | (S) or (R)-3-fluoro-N'-((1,2,3,5,6,7-hexahydro-s-indacen-4-yl)carbamoyl)-5-(2-hydroxypropan-2-yl)thiophene-2-sulfonimidamide | CHIRALPAK IG, 20*250 mm, 5 um | IPA in Hex (8 mM $NH_3$-MeOH) | 438 |
| 387 | 330a | 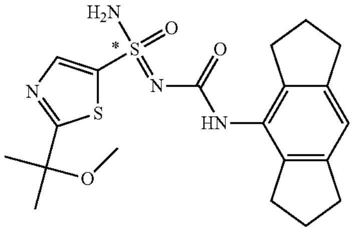 | (S) or (R)-N'-((1,2,3,5,6,7-hexahydro-s-indacen-4-yl)carbamoyl)-2-(2-methoxypropan-2-yl)thiazole-5-sulfonimidamide | CHIRAL ART Cellulose-SB, 2*25 cm, 5 um | EtOH in Hex (8 mM $NH_3$-MeOH) | 435 |
| 388 | 330b | 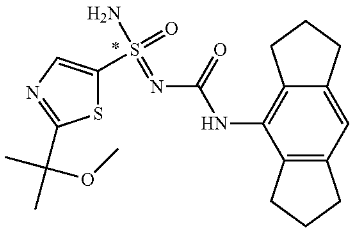 | (R) or (S)-N'-((1,2,3,5,6,7-hexahydro-s-indacen-4-yl)carbamoyl)-2-(2-methoxypropan-2-yl)thiazole-5-sulfonimidamide | CHIRAL ART Cellulose-SB, 2*25 cm, 5 um | EtOH in Hex (8 mM $NH_3$-MeOH) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 389 | 341a | 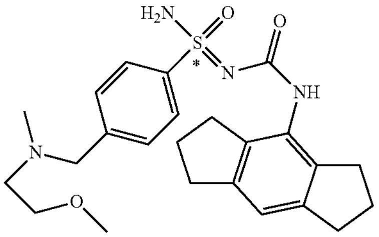 | (S) or (R)-N'-((1,2,3,5,6,7-hexahydro-s-indacen-4-yl) carbamoyl)-4-(((2-methoxy-ethyl) (methyl) amino) methyl) benzene-sulfonimi-damide | CHIRAL-Cellu-lose-SB 4.6*100 mm 3 um | Hex (0.1% DEA): EtOH = 70:30 | 457 |
| 390 | 341b | 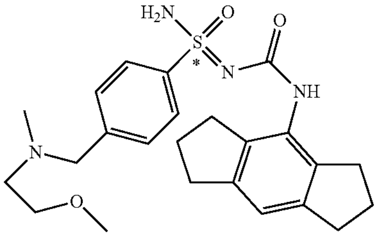 | (R) or (S)-N'-((1,2,3,5,6,7-hexahydro-s-indacen-4-yl) carbamoyl)-4-(((2-methoxy-ethyl) (methyl) amino) methyl) benzene-sulfonimi-damide | CHIRAL-Cellu-lose-SB 4.6*100 mm 3 um | Hex (0.1% DEA): EtOH = 70:30 | 457 |
| 391 | 360ba | 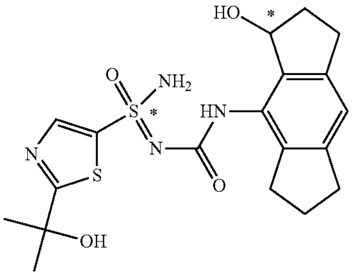 | (R,R) or (R,S) or (S,S) or (S,R)-N'-((3-hydroxy-1,2,3,5,6,7-hexahydro-s-indacen-4-yl) carbamoyl)-2-(2-hydroxy-propan-2-yl) thiazole-5-sulfonimi-damide (from Example 370) | CHIRAL-PAK IG, 20*250 mm, 5 um | EtOH in MTBE (10 mM $NH_3$-MeOH) | 437 |
| 392 | 360bb | 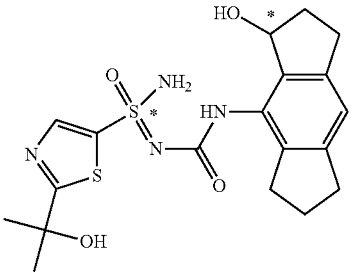 | (R,S) or (R,R) or (S,R) or (S,S)-N'-((3-hydroxy-1,2,3,5,6,7-hexahydro-s-indacen-4-yl) carbamoyl)-2-(2-hydroxy-propan-2-yl) thiazole-5-sulfonimi-damide (from Example 370) | CHIRAL-PAK IG, 20*250 mm, 5 um | EtOH in MTBE (10 mM $NH_3$-MeOH) | 437 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M + H]^+$ |
|---|---|---|---|---|---|---|
| 393 | 363b | 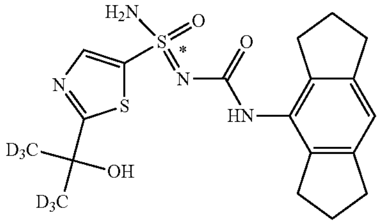 | (R)-N'-((1,2,3,5,6,7-hexahydro-s-indacen-4-yl) carbamoyl)-2-(2-hydroxy-propan-2-yl-1,1,1,3,3,3-$d_6$)thiazole-5-sulfonimidamide | CHIRAL-PAK IF, 2*25 cm, 5 um | 40% MeOH in $CO_2$ | 427 |
| 394 | 363a | 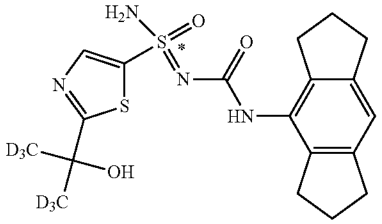 | (S)-N'-((1,2,3,5,6,7-hexahydro-s-indacen-4-yl) carbamoyl)-2-(2-hydroxy-propan-2-yl-1,1,1,3,3,3-$d_6$)thiazole-5-sulfonimidamide | CHIRAL-PAK IF, 2*25 cm, 5 um | 40% MeOH in $CO_2$ | 427 |
| 395 | 343a | 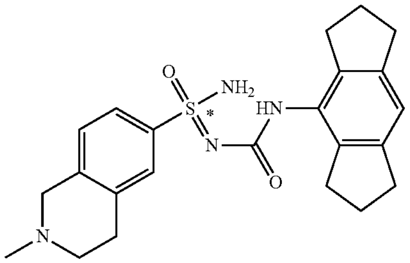 | (R) or (S)-N'-((1,2,3,5,6,7-hexahydro-s-indacen-4-yl) carbamoyl)-2-methyl-1,2,3,4-tetrahydro-isoquinoline-6-sulfonimidamide | CHIRAL-PAK IG, 20*250 mm, 5 um | EtOH in Hex (8 mM $NH_3$-MeOH | 425 |
| 396 | 343b | 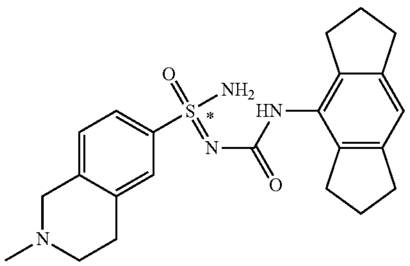 | (S) or (R)-N'-((1,2,3,5,6,7-hexahydro-s-indacen-4-yl) carbamoyl)-2-methyl-1,2,3,4-tetrahydro-isoquinoline-6-sulfonimidamide | CHIRAL-PAK IG, 20*250 mm, 5 um | EtOH in Hex (8 mM $NH_3$-MeOH | 425 |
| 397 | 359a | 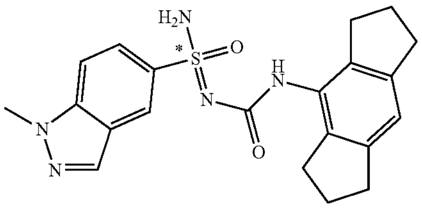 | (R) or (S)-N'-((1,2,3,5,6,7-hexahydro-s-indacen-4-yl) carbamoyl)-1-methyl-1H-indazole-5-sulfonimidamide | Chiral-pakID, 2*25 cm, 5 um | IPA in Hex: DCM = 3:1 (10 mM $NH_2$-MeOH) | 410 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 398 | 359b | 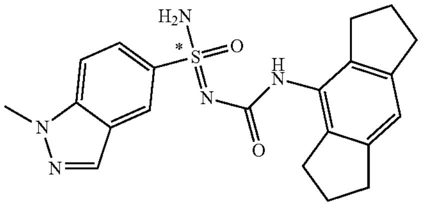 | (S) or (R)-N'-((1,2,3,5,6,7-hexahydro-s-indacen-4-yl) carbamoyl)-1-methyl-1H-indazole-5-sulfonimidamide | Chiral-pakID, 2*25 cm, 5 um | IPA in Hex: DCM = 3:1 (10 mM $NH_2$-MeOH) | 410 |
| 399 | 352a | 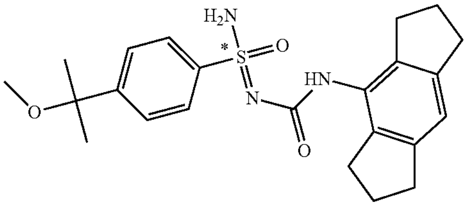 | (R) or (S)-N'-((1,2,3,5,6,7-hexahydro-s-indacen-4-yl) carbamoyl)-4-(2-methoxy-propan-2-yl) benzene-sulfonimidamide | CHIRAL-PAK IG, 2.0*25 cm (5 um) | Hex (0.1% DEA): IPA = 70:30 | 428 |
| 400 | 352b | 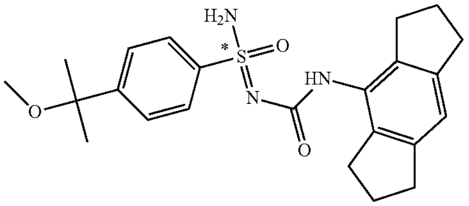 | (S) or (R)-N'-((1,2,3,5,6,7-hexahydro-s-indacen-4-yl) carbamoyl)-4-(2-methoxy-propan-2-yl) benzene-sulfonimidamide | CHIRAL-PAK IG, 2.0*25 cm (5 um) | Hex (0.1% DEA): IPA = 70:30 | 428 |
| 401 | 383a | 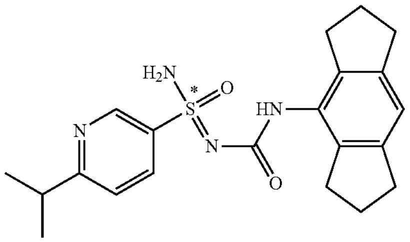 | (R) or (S)-N'-((1,2,3,5,6,7-hexahydro-s-indacen-4-yl) carbamoyl)-6-isopropyl-pyridine-3-sulfonimidamide | CHIRAL-PAK IG, 2*25 cm, 5 um | EtOH in Hex (8 mM $NH_3$-MeOH) | 399 |
| 402 | 383b | 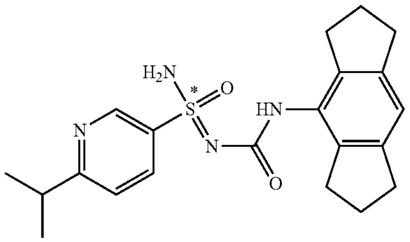 | (S) or (R)-N'-((1,2,3,5,6,7-hexahydro-s-indacen-4-yl) carbamoyl)-6-isopropyl-pyridine-3-sulfonimidamide | CHIRAL-PAK IG, 2*25 cm, 5 um | EtOH in Hex (8 mM $NH_3$-MeOH) | 399 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M+H]^+$ |
|---|---|---|---|---|---|---|
| 403 | 382a | 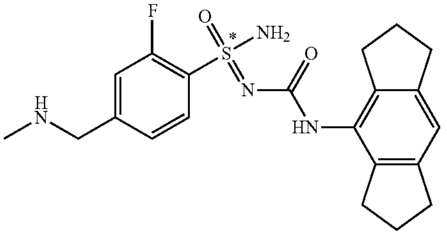 | (R) or (S)-2-fluoro-N'-((1,2,3,5,6,7-hexahydro-s-indacen-4-yl) carbamoyl)-4-((methyl-amino) methyl) benzene-sulfonimi-damide | CHIRAL-PAK IG, 2*25 cm, 5 um | EtOH in Hex (8 mM $NH_3$-MeOH) | 417 |
| 404 | 382b | 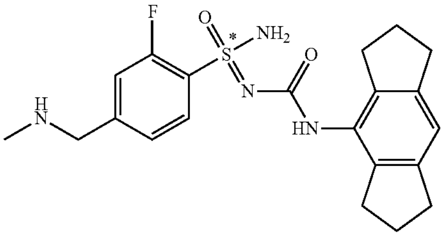 | (S) or (R)-2-fluoro-N'-((1,2,3,5,6,7-hexahydro-s-indacen-4-yl) carbamoyl)-4-((methyl-amino) methyl) benzene-sulfonimi-damide | CHIRAL-PAK IG, 2*25 cm, 5 um | EtOH in Hex (8 mM $NH_3$• MeOH) | 417 |
| 405 | 379a | 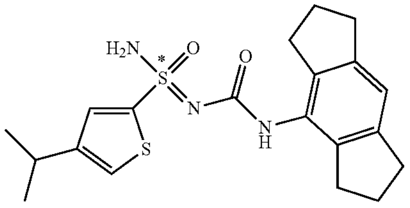 | (R) or (S)-N'-((1,2,3,5,6,7-hexahydro-s-indacen-4-yl) carbamoyl)-4-isopropyl-thiophene-2-sulfonimi-damide | CHIRAL-PAK IG, 2.0*25 cm (5 um) | EtOH in Hex (8 mM $NH_3$-MeOH) | 404 |
| 406 | 379b | 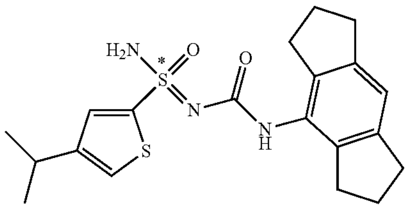 | (S) or (R)-N'-((1,2,3,5,6,7-hexahydro-s-indacen-4-yl) carbamoyl)-4-isopropyl-thiophene-2-sulfonimi-damide | CHIRAL-PAK IG, 2.0*25 cm (5 um) | EtOH in Hex (8 mM $NH_3$-MeOH) | 404 |
| 407 | 380a | 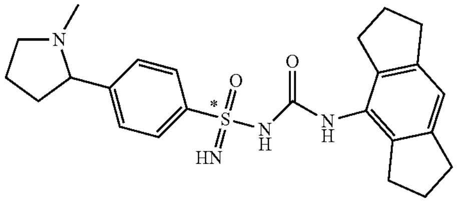 | (R,R) or (R,S) or (S,S) or (S,R)-N-((1,2,3,5,6,7-hexahydro-s-indacen-4-yl) carbamoyl)-4-(1-methyl-pyrrolidin-2-yl)benzene-sulfonimi-damide | CHIRAL-PAK IG, 20*250 mm, 5 um | IPA in Hex: DCM = 5:1 (10 mM $NH_3$-MeOH) | 439 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 408 | 380b | 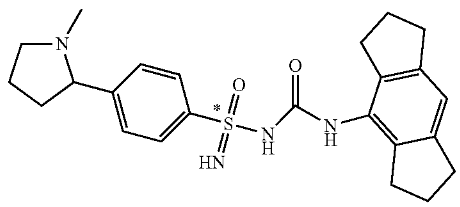 | (S,R) or (S,S) or (R,S) or (R,R)-N-((1,2,3,5,6,7-hexahydro-s-indacen-4-yl) carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM $NH_3$-MeOH) | 439 |
| 409 | 380c | 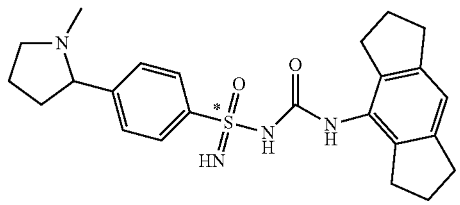 | (R,S) or (S,R) or (S,R) or (R,R)-N-((1,2,3,5,6,7-hexahydro-s-indacen-4-yl) carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM $NH_3$-MeOH) | 439 |
| 410 | 380d | 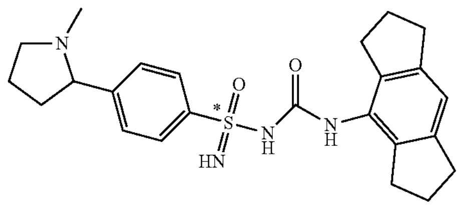 | (R,S) or (S,R) or (R,S or (S,S)-N-((1,2,3,5,6,7-hexahydro-s-indacen-4-yl) carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM $NH_3$-MeOH) | 439 |
| 411 | 384a | 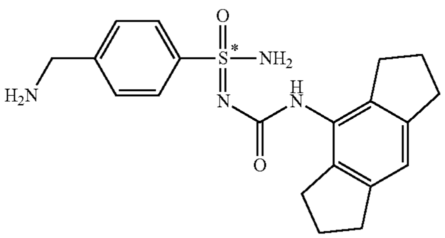 | (R) or (S)-4-(amino-methyl)-N'-((1,2,3,5,6,7-hexahydro-s-indacen-4-yl) carbamoyl) benzene-sulfonimidamide | CHIRAL-PAK IG, 2*25 cm, 5 um | EtOH in Hex (8 mM $NH_3$-MeOH) | 385 |
| 412 | 384b | 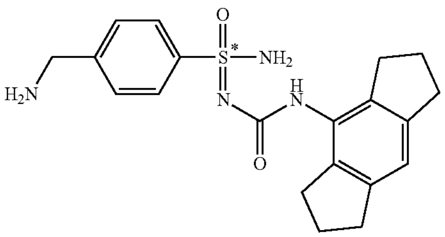 | (S) or (R)-4-(amino-methyl)-N'-((1,2,3,5,6,7-hexahydro-s-indacen-4-yl) carbamoyl) benzene-sulfonimidamide | CHIRAL-PAK IG, 2*25 cm, 5 um | EtOH in Hex (8 mM $NH_3$-MeOH) | 385 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS $[M + H]^+$ |
|---|---|---|---|---|---|---|
| 413 | 357a | 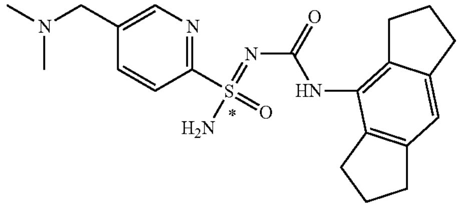 | (R) or (S)-5-((dimethyl-amino) methyl)-N'-((1,2,3,5,6,7-hexahydro-s-indacen-4-yl) carbamoyl) pyridine-2-sulfonimi-damide | CHIRAL-PAK AD-H, 2.0.*25 cm | EtOH in Hex (8 mM $NH_3$-MeOH) | 414 |
| 414 | 357b | 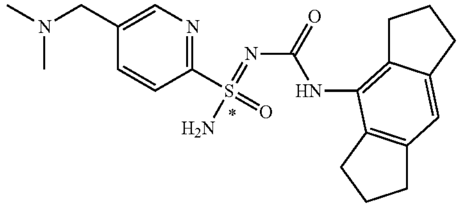 | (S) or (R)-5-((dimethyl-amino) methyl)-N'-((1,2,3,5,6,7-hexahydro-s-indacen-4-yl) carbamoyl) pyridine-2-sulfonimi-damide | CHIRAL-PAK AD-H, 2.0.*25 cm | EtOH in Hex (8 mM $NH_3$-MeOH) | 414 |
| 415 | 354a | 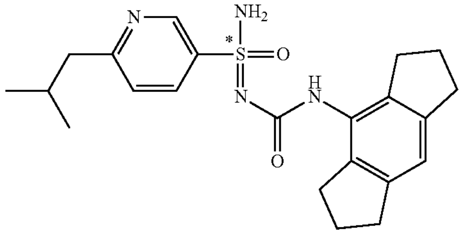 | (R) or (S)-N'-((1,2,3,5,6,7-hexahydro-s-indacen-4-yl) carbamoyl)-6-isobutyl-pyridine-3-sulfonimi-damide | CHIRAL ART Cellu-lose-SB, 2*25 cm, 5 um | EtOH in Hex (0.1% DEA) | 413 |
| 416 | 354b | 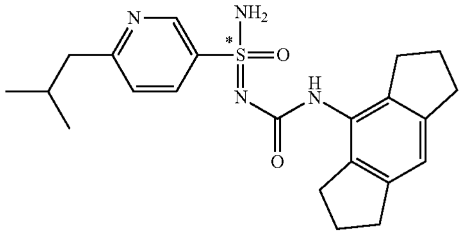 | (S) or (R)-N'-((1,2,3,5,6,7-hexahydro-s-indacen-4-yl) carbamoyl)-6-isobutyl-pyridine-3-sulfonimi-damide | CHIRAL ART Cellu-lose-SB, 2*25 cm, 5 um | EtOH in Hex (0.1% DEA) | 413 |
| 417 | 387a | 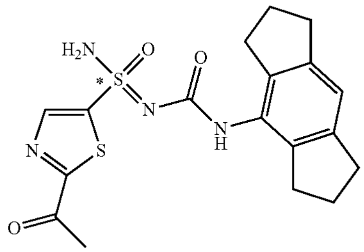 | (R) or (S)-2-acetyl-N'-((1,2,3,5,6,7-hexahydro-s-indacen-4-yl) carbamoyl) thiazole-5-sulfonimi-damide | CHIRAL ART Cellu-lose-SB, 2*25 cm, 5 um | IPA in $CO_2$ | 405 |

TABLE 28-continued

| Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2. | | | | | | |
|---|---|---|---|---|---|---|
| Ex. # | Final Target Number | Structure | IUPAC Name | Column | Eluents | LC-MS [M + H]+ |
| 418 | 387b | 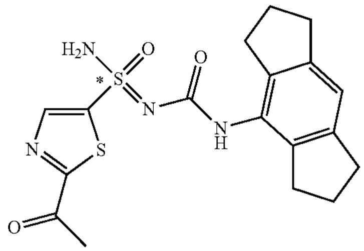 | (S) or (R)-2-acetyl-N'-((1,2,3,5,6,7-hexahydro-s-indacen-4-yl) carbamoyl) thiazole-5-sulfonimidamide | CHIRAL ART Cellulose-SB, 2*25 cm, 5 um | IPA in $CO_2$ | 405 |
| 419 | 333a | 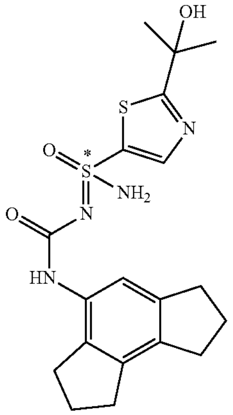 | (R) or (S)-N'-((1,2,3,6,7,8-hexahydro-as-indacen-4-yl) carbamoyl)-2-(2-hydroxy-propan-2-yl) thiazole-5-sulfonimidamide | CHIRAL-PAK IF, 5*25 cm, 5 um | EtOH in Hex (8 mM $NH_3$-MeOH) | 421 |
| 420 | 333b | 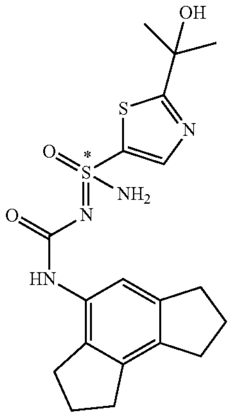 | (S) or (R)-N'-((1,2,3,6,7,8-hexahydro-as-indacen-4-yl) carbamoyl)-2-(2-hydroxy-propan-2-yl) thiazole-5-sulfonimidamide | CHIRAL-PAK IF, 5*25 cm, 5 um | EtOH in Hex (8 mM $NH_3$-MeOH) | 421 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 421 | 375a | 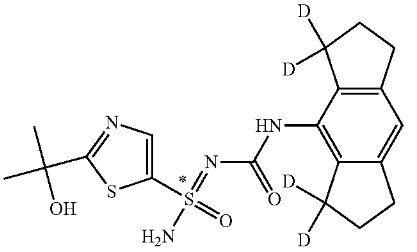 | (R) or (S)-N'-((1,2,3,5,6,7-hexahydro-s-indacen-4-yl-3,3,5,5-$d_4$) carbamoyl)-2-(2-hydroxy-propan-2-yl) thiazole-5-sulfonimidamide | CHIRAL-PAK IF, 2*25 cm, 5 um | MeOH (2 mM $NH_3$-MeOH) in $CO_2$ | 425 |
| 422 | 375b | 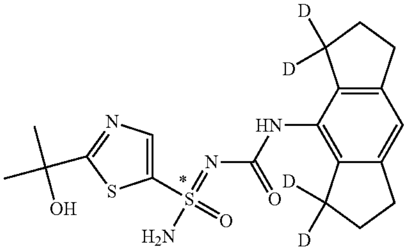 | (S) or (R)-N'-((1,2,3,5,6,7-hexahydro-s-indacen-4-yl-3,3,5,5-$d_4$) carbamoyl)-2-(2-hydroxy-propan-2-yl) thiazole-5-sulfonimidamide | CHIRAL-PAK IF, 2*25 cm, 5 um | MeOH (2 mM $NH_3$-MeOH) in $CO_2$ | 425 |
| 423 | 376a | 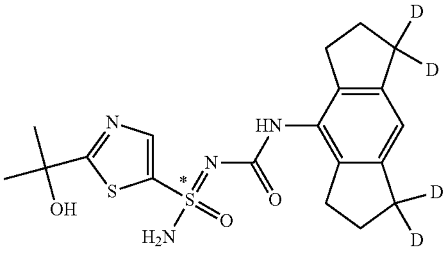 | (R) or (S)-N'-((1,2,3,5,6,7-hexahydro-s-indacen-4-yl-1,1,7,7-$d_4$) carbamoyl)-2-(2-hydroxy-propan-2-yl) thiazole-5-sulfonimidamide | CHIRAL-PAK ID, 2*25 cm (5 um) | MeOH (2 mM $NH_3$-MeOH) in $CO_2$ | 425 |
| 424 | 376b | 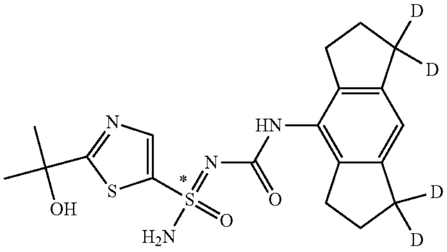 | (S) or (R)-N'-((1,2,3,5,6,7-hexahydro-s-indacen-4-yl-1,1,7,7-$d_4$) carbamoyl)-2-(2-hydroxy-propan-2-yl) thiazole-5-sulfonimidamide | CHIRAL-PAK ID, 2*25 cm (5 um) | MeOH (2 mM $NH_3$-MeOH) in $CO_2$ | 425 |

#The amount of $NH_3$ in this chiral chromatographic solvent and similar solvents were adjusted by adding 2M $NH_3$ in methanol to the desired $NH_3$ concentration. In this case, the resulting concentration of $NH_3$ in methanol is 8 mM.

Example 425 (Compound 318)

1-{Amino[5-(2-hydroxypropan-2-yl)-1,3-thiazol-2-yl]oxo-λ$^6$-sulfanylidene}-3-(8-bromo-1,2,3,5,6,7-hexahydro-s-indacen-4-yl)urea

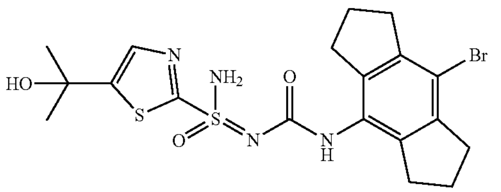

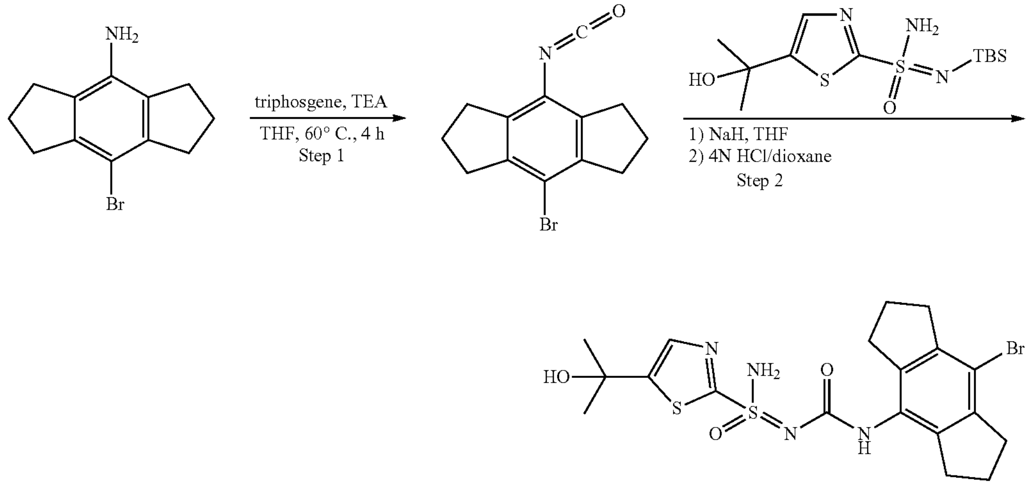

Step 1: 4-Bromo-1,2,3,5,6,7-hexahydro-8-isocyanato-s-indacene

To a solution of 8-bromo-1,2,3,5,6,7-hexahydros-indacen-4-amine (1.5 g, 5.94 mmol) in anhydrous THF (50 mL) was added triethylamine (1.07 mL, 7.73 mmol) and triphosgene (882 mg, 2.97 mmol) at room temperature. The resulting mixture was then stirred at 60° C. for 4 h. Reaction mixture was then brought to room temperature and used directly in the next step.

Step 2: 1-{Amino[5-(2-hydroxypropan-2-yl)-1,3-thiazol-2-yl]oxo-λ$^6$-sulfanylidene}-3-(8-bromo-1,2,3,5,6,7-hexahydro-s-indacen-4-yl)urea To a solution of N-(tert-butyldimethylsilyl)-5-(2-hydroxypropan-2-yl)-1,3-thiazole-2-sulfonoimidamide (400 mg, 1.2 mmol) in anhydrous THF (10 mL) was added NaH (60% wt. oil dispersioin, 96 mg, 2.4 mmol) at room temperature. After 5 min, a solution of 4-bromo-1,2,3,5,6,7-hexahydro-8-isocyanato-s-indacene (2 mL, 2 mmol, from Step 1) was added drop wise. The resulting mixture was stirred at room temperature for 20 min before quenching carefully with 4 M HCl solution in dioxane (3 mL). Saturated aqueous ammonium chloride was added and the mixture was extracted with dichloromethane (15 mL×3). The combined organic layers were washed with brine, dried over $MgSO_4$, filtered, and concentrated in vacuo. The crude product was purified by prep-HPLC to obtain the titled compound (280 mg, 47%). LCMS: $[M+H]^+$=499.3.

Example 426 (Compound 313)

1-{Amino[5-(2-hydroxypropan-2-yl)-1,3-thiazol-2-yl]oxo-λ$^6$-sulfanylidene}-3-[7-(3,4-dimethylphenyl)-2,3-dihydro-1H-inden-4-yl]urea

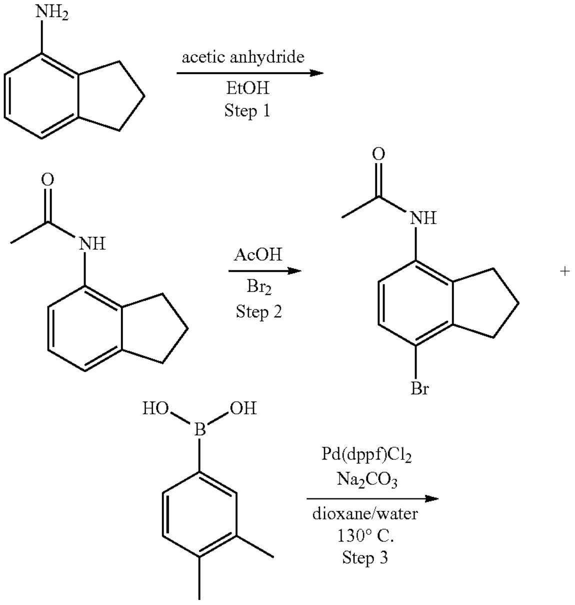

-continued

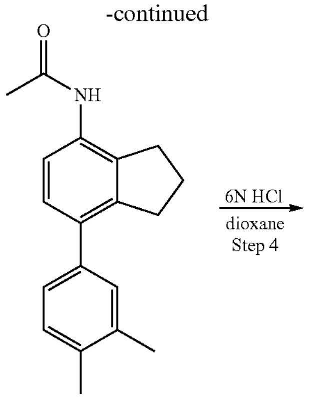

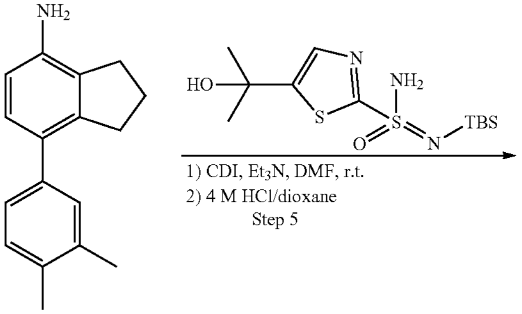

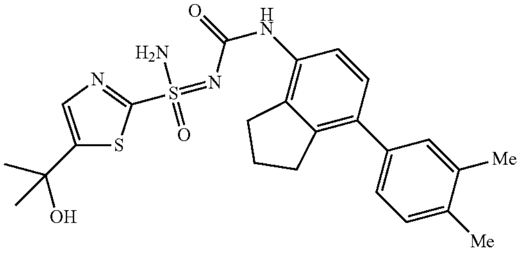 [SMILES: Cc1ccc(-c2ccc(NC(=O)N=S(N)(=O)c3ncc(C(C)(C)O)s3)c3c2CCC3)cc1C]

Step 1: N-(2,3-dihydro-1H-inden-4-yl)acetamide

To a solution of 2,3-dihydro-1H-inden-4-amine (3.4 g, 26 mmol) in ethanol (45 mL) was added a solution of acetic anhydride (4.9 mL, 52 mmol) in ethanol (15 mL) dropwise at 0° C. The resulting mixture was gradually warmed up to RT and stirred for 15 h. Solvent was removed under reduced pressure and the residue was triturated with diethyl ether to afford titled compound as off white solid (3 g, 66%). LCMS $[M+H]^+$=176.3.

Step 2: N-(4-bromo-2,3-dihydro-1H-inden-7-yl)acetamide

Into a 250-mL round-bottom flask was added N-(2,3-dihydro-1H-inden-4-yl)acetamide (3 g, 17.1 mmol) and acetic acid (45 mL). The resulting solution was cooled to 0° C. and then a solution of bromine (5.4 g, 34.2 mmol) in acetic acid (12 mL) was added dropwise with stirring over 10 min. The cooling bath was removed and the reaction mixture was stirred at RT for 1 h. Water was added and the resulting precipitates of product were collected by filtration and dried under vacuum to afford titled compound as off white solid (3.9 g, 90%). LCMS $[M+H]^+$=254.4.

Step 3: N-(2,3-dihydro-4-(3,4-dimethylphenyl)-1H-inden-7-yl)acetamide

A mixture of N-(4-bromo-2,3-dihydro-1H-inden-7-yl)acetamide (1 g, 3.9 mmol), 3,4-dimethylphenylboronic acid (700 mg, 4.68 mmol), Pd(dppf)$Cl_2$.DCM (160 mg, 0.19 mmol), sodium carbonate (900 mg, 8.58 mmol as 2 M aqueous solution) in dioxane (12 mL) was stirred at 100° C. in an oil bath for 72 h. The reaction mixture was brought to RT, water (20 mL) was added and extracted with EtOAc (15 mL×3). The combined organic layers were washed with brine, dried over $MgSO_4$, filtered, and concentrated in vacuo. The crude product was purified by silica gel flash chromatography using 0-30% gradient of EtOAc in hexanes to afford titled compound (880 mg, 81%). LCMS $[M+H]^+$=280.6.

Step 4: 2,3-Dihydro-7-(3,4-dimethylphenyl)-1H-inden-4-amine

A solution of N-(2,3-dihydro-4-(3,4-dimethylphenyl)-1H-inden-7-yl)acetamide (880 mg, 3.15 mmol) in 6 N HCl (20 mL) was stirred at 100° C. for 40 h. After consumption of the starting material, the reaction mixture was cooled to 0° C. and adjusted to pH=8 with 10 M aqueous sodium hydroxide solution. The precipitates formed were collected, washed with water and dried under vacuum to afford the titled compound (81 mg, 67%) as tan colored powder. LCMS $[M+H]^+$=238.3.

Step 5: 1-{Amino[5-(2-hydroxypropan-2-yl)-1,3-thiazol-2-yl]oxo-$\lambda^6$-sulfanylidene}-3-[7-(3,4-dimethylphenyl)-2,3-dihydro-1H-inden-4-yl]urea To a solution of N-(tert-butyldimethylsilyl)-5-(2-hydroxypropan-2-yl)-1,3-thiazole-2-sulfonoimidamide (42 mg, 0.13 mmol) in DMF (1 mL) was added $Et_3N$ (35 uL, 0.25 mmol) and the resulting mixture was stirred at room temperature for 10 min, followed by the addition of CDI (41 mg, 0.25 mmol). The reaction mixture was further stirred at RT for 1 h, and then 2,3-dihydro-7-(3,4-dimethylphenyl)-1H-inden-4-amine (30 mg, 0.13 mmol) was added. The resulting reaction mixture was stirred overnight at room temperature. The presence of desired product was then confirmed by LC-MS. The reaction mixture was quenched with 4 M HCl in dioxane (1 mL) and stirred for 30 min to de-protect the TBS group which indicated the formation of desired product on LCMS. The crude product was purified by preparative HPLC to provide titled compound (16.4 mg, 27%). LCMS $[M+H]^+$=485.49.

Example 427 (Compound 314)

1-{Amino[5-(2-hydroxypropan-2-yl)-1,3-thiazol-2-yl]oxo-$\lambda^6$-sulfanylidene}-3-[8-(3,4-dimethylphenyl)-1,2,3,5,6,7-hexahydro-s-indacen-4-yl]urea

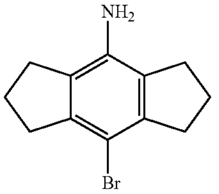

+

-continued

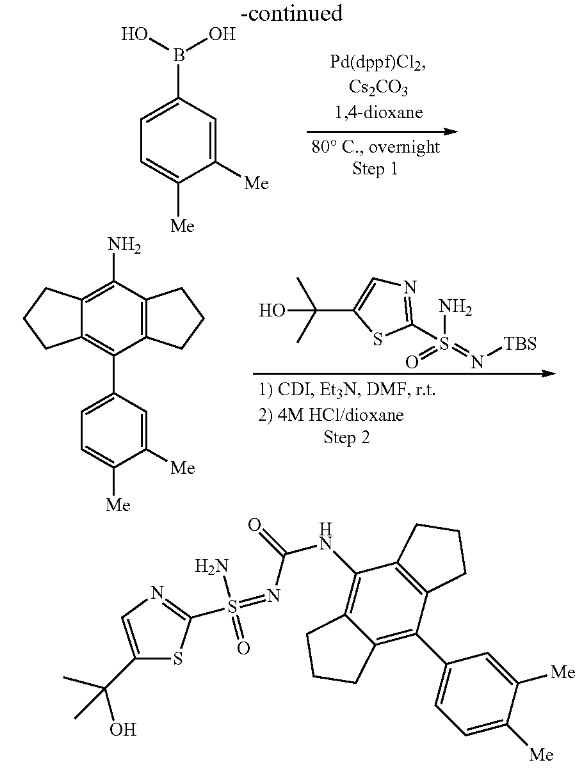

Step 1: 1,2,3,5,6,7-Hexahydro-8-(3,4-dimethylphenyl)-s-indacen-4-amine

8-Bromo-1,2,3,5,6,7-hexahydro-s-indacen-4-amine (105 mg, 0.42 mmol), 3,4-dimethylphenyl-boronic acid (187 mg, 1.25 mmol), $Pd(dppf)Cl_2$ (30.4 mg, 0.04 mmol) and dioxane (1.5 mL) were added to a reaction vial. Cesium carbonate (1.24 mL, 1 M in $H_2O$) was then added and the reaction mixture was stirred at 80° C. for 16 h. Reaction mixture was brought to RT and filtered through a small bed of Celite and rinsed with dioxane (5 mL). Water (5 mL) was added to the filtrates and extracted with diethyl ether (5 mL×3). The combined organic layers were washed with brine, dried over anhydrous $MgSO_4$, filtered, and concentrated in vacuo to provide titled compound which was used in the next step without any purification. LCMS $[M+H]^+$=278.4.

Step 2: 1-{Amino[5-(2-hydroxypropan-2-yl)-1,3-thiazol-2-yl]oxo-λ$^6$-sulfanylidene}-3-[8-(3,4-dimethylphenyl)-1,2,3,5,6,7-hexahydro-s-indacen-4-yl]urea

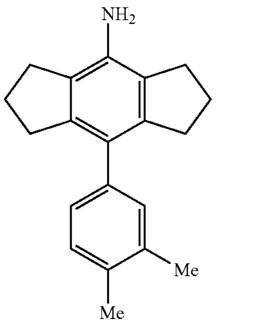

+

-continued

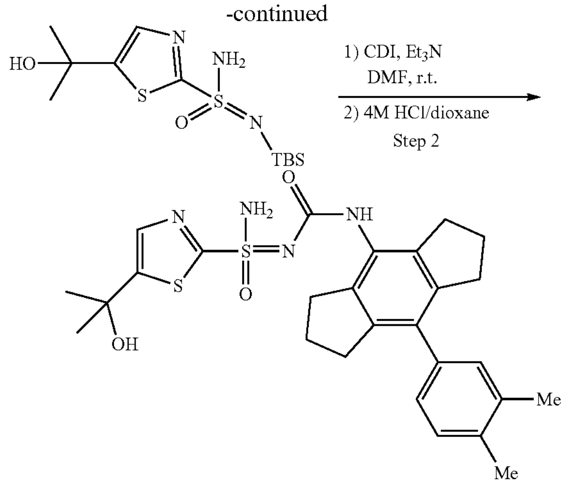

The title product was obtained using similar procedure as in Step 5 Example 426. LCMS: $[M+H]^+$=525.42.

Example 428 (Compound 309)

3-[Amino(dimethyl-1,3-thiazol-5-yl)oxo-λ$^6$-sulfanylidene]-1-[4-fluoro-2,6-bis(propan-2-yl)phenyl]urea

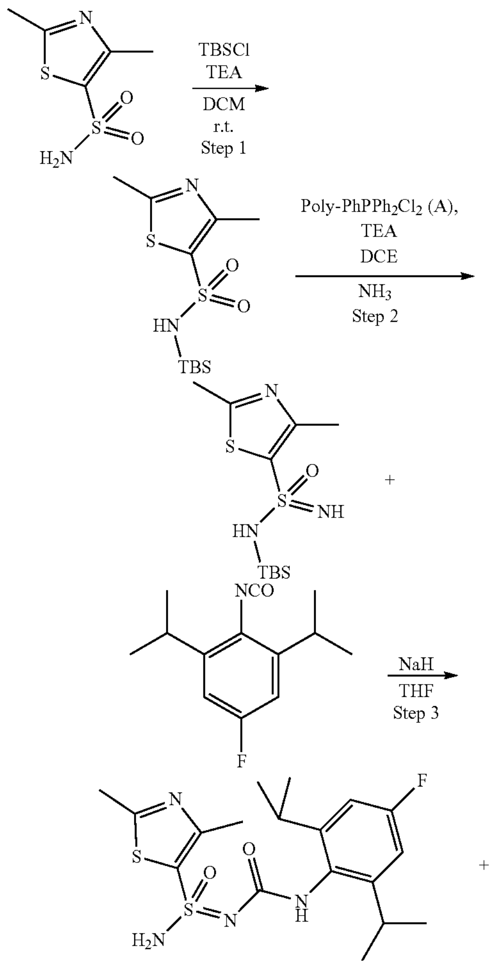

-continued

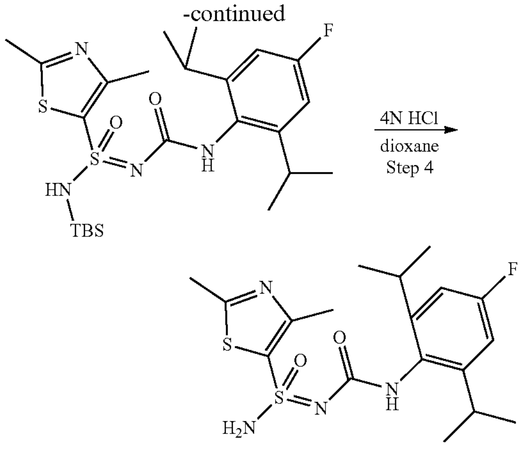

Step 1: N-(tert-butyldimethylsilyl)-2,4-dimethyl-1,3-thiazole-5-sulfonamide

Dimethyl-1,3-thiazole-5-sulfonamide (41.4 mg, 0.22 mmol) was dissolved in anhydrous $CH_2Cl_2$ (2 mL). Triethylamine (0.090 mL, 0.65 mmol) and TBSCl (38 mg, 0.25 mol) were added and the resulting mixture was stirred at 50° C. for 18 h. Reaction mixture was brought to RT and used directly in the next step. LCMS: $[M+H]^+$=307.2.

Step 2: N-(tert-butyldimethylsilyl)-2,4-dimethyl-1,3-thiazole-5-sulfonoimidamide Polymer bound dichlorotriphenylphosphorane reaction mixture (described for Reagent 2) was cooled in an ice/water bath under nitrogen. Triethylamine (0.1 mL, 0.72 mmol, 2.25 equiv.) was added slowly via syringe. Resulting mixture was stirred at 0° C. for 10 min and then the reaction mixture from Step 1 above was added dropwise via syringe.

This reaction mixture was further stirred at 0° C. for 30 min and then a steady stream of anhydrous ammonia was bubbled into the reaction mixture for 3 min. Reaction vial was screw capped and stirred in ice/water bath for 2 h. Reaction mixture was warmed up to room temperature, carefully opened and filtered to remove resin. The cloudy filtrate was centrifuged to remove any solids. Supernatant was concentrated in vacuo and dried under high vacuum for 1 h and used directly in the next step. LCMS: $[M+H]^+$=306.8.

Step 3: 3-{[(Tert-butyldimethylsilyl)amino](dimethyl-1,3-thiazol-5-yl)oxo-λ$^6$-sulfanylidene}-1-[4-fluoro-2,6-bis(propan-2-yl)phenyl]urea To the crude reaction mixture from Step 2 was added anhydrous THF (1.5 mL) and the resulting mixture was stirred in an ice/water bath for 5 min. NaH (17 mg, 0.44 mmol) was added and after 2 min of stirring a solution of isocyanate (0.165 mmol) in THF (3 ml) was added dropwise at 0° C. The resulting mixture was brought to RT and stirred for 15 min to give a mixture of crude products. LCMS: $[M+H]^+$=527.5; for de-protected product, $[M+H]^+$=413.5.

Step 4: 3-[amino(dimethyl-1,3-thiazol-5-yl)oxo-λ$^6$-sulfanylidene]-1-[4-fluoro-2,6-bis(propan-2-yl)phenyl]urea To the reaction from Step 3 was carefully added 4N HCl in dioxane (0.3 mL) and the resulting mixture was stirred at RT for 30 min or till the completion of reaction as determined by the LCMS analysis ($[M+H]^+$=413.5). Reaction mix was then concentrated in vacuo. DMSO (0.8 mL) was added to the residue and purified by prep-HPLC to afford titled compound (10 mg).

Examples in the following table were prepared using similar procedures described in Example 428.

TABLE 29

| Example # | Final Target # | IUPAC Name | Structure | LCMS: $[M + H]^+$ |
|---|---|---|---|---|
| 428 | 309 | 3-[amino(dimethyl-1,3-thiazol-5-yl)oxo-λ$^6$-sulfanylidene]-1-[4-fluoro-2,6-bis(propan-2-yl)phenyl]urea | 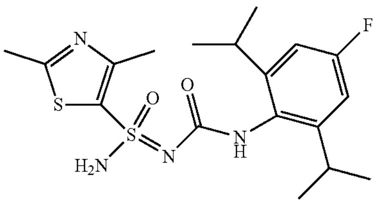 [SMILES: Cc1nc(C)c(S(N)(=O)=NC(=O)Nc2c(C(C)C)cc(F)cc2C(C)C)s1] | 413.16 |
| 430 | 310 | 3-[amino({1-methyl-1H-pyrazolo[3,4-b]pyridin-5-yl})oxo-λ$^6$-sulfanylidene]-1-[4-fluoro-2,6-bis(propan-2-yl)phenyl]urea | 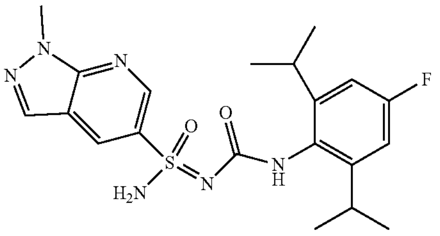 [SMILES: CC(C)c1cc(F)cc(C(C)C)c1NC(=O)N=S(N)(=O)c1cnc2c(cnn2C)c1] | 433.27 |

TABLE 29-continued

| Example # | Final Target # | IUPAC Name | Structure | LCMS: [M + H]+ |
|---|---|---|---|---|
| 431 | 306 | 1-{amino[5-(dimethylamino)naphthalen-1-yl]oxo-λ6 sulfanylidene}-3-[4-fluoro-2,6-bis(propan-2-yl)phenyl]urea | 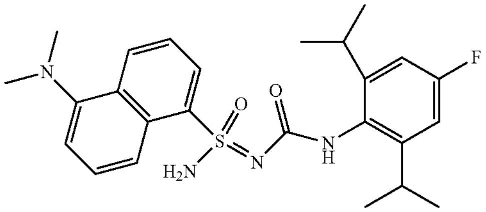 [SMILES: CC(C)c1cc(F)cc(C(C)C)c1NC(=O)N=S(N)(=O)c1cccc2c(N(C)C)cccc12] | 471.70 |

The following protocol is suitable for testing the activity of the compounds disclosed herein.

Procedure 1: IL-1β Production in PMA-Differentiated THP-1 Cells Stimulated with Gramicidin THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g. 100, 33, 11, 3.7, 1.2, 0.41, 0.14, 0.046, 0.015, 0.0051, 0.0017 μM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 μg/ml). The cells were plated in the 384-well assay plate containing the spotted compounds at a density of 50,000 cells/well (final assay volume 50 μl). Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 2: IL-1β Production in PMA-Differentiated THP-1 Cells Stimulated with Gramicidin THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were first dissolved in assay medium to obtain a 5× top concentration of 500 μM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 M). Final DMSO concentration was at 0.37%. Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 3

1. Experimental Procedure 1.1 Cell Culture

1) Culture THP-1 cells in the complete RPMI-1640 medium with 10% FBS at 37° C., 5% $CO_2$.

2) Passage the cells every 3 days by inoculating $3\times10^5$ cells per ml.

1.2 Compound Preparation

Figure 3:
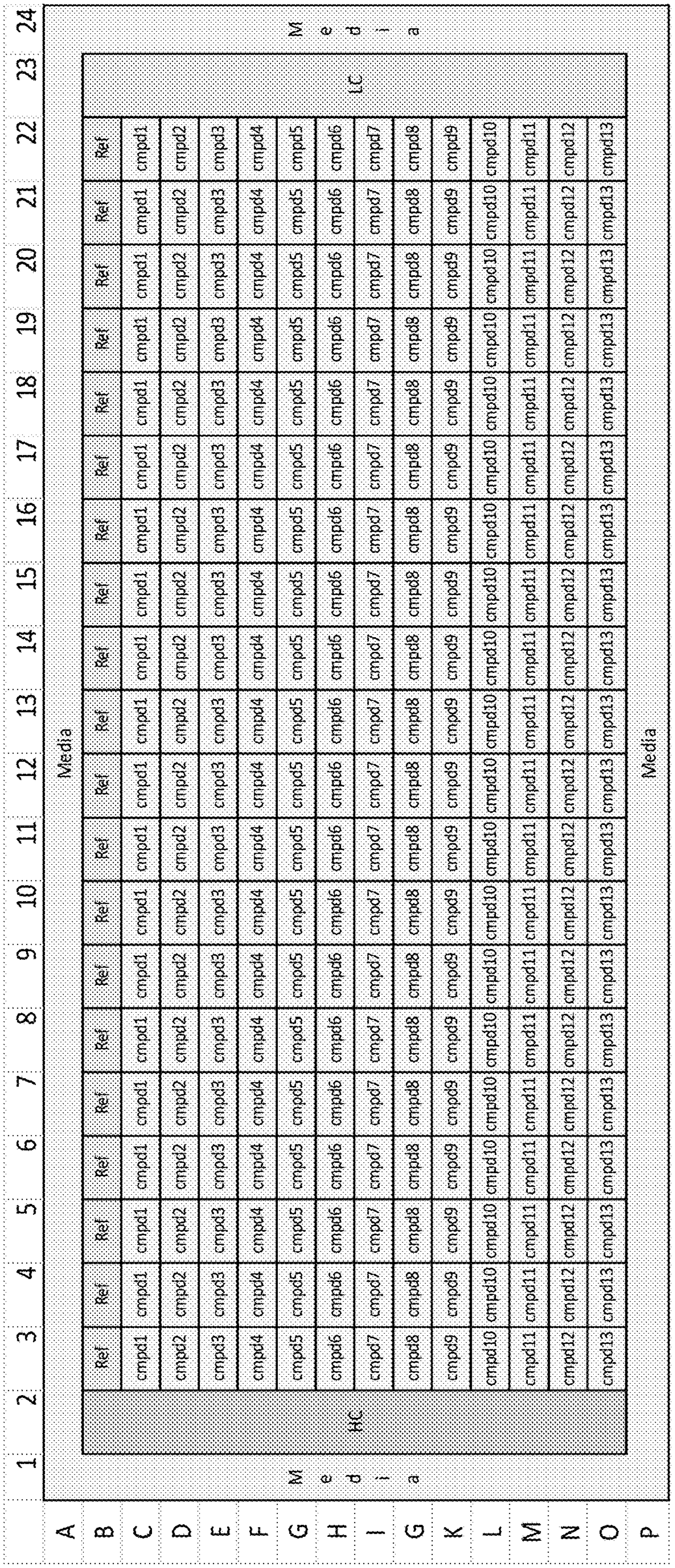
FIG. 3 depicts the layout of the microplate used in an hTHP-1 assay.

Prepare the 3-fold serial dilution of the compounds with DMSO in a 384-well LDV Microplate using TECAN EVO system to generate the compound source plate with 10 concentrations. Top concentration is 30 mM. FIG. 3 depicts the layout of the microplate.

1.3 Cell Preparation

1) Centrifuge THP-1 cells at 350 g for 5 min.

2) Re-suspend cells with complete RMPI-1640 medium, and count cells.

3) Seed cells in T225 flask, about 2.5×$10^7$ per flask, treat cells with 20 ng/ml PMA (final DMSO concentration<1%).

4) Incubate overnight.

1.4 THP-1 Stimulation

1) Wash adherent THP-1 cells with PBS, and detach cells with 4 ml trypsin for T225 flask.

2) Centrifuge cells at 350 g for 5 min, re-suspend cells with RPMI-1640 containing 2% FBS and count cells with trypan blue.

3) Transfer 50 nl/well the serial dilution of test compound to 384-well plate by Echo; For the high control and first point of CRID3 (MCC950), transfer 165 nl, then back-fill to make the DMSO concentration is consistent in all wells, the plate layout is as below.

4) Seed 50k cells in 40 ul RPMI-1640 with 2% FBS per well in 384-well plate.

5) Incubate for 1 h at 37° C., 5% $CO_2$.

6) Prepare 5× gramicidin, add 10 µl per well, the final concentration is 5 µM, incubate for 2 hrs at 37° C., 5% $CO_2$.

7) Centrifuge at 350 g for 1 min.

8) Pipet 16 µl supernatant by apricot, and transfer into white 384 proxiplate. FIG. 3 depicts the layout of the plates: HC: 100 µM CRID3 (MCC950)+5 µM gramicidin LC: 5 µM Gramicidin.

1.5 IL-1β Detection

1) Homogenize the 5× diluent #5 with a vortex and add 1 volume of stock solution in 4 volumes of distilled water.

2) Thaw 20× stock solution of anti-IL1β-Cryptate-antibody and anti-IL1β XL-antibody. Dilute these two antibodies to 1× with detection buffer #3.

3) Pre-mix the two ready-to-use antibody solutions just prior to use.

4) Dispense 4 ul of pre-mixed Anti-IL1β antibodies working solution into all wells.

5) Seal the plate and incubate overnight at 4° C.

6) Read the cell plate using EnVison and plot Readout vs. the test compound concentration to calculate the $IC_{50}$.

2. Data Analysis

1. $IC_{50}$ of compounds can be calculated using the following formulas Formula for $IC_{50}$ $$\%\ inhibition=100-100\times[HC_{ave}-Readout/(HC_{ave}-LC_{ave})]$$

2. Fit the normalized data in a dose-response manner using XLfit, and calculate the compound concentration.

Table 30 shows the biological activity of compounds in hTHP-1 assay containing 2% fetal bovine serum: <0.008 µM="++++++"; >0.008 and <0.04 µM="+++++"; ≥0.04 and <0.2 µM="++++"; ≥0.2 and <1 µM="+++"; ≥1 and <5 µM="++"; ≥5 and <30 µM="+".

TABLE 30

Average $IC_{50}$ of compounds in hTHP-1 assay

| Example # | Compound Number | hTHP-1 $IC_{50}$ |
|---|---|---|
| 1 | 181 | +++++ |
| 2 | 181a | +++++ |
| 3 | 181b | +++ |
| 4 | 101' | ++++ |
| 5 | 101 or 102 | +++ |
| 6 | 102 or 101 | +++++ |
| 7 | 194 | +++ |
| 8 | 270 | + |
| 9 | 204 | >30 µM |
| 10 | 180 | ++++ |
| 11 | 190 | + |
| 12 | 182 | ++++ |
| 13 | 191 | ++++ |
| 14 | 177 | +++++ |
| 15 | 185 | ++++ |
| 16 | 186 | ++++ |
| 17 | 187 | +++++ |
| 18 | 188 | +++ |
| 19 | 192 | ++ |
| 20 | 189 | ++++ |
| 21 | 178 | ++++ |
| 22 | 193 | ++ |
| 23 | 170 | ++++ |
| 24 | 168 | ++ |
| 25 | 171 | ++++ |
| 26 | 122 | ++++ |
| 27 | 120 | +++ |
| 28 | 125 | ++++ |
| 29 | 129 | + |
| 30 | 213 | +++++ |
| 31 | 207 | ++++ |
| 32 | 195 | +++++ |
| 33 | 179 | ++++ |
| 34 | 105 | ++ |
| 35 | 121 | +++ |
| 36 | 145 | ++ |
| 37 | 131 | ++ |
| 38 | 132 | ++++ |
| 39 | 144 | +++ |
| 40 | 149 | ++++ |
| 41 | 152 | ++++ |
| 42 | 150 | + |
| 43 | 167 | ++++ |
| 44 | 106 | +++++ |
| 45 | 107 | ++++++ |
| 46 | 110 | ++ |
| 47 | 151 | +++ |
| 48 | 154 | ++++ |
| 49 | 148 | +++ |
| 50 | 153 | ++ |
| 51 | 109 | ++ |
| 52 | 135 | +++ |
| 53 | 134 | +++++ |
| 54 | 130 | ++ |
| 55 | 212 | +++ |
| 56 | 205 | +++ |
| 57 | 143 | +++ |
| 58 | 206 | ++ |
| 59 | 108 | +++++ |
| 60 | 202 | ++ |
| 61 | 208 | +++++ |
| 62 | 197 | ++++ |
| 63 | 196 | ++ |
| 64 | 124 | ++++ |
| 65 | 173 | ++++ |
| 66 | 172 | + |
| 67 | 174 | +++ |
| 68 | 158 | ++ |
| 69 | 220 | ++ |
| 70 | 157 | ++ |
| 71 | 161 | ++ |
| 72 | 159 | +++ |
| 73 | 165 | ++ |
| 74 | 183 | +++++ |
| 75 | 176 | +++++ |
| 76 | 136 | +++++ |
| 77 | 209 | ++++ |
| 78 | 203 | >30 µM |

TABLE 30-continued

Average $IC_{50}$ of compounds in hTHP-1 assay

| Example # | Compound Number | hTHP-1 $IC_{50}$ |
|---|---|---|
| 79 | 180b or 180a | +++++ |
| 80 | 180a or 180b | +++ |
| 81 | 179b | +++++ |
| 82 | 179a | +++ |
| 83 | 190a or 190b | ++ |
| 84 | 190b or 190a | >30 μM |
| 85 | 182a or 182b | +++++ |
| 86 | 182b or 182a | +++ |
| 87 | 191b or 191a | ++++ |
| 88 | 191a or 191b | ++ |
| 89 | 177b or 177a | +++++ |
| 90 | 177a or 177b | +++ |
| 91 | 185b or 185a | ++++ |
| 92 | 185a or 185b | ++ |
| 93 | 186a or 186b | ++++ |
| 94 | 186b or 186a | ++ |
| 95 | 187a or 187b | ++++++ |
| 96 | 187b or 187a | +++ |
| 97 | 188b or 188a | ++++ |
| 98 | 188a or 188b | + |
| 99 | 192b or 192a | +++ |
| 100 | 192a or 192b | + |
| 101 | 189b or 189a | ++++ |
| 102 | 189a or 189b | ++ |
| 103 | 178b or 178a | ++++ |
| 104 | 178a or 178b | ++ |
| 105 | 193b or 193a | +++ |
| 106 | 193a or 193b | + |
| 107 | 170b or 170a | + |
| 108 | 170a or 170b | ++++ |
| 109 | 168b or 168a | +++ |
| 110 | 168a or 168b | >30 μM |
| 111 | 171b or 171a | ++++ |
| 112 | 171a or 171b | + |
| 113 | 122b or 122a | +++++ |
| 114 | 122a or 122b | ++ |
| 115 | 120b or 120a | ++ |
| 116 | 120a or 120b | ++++ |
| 117 | 125b or 125a | ++++ |
| 118 | 125a or 125b | ++ |
| 119 | 129b or 129a | + |
| 120 | 129a or 129b | >30 μM |
| 121 | 112b or 112a | +++++ |
| 122 | 112a or 112b | +++ |
| 123 | 207c | ++++ |
| 124 | 207aa | ++ |
| 125 | 207b | ++++ |
| 126 | 195a or 195e | ++ |
| 127 | 195e or 195a | ++++ |
| 128 | 105b or 105a | +++ |
| 129 | 105a or 105b | + |
| 130 | 121b or 121a | ++++ |
| 131 | 121a or 121b | ++ |
| 132 | 145b or 145a | ++ |
| 133 | 145a or 145b | >30 μM |
| 134 | 131b or 131a | >30 μM |
| 135 | 131a or 131b | ++ |
| 136 | 225b or 225a | ++ |
| 137 | 225a or 225b | ++++ |
| 138 | 144b or 144a | ++ |
| 139 | 144a or 144b | ++++ |
| 140 | 149b or 149a | +++++ |
| 141 | 149a or 149b | ++ |
| 142 | 152b or 152a | ++++ |
| 143 | 152a or 152b | + |
| 144 | 151b' or 151a' | >30 μM |
| 145 | 151a' or 151b' | + |
| 146 | 167b or 167a | ++ |
| 147 | 167a or 167b | +++ |
| 148 | 107b or 107a | ++++++ |
| 149 | 107a or 107b | +++ |
| 150 | 110b or 110a | + |
| 151 | 110a or 110b | +++ |
| 152 | 151b or 151a | ++++ |
| 153 | 151a or 151b | ++ |
| 154 | 154b or 154a | ++++ |

TABLE 30-continued

Average $IC_{50}$ of compounds in hTHP-1 assay

| Example # | Compound Number | hTHP-1 $IC_{50}$ |
|---|---|---|
| 155 | 154a or 154b | ++ |
| 156 | 148b or 148a | +++ |
| 157 | 148a or 148b | + |
| 158 | 153b or 153a | ++ |
| 159 | 153a or 153b | + |
| 160 | 109b or 109a | +++ |
| 161 | 109a or 109b | + |
| 162 | 135b or 135a | +++ |
| 163 | 135a or 135b | + |
| 164 | 134b or 134a | +++++ |
| 165 | 134a or 134b | ++ |
| 166 | 130b or 130a | +++ |
| 167 | 130a or 130b | >11.2150 |
| 168 | 212b or 212a | +++ |
| 169 | 212a or 212b | >5.5915 |
| 170 | 205b or 205a | ++ |
| 171 | 205a or 205b | +++ |
| 172 | 143b or 143a | +++ |
| 173 | 143a or 143b | ++ |
| 174 | 206b or 206a | +++ |
| 175 | 206a or 206b | ++ |
| 176 | 108b or 108a | +++++ |
| 177 | 108a or 108b | ++ |
| 178 | 202b or 202a | + |
| 179 | 202a or 202b | ++ |
| 180 | 116b or 116a | ++ |
| 181 | 116a or 116b | + |
| 182 | 173a or 173b | +++++ |
| 183 | 173b or 173a | +++ |
| 184 | 174b or 174a | +++ |
| 185 | 174a or 174b | + |
| 186 | 223b or 223a | ++++ |
| 187 | 223a or 223b | + |
| 188 | 158b or 158a | ++ |
| 189 | 158a or 158b | >30 μM |
| 190 | 220b or 220a | +++ |
| 191 | 220a or 220b | + |
| 192 | 157a or 157b | +++ |
| 193 | 157b or 157a | >30 μM |
| 194 | 161b or 161a | ++ |
| 195 | 161a or 161b | + |
| 196 | 165b or 165a | + |
| 197 | 165a or 165b | >30 μM |
| 198 | 172b or 172a | + |
| 199 | 172a or 172b | >30 μM |
| 200 | 106a or 106b | +++++ |
| 201 | 106b or 106a | +++ |
| 202 | 136b or 136a | ++ |
| 203 | 136a or 136b | ++++++ |
| 204 | 183a or 183b | +++ |
| 205 | 183b or 183a | +++++ |
| 206 | 176b or 176a | +++++ |
| 207 | 176a or 176b | +++ |
| 208 | 221 | + |
| 209 | 219 | >30 μM |
| 210 | 217 | >30 μM |
| 211 | 216 | + |
| 212 | 215 | >30 μM |
| 213 | 218 | >30 μM |
| 214 | 214 | >30 μM |
| 215 | 211 | + |
| 216 | 210 | >30 μM |
| 217 | 201 | + |
| 218 | 200 | ++ |
| 219 | 199 | >30 μM |
| 220 | 198 | + |
| 221 | 141 | ++++ |
| 222 | 140 | +++ |
| 223 | 321 | +++++ |
| 224 | 321b or 321a | +++++ |
| 225 | 321a or 321b | ++ |
| 226 | 329 | +++++ |
| 227 | 375 | ++++ |
| 228 | 376 | ++++ |
| 229 | 307 | ++ |
| 230 | 323 | ++ |

TABLE 30-continued

Average $IC_{50}$ of compounds in hTHP-1 assay

| Example # | Compound Number | hTHP-1 $IC_{50}$ |
|---|---|---|
| 231 | 338 | ++ |
| 232 | 341 | ++ |
| 233 | 342 | ++ |
| 234 | 345 | ++ |
| 235 | 346 | ++ |
| 236 | 347 | ++ |
| 237 | 348 | ++ |
| 238 | 403 | ++ |
| 239 | 402 | ++ |
| 240 | 350 | ++ |
| 241 | 322 | ++ |
| 242 | 351 | ++ |
| 243 | 358 | ++ |
| 244 | 401 | + |
| 245 | 404 | + |
| 246 | 331 | + |
| 247 | 339 | + |
| 248 | 405 | + |
| 249 | 406 | >30 μM |
| 250 | 324 | + |
| 251 | 407 | ++ |
| 252 | 410 | >30 μM |
| 253 | 408 | |
| 254 | 308 | ++ |
| 255 | 311 | + |
| 256 | 312 | >30 μM |
| 257 | 327 | ++++ |
| 258 | 326 | ++++ |
| 259 | 139 | +++ |
| 260 | 137 | +++ |
| 261 | 409 | ++ |
| 262 | 303 | +++++ |
| 263 | 325 | +++++ |
| 264 | 138 | ++ |
| 265 | 332 | ++++ |
| 266 | 334 | ++++ |
| 267 | 335 | ++++ |
| 268 | 337 | ++ |
| 269 | 113 | +++++ |
| 270 | 343 | ++ |
| 271 | 349 | ++ |
| 272 | 344 | +++ |
| 273 | 359 | + |
| 274 | 352 | +++ |
| 275 | 354 | ++ |
| 276 | 355 | +++ |
| 277 | 356 | >30 μM |
| 278 | 357 | +++ |
| 279 | 340 | +++++ |
| 280 | 377 | +++ |
| 281 | 378 | +++++ |
| 282 | 379 | +++ |
| 283 | 380 | +++ |
| 284 | 353 | + |
| 285 | 333 | ++++ |
| 287 | 382 | ++ |
| 288 | 383 | ++ |
| 289 | 315 | ++++ |
| 290 | 316 | ++ |
| 291 | 317 | ++++ |
| 292 | 319 | ++++ |
| 293 | 320 | +++ |
| 294 | 336 | ++++ |
| 295 | 330 | ++++ |
| 296 | 364a | ++++++ |
| 297 | 364b | +++ |
| 298 | 365a | ++++ |
| 299 | 365b | ++ |
| 300 | 308a | +++ |
| 301 | 308b | + |
| 302 | 195ba or 195bb | +++ |
| 303 | 195bb or 195ba | +++++ |
| 304 | 207a or 207bb | ++++ |
| 305 | 207bb or 207a | +++++ |
| 306 | 366a | ++++++ |
| 307 | 366b | ++++ |

TABLE 30-continued

Average $IC_{50}$ of compounds in hTHP-1 assay

| Example # | Compound Number | hTHP-1 $IC_{50}$ |
|---|---|---|
| 308 | 139a | ++ |
| 309 | 139b | ++++ |
| 310 | 367a | +++++ |
| 311 | 367b | +++ |
| 312 | 409b | ++ |
| 313 | 409a | ++ |
| 314 | 369a | +++ |
| 315 | 369b | + |
| 316 | 159a | +++ |
| 317 | 159ab | ++ |
| 318 | 159ba | +++ |
| 319 | 137a | ++ |
| 320 | 137b | ++++ |
| 321 | 317ab | ++ |
| 322 | 317aa | +++ |
| 323 | 317bb | ++++ |
| 324 | 317ba | +++++ |
| 325 | 316a | >28.4352 |
| 326 | 316b | + |
| 327 | 373a | >30 μM |
| 328 | 373b | ++ |
| 329 | 374a | >30 μM |
| 330 | 374b | >30 μM |
| 331 | 319ab | + |
| 332 | 319aa | +++ |
| 333 | 319bb | ++ |
| 334 | 319ba | +++++ |
| 335 | 320a | ++ |
| 336 | 320b | +++ |
| 337 | 323ab | ++ |
| 338 | 323bb | ++ |
| 339 | 323aa | ++ |
| 340 | 323ba | ++ |
| 341 | 303a | ++++++ |
| 342 | 303b | +++ |
| 343 | 315a | ++++ |
| 344 | 315b | ++ |
| 345 | 138a | +++ |
| 346 | 138b | + |
| 347 | 328a | +++++ |
| 348 | 328b | ++ |
| 349 | 326b | ++ |
| 350 | 326a | ++++ |
| 351 | 318a | +++ |
| 352 | 318b | ++++ |
| 353 | 325a | ++ |
| 354 | 325b | +++++ |
| 355 | 329a | ++++++ |
| 356 | 329b | +++ |
| 357 | 404b | + |
| 358 | 404a | >30 μM |
| 359 | 332a | +++++ |
| 360 | 332b | +++ |
| 361 | 335a | ++++ |
| 362 | 335b | ++ |
| 363 | 336a | ++ |
| 364 | 336b | ++++ |
| 365 | 337a | >30 μM |
| 366 | 337b | ++ |
| 367 | 371a | >30 μM |
| 368 | 371b | ++ |
| 369 | 372a | >30 μM |
| 370 | 372b | +++ |
| 371 | 334a | + |
| 372 | 334b | ++++ |
| 373 | 339a | + |
| 374 | 339b | +++++ |
| 375 | 334ab | + |
| 376 | 334aa | + |
| 377 | 334bb | ++++ |
| 378 | 334ba | +++ |
| 379 | 338a | ++ |
| 380 | 338b | >30 μM |
| 381 | 340a | +++++ |
| 382 | 340b | ++ |
| 383 | 361b | >30 μM |

TABLE 30-continued

| Average $IC_{50}$ of compounds in hTHP-1 assay | | |
|---|---|---|
| Example # | Compound Number | hTHP-1 $IC_{50}$ |
| 384 | 361a | >30 μM |
| 385 | 113a | +++++ |
| 386 | 113b | +++ |
| 387 | 330a | ++ |
| 388 | 330b | ++++ |
| 389 | 341a | >30 μM |
| 390 | 341b | ++ |
| 391 | 360ba | +++ |
| 392 | 360bb | +++ |
| 393 | 363b | +++++ |
| 394 | 363a | +++ |
| 395 | 343a | ++ |
| 396 | 343b | >30 μM |
| 397 | 359a | ++ |
| 398 | 359b | >30 μM |
| 399 | 352a | +++ |
| 400 | 352b | + |
| 401 | 383a | >30 μM |
| 402 | 383b | ++ |
| 403 | 382a | +++ |
| 404 | 382b | + |
| 405 | 379a | |
| 406 | 379b | >30 μM |
| 407 | 380a | + |
| 408 | 380b | ++ |
| 409 | 380c | +++ |
| 410 | 380d | ++++ |

TABLE 30-continued

| Average $IC_{50}$ of compounds in hTHP-1 assay | | |
|---|---|---|
| Example # | Compound Number | hTHP-1 $IC_{50}$ |
| 411 | 384a | ++ |
| 412 | 384b | >30 μM |
| 413 | 357a | +++ |
| 414 | 357b | + |
| 415 | 354a | >30 μM |
| 416 | 354b | +++ |
| 417 | 387a | ++ |
| 418 | 387b | ++++ |
| 419 | 333a | ++++ |
| 420 | 333b | ++ |
| 421 | 375a | +++++ |
| 422 | 375b | |
| 423 | 376a | +++++ |
| 424 | 376b | |
| 425 | 318 | +++ |
| 426 | 313 | + |
| 427 | 314 | + |
| 428 | 309 | + |
| 430 | 310 | + |
| 431 | 306 | + |

A number of embodiments of the invention have been described. Nevertheless, it will be understood that various modifications may be made without departing from the spirit and scope of the invention. Accordingly, other embodiments are within the scope of the following claims.

We claim:

1. A compound of Formula AA

Formula AA

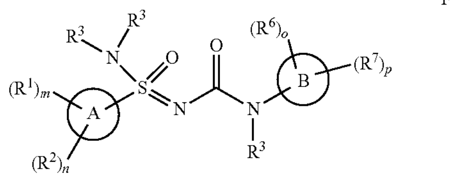

wherein m=0, 1, or 2;

n=0, 1, or 2;

o=1 or 2;

p=0, 1, 2, or 3;

wherein

A is a 5-10-membered heteroaryl or a $C_6$-$C_{10}$ aryl;

B is a 5-10-membered heteroaryl or a $C_6$-$C_{10}$ aryl;

wherein at least one $R^6$ is ortho to the bond connecting the B ring to the $NR^3$(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO-$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5-to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C═$NR^3$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $COOC_1$-$C_6$ alkyl, $NR^8R^9$, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;

wherein the 3- to 7-membered heterocycloalkyl, $C_6$-$C_{10}$ aryl, or 5- to 10-membered heteroaryl, of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, oxo, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, ═$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_7$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, ═$NR^{10}$, —$COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 4-to 8-membered heterocyclic ring containing 1 or 2 heteroatoms independently selected from O, N, $NR^{20}$, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of $R^4$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, $C_2$-$C_6$alkenyl, $C_2$-$C_6$ alkynyl, $(C{=}NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl, $C_2$-$C_6$ alkenyl, or $C_2$-$C_6$ alkynyl is optionally substituted with one or more hydroxy, halo, oxo, $C_1$-$C_6$ alkoxy, $C_2$-$C_6$ alkynyl, $C_{02}R^{13}$, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

each $R^3$ is independently selected from hydrogen, cyano, hydroxy, $C_1$-$C_6$ alkoxy, $C_1$-$C_6$ alkyl, $CO_2C_1$-$C_6$ alkyl, and

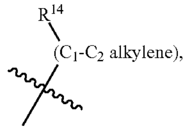

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

2. The compound of claim 1, wherein A is a 5- to 10-membered monocyclic or bicyclic heteroaryl or a $C_6$-$C_{10}$ monocyclic or bicyclic aryl.

3. The compound of claim 2, wherein A is:

naphthyl optionally substituted with 1 or 2 $R^1$ and optionally substituted with 1 or 2 $R^2$, pyridyl optionally substituted with 1 or 2 $R^1$ and optionally substituted with 1 or 2 $R^2$, indazolyl optionally substituted with 1 or 2 $R^1$ and optionally substituted with 1 or 2 $R^2$, or phenyl substituted with 1 $R^1$ and optionally substituted with 1 $R^2$.

4. The compound of claim 2, wherein A is:

phenyl, m is 0 or 1, and n is 0, 1, or 2, furanyl, m is 0 or 1, and n is 0, 1, or 2, thiophenyl, m is 0 or 1, and n is 0, 1, or 2, oxazolyl, m is 0 or 1, and n is 0, 1, or 2, thiazolyl, m is 0 or 1, and n is 0, 1, or 2, pyrazolyl, m is 0 or 1, and n is 0, 1, or 2, pyridyl, m is 0 or 1, and n is 0, 1, or 2, or indazolyl, m is 0 Or 1, and n is 0, 1, or 2.

5. The compound of claim 2, wherein A is:

naphthyl substituted with 1 $R^1$ and optionally substituted with 1 $R^2$, furanyl substituted with 1 $R^1$ and optionally substituted with 1 $R^2$, thiophenyl substituted with 1 $R^1$ and optionally substituted with 1 $R^2$, oxazolyl substituted with 1 $R^1$ and optionally substituted with 1 $R^2$, thiazolyl substituted with 1 $R^1$ and optionally substituted with 1 $R^2$, pyrazolyl substituted with 1 $R^1$ and optionally substituted with 1 $R^2$, pyridyl substituted with 1 $R^1$ and optionally substituted with 1 $R^2$, or indazolyl optionally substituted with 1 $R^1$ and optionally substituted with 1 $R^2$.

6. The compound of claim 2, wherein A is:

phenyl substituted with 1 $R^1$ and substituted with 1 $R^2$,

A is furanyl substituted with 1 $R^1$ and substituted with 1 $R^2$, thiophenyl substituted with 1 $R^1$ and substituted with 1 $R^2$, oxazolyl substituted with 1 $R^1$ and substituted with 1 $R^2$, thiazolyl substituted with 1 $R^1$ and substituted with 1 $R^2$, pyrazolyl substituted with 1 $R^1$ and substituted with 1 $R^2$, or pyridyl substituted with 1 $R^1$ and substituted with 1 $R^2$.

7. The compound of claim 4, wherein the optionally substituted ring A is

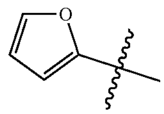

,

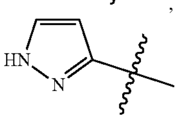

,

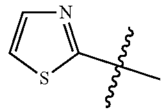

,

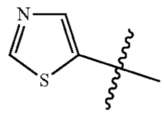

,

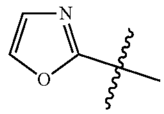

,

-continued
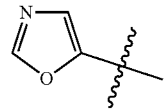
,
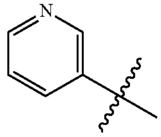
,
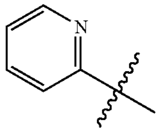
, or
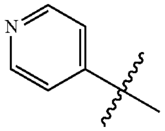
.
8. The compound of claim 6, wherein the optionally substituted ring A is
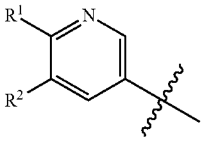
,
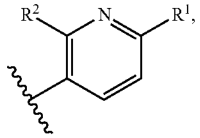
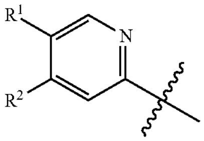
,
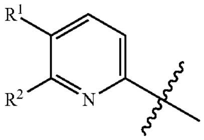
,
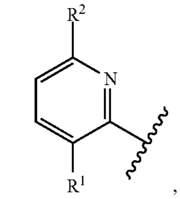
,
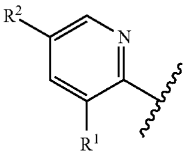
,
-continued
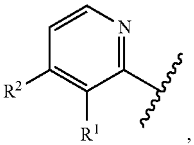
,
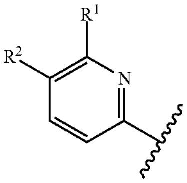
,
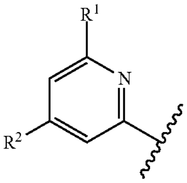
,
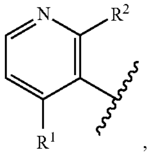
,
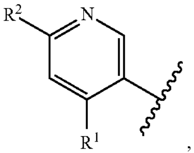
,
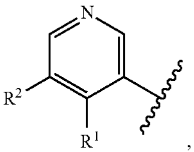
,
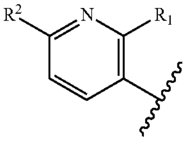
,
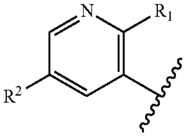
,
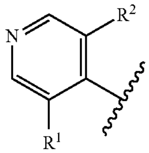
,
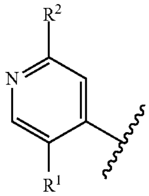
, -continued

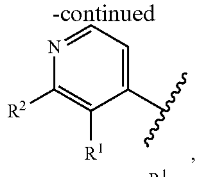

,

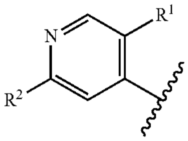

, or

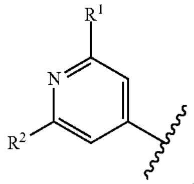

.

9. The compound of claim 4, wherein the optionally substituted ring A is

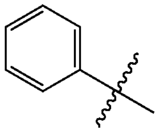

,

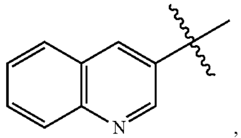

,

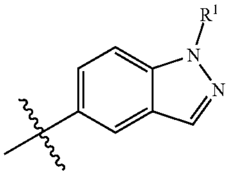

, or

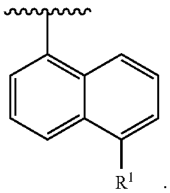

.

10. The compound of claim 1, wherein $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO-$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5-to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

11. The compound of claim 1, wherein m=1; n=0; and $R^1$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$ $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

12. The compound of claim 11, wherein m=1; n=0; and $R^1$ is selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

13. The compound of claim 1, wherein m=1; n=1; and $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO-$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5-to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, N($C_1$-$C_6$ alkyl)$_2$, $CONR^8R^9$, $SF_5$, $SC_1$-$C_6$ alkyl, S($O_2$)$C_1$-$C_6$ alkyl, S($O_2$)$NR^{11}R^{12}$, S(O)$C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5-to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

14. The compound of claim 13, wherein m=1; n=1; and, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, S(O)$C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

15. The compound of claim 13, wherein m=1; n=1; and $R^1$ and $R^2$ are on adjacent atoms, and taken together with the atoms connecting them, form a $C_4$-$C_8$ carbocyclic ring or a 5- to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

16. The compound of claim 15, wherein m=1; n=1; and $R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

17. The compound of claim 16, wherein m=1; n=1; and $R^1$ and $R^2$ are on adjacent atoms, and taken together with the atoms connecting them, form a $C_5$ carbocyclic ring or a 5- to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $COOC_1$-$C_6$ alkyl, $C_6$-$C_{10}$ aryl, and $CONR^8R^9$.

18. The compound of claim 17, wherein m=1; n=1; and $R^1$ and $R^2$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

19. A method of treating a subject in need thereof having a disease, disorder or condition in which NLRP3 signaling contributes to the pathology and/or symptoms and/or progression of the disease disorder or condition, comprising administering to the subject an effective amount of a compound according to claim 1.

20. The method according to claim 19, further comprising administering a therapeutically effective amount of an anti-TNFα agent to the subject.

* * * * *

SEQUENCE LISTING

```
<160> NUMBER OF SEQ ID NOS: 37

<210> SEQ ID NO 1
<211> LENGTH: 702
<212> TYPE: DNA
<213> ORGANISM: Homo sapiens

<400> SEQUENCE: 1

atgagcactg aaagcatgat ccgggacgtg gagctggccg aggaggcgct ccccaagaag     60

acagggggc cccagggctc caggcggtgc ttgttcctca gcctcttctc cttcctgatc     120

gtggcaggcg ccaccacgct cttctgcctg ctgcactttg gagtgatcgg cccccagagg    180

gaagagttcc ccagggacct ctctctaatc agccctctgg cccaggcagt cagatcatct    240

tctcgaaccc cgagtgacaa gcctgtagcc catgttgtag caaaccctca agctgagggg    300

cagctccagt ggctgaaccg ccgggccaat gccctcctgg ccaatggcgt ggagctgaga    360

gataaccagc tggtggtgcc atcagagggc ctgtacctca tctactccca ggtcctcttc    420

aagggccaag gctgcccctc cacccatgtg ctcctcaccc acaccatcag ccgcatcgcc    480

gtctcctacc agaccaaggt caacctcctc tctgccatca agagcccctg ccagagggag    540

accccagagg gggctgaggc caagccctgg tatgagccca tctatctggg aggggtcttc    600

cagctggaga agggtgaccg actcagcgct gagatcaatc ggcccgacta tctcgacttt    660

gccgagtctg ggcaggtcta ctttgggatc attgccctgt ga                       702


<210> SEQ ID NO 2
<211> LENGTH: 1368
<212> TYPE: DNA
<213> ORGANISM: Homo sapiens

<400> SEQUENCE: 2

atgggcctct ccaccgtgcc tgacctgctg ctgccactgg tgctcctgga gctgttggtg     60
```

```
ggaatatacc cctcaggggt tattggactg gtccctcacc taggggacag ggagaagaga    120
gatagtgtgt gtccccaagg aaaatatatc caccctcaaa ataattcgat ttgctgtacc    180
aagtgccaca aaggaaccta cttgtacaat gactgtccag gcccggggca ggatacggac    240
tgcagggagt gtgagagcgg ctccttcacc gcttcagaaa accacctcag acactgcctc    300
agctgctcca aatgccgaaa ggaaatgggt caggtggaga tctcttcttg cacagtggac    360
cgggacaccg tgtgtggctg caggaagaac cagtaccggc attattggag tgaaaacctt    420
ttccagtgct tcaattgcag cctctgcctc aatgggaccg tgcacctctc ctgccaggag    480
aaacagaaca ccgtgtgcac ctgccatgca ggtttctttc taagagaaaa cgagtgtgtc    540
tcctgtagta actgtaagaa aagcctggag tgcacgaagt tgtgcctacc ccagattgag    600
aatgttaagg gcactgagga ctcaggcacc acagtgctgt tgccccctggt catttctttt    660
ggtctttgcc ttttatccct cctcttcatt ggtttaatgt atcgctacca acggtggaag    720
tccaagctct actccattgt ttgtgggaaa tcgacacctg aaaaagaggg ggagcttgaa    780
ggaactacta ctaagcccct ggccccaaac ccaagcttca gtcccactcc aggcttcacc    840
cccaccctgg gcttcagtcc cgtgcccagt tccaccttca cctccagctc cacctatacc    900
cccggtgact gtcccaactt tgcggctccc cgcagagagg tggcaccacc ctatcagggg    960
gctgacccca tccttgcgac agccctcgcc tccgacccca tccccaaccc ccttcagaag   1020
tgggaggaca gcgcccacaa gccacagagc ctagacactg atgaccccgc gacgctgtac   1080
gccgtggtgg agaacgtgcc cccgttgcgc tggaaggaat tcgtgcggcg cctagggctg   1140
agcgaccacg agatcgatcg gctggagctg cagaacgggc gctgcctgcg cgaggcgcaa   1200
tacagcatgc tggcgacctg gaggcggcgc acgccgcggc gcgaggccac gctggagctg   1260
ctgggacgcg tgctccgcga catggacctg ctgggctgcc tggaggacat cgaggaggcg   1320
ctttgcggcc ccgccgccct cccgcccgcg cccagtcttc tcagatga                 1368
```

```
<210> SEQ ID NO 3
<211> LENGTH: 281
<212> TYPE: DNA
<213> ORGANISM: Homo sapiens

<400> SEQUENCE: 3

attcttcccc tggtggccat gggacccagg tcaatgtcac ctgcatcgtg aacgtctgta     60
gcagctctga ccacagctca cagtgctcct cccaagccag ctccacaatg ggagacacag    120
attccagccc ctcggagtcc ccgaaggacg agcaggtccc cttctccaag gaggaatgtg    180
cctttcggtc acagctggag acgccagaga ccctgctggg gagcaccgaa gagaagcccc    240
tgccccttgg agtgcctgat gctgggatga agcccagtta a                        281
```

```
<210> SEQ ID NO 4
<211> LENGTH: 939
<212> TYPE: DNA
<213> ORGANISM: Homo sapiens

<400> SEQUENCE: 4

atggcagctg ggcaaaatgg gcacgaagag tgggtgggca gcgcatacct gtttgtggag     60
tcctcgctgg acaaggtggt cctgtcggat gcctacgcgc acccccagca gaaggtggca    120
gtgtacaggg ctctgcaggc tgccttggca gagagcggcg ggagcccgga cgtgctgcag    180
atgctgaaga tccaccgcag cgacccgcag ctgatcgtgc agctgcgatt ctgcgggcgg    240
```

```
cagccctgtg gccgcttcct ccgcgcctac cgcgaggggg cgctgcgcgc cgcgctgcag    300

aggagcctgg cggccgcgct cgcccagcac tcggtgccgc tgcaactgga gctgcgcgcc    360

ggcgccgagc ggctggacgc tttgctggcg gacgaggagc gctgtttgag ttgcatccta    420

gcccagcagc ccgaccggct ccgggatgaa gaactggctg agctggagga tgcgctgcga    480

aatctgaagt gcggctcggg ggcccggggt ggcgacgggg aggtcgcttc ggcccccttg    540

cagcccccgg tgccctctct gtcggaggtg aagccgccgc cgccgccgcc acctgcccag    600

acttttctgt tccagggtca gcctgtagtg aatcggccgc tgagcctgaa ggaccaacag    660

acgttcgcgc gctctgtggg tctcaaatgg cgcaaggtgg ggcgctcact gcagcgaggc    720

tgccgggcgc tgcgggaccc ggcgctggac tcgctggcct acgagtacga gcgcgaggga    780

ctgtacgagc aggccttcca gctgctgcgg cgcttcgtgc aggccgaggg ccgccgcgcc    840

acgctgcagc gcctggtgga ggcactcgag gagaacgagc tcaccagcct ggcagaggac    900

ttgctgggcc tgaccgatcc caatggcggc ctggcctag                           939
```

<210> SEQ ID NO 5
<211> LENGTH: 1506
<212> TYPE: DNA
<213> ORGANISM: Homo sapiens

<400> SEQUENCE: 5

```
atggctgcag ctagcgtgac cccccctggc tccctggagt tgctacagcc cggcttctcc     60

aagaccctcc tggggaccaa gctggaagcc aagtacctgt gctccgcctg cagaaacgtc    120

ctccgcaggc ccttccaggc gcagtgtggc caccggtact gctccttctg cctggccagc    180

atcctcagct ctgggcctca gaactgtgct gcctgtgttc acgagggcat atatgaagaa    240

ggcatttcta ttttagaaag cagttcggcc ttcccagata atgctgcccg cagggaggtg    300

gagagcctgc cggccgtctg tcccagtgat ggatgcacct ggaaggggac cctgaaagaa    360

tacgagagct gccacgaagg ccgctgcccg ctcatgctga ccgaatgtcc cgcgtgcaaa    420

ggcctggtcc gccttggtga aaaggagcgc cacctggagc acgagtgccc ggagagaagc    480

ctgagctgcc ggcattgccg ggcaccctgc tgcggagcag acgtgaaggc gcaccacgag    540

gtctgcccca agttcccctt aacttgtgac ggctgcggca agaagaagat cccccgggag    600

aagtttcagg accacgtcaa gacttgtggc aagtgtcgag tcccttgcag attccacgcc    660

atcggctgcc tcgagacggt agagggtgag aaacagcagg agcacgaggt gcagtggctg    720

cgggagcacc tggccatgct actgagctcg gtgctggagg caaagcccct cttgggagac    780

cagagccacg cggggtcaga gctcctgcag aggtgcgaga gcctggagaa gaagacggcc    840

acttttgaga acattgtctg cgtcctgaac cgggaggtgg agagggtggc catgactgcc    900

gaggcctgca gccggcagca ccggctggac caagacaaga ttgaagccct gagtagcaag    960

gtgcagcagc tggagaggag cattggcctc aaggacctgg cgatggctga cttggagcag   1020

aaggtcttgg agatggaggc atccacctac gatggggtct tcatctggaa gatctcagac   1080

ttcgccagga agcgccagga agctgtggct ggccgcatac ccgccatctt ctccccagcc   1140

ttctacacca gcaggtacgg ctacaagatg tgtctgcgta tctacctgaa cggcgacggc   1200

accgggcgag gaacacacct gtccctcttc tttgtggtga tgaagggccc gaatgacgcc   1260

ctgctgcggt ggcccttcaa ccagaaggtg accttaatgc tgctcgacca gaataaccgg   1320

gagcacgtga ttgacgcctt caggcccgac gtgacttcat cctcttttca gaggccagtc   1380

aacgacatga acatcgcaag cggctgcccc ctcttctgcc ccgtctccaa gatggaggca   1440
```

aagaattcct acgtgcggga cgatgccatc ttcatcaagg ccattgtgga cctgacaggg 1500
ctctaa 1506

<210> SEQ ID NO 6
<211> LENGTH: 1044
<212> TYPE: DNA
<213> ORGANISM: Homo sapiens

<400> SEQUENCE: 6
atggaaacac ccttctacgg cgatgaggcg ctgagcggcc tgggcggcgg cgccagtggc 60
agcggcggca gcttcgcgtc cccgggccgc ttgttccccg gggcgccccc gacggccgcg 120
gccggcagca tgatgaagaa ggacgcgctg acgctgagcc tgagtgagca ggtggcggca 180
gcgctcaagc ctgcggccgc gccgcctcct accccccctgc gcgccgacgg cgccccccagc 240 gcggcacccc ccgacggcct gctcgcctct cccgacctgg ggctgctgaa gctggcctcc 300
cccgagctcg agcgcctcat catccagtcc aacgggctgg tcaccaccac gccgacgagc 360
tcacagttcc tctaccccaa ggtggcggcc agcgaggagc aggagttcgc cgagggcttc 420
gtcaaggccc tggaggattt acacaagcag aaccagctcg gcgcgggcgc ggccgctgcc 480
gccgccgccg ccgccgccgg ggggccctcg ggcacggcca cgggctccgc gccccccggc 540
gagctggccc cggcggcggc cgcgcccgaa gcgcctgtct acgcgaacct gagcagctac 600
gcgggcggcg ccgggggcgc gggggcgcc gcgacggtcg ccttcgctgc cgaacctgtg 660
cccttcccgc cgccgccacc cccaggcgcg ttggggccgc cgcgcctggc tgcgctcaag 720
gacgagccac agacggtgcc cgacgtgccg agcttcggcg agagcccgcc gttgtcgccc 780
atcgacatgg acacgcagga gcgcatcaag gcggagcgca agcggctgcg caaccgcatc 840
gccgcctcca agtgccgcaa gcgcaagctg gagcgcatct cgcgcctgga agagaaagtg 900
aagaccctca agagtcagaa cacggagctg gcgtccacgg cgagcctgct gcgcgagcag 960
gtggcgcagc tcaagcagaa agtcctcagc cacgtcaaca gcggctgcca gctgctgccc 1020
cagcaccagg tgcccgcgta ctga 1044

<210> SEQ ID NO 7
<211> LENGTH: 4124
<212> TYPE: DNA
<213> ORGANISM: Homo sapiens

<400> SEQUENCE: 7
atgagcacgg aggcggacga gggcatcact ttctctgtgc caccccttcgc cccctcgggc 60 ttctgcacca tccccgaggg cggcatctgc aggaggggag gagcggcggc ggtgggcgag 120
ggcgaggagc accagctgcc accgccgccg ccgggcagtt tctggaacgt ggagagcgcc 180
gctgcccctg gcatcggttg tccggcggcc acctcctcga gcagtgccac ccgaggccgg 240
ggcagctctg ttggcggggg cagccgacgg accacggtgg catatgtgat caacgaagcg 300
agccaagggc aactggtggt ggccgagagc gaggccctgc agagcttgcg ggaggcgtgc 360
gagacagtgg gcgccaccct ggaaccctgc attttgggaa actcgacttt ggagaaacca 420
ccgtgctgga ccgcttttac aatgcagata ttgcggtggt ggagatgagc gatgccttcc 480
ggcagccgtc cttgttttac caccttgggg tgagagaaag tttcagcatg gccaacaaca 540
tcatcctcta ctgcgatact aactcggact ctctgcagtc actgaaggaa atcatttgcc 600
agaagaatac tatgtgcact gggaactaca cctttgttcc ttacatgata actccacata 660

-continued

```
acaaagtcta ctgctgtgac agcagcttca tgaaggggtt gacagagctc atgcaaccga    720
acttcgagct gcttcttgga cccatctgct tacctcttgt ggatcgtttt attcaacttt    780
tgaaggtggc acaagcaagt tctagccagt acttccggga atctatactc aatgacatca    840
ggaaagctcg taatttatac actggtaaag aattggcagc tgagttggca agaattcggc    900
agcgagtaga taatatcgaa gtcttgacag cagatattgt cataaatctg ttactttcct    960
acagagatat ccaggactat gattctattg tgaagctggt agagacttta gaaaaactgc   1020
caacctttga tttggcctcc catcaccatg tgaagtttca ttatgcattt gcactgaata   1080
ggagaaatct ccctggtgac agagcaaaag ctcttgatat tatgattccc atggtgcaaa   1140
gcgaaggaca agttgcttca gatatgtatt gcctagttgg tcgaatctac aaagatatgt   1200
ttttggactc taatttcacg gacactgaaa gcagagacca tggagcttct tggttcaaaa   1260
aggcatttga atctgagcca acactacagt caggaattaa ttatgcggtc ctcctcctgg   1320
cagctggaca ccagtttgaa tcttcctttg agctccggaa agttggggtg aagctaagta   1380
gtcttcttgg taaaaaggga aacttggaaa aactccagag ctactgggaa gttggatttt   1440
ttctgggggc cagcgtccta gccaatgacc acatgagagt cattcaagca tctgaaaagc   1500
tttttaaact gaagacacca gcatggtacc tcaagtctat tgtagagaca attttgatat   1560
ataagcattt tgtgaaactg accacagaac agcctgtggc caagcaagaa cttgtggact   1620
tttggatgga tttcctggtc gaggccacaa agacagatgt tactgtggtt aggtttccag   1680
tattaatatt agaaccaacc aaaatctatc aaccttctta tttgtctatc aacaatgaag   1740
ttgaggaaaa gacaatctct atttggcacg tgcttcctga tgacaagaaa ggtatacatg   1800
agtggaattt tagtgcctct tctgtcaggg gagtgagtat ttctaaattt gaagaaagat   1860
gctgctttct ttatgtgctt cacaattctg atgatttcca aatctatttc tgtacagaac   1920
ttcattgtaa aaagtttttt gagatggtga acaccattac cgaagagaag gggagaagca   1980
cagaggaagg agactgtgaa agtgacttgc tggagtatga ctatgaatat gatgaaaatg   2040
gtgacagagt cgttttagga aaaggcactt atgggatagt ctacgcaggt cgggacttga   2100
gcaaccaagt cagaattgct attaaggaaa tcccagagag agacagcaga tactctcagc   2160
ccctgcatga agaaatagca ttgcataaac acctgaagca caaaaatatt gtccagtatc   2220
tgggctcttt cagtgagaat ggtttcatta aaatcttcat ggagcaggtc cctggaggaa   2280
gtctttctgc tctccttcgt tccaaatggg gtccattaaa agacaatgag caaacaattg   2340
gcttttatac aaagcaaata ctggaaggat taaaatatct ccatgacaat cagatagttc   2400
accgggacat aaagggtgac aatgtgttga ttaataccta cagtggtgtt ctcaagatct   2460
ctgacttcgg aacatcaaag aggcttgctg gcataaaccc ctgtactgaa acttttactg   2520
gtaccctcca gtatatggca ccagaaataa tagataaagg accaagaggc tacggaaaag   2580
cagcagacat ctggtctctg ggctgtacaa tcattgaaat ggccacagga aaacccccat   2640
tttatgaact gggagaacca caagcagcta tgttcaaggt gggaatgttt aaagtccacc   2700
ctgagatccc agagtccatg tctgcagagg ccaaggcatt catactgaaa tgttttgaac   2760
cagatcctga caagagagcc tgtgctaacg acttgcttgt tgatgagttt ttaaaagttt   2820
caagcaaaaa gaaaaagaca caacctaagc tttcagctct ttcagctgga tcaaatgaat   2880
atctcaggag tatatccttg ccggtacctg tgctggtgga ggacaccagc agcagcagtg   2940
agtacggctc agtttcaccc gacacggagt tgaaagtgga ccccttctct ttcaaaacaa   3000
gagccaagtc ctgcggagaa agagatgtca agggaattcg gacactcttt ttgggcattc   3060
```

```
cagatgagaa ttttgaagat cacagtgctc ctccttcccc tgaagaaaaa gattctggat   3120
tcttcatgct gaggaaggac agtgagaggc gagctaccct tcacaggatc ctgacggaag   3180
accaagacaa aattgtgaga aacctaatgg aatctttagc tcagggggct gaagaaccga   3240
aactaaaatg ggaacacatc acaaccctca ttgcaagcct cagagaattt gtgagatcca   3300
ctgaccgaaa aatcatagcc accacactgt caaagctgaa actggagctg gacttcgaca   3360
gccatggcat tagccaagtc caggtggtac tctttggttt tcaagatgct gtcaataaag   3420
ttcttcggaa tcataacatc aagccgcact ggatgtttgc cttagacagt atcattcgga   3480
aggcggtaca gacagccatt accatcctgg ttccagaact aaggccacat ttcagccttg   3540
catctgagag tgatactgct gatcaagaag acttggatgt agaagatgac catgaggaac   3600
agccttcaaa tcaaactgtc cgaagacctc aggctgtcat tgaagatgct gtggctacct   3660
caggcgtgag cacgctcagt tctactgtgt ctcatgattc ccagagtgct caccggtcac   3720
tgaatgtaca gcttggaagg atgaaaatag aaaccaatag attactggaa gaattggttc   3780
ggaaagagaa agaattacaa gcactccttc atcgagctat tgaagaaaaa gaccaagaaa   3840
ttaaacacct gaagcttaag tcccaaccca tagaaattcc tgaattgcct gtatttcatc   3900
taaattcttc tggcacaaat actgaagatt ctgaacttac cgactggctg agagtgaatg   3960
gagctgatga agacactata agccggtttt tggctgaaga ttatacacta ttggatgttc   4020
tctactatgt tacacgtgat gacttaaaat gcttgagact aaggggaggg atgctgtgca   4080
cactgtggaa ggctatcatt gactttcgaa acaaacagac ttga                    4124
```

<210> SEQ ID NO 8
<211> LENGTH: 1128
<212> TYPE: DNA
<213> ORGANISM: Homo sapiens

<400> SEQUENCE: 8

```
atggagcgcg cgtcctgctt gttgctgctg ctgctgccgc tggtgcacgt ctctgcgacc     60
acgccagaac cttgtgagct ggacgatgaa gatttccgct gcgtctgcaa cttctccgaa    120
cctcagcccg actggtccga agccttccag tgtgtgtctg cagtagaggt ggagatccat    180
gccggcggtc tcaacctaga gccgtttcta aagcgcgtcg atgcggacgc cgacccgcgg    240
cagtatgctg acacggtcaa ggctctccgc gtgcggcggc tcacagtggg agccgcacag    300
gttcctgctc agctactggt aggcgccctg cgtgtgctag cgtactcccg cctcaaggaa    360
ctgacgctcg aggacctaaa gataaccggc accatgcctc cgctgcctct ggaagccaca    420
ggacttgcac tttccagctt gcgcctacgc aacgtgtcgt gggcgacagg gcgttcttgg    480
ctcgccgagc tgcagcagtg gctcaagcca ggcctcaagg tactgagcat tgcccaagca    540
cactcgcctg ccttttcctg cgaacaggtt cgcgccttcc cggcccttac cagcctagac    600
ctgtctgaca atcctggact gggcgaacgc ggactgatgg cggctctctg tccccacaag    660
ttcccggcca tccagaatct agcgctgcgc aacacaggaa tggagacgcc cacaggcgtg    720
tgcgccgcac tggcggcggc aggtgtgcag ccccacagcc tagacctcag ccacaactcg    780
ctgcgcgcca ccgtaaaccc tagcgctccg agatgcatgt ggtccagcgc cctgaactcc    840
ctcaatctgt cgttcgctgg gctggaacag gtgcctaaag gactgccagc caagctcaga    900
gtgctcgatc tcagctgcaa cagactgaac agggcgccgc agcctgacga gctgcccgag    960
gtggataacc tgacactgga cgggaatccc ttcctggtcc ctggaactgc cctcccccac   1020
```

-continued

```
gagggctcaa tgaactccgg cgtggtccca gcctgtgcac gttcgaccct gtcggtgggg   1080

gtgtcgggaa ccctggtgct gctccaaggg gcccggggct ttgcctaa                 1128


<210> SEQ ID NO 9
<211> LENGTH: 1140
<212> TYPE: DNA
<213> ORGANISM: Homo sapiens

<400> SEQUENCE: 9

atggcggcgg cggcggctca gggggcgggg ggcggggagc cccgtagaac cgagggggtc     60

ggcccggggg tcccggggga ggtggagatg gtgaaggggc agccgttcga cgtgggcccg    120

cgctacacgc agttgcagta catcggcgag ggcgcgtacg gcatggtcag ctcggcctat    180

gaccacgtgc gcaagactcg cgtggccatc aagaagatca gccccttcga acatcagacc    240

tactgccagc gcacgctccg ggagatccag atcctgctgc gcttccgcca tgagaatgtc    300

atcggcatcc gagacattct gcgggcgtcc accctggaag ccatgagaga tgtctacatt    360

gtgcaggacc tgatggagac tgacctgtac aagttgctga aaagccagca gctgagcaat    420

gaccatatct gctacttcct ctaccagatc ctgcggggcc tcaagtacat ccactccgcc    480

aacgtgctcc accgagatct aaagccctcc aacctgctca tcaacaccac ctgcgacctt    540

aagatttgtg atttcggcct ggcccggatt gccgatcctg agcatgacca caccggcttc    600

ctgacggagt atgtggctac gcgctggtac cgggccccag agatcatgct gaactccaag    660

ggctatacca agtccatcga catctggtct gtgggctgca ttctggctga gatgctctct    720

aaccggccca tcttccctgg caagcactac ctggatcagc tcaaccacat tctgggcatc    780

ctgggctccc catcccagga ggacctgaat tgtatcatca acatgaaggc ccgaaactac    840

ctacagtctc tgccctccaa gaccaaggtg gcttgggcca agcttttccc caagtcagac    900

tccaaagccc ttgacctgct ggaccggatg ttaaccttta accccaataa acggatcaca    960

gtggaggaag cgctggctca cccctacctg gagcagtact atgacccgac ggatgagcca   1020

gtggccgagg agcccttcac cttcgccatg gagctggatg acctacctaa ggagcggctg   1080

aaggagctca tcttccagga gacagcacgc ttccagcccg gagtgctgga ggcccccctag   1140


<210> SEQ ID NO 10
<211> LENGTH: 1083
<212> TYPE: DNA
<213> ORGANISM: Homo sapiens

<400> SEQUENCE: 10

atggcggcgg cggcggcggc gggcgcgggc ccggagatgg tccgcgggca ggtgttcgac     60

gtggggccgc gctacaccaa cctctcgtac atcggcgagg gcgcctacgg catggtgtgc    120

tctgcttatg ataatgtcaa caaagttcga gtagctatca agaaaatcag ccccttttgag    180

caccagacct actgccagag aaccctgagg gagataaaaa tcttactgcg cttcagacat    240

gagaacatca ttggaatcaa tgacattatt cgagcaccaa ccatcgagca aatgaaagat    300

gtatatatag tacaggacct catggaaaca gatctttaca agctcttgaa gacacaacac    360

ctcagcaatg accatatctg ctattttctc taccagatcc tcagagggtt aaaatatatc    420

cattcagcta acgttctgca ccgtgacctc aagccttcca acctgctgct caacaccacc    480

tgtgatctca agatctgtga ctttggcctg gcccgtgttg cagatccaga ccatgatcac    540

acagggttcc tgacagaata tgtggccaca cgttggtaca gggctccaga aattatgttg    600

aattccaagg gctacaccaa gtccattgat atttggtctg taggctgcat tctggcagaa    660
```

-continued

```
atgctttcta acaggcccat ctttccaggg aagcattatc ttgaccagct gaaccacatt    720

ttgggtattc ttggatcccc atcacaagaa gacctgaatt gtataataaa tttaaaagct    780

aggaactatt tgctttctct tccacacaaa aataaggtgc catggaacag gctgttccca    840

aatgctgact ccaaagctct ggacttattg gacaaaatgt tgacattcaa cccacacaag    900

aggattgaag tagaacaggc tctggcccac ccatatctgg agcagtatta cgacccgagt    960

gacgagccca tcgccgaagc accattcaag ttcgacatgg aattggatga cttgcctaag   1020

gaaaagctca aagaactaat tttgaagag actgctagat tccagccagg atacagatct   1080

taa                                                                 1083
```

<210> SEQ ID NO 11
<211> LENGTH: 2265
<212> TYPE: DNA
<213> ORGANISM: Homo sapiens

<400> SEQUENCE: 11

```
atgttttcag gggggtgtca tagccccggg tttggccgcc ccagccccgc cttccccgcc     60

ccggggagcc cgccccctgc cccgcgtccc tgccgacagg aaacaggtga gcagattgcc    120

atcaagcagt gccggcagga gctcagcccc cggaaccgag agcggtggtg cctggagatc    180

cagatcatga gaaggctgac ccaccccaat gtggtggctg cccgagatgt ccctgagggg    240

atgcagaact tggcgcccaa tgacctgccc ctgctggcca tggagtactg ccaaggagga    300

gatctccgga agtacctgaa ccagtttgag aactgctgtg gtctgcggga aggtgccatc    360

ctcaccttgc tgagtgacat tgcctctgcg cttagatacc ttcatgaaaa cagaatcatc    420

catcgggatc taaagccaga aaacatcgtc ctgcagcaag gagaacagag gttaatacac    480

aaaattattg acctaggata tgccaaggag ctggatcagg gcagtctttg cacatcattc    540

gtggggaccc tgcagtacct ggccccagag ctactggagc agcagaagta cacagtgacc    600

gtcgactact ggagcttcgg caccctggcc tttgagtgca tcacgggctt ccggcccttc    660

ctccccaact ggcagcccgt gcagtggcat tcaaaagtgc ggcagaagag tgaggtggac    720

attgttgtta gcgaagactt gaatggaacg gtgaagtttt caagctcttt accctacccc    780

aataatctta acagtgtcct ggctgagcga ctggagaagt ggctgcaact gatgctgatg    840

tggcaccccc gacagagggg cacggatccc acgtatgggc ccaatggctg cttcaaggcc    900

ctggatgaca tcttaaactt aaagctggtt catatcttga acatggtcac gggcaccatc    960

cacacctacc ctgtgacaga ggatgagagt ctgcagagct tgaaggccag aatccaacag   1020

gacacgggca tcccagagga ggaccaggag ctgctgcagg aagcgggcct ggcgttgatc   1080

cccgataagc ctgccactca gtgtatttca gacggcaagt taaatgaggg ccacacattg   1140

gacatggatc ttgtttttct ctttgacaac agtaaaatca cctatgagac tcagatctcc   1200

ccacggcccc aacctgaaag tgtcagctgt atccttcaag agcccaagag gaatctcgcc   1260

ttcttccagc tgaggaaggt gtggggccag gtctggcaca gcatccagac cctgaaggaa   1320

gattgcaacc ggctgcagca gggacagcga gccgccatga tgaatctcct ccgaaacaac   1380

agctgcctct ccaaaatgaa gaattccatg gcttccatgt ctcagcagct caaggccaag   1440

ttggatttct tcaaaaccag catccagatt gacctggaga agtacagcga gcaaaccgag   1500

tttgggatca catcagataa actgctgctg gcctggaggg aaatggagca ggctgtggag   1560

ctctgtgggc gggagaacga agtgaaactc ctggtagaac ggatgatggc tctgcagacc   1620
```

-continued

```
gacattgtgg acttacagag gagccccatg ggccggaagc aggggggaac gctggacgac   1680

ctagaggagc aagcaaggga gctgtacagg agactaaggg aaaaacctcg agaccagcga   1740

actgagggtg acagtcagga aatggtacgg ctgctgcttc aggcaattca gagcttcgag   1800

aagaaagtgc gagtgatcta tacgcagctc agtaaaactg tggtttgcaa gcagaaggcg   1860

ctggaactgt tgcccaaggt ggaagaggtg gtgagcttaa tgaatgagga tgagaagact   1920

gttgtccggc tgcaggagaa gcggcagaag gagctctgga atctcctgaa gattgcttgt   1980

agcaaggtcc gtggtcctgt cagtggaagc ccggatagca tgaatgcctc tcgacttagc   2040

cagcctgggc agctgatgtc tcagccctcc acggcctcca acagcttacc tgagccagcc   2100

aagaagagtg aagaactggt ggctgaagca cataacctct gcaccctgct agaaaatgcc   2160

atacaggaca ctgtgaggga acaagaccag agtttcacgg ccctagactg gagctggtta   2220

cagacggaag aagaagagca cagctgcctg gagcaggcct catga                   2265
```

<210> SEQ ID NO 12
<211> LENGTH: 954
<212> TYPE: DNA
<213> ORGANISM: Homo sapiens

<400> SEQUENCE: 12

```
atgttccagg cggccgagcg cccccaggag tgggccatgg agggcccccg cgacgggctg     60

aagaaggagc ggctactgga cgaccgccac gacagcggcc tggactccat gaaagacgag    120

gagtacgagc agatggtcaa ggagctgcag gagatccgcc tcgagccgca ggaggtgccg    180

cgcggctcgg agccctggaa gcagcagctc accgaggacg gggactcgtt cctgcacttg    240

gccatcatcc atgaagaaaa ggcactgacc atggaagtga tccgccaggt gaagggagac    300

ctggccttcc tcaacttcca gaacaacctg cagcagactc cactccactt ggctgtgatc    360

accaaccagc cagaaattgc tgaggcactt ctgggagctg gctgtgatcc tgagctccga    420

gactttcgag gaaatacccc cctacacctt gcctgtgagc agggctgcct ggccagcgtg    480

ggagtcctga ctcagtcctg caccaccccg cacctccact ccatcctgaa ggctaccaac    540

tacaatggcc acacgtgtct acacttagcc tctatccatg gctacctggg catcgtggag    600

cttttggtgt ccttgggtgc tgatgtcaat gctcaggagc cctgtaatgg ccggactgcc    660

cttcacctcg cagtggacct gcaaaatcct gacctggtgt cactcctgtt gaagtgtggg    720

gctgatgtca acagagttac ctaccagggc tattctccct accagctcac ctggggccgc    780

ccaagcaccc ggatacagca gcagctgggc cagctgacac tagaaaacct tcagatgctg    840

ccagagagtg aggatgagga gagctatgac acagagtcag agttcacgga gttcacagag    900

gacgagctgc cctatgatga ctgtgtgttt ggaggccagc gtctgacgtt atga          954
```

<210> SEQ ID NO 13
<211> LENGTH: 2139
<212> TYPE: DNA
<213> ORGANISM: Homo sapiens

<400> SEQUENCE: 13

```
atggccgggg ggccgggccc gggggagccc gcagcccccg gcgcccagca cttcttgtac     60

gaggtgccgc cctgggtcat gtgccgcttc tacaaagtga tggacgccct ggagcccgcc    120

gactggtgcc agttcgccgc cctgatcgtg cgcgaccaga ccgagctgcg gctgtgcgag    180

cgctccgggc agcgcacggc cagcgtcctg tggccctgga tcaaccgcaa cgcccgtgtg    240

gccgacctcg tgcacatcct cacgcacctg cagctgctcc gtgcgcggga catcatcaca    300
```

-continued gcctggcacc ctcccgcccc gcttccgtcc ccaggcacca ctgccccgag gcccagcagc 360
atccctgcac ccgccgaggc cgaggcctgg agcccccgga agttgccatc ctcagcctcc 420
accttcctct ccccagcttt tccaggctcc cagacccatt cagggcctga gctcggcctg 480
gtcccaagcc ctgcttccct gtggcctcca ccgccatctc cagccccttc ttctaccaag 540
ccaggcccag agagctcagt gtccctcctg cagggagccc gcccctttcc gttttgctgg 600
cccctctgtg agatttcccg gggcacccac aacttctcgg aggagctcaa gatcggggag 660
ggtggctttg ggtgcgtgta ccgggcggtg atgaggaaca cggtgtatgc tgtgaagagg 720
ctgaaggaga acgctgacct ggagtggact gcagtgaagc agagcttcct gaccgaggtg 780
gagcagctgt ccaggtttcg tcacccaaac attgtggact ttgctggcta ctgtgctcag 840
aacggcttct actgcctggt gtacggcttc ctgcccaacg gctccctgga ggaccgtctc 900
cactgccaga cccaggcctg cccacctctc tcctggcctc agcgactgga catccttctg 960
ggtacagccc gggcaattca gtttctacat caggacagcc ccagcctcat ccatggagac 1020
atcaagagtt ccaacgtcct tctggatgag aggctgacac ccaagctggg agactttggc 1080
ctggcccggt tcagccgctt tgccgggtcc agccccagcc agagcagcat ggtggcccgg 1140
acacagacag tgcggggcac cctggcctac ctgcccgagg agtacatcaa gacgggaagg 1200
ctggctgtgg acacggacac cttcagcttt ggggtggtag tgctagagac cttggctggt 1260
cagagggctg tgaagacgca cggtgccagg accaagtatc tgaaagacct ggtggaagag 1320
gaggctgagg aggctggagt ggctttgaga agcacccaga gcacactgca agcaggtctg 1380
gctgcagatg cctgggctgc tcccatcgcc atgcagatct acaagaagca cctggacccc 1440
aggcccgggc cctgcccacc tgagctgggc ctgggcctgg gccagctggc ctgctgctgc 1500
ctgcaccgcc gggccaaaag gaggcctcct atgacccagg tgtacgagag gctagagaag 1560
ctgcaggcag tggtggcggg ggtgcccggg cattcggagg ccgccagctg catcccccct 1620
tccccgcagg agaactccta cgtgtccagc actggcagag cccacagtgg ggctgctcca 1680
tggcagcccc tggcagcgcc atcaggagcc agtgcccagg cagcagagca gctgcagaga 1740
ggccccaacc agcccgtgga gagtgacgag agcctaggcg gcctctctgc tgccctgcgc 1800
tcctggcact tgactccaag ctgccctctg gacccagcac ccctcaggga ggccggctgt 1860
cctcaggggg acacggcagg agaatcgagc tgggggagtg gcccaggatc ccggcccaca 1920
gccgtggaag gactggccct tggcagctct gcatcatcgt cgtcagagcc accgcagatt 1980
atcatcaacc ctgcccgaca gaagatggtc cagaagctgg ccctgtacga ggatggggcc 2040
ctggacagcc tgcagctgct gtcgtccagc tccctcccag gcttgggcct ggaacaggac 2100
aggcaggggc ccgaagaaag tgatgaattt cagagctga 2139

<210> SEQ ID NO 14
<211> LENGTH: 1284
<212> TYPE: DNA
<213> ORGANISM: Homo sapiens

<400> SEQUENCE: 14
atgagcagaa gcaagcgtga caacaatttt tatagtgtag agattggaga ttctacattc 60
acagtcctga aacgatatca gaatttaaaa cctataggct caggagctca aggaatagta 120
tgcgcagctt atgatgccat tcttgaaaga aatgttgcaa tcaagaagct aagccgacca 180
tttcagaatc agactcatgc caagcgggcc tacagagagc tagttcttat gaaatgtgtt 240
aatcacaaaa atataattgg ccttttgaat gttttcacac cacagaaatc cctagaagaa 300
tttcaagatg tttacatagt catggagctc atggatgcaa atctttgcca agtgattcag 360
atggagctag atcatgaaag aatgtcctac cttctctatc agatgctgtg tggaatcaag 420
caccttcatt ctgctggaat tattcatcgg gacttaaagc ccagtaatat agtagtaaaa 480
tctgattgca ctttgaagat tcttgacttc ggtctggcca ggactgcagg aacgagtttt 540
atgatgacgc cttatgtagt gactcgctac tacagagcac ccgaggtcat ccttggcatg 600
ggctacaagg aaaacgttga catttggtca gttgggtgca tcatgggaga aatgatcaaa 660
ggtggtgttt tgttcccagg tacagatcat attgatcagt ggaataaagt tattgaacag 720
cttggaacac catgtcctga attcatgaag aaactgcaac caacagtaag gacttacgtt 780
gaaaacagac ctaaatatgc tggatatagc tttgagaaac tcttccctga tgtccttttc 840
ccagctgact cagaacacaa caaacttaaa gccagtcagg caagggattt gttatccaaa 900
atgctggtaa tagatgcatc taaaaggatc tctgtagatg aagctctcca acacccgtac 960
atcaatgtct ggtatgatcc ttctgaagca gaagctccac caccaaagat ccctgacaag 1020
cagttagatg aaagggaaca cacaatagaa gagtggaaag aattgatata taaggaagtt 1080
atggacttgg aggagagaac caagaatgga gttatacggg ggcagccctc tcctttaggt 1140
gcagcagtga tcaatggctc tcagcatcca tcatcatcgt cgtctgtcaa tgatgtgtct 1200
tcaatgtcaa cagatccgac tttggcctct gatacagaca gcagtctaga agcagcagct 1260
gggcctctgg gctgctgtag atga 1284

<210> SEQ ID NO 15
<211> LENGTH: 1446
<212> TYPE: DNA
<213> ORGANISM: Homo sapiens

<400> SEQUENCE: 15
atgggggcct tggccagagc cctgccgtcc atactgctgg cattgctgct tacgtccacc 60
ccagaggctc tgggtgccaa ccccggcttg gtcgccagga tcaccgacaa gggactgcag 120
tatgcggccc aggaggggct attagctctg cagagtgagc tgctcaggat cacgctgcct 180
gacttcaccg gggacttgag gatcccccac gtcggccgtg ggcgctatga gttccacagc 240
ctgaacatcc acagctgtga gctgcttcac tctgcgctga ggcctgtccc tggccagggc 300
ctgagtctca gcatctccga ctcctccatc cgggtccagg gcaggtggaa ggtgcgcaag 360
tcattcttca aactacaggg ctcctttgat gtcagtgtca agggcatcag catttcggtc 420
aacctcctgt tgggcagcga gtcctccggg aggcccacag ttactgcctc cagctgcagc 480
agtgacatcg ctgacgtgga ggtggacatg tcgggagact tggggtggct gttgaacctc 540
ttccacaacc agattgagtc caagttccag aaagtactgg agagcaggat ttgcgaaatg 600
atccagaaat cggtgtcctc cgatctacag ccttatctcc aaactctgcc agttacaaca 660
gagattgaca gtttcgccga cattgattat agcttagtgg aagcccctcg ggcaacagcc 720
cagatgctgg aggtgatgtt taagggtgaa atctttcatc gtaaccaccg ttctccagtt 780
accctccttg ctgcagtcat gagccttcct gaggaacaca acaaaatggt ctactttgcc 840
atctcggatt atgtcttcaa cacggccagc ctggtttatc atgaggaagg atatctgaac 900
ttctccatca cagatgacat gataccgcct gactctaata tccgactgac caccaagtcc 960
ttccgaccct tcgtcccacg gttagccagg ctctacccca acatgaacct ggaactccag 1020
ggatcagtgc cctctgctcc gctcctgaac ttcagccctg ggaatctgtc tgtggacccc 1080

-continued tatatggaga tagatgcctt tgtgctcctg cccagctcca gcaaggagcc tgtcttccgg 1140
ctcagtgtgg ccactaatgt gtccgccacc ttgaccttca ataccagcaa gatcactggg 1200
ttcctgaagc caggaaaggt aaaagtggaa ctgaaagaat ccaaagttgg actattcaat 1260
gcagagctgt tggaagcgct cctcaactat tacatcctta acaccctcta ccccaagttc 1320
aatgataagt tggccgaagg cttccccctt cctctgctga agcgtgttca gctctacgac 1380
cttgggctgc agatccataa ggacttcctg ttcttgggtg ccaatgtcca atacatgaga 1440
gtttga 1446

<210> SEQ ID NO 16
<211> LENGTH: 1182
<212> TYPE: DNA
<213> ORGANISM: Homo sapiens

<400> SEQUENCE: 16
atgcccaaga agaagccgac gcccatccag ctgaacccgg cccccgacgg ctctgcagtt 60
aacgggacca gctctgcgga gaccaacttg gaggccttgc agaagaagct ggaggagcta 120
gagcttgatg agcagcagcg aaagcgcctt gaggcctttc ttacccagaa gcagaaggtg 180
ggagaactga aggatgacga ctttgagaag atcagtgagc tgggggctgg caatggcggt 240
gtggtgttca aggtctccca caagccttct ggcctggtca tggccagaaa gctaattcat 300
ctggagatca aacccgcaat ccggaaccag atcataaggg agctgcaggt tctgcatgag 360
tgcaactctc cgtacatcgt gggcttctat ggtgcgttct acagcgatgg cgagatcagt 420
atctgcatgg agcacatgga tggaggttct ctggatcaag tcctgaagaa agctggaaga 480
attcctgaac aaattttagg aaaagttagc attgctgtaa taaaaggcct gacatatctg 540
agggagaagc acaagatcat gcacagagat gtcaagccct ccaacatcct agtcaactcc 600
cgtggggaga tcaagctctg tgactttggg gtcagcgggc agctcatcga ctccatggcc 660
aactccttcg tgggcacaag gtcctacatg tcgccagaaa gactccaggg gactcattac 720
tctgtgcagt cagacatctg gagcatggga ctgtctctgg tagagatggc ggttgggagg 780
tatcccatcc ctcctccaga tgccaaggag ctggagctga tgtttgggtg ccaggtggaa 840
ggagatgcgg ctgagacccc acccaggcca aggacccccg ggaggcccct tagctcatac 900
ggaatggaca gccgacctcc catggcaatt tttgagttgt tggattacat agtcaacgag 960
cctcctccaa aactgcccag tggagtgttc agtctggaat ttcaagattt tgtgaataaa 1020
tgcttaataa aaaaccccgc agagagagca gatttgaagc aactcatggt tcatgctttt 1080
atcaagagat ctgatgctga ggaagtggat tttgcaggtt ggctctgctc caccatcggc 1140
cttaaccagc ccagcacacc aacccatgct gctggcgtct aa 1182

<210> SEQ ID NO 17
<211> LENGTH: 1203
<212> TYPE: DNA
<213> ORGANISM: Homo sapiens

<400> SEQUENCE: 17
atgctggccc ggaggaagcc ggtgctgccg gcgctcacca tcaaccctac catcgccgag 60
ggcccatccc ctaccagcga gggcgcctcc gaggcaaacc tggtggacct gcagaagaag 120
ctggaggagc tggaacttga cgagcagcag aagaagcggc tggaagcctt tctcacccag 180
aaagccaagg tcggcgaact caaagacgat gacttcgaaa ggatctcaga gctgggcgcg 240

```
ggcaacggcg gggtggtcac caaagtccag cacagaccct cgggcctcat catggccagg    300

aagctgatcc accttgagat caagccggcc atccggaacc agatcatccg cgagctgcag    360

gtcctgcacg aatgcaactc gccgtacatc gtgggcttct acggggcctt ctacagtgac    420

ggggagatca gcatttgcat ggaacacatg gacggcggct ccctggacca ggtgctgaaa    480

gaggccaaga ggattcccga ggagatcctg ggaaagtca gcatcgcggt tctccggggc    540

ttggcgtacc tccgagagaa gcaccagatc atgcaccgag atgtgaagcc ctccaacatc    600

ctcgtgaact ctagagggga gatcaagctg tgtgacttcg gggtgagcgg ccagctcatc    660

gactccatgg ccaactcctt cgtgggcacg cgctcctaca tggctccgga gcggttgcag    720

ggcacacatt actcggtgca gtcggacatc tggagcatgg gcctgtccct ggtggagctg    780

gccgtcggaa ggtaccccat ccccccgccc gacgccaaag agctggaggc catctttggc    840

cggcccgtgg tcgacgggga agaaggagag cctcacagca tctcgcctcg gccgaggccc    900

cccgggcgcc ccgtcagcgg tcacgggatg gatagccggc ctgccatggc catctttgaa    960

ctcctggact atattgtgaa cgagccacct cctaagctgc ccaacggtgt gttcaccccc   1020

gacttccagg agtttgtcaa taaatgcctc atcaagaacc cagcggagcg ggcggacctg   1080

aagatgctca caaaccacac cttcatcaag cggtccgagg tggaagaagt ggattttgcc   1140

ggctggttgt gtaaaaccct gcggctgaac cagcccggca cacccacgcg caccgccgtg   1200

tga                                                                 1203
```

<210> SEQ ID NO 18
<211> LENGTH: 957
<212> TYPE: DNA
<213> ORGANISM: Homo sapiens

<400> SEQUENCE: 18

```
atgtccaagc cacccgcacc caaccccaca cccccccgga acctggactc ccggaccttc     60

atcaccattg gagacagaaa ctttgaggtg gaggctgatg acttggtgac catctcagaa    120

ctgggccgtg gagcctatgg ggtggtagag aaggtgcggc acgcccagag cggcaccatc    180

atggccgtga agcggatccg ggccaccgtg aactcacagg agcagaagcg gctgctcatg    240

gacctggaca tcaacatgcg cacggtcgac tgtttctaca ctgtcacctt ctacggggca    300

ctattcagag agggagacgt gtggatctgc atggagctca tggacacatc cttggacaag    360

ttctaccgga aggtgctgga taaaaacatg acaattccag aggacatcct tggggagatt    420

gctgtgtcta tcgtgcgggc cctggagcat ctgcacagca agctgtcggt gatccacaga    480

gatgtgaagc cctccaatgt ccttatcaac aaggagggcc atgtgaagat gtgtgacttt    540

ggcatcagtg gctacttggt ggactctgtg gccaagacga tggatgccgg ctgcaagccc    600

tacatggccc ctgagaggat caacccagag ctgaaccaga agggctacaa tgtcaagtcc    660

gacgtctgga gcctgggcat caccatgatt gagatggcca tcctgcggtt cccttacgag    720

tcctggggga ccccgttcca gcagctgaag caggtggtgg aggagccgtc cccccagctc    780

ccagccgacc gtttctcccc cgagtttgtg gacttcactg ctcagtgcct gaggaagaac    840

cccgcagagc gtatgagcta cctggagctg atggagcacc ccttcttcac cttgcacaaa    900

accaagaaga cggacattgc tgccttcgtg aaggagatcc tgggagaaga ctcatag       957
```

<210> SEQ ID NO 19
<211> LENGTH: 1005
<212> TYPE: DNA
<213> ORGANISM: Homo sapiens

<400> SEQUENCE: 19
atgtctcagt cgaaaggcaa gaagcgaaac cctggcctta aaattccaaa agaagcattt 60
gaacaacctc agaccagttc cacaccacct cgagatttag actccaaggc ttgcatttct 120
attggaaatc agaactttga ggtgaaggca gatgacctgg agcctataat ggaactggga 180
cgaggtgcgt acggggtggt ggagaagatg cggcacgtgc ccagcgggca gatcatggca 240
gtgaagcgga tccgagccac agtaaatagc caggaacaga aacggctact gatggatttg 300
gatatttcca tgaggacggt ggactgtcca ttcactgtca ccttttatgg cgcactgttt 360
cgggagggtg atgtgtggat ctgcatggag ctcatggata catcactaga taaattctac 420
aaacaagtta ttgataaagg ccagacaatt ccagaggaca tcttagggaa aatagcagtt 480
tctattgtaa aagcattaga acatttacat agtaagctgt ctgtcattca cagagacgtc 540
aagccttcta atgtactcat caatgctctc ggtcaagtga agatgtgcga ttttggaatc 600
agtggctact tggtggactc tgttgctaaa acaattgatg caggttgcaa accatacatg 660
gcccctgaaa gaataaaccc agagctcaac cagaagggat acagtgtgaa gtctgacatt 720
tggagtctgg gcatcacgat gattgagttg gccatccttc gatttcccta tgattcatgg 780
ggaactccat ttcagcagct caaacaggtg gtagaggagc catcgccaca actcccagca 840
gacaagttct ctgcagagtt tgttgacttt acctcacagt gcttaaagaa gaattccaaa 900
gaacggccta catacccaga gctaatgcaa catccatttt tcaccctaca tgaatccaaa 960
ggaacagatg tggcatcttt tgtaaaactg attcttggag actaa 1005

<210> SEQ ID NO 20
<211> LENGTH: 4539
<212> TYPE: DNA
<213> ORGANISM: Homo sapiens

<400> SEQUENCE: 20
atggcggcgg cggcggggaa tcgcgcctcg tcgtcgggat tcccgggcgc cagggctacg 60
agccctgagg caggcggcgg cggaggagcc ctcaaggcga gcagcgcgcc cgcggctgcc 120
gcgggactgc tgcgggaggc gggcagcggg ggccgcgagc gggcggactg gcggcggcgg 180
cagctgcgca aagtgcggag tgtggagctg gaccagctgc ctgagcagcc gctcttcctt 240
gccgcctcac cgccggcctc ctcgacttcc ccgtcgccgg agcccgcgga cgcagcgggg 300
agtgggaccg gcttccagcc tgtggcggtg ccgccgcccc acggagccgc gagccgcggc 360
ggcgcccacc ttaccgagtc ggtggcggcg ccggacagcg gcgcctcgag tcccgcagcg 420
gccgagcccg gggagaagcg ggcgcccgcc gccgagccgt ctcctgcagc ggcccccgcc 480
ggtcgtgaga tggagaataa agaaactctc aaagggttgc acaagatgga tgatcgtcca 540
gaggaacgaa tgatcaggga gaaactgaag gcaacctgta tgccagcctg gaagcacgaa 600
tggttggaaa ggagaaatag gcgagggcct gtggtggtaa aaccaatccc agttaaagga 660
gatggatctg aaatgaatca cttagcagct gagtctccag gagaggtcca ggcaagtgcg 720
gcttcaccag cttccaaagg ccgacgcagt ccttctcctg gcaactcccc atcaggtcgc 780
acagtgaaat cagaatctcc aggagtaagg agaaaaagag tttccccagt gccttttcag 840
agtggcagaa tcacaccacc ccgaagagcc ccttcaccag atggcttctc accatatagc 900
cctgaggaaa caaaccgccg tgttaacaaa gtgatgcggg ccagactgta cttactgcag 960
cagatagggc ctaactcttt cctgattgga ggagacagcc cagacaataa ataccgggtg 1020

-continued

```
tttattgggc ctcagaactg cagctgtgca cgtggaacat tctgtattca tctgctattt   1080
gtgatgctcc gggtgtttca actagaacct tcagacccaa tgttatggag aaaaacttta   1140
aagaattttg aggttgagag tttgttccag aaatatcaca gtaggcgtag ctcaaggatc   1200
aaagctccat ctcgtaacac catccagaag tttgtttcac gcatgtcaaa ttctcataca   1260
ttgtcatcat ctagtacttc tacgtctagt tcagaaaaca gcataaagga tgaagaggaa   1320
cagatgtgtc ctatttgctt gttgggcatg cttgatgaag aaagtcttac agtgtgtgaa   1380
gacggctgca ggaacaagct gcaccaccac tgcatgtcaa tttgggcaga agagtgtaga   1440
agaaatagag aacctttaat atgtcccctt tgtagatcta agtggagatc tcatgatttc   1500
tacagccacg agttgtcaag tcctgtggat tccccttctt ccctcagagc tgcacagcag   1560
caaaccgtac agcagcagcc tttggctgga tcacgaagga atcaagagag caattttaac   1620
cttactcatt atggaactca gcaaatccct cctgcttaca aagatttagc tgagccatgg   1680
attcaggtgt ttggaatgga actcgttggc tgcttatttt ctagaaactg gaatgtgaga   1740
gagatggccc tcaggcgtct ttcccatgat gtcagtgggg ccctgctgtt ggcaaatggg   1800
gagagcactg gaaattctgg gggcagcagt ggaagcagcc cgagtggggg agccaccagt   1860
gggtcttccc agaccagtat ctcaggagat gtggtggagg catgctgcag cgttctgtca   1920
atggtctgtg ctgaccctgt ctacaaagtg tacgttgctg ctttaaaaac attgagagcc   1980
atgctggtat atactccttg ccacagttta gcggaaagaa tcaaacttca gagacttctc   2040
cagccagttg tagacaccat cctagtcaaa tgtgcagatg ccaatagccg cacaagtcag   2100
ctgtccatat caacactgtt ggaactgtgc aaaggccaag caggagagtt ggcagttggc   2160
agagaaatac taaaagctgg atccattggt attggtggtg ttgattatgt cttaaattgt   2220
attcttggaa accaaactga atcaaacaat tggcaagaac ttcttggccg cctttgtctt   2280
atagatagac tgttgttgga atttcctgct gaattttatc ctcatattgt cagtactgat   2340
gtttcacaag ctgagcctgt tgaaatcagg tataagaagc tgctgtccct cttaaccttt   2400
gctttgcagt ccattgataa ttcccactca atggttggca aactttccag aaggatctac   2460
ttgagttctg caagaatggt tactacagta ccccatgtgt tttcaaaact gttagaaatg   2520
ctgagtgttt ccagttccac tcacttcacc aggatgcgtc gccgtttgat ggctattgca   2580
gatgaggtgg aaattgccga agccatccag ttgggcgtag aagacacttt ggatggtcaa   2640
caggacagct tcttgcaggc atctgttccc aacaactatc tggaaaccac agagaacagt   2700
tcccctgagt gcacagtcca tttagagaaa actggaaaag gattatgtgc tacaaaattg   2760
agtgccagtt cagaggacat ttctgagaga ctggccagca tttcagtagg accttctagt   2820
tcaacaacaa caacaacaac aacaacagag caaccaaagc caatggttca aacaaaaggc   2880
agaccccaca gtcagtgttt gaactcctct cctttatctc atcattccca attaatgttt   2940
ccagccttgt caacccccttc ttcttctacc ccatctgtac cagctggcac tgcaacagat   3000
gtctctaagc atagacttca gggattcatt ccctgcagaa taccttctgc atctcctcaa   3060
acacagcgca agttttctct acaattccac agaaactgtc ctgaaaacaa agactcagat   3120
aaactttccc cagtctttac tcagtcaaga cccttgccct ccagtaacat acacaggcca   3180
aagccatcta gacctacccc aggtaataca agtaaacagg gagatccctc aaaaaatagc   3240
atgacacttg atctgaacag tagttccaaa tgtgatgaca gctttggctg tagcagcaat   3300
agtagtaatg ctgttatacc cagtgacgag acagtgttca ccccagtaga ggagaaatgc   3360
agattagatg tcaatacaga gctcaactcc agtattgagg accttcttga agcatctatg   3420
```

```
ccttcaagtg atacaacagt aacttttaag tcagaagttg ctgtcctgtc tcctgaaaag   3480
gctgaaaatg atgataccta caaagatgat gtgaatcata atcaaaagtg caaagagaag   3540
atggaagctg aagaagaaga agctttagca attgccatgg caatgtcagc gtctcaggat   3600
gccctcccca tagttcctca gctgcaggtt gaaaatggag aagatatcat cattattcaa   3660
caggatacac cagagactct accaggacat accaaagcaa aacaaccgta tagagaagac   3720
actgaatggc tgaaaggtca acagataggc cttggagcat ttcttcttg ttatcaggct    3780
caagatgtgg gaactggaac tttaatggct gttaaacagg tgacttatgt cagaaacaca   3840
tcttctgagc aagaagaagt agtagaagca ctaagagaag agataagaat gatgagccat   3900
ctgaatcatc caaacatcat taggatgttg ggagccacgt gtgagaagag caattacaat   3960
ctcttcattg aatggatggc agggggatcg gtggctcatt tgctgagtaa atatggagcc   4020
ttcaaagaat cagtagttat taactacact gaacagttac tccgtggcct ttcgtatctc   4080
catgaaaacc aaatcattca cagagatgtc aaaggtgcca atttgctaat tgacagcact   4140
ggtcagagac taagaattgc agattttgga gctgcagcca ggttggcatc aaaaggaact   4200
ggtgcaggag agtttcaggg acaattactg ggacaattg catttatggc acctgaggta    4260
ctaagaggtc aacagtatgg aaggagctgt gatgtatgga gtgttggctg tgctattata   4320
gaaatggctt gtgcaaaacc accatggaat gcagaaaaac actccaatca tcttgctttg   4380
atatttaaga ttgctagtgc aactactgct ccatcgatcc cttcacattt gtctcctggt   4440
ttacgagatg tggctcttcg ttgtttagaa cttcaacctc aggacagacc tccatcaaga   4500
gagctactga agcatccagt ctttcgtact acatggtag                          4539
```

<210> SEQ ID NO 21
<211> LENGTH: 1974
<212> TYPE: DNA
<213> ORGANISM: Homo sapiens

<400> SEQUENCE: 21

```
atggacgaac aggaggcatt gaactcaatc atgaacgatc tggtggccct ccagatgaac     60
cgacgtcacc ggatgcctgg atatgagacc atgaagaaca aagacacagg tcactcaaat    120
aggcagaaaa aacacaacag cagcagctca gcccttctga acagccccac agtaacaaca    180
agctcatgtg caggggccag tgagaaaaag aaatttttga gtgacgtcag aatcaagttc    240
gagcacaacg gggagaggcg aattatagcg ttcagccggc ctgtgaaata tgaagatgtg    300
gagcacaagg tgacaacagt atttggacaa cctcttgatc tacattacat gaacaatgag    360
ctctccatcc tgctgaaaaa ccaagatgat cttgataaag caattgacat tttagataga    420
agctcaagca tgaaaagcct taggatattg ctgttgtccc aggacagaaa ccataacagt    480
tcctctcccc actctggggt gtccagacag gtgcggatca aggcttccca gtccgcaggg    540
gatataaata ctatctacca gccccccgag cccagaagca ggcacctctc tgtcagctcc    600
cagaaccctg gccgaagctc acctcccct ggctatgttc ctgagcggca gcagcacatt     660
gcccggcagg ggtcctacac cagcatcaac agtgaggggg agttcatccc agagaccagc    720
gagcagtgca tgctggatcc cctgagcagt gcagaaaatt ccttgtctgg aagctgccaa    780
tccttggaca ggtcagcaga cagcccatcc ttccggaaat cacgaatgtc ccgtgcccag    840
agcttccctg acaacagaca ggaatactca gatcgggaaa ctcagcttta tgacaaaggg    900
gtcaaaggtg gaacctaccc ccggcgctac cacgtgtctg tgcaccacaa ggactacagt    960
```

-continued

```
gatggcagaa gaacatttcc ccgaatacgg cgtcatcaag gcaacttgtt caccctggtg   1020

ccctccagcc gctccctgag cacaaatggc gagaacatgg gtctggctgt gcaatacctg   1080

gacccccgtg ggcgcctgcg gagtgcggac agcgagaatg ccctctctgt gcaggagagg   1140

aatgtgccaa ccaagtctcc cagtgccccc atcaactggc gccggggaaa gctcctgggc   1200

cagggtgcct tcggcagggt ctatttgtgc tatgacgtgg acacgggacg tgaacttgct   1260

tccaagcagg tccaatttga tccagacagt cctgagacaa gcaaggaggt gagtgctctg   1320

gagtgcgaga tccagttgct aaagaacttg cagcatgagc gcatcgtgca gtactatggc   1380

tgtctgcggg accgcgctga gaagaccctg accatcttca tggagtacat gccagggggc   1440

tcggtgaaag accagttgaa ggcttacggt gctctgacag agagcgtgac ccgaaagtac   1500

acgcggcaga tcctggaggg catgtcctac ctgcacagca acatgattgt tcaccgggac   1560

attaagggag ccaacatcct ccgagactct gctgggaatg taaagctggg ggactttggg   1620

gccagcaaac gcctgcagac gatctgtatg tcggggacgg gcatgcgctc cgtcactggc   1680

acaccctact ggatgagccc tgaggtgatc agcggcgagg gctatggaag gaaagcagac   1740

gtgtggagcc tgggctgcac tgtggtggag atgctgacag agaaaccacc gtgggcagag   1800

tatgaagcta tggccgccat cttcaagatt gccacccagc ccaccaatcc tcagctgccc   1860

tcccacatct ctgaacatgg ccgggacttc ctgaggcgca tttttgtgga ggctcgccag   1920

agaccttcag ctgaggagct gctcacacac cactttgcac agctcatgta ctga         1974
```

<210> SEQ ID NO 22
<211> LENGTH: 4826
<212> TYPE: DNA
<213> ORGANISM: Homo sapiens

<400> SEQUENCE: 22

```
atgagagaag ccgctgccgc gctggtccct cctcccgcct ttgccgtcac gcctgccgcc     60

gccatggagg agccgccgcc accgccgccg ccgccaccac cgccaccgga acccgagacc    120

gagtcagaac ccgagtgctg cttggcggcg aggcaagagg gcacattggg agattcagct    180

tgcaagagtc ctgaatctga tctagaagac ttctccgatg aaacaaatac agagaatctt    240

tatggtacct ctcccccccag cacacctcga cagatgaaac gcatgtcaac caaacatcag    300

aggaataatg tggggaggcc agccagtcgg tctaatttga aagaaaaaat gaatgcacca    360

aatcagcctc cacataaaga cactggaaaa acagtggaga atgtggaaga atacagctat    420

aagcaggaga aaaagatccg agcagctctt agaacaacag agcgtgatca taaaaaaaat    480

gtacagtgct cattcatgtt agactcagtg ggtggatctt tgccaaaaaa atcaattcca    540

gatgtggatc tcaataagcc ttacctcagc cttggctgta gcaatgctaa gcttccagta    600

tctgtgccca tgcctatagc cagacctgca cgccagactt ctaggactga ctgtccagca    660

gatcgtttaa agtttttga aactttacga cttttgctaa agcttacctc agtctcaaag    720

aaaaaagaca gggagcaaag aggacaagaa aatacgtctg gtttctggct taaccgatct    780

aacgaactga tctggttaga gctacaagcc tggcatgcag gacggacaat taacgaccag    840

gacttctttt tatatacagc ccgtcaagcc atcccagata ttattaatga aatccttact    900

ttcaaagtcg actatgggag cttcgccttt gttagagata gagctggttt taatggtact    960

tcagtagaag ggcagtgcaa agccactcct ggaacaaaga ttgtaggtta ctcaacacat   1020

catgagcatc tccaacgcca gagggtctca tttgagcagg taaaacggat aatggagctg   1080

ctagagtaca tagaagcact ttatccatca ttgcaggctc ttcagaagga ctatgaaaaa   1140
```

-continued

```
tatgctgcaa aagacttcca ggacagggtg caggcactct gtttgtggtt aaacatcaca   1200
aaagacttaa atcagaaatt aaggattatg ggcactgttt tgggcatcaa gaatttatca   1260
gacattggct ggccagtgtt tgaaatccct tcccctcgac catccaaagg taatgagccg   1320
gagtatgagg gtgatgacac agaaggagaa ttaaaggagt tggaaagtag tacggatgag   1380
agtgaagaag aacaaatctc tgatcctagg gtaccggaaa tcagacagcc catagataac   1440
agcttcgaca tccagtcgcg ggactgcata tccaagaagc ttgagaggct cgaatctgag   1500
gatgattctc ttggctgggg agcaccagac tggagcacag aagcaggctt tagtagacat   1560
tgtctgactt ctatttatag accatttgta gacaaagcac tgaagcagat ggggttaaga   1620
aagttaattt taagacttca caagctaatg gatggttcct tgcaaagggc acgtatagca   1680
ttggtaaaga acgatcgtcc agtggagttt tctgaatttc cagatcccat gtggggttca   1740
gattatgtgc agttgtcaag gacaccacct tcatctgagg agaaatgcag tgctgtgtcg   1800
tgggaggagc tgaaggccat ggatttacct tcattcgaac ctgccttcct agttctctgc   1860
cgagtccttc tgaatgtcat acatgagtgt ctgaagttaa gattggagca gagacctgct   1920
ggagaaccat ctctcttgag tattaagcag ctggtgagag agtgtaagga ggtcctgaag   1980
ggcggcctgc tgatgaagca gtactaccag ttcatgctgc aggaggttct ggaggacttg   2040
gagaagcccg actgcaacat tgacgctttt gaagaggatc tacataaaat gcttatggtg   2100
tattttgatt acatgagaag ctggatccaa atgctacagc aattacctca agcatcgcat   2160
agtttaaaaa atctgttaga agaagaatgg aatttcacca aagaaataac tcattacata   2220
cggggaggag aagcacaggc cgggaagctt ttctgtgaca ttgcaggaat gctgctgaaa   2280
tctacaggaa gtttttttaga atttggctta caggagagct gtgctgaatt ttggactagt   2340
gcggatgaca gcagtgcttc cgacgaaatc aggaggtctg ttatagagat cagtcgagcc   2400
ctgaaggagc tcttccatga agccagagaa agggcttcca aagcacttgg atttgctaaa   2460
atgttgagaa aggacctgga aatagcagca gaattcaggc tttcagcccc agttagagac   2520
ctcctggatg ttctgaaatc aaaacagtat gtcaaggtgc aaattcctgg gttagaaaac   2580
ttgcaaatgt ttgttccaga cactcttgct gaggagaaga gtattatttt gcagttactc   2640
aatgcagctg caggaaagga ctgttcaaaa gattcagatg acgtactcat cgatgcctat   2700
ctgcttctga ccaagcacgg tgatcgagcc cgtgattcag aggacagctg gggcacctgg   2760
gaggcacagc ctgtcaaagt cgtgcctcag gtggagactg ttgacaccct gagaagcatg   2820
caggtggata atcttttact agttgtcatg cagtctgcgc atctcacaat tcagagaaaa   2880
gctttccagc agtccattga gggacttatg actctgtgcc aggagcagac atccagtcag   2940
ccggtcatcg ccaaagcttt gcagcagctg aagaatgatg cattggagct atgcaacagg   3000
ataagcaatg ccattgaccg cgtggaccac atgttcacat cagaatttga tgctgaggtt   3060
gatgaatctg aatctgtcac cttgcaacag tactaccgag aagcaatgat tcaggggtac   3120
aattttggat ttgagtatca taaagaagtt gttcgtttga tgtctgggga gtttagacag   3180
aagataggag acaaatatat aagctttgcc cggaagtgga tgaattatgt cctgactaaa   3240
tgtgagagtg gtagaggtac aagacccagg tgggcgactc aaggatttga ttttctacaa   3300
gcaattgaac ctgcctttat ttcagcttta ccagaagatg acttcttgag tttacaagcc   3360
ttgatgaatg aatgcattgg ccatgtcata ggaaaaccac acagtcctgt tacaggtttg   3420
taccttgcca ttcatcggaa cagcccccgt cctatgaagg tacctcgatg ccatagtgac   3480
```

```
cctcctaacc cacacctcat tatccccact ccagagggat tcagcactcg gagcatgcct   3540

tccgacgcgc ggagccatgg cagccctgct gctgctgctg ctgctgctgc tgctgctgtt   3600

gctgccagtc ggcccagccc ctctggtggt gactctgtgc tgcccaaatc catcagcagt   3660

gcccatgata ccaggggttc cagcgttcct gaaaatgatc gattggcttc catagctgct   3720

gaattgcagt ttaggtccct gagtcgtcac tcaagcccca cggaggagcg agatgaacca   3780

gcatatccaa gaggagattc aagtgggtcc acaagaagaa gttgggaact tcggacacta   3840

atcagccaga gtaaagatac tgcttctaaa ctaggaccca tagaagctat ccagaagtca   3900

gtccgattgt ttgaagaaaa gaggtaccga gaaatgagga gaaagaatat cattggtcaa   3960

gtttgtgata cgcctaagtc ctatgataat gttatgcacg ttggcttgag gaaggtgacc   4020

ttcaaatggc aaagaggaaa caaaattgga gaaggccagt atgggaaggt gtacacctgc   4080

atcagcgtcg acaccgggga gctgatggcc atgaaagaga ttcgatttca acctaatgac   4140

cataagacta tcaaggaaac tgcagacgaa ttgaaaatat tcgaaggcat caaacacccc   4200

aatctggttc ggtattttgg tgtggagctc catagagaag aaatgtacat cttcatggag   4260

tactgcgatg aggggacttt agaagaggtg tcaaggctgg gacttcagga acatgtgatt   4320

aggctgtatt caaagcagat caccattgcg atcaacgtcc tccatgagca tggcatagtc   4380

caccgtgaca ttaaaggtgc caatatcttc cttacctcat ctggattaat caaactggga   4440

gattttggat gttcagtaaa gctcaaaaac aatgcccaga ccatgcctgg tgaagtgaac   4500

agcaccctgg ggacagcagc atacatggca cctgaagtca tcactcgtgc caaaggagag   4560

ggccatgggc gtgcggccga catctggagt ctggggtgtg ttgtcataga gatggtgact   4620

ggcaagaggc cttggcatga gtatgagcac aactttcaaa ttatgtataa agtggggatg   4680

ggacataagc caccaatccc tgaaagatta agccctgaag gaaaggactt cctttctcac   4740

tgccttgaga gtgacccaaa gatgagatgg accgccagcc agctcctcga ccattcgttt   4800

gtcaaggttt gcacagatga agaatg                                        4826
```

<210> SEQ ID NO 23
<211> LENGTH: 3867
<212> TYPE: DNA
<213> ORGANISM: Homo sapiens

<400> SEQUENCE: 23

```
atggcggggc cgtgtccccg gtccggggcg gagcgcgccg gcagctgctg gcaggacccg     60

ctggccgtgg cgctgagccg gggccggcag ctcgcggcgc ccccgggccg gggctgcgcg    120

cggagccggc cgctcagcgt ggtctacgtg ctgacccggg agccgcagcc cgggctcgag    180

cctcgggagg gaaccgaggc ggagccgctg cccctgcgct gcctgcgcga ggcttgcgcg    240

caggtccccc ggccgcggcc gcccccgcag ctgcgcagcc tgcccttcgg gacgctggag    300

ctaggcgaca ccgcggctct ggatgccttc tacaacgcgg atgtggtggt gctggaggtg    360

agcagctcgc tggtacagcc ctccctgttc taccaccttg gtgtgcgtga gagcttcagc    420

atgaccaaca atgtgctcct ctgctcccag gccgacctcc ctgacctgca ggccctgcgg    480

gaggatgttt tccagaagaa ctcggattgc gttggcagct acacactgat cccctatgtg    540

gtgacggcca ctggtcgggt gctgtgtggt gatgcaggcc ttctgcgggg cctggctgat    600

gggctggtac aggctggagt ggggaccgag gccctgctca ctcccctggt gggccggctt    660

gcccgcctgc tggaggccac acccacagac tcttgtggct atttccggga gaccattcgg    720

cgggacatcc ggcaggcgcg ggagcggttc agtgggccac agctgcggca ggagctggct    780
```

-continued

```
cgcctgcagc ggagactgga cagcgtggag ctgctgagcc ccgacatcat catgaacttg    840
ctgctctcct accgcgatgt gcaggactac tcggccatca ttgagctggt ggagacgctg    900
caggccttgc ccacctgtga tgtggccgag cagcataatg tctgcttcca ctacactttt    960
gccctcaacc ggaggaacag gcctggggac cgggcgaagg ccctgtctgt gctgctgccg   1020
ctggtacagc ttgagggctc tgtggcgccc gatctgtact gcatgtgtgg ccgtatctac   1080
aaggacatgt tcttcagctc gggtttccag gatgctgggc accgggagca ggcctatcac   1140
tggtatcgca aggcttttga cgtagagccc agccttcact caggcatcaa tgcagctgtg   1200
ctcctcattg ctgccgggca gcactttgag gattccaaag agctccggct aataggcatg   1260
aagctgggct gcctgctggc ccgcaaaggc tgcgtggaga agatgcagta ttactgggat   1320
gtgggtttct acctgggagc ccagatcctc gccaatgacc ccacccaggt ggtgctggct   1380
gcagagcagc tgtataagct caatgccccc atatggtacc tggtgtccgt gatggagacc   1440
ttcctgctct accagcactt caggcccacg ccagagcccc ctggagggcc accacgccgt   1500
gcccacttct ggctccactt cttgctacag tcctgccaac cattcaagac agcctgtgcc   1560
cagggcgacc agtgcttggt gctggtcctg gagatgaaca aggtgctgct gcctgcaaag   1620
ctcgaggttc ggggtactga cccagtaagc acagtgaccc tgagcctgct ggagcctgag   1680
acccaggaca ttccctccag ctggaccttc ccagtcgcct ccatatgcgg agtcagcgcc   1740
tcaaagcgcg acgagcgctg ctgcttcctc tatgcactcc ccccggctca ggacgtccag   1800
ctgtgcttcc ccagcgtagg gcactgccag tggttctgcg gcctgatcca ggcctgggtg   1860
acgaacccgg attccacggc gcccgcggag gaggcggagg gcgcggggga gatgttggag   1920
tttgattatg agtacacgga gacgggcgag cggctggtgc tgggcaaggg cacgtatggg   1980
gtggtgtacg cgggccgcga tcgccacacg agggtgcgca tcgccatcaa ggagatcccg   2040
gagcgggaca gcaggttctc tcagcccctg catgaagaga tcgctcttca cagacgcctg   2100
cgccacaaga acatagtgcg ctatctgggc tcagctagcc agggcggcta ccttaagatc   2160
ttcatggagg aagtgcctgg aggcagcctg tcctccttgc tgcggtcggt gtggggaccc   2220
ctgaaggaca acgagagcac catcagtttc tacacccgcc agatcctgca gggacttggc   2280
tacttgcacg acaaccacat cgtgcacagg gacataaaag gggacaatgt gctgatcaac   2340
accttcagtg ggctgctcaa gatttctgac ttcggcacct ccaagcggct ggcaggcatc   2400
acaccttgca ctgagacctt cacaggaact ctgcagtata tggccccaga aatcattgac   2460
cagggcccac gcgggtatgg gaaagcagct gacatctggt cactgggctg cactgtcatt   2520
gagatggcca caggtcgccc cccctccac gagctcggga gcccacaggc tgccatgttt   2580
caggtgggta tgtacaaggt ccatccgcca atgcccagct ctctgtcggc cgaggcccaa   2640
gcctttctcc tccgaacttt tgagccagac ccccgcctcc gagccagcgc ccagacactg   2700
ctgggggacc ccttcctgca gcctgggaaa aggagccgca gccccagctc ccccacgacat   2760
gctccacggc cctcagatgc cccttctgcc agtcccactc cttcagccaa ctcaaccacc   2820
cagtctcaga cattcccgtg ccctcaggca ccctctcagc acccacccag ccccccgaag   2880
cgctgcctca gttatggggg caccagccag ctccgggtgc ccgaggagcc tgcggccgag   2940
gagcctgcgt ctccggagga gagttcgggg ctgagcctgc tgcaccagga gagcaagcgt   3000
cgggccatgc tggccgcagt attggagcag gagctgccag cgctggcgga gaatctgcac   3060
caggagcaga agcaagagca gggggcccgt ctgggcagaa accatgtgga agagctgctg   3120
```

```
cgctgcctcg gggcacacat ccacactccc aaccgccggc agctcgccca ggagctgcgg   3180
gcgctgcaag gacggctgag ggcccagggc cttgggcctg cgcttctgca cagaccgctg   3240
tttgccttcc cggatgcggt gaagcagatc ctccgcaagc gccagatccg tccacactgg   3300
atgttcgttc tggactcact gctcagccgt gctgtgcggg cagccctggg tgtgctagga   3360
ccggaggtgg agaaggaggc ggtctcaccg aggtcagagg agctgagtaa tgaaggggac   3420
tcccagcaga gcccaggcca gcagagcccg cttccggtgg agcccgagca gggccccgct   3480
cctctgatgg tgcagctgag cctcttgagg gcagagactg atcggctgcg cgaaatcctg   3540
gcggggaagg aacgggagta ccaggccctg gtgcagcggg ctctacagcg gctgaatgag   3600
gaagcccgga cctatgtcct ggccccagag cctccaactg ctctttcaac ggaccagggc   3660
ctggtgcagt ggctacagga actgaatgtg gattcaggca ccatccaaat gctgttgaac   3720
catagcttca ccctccacac tctgctcacc tatgccactc gagatgacct catctacacc   3780
cgcatcaggg gagggatggt atgccgcatc tggagggcca tcttggcaca gcgagcagga   3840
tccacaccag tcacctctgg accctga                                       3867
```

<210> SEQ ID NO 24
<211> LENGTH: 1740
<212> TYPE: DNA
<213> ORGANISM: Homo sapiens

<400> SEQUENCE: 24

```
atgtctacag cctctgccgc ctcctcctcc tcctcgtctt cggccggtga gatgatcgaa     60
gccccttccc aggtcctcaa ctttgaagag atcgactaca aggagatcga ggtggaagag    120
gttgttggaa gaggagcctt tggagttgtt tgcaaagcta agtggagagc aaaagatgtt    180
gctattaaac aaatagaaag tgaatctgag aggaaagcgt ttattgtaga gcttcggcag    240
ttatcccgtg tgaaccatcc taatattgta aagctttatg gagcctgctt gaatccagtg    300
tgtcttgtga tggaatatgc tgaagggggc tctttatata atgtgctgca tggtgctgaa    360
ccattgccat attatactgc tgcccacgca atgagttggt gtttacagtg ttcccaagga    420
gtggcttatc ttcacagcat gcaacccaaa gcgctaattc acagggacct gaaaccacca    480
aacttactgc tggttgcagg ggggacagtt ctaaaaattt gtgattttgg tacagcctgt    540
gacattcaga cacacatgac caataacaag gggagtgctg cttggatggc acctgaagtt    600
tttgaaggta gtaattacag tgaaaaatgt gacgtcttca gctggggtat tattctttgg    660
gaagtgataa cgcgtcggaa accctttgat gagattggtg gcccagcttt ccgaatcatg    720
tgggctgttc ataatggtac tcgaccacca ctgataaaaa atttacctaa gcccattgag    780
agcctgatga ctcgttgttg gtctaaagat ccttcccagc gcccttcaat ggaggaaatt    840
gtgaaaataa tgactcactt gatgcggtac tttccaggag cagatgagcc attacagtat    900
ccttgtcagt attcagatga aggacagagc aactctgcca ccagtacagg ctcattcatg    960
gacattgctt ctacaaatac gagtaacaaa agtgacacta atatggagca agttcctgcc   1020
acaaatgata ctattaagcg cttagaatca aaattgttga aaaatcaggc aaagcaacag   1080
agtgaatctg gacgtttaag cttgggagcc tcccgtggga gcagtgtgga gagcttgccc   1140
ccaacctctg agggcaagag gatgagtgct gacatgtctg aaatagaagc taggatcgcc   1200
gcaaccacag gcaacggaca gccaagacgt agatccatcc aagacttgac tgtaactgga   1260
acagaacctg gtcaggtgag cagtaggtca tccagtccca gtgtcagaat gattactacc   1320
tcaggaccaa cctcagaaaa gccaactcga agtcatccat ggacccctga tgattccaca   1380
```

gataccaatg gatcagataa ctccatccca atggcttatc ttacactgga tcaccaacta 1440
cagcctctag caccgtgccc aaactccaaa gaatctatgg cagtgtttga acagcattgt 1500
aaaatggcac aagaatatat gaaagttcaa acagaaattg cattgttatt acagagaaag 1560
caagaactag ttgcagaact ggaccaggat gaaaaggacc agcaaaatac atctcgcctg 1620
gtacaggaac ataaaaagct tttagatgaa aacaaaagcc tttctactta ctaccagcaa 1680
tgcaaaaaac aactagaggt catcagaagt cagcagcaga aacgacaagg cacttcatga 1740

<210> SEQ ID NO 25
<211> LENGTH: 1113
<212> TYPE: DNA
<213> ORGANISM: Homo sapiens

<400> SEQUENCE: 25
atgctgtcca actcccaggg ccagagcccg ccggtgccgt tccccgcccc ggccccgccg 60
ccgcagcccc ccacccctgc cctgccgcac cccccggcgc agccgccgcc gccgcccccg 120
cagcagttcc cgcagttcca cgtcaagtcc ggcctgcaga tcaagaagaa cgccatcatc 180
gatgactaca aggtcaccag ccaggtcctg gggctgggca tcaacggcaa agttttgcag 240
atcttcaaca agaggaccca ggagaaattc gccctcaaaa tgcttcagga ctgccccaag 300
gcccgcaggg aggtggagct gcactggcgg gcctcccagt gcccgcacat cgtacggatc 360
gtggatgtgt acgagaatct gtacgcaggg aggaagtgcc tgctgattgt catggaatgt 420
ttggacggtg gagaactctt tagccgaatc caggatcgag gagaccaggc attcacagaa 480
agagaagcat ccgaaatcat gaagagcatc ggtgaggcca tccagtatct gcattcaatc 540
aacattgccc atcgggatgt caagcctgag aatctcttat acacctccaa aaggcccaac 600
gccatcctga aactcactga ctttggcttt gccaaggaaa ccaccagcca caactctttg 660
accactcctt gttatacacc gtactatgtg gctccagaag tgctgggtcc agagaagtat 720
gacaagtcct gtgacatgtg gtccctgggt gtcatcatgt acatcctgct gtgtgggtat 780
ccccccttct actccaacca cggccttgcc atctctccgg gcatgaagac tcgcatccga 840
atgggccagt atgaatttcc caacccagaa tggtcagaag tatcagagga agtgaagatg 900
ctcattcgga atctgctgaa aacagagccc acccagagaa tgaccatcac cgagtttatg 960
aaccaccctt ggatcatgca atcaacaaag gtccctcaaa ccccactgca caccagccgg 1020
gtcctgaagg aggacaagga gcggtgggag gatgtcaagg ggtgtcttca tgacaagaac 1080
agcgaccagg ccacttggct gaccaggttg tga 1113

<210> SEQ ID NO 26
<211> LENGTH: 954
<212> TYPE: DNA
<213> ORGANISM: Homo sapiens

<400> SEQUENCE: 26
atgcgacccg accgcgctga ggctccagga ccgcccgcca tggctgcagg aggtcccggc 60
gcggggtctg cggccccggt ctcctccaca tcctcccttc ccctggctgc tctcaacatg 120
cgagtgcggc gccgcctgtc tctgttcttg aacgtgcgga cacaggtggc ggccgactgg 180
accgcgctgg cggaggagat ggactttgag tacttggaga tccggcaact ggagacacaa 240
gcggacccca ctggcaggct gctggacgcc tggcagggac gccctggcgc ctctgtaggc 300
cgactgctcg agctgcttac caagctgggc cgcgacgacg tgctgctgga gctgggaccc 360

-continued agcattgagg aggattgcca aaagtatatc ttgaagcagc agcaggagga ggctgagaag 420
cctttacagg tggccgctgt agacagcagt gtcccacgga cagcagagct ggcgggcatc 480
accacacttg atgacccct ggggcatatg cctgagcgtt tcgatgcctt catctgctat 540
tgccccagcg acatccagtt tgtgcaggag atgatccggc aactggaaca gacaaactat 600
cgactgaagt tgtgtgtgtc tgaccgcgat gtcctgcctg gcacctgtgt ctggtctatt 660
gctagtgagc tcatcgaaaa gaggttggct agaaggccac ggggtgggtg ccgccggatg 720
gtggtggttg tctctgatga ttacctgcag agcaaggaat gtgacttcca gaccaaattt 780
gcactcagcc tctctccagg tgcccatcag aagcgactga tccccatcaa gtacaaggca 840
atgaagaaag agttccccag catcctgagg ttcatcactg tctgcgacta caccaacccc 900
tgcaccaaat cttggttctg gactcgcctt gccaaggcct tgtccctgcc ctga 954

<210> SEQ ID NO 27
<211> LENGTH: 2907
<212> TYPE: DNA
<213> ORGANISM: Homo sapiens

<400> SEQUENCE: 27
atggcagaag atgatccata tttgggaagg cctgaacaaa tgtttcattt ggatccttct 60
ttgactcata caatatttaa tccagaagta tttcaaccac agatggcact gccaacagat 120
ggcccatacc ttcaaatatt agagcaacct aaacagagag gatttcgttt ccgttatgta 180
tgtgaaggcc catcccatgg tggactacct ggtgcctcta gtgaaaagaa caagaagtct 240
taccctcagg tcaaaatctg caactatgtg ggaccagcaa aggttattgt tcagttggtc 300
acaaatggaa aaaatatcca cctgcatgcc cacagcctgg tgggaaaaca ctgtgaggat 360
gggatctgca ctgtaactgc tggacccaag gacatggtgg tcggcttcgc aaacctgggt 420
atacttcatg tgacaaagaa aaaagtattt gaaacactgg aagcacgaat gacagaggcg 480
tgtataaggg gctataatcc tggactcttg gtgcaccctg accttgccta tttgcaagca 540
gaaggtggag gggaccggca gctgggagat cgggaaaaag agctaatccg ccaagcagct 600
ctgcagcaga ccaaggagat ggacctcagc gtggtgcggc tcatgtttac agcttttctt 660
ccggatagca ctggcagctt cacaaggcgc ctggaacccg tggtatcaga cgccatctat 720
gacagtaaag cccccaatgc atccaacttg aaaattgtaa gaatggacag gacagctgga 780
tgtgtgactg gaggggagga aatttatctt ctttgtgaca aagttcagaa agatgacatc 840
cagattcgat tttatgaaga ggaagaaaat ggtggagtct gggaaggatt tggagatttt 900
tcccccacag atgttcatag acaatttgcc attgtcttca aaactccaaa gtataaagat 960
attaatatta caaaaccagc ctctgtgttt gtccagcttc ggaggaaatc tgacttggaa 1020
actagtgaac caaaaccttt cctctactat cctgaaatca aagataaaga agaagtgcag 1080
aggaaacgtc agaagctcat gcccaatttt tcggatagtt tcggcggtgg tagtggtgct 1140
ggagctggag gcggaggcat gtttggtagt ggcggtggag gagggggcac tggaagtaca 1200
ggtccagggt atagcttccc acactatgga tttcctactt atggtgggat tactttccat 1260
cctggaacta ctaaatctaa tgctgggatg aagcatggaa ccatggacac tgaatctaaa 1320
aaggaccctg aaggttgtga caaaagtgat gacaaaaaca ctgtaaacct ctttgggaaa 1380
gttattgaaa ccacagagca agatcaggag cccagcgagg ccaccgttgg gaatggtgag 1440
gtcactctaa cgtatgcaac aggaacaaaa gaagagagtg ctggagttca ggataacctc 1500
tttctagaga aggctatgca gcttgcaaag aggcatgcca atgccctttt cgactacgcg 1560
gtgacaggag acgtgaagat gctgctggcc gtccagcgcc atctcactgc tgtgcaggat 1620
gagaatgggg acagtgtctt acacttagca atcatccacc ttcattctca acttgtgagg 1680
gatctactag aagtcacatc tggtttgatt tctgatgaca ttatcaacat gagaaatgat 1740
ctgtaccaga cgcccttgca cttggcagtg atcactaagc aggaagatgt ggtggaggat 1800
ttgctgaggg ctggggccga cctgagcctt ctggaccgct tgggtaactc tgttttgcac 1860
ctagctgcca aagaaggaca tgataaagtt ctcagtatct tactcaagca caaaaaggca 1920
gcactacttc ttgaccaccc caacggggac ggtctgaatg ccattcatct agccatgatg 1980
agcaatagcc tgccatgttt gctgctgctg gtggccgctg gggctgacgt caatgctcag 2040
gagcagaagt ccgggcgcac agcactgcac ctggctgtgg agcacgacaa catctcattg 2100
gcaggctgcc tgctcctgga gggtgatgcc catgtggaca gtactaccta cgatggaacc 2160
acacccctgc atatagcagc tgggagaggg tccaccaggc tggcagctct tctcaaagca 2220
gcaggagcag atcccctggt ggagaacttt gagcctctct atgacctgga tgactcttgg 2280
gaaaatgcag gagaggatga aggagttgtg cctggaacca cgcctctaga tatggccacc 2340
agctggcagg tatttgacat attaaatggg aaaccatatg agccagagtt tacatctgat 2400
gatttactag cacaaggaga catgaaacag ctggctgaag atgtgaagct gcagctgtat 2460
aagttactag aaattcctga tccagacaaa aactgggcta ctctggcgca gaaattaggt 2520
ctggggatac ttaataatgc cttccggctg agtcctgctc cttccaaaac acttatggac 2580
aactatgagg tctctggggg tacagtcaga gagctggtgg aggccctgag acaaatgggc 2640
tacaccgaag caattgaagt gatccaggca gcctccagcc cagtgaagac cacctctcag 2700
gcccactcgc tgcctctctc gcctgcctcc acaaggcagc aaatagacga gctccgagac 2760
agtgacagtg tctgcgacag cggcgtggag acatccttcc gcaaactcag ctttaccgag 2820
tctctgacca gtggtgcctc actgctaact ctcaacaaaa tgccccatga ttatgggcag 2880
gaaggacctc tagaaggcaa aatttag 2907

<210> SEQ ID NO 28
<211> LENGTH: 2844
<212> TYPE: DNA
<213> ORGANISM: Homo sapiens

<400> SEQUENCE: 28
atggcagtga tggaaatggc ctgcccaggt gcccctggct cagcagtggg gcagcagaag 60
gaactcccca aagccaagga gaagacgccg ccactgggga agaaacagag ctccgtctac 120
aagcttgagg ccgtggagaa gagccctgtg ttctgcggaa agtgggagat cctgaatgac 180
gtgattacca agggcacagc caaggaaggc tccgaggcag ggccagctgc catctctatc 240
atcgcccagg ctgagtgtga gaatagccaa gagttcagcc ccaccttttc agaacgcatt 300
ttcatcgctg ggtccaaaca gtacagccag tccgagagtc ttgatcagat ccccaacaat 360
gtggcccatg ctacagaggg caaaatggcc cgtgtgtgtt ggaagggaaa gcgtcgcagc 420
aaagcccgga agaaacggaa gaagaagagc tcaaagtccc tggctcatgc aggagtggcc 480
ttggccaaac ccctccccag gacccctgag caggagagct gcaccatccc agtgcaggag 540
gatgagtctc cactcggcgc cccatatgtt agaaacaccc cgcagttcac caagcctctg 600
aaggaaccag gccttgggca actctgtttt aagcagcttg gcgagggcct acggccggct 660
ctgcctcgat cagaactcca caaactgatc agccccttgc aatgtctgaa ccacgtgtgg 720

```
aaactgcacc acccccagga cggaggcccc ctgcccctgc ccacgcaccc cttcccctat    780

agcagactgc ctcatccctt cccattccac cctctccagc cctggaaacc tcaccctctg    840

gagtccttcc tgggcaaact ggcctgtgta gacagccaga aacccttgcc tgacccacac    900

ctgagcaaac tggcctgtgt agacagtcca aagcccctgc ctggcccaca cctggagccc    960

agctgcctgt ctcgtggtgc ccatgagaag ttttctgtgg aggaatacct agtgcatgct   1020

ctgcaaggca gcgtgagctc aggccaggcc cacagcctga ccagcctggc caagacctgg   1080

gcagcaaggg gctccagatc ccgggagccc agccccaaaa ctgaggacaa cgagggtgtc   1140

ctgctcactg agaaactcaa gccagtggat tatgagtacc gagaagaagt ccactgggcc   1200

acgcaccagc tccgcctggg cagaggctcc ttcggagagg tgcacaggat ggaggacaag   1260

cagactggct tccagtgcgc tgtcaaaaag gtgcggctgg aagtatttcg ggcagaggag   1320

ctgatggcat gtgcaggatt gacctcaccc agaattgtcc ctttgtatgg agctgtgaga   1380

gaagggcctt gggtcaacat cttcatggag ctgctggaag gtggctccct gggccagctg   1440

gtcaaggagc agggctgtct cccagaggac cgggccctgt actacctggg ccaggccctg   1500

gagggtctgg aatacctcca ctcacgaagg attctgcatg gggacgtcaa agctgacaac   1560

gtgctcctgt ccagcgatgg gagccacgca gccctctgtg actttggcca tgctgtgtgt   1620

cttcaacctg atggcctggg aaagtccttg ctcacagggg actacatccc tggcacagag   1680

acccacatgg ctccggaggt ggtgctgggc aggagctgcg acgccaaggt ggatgtctgg   1740

agcagctgct gtatgatgct gcacatgctc aacggctgcc acccctggac tcagttcttc   1800

cgagggccgc tctgcctcaa gattgccagc gagcctccgc ctgtgaggga gatcccaccc   1860

tcctgcgccc ctctcacagc ccaggccatc caagaggggc tgaggaaaga gcccatccac   1920

cgcgtgtctg cagcggagct gggagggaag gtgaaccggg cactacagca agtgggaggt   1980

ctgaagagcc cttggagggg agaatataaa gaaccaagac atccaccgcc aaatcaagcc   2040

aattaccacc agaccctcca tgcccagccg agagagcttt cgccaagggc cccagggccc   2100

cggccagctg aggagacaac aggcagagcc cctaagctcc agcctcctct cccaccagag   2160

cccccagagc caaacaagtc tcctcccttg actttgagca aggaggagtc tgggatgtgg   2220

gaacccttac ctctgtcctc cctggagcca gcccctgcca gaaaccccag ctcaccagag   2280

cggaaagcaa ccgtcccgga gcaggaactg cagcagctgg aaatagaatt attcctcaac   2340

agcctgtccc agccattttc tctggaggag caggagcaaa ttctctcgtg cctcagcatc   2400

gacagcctct ccctgtcgga tgacagtgag aagaacccat caaaggcctc tcaaagctcg   2460

cgggacaccc tgagctcagg cgtacactcc tggagcagcc aggccgaggc tcgaagctcc   2520

agctggaaca tggtgctggc ccgggggcgg cccaccgaca ccccaagcta tttcaatggt   2580

gtgaaagtcc aaatacagtc tcttaatggt gaacacctgc acatccggga gttccaccgg   2640

gtcaaagtgg gagacatcgc cactggcatc agcagccaga tcccagctgc agccttcagc   2700

ttggtcacca aagacgggca gcctgttcgc tacgacatgg aggtgccaga ctcgggcatc   2760

gacctgcagt gcacactggc ccctgatggc agcttcgcct ggagctggag ggtcaagcat   2820

ggccagctgg agaacaggcc ctaa                                          2844
```

<210> SEQ ID NO 29
<211> LENGTH: 1083
<212> TYPE: DNA
<213> ORGANISM: Homo sapiens

<400> SEQUENCE: 29

-continued

```
atgtctcagg agaggcccac gttctaccgg caggagctga acaagacaat ctgggaggtg     60

cccgagcgtt accagaacct gtctccagtg ggctctggcg cctatggctc tgtgtgtgct    120

gcttttgaca caaaaacggg gttacgtgtg gcagtgaaga agctctccag accatttcag    180

tccatcattc atgcgaaaag aacctacaga gaactgcggt tacttaaaca tatgaaacat    240

gaaaatgtga ttggtctgtt ggacgttttt acacctgcaa ggtctctgga ggaattcaat    300

gatgtgtatc tggtgaccca tctcatgggg gcagatctga acaacattgt gaaatgtcag    360

aagcttacag atgaccatgt tcagttcctt atctaccaaa ttctccgagg tctaaagtat    420

atacattcag ctgacataat tcacagggac ctaaaaccta gtaatctagc tgtgaatgaa    480

gactgtgagc tgaagattct ggattttgga ctggctcggc acacagatga tgaaatgaca    540

ggctacgtgg ccactaggtg gtacagggct cctgagatca tgctgaactg gatgcattac    600

aaccagacag ttgatatttg gtcagtggga tgcataatgg ccgagctgtt gactggaaga    660

acattgtttc ctggtacaga ccatattaac cagcttcagc agattatgcg tctgacagga    720

acacccccg cttatctcat taacaggatg ccaagccatg aggcaagaaa ctatattcag    780

tctttgactc agatgccgaa gatgaacttt gcgaatgtat ttattggtgc caatcccctg    840

gctgtcgact tgctggagaa gatgcttgta ttggactcag ataagagaat tacagcggcc    900

caagcccttg cacatgccta ctttgctcag taccacgatc ctgatgatga accagtggcc    960

gatccttatg atcagtcctt tgaaagcagg gacctcctta tagatgagtg gaaaagcctg   1020

acctatgatg aagtcatcag ctttgtgcca ccaccccttg accaagaaga gatggagtcc   1080

tga                                                                 1083
```

<210> SEQ ID NO 30
<211> LENGTH: 1656
<212> TYPE: DNA
<213> ORGANISM: Homo sapiens

<400> SEQUENCE: 30

```
atggctggtg atctttcagc aggtttcttc atggaggaac ttaatacata ccgtcagaag     60

cagggagtag tacttaaata tcaagaactg cctaattcag gacctccaca tgataggagg    120

tttacatttc aagttataat agatggaaga gaatttccag aaggtgaagg tagatcaaag    180

aaggaagcaa aaaatgccgc agccaaatta gctgttgaga tacttaataa ggaaaagaag    240

gcagttagtc ctttattatt gacaacaacg aattcttcag aaggattatc catggggaat    300

tacataggcc ttatcaatag aattgcccag aagaaaagac taactgtaaa ttatgaacag    360

tgtgcatcgg gggtgcatgg gccagaagga tttcattata aatgcaaaat gggacagaaa    420

gaatatagta ttggtacagg ttctactaaa caggaagcaa aacaattggc cgctaaactt    480

gcatatcttc agatattatc agaagaaacc tcagtgaaat ctgactacct gtcctctggt    540

tcttttgcta ctacgtgtga gtcccaaagc aactctttag tgaccagcac actcgcttct    600

gaatcatcat ctgaaggtga cttctcagca gatacatcag agataaattc taacagtgac    660

agtttaaaca gttcttcgtt gcttatgaat ggtctcagaa ataatcaaag gaaggcaaaa    720

agatctttgg cacccagatt tgaccttcct gacatgaaag aaacaaagta tactgtggac    780

aagaggtttg gcatggattt taaagaaata gaattaattg gctcaggtgg atttggccaa    840

gttttcaaag caaaacacag aattgacgga aagacttacg ttattaaacg tgttaaatat    900

aataacgaga aggcggagcg tgaagtaaaa gcattggcaa aacttgatca tgtaaatatt    960
```

-continued gttcactaca atggctgttg ggatggattt gattatgatc ctgagaccag tgatgattct 1020
cttgagagca gtgattatga tcctgagaac agcaaaaata gttcaaggtc aaagactaag 1080
tgccttttca tccaaatgga attctgtgat aaagggacct tggaacaatg gattgaaaaa 1140
agaagaggcg agaaactaga caaagttttg gctttggaac tctttgaaca aataacaaaa 1200
ggggtggatt atatacattc aaaaaaatta attcatagag atcttaagcc aagtaatata 1260
ttcttagtag atacaaaaca agtaaagatt ggagactttg gacttgtaac atctctgaaa 1320
aatgatggaa agcgaacaag gagtaaggga actttgcgat acatgagccc agaacagatt 1380
tcttcgcaag actatggaaa ggaagtggac ctctacgctt tggggctaat tcttgctgaa 1440
cttcttcatg tatgtgacac tgcttttgaa acatcaaagt ttttcacaga cctacgggat 1500
ggcatcatct cagatatatt tgataaaaaa gaaaaaactc ttctacagaa attactctca 1560
aagaaacctg aggatcgacc taacacatct gaaatactaa ggaccttgac tgtgtggaag 1620
aaaagcccag agaaaaatga acgacacaca tgttag 1656

<210> SEQ ID NO 31
<211> LENGTH: 1443
<212> TYPE: DNA
<213> ORGANISM: Homo sapiens

<400> SEQUENCE: 31
atgagcgacg tggctattgt gaaggagggt tggctgcaca aacgagggga gtacatcaag 60
acctggcggc cacgctactt cctcctcaag aatgatggca ccttcattgg ctacaaggag 120
cggccgcagg atgtggacca acgtgaggct cccctcaaca acttctctgt ggcgcagtgc 180
cagctgatga agacggagcg gccccggccc aacaccttca tcatccgctg cctgcagtgg 240
accactgtca tcgaacgcac cttccatgtg gagactcctg aggagcggga ggagtggaca 300
accgccatcc agactgtggc tgacggcctc aagaagcagg aggaggagga gatggacttc 360
cggtcgggct cacccagtga caactcaggg gctgaagaga tggaggtgtc cctggccaag 420
cccaagcacc gcgtgaccat gaacgagttt gagtacctga agctgctggg caagggcact 480
ttcggcaagg tgatcctggt gaaggagaag gccacaggcc gctactacgc catgaagatc 540
ctcaagaagg aagtcatcgt ggccaaggac gaggtggccc acacactcac cgagaaccgc 600
gtcctgcaga actccaggca ccccttcctc acagccctga agtactcttt ccagacccac 660
gaccgcctct gctttgtcat ggagtacgcc aacgggggcg agctgttctt ccacctgtcc 720
cgggagcgtg tgttctccga ggaccgggcc cgcttctatg gcgctgagat tgtgtcagcc 780
ctggactacc tgcactcgga gaagaacgtg gtgtaccggg acctcaagct ggagaacctc 840
atgctggaca aggacgggca cattaagatc acagacttcg ggctgtgcaa ggaggggatc 900
aaggacggtg ccaccatgaa gaccttttgc ggcacacctg agtacctggc ccccgaggtg 960
ctggaggaca atgactacgg ccgtgcagtg gactggtggg ggctgggcgt ggtcatgtac 1020
gagatgatgt gcggtcgcct gcccttctac aaccaggacc atgagaagct tttgagctc 1080 atcctcatgg aggagatccg cttcccgcgc acgcttggtc ccgaggccaa gtccttgctt 1140
tcagggctgc tcaagaagga ccccaagcag aggcttggcg gggctccga ggacgccaag 1200 gagatcatgc agcatcgctt ctttgccggt atcgtgtggc agcacgtgta cgagaagaag 1260
ctcagcccac ccttcaagcc ccaggtcacg tcggagactg acaccaggta ttttgatgag 1320
gagttcacgg cccagatgat caccatcaca ccacctgacc aagatgacag catggagtgt 1380
gtggacagcg agcgcaggcc ccacttcccc cagttctcct actcggccag cggcacggcc 1440
tga 1443

<210> SEQ ID NO 32
<211> LENGTH: 2514
<212> TYPE: DNA
<213> ORGANISM: Homo sapiens

<400> SEQUENCE: 32
atggctagca aacgaaaatc tacaactcca tgcatggttc ggacatcaca agtagtagaa 60
caagatgtgc ccgaggaagt agacagggcc aaagagaaag gaatcggcac accacagcct 120
gacgtggcca aggacagttg ggcagcagaa cttgaaaact cttccaaaga aaacgaagtg 180
atagaggtga aatctatggg ggaaagccag tccaaaaaac tccaaggtgg ttatgagtgc 240
aaatactgcc cctactccac gcaaaacctg aacgagttca cggagcatgt cgacatgcag 300
catcccaacg tgattctcaa ccccctctac gtgtgtgcag aatgtaactt cacaaccaaa 360
aagtacgact ccctatccga ccacaactcc aagttccatc ccggggaggc caacttcaag 420
ctgaagttaa ttaaacgcaa taatcaaact gtcttggaac agtccatcga aaccaccaac 480
catgtcgtgt ccatcaccac cagtggccct ggaactggtg acagtgattc tgggatctcg 540
gtgagtaaaa cccccatcat gaagcctgga aaaccaaaag cggatgccaa gaaggtgccc 600
aagaagcccg aggagatcac ccccgagaac cacgtggaag ggaccgcccg cctggtgaca 660
gacacagctg agatcctctc gagactcggc ggggtggagc tcctccaaga cacattagga 720
cacgtcatgc cttctgtaca gctgccacca aatatcaacc ttgtgcccaa ggtccctgtc 780
ccactaaata ctaccaaata caactctgcc ctggatacaa atgccacgat gatcaactct 840
ttcaacaagt ttccttaccc gacccaggct gagttgtcct ggctgacagc tgcctccaaa 900
cacccagagg agcacatcag aatctggttt gccacccagc gcttaaagca tggcatcagc 960
tggtccccag aagaggtgga ggaggcccgg aagaagatgt tcaacggcac catccagtca 1020
gtacccccga ccatcactgt gctgcccgcc cagttggccc ccacaaaggt gacgcagccc 1080
atcctccaga cggctctacc gtgccagatc ctcggccaga ctagcctggt gctgactcag 1140
gtgaccagcg ggtcaacaac cgtctcttgc tcccccatca cacttgccgt ggcaggagtc 1200
accaaccatg gccagaagag acccttggtg actccccaag ctgcccccga acccaagcgt 1260
ccacacatcg ctcaggtgcc agagccccca cccaaggtgg ccaacccccc gctcacacca 1320
gccagtgacc gcaagaagac aaaggagcag atagcacatc tcaaggccag ctttctccag 1380
agccagttcc ctgacgatgc cgaggtttac cggctcatcg aggtgactgg ccttgccagg 1440
agcgagatca agaagtggtt cagtgaccac cgatatcggt gtcaaagggg catcgtccac 1500
atcaccagcg aatcccttgc caaagaccag ttggccatcg cggcctcccg acacggtcgc 1560
acgtatcatg cgtacccaga ctttgccccc cagaagttca aagagaaaac acagggtcag 1620
gttaaaatct tggaagacag ctttttgaaa agttcttttc ctacccaagc agaactggat 1680
cggctaaggg tggagaccaa gctgagcagg agagagatcg actcctggtt ctcggagagg 1740
cggaagcttc gagacagcat ggaacaagct gtcttggatt ccatggggtc tggcaaaaaa 1800
ggccaagatg tgggagcccc caatggtgct ctgtctcgac tcgaccagct ctccggtgcc 1860
cagttaacaa gttctctgcc cagcccttcg ccagcaattg caaaaagtca agaacaggtt 1920
catctcctga ggagcacgtt tgcaagaacc cagtggccta ctccccagga gtacgaccag 1980
ttagcggcca agactggcct ggtccgaact gagattgtgc gttggttcaa ggagaacaga 2040

-continued

```
tgcttgctga aaacgggaac cgtgaagtgg atggagcagt accagcacca gcccatggca   2100

gatgatcacg gctacgatgc cgtagcaagg aaagcaacaa aacccatggc cgagagccca   2160

aagaacgggg gtgatgtggt tccacaatat tacaaggacc ccaaaaagct ctgcgaagag   2220

gacttggaga agttggtgac cagggtaaaa gtaggcagcg agccagcaaa agactgtttg   2280

ccagcaaagc cctcagaggc cacctcagac cggtcagagg gcagcagccg ggacggccag   2340

ggtagcgacg agaacgagga gtcgagcgtt gtggattacg tggaggtgac ggtcggggag   2400

gaggatgcga tctcagatag atcagatagc tggagtcagg ctgcggcaga aggtgtgtcg   2460

gaactggctg aatcagactc cgactgcgtc cctgcagagg ctggccaggc ctag         2514
```

<210> SEQ ID NO 33
<211> LENGTH: 567
<212> TYPE: DNA
<213> ORGANISM: Homo sapiens

<400> SEQUENCE: 33

```
atgactgaat ataaacttgt ggtagttgga gctggtggcg taggcaagag tgccttgacg     60

atacagctaa ttcagaatca ttttgtggac gaatatgatc caacaataga ggattcctac    120

aggaagcaag tagtaattga tggagaaacc tgtctcttgg atattctcga cacagcaggt    180

caagaggagt acagtgcaat gagggaccag tacatgagga ctggggaggg ctttctttgt    240

gtatttgcca taaataatac taaatcattt gaagatattc accattatag agaacaaatt    300

aaaagagtta aggactctga agatgtacct atggtcctag taggaaataa atgtgatttg    360

ccttctagaa cagtagacac aaaacaggct caggacttag caagaagtta tggaattcct    420

tttattgaaa catcagcaaa gacaagacag ggtgttgatg atgccttcta tacattagtt    480

cgagaaattc gaaaacataa agaaaagatg agcaaagatg gtaaaaagaa gaaaaagaag    540

tcaaagacaa agtgtgtaat tatgtaa                                        567
```

<210> SEQ ID NO 34
<211> LENGTH: 570
<212> TYPE: DNA
<213> ORGANISM: Homo sapiens

<400> SEQUENCE: 34

```
atgactgagt acaaactggt ggtggttgga gcaggtggtg ttgggaaaag cgcactgaca     60

atccagctaa tccagaacca ctttgtagat gaatatgatc ccaccataga ggattcttac    120

agaaaacaag tggttataga tggtgaaacc tgtttgttgg acatactgga tacagctgga    180

caagaagagt acagtgccat gagagaccaa tacatgagga caggcgaagg cttcctctgt    240

gtatttgcca tcaataatag caagtcattt gcggatatta acctctacag ggagcagatt    300

aagcgagtaa aagactcgga tgatgtacct atggtgctag tgggaaacaa gtgtgatttg    360

ccaacaagga cagttgatac aaaacaagcc cacgaactgg ccaagagtta cgggattcca    420

ttcattgaaa cctcagccaa gaccagacag ggtgttgaag atgcttttta cacactggta    480

agagaaatac gccagtaccg aatgaaaaaa ctcaacagca gtgatgatgg gactcagggt    540

tgtatgggat tgccatgtgt ggtgatgtaa                                     570
```

<210> SEQ ID NO 35
<211> LENGTH: 2016
<212> TYPE: DNA
<213> ORGANISM: Homo sapiens

<400> SEQUENCE: 35

-continued atgcaaccag acatgtcctt gaatgtcatt aagatgaaat ccagtgactt cctggagagt 60
gcagaactgg acagcggagg ctttgggaag gtgtctctgt gtttccacag aacccaggga 120
ctcatgatca tgaaaacagt gtacaagggg cccaactgca ttgagcacaa cgaggccctc 180
ttggaggagg cgaagatgat gaacagactg agacacagcc gggtggtgaa gctcctgggc 240
gtcatcatag aggaagggaa gtactccctg gtgatggagt acatggagaa gggcaacctg 300
atgcacgtgc tgaaagccga gatgagtact ccgctttctg taaaaggaag gataattttg 360
gaaatcattg aaggaatgtg ctacttacat ggaaaaggcg tgatacacaa ggacctgaag 420
cctgaaaata tccttgttga taatgacttc cacattaaga tcgcagacct cggccttgcc 480
tcctttaaga tgtggagcaa actgaataat gaagagcaca atgagctgag ggaagtggac 540
ggcaccgcta agaagaatgg cggcaccctc tactacatgg cgcccgagca cctgaatgac 600
gtcaacgcaa agcccacaga gaagtcggat gtgtacagct ttgctgtagt actctgggcg 660
atatttgcaa ataaggagcc atatgaaaat gctatctgtg agcagcagtt gataatgtgc 720
ataaaatctg ggaacaggcc agatgtggat gacatcactg agtactgccc aagagaaatt 780
atcagtctca tgaagctctg ctgggaagcg aatccggaag ctcggccgac atttcctggc 840
attgaagaaa aatttaggcc tttttattta agtcaattag aagaaagtgt agaagaggac 900
gtgaagagtt taaagaaaga gtattcaaac gaaaatgcag ttgtgaagag aatgcagtct 960
cttcaacttg attgtgtggc agtaccttca agccggtcaa attcagccac agaacagcct 1020
ggttcactgc acagttccca gggacttggg atgggtcctg tggaggagtc ctggtttgct 1080
ccttccctgg agcacccaca agaagagaat gagcccagcc tgcagagtaa actccaagac 1140
gaagccaact accatcttta tggcagccgc atggacaggc agacgaaaca gcagcccaga 1200
cagaatgtgg cttacaacag agaggaggaa aggagacgca gggtctccca tgaccctttt 1260
gcacagcaaa gaccttacga gaattttcag aatacagagg gaaaaggcac tgcttattcc 1320
agtgcagcca gtcatggtaa tgcagtgcac cagccctcag ggctcaccag ccaacctcaa 1380
gtactgtatc agaacaatgg attatatagc tcacatggct ttggaacaag accactggat 1440
ccaggaacag caggtcccag agtttggtac aggccaattc caagtcatat gcctagtctg 1500
cataatatcc cagtgcctga gaccaactat ctaggaaata cacccaccat gccattcagc 1560
tccttgccac caacagatga atctataaaa tataccatat acaatagtac tggcattcag 1620
attggagcct acaattatat ggagattggt gggacgagtt catcactact agacagcaca 1680
aatacgaact tcaaagaaga gccagctgct aagtaccaag ctatctttga taataccact 1740
agtctgacgg ataaacacct ggacccaatc agggaaaatc tgggaaagca ctggaaaaac 1800
tgtgcccgta aactgggctt cacacagtct cagattgatg aaattgacca tgactatgag 1860
cgagatggac tgaaagaaaa ggtttaccag atgctccaaa agtgggtgat gagggaaggc 1920
ataaagggag ccacggtggg gaagctggcc caggcgctcc accagtgttc caggatcgac 1980
cttctgagca gcttgattta cgtcagccag aactaa 2016

<210> SEQ ID NO 36
<211> LENGTH: 1569
<212> TYPE: DNA
<213> ORGANISM: Homo sapiens

<400> SEQUENCE: 36
atgagtctgc taaactgtga aaacagctgt ggatccagcc agtctgaaag tgactgctgt 60

```
gtggccatgg ccagctcctg tagcgctgta acaaaagatg atagtgtggg tggaactgcc    120
agcacgggga acctctccag ctcatttatg gaggagatcc agggatatga tgtagagttt    180
gacccacccc tggaaagcaa gtatgaatgc cccatctgct tgatggcatt acgagaagca    240
gtgcaaacgc catgcggcca taggttctgc aaagcctgca tcataaaatc aataagggat    300
gcaggtcaca aatgtccagt tgacaatgaa atactgctgg aaaatcaact atttccagac    360
aattttgcaa aacgtgagat tctttctctg atggtgaaat gtccaaatga aggttgtttg    420
cacaagatgg aactgagaca tcttgaggat catcaagcac attgtgagtt tgctcttatg    480
gattgtcccc aatgccagcg tcccttccaa aaattccata ttaatattca cattctgaag    540
gattgtccaa ggagacaggt ttcttgtgac aactgtgctg catcaatggc atttgaagat    600
aaagagatcc atgaccagaa ctgtcctttg gcaaatgtca tctgtgaata ctgcaatact    660
atactcatca gagaacagat gcctaatcat tatgatctag actgccctac agccccaatt    720
ccatgcacat tcagtacttt tggttgccat gaaaagatgc agaggaatca cttggcacgc    780
cacctacaag agaacaccca gtcacacatg agaatgttgg cccaggctgt tcatagtttg    840
agcgttatac ccgactctgg gtatatctca gaggtccgga atttccagga aactattcac    900
cagttagagg gtcgccttgt aagacaagac catcaaatcc gggagctgac tgctaaaatg    960
gaaactcaga gtatgtatgt aagtgagctc aaacgaacca ttcgaaccct tgaggacaaa   1020
gttgctgaaa tcgaagcaca gcagtgcaat ggaatttata tttggaagat tggcaacttt   1080
ggaatgcatt tgaaatgtca agaagaggag aaacctgttg tgattcatag ccctggattc   1140
tacactggca aacccgggta caaactgtgc atgcgcttgc accttcagtt accgactgct   1200
cagcgctgtg caaactatat atcccttttt gtccacacaa tgcaaggaga atatgacagc   1260
cacctccctt ggcccttcca gggtacaata cgccttacaa ttcttgatca gtctgaagca   1320
cctgtaaggc aaaaccacga agagataatg gatgccaaac cagagctgct tgctttccag   1380
cgacccacaa tcccacggaa cccaaaaggt tttggctatg taacttttat gcatctggaa   1440
gccctaagac aaagaacttt cattaaggat gacacattat tagtgcgctg tgaggtctcc   1500
acccgctttg acatgggtag ccttcggagg gagggttttc agccacgaag tactgatgca   1560
ggggtatag                                                           1569
```

<210> SEQ ID NO 37
<211> LENGTH: 999
<212> TYPE: DNA
<213> ORGANISM: Homo sapiens

<400> SEQUENCE: 37

```
atggccaacc gttacaccat ggatctgact gccatctacg agagcctcct gtcgctgagc     60
cctgacgtgc ccgtgccatc cgaccatgga gggactgagt ccagcccagg ctggggctcc    120
tcgggaccct ggagcctgag cccctccgac tccagcccgt ctggggtcac ctcccgcctg    180
cctggccgct ccaccagcct agtggagggc cgcagctgtg gctgggtgcc cccacccccct    240
ggcttcgcac cgctggctcc ccgcctgggc cctgagctgt caccctcacc cacttcgccc    300
actgcaacct ccaccacccc ctcgcgctac aagactgagc tatgtcggac cttctcagag    360
agtgggcgct gccgctacgg ggccaagtgc cagtttgccc atggcctggg cgagctgcgc    420
caggccaatc gccaccccaa atacaagacg gaactctgtc acaagttcta cctccagggc    480
cgctgcccct acggctctcg ctgccacttc atccacaacc ctagcgaaga cctggcggcc    540
ccgggccacc ctcctgtgct tcgccagagc atcagcttct ccggcctgcc ctctggccgc    600
```

-continued

```
cggacctcac caccaccacc aggcctggcc ggcccttccc tgtcctccag ctccttctcg    660

ccctccagct ccccaccacc acctggggac cttccactgt caccctctgc cttctctgct    720

gcccctggca cccccctggc tcgaagagac cccaccccag tctgttgccc ctcctgccga    780

agggccactc ctatcagcgt ctgggggccc ttgggtggcc tggttcggac cccctctgta    840

cagtccctgg gatccgaccc tgatgaatat gccagcagcg gcagcagcct ggggggctct    900

gactctcccg tcttcgaggc gggagttttt gcaccacccc agcccgtggc agccccccgg    960

cgactcccca tcttcaatcg catctctgtt tctgagtga                           999
```